US011685906B2

(12) United States Patent
Perez-Garcia et al.

(10) Patent No.: US 11,685,906 B2
(45) Date of Patent: Jun. 27, 2023

(54) COMPOSITIONS AND METHODS FOR TREATING ORNITHINE TRANSCARBAMYLASE DEFICIENCY

(71) Applicant: Arcturus Therapeutics, Inc., San Diego, CA (US)

(72) Inventors: Carlos G. Perez-Garcia, San Diego, CA (US); Kiyoshi Tachikawa, San Diego, CA (US); Daiki Matsuda, San Diego, CA (US); Padmanabh Chivukula, San Diego, CA (US)

(73) Assignee: ARCTURUS THERAPEUTICS, INC., San Diego, CA (US)

( * ) Notice: Subject to any disclaimer, the term of this patent is extended or adjusted under 35 U.S.C. 154(b) by 582 days.

(21) Appl. No.: 16/705,102

(22) Filed: Dec. 5, 2019

(65) Prior Publication Data

US 2020/0181584 A1 Jun. 11, 2020

Related U.S. Application Data

(60) Provisional application No. 62/776,302, filed on Dec. 6, 2018.

(51) Int. Cl.

| | |
|---|---|
| ***C07H 21/02*** | (2006.01) |
| ***C07H 21/04*** | (2006.01) |
| ***C12N 9/10*** | (2006.01) |
| ***A61P 9/00*** | (2006.01) |
| *A61K 48/00* | (2006.01) |

(52) U.S. Cl.

CPC .............. *C12N 9/1018* (2013.01); *A61P 9/00* (2018.01); *C12Y 201/03003* (2013.01); *A61K 48/00* (2013.01)

(58) Field of Classification Search

CPC .............................................. C12Y 201/03003

See application file for complete search history.

(56) References Cited

U.S. PATENT DOCUMENTS

| | | | |
|---|---|---|---|
| 8,058,069 | B2 | 11/2011 | Yaworski et al. |
| 8,093,367 | B2 | 1/2012 | Kore et al. |
| 8,158,601 | B2 | 4/2012 | Chen et al. |
| 8,278,036 | B2 | 10/2012 | Kariko et al. |
| 8,304,529 | B2 | 11/2012 | Kore et al. |
| 8,492,359 | B2 | 7/2013 | Yaworski et al. |
| 8,691,966 | B2 | 4/2014 | Kariko et al. |
| 8,748,089 | B2 | 6/2014 | Kariko et al. |
| 8,822,668 | B2 | 9/2014 | Yaworski et al. |
| 9,006,191 | B2 | 4/2015 | Maclachlan et al. |
| 9,006,417 | B2 | 4/2015 | Yaworski et al. |
| 9,364,435 | B2 | 6/2016 | Yaworski et al. |
| 9,404,127 | B2 | 8/2016 | Yaworski et al. |
| 9,428,535 | B2 | 8/2016 | De Fougerolles et al. |
| 9,518,272 | B2 | 12/2016 | Yaworski et al. |
| 9,572,874 | B2 | 2/2017 | Fotin-Mleczek et al. |
| 9,750,824 | B2 | 9/2017 | Kariko et al. |
| 9,751,925 | B2 | 9/2017 | Hoge et al. |
| 9,890,365 | B2 | 2/2018 | Wang et al. |
| 9,896,413 | B2 | 2/2018 | Payne et al. |
| 10,072,057 | B2 | 9/2018 | Hoge et al. |
| 10,143,758 | B2 | 12/2018 | Guild et al. |
| 10,167,454 | B2 | 1/2019 | Wang et al. |
| 10,188,748 | B2 | 1/2019 | Von Der Mülbe et al. |
| 10,201,620 | B2 | 2/2019 | Meis et al. |
| 10,232,055 | B2 | 3/2019 | Kariko et al. |
| 10,238,754 | B2 | 3/2019 | Guild et al. |
| 10,487,105 | B2 | 11/2019 | Chivukula et al. |
| 10,501,512 | B2 | 12/2019 | De Fougerolles et al. |
| 10,526,284 | B2 | 1/2020 | Payne et al. |
| 10,568,972 | B2 | 2/2020 | Von Der Mülbe et al. |
| 2005/0147993 | A1 | 7/2005 | Khan |
| 2007/0196334 | A1 | 8/2007 | Khan |
| 2011/0256175 | A1 | 10/2011 | Hope et al. |
| 2012/0027803 | A1 | 2/2012 | Manoharan et al. |
| 2012/0128760 | A1 | 5/2012 | Manoharan et al. |
| 2014/0090108 | A1 | 3/2014 | Garabagi et al. |
| 2015/0064235 | A1 | 3/2015 | Bangel et al. |
| 2015/0104476 | A1 | 4/2015 | Von Der Mülbe et al. |
| 2016/0089451 | A1 | 3/2016 | Armstrong |
| 2016/0136301 | A1 | 5/2016 | Von Der Mülbe et al. |
| 2016/0161403 | A1 | 6/2016 | Sugimoto |
| 2016/0354493 | A1 | 12/2016 | Roy et al. |

(Continued)

FOREIGN PATENT DOCUMENTS

| | | | |
|---|---|---|---|
| SG | 11201903460 | A | 5/2019 |
| WO | 9207065 | A1 | 4/1992 |
| WO | 9315187 | A1 | 8/1993 |
| WO | 2009086558 | A1 | 7/2009 |
| WO | 2009127060 | A1 | 10/2009 |
| WO | 2010048536 | A2 | 4/2010 |
| WO | 2010054406 | A1 | 5/2010 |
| WO | 2010129709 | A1 | 11/2010 |

(Continued)

OTHER PUBLICATIONS

Kwok et al. (Biochem J, 2015, 467, 91-102).*

Federation of Experimental Biologists Society Letter, 1978, 96:1-11.

Remington's Pharmaceutical Sciences, Mack Publishing Company, 17th edition, 1985, 4 pages.

(Continued)

*Primary Examiner* — Amy H Bowman

(74) *Attorney, Agent, or Firm* — Mintz, Levin, Cohn, Ferris, Glovsky and Popeo P.C.

(57) ABSTRACT

The present disclosure provides a modified human OTC protein having improved properties for the treatment of OTC deficiency in a patient. Preferably, the protein of the disclosure is produced from a codon optimized mRNA suitable for administration to a patient suffering from OTC deficiency wherein upon administration of the mRNA to the patient, the protein of the disclosure is expressed in the patient in therapeutically effective amounts to treat OTC deficiency. The present disclosure also provides codon optimized mRNA sequences encoding wild type human OTC comprising a 5' UTR derived from a gene expressed by *Arabidopsis thaliana* for use in treating OTC deficiency in a patient.

25 Claims, 15 Drawing Sheets

Specification includes a Sequence Listing.

(56) References Cited

U.S. PATENT DOCUMENTS

| | | | |
|---|---|---|---|
| 2017/0056528 | A1 | 3/2017 | De Fougerolles et al. |
| 2017/0130216 | A1 | 5/2017 | Armstrong |
| 2017/0252461 | A1 | 9/2017 | Chakraborty et al. |
| 2017/0362627 | A1 | 12/2017 | Reynders et al. |
| 2018/0135030 | A1 | 5/2018 | Wang et al. |
| 2018/0169268 | A1 | 6/2018 | Payne et al. |
| 2018/0222863 | A1 | 8/2018 | Payne et al. |
| 2018/0273576 | A1 | 9/2018 | Hogrefe et al. |
| 2018/0327471 | A1 | 11/2018 | Limphong et al. |
| 2018/0353618 | A1 | 12/2018 | Burkhardt et al. |
| 2019/0002906 | A1 | 1/2019 | Limphong et al. |
| 2019/0192688 | A1 | 6/2019 | Askew et al. |
| 2019/0307897 | A1 | 10/2019 | Angel et al. |
| 2020/0297634 | A1 | 3/2020 | Karmali et al. |

FOREIGN PATENT DOCUMENTS

| | | | | |
|---|---|---|---|---|
| WO | WO 2011/025242 | A2 * | 3/2011 | ......... A61K 31/7105 |
| WO | 2011068810 | A1 | 6/2011 | |
| WO | 2011153493 | A2 | 12/2011 | |
| WO | 2015051169 | A2 | 4/2015 | |
| WO | 2015061491 | A1 | 4/2015 | |
| WO | 2015074085 | A1 | 5/2015 | |
| WO | 2015138348 | A1 | 9/2015 | |
| WO | 2015138357 | A2 | 9/2015 | |
| WO | 2016070166 | A2 | 5/2016 | |
| WO | 2016081029 | A1 | 5/2016 | |
| WO | 2017023817 | A1 | 2/2017 | |
| WO | 2017117530 | A1 | 7/2017 | |
| WO | 2017218524 | A1 | 12/2017 | |
| WO | 2018078053 | A1 | 5/2018 | |
| WO | 2018118102 | A1 | 6/2018 | |
| WO | 2018119163 | A1 | 6/2018 | |
| WO | 2018222890 | A1 | 12/2018 | |
| WO | 2018222926 | A1 | 12/2018 | |
| WO | WO 2019/104152 | A1 * | 5/2019 | ..... C12Y 201/03003 |
| WO | 2010088537 | A2 | 8/2020 | |

OTHER PUBLICATIONS

Altschul et al. (1990) "Basic Local Alignment Search Tool", Journal of Molecular Biology, 215(3):403-410.
Berge et al. (Jan. 1977) "Pharmaceutical Salts", Journal of Pharmaceutical Sciences, 66(1):1-19.
Bochicchio et al. (2014) "Liposomes as siRNA Delivery Vectors", Current Drug Metabolism, 15(9):882-892.
Both et al. (Mar. 1, 1975) "Methylation-Dependent Translation Of Viral Messenger RNAs In Vitro", Proceedings of the National Academy of Sciences, 72(3):1189-1193.
Bouloy et al. (Jul. 1, 1980) "Both The 7-Methyl And The 2'-O-Methyl Groups in The Cap of mRNA Strongly Influence Its Ability to Act as Primer For Influenza Virus RNA Transcription", Proceedings of the National Academy of Sciences, 77(7):3952-3956.
Burgin et al. (1996) "Chemically Modified Hammerhead Ribozymes with Improved Catalytic Rates", Biochemistry, 35(45):14090-14097.
Carillo et al. (Oct. 1988) "The Multiple Sequence Alignment Problem in Biology", SIAM Journal on Applied Mathematics, 48(5):1073-1082.
Dabkowska et al. (Mar. 7, 2012) "The Effect Of Neutral Helper Lipids on The Structure of Cationic Lipid Monolayers", Journal of the Royal Society Interface, 9(68):548-561.
Dam et al. (Mar. 6, 1998) "Garlic (*Allium sativum*) Lectins Bind to High Mannose Oligosaccharide Chains", Journal of Biological Chemistry, 273(10):5528-5535.
Devereux et al. (Jan. 11, 1984) "A Comprehensive Set of Sequence Analysis Programs for the VAX", Nucleic Acids Research, 12(1 Pt 1):387-395.
Furuichi et al. (1977) "5'-Terminal structure and mRNA stability", Nature, 266:235-239.
Gingras et al. (1999) "elF4 Initiation Factors: Effectors of mRNA Recruitment To Ribosomes And Regulators Of Translation", Annual Review of Biochemistry, 68:913-963.
Gordon Neil (May 2003) "Ornithine Transcarbamylase Deficiency: a Urea Cycle Defect", European Journal of Paediatric Neurology, 7(3):115-121.
Gustafsson et al. (Jul. 2004) "Codon Bias and Heterologous Protein Expression", Trends in Biotechnology, 22 (7):346-353.
Hata et al. (1986) "Isolation and Characterization of the Human Ornithine Transcarbamylase Gene: Structure of the 5'-End Region", Journal of Biochemistry, 100:717-725.
Horwich et al. (Jun. 8, 1984) "Structure and Expression of a Complementary DNA For The Nuclear Coded Precursor Of Human Mitochondrial Ornithine Transcarbamylase", Science, 224(4653):1068-1074.
Horwich (Feb. 14, 1986) "Targeting Of Pre-Ornithine Transcarbamylase To Mitochondria: Definition Of Critical Regions And Residues In The Leader Peptide", Cell, 44(3):451-459.
Huang et al. (Aug. 2011) "In Vivo Delivery of RNAi with Lipid-Based Nanoparticles", Annual Review of Biomedical Engineering, 13:507-530.
Ishikawa et al. (Sep. 27, 2009) "Preparation of Eukaryotic mRNA having Differently Methylated Adenosine at the 5'-Terminus and the Effect of the Methyl Group in Translation", Nucleic Acids Symposium, 53(1):129-130.
Jokerst et al. (Jun. 2011) "Nanoparticle PEGylation for Imaging and Therapy", Nanomedicine (Lond), 6(4):715-728.
Kawabata et al. (1995) "The Fate of Plasmid DNA After Intravenous Injection in Mice: Involvement of Scavenger Receptors in Its Hepatic Uptake", Pharmaceutical Research, 12:825-830.
Kozak Marilyn (1988) "Leader Length And Secondary Structure Modulate Mrna Function Under Conditions Of Stress.", Molecular and Cellular Biology, 8:2737-2744.
Kozak Marilyn (Oct. 25, 1991) "Structural Features In Eukaryotic mRNAs that Modulate the Initiation of Translation", Journal of Biological Chemistry, 266(30):19867-19870.
Kratz Marilyn (Nov. 1990) "Downstream Secondary Structure Facilitates Recognition of Initiator Codons By Eukaryotic Ribosomes", Proceedings of the National Academy of Sciences of the United States of America, 87:8301-8305.
Kratz Marilyn (Feb. 1989) "The Scanning Model For Translation: An Update", Journal of Cell Biology, 108 (2):229-241.
Lasic Dand (Jul. 1, 1998) "Novel Applications of Liposomes", Trends in Biotechnology, 16(7):307-321.
Li et al. (Aug. 3, 2010) "Stealth Nanoparticles: High Density but Sheddable PEG is a Key for Tumor Targeting", Journal of Controlled Release, 145(3):178-181.
Limbach et al. (Jun. 25, 1994) "Summary: the modified nucleosides of RNA", Nucleic Acids Research, 22(12):2183-2196.
Lin et al. (2014) "Lipid-Based Nanoparticles in the Systemic Delivery of siRNA", Nanomedicine, 9(1):105-120.
Lindgren et al. (Nov. 9, 1984) "Human Ornithine Transcarbamylase Locus Mapped to Band Xp21.1 Near the Duchenne Muscular Dystrophy Locus", Science, 226(4675)698-700.
Muthukrishnan et al. (1975) "5'-Terminal 7-Methylguanosine in Eukaryotic mRNA is Required for Translation", Nature, 255:33-37.
Myers et al. (1988) "Optimal Alignments in Linear Space", Computer Applications in the Biosciences, 4(1):11-17.
Patil et al. (Jan. 2014) "Novel Methods for Liposome Preparation", Chemistry and Physics of Lipids, 177:8-18.
Rhoads R.E. (Oct. 22, 1999) "Signal Transduction Pathways That Regulate Eukaryotic Protein Synthesis", Journal of Biological Chemistry, 274(43):30337-30340.
Rodriguez-Gascon et al. (2014) "Development Of Nucleic Acid Vaccines: Use of Self-Amplifying RNA In Lipid Nanoparticles", International Journal of Nanomedicine, 9:1833-1843.
Sablad et al. (2019) "mRNA Therapy For Ornithine Transcarbamlyse Deficiency", Poster presented at 41st Annual Meeting for the Society for Inherited Metabolic Disorders, 1 pages.
Shatkin Aaronj. (Dec. 1976) "Capping of Eucaryotic mRNAs", Cell, 9(4 PT 2):645-53.
Shatkin A.J. (Feb. 1985) "mRNA Cap Binding Proteins: Essential Factors for Initiating Translation", 40 (2):223-224.

(56) References Cited

OTHER PUBLICATIONS

Sonenberg Nahum (1988) "Cap-Binding Proteins of Eukaryotic Messenger RNA: Functions in Initiation and Control of Translation", Progress in Nucleic Acid Research and Molecular Biology, 35:173-207.

Taverniti et al. (Jan. 9, 2015) "Elimination of Cap Structures Generated by mRNA Decay Involves the New Scavenger mRNA Decapping Enzyme Aph1/FHIT Together with DcpS", Nucleic Acids Research, 43(1):482-492.

Villalobos et al. (2006) "Gene Designer: A Synthetic Biology Tool For Constructing Artificial DNA Segments", BMC Bioinformatics, 7:285.

Jemielity et al. (2003) "Novel "Anti-Reverse" Cap Analogs with Superior Translational Properties", RNA, 9 (9):1108-1122.

Cunningham, et al., Induction and prevention of severe hyperammonemia in the spfash mouse model of ornithine transcarbamylase deficiency using shRNA and rAAV-mediated gene delivery, The American Society of Gene & Cell Therapy, Mol Ther., 2011, 854-9.

International Searching Authority, International Search Report and Written Opinion for PCT/US2019/64786, dated Apr. 16, 2020, 15 pages.

Lichter-Koneki, et al., Ornithine transcarbamylase deficiency, GeneReviews® [Internet], University of Washington, Seattle, 2016, 28 pages.

Love, et al., Lipid-like materials for low-dose, In Vivo Gene Silencing, PNAS, 2010, pp. 1864-1869, vol. 107, No. 5.

Prieve, et al., Targeted mRNA therapy for Ornithine Transcarbamylase Deficiency, Mol. Ther., 2018, pp. 801-813, vol. 26, No. 3.

* cited by examiner

3A

3B

4A

4B

SEQUENCE LISTING

<160> NUMBER OF SEQ ID NOS: 253

<210> SEQ ID NO 1
<211> LENGTH: 1065
<212> TYPE: RNA
<213> ORGANISM: Homo sapiens

<400> SEQUENCE: 1
augcuguuua aucugaggau ccuguuaaac aaugcagcuu uuagaaaugg ucacaacuuc 60
augguucgaa auuuucggug uggacaacca cuacaaaaua aagugcagcu gaagggccgu 120
gaccuucuca cucuaaaaaa cuuuaccgga gaagaaauua aauauaugcu auggcuauca 180
gcagaucuga aauuuaggau aaaacagaaa ggagaguauu ugccuuuauu gcaagggaag 240
uccuuaggca ugauuuuuga gaaaagaagu acucgaacaa gauugucuac agaaacaggc 300
uuugcacuuc ugggaggaca uccuuguuuu cuuaccacac aagauauuca uuugggugug 360

```
aaugaaaguc ucacggacac ggcccgugua uugucuagca uggcagaugc aguauuggcu    420

cgaguguaua aacaaucaga uuuggacacc cuggcuaaag aagcauccau cccaauuauc    480

aaugggcugu cagauuugua ccauccuauc cagauccugg cugauuaccu cacgcuccag    540

gaacacuaua gcucucugaa aggucuuacc cucagcugga ucggggaugg gaacaauauc    600

cugcacucca ucaugaugag cgcagcgaaa uucggaaugc accuucaggc agcuacucca    660

aaggguuaug agccggaugc uaguguaacc aaguuggcag agcaguaugc caaagagaau    720

gguaccaagc uguugcugac aaaugaucca uuggaagcag cgcauggagg caauguauua    780

auuacagaca cuuggauaag caugggacaa gaagaggaga agaaaaagcg gcuccaggcu    840

uuccaagguu accagguuac aaugaagacu gcuaaaguug cugccucuga cuggacauuu    900

uuacacugcu ugcccagaaa gccagaagaa guggaugaug aagucuuuua uucuccucga    960

ucacuagugu ucccagaggc agaaaacaga aaguggacaa ucauggcugu cauggugucc   1020

cugcugacag auuacucacc ucagcuccag aagccuaaau uuuga                   1065
```

<210> SEQ ID NO 2
<211> LENGTH: 1065
<212> TYPE: DNA
<213> ORGANISM: Homo sapiens

<400> SEQUENCE: 2

```
atgctgttta atctgaggat cctgttaaac aatgcagctt ttagaaatgg tcacaacttc     60

atggttcgaa attttcggtg tggacaacca ctacaaaata aagtgcagct gaagggccgt    120

gaccttctca ctctaaaaaa ctttaccgga gaagaaatta aatatatgct atggctatca    180

gcagatctga aatttaggat aaaacagaaa ggagagtatt tgcctttatt gcaagggaag    240

tccttaggca tgatttttga gaaaagaagt actcgaacaa gattgtctac agaaacaggc    300

tttgcacttc tgggaggaca tccttgtttt cttaccacac aagatattca tttgggtgtg    360

aatgaaagtc tcacggacac ggcccgtgta ttgtctagca tggcagatgc agtattggct    420

cgagtgtata aacaatcaga tttggacacc ctggctaaag aagcatccat cccaattatc    480

aatgggctgt cagatttgta ccatcctatc cagatcctgg ctgattacct cacgctccag    540

gaacactata gctctctgaa aggtcttacc ctcagctgga tcggggatgg gaacaatatc    600

ctgcactcca tcatgatgag cgcagcgaaa ttcggaatgc accttcaggc agctactcca    660

aagggttatg agccggatgc tagtgtaacc aagttggcag agcagtatgc caaagagaat    720

ggtaccaagc tgttgctgac aaatgatcca ttggaagcag cgcatggagg caatgtatta    780

attacagaca cttggataag catgggacaa gaagaggaga agaaaaagcg gctccaggct    840

ttccaaggtt accaggttac aatgaagact gctaaagttg ctgcctctga ctggacattt    900

ttacactgct tgcccagaaa gccagaagaa gtggatgatg aagtctttta ttctcctcga    960

tcactagtgt tcccagaggc agaaaacaga aagtggacaa tcatggctgt catggtgtcc   1020

ctgctgacag attactcacc tcagctccag aagcctaaat tttga                   1065
```

<210> SEQ ID NO 3
<211> LENGTH: 353
<212> TYPE: PRT
<213> ORGANISM: Homo sapiens

<400> SEQUENCE: 3

```
Met Leu Phe Asn Leu Arg Ile Leu Leu Asn Asn Ala Ala Phe Arg Asn
1               5                   10                  15
```

-continued

```
Gly His Asn Phe Met Val Arg Asn Phe Arg Cys Gly Gln Pro Leu Gln
            20                  25                  30

Asn Lys Val Gln Leu Lys Gly Arg Asp Leu Leu Thr Leu Lys Asn Phe
        35                  40                  45

Thr Gly Glu Glu Ile Lys Tyr Met Leu Trp Leu Ser Ala Asp Leu Lys
    50                  55                  60

Phe Arg Ile Lys Gln Lys Gly Glu Tyr Leu Pro Leu Leu Gln Gly Lys
65                  70                  75                  80

Ser Leu Gly Met Ile Phe Glu Lys Arg Ser Thr Arg Thr Arg Leu Ser
                85                  90                  95

Thr Glu Thr Gly Phe Ala Leu Leu Gly Gly His Pro Cys Phe Leu Thr
            100                 105                 110

Thr Gln Asp Ile His Leu Gly Val Asn Glu Ser Leu Thr Asp Thr Ala
        115                 120                 125

Arg Val Leu Ser Ser Met Ala Asp Ala Val Leu Ala Arg Val Tyr Lys
    130                 135                 140

Gln Ser Asp Leu Asp Thr Leu Ala Lys Glu Ala Ser Ile Pro Ile Phe
145                 150                 155                 160

Gly Leu Ser Asp Leu Tyr His Pro Ile Gln Ile Leu Ala Asp Tyr Leu
                165                 170                 175

Thr Leu Gln Glu His Tyr Ser Ser Leu Lys Gly Leu Thr Leu Ser Trp
            180                 185                 190

Ile Gly Asp Gly Asn Asn Ile Leu His Ser Ile Met Met Ser Ala Ala
        195                 200                 205

Lys Phe Gly Met His Leu Gln Ala Ala Thr Pro Lys Gly Tyr Glu Pro
    210                 215                 220

Asp Ala Ser Val Thr Lys Leu Ala Glu Gln Tyr Ala Lys Glu Asn Gly
225                 230                 235                 240

Thr Lys Leu Leu Leu Thr Asn Asp Pro Leu Glu Ala Ala His Gly Gly
                245                 250                 255

Asn Val Leu Ile Thr Asp Thr Trp Ile Ser Met Gly Gln Glu Glu Glu
            260                 265                 270

Lys Lys Lys Arg Leu Gln Ala Phe Gln Gly Tyr Gln Val Thr Met Lys
        275                 280                 285

Thr Ala Lys Val Ala Ala Ser Asp Trp Thr Phe Leu His Cys Leu Pro
    290                 295                 300

Arg Lys Pro Glu Glu Val Asp Asp Glu Val Phe Tyr Ser Pro Arg Ser
305                 310                 315                 320

Leu Val Phe Pro Glu Ala Glu Asn Arg Lys Trp Thr Ile Met Ala Val
                325                 330                 335

Met Val Ser Leu Leu Thr Asp Tyr Ser Pro Gln Leu Gln Lys Pro Lys
            340                 345                 350

Phe


<210> SEQ ID NO 4
<211> LENGTH: 355
<212> TYPE: PRT
<213> ORGANISM: Artificial Sequence
<220> FEATURE:
<223> OTHER INFORMATION: Synthetic construct

<400> SEQUENCE: 4

Met Leu Val Phe Asn Leu Arg Ile Leu Leu Asn Asn Ala Ala Phe Arg
1               5                   10                  15

Asn Gly His Asn Phe Met Val Arg Asn Phe Arg Cys Gly Gln Pro Leu
```

```
            20                  25                  30

Gln Asn Arg Val Gln Leu Lys Gly Arg Asp Leu Leu Thr Leu Lys Asn
        35                  40                  45

Phe Thr Gly Glu Glu Ile Arg Tyr Met Leu Trp Leu Ser Ala Asp Leu
    50                  55                  60

Lys Phe Arg Ile Lys Gln Lys Gly Glu Tyr Leu Pro Leu Leu Gln Gly
65                  70                  75                  80

Lys Ser Leu Gly Met Ile Phe Glu Lys Arg Ser Thr Arg Thr Arg Leu
                85                  90                  95

Ser Thr Glu Thr Gly Phe Ala Leu Leu Gly Gly His Pro Cys Phe Leu
            100                 105                 110

Thr Thr Gln Asp Ile His Leu Gly Val Asn Glu Ser Leu Thr Asp Thr
        115                 120                 125

Ala Arg Val Leu Ser Ser Met Ala Asp Ala Val Leu Ala Arg Val Tyr
    130                 135                 140

Lys Gln Ser Asp Leu Asp Thr Leu Ala Lys Glu Ala Ser Ile Pro Ile
145                 150                 155                 160

Ile Asn Gly Leu Ser Asp Leu Tyr His Pro Ile Gln Ile Leu Ala Asp
                165                 170                 175

Tyr Leu Thr Leu Gln Glu His Tyr Ser Ser Leu Lys Gly Leu Thr Leu
            180                 185                 190

Ser Trp Ile Gly Asp Gly Asn Asn Ile Leu His Ser Ile Met Met Ser
        195                 200                 205

Ala Ala Lys Phe Gly Met His Leu Gln Ala Ala Thr Pro Lys Gly Tyr
    210                 215                 220

Glu Pro Asp Ala Ser Val Thr Lys Leu Ala Glu Gln Tyr Ala Lys Glu
225                 230                 235                 240

Asn Gly Thr Lys Leu Leu Leu Thr Asn Asp Pro Leu Glu Ala Ala His
                245                 250                 255

Gly Gly Asn Val Leu Ile Thr Asp Thr Trp Ile Ser Met Gly Gln Glu
            260                 265                 270

Glu Glu Lys Lys Lys Arg Leu Gln Ala Phe Gln Gly Tyr Gln Val Thr
        275                 280                 285

Met Lys Thr Ala Lys Val Ala Ala Ser Asp Trp Thr Phe Leu His Cys
    290                 295                 300

Leu Pro Arg Lys Pro Glu Glu Val Asp Asp Glu Val Phe Tyr Ser Pro
305                 310                 315                 320

Arg Ser Leu Val Phe Pro Glu Ala Glu Asn Arg Lys Trp Thr Ile Met
                325                 330                 335

Ala Val Met Val Ser Leu Leu Thr Asp Tyr Ser Pro Gln Leu Gln Lys
            340                 345                 350

Pro Lys Phe
        355
```

<210> SEQ ID NO 5
<211> LENGTH: 129
<212> TYPE: RNA
<213> ORGANISM: Artificial Sequence
<220> FEATURE:
<223> OTHER INFORMATION: Synthetic construct

<400> SEQUENCE: 5

```
ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120
```

gaacgauag 129

<210> SEQ ID NO 6
<211> LENGTH: 28
<212> TYPE: RNA
<213> ORGANISM: Artificial Sequence
<220> FEATURE:
<223> OTHER INFORMATION: Synthetic construct

<400> SEQUENCE: 6
auuauuacau caaaacaaaa agccgcca 28

<210> SEQ ID NO 7
<211> LENGTH: 245
<212> TYPE: RNA
<213> ORGANISM: Artificial Sequence
<220> FEATURE:
<223> OTHER INFORMATION: Synthetic construct

<400> SEQUENCE: 7
cuuaaggggg cgcugccuac ggagguggca gccaucuccu ucucggcauc aagcuuacca 60
uggugcccca ggcccugcuc uugguccccgc ugcugguguu ccccucugc uucggcaagu 120 uccccaucua caccaucccc gacaagcugg ggccguggag ccccaucgac auccaccacc 180
uguccugccc caacaaccuc gugggucgagg acgagggcug caccaaccug agcggguucu 240
ccuac 245

<210> SEQ ID NO 8
<211> LENGTH: 177
<212> TYPE: RNA
<213> ORGANISM: Artificial Sequence
<220> FEATURE:
<223> OTHER INFORMATION: Synthetic construct

<400> SEQUENCE: 8
ugagugucgu acagccucca ggcccccccc ucccgggaga gccauagugg ucugcggaac 60
cggugaguac accggaauug ccgggaagac ugggguccuuu cuuggauaaa cccacucuau 120
gcccggccau uugggcgugc ccccgcaaga cugcuagccg aguaguguug gguugcg 177

<210> SEQ ID NO 9
<211> LENGTH: 89
<212> TYPE: RNA
<213> ORGANISM: Artificial Sequence
<220> FEATURE:
<223> OTHER INFORMATION: Synthetic construct

<400> SEQUENCE: 9
aauuauuggu uaaagaagua uauuagugcu aauuucccuc cguuuguccu agcuuuucuc 60
uucugucaac cccacacgcc uuuggcaca 89

<210> SEQ ID NO 10
<211> LENGTH: 569
<212> TYPE: RNA
<213> ORGANISM: Artificial Sequence
<220> FEATURE:
<223> OTHER INFORMATION: Synthetic construct

<400> SEQUENCE: 10 cuccccuccccc cccccccuaac guuacuggcc gaagccgcuu ggaauaaggc cggugugcgu 60
uugucuauau guuauuuucc accauauugc cgucuuuugg caaugugagg gcccggaaac 120
cuggcccugu cuucuugacg agcauuccua ggggucuuuc cccucucgcc aaaggaaugc 180
aaggucuguu gaaugucgug aaggaagcag uuccucugga agcuucuuga agacaaacaa 240
cgucuguagc gacccuuugc aggcagcgga acccccccacc uggcgacagg ugccucugcg 300
gccaaaagcc acguguauaa gauacaccug caaaggcggc acaaccccag ugccacguug 360
ugaguuggau aguuguggaa agagucaaau ggcucuccuc aagcguauuc aacaaggggc 420
ugaaggaugc ccagaaggua ccccauugua ugggaucuga ucuggggccu cggugcacau 480
gcuuuacgug uguuuagucg agguuaaaaa acgucuaggc cccccgaacc acggggacgu 540
gguuuuccuu ugaaaaacac gaugauaau 569

<210> SEQ ID NO 11
<211> LENGTH: 44
<212> TYPE: RNA
<213> ORGANISM: Artificial Sequence
<220> FEATURE:
<223> OTHER INFORMATION: Synthetic construct

<400> SEQUENCE: 11
gucagcuuuc aaacucuuug uuucuuguuu guugauugag aaua 44

<210> SEQ ID NO 12
<211> LENGTH: 54
<212> TYPE: RNA
<213> ORGANISM: Artificial Sequence
<220> FEATURE:
<223> OTHER INFORMATION: Synthetic construct

<400> SEQUENCE: 12
cucucgccug agaaaaaaaa uccacgaacc aauuucucag caaccagcag cacg 54

<210> SEQ ID NO 13
<211> LENGTH: 52
<212> TYPE: RNA
<213> ORGANISM: Artificial Sequence
<220> FEATURE:
<223> OTHER INFORMATION: Synthetic construct

<400> SEQUENCE: 13
accugugagg guucgaagga aguagcagug uuuuuuguuc cuagaggaag ag 52

<210> SEQ ID NO 14
<211> LENGTH: 71
<212> TYPE: RNA
<213> ORGANISM: Artificial Sequence
<220> FEATURE:
<223> OTHER INFORMATION: Synthetic construct

<400> SEQUENCE: 14
acacagaaac auucgcaaaa acaaaauccc aguaucaaaa uucuucucuu uuuuucauau 60
uucgcaaaga c 71

<210> SEQ ID NO 15
<211> LENGTH: 52
<212> TYPE: RNA
<213> ORGANISM: Artificial Sequence
<220> FEATURE:
<223> OTHER INFORMATION: Synthetic construct

<400> SEQUENCE: 15
cagaaaaauu ugcuacauug uuucacaaac uucaaauauu auucauuuau uu 52

<210> SEQ ID NO 16

<211> LENGTH: 158
<212> TYPE: RNA
<213> ORGANISM: Artificial Sequence
<220> FEATURE:
<223> OTHER INFORMATION: Synthetic construct

<400> SEQUENCE: 16
cuagugacug acuaggaucu gguuaccacu aaaccagccu caagaacacc cgaauggagu 60
cucuaagcua cauaauacca acuuacacuu acaaaauguu guccccccaaa auguagccau 120 ucguaucugc uccuaauaaa aagaaaguuu cuucacau 158

<210> SEQ ID NO 17
<211> LENGTH: 166
<212> TYPE: RNA
<213> ORGANISM: Artificial Sequence
<220> FEATURE:
<223> OTHER INFORMATION: Synthetic construct

<400> SEQUENCE: 17
ugcaaggcug gccggaagcc cuugccugaa agcaagauuu cagccuggaa gagggcaaag 60
uggacgggag uggacaggag uggaugcgau aagauguggu uugaagcuga ugggugccag 120
cccugcauug cugagucaau caauaaagag cuuucuuuug acccau 166

<210> SEQ ID NO 18
<211> LENGTH: 143
<212> TYPE: RNA
<213> ORGANISM: Artificial Sequence
<220> FEATURE:
<223> OTHER INFORMATION: Synthetic construct

<400> SEQUENCE: 18
acgccgaagc cugcagccau gcgaccccac gccaccccgu gccuccugcc uccgcgcagc 60
cugcagcggg agacccuguc cccgccccag ccguccuccu ggggguggacc cuaguuuaau 120 aaagauucac caaguuucac gca 143

<210> SEQ ID NO 19
<211> LENGTH: 220
<212> TYPE: RNA
<213> ORGANISM: Artificial Sequence
<220> FEATURE:
<223> OTHER INFORMATION: Synthetic construct

<400> SEQUENCE: 19
uagagcggca aacccuagcu acacuccaua gcuaguuucu uuuuuuuuug uuuuuuuuuu 60
uuuuuuuuuu uuuuuuuuuu uuuuuuuuuc cuuucuuuuc cuucuuuuuu uccucuuuuc 120
uugguggcuc caucuuagcc cuagucacgg cuagcuguga aagguccgug agccgcauga 180
cugcagagag ugccguaacu ggucucucug cagaucaugu 220

<210> SEQ ID NO 20
<211> LENGTH: 170
<212> TYPE: RNA
<213> ORGANISM: Artificial Sequence
<220> FEATURE:
<223> OTHER INFORMATION: Synthetic construct

<400> SEQUENCE: 20
acacaucaca accacaaccu ucucaggcua cccugagaaa aaaagacaug aagacucagg 60
acucaucuuu ucuguuggug uaaaaucaac acccuaagga acacaaauuu cuuuaaacau 120
uugacuucuu gucucugugc ugcaauuaau aaaaaaugga aagaaucuac 170

<210> SEQ ID NO 21
<211> LENGTH: 110
<212> TYPE: RNA
<213> ORGANISM: Artificial Sequence
<220> FEATURE:
<223> OTHER INFORMATION: Synthetic construct

<400> SEQUENCE: 21
gcuggagccu cgguagccgu uccuccugcc cgcugggccu cccaacgggc ccuccucccc 60
uccuugcacc ggcccuuccu ggucuuugaa uaaagucuga gugggcagca 110

<210> SEQ ID NO 22
<211> LENGTH: 123
<212> TYPE: RNA
<213> ORGANISM: Artificial Sequence
<220> FEATURE:
<223> OTHER INFORMATION: Synthetic construct

<400> SEQUENCE: 22
uagugcaguc acuggcacaa cgcguugccc gguaagccaa ucggguauac acggucguca 60
uacugcagac aggguucuuc uacuuugcaa gauagucuag aguaguaaaa uaaauaguau 120
aag 123

<210> SEQ ID NO 23
<211> LENGTH: 6
<212> TYPE: RNA
<213> ORGANISM: Artificial Sequence
<220> FEATURE:
<223> OTHER INFORMATION: Synthetic construct

<400> SEQUENCE: 23 gccacc 6

<210> SEQ ID NO 24
<211> LENGTH: 4
<212> TYPE: RNA
<213> ORGANISM: Artificial Sequence
<220> FEATURE:
<223> OTHER INFORMATION: Synthetic construct

<400> SEQUENCE: 24 gcca 4

<210> SEQ ID NO 25
<211> LENGTH: 9
<212> TYPE: RNA
<213> ORGANISM: Artificial Sequence
<220> FEATURE:
<223> OTHER INFORMATION: Synthetic construct

<400> SEQUENCE: 25 auaagugaa 9

<210> SEQ ID NO 26
<211> LENGTH: 1368
<212> TYPE: RNA
<213> ORGANISM: Artificial Sequence
<220> FEATURE:
<223> OTHER INFORMATION: Synthetic construct

<400> SEQUENCE: 26
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uuuaaucuga ggauccuguu aaacaaugca gcuuuuagaa 180
auggucacaa cuucaugguu cgaaauuuuc gguguggaca accacuacaa aauaaagugc 240
agcugaaggg ccgugaccuu cucacucuaa aaaacuuuac cggagaagaa auuaaauaua 300
ugcuauggcu aucagcagau cugaaauuua ggauaaaaca gaaaggagag uauuugccuu 360
uauugcaagg gaaguccuua ggcaugauuu uugagaaaag aaguacucga acaagauugu 420
cuacagaaac aggcuuugca cuucugggag gacauccuug uuuucuuacc acacaagaua 480
uucauuuggg ugugaaugaa agucucacgg acacggcccg uguauugucu agcauggcag 540
augcaguauu ggcucgagug uauaaacaau cagauuugga cacccuggcu aaagaagcau 600
ccaucccaau uaucaauggg cugucagauu uguaccaucc uauccagauc cuggcugauu 660
accucacgcu ccaggaacac uauagcucuc ugaaaggucu uacccucagc uggaucgggg 720
augggaacaa uauccugcac uccaucauga ugagcgcagc gaaauucgga augcaccuuc 780
aggcagcuac uccaaagggu uaugagccgg augcuagugu aaccaaguug gcagagcagu 840
augccaaaga gaaugguacc aagcuguugc ugacaaauga uccauuggaa gcagcgcaug 900
gaggcaaugu auuaauuaca gacacuugga uaagcauggg acaagaagag gagaagaaaa 960
agcggcucca ggcuuuccaa gguuaccagg uuacaaugaa gacugcuaaa guugcugccu 1020
cugacuggac auuuuuacac ugcuugccca gaaagccaga agaaguggau gaugaagucu 1080
uuuauucucc ucgaucacua guguucccag aggcagaaaa cagaaagugg acaaucaugg 1140
cugucauggu gucccugcug acagauuacu caccucagcu ccagaagccu aaauuuugac 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 27
<211> LENGTH: 1368
<212> TYPE: RNA
<213> ORGANISM: Artificial Sequence
<220> FEATURE:
<223> OTHER INFORMATION: Synthetic construct

<400> SEQUENCE: 27
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuc uuuaaucugc gcaucuuacu gaacaacgcc gcauuccgga 180
acggucacaa cuucaugguc cgcaauuucc gcuguggcca gccgcuucaa aacaaggucc 240
agcugaaggg acgggaucug cugacacuga agaacuucac cggagaagag aucaaguaca 300
ugcuguggcu cagcgcagac uugaaguucc ggaucaagca gaagggagaa uacuugcccc 360
ugcugcaagg aaagucgcug ggaaugauuu uugagaagcg gucaacucgc accagacucu 420
ccaccgaaac ugguuucgca cugcuuggcg ggcacccuug cuuccugacg acucaggaca 480
uccaccucgg cgugaacgaa ucgcuaaccg auaccgccag agugcuuucu uccauggccg 540
acgcggugcu ggccagggug uacaagcagu ccgaccucga uaccuuggca aaggaggcuu 600
ccauucccau caucaacggc cugagcgacc uguaccaccc aauccaaauc cuggcugacu 660
accugacccu gcaagagcac uacagcagcc ugaagggucu gacccuguca uggauuggcg 720
auggaaacaa uauucugcac uccaucauga uguccgccgc gaaguucgga augcaucugc 780
aagccgccac uccaaaagga uacgaaccgg augcguccgu gaccaaguug gcggaacagu 840
acgcgaagga gaacggaacc aagcuucugc ugacuaacga cccccucgag gcugcgcaug 900
ggggcaacgu gcugauuacc gacaccugga ucuccauggg gcaggaggaa gagaagaaga 960
agagacugca ggcauuccag ggguaccagg ucaccaugaa aaccgcaaaa guggcagcuu 1020
cggacuggac uuuccugcau ugccugccga ggaagccgga ggaagucgac gacgaagugu 1080
ucuacucgcc ucgguccug guguuccccg aggccgaaaa ccggaagugg accaucaugg 1140
ccgugauggu guccuugcug acugacuaua gcccgcagcu gcagaagccu aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 28
<211> LENGTH: 1368
<212> TYPE: RNA
<213> ORGANISM: Artificial Sequence
<220> FEATURE:
<223> OTHER INFORMATION: Synthetic construct

<400> SEQUENCE: 28
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uuuaaccuac guauuuugcu caacaaugca gccuuuagaa 180
acggacauaa cuuuaugguu cgaaacuuuc gcugcgggca gccacugcag aacaaggucc 240
agcugaaagg gagagauuug cucacgcuga agaacuuuac uggcgaagaa aucaaguaua 300
ugcugugguu guccgcggac cucaaguuuc ggauuaagca gaaaggggag uaucugccac 360
ugcugcaagg aaagagccuc ggcaugaucu ucgagaagcg gagcacucgg accaggcuga 420
guaccgaaac uggcuucgca uuguugggug gacauccaug uuuucugaca acgcaggaca 480
uucaucuggg cgugaacgag agucugacgg acacagcucg cguucugucc ucuauggcug 540 augcggugu u ggcccggguc uauaagcagu ccgauuugga caccuuggcu aaggaagcua 600
gcauaccgau uaucaauggg cuguccgacc uguaucaccc uauucaaauc cuggccgacu 660
accucacacu gcaagaacac uauagcucau ugaagggacu gacccugagc uggauagggg 720
acggaaacaa cauccuacau agcauuauga uguccgcugc caaguuuggc augcaucuuc 780
aagccgccac gccaaagggu uaugagcccg acgcgucagu gacaaagcug gccgagcagu 840
acgcuaagga gaaugguacc aaauuacugc ugacuaauga uccacuggag gcugcacaug 900
gcggcaaugu acugaucacc gacacaugga ucucgauggg ccaggaggaa gaaaagaaga 960
agaggcuuca ggccuuccaa ggcuaccagg ucaccaugaa aacagcuaag guugcagcau 1020
cugauuggac cuuucugcac ugucugccaa ggaagcccga agagguggac gaugaaguau 1080
ucuauagccc acggaguuug guguucccug aggcugaaaa uaggaagugg acaauuaugg 1140
ccguaauggu gucccuguua accgacuacu cuccgcaacu gcagaaaccu aaguuuuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 29

<211> LENGTH: 1368
<212> TYPE: RNA
<213> ORGANISM: Artificial Sequence
<220> FEATURE:
<223> OTHER INFORMATION: Synthetic construct

<400> SEQUENCE: 29
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uuuaacuuaa ggauccugcu gaacaacgcc gcuuuucgua 180
acggucauaa cuuuaugguc cggaacuuua gauguggcca gccgcugcag aacaagguuc 240
agcugaaggg gagggaucug cugaccuuga agaacuuuac cggcgaagag aucaaguaca 300
uguuguggcu gagcgccgau cugaaguuua ggauuaagca gaagggggag uauuugccac 360
ugcugcaagg aaaauccuug gggaugaucu ucgagaagcg cuccacuaga acccggcuaa 420
gcacagaaac cggcuucgca cuucugggug gacaucccug uuuucugacg acgcaggaua 480
uacaccuggg cgugaaugag agucugacgg acacagcuag gguguugagc agcauggccg 540
augcaguacu ggcccgcguu uauaagcaga gcgacuugga cacacuggcc aaggaagcgu 600
caauuccgau uaucaauggg cugucagacc uguaucaucc cauucaaauc uuggcugacu 660
aucugacccu gcaagaacau uacagcuccc ugaagggccu cacguugucc uggauuggcg 720
acggaaacaa cauucugcau ucgaucauga ugagcgcugc uaaguuuggc augcaccucc 780
aagccgcuac accuaaggga uaugagccug augccagcgu aaccaagcug gccgaacagu 840
acgcgaagga gaauggcacg aaacugcugu ugacaaauga cccacuggag gcagcucacg 900
guggcaacgu gcugaucacc gacacgugga uaucuauggg acaggaagaa gagaagaaga 960
agcggcugca ggcauuccaa ggguaucagg ucaccaugaa aacggccaag guugcugcau 1020
ccgacuggac auuucugcau ugcuugcccc gcaaaccaga agaaguagac gacgaagucu 1080
uuuauucccc acggucgcug guguuccccg aggcggagaa ucgaaagugg acgauuaugg 1140
ccgugauggu gucccugcug acugauuacu cuccccaacu gcaaaagccu aaguuuuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 30
<211> LENGTH: 1368
<212> TYPE: RNA
<213> ORGANISM: Artificial Sequence
<220> FEATURE:
<223> OTHER INFORMATION: Synthetic construct

<400> SEQUENCE: 30
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaccuga ggauccuccu gaacaacgcc gccuuucgca 180
auggucacaa cuuuaugguc cggaacuuca gaugcggcca gccgcugcag aacaaggucc 240
agcugaaggg acgggaucug cugacucuga agaacuucac cggagaagag aucaaguaca 300
ugcuguggcu gucggccgac cugaaguuca ggaucaagca gaagggagaa uaccucccgc 360
ugcugcaagg aaagucccug ggcaugauuu ucgagaagcg cucgaccaga acucgguugu 420
ccaccgaaac cggguuugcg cugcugggcg gacauccuug cuuccugacg acucaggaua 480

```
uucaccuggg agugaacgag ucgcugaccg acaccgccag agugcugagc ucgauggccg    540

acgccguguu ggcacgcgug uacaagcagu ccgaucugga uacccuggcc aaagaagcuu    600

ccaucccgau cauuaacggg cugagcgacc ucuaccaccc cauucaaauc cuggccgacu    660

accugacucu gcaagaacac uacagcucgc ugaaggggau gacucugucc uggaucggcg    720

acggaaacaa cauccugcac uccaucauga ugucggccgc aaaguucggc augcauuugc    780

aagccgccac cccaaagggc uacgaaccag acgcgagcgu caccaagcug gccgaacagu    840

acgcgaagga aaaugguacu aagcugcugc ugaccaacga cccauuggaa gcugcccaug    900

guggaaacgu gcugaucacc gacaccugga ucucgauggg ccaggaagag gagaagaaga    960

agcggcugca ggcguuccag ggguaucagg ucaccaugaa aacagccaaa guggcagcgu   1020

cagacuggac cuuccuccac ugucugccuc gcaagccaga ggagguggac gacgaggugu   1080

ucuacucccc ucggucccuc guguucccug aggcugagaa ccggaagugg accauuaugg   1140

ccgugauggu gucacuccug acugauuacu ccccgcaacu gcagaagccc aaguucuagc   1200

ucgagcuagu gacugacuag gaucugguua ccacuaaacc agccucaaga acacccgaau   1260

ggagucucua agcuacauaa uaccaacuua cacuuacaaa auguuguccc ccaaaaugua   1320

gccauucgua ucugcuccua auaaaaagaa aguuucuuca cauucuag                1368
```

<210> SEQ ID NO 31
<211> LENGTH: 1368
<212> TYPE: RNA
<213> ORGANISM: Artificial Sequence
<220> FEATURE:
<223> OTHER INFORMATION: Synthetic construct

<400> SEQUENCE: 31

```
ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc caccaugcug uuuaaccuga ggauccuauu gaacaaugcu gcuuuucgua    180

auggccauaa cuuuaugguu cggaacuuua gaugcgggca gccacugcag aacaaggucc    240

aguugaaagg ccgcgaucug uugacauuga agaacuuuac cggcgaagag auuaaguaua    300

ugcuguggcu gucugcugac cucaaguuuc gaaucaagca gaagggcgaa uaucuccccc    360

ugcugcaagg aaagucucuc ggcaugaucu uugagaagcg gaguacccga acacggcuga    420

gcaccgaaac gggcuucgca cugcuggggg gccaucccug uuuucugaca acgcaggaca    480

uccacuuggg gguuaacgaa ucauugacug auaccgcccg cguacuguca uccauggccg    540

acgcugugcu ggcuagggug uacaagcagu cagaucugga uacacuggcc aaggaagcua    600

gcauaccaau caucaaugga cugagugacc uuuaucaccc gauucaaaua cuagccgauu    660

aucugacccu gcaagagcau uacuccucgc ugaaaggccu cacgcugucc uggaucggcg    720

acggcaacaa cauucugcau aguauuauga ugucugcugc caaauucggc augcaucugc    780

aagcugcuac gccgaagggu uaugaacccg acgcgucagu uacgaagcuc gcugagcagu    840

augcaaagga gaauggcaca aagcuguugc uuaccaacga uccccuggaa gcugcucaug    900

gcggcaaugu gcugauuacu gacaccugga uuucaauggg ccaggaggag gagaagaaga    960

agagguuaca ggcuuuucaa gguuaccaag ucacgaugaa aaccgcuaag gucgcagcca   1020

gcgacuggac auuccugcac ugucugccaa gaaagccgga agaaguggac gacgaggugu   1080

ucuauucccc gcggucuuug guguuuccgg aggccgaaaa caggaaaugg accauuaugg   1140
```

ccgugauggu aucguugcug acggacuaca gcccucaguu gcaaaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 32
<211> LENGTH: 1368
<212> TYPE: RNA
<213> ORGANISM: Artificial Sequence
<220> FEATURE:
<223> OTHER INFORMATION: Synthetic construct

<400> SEQUENCE: 32
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuc uuuaaccucc gcauccuccu caacaacgcc gccuuccgga 180
augggcauaa cuucaugguc cggaacuuca gaugcggcca gccccugcaa aacaaggucc 240
aguugaaggg acgggaccuc cuuacgcuga agaacuuuac cggagaagag auuaaguaca 300 ugcuguggu guccgcugac cucaaguucc gcauuaagca gaagggagaa uaucugccgc 360
ugcugcaagg aaagagccug ggcaugaucu ucgaaaagcg cuccacuaga acccggcugu 420
cgacugagac uggauucgcc uugcucggug gacacccgug cuuccugacg acccaggaca 480
uccaccuggg agugaacgag ucacuuacgg auaccgcgag ggugcugucc ucaauggccg 540
acgcagugcu cgcgcgcgug uacaagcagu cagaucugga uacccuggcc aaggaagcca 600
gcauucccau caucaacgga cugagcgacc uuuaccaccc aauccagauc cucgccgacu 660
acuuaacccu gcaagagcac uacagcuccc ugaagggacu gacucugucc uggaucgggg 720
auggaaacaa cauccugcac uccaucauga ugucugccgc uaaguuuggg augcaucugc 780
aagccgcaac cccuaaggga uacgagcccg acgccucggu gaccaaacuu gcggaacagu 840
acgccaagga aaacgguacc aagcugcugc ugaccaacga cccucuggaa gcggcccacg 900
gaggaaaugu gcugauuacc gacaccugga uuucgauggg ccaggaggag gagaagaaga 960
agagacugca ggcguuccag ggauaucagg ucaccaugaa aaccgccaag gucgccgcca 1020
gcgacuggac cuuccugcac ugucucccuc ggaaaccgga agaaguggau gacgaggugu 1080
ucuacucccc gcgcucgcug guguucccgg aggcugaaaa caggaagugg acaaucaugg 1140
ccgugauggu gucccuguug accgacuacu ccccacaacu gcagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 33
<211> LENGTH: 1368
<212> TYPE: RNA
<213> ORGANISM: Artificial Sequence
<220> FEATURE:
<223> OTHER INFORMATION: Synthetic construct

<400> SEQUENCE: 33
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucugc gcauccuccu gaacaacgcc gccuuccgca 180
auggacacaa cuuuauggue cgcaacuucc gcugugggca gccgcugcag aacaaggucc 240
agcucaaggg gagagaucuc cugacccuga agaacuucac uggagaggag aucaaguaca 300
ugcuguggcu guccgccgac cugaaauuuc ggauuaagca gaagggcgaa uaccucccac 360
ugcugcaagg aaagucuuug ggcaugaucu ucgaaaagag aagcacccgg acccgguuga 420
gcaccgaaac uggguucgcg cuccucggug gacacccgug cuuccugacc acccaagaua 480
uucaucuggg ugucaacgaa agccugaccg acaccgccag ggugcuguca uccauggcug 540
acgcagugcu cgcccgggug uacaagcagu cagaccugga cacccucgcc aaggaagcuu 600
cgaucccuau caucaacgga cuuuccgacc uguaccaccc cauccaaauu cuggccgacu 660
accugacucu gcaagaacac uauagcucgc ugaaaggacu uacucugucc uggaucgggg 720
acggcaacaa cauucuccau uccaucauga uguccgcugc caaguucgga augcaccuuc 780
aagcagcgac ucccaaggga uacgaaccug augccuccgu gacuaagcug gcagagcagu 840
acgccaagga gaacgguaca aagcugcugc ucacgaacga cccccuggag gcggcccacg 900
gcggaaacgu gcugauuacc gauaccugga ucucaauggg ccaggaagag gagaagaaga 960
agcggcucca ggcguuucaa ggcuaccagg ucaccaugaa aaccgcgaag gucgccgccu 1020
ccgacuggac uuucuugcac ugccugccgc ggaagcccga ggaaguggau gacgaagugu 1080
ucuacucgcc gagaucguug guguucccug aggccgaaaa caggaagugg accaucaugg 1140
ccgugauggu gucccugcug acugauuaca gcccacagcu gcagaagccu aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 34
<211> LENGTH: 1368
<212> TYPE: RNA
<213> ORGANISM: Artificial Sequence
<220> FEATURE:
<223> OTHER INFORMATION: Synthetic construct

<400> SEQUENCE: 34
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggccacaa cuucauggue cggaacuuca gauguggcca gccgcuucaa aacaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 35
<211> LENGTH: 1368
<212> TYPE: RNA
<213> ORGANISM: Artificial Sequence
<220> FEATURE:
<223> OTHER INFORMATION: Synthetic construct

<400> SEQUENCE: 35
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaccuga gaauccuccu gaacaacgcc gccuuccgca 180
auggucauaa cuucaugguc cgcaacuuuc gcugcggaca gccucuccaa aacaaggucc 240
agcucaaggg gcgcgaccuc cucacacuga agaacuucac uggagaagaa aucaaguaca 300
ugcuguggcu gagcgccgau cugaaguucc ggaucaagca gaagggagag uaccuuccuc 360
ugcugcaagg gaaguccuug ggaaugauuu ucgagaagcg guccacccgg accaggcuga 420
gcacugaaac uggcuucgcc cugcugggag gccacccuug uuuccugacc acucaggaca 480
uccaccuggg cgugaacgag ucccugaccg auacugccag agugcugucc uccauggccg 540
acgccgugcu cgcccgggug uacaagcagu cagaccucga uacgcuggcc aaggaagccu 600
ccauucccau uaucaauggu cugucggacc ucuaccaucc aauccaaauc cucgccgacu 660
accugacucu gcaagaacac uacagcucac ucaagggccu cacccucucc uggaucggcg 720
acggaaacaa cauccuucac ucgauuauga ugucggccgc gaaguucggg augcaccucc 780
aagcugccac uccaaaaggc uacgagccgg augccucagu gacuaaguug gcggaacagu 840
augcgaagga gaacgguacc aagcuccugc ugacuaacga cccgcuggag gccgcccacg 900
ggggaaacgu gcucaucacc gauacuugga uuuccauggg acaggaggaa gagaagaaga 960
agcgguugca ggcauuucag ggcuaccagg ucaccaugaa aacugccaaa gucgccgcca 1020
gcgacuggac cuuccugcac ugccugcccc gcaagccuga agaaguggac gacgaggugu 1080
ucuacucucc ccggucccuc guguucccug aggccgaaaa caggaagugg accaucaugg 1140
cugugauggu gucccuccug accgacuaca gcccucagcu ccaaaaaccc aaguuuuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 36
<211> LENGTH: 1368
<212> TYPE: RNA
<213> ORGANISM: Artificial Sequence
<220> FEATURE:
<223> OTHER INFORMATION: Synthetic construct

<400> SEQUENCE: 36
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaccuga gaauccucuu gaacaaugcu gcuuuucgga 180
auggccacaa cuuuaugguu cggaacuucc guugcggcca gccuuuacaa aacaaggucc 240
agcugaaggg ccgggauuug cucacacuga agaacuuuac uggggaggag auuaaguaua 300
ugcuguggcu guccgcugac cugaaguuua ggaucaagca gaagggcgaa uaucugccgc 360
ugcugcaagg gaaaagucug ggcaugauuu uugaaaagcg cucuacccgg accagacugu 420
cuacggaaac aggcuuugcc cugcugggcg gccacccug uuuucugaca acgcaggaca 480
uccaucuggg cgugaacgaa ucacugaccg auacugcucg gguacucagu ucuauggcug 540
acgcagugcu ggcuagggug uacaagcaga gcgacuugga cacacuggcu aaggaggcca 600 gcaucccau uaucaauggc cugucugauu uguaccaucc cauucaaauc cuggcugauu 660
aucugacacu acaagagcau uacucaaguc ugaaggguuu gacucucucc uggaucggcg 720
acggcaacaa cauuuuacau uccauuauga ugagugcugc uaaguuuggc augcauuugc 780
aagcugcuac cccaaagggc uaugaaccug acgcuagcgu aaccaaguug gccgaacagu 840
augcuaaaga gaauggcacc aagcugcucc ugacgaauga cccccuggaa gcugcucaug 900
gcggaaacgu acuuauaacu gauacaugga uuagcauggg ccaggaagag gagaagaaga 960
agagacugca ggccuuccaa ggcuaucagg ucaccaugaa aacugccaag guugcagcua 1020
gcgacuggac cuuccugcac uguuugccga ggaaacccga ggagguggac gaugaagucu 1080
uuuauucucc ccgcuccuug guguuucccg aggcugaaaa ucgaaagugg acgauaaugg 1140
cagugauggu gucccuacug accgacuauu cuccacaacu gcagaagccu aaauucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 37
<211> LENGTH: 1368
<212> TYPE: RNA
<213> ORGANISM: Artificial Sequence
<220> FEATURE:
<223> OTHER INFORMATION: Synthetic construct

<400> SEQUENCE: 37
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucuga ggauccugcu gaacaacgcu gcuuuucgca 180
acggucauaa cuuuaugguu cgcaauuuuc guuguggcca gccgcugcag aacaagguuc 240
agcugaaggg cagagaucug cugacucuga agaacuucac uggggaagaa aucaaguaua 300
uguuauggcu guccgcggau cugaaauuuc gaaucaagca gaagggcgaa uaucuucccc 360
ugcugcaagg gaaauccuug ggcaugauuu uugagaagag gagcacuagg acuagauugu 420
caacagaaac aggcuuugcu uuguugggcg gacaucccug cuuucugacg acacaggaua 480
uccaccucgg cguaaacgag ucccucaccg acacugcuag gguacugagc agcauggccg 540
acgcugugcu agcccggguu uacaagcagu cagaccugga cacccuugcc aaggaagcuu 600
cuauuccaau uaucaacggc cugagugacc uguaucaccc uauucaaaua cucgccgacu 660
auuugacgcu ucaagaacau uacagcagcc ucaagggcuu aaccuugagu uggauaggcg 720
acggcaacaa uauccugcau uccauuauga ugucugccgc uaaguuuggc augcaucuac 780
aagccgcaac acccaagggc uaugaacccg acgcuagcgu gaccaagcug gccgagcagu 840
augcuaagga aaauggcaca aagcuccuuc uuaccaacga uccccuggag gcugcucacg 900
gcggcaacgu gcugauuacc gauacaugga uuagcauggg ccaggaggag gagaaaaaga 960
agcggcucca ggcuuuucaa ggcuaucagg ucaccaugaa aacugcaaag gucgcugccu 1020
ccgacuggac uuuccugcau ugucuacccc gcaagccuga ggaaguggac gaugaggugu 1080
ucuacucccc acggagucug guguucccgg aagcagagaa ucggaagugg accaucaugg 1140
cugucauggu gucgcucuug acugacuauu cuccccaacu gcaaaaaccc aaguuuuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 38
<211> LENGTH: 1368
<212> TYPE: RNA
<213> ORGANISM: Artificial Sequence
<220> FEATURE:
<223> OTHER INFORMATION: Synthetic construct

<400> SEQUENCE: 38
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccauguua uucaaccuuc guauccugcu aaacaaugcu gcuuuucgca 180
auggccauaa cuuuaugguu cgcaacuuua gaugcggcca gccgcugcag aacaagguuc 240
agcugaaggg ccgggacuug cugacgcuga aaaacuuuac cggggaagag auuaaguaua 300
ugcuguggcu aagcgcugau cugaaguuua ggaucaagca gaagggcgaa uaucugccac 360
ugcugcaagg gaagagucuu ggcaugauuu uugaaaagcg gucuaccaga acccggcugu 420
cgaccgagac agguuuugcu cugcuggggg gccaucccug uuuucugaca acucaggaca 480
uucaccuggg cgugaaugag ucccugaccg auacugcuag gguguugagu agcauggccg 540
acgcuguacu cgcucgagug uauaagcagu cugaucugga cacucuggcu aaggaagcuu 600
ccauuccuau uaucaacggc uugagcgacc uguaccaccc cauucaaauc cucgcugauu 660
acuugacuuu gcaagaacau uacagcagcu ugaagggcuu aacacugagc uggauaggcg 720
acggaaacaa caucuugcau uccauaauga uguccgccgc uaaguucggg augcaccucc 780
aagcagccac acccaagggc uaugaaccgg augcuuccgu gacaaaacug gcugagcagu 840
augcuaagga gaauggcacg aaacugcugc ucaccaacga cccauuggaa gcugcacaug 900
guggcaacgu acugaucacu gacacuugga ucucaauggg ccaggaggaa gagaagaaga 960
aaaggcugca ggcauuucag ggauaccaag ucacuaugaa aacugccaag gucgcugccu 1020
ccgacuggac auuccugcau ugucugccac ggaagccuga ggaagucgau gacgaagugu 1080
ucuauagccc acgaagcuug guguuucccg aggcugagaa uaggaagugg accauuaugg 1140
cuguuauggu gucccugcuc accgacuauu ccccucaacu gcaaaaaccc aaguuuuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 39
<211> LENGTH: 1365
<212> TYPE: RNA
<213> ORGANISM: Artificial Sequence
<220> FEATURE:
<223> OTHER INFORMATION: Synthetic construct

<400> SEQUENCE: 39
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caugcuuuuu aaucuccgca uccuccuuaa caacgccgcg uuuagaaacg 180
gccacaacuu cauggucegg aacuucagau guggccagcc gcuucaaaac aagguccagc 240
ugaagggccg ggaucuucug acccugaaga acuuuacugg cgaagagauc aaguacaugc 300
ucuggcucuc cgcggacuug aaguuccgca uuaagcagaa gggggaauac cuuccgcugc 360
uucaaggaaa gagccucggc augaucuuug agaagcgcuc aaccaggacc cgccuuucua 420
cugaaacugg guucgcgcug cucgguggcc accccugcuu ccugacgacc caggacaucc 480
accucggagu gaacgaaucc cucaccgaua ccgcccgggu guuaucgagc auggcagaug 540
ccgugcuggc cagggugugac aaacaguccg aucuggacac ucuggccaag gaggcgucaa 600
uucccaucau caacggccug agcgaccugu accacccaau ccaaauccug gcugacuacc 660
ugacccugca agagcacuac agcagccuga agggucugac ccugucaugg auuggcgaug 720
gaaacaauau ucugcacucc aucaugaugu ccgccgcgaa guucggaaug caucugcaag 780
ccgccacgcc aaaaggauac gaaccggaug cguccgugac gaaguuggcg gaacaguacg 840
cgaaggagaa cggaaccaag cuucugcuga cuaacgaccc ccucgaggcu gcgcaugggg 900
gcaacgugcu gauuaccgac accuggaucu ccauggggca ggaggaagag aagaagaaga 960
gacugcaggc auuccagggg uaccagguca ccaugaaaac cgcaaaagug gcagcuucgg 1020
acuggacuuu ccugcauugc cugccgagga agccggagga agucgacgac gaaguguucu 1080
acucgccucg gucccuggug uuccccgagg ccgaaaaccg gaaguggacc aucauggccg 1140 ugauggugucc cuugcugacu gacuauagcc cgcagcugca gaagccuaag uucuagcucg 1200
agcuagugac ugacuaggau cugguuacca cuaaaccagc cucaagaaca cccgaaugga 1260
gucucuaagc uacauaauac caacuuacac uuacaaaaug uuguccccca aaauguagcc 1320
auucguaucu gcuccuaaua aaaagaaagu uucuucacau ucuag 1365

<210> SEQ ID NO 40
<211> LENGTH: 1365
<212> TYPE: RNA
<213> ORGANISM: Artificial Sequence
<220> FEATURE:
<223> OTHER INFORMATION: Synthetic construct

<400> SEQUENCE: 40
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caugcuuuuc aaccugagaa uccucuugaa caaugcugcu uuucggaaug 180
gccacaacuu uaugguucgg aacuuccguu gcggccagcc uuuacaaaac aagguccagc 240

-continued

```
ugaagggccg ggauuugcuc acacugaaga acuuuacugg agaagagauc aaguacaugc    300

uguggcuguc ggccgaccug aaguucagga ucaagcagaa gggagaauac cuuccgcugc    360

uucaaggaaa gagccucggc augaucuuug agaagcgcuc aaccaggacc cgccuuucua    420

cugaaacugg guucgcgcug cucgguggcc accccugcuu ccugacgacc caggacaucc    480

accucggagu gaacgaaucc cucaccgaua ccgcccgggu guuaucgagc auggcagaug    540

ccgugcuggc cagggguguac aaacaguccg aucucgauac cuuggcaaag gaggcuucca    600

uucccaucau caacggccug agcgaccugu accacccaau ccaaauccug gcugacuacc    660

ugacccugca agagcacuac agcagccuga agggucugac ccugucaugg auuggcgaug    720

gaaacaauau ucugcacucc aucaugaugu ccgccgcgaa guucggaaug caucugcaag    780

ccgccacucc aaaaggauac gaaccggaug cguccgugac caaguuggcg gaacaguacg    840

cgaaggagaa cggaaccaag cuucugcuga cuaacgaccc ccucgaggcu gcgcaugggg    900

gcaacgugcu gauuaccgac accuggaucu ccauggggca ggaggaagag aagaagaaga    960

gacugcaggc auuccagggg uaccagguca ccaugaaaac cgcaaaagug gcagcuucgg   1020

acuggacuuu ccugcauugc cugccgagga agccggagga agucgacgac gaaguguucu   1080

acucgccucg gucccuggug uuccccgagg ccgaaaaccg gaaguggacc aucauggccg   1140

ugauggugue cuugcugacu gacuauagcc cgcagcugca gaagccuaag uucuagcucg   1200

agcuagugac ugacuaggau cugguuacca cuaaaccagc cucaagaaca cccgaaugga   1260

gucucuaagc uacauaauac caacuuacac uuacaaaaug uuguccccca aaauguagcc   1320

auucguaucu gcuccuaaua aaaagaaagu uucuucacau ucuag                   1365
```

```
<210> SEQ ID NO 41
<211> LENGTH: 1365
<212> TYPE: RNA
<213> ORGANISM: Artificial Sequence
<220> FEATURE:
<223> OTHER INFORMATION: Synthetic construct

<400> SEQUENCE: 41

ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc caugcuuuuc aaccugagaa uccucuugaa caaugcugcu uuucggaaug    180

gccacaacuu uaugguucgg aacuuccguu gcggccagcc uuuacaaaac aagguccagc    240

ugaagggccg ggauuugcuc acacuaaaga acuuuacugg agaagagauc aaguacaugc    300

uauggcuguc ggccgaccug aaguuccgua ucaagcagaa gggagaauac cuuccgcugc    360

uucaaggaaa gagccucggc augaucuuug agaagcgcuc aaccaggacc cgccuuucua    420

cugaaacugg guucgcgcug cucgguggcc accccugcuu ccugacgacc caggacaucc    480

accucggagu gaacgaaucc cucaccgaua ccgcccgggu guuaucgagc auggcagaug    540

ccgugcuggc caggguguac aaacaguccg aucucgauac cuuggcaaag gaggcuucca    600

uucccaucau caacggccug agcgaccugu accacccaau ccaaauccug gcugacuacc    660

ugacccugca agagcacuac agcagccuga agggucugac ccugucaugg auuggcgaug    720

gaaacaauau ucugcacucc aucaugaugu ccgccgcgaa guucggaaug caucugcaag    780

ccgccacucc aaaaggauac gaaccggaug cauccgugac caaguuggcg gaacaguacg    840

cgaaggagaa cggaaccaag cuccugcuga cuaacgaccc gcucgaggcu gcgcaugggg    900

guaacgugcu gauuacggac accuggaucu ccauggggca ggaggaagag aagaagaaga    960
```

gacugcaggc auuccagggg uaccagguca ccaugaaaac cgcaaaagug gcagcuucgg 1020
acuggacuuu ccugcauugc cugccgagga agccggagga agucgacgac gaaguguucu 1080
acucgccucg gucccuggug uuccccgagg ccgaaaaccg gaaguggacc aucauggccg 1140 ugauggugue cuugcugacu gacuauagcc cgcagcugca gaagccuaag uucuagcucg 1200
agcuagugac ugacuaggau cugguuacca cuaaaccagc cucaagaaca cccgaaugga 1260
gucucuaagc uacauaauac caacuuacac uuacaaaaug uuguccccca aaauguagcc 1320
auucguaucu gcuccuaaua aaaagaaagu uucuucacau ucuag 1365

<210> SEQ ID NO 42
<211> LENGTH: 1365
<212> TYPE: RNA
<213> ORGANISM: Artificial Sequence
<220> FEATURE:
<223> OTHER INFORMATION: Synthetic construct

<400> SEQUENCE: 42
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caugcuuuuc aaccugagaa uccucuugaa caaugcugcu uuucggaaug 180
gccacaacuu uaugguucgg aacuuccguu gcggccagcc uuuacaaaac aagguccagc 240
ugaagggccg ggauuugcuc acacuaaaga acuuuacugg agaagagauc aaguacaugc 300
uauggcuguc ggccgaccug aaguuccgua ucaagcagaa gggagaauac cuuccgcugc 360
uucaaggaaa gagccucggc augaucuuug agaagcgcuc aaccaggacc cgccuuucua 420
cugaaacugg guucgcgcug cucgguggcc accccugcuu ccugacgacc caggacaucc 480
accucggagu gaacgaaucc cucaccgaua ccgcccgggu guuaucgagc auggcagaug 540
ccgugcuggc cagggguguac aaacaguccg aucucgauac cuuggcaaag gaggcuucca 600
uucccaucau caacggccug agcgaccugu accacccaau ccaaauccug gcugacuacc 660
ugacccugca agagcacuac agcagccuga agggucugac ccugucaugg auuggcgaug 720
gaaacaauau ucugcacucc aucaugaugu ccgccgcgaa guucggaaug caucugcaag 780
ccgccacucc aaaaggauac gaaccggaug cguccgugac caaguuggcg gaacaguacg 840
cgaaggagaa cggaaccaag cuucugcuga cuaacgaccc ccucgaggcu gcgcaugggg 900
gcaacgugcu gauuaccgac accuggaucu ccaugggggca ggaggaagag aagaagaaga 960
gacugcaggc auuccagggg uaccagguca ccaugaaaac cgcaaaagug gcagcuucgg 1020
acuggacuuu ccugcauugc cugccgagga agccggagga agucgacgac gaaguguucu 1080
acucgccucg gucccuggug uuccccgagg ccgaaaaccg gaaguggacc aucauggccg 1140 ugauggugue cuugcugacu gacuauagcc cgcagcugca gaagccuaag uucuagcucg 1200
agcuagugac ugacuaggau cugguuacca cuaaaccagc cucaagaaca cccgaaugga 1260
gucucuaagc uacauaauac caacuuacac uuacaaaaug uuguccccca aaauguagcc 1320
auucguaucu gcuccuaaua aaaagaaagu uucuucacau ucuag 1365

<210> SEQ ID NO 43
<211> LENGTH: 1371
<212> TYPE: RNA
<213> ORGANISM: Artificial Sequence
<220> FEATURE:
<223> OTHER INFORMATION: Synthetic construct

<400> SEQUENCE: 43
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccugc gaauccugcu gaacaacgcc gcuuuucgga 180
acgggcacaa cuuuauggug aggaacuuuc gcugcggaca gccccuccag aauaaggucc 240
agcugaaggg cagggaccug cugacccuga aaaauuucac aggggaggaa aucaaguaua 300
ugcuguggcu gucagcugau cugaaguucc ggaucaagca gaagggcgaa uaucugccuc 360
ugcuccaggg caaaagccug ggaugaucu ucgaaaagcg caguacucgg accagacugu 420
caaccgagac uggauucgcu cugcugggag gacacccuug uuuucugacc acucaggaca 480
uucaccuggg agugaacgag ucccugaccg acacugcucg cguccugagc ucuauggccg 540
acgcugugcu ggcucgaguc uacaaacagu ccgaccugga uacccuggcc aaggaagcuu 600
cuaucccaau uauuaacggc cugucagacc uguaucaccc cauccagauu cuggccgauu 660
accugacccu ccaggagcac uauucuaguc ugaaagggcu gacacugagu uggauugggg 720
acggaaacaa uauccugcac ucuauuauga ugucagccgc caaguuugga augcaccucc 780
aggcugcaac cccaaaaggc uacgaacccg augccucagu gacaaagcug gcugaacagu 840
acgccaaaga gaacggcacu aagcugcugc ugaccaacga cccucuggag gccgcucacg 900
gaggcaacgu gcugaucacc gauaccugga uuaguauggg acaggaggaa gagaagaaga 960
agcggcucca ggccuuccag ggcuaccagg ugacaaugaa aaccgcuaag gucgcagcca 1020
gcgauuggac cuuucugcac ugccugccca gaaagcccga agagguggac gacgaggucu 1080
ucuacucucc cagaagccug guguuucccg aagcugagaa uaggaagugg acaauuaugg 1140
cagugauggu cagccugcug acugauuauu caccucagcu ccagaaacca aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 44
<211> LENGTH: 1371
<212> TYPE: RNA
<213> ORGANISM: Artificial Sequence
<220> FEATURE:
<223> OTHER INFORMATION: Synthetic construct

<400> SEQUENCE: 44
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccugc gcauccugcu gaacaacgcc gccuuccgca 180
acggccacaa cuucauggug cgcaacuucc gcugcggcca gccccugcag aacaaggugc 240
agcugaaggg ccgcgaccug cugacccuga agaacuucac cggcgaggag aucaaguaca 300
ugcuguggcu gagcgccgac cugaaguucc gcaucaagca gaagggcgag uaccugcccc 360
ugcugcaggg caagagccug ggcaugaucu ucgagaagcg cagcacccgc acccgccuga 420
gcaccgagac aggccuggcc cugcugggcg gccaccccug cuuccugacc acccaggaca 480
uccaccuggg cgugaacgag agccugaccg acaccgcccg cgugcugagc agcauggccg 540
acgccgugcu ggcccgcgug uacaagcaga gcgaccugga cacccuggcc aaggaggcca 600
gcauccccau caucaacggc cugagcgacc uguaccaccc cauccagauc cuggccgacu 660
accugacccu gcaggagcac uacagcagcc ugaagggccu gacccugagc uggaucggcg 720
acggcaacaa cauccugcac agcaucauga ugagcgccgc caaguucggc augcaccugc 780
aggccgccac ccccaagggc uacgagcccg acgccagcgu gaccaagcug gccgagcagu 840
acgccaagga gaacggcacc aagcugcugc ugaccaacga cccccuggag gccgcccacg 900
gcggcaacgu gcugaucacc gacaccugga ucagcauggg ccaggaggag gagaagaaga 960
agcgccugca ggccuuccag ggcuaccagg ugaccaugaa gaccgccaag guggccgcca 1020
gcgacuggac cuuccugcac ugccugcccc gcaagcccga ggagguggac gacgaggugu 1080
ucuacagccc ccgcagccug guguuccccg aggccgagaa ccgcaagugg accaucaugg 1140
ccgugauggu gagccugcug accgacuaca gcccccagcu gcagaagccc aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 45
<211> LENGTH: 1371
<212> TYPE: RNA
<213> ORGANISM: Artificial Sequence
<220> FEATURE:
<223> OTHER INFORMATION: Synthetic construct

<400> SEQUENCE: 45
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccugc gaauccugcu gaacaacgcc gcuuuucgga 180
acgggcacaa cuuuauggug aggaacuuuc gcugcggaca gccccuccag aauaagaucc 240
agcugaaggg cagggaccug cugacccuga aaaauuucac aggggaggaa aucaaguaua 300
ugcuguggcu gucagcugau cugaaguucc ggaucaagca gaagggcgaa uaucugccuc 360
ugcuccaggg caaaagccug ggaugaucu ucgaaaagcg caguacucgg accagacugu 420
caaccgagac uggauucgcu cugcugggag gacacccuug uuuucugacc acucaggaca 480
uucaccuggg agugaacgag ucccugaccg acacugcucg cguccugagc ucuauggccg 540
acgcugugcu agcucgaguc uacaaacagu ccgaccugga uacccuggcc aaggaagcuu 600
cuaucccaau uauuaacggc cugucagacc uguaucaccc cauccagauu cuggccgauu 660
accugacccu ccaggagcac uauucuaguc ugaaagggcu gacacugagu uggauugggg 720
acggaaacaa uauccugcac ucuauuauga ugucagccgc caaguuugga augcaccucc 780
aggcugcaac cccaaaaggc uacgaacccg augccucagu gacaaagcug gcugaacagu 840
acgccaaaga gaacggcacu aagcugcugc ugaccaacga cccucuggag gccgcucacg 900
gaggcaacgu gcugaucacc gauaccugga uuaguauggg acaggaggaa gagaagaaga 960
agcggcucca ggccuuccag ggcuaccagg ugacaaugaa aaccgcuaag gucgcagcca 1020
gcgauuggac cuuucugcac ugccugccca gaaagcccga agagguggac gacgaggucu 1080
ucuacucucc cagaagccug guguuucccg aagcugagaa uaggaagugg acaauuaugg 1140
cagugauggu cagccugcug acugauuauu caccucagcu ccagaaacca aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 46
<211> LENGTH: 1371
<212> TYPE: RNA
<213> ORGANISM: Artificial Sequence
<220> FEATURE:
<223> OTHER INFORMATION: Synthetic construct

<400> SEQUENCE: 46
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccugc gaauccugcu gaacaaugcc gcuuuucgga 180
acgggcacaa uuucauggug aggaacuuuc gcugcggaca gccccuccag aacaaggucc 240
agcugaaggg cagggaccug cugacccuga aaaauuucac aggggaggaa aucaaguaca 300
ugcuguggcu gucagccgau cugaaguucc ggaucaagca gaagggcgaa uaucugccuc 360
ugcuccaggg caaaagccug ggaugaucu ucgaaaagcg caguacucgg accagacugu 420
caacagagac uggauucgca cugcugggag gacacccaug uuuucugacc acacaggaca 480
uucaucuggg agugaacgag ucccugaccg acacagcacg cguccugagc uccauggcug 540
augcagugcu ggcucgaguc uacaaacagu cugaccugga uacccuggcc aaggaagcuu 600
cuaucccaau cauuaauggc cugagugacc uguaucaccc cauccagauu cuggccgauu 660
accugacccu ccaggagcau uauucuaguc ugaaagggcu gacacugagc uggauugggg 720
acggaaacaa uauccugcac uccauuauga ugagcgccgc caaguuugga augcaccucc 780
aggcugcaac cccaaaaggc uacgaacccg augccuccgu gacaaagcug gcagaacagu 840
augccaaaga gaacggcacu aagcugcugc ugaccaauga cccucuggag gccgcucacg 900
gaggcaacgu gcugaucacu gauaccugga uuaguauggg acaggaggaa gagaagaaga 960
agcggcucca ggccuuccag ggcuaccagg ugacaaugaa aacugcuaag gucgcagcca 1020
gcgacuggac cuuucugcau ugccugccca gaaagccuga agagguggac gaugaggucu 1080
ucuacucacc cagaagccug guguuuccug aagcugagaa uaggaagugg acaaucaugg 1140
cagugauggu cagccugcug acugauuauu ccccucagcu ccagaaacca aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 47
<211> LENGTH: 1368
<212> TYPE: RNA
<213> ORGANISM: Artificial Sequence
<220> FEATURE:
<223> OTHER INFORMATION: Synthetic construct

<400> SEQUENCE: 47
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaccuuc gcauucuccu caacaacgcc gcguuuagaa 180
acggacacaa cuucaugguc cgcaacuucc gcugcggaca gccgcugcag aacaaggucc 240
agcucaaggg ucgggaucuc cugacgcuga agaacuuuac cggcgaagag auuaaguaca 300
ugcuguggcu guccgccgac cuuaaguucc ggaucaagca gaagggcgaa uaccuucccc 360

```
ugcugcaagg aaagucccug ggcaugaucu ucgagaagcg caguaccaga accagacucu    420
ccacugaaac cggguucgcg cugcuuggcg gccacccgug uuuccucacu acgcaagaca    480
uccaucuugg cgugaacgag ucccuuaccg acaccgccag ggugcuguca agcauggccg    540
acgccguccu ugcgcgcgug uacaagcagu cagaccuuga uacucuggcc aaggaagccu    600
ccaucccuau uaucaacggc cuauccgacc uuuaccaccc gauccagauc cucgcugacu    660
accugacccu gcaagaacac uacagcagcc ucaagggacu gacucugucc uggaucggcg    720
acgggaacaa cauccugcac ucaaucauga ugagcgcagc caaguucggc augcaucucc    780
aagccgcuac acccaagggu uaugaaccgg acgccucugu gaccaaguug gcagaacagu    840
acgccaagga gaacgguacu aagcuccuuu uaaccaacga cccccucgaa gcagcccaug    900
gcgggaaugu gcucauuacc gauaccugga uuucgauggg ccaggaggag gagaagaaga    960
agcggcugca ggcguuccag ggcuaccagg ucaccaugaa aacugccaaa guggccgccu   1020
cggauuggac cuuucuccac ugccugccuc ggaagccuga ggagguggac gacgaagugu   1080
ucuacucccc acggucccuc guguuccccg aggccgaaaa uaggaagugg accaucaugg   1140
ccgugauggu gucccucuug accgauuaca gcccgcagcu ucagaagccu aaauucuagc   1200
ucgagcuagu gacugacuag gaucugguua ccacuaaacc agccucaaga acacccgaau   1260
ggagucucua agcuacauaa uaccaacuua cacuuacaaa auguuguccc ccaaaaugua   1320
gccauucgua ucugcuccua auaaaaagaa aguuucuuca cauucuag                1368
```

<210> SEQ ID NO 48
<211> LENGTH: 1368
<212> TYPE: RNA
<213> ORGANISM: Artificial Sequence
<220> FEATURE:
<223> OTHER INFORMATION: Synthetic construct

<400> SEQUENCE: 48

```
ucaacacaac auauacaaaa caaacgaauc ucaagcaauc aagcauucua cuucuauugc     60
agcaauuuaa aucauuucuu uuaaagcaaa agcaauuuuc ugaaaauuuu caccauuuac    120
gaacgauagc caccaugcuu uucaaucuuc gcauccuguu gaacaacgcc gccuuccgca    180
auggucacaa cuucaugguc cggaacuuca gauguggaca gccucuccaa aacaaggucc    240
agcugaaggg aagggaccuc uuaacccuca aaaacuuuac uggagaggag aucaaguaca    300
ugcuguggcu uagcgccgac cuuaaguucc ggaucaagca gaagggagag uaccucccgc    360
ugcugcaagg aaagagucuu ggaaugaucu ucgagaagcg guccaccaga acucgccucu    420
ccacugaaac cggauucgca cuccugggug gacacccgug cuuucugacc acccaagaca    480
uccaccucgg agugaacgag agccucacgg acaccgcgag agugcuguca uccauggccg    540
acgccgugcu ugcacggguc uacaagcagu ccgaucugga cacucuugcc aaggaagccu    600
ccauuccuau cauuaacggu cugucggauc uguaccaccc gauucagauc cuugcggacu    660
accucacacu ucaagaacac uauucaagcc uaaagggucu gacccugucc uggaucggag    720
auggaaacaa cauucuccau uccaucauga ugagcgcugc caaguucgga augcaucucc    780
aagcagcgac uccuaagggu uacgagccgg acgccucagu gacuaagcug gccgagcagu    840
acgccaagga gaacgguacc aaacuguugc uuacuaacga cccgcuugaa gcggcccaug    900
gaggaaacgu gcugauuacc gacaccugga uuucgauggg acaggaagag gagaagaaga    960
agcggcucca ggcguuccag ggauaccagg ucaccaugaa aacggccaaa guggccgcua   1020
```

gcgauuggac cuuucugcac ugccuccccgc gcaagccuga agaaguggac gacgaagugu 1080
ucuacucccc ucgcucucuu guguucccgg aagccgaaaa caggaagugg accaucaugg 1140
ccgugauggu gucccuccug accgauuaca gcccgcagcu gcagaagccu aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 49
<211> LENGTH: 1368
<212> TYPE: RNA
<213> ORGANISM: Artificial Sequence
<220> FEATURE:
<223> OTHER INFORMATION: Synthetic construct

<400> SEQUENCE: 49
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu caacaacgcc gcguuuagaa 180
acggccacaa cuucaugguc cggaacuuca gauguggcca gccgcuucag aacaagoucc 240 agcucaaggg ccgggaucuu cugacccuga agaacuuuac uggcgaagaa aucaaguaca 300
ugcucuggcu cuccgccgac uugaaguucc gcauuaagca gaagggggaa uaccuuccgc 360
ugcugcaagg aaagucgcuc ggcaugaucu uugagaagcg cucaacccgc accaggcugu 420
ccacugaaac cgguucgcg cugcuuggug gccaccccug cuuccugacc acccaagaca 480
uucaccucgg agugaacgaa ucgcucacug auacugcccg ggugcugucg ucgauggccg 540
augcagugcu ggccagggug uacaaacagu ccgaucugga cacucuggcc aaggaggcgu 600
ccaucccuau uaucaacggc cuuuccgacc ucuaccaccc gauucagauc cuugccgauu 660
accucacccu gcaagaacac uacucgucac ugaagggucu gaccuugucc uggaucggcg 720
acggcaacaa cauccuccau uccauuauga uguccgccgc caaauucggc augcaucuuc 780
aagccgcaac ccccuaagggu uacgagccgg acgcuuccgu gaccaagcuc gccgagcagu 840
acgcuaagga gaacggaacc aagcuucugc ugacuaacga cccccuagag gcagcccacg 900
ggggcaacgu gcuuauuacu gacaccugga ucuccauggg acaggaagaa gagaagaaga 960
agcgguuaca ggcguuccag ggcuaucagg ucaccaugaa aaccgccaag gucgcugccu 1020
cggacuggac cuuccugcau ugccugccuc gcaagcccga agaaguggac gacgaggugu 1080
ucuacucgcc acggucccuu guguucccug aggccgagaa uagaaagugg accauuaugg 1140
ccgugauggu gucccuucuc accgacuacu cgccgcaacu gcagaaaccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 50
<211> LENGTH: 1368
<212> TYPE: RNA
<213> ORGANISM: Artificial Sequence
<220> FEATURE:
<223> OTHER INFORMATION: Synthetic construct

<400> SEQUENCE: 50
ucaacacaac auauacaaaa caaacgaauc ucaagcaauc aagcauucua cuucuauugc 60

-continued agcaauuuaa aucauuucuu uuaaagcaaa agcaauuuuc ugaaaauuuu caccauuuac 120
gaacgauagc caccaugcuu uucaaucuuc gcauccuccu caacaacgcc gccuuccgga 180
acggucacaa cuucauggucc cggaacuucc gcugcggcca gccgcuccaa aacaaagugc 240
agcuuaaggg ccgcgaucuc cugacccuga agaacuucac cggagaggaa aucaaguaca 300
ugcuguggcu cucggcggac cugaaguuua ggauuaagca gaagggggag uaucugccgc 360
ugcuccaagg gaagucccuu ggcaugaucu ucgaaaagag guccacccgg acucggcuca 420
gcaccgaaac agguuuugca cuucuggggg gccacccgug cuuccugacg acccaggaca 480
uccaucuggg ugucaacgag aguuugaccg acacugccag agugcuguca uccauggcgg 540
acgcggugcu cgcgagagug uacaagcagu ccgaucuuga cacccuggca aaagaggcuu 600
caaucccgau cauuaacgga cucucggauc uguaccaccc uauccaaauc uuggccgacu 660
accugacccu gcaagaacac uacagcuccc ugaagggccu gacucuuucc uggauuggcg 720
auggaaacaa cauucuccau ucuauuauga uguccgccgc caaguucggc augcaccuuc 780
aagccgccac cccgaagggc uacgaaccug acgccuccgu gacuaagcua gccgaacagu 840
acgcuaagga gaacggcacu aagcuucucc uuaccaacga uccgcuggag gcggcccaug 900
gcggaaaugu gcuuaucacc gacaccugga uuagcauggg gcaggaagaa gagaagaaga 960
aacggcucca ggcauuccag ggcuaccagg ucaccaugaa aacugccaag gucgccgcua 1020
gcgacuggac cuuccuccac ugucugccuc gcaagccuga agaaguggac gacgaggugu 1080
ucuacucccc gcgcucccuc guguuuccug aggccgagaa cagaaagugg accaucaugg 1140
ccgugauggu gucauuacuu acggacuaca gcccgcagcu gcagaagccg aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 51
<211> LENGTH: 1368
<212> TYPE: RNA
<213> ORGANISM: Artificial Sequence
<220> FEATURE:
<223> OTHER INFORMATION: Synthetic construct

<400> SEQUENCE: 51
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uuuaacuuga gaauccuucu gaacaacgcc gcuuuccgca 180
acggucauaa cuucaugguc cggaacuuca gauguggcca gccccuccaa aacaaagugc 240
agcugaaggg ccgggaccuu cuuacgcuga agaauuucac cggcgaagaa aucaaguaca 300
ugcucuggcu guccgccgau cuuaaguucc gcauuaagca gaagggggaa uaccucccgc 360
ugcugcaagg gaagucgcug ggcaugauuu uugagaagcg gucaacucgc acccgccugu 420
ccacugaaac uggauucgca cugcucggug gccaucccug cuuccugacc acccaagaca 480
uccaccucgg cgugaacgag ucccugacug acaccgcccg ggucuuaucc ucgauggccg 540
augcugugcu ugcgagggug uacaagcagu ccgaccucga cacacucgcg aaggaggccu 600
ccauccccau caucaacggc cuguccgacc uuuaccaccc aauucagauc cucgccgauu 660
accugacccu gcaagagcac uacucgucgc ucaaggggcu uacccucucg uggauuggcg 720

-continued acggcaacaa cauccuucac uccaucauga ugucggcagc gaaguucggc augcaucugc 780
aagccgccac gccuaagggu uaugaaccgg augccucagu gaccaagcuc gccgaacagu 840
acgcgaaaga gaauggaacc aagcuacuuc ugaccaacga cccccuggag gccgcucacg 900
gcggcaacgu ccucauuacc gauacuugga uuucgauggg acaggaagag gaaaagaaga 960
agagacugca ggcguuccag ggauaccagg ucaccaugaa aacugccaaa guggcagccu 1020
ccgacuggac cuuccuucac ugccugccga ggaagccuga agagguggac gacgaggugu 1080
ucuacucccc gcgcuccuug guguuuccug aggccgaaaa ccggaagugg acuaucaugg 1140
ccgugauggu gucccuccuc accgacuacu cgccgcaacu gcagaagccu aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 52
<211> LENGTH: 1368
<212> TYPE: RNA
<213> ORGANISM: Artificial Sequence
<220> FEATURE:
<223> OTHER INFORMATION: Synthetic construct

<400> SEQUENCE: 52
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccauguua uucaaccuua gaauucuccu uaacaacgcc gccuuccgga 180
augggcauaa cuuuaugguc cgcaauuucc gcuguggaca gccucugcaa aacaaggucc 240
agcucaaggg ccgggaucug cugacucuca agaacuucac uggggaagaa aucaaguaca 300
ugcucuggcu gagcgccgac cucaaguucc gcaucaagca gaagggagag uaccucccgc 360
ugcuccaagg gaagucccug ggcaugaucu ucgagaagag auccacccgc accagacuuu 420
ccacugagac uggcuucgcc uugcugggag gccacccaug cuuccugacg acccaggaca 480
uucaccuugg cgugaacgag ucccugacug acaccgcaag gguguugucc ucgauggccg 540
acgccgugcu ugcccgggug uacaagcaga gcgaucuuga cacccuggcu aaggaagcuu 600
ccauucccau caucaacggu cugagcgacc uguaccaccc gauucagauc cuggcggacu 660
accuaacccu gcaagagcac uauagcuccc ugaagggccu cacacuuuca uggaucggcg 720
acggcaacaa cauccugcac ucuauuauga ugagcgcugc caaauucggc augcaccucc 780
aagccgccac gccuaaaggc uacgagcccg acgccucggu gaccaagcuu gcggagcagu 840
acgcgaagga aaacggcacc aagcugcuuc ucaccaacga uccucuggaa gcggcccaug 900
guggcaacgu gcucauuacc gacacuugga ucuccauggg acaggaggag gaaaagaaga 960
agcggcucca ggcguuucag gguuaccagg ucaccaugaa aaccgccaag gucgcagccu 1020
ccgacuggac cuuccuucau ugccuucccgc gcaagcccga agaaguggac gaugaagugu 1080
uuuacucacc ucggucacuc guguucccgg aagcagagaa caggaaaugg accauuaugg 1140
ccgugauggu gucccugcuc accgauuaca guccgcaacu gcagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 53
<211> LENGTH: 1368
<212> TYPE: RNA
<213> ORGANISM: Artificial Sequence
<220> FEATURE:
<223> OTHER INFORMATION: Synthetic construct

<400> SEQUENCE: 53
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggccacaa cuucaugguc cggaacuuca gauguggcca gccgcuucaa aacaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucaaauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccuaagggu uacgaacccg acgcuuccgu gacuaagcuc gccgagcagu 840
acgcuaagga gaacggaacc aagcugcugc ugacuaacga cccgcuagaa gcagcccacg 900
ggggcaacgu gcuuauuacu gacaccugga ucuccauggg ccaggaggaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacuucuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 54
<211> LENGTH: 1368
<212> TYPE: RNA
<213> ORGANISM: Artificial Sequence
<220> FEATURE:
<223> OTHER INFORMATION: Synthetic construct

<400> SEQUENCE: 54
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggccacaa cuucaugguc cggaacuuca gauguggcca gccgcuucaa aacaaggucc 240
agcuuaaggg ccgggaucuc cucacccuua aaaacuucac cggcgaagag aucaaguaca 300
ugcucuggcu cuccgcggac cuuaaguucc gcauuaagca gaagggggaa uaccuuccgc 360
ugcuucaagg aaagagccuc ggcaugaucu uugagaagcg cucaaccagg accaggcuuu 420
cuacugaaac uggguucgcg cuucucggcg gucaucccug cuuccucacg acccaagaca 480
uccaccucgg agugaacgaa ucccucacgg auacugcccg cgugcuuucg agcauggcag 540
acgccgugcu cgcccgggug uacaaacagu ccgaucucga cacucucgcc aaggaggcgu 600
caauuccuau uaucaacggu cuuagugacc uuuaccaccc gauccagauc cucgccgauu 660
accucacacu ccaagaacac uacagcuccc uuaagggucu uacccucucc uggaucggcg 720
acggcaacaa cauucuccac uccaucauga uguccgccgc aaaguucggc augcaucuuc 780
aagccgccac cccgaagggc uacgagccug augcuuccgu gacuaagcuc gccgagcagu 840
acgcuaagga gaacggaacc aagcuucuuc ucacuaacga cccacucgaa gcagcccaug 900
ggggcaacgu gcuuaucacu gacaccugga ucuccauggg ccaggaagaa gagaagaaga 960
agcggcucca ggcguuccag ggauaucagg ucaccaugaa aaccgccaag gucgcugccu 1020
ccgacuggac cuuucuccac ugccucccuc gcaaaccuga agaaguggac gacgaggugu 1080
ucuacucgcc ccggagccuc guguuccccg aggccgagaa uagaaagugg accauuaugg 1140
ccgugauggu gucacuccuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 55
<211> LENGTH: 1368
<212> TYPE: RNA
<213> ORGANISM: Artificial Sequence
<220> FEATURE:
<223> OTHER INFORMATION: Synthetic construct

<400> SEQUENCE: 55
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggacauaa cuucaugguc cggaacuuca gauguggaca gccgcuucaa aacaaggucc 240
agcugaaggg ucgggaucuu cugacccuga agaacuuuac cggagaagag aucaaguaca 300
ugcucuggcu cuccgcggac uugaaguucc gcauuaagca gaagggagaa uaccuccccgc 360 ugcuucaagg aaagagccuc ggaaugauuu uugagaagcg cucaaccagg acccgccuuu 420
cuacugaaac uggauucgcg cugcugggug gacaccccug cuuccugacg acccaggaca 480
uccaccucgg agugaacgaa ucccucacug auaccgcccg gguguuaucg agcauggcag 540
augccgugcu ggccagggug uacaaacagu ccgaucugga cacucuggcc aaggaggcgu 600
caauuccuau caucaacgga cuuagugacc ucuaccaucc gauucaaauc cuggccgacu 660
accucacccu gcaagaacac uacagcuccc ugaagggucu gacauugucc uggaucggag 720
auggaaacaa cauucuccac uccaucauga uguccgccgc aaaauucgga augcaucuuc 780
aagccgccac gccuaagggu uacgaacccg acgcuuccgu gacuaagcuc gccgagcagu 840
acgcuaagga gaacgguacc aagcuucucc ugaccaacga cccacuagaa gcagcccacg 900
guggaaacgu gcuuauuacu gacacuugga ucuccauggg acaggaggaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc gcggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 56
<211> LENGTH: 1368
<212> TYPE: RNA
<213> ORGANISM: Artificial Sequence
<220> FEATURE:
<223> OTHER INFORMATION: Synthetic construct

<400> SEQUENCE: 56
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaccucc gcauucuccu caacaacgcu gccuuccgga 180
auggacauaa cuucaugguc cggaacuuca gaugcggaca gccgcuucag aacaaggucc 240
agcuuaaggg gagagaucuc cuuacccuca aaaacuucac uggcgaagaa aucaaguaca 300
ugcucuggcu uagugcggau cucaaguucc gcaucaagca gaagggagaa uaccucccgc 360
uccuucaagg aaagagccuc ggcaugauuu uugagaagag guccaccaga acucgccuuu 420
caaccgagac uggguucgcc cugcuuggcg gucaccccug cuuccucacu acccaagaca 480
uccaccucgg cgugaacgag agccuuaccg acaccgcccg cgugcucucc ucaauggccg 540
acgcugugcu cgcccgggug uacaagcagu ccgaccuuga uacucucgcc aaggaggccu 600
ccaucccaau uaucaacggg cucucugauc ucuaccaccc uauccaaauc cucgcggacu 660
accucacccu ccaagagcac uauagcucgc ucaagggccu cacccuuucc uggauuggcg 720
acggcaacaa cauucuucac ucgaucauga uguccgccgc caaguucggc augcaucucc 780
aagccgcgac ccccaagggc uacgagccug acgcauccgu gaccaagcuc gccgagcagu 840
acgcgaagga aaauggcacc aagcuucuuc ucaccaacga cccccuugag gccgcucaug 900
gcggcaacgu gcucaucacu gacacuugga ucagcauggg ccaggaggag gaaaagaaga 960
agcgccuuca ggcauuccag gguuaccagg ucaccaugaa aaccgccaaa guggccgccu 1020
ccgacuggac cuuucuucac ugucuccccgc ggaagccuga agaaguggau gacgaagugu 1080
uuuacucccc ucggucacuc guguucccgg aagcagaaaa caggaagugg accauuaugg 1140
cggucauggu gucccuccuc accgacuaca gcccgcagcu ucagaaaccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 57
<211> LENGTH: 1368
<212> TYPE: RNA
<213> ORGANISM: Artificial Sequence
<220> FEATURE:
<223> OTHER INFORMATION: Synthetic construct

<400> SEQUENCE: 57
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgca gcguuuagaa 180
acggucacaa cuucaugguc cggaacuucc gcuguggaca gccgcuucaa aacaaggucc 240
agcugaaggg ucgggaccuu cugacccuga agaacuuuac uggagaagag aucaaguaca 300
ugcuuuggcu guccgcggac uugaaguucc gcauuaagca gaagggagaa uaccuuccgc 360
ugcuccaagg aaagagccug ggaaugaucu uugagaagcg cucaaccagg acccgccuuu 420
cuacugaaac uggauucgcg cugcugggug gucacccuug cuuccugacg acccaggaca 480
uucaccucgg agugaacgag ucccucacug auaccgccag aguguuaucg agcauggcag 540
augccgugcu ggcuagggug uacaaacagu ccgaucugga cacccuggcc aaggaggcau 600
caauuccuau uaucaacgga cuuagugacc ucuaccaucc gauucaaauc cuggccgauu 660
accucacccu gcaagaacac uacagcuccc ugaagggucu gacauugucc uggaucggag 720
auggaaacaa cauucuccau uccaucauga uguccgcggc caaguucgga augcaucucc 780
aagccgccac gccgaaagga uacgagccgg acgcuuccgu gacuaagcuc gccgagcagu 840
acgcuaagga gaacggaacc aagcuucugc ugacuaacga cccgcuagaa gccgcccacg 900
guggaaacgu gcuuauuacu gacaccugga ucuccauggg acaggaagaa gagaaaaaga 960
agcggcugca ggcguuccag ggauaucagg ucaccaugaa aaccgccaag gucgccgccu 1020
ccgacuggac cuuccuucac ugccugccuc ggaagccuga agaaguggac gacgaggugu 1080
ucuacucgcc gcggagccuc guguucccug aggccgagaa uagaaagugg accaucaugg 1140
ccgugauggu gucacuccuc accgacuaca gcccgcagcu ucagaagccu aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 58
<211> LENGTH: 1368
<212> TYPE: RNA
<213> ORGANISM: Artificial Sequence
<220> FEATURE:
<223> OTHER INFORMATION: Synthetic construct

<400> SEQUENCE: 58
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauucuccu caacaacgca gccuuuagaa 180
acggccacaa cuucaugguc cggaacuuca gauguggcca gccgcuucag aacaaggucc 240
agcucaaggg ccgggaccuc cucacccuca aaaacuuuac cggcgaagag aucaaguaca 300
ugcucuggcu uucggccgac cuuaaguucc gcaucaagca gaagggggaa uaccuuccgc 360
ugcuucaagg aaagucccuc ggcaugaucu uugaaaagcg cucgaccagg acccgccuuu 420
ccacugaaac cggguucgcg cuucucggug gccaccccug cuuccucacc acccaagaca 480
uucaccucgg agugaacgaa ucccuuaccg auaccgcaag agugcuuucg ucgauggccg 540
augccgugcu ugcgcgggug uacaagcagu cagaucucga cacucucgcc aaggaggcgu 600
ccauuccuau uaucaacggc cuuuccgacc uuuaccaccc gauucagauc cucgccgauu 660
accucacccu gcaagagcac uacucgucac ucaagggucu uacccucucc uggaucggcg 720
acggaaacaa cauccuccau ucgaucauga uguccgccgc caaauucggc augcaccucc 780
aagccgcgac cccgaagggu uacgagcccg acgcuuccgu gaccaagcuc gccgaacagu 840
acgcuaagga aaacggcacc aagcuccucc ucacuaacga cccucucgaa gcagcccaug 900
ggggcaacgu gcucauuacu gacacuugga ucucgauggg ccaggaagag gagaaaaaga 960
agcggcuuca ggcguuccag ggauaucagg ucaccaugaa aaccgccaag gucgcugccu 1020
cggacuggac cuuccuucac ugccuucccgc gcaagccuga agagguggac gaugaggugu 1080
ucuacucccc acgguccuu guguuccccg aggccgagaa uaggaagugg accaucaugg 1140
ccgugauggu gucgcuccuc acugacuacu ccccgcaacu ucagaagccu aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 59
<211> LENGTH: 1368
<212> TYPE: RNA
<213> ORGANISM: Artificial Sequence
<220> FEATURE:
<223> OTHER INFORMATION: Synthetic construct

<400> SEQUENCE: 59
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uuuaaucuga gaauacuucu aaacaacgcc gccuuccgga 180
auggccauaa cuuuaugguu cggaauuucc gcugcggcca gccgcugcag aacaaggucc 240
agcugaaggg aagagacuug cugacccuca agaacuucac cggagaagaa aucaaguaua 300
ugcuguggcu guccgccgac cugaaauucc gcaucaagca gaagggcgaa uaucugccgc 360
uguugcaagg gaagucccug gggaugaucu ucgagaagag guccaccaga acacggcuuu 420
caaccgaaac cggguuugca cugcugggug gacaccccug uuuucugacc acucaagaua 480
uccaccuggg cgugaacgag ucccuuaccg acacugcuag gguguugucc agcauggccg 540
augccguccu ggcucgcgug uacaagcagu ccgaccugga uacccuggca aaggaagcgu 600
ccauucccau uaucaacggg cuguccgacc uguaccaucc gauucaaauc cuggcggacu 660
accugacucu gcaagagcau uacagcagcu ugaaggggcu uacucucucg uggaucggcg 720
acgggaacaa cauccugcac uccaucauga uguccgccgc caaguucggg augcauuugc 780
aagcugcgac cccgaaaggu uacgagcccg augcuagcgu aacuaagcuu gccgaacagu 840
acgccaaaga gaaugguaca aaacugcuuc ugacuaacga cccgcuggaa gcagcccacg 900
gcgggaacgu gcugauaacc gacaccugga uuucaauggg gcaggaggaa gagaagaaga 960
agcgacugca ggcguuccaa ggcuaucagg uuaccaugaa aaccgccaaa guggcagcca 1020
gcgauuggac uuuccugcac ugucugccgc ggaagcccga ggaaguugau gacgaaguau 1080
ucuacucacc ccggagccuc guguuccccg aggccgaaaa ccggaagugg acuauuaugg 1140
ccgugauggu gucgcuguug accgacuaca gcccgcaacu gcagaagccg aaguuuuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 60
<211> LENGTH: 1368
<212> TYPE: RNA

<213> ORGANISM: Artificial Sequence
<220> FEATURE:
<223> OTHER INFORMATION: Synthetic construct

<400> SEQUENCE: 60
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaccuga ggauccuuuu gaacaacgcc gccuuucgca 180
acggccacaa cuuuaugguc cgcaauuucc gcugcgggca gccgcugcag aacaaggucc 240
agcugaaggg ccgggaucug cugacccuga agaacuucac cggggaggaa aucaaguaca 300
ugcuuuggcu cuccgccgau cugaaguuca gaaucaagca gaagggagag uaccuccccgu 360 ugcugcaagg aaagucacuc ggaaugauuu ucgaaaagag aagcacuagg acccgccucu 420
caacugaaac cgguucgcg cugcucgggg gccauccgug uuuccugacu acccaagaca 480
uccaccuggg agugaacgag ucgcugaccg acaccgcacg cgugcuguca uccauggcgg 540
acgcagugcu ugcccgggug uacaagcagu cggaccugga cacucuugcc aaggaggcau 600
caauccccau cauuaacgga cuguccgauc ucuaccaccc gauucagauc cuggcugacu 660
accuaacccu gcaagagcac uacucaagcc ugaaggggcu gacccugucg uggaucgggg 720
acggcaacaa cauucugcac uccaucauga ugucggcggc uaaguucggg augcauuugc 780
aagcggcaac uccgaagggu uaugaacccg acgccuccgu gaccaagcug gccgaacagu 840
acgccaagga aaacggaacc aaguugcugc ugacuaauga uccccuggag gcggcccacg 900
gggggaacgu gcugauaacc gauaccugga ucuccauggg gcaggaagaa gagaagaaaa 960
agcggcugca ggcauuccag ggauaccagg ucaccaugaa aaccgcaaaa guggcagcca 1020
gcgacuggac uuuccuccau ugccugccgc gaaagccgga ggaggucgau gacgaggugu 1080
ucuacucccc gcggucgcug guguucccgg aggcggaaaa ccggaagugg accauuaugg 1140
ccgugauggu gucacuccug acugacuaca gcccgcaacu gcagaagccg aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 61
<211> LENGTH: 1496
<212> TYPE: RNA
<213> ORGANISM: Artificial Sequence
<220> FEATURE:
<223> OTHER INFORMATION: Synthetic construct

<400> SEQUENCE: 61
cuuaaggggg cgcugccuac ggagguggca gccaucuccu ucucggcauc aagcuuacca 60
uggugcccca ggcccugcuc uugguccccgc ugcugguguu cccccucugc uucggcaagu 120
uccccaucua caccaucccc gacaagcugg ggccguggag ccccaucgac auccaccacc 180
uguccugccc caacaaccuc gugggucgagg acgagggcug caccaaccug agcggguucu 240
ccuacaugcu uuucaaucuc cgcauccucc uuaacaacgc cgcguuuaga aacggccaca 300
acuucauggu ccggaacuuc agauguggcc agccgcuuca aaacaagguc cagcugaagg 360
gccgggaucu ucugacccug aagaacuuua cuggcgaaga gaucaaguac augcucuggc 420
ucuccgcgga cuugaaguuc cgcauuaagc agaaggggga auaccuuccg cugcuucaag 480
gaaagagccu cggcaugauc uuugagaagc gcucaaccag gacccgccuu ucuacugaaa 540
cuggguucgc gcugcucggu ggccaccccu gcuuccugac gacccaggac auccaccucg 600
gagugaacga aucccucacc gauaccgccc ggguguuauc gagcauggca gaugccgugc 660
uggccagggu guacaaacag uccgaucugg acacucuggc caaggaggcg ucaauuccua 720
uuaucaacgg ccuuagugac cucuaccauc cgauucagau ccuggccgau uaccucaccc 780
ugcaagaaca cuacagcucc cugaagggguc ugacauuguc cuggaucggc gacggcaaca 840
acauucucca uuccaucaug auguccgccg caaaauucgg caugcaucuu caagccgcca 900
cgccgaaggg uuacgagccc gacgcuuccg ugacuaagcu cgccgagcag uacgcuaagg 960
agaacggaac caagcuucug cugacuaacg acccacuaga agcagcccac gggggcaacg 1020
ugcuuauuac ugacaccugg aucuccaugg gccaggaaga agagaaaaag aagcggcugc 1080
aggcguucca gggauaucag gucaccauga aaaccgccaa ggucgcugcc uccgacugga 1140
ccuuccugca cugccugccu cgcaagccug aagaagugga cgacgaggug uucuacucgc 1200
cacggagccu cguguucccc gaggccgaga auagaaagug gaccaucaug gccgugaugg 1260
ugucacugcu caccgacuac agcccgcagc uucagaagcc caaguucuag auaagugaau 1320
gcaaggcugg ccggaagccc uugccugaaa gcaagauuuc agccuggaag agggcaaagu 1380
ggacgggagu ggacaggagu ggaugcgaua agaugugguu ugaagcugau gggugccagc 1440
ccugcauugc ugagucaauc aauaaagagc uuucuuuuga cccauucuag aucuag 1496

<210> SEQ ID NO 62
<211> LENGTH: 1368
<212> TYPE: RNA
<213> ORGANISM: Artificial Sequence
<220> FEATURE:
<223> OTHER INFORMATION: Synthetic construct

<400> SEQUENCE: 62
aggaaacuua agauuauuac aucaaaacaa aaagccgcca augcuguuca accugcgcau 60
ccugcugaac aacgccgccu uccgcaacgg ccacaacuuc auggugcgca acuuccgcug 120
cggccagccc cugcagaaca aggugcagcu gaagggccgc gaccugcuga cccugaagaa 180
cuucaccggc gaggagauca aguacaugcu guggcugagc gccgaccuga aguuccgcau 240
caagcagaag ggcgaguacc ugccccugcu gcagggcaag agccugggca ugaucuucga 300
gaagcgcagc acccgcaccc gccugagcac cgagacaggc cuggcccugc ugggcggcca 360
ccccugcuuc cugaccaccc aggacaucca ccugggcgug aacgagagcc ugaccgacac 420
cgcccgcgug cugagcagca uggccgacgc cgugcuggcc cgcguguaca agcagagcga 480
ccuggacacc cuggccaagg aggccagcau ccccaucauc aacggccuga gcgaccugua 540
ccaccccauc cagauccugg ccgacuaccu gacccugcag gagcacuaca gcagccugaa 600
gggccugacc cugagcugga ucggcgacgg caacaacauc cugcacagca ucaugaugag 660
cgccgccaag uucggcaugc accugcaggc cgccaccccc aagggcuacg agcccgacgc 720
cagcgugacc aagcuggccg agcaguacgc caaggagaac ggcaccaagc ugcugcugac 780
caacgacccc cuggaggccg cccacggcgg caacgugcug aucaccgaca ccuggaucag 840
caugggccag gaggaggaga agaagaagcg ccugcaggcc uuccagggcu accaggugac 900
caugaagacc gccaaggugg ccgccagcga cuggaccuuc cugcacugcc ugccccgcaa 960
gcccgaggag guggacgacg agguguucua cagcccccgc agccuggugu uccccgaggc 1020
cgagaaccgc aaguggacca ucauggccgu gauggugagc cugcugaccg acuacagccc 1080

```
ccagcugcag aagcccaagu ucugaacgcc gaagccugca gccaugcgac cccacgccac   1140

cccgugccuc cugccuccgc gcagccugca gcgggagacc cuguccccgc cccagccguc   1200

cuccuggggu ggacccuagu uuaauaaaga uucaccaagu uucacgcaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaa                1368
```

<210> SEQ ID NO 63
<211> LENGTH: 1495
<212> TYPE: RNA
<213> ORGANISM: Artificial Sequence
<220> FEATURE:
<223> OTHER INFORMATION: Synthetic construct

<400> SEQUENCE: 63

```
cuuaaggggg cgcugccuac ggagguggca gccaucuccu ucucggcauc aagcuuacca     60

uggugcccca ggcccugcuc uugguccccgc ugcugguguu cccccucugc uucggcaagu   120

uccccaucua caccaucccc gacaagcugg ggccguggag ccccaucgac auccaccacc   180

uguccugccc caacaaccuc gugggucgagg acgagggcug caccaaccug agcggguucu   240

ccuacaugcu guucaaccug cgcauccugc ugaacaacgc cgccuuccgc aacggccaca   300

acuucauggu gcgcaacuuc cgcugcggcc agccccugca gaacaaggug cagcugaagg   360

gccgcgaccu gcugacccug aagaacuuca ccggcgagga gaucaaguac augcuguggc   420

ugagcgccga ccugaaguuc cgcaucaagc agaagggcga guaccugccc cugcugcagg   480

gcaagagccu gggcaugauc uucgagaagc gcagcacccg cacccgccug agcaccgaga   540

caggccuggc ccugcugggc ggccaccccu gcuuccugac cacccaggac auccaccugg   600

gcgugaacga gagccugacc gacaccgccc gcgugcugag cagcauggcc gacgccgugc   660

uggcccgcgu guacaagcag agcgaccugg acacccuggc caaggaggcc agcaucccca   720

ucaucaacgg ccugagcgac cuguaccacc ccauccagau ccuggccgac uaccugaccc   780

ugcaggagca cuacagcagc cugaagggcc ugacccugag cuggaucggc gacggcaaca   840

acauccugca cagcaucaug augagcgccg ccaaguucgg caugcaccug caggccgcca   900

cccccaaggg cuacgagccc gacgccagcg ugaccaagcu ggccgagcag uacgccaagg   960

agaacggcac caagcugcug cugaccaacg acccccugga ggccgcccac ggcggcaacg  1020

ugcugaucac cgacaccugg aucagcaugg gccaggagga ggagaagaag aagcgccugc  1080

aggccuucca gggcuaccag gugaccauga agaccgccaa gguggccgcc agcgacugga  1140

ccuuccugca cugccugccc cgcaagcccg aggaggugga cgacgaggug uucuacagcc  1200

cccgcagccu gguguucccc gaggccgaga accgcaagug gaccaucaug gccgugaugg  1260

ugagccugcu gaccgacuac agcccccagc ugcagaagcc caaguucuga auaagugaug  1320

caaggcuggc cggaagcccu ugccugaaag caagauuuca gccuggaaga gggcaaagug  1380

gacgggagug gacaggagug gaugcgauaa gauguggguuu gaagcugaug ggugccagcc  1440

cugcauugcu gagucaauca auaaagagcu uucuuuugac ccauucuaga ucuag        1495
```

<210> SEQ ID NO 64
<211> LENGTH: 1368
<212> TYPE: RNA
<213> ORGANISM: Artificial Sequence
<220> FEATURE:
<223> OTHER INFORMATION: Synthetic construct

<400> SEQUENCE: 64
aggaaacuua agauuauuac aucaaaacaa aaagccgcca augcuuuuca aucuccgcau 60
ccuccuuaac aacgccgcgu uuagaaacgg ccacaacuuc augguccgga acuucagaug 120
uggccagccg cuucaaaaca agguccagcu gaagggccgg gaucuucuga cccugaagaa 180
cuuuacuggc gaagagauca aguacaugcu cuggcucucc gcggacuuga aguuccgcau 240
uaagcagaag ggggaauacc uuccgcugcu ucaaggaaag agccucggca ugaucuuuga 300
gaagcgcuca accaggaccc gccuuucuac ugaaacuggg uucgcgcugc ucgguggcca 360
ccccugcuuc cugacgaccc aggacaucca ccucggagug aacgaauccc ucaccgauac 420
cgcccgggug uuaucgagca uggcagaugc cgugcuggcc aggguguaca aacaguccga 480
ucuggacacu cuggccaagg aggcgucaau uccuauuauc aacggccuua gugaccucua 540
ccauccgauu cagauccugg ccgauuaccu cacccugcaa gaacacuaca gcucccugaa 600
gggucugaca uuguccugga ucggcgacgg caacaacauu cuccauucca ucaugauguc 660
cgccgcaaaa uucggcaugc aucuucaagc cgccacgccg aaggguuacg agcccgacgc 720
uuccgugacu aagcucgccg agcaguacgc uaaggagaac ggaaccaagc uucugcugac 780
uaacgaccca cuagaagcag cccacggggg caacgugcuu auuacugaca ccuggaucuc 840
caugggccag gaagaagaga aaaagaagcg gcugcaggcg uuccagggau aucaggucac 900
caugaaaacc gccaaggucg cugccuccga cuggaccuuc cugcacugcc ugccucgcaa 960
gccugaagaa guggacgacg agguguucua cucgccacgg agccucgugu uccccgaggc 1020
cgagaauaga aaguggacca ucauggccgu gaugguguca cugcucaccg acuacagccc 1080
gcagcuucag aagcccaagu ucuagacgcc gaagccugca gccaugcgac cccacgccac 1140
cccgugccuc cugccuccgc gcagccugca gcgggagacc cuguccccgc cccagccguc 1200
cuccuggggu ggacccuagu uuaauaaaga uucaccaagu uucacgcaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaaaaaaa aaaaaaaaaa aaaaaaaaaa aaaaaaaa 1368

<210> SEQ ID NO 65
<211> LENGTH: 1495
<212> TYPE: RNA
<213> ORGANISM: Artificial Sequence
<220> FEATURE:
<223> OTHER INFORMATION: Synthetic construct

<400> SEQUENCE: 65
cuuaaggggg cgcugccuac ggagguggca gccaucuccu ucucggcauc aagcuuacca 60
uggugcccca ggcccugcuc uugguccgc ugcugguguu cccccucugc uucggcaagu 120
uccccaucua caccaucccc gacaagcugg ggccguggag ccccaucgac auccaccacc 180
uguccugccc caacaaccuc guggucgagg acgagggcug caccaaccug agcggguucu 240
ccuacaugcu uuucaaccug agaauccucu ugaacaaugc ugcuuuucgg aauggccaca 300
acuuuauggu ucggaacuuc cguugcggcc agccuuuaca aaacaagguc cagcugaagg 360
gccgggauuu gcucacacua aagaacuuua cuggagaaga gaucaaguac augcuauggc 420
ugucggccga ccugaaguuc cguaucaagc agaagggaga auaccuuccg cugcuucaag 480
gaaagagccu cggcaugauc uuugagaagc gcucaaccag gacccgccuu ucuacugaaa 540
cuggguucgc gcugcucggu ggccaccccu gcuuccugac gacccaggac auccaccucg 600
gagugaacga aucccucacc gauaccgccc ggguguuauc gagcauggca gaugccgugc 660
uggccagggu guacaaacag uccgaucucg auaccuuggc aaaggaggcu uccauuccca 720
ucaucaacgg ccugagcgac cuguaccacc caauccaaau ccuggcugac uaccugaccc 780
ugcaagagca cuacagcagc cugaagggu c ugacccuguc auggauuggc gauggaaaca 840
auauucugca cuccaucaug auguccgccg cgaaguucgg aaugcaucug caagccgcca 900
cuccaaaagg auacgaaccg gaugcauccg ugaccaaguu ggcggaacag uacgcgaagg 960
agaacggaac caagcuccug cugacuaacg acccgcucga ggcugcgcau gggggauaacg 1020 ugcugauuac ggacaccugg aucuccaugg ggcaggagga agagaagaag aagagacugc 1080
aggcauucca gggguaccag gucaccauga aaaccgcaaa aguggcagcu ucggacugga 1140
cuuuccugca uugccugccg aggaagccgg aggaagucga cgacgaagug uucuacucgc 1200 cucgguccu ggguguucccc gaggccgaaa accggaagug gaccaucaug gccgugaugg 1260
uguccuugcu gacugacuau agcccgcagc ugcagaagcc uaaguucuag auaagugaug 1320
caaggcuggc cggaagcccu ugccugaaag caagauuuca gccuggaaga gggcaaagug 1380
gacgggagug gacaggagug gaugcgauaa gauguggguuu gaagcugaug ggugccagcc 1440
cugcauugcu gagucaauca auaaagagcu uucuuuugac ccauucuaga ucuag 1495

<210> SEQ ID NO 66
<211> LENGTH: 1475
<212> TYPE: RNA
<213> ORGANISM: Artificial Sequence
<220> FEATURE:
<223> OTHER INFORMATION: Synthetic construct

<400> SEQUENCE: 66
ugagugucgu acagccucca ggcccccccc ucccgggaga gccauagugg ucugcggaac 60
cggugaguac accggaauug ccgggaagac ugggguccuuu cuuggauaaa cccacucuau 120
gcccggccau uugggcgugc ccccgcaaga cugcuagccg aguaguguug gguugcgaug 180
cuguucaacc ugcgcauccu gcugaacaac gccgccuucc gcaacggcca caacuucaug 240
gugcgcaacu uccgcugcgg ccagccccug cagaacaagg ugcagcugaa gggccgcgac 300
cugcugaccc ugaagaacuu caccggcgag gagaucaagu acaugcugug gcugagcgcc 360
gaccugaagu uccgcaucaa gcagaagggc gaguaccugc cccugcugca gggcaagagc 420
cugggcauga ucuucgagaa gcgcagcacc cgcacccgcc ugagcaccga gacaggccug 480
gcccugcugg gcggccaccc cugcuuccug accacccagg acauccaccu gggcgugaac 540
gagagccuga ccgacaccgc ccgcgugcug agcagcaugg ccgacgccgu gcuggcccgc 600
guguacaagc agagcgaccu ggacacccug gccaaggagg ccagcauccc caucaucaac 660
ggccugagcg accuguacca ccccauccag auccuggccg acuaccugac ccugcaggag 720
cacuacagca gccugaaggg ccugacccug agcuggaucg gcgacggcaa caacauccug 780
cacagcauca ugaugagcgc cgccaaguuc ggcaugcacc ugcaggccgc cacccccaag 840
ggcuacgagc ccgacgccag cgugaccaag cuggccgagc aguacgccaa ggagaacggc 900
accaagcugc ugcugaccaa cgacccccug gaggccgccc acggcggcaa cgugcugauc 960
accgacaccu ggaucagcau gggccaggag gaggagaaga agaagcgccu gcaggccuuc 1020
cagggcuacc aggugaccau gaagaccgcc aagguggccg ccagcgacug gaccuuccug 1080
cacugccugc cccgcaagcc cgaggaggug gacgacgagg uguucuacag cccccgcagc 1140
cugguguucc ccgaggccga gaaccgcaag uggaccauca uggccgugau ggugagccug 1200
cugaccgacu acagccccca gcugcagaag cccaaguucu gaauaaguga uagagcggca 1260
aacccuagcu acacuccaua gcuaguuucu uuuuuuuuug uuuuuuuuuu uuuuuuuuuu 1320
uuuuuuuuuu uuuuuuuuuc cuuucuuuuc cuucuuuuuu uccucuuuuc uugguggcuc 1380
caucuuagcc cuagucacgg cuagcuguga aagguccgug agccgcauga cugcagagag 1440
ugccguaacu ggccucucug cagaucaugu ucuag 1475

<210> SEQ ID NO 67
<211> LENGTH: 1335
<212> TYPE: RNA
<213> ORGANISM: Artificial Sequence
<220> FEATURE:
<223> OTHER INFORMATION: Synthetic construct

<400> SEQUENCE: 67
aggaaacuua agauuauuac aucaaaacaa aaagccgcca augcuuuuca aucuccgcau 60
ccuccuuaac aacgccgcgu uuagaaacgg ccacaacuuc augguccgga acuucagaug 120
uggccagccg cuucaaaaca agguccagcu gaagggccgg gaucuucuga cccugaagaa 180
cuuuacuggc gaagagauca aguacaugcu cuggcucucc gcggacuuga aguuccgcau 240
uaagcagaag gggggaauacc uuccgcugcu ucaaggaaag agccucggca ugaucuuuga 300
gaagcgcuca accaggaccc gccuuucuac ugaaacuggg uucgcgcugc ucgguggcca 360
ccccugcuuc cugacgaccc aggacaucca ccucggagug aacgaauccc ucaccgauac 420
cgcccgggug uuaucgagca uggcagaugc cgugcuggcc aggguguaca aacaguccga 480
ucuggacacu cuggccaagg aggcgucaau uccuauuauc aacggccuua gugaccucua 540
ccauccgauu cagauccugg ccgauuaccu cacccugcaa gaacacuaca gcucccugaa 600
gggucugaca uuguccugga ucggcgacgg caacaacauu cuccauucca ucaugauguc 660
cgccgcaaaa uucggcaugc aucuucaagc cgccacgccg aaggguuacg agcccgacgc 720
uuccgugacu aagcucgccg agcaguacgc uaaggagaac ggaaccaagc uucugcugac 780
uaacgaccca cuagaagcag cccacggggg caacgugcuu auuacugaca ccuggaucuc 840
caugggccag gaagaagaga aaaagaagcg gcugcaggcg uuccagggau aucaggucac 900
caugaaaacc gccaaggucg cugccuccga cuggaccuuc cugcacugcc ugccucgcaa 960
gccugaagaa guggacgacg agguguucua cucgccacgg agccucgugu uccccgaggc 1020
cgagaauaga aaguggacca ucauggccgu gaugguguca cugcucaccg acuacagccc 1080
gcagcuucag aagcccaagu ucuaggcugg agccucggua gccguuccuc cugcccgcug 1140
ggccucccaa cgggcccucc ucccucccuu gcaccggccc uuccuggucu uugaauaaag 1200
ucugaguggg cagcaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaa 1335

<210> SEQ ID NO 68
<211> LENGTH: 1335
<212> TYPE: RNA
<213> ORGANISM: Artificial Sequence
<220> FEATURE:
<223> OTHER INFORMATION: Synthetic construct

<400> SEQUENCE: 68
aggaaacuua agauuauuac aucaaaacaa aaagccgcca augcuguuca accugcgcau 60
ccugcugaac aacgccgccu uccgcaacgg ccacaacuuc auggugcgca acuuccgcug 120
cggccagccc cugcagaaca aggugcagcu gaagggccgc gaccugcuga cccugaagaa 180
cuucaccggc gaggagauca aguacaugcu guggcugagc gccgaccuga aguuccgcau 240
caagcagaag ggcgaguacc ugccccugcu gcagggcaag agccugggca ugaucuucga 300
gaagcgcagc acccgcaccc gccugagcac cgagacaggc cuggcccugc ugggcggcca 360
ccccugcuuc cugaccaccc aggacaucca ccugggcgug aacgagagcc ugaccgacac 420
cgcccgcgug cugagcagca uggccgacgc cgugcuggcc cgcguguaca agcagagcga 480
ccuggacacc cuggccaagg aggccagcau ccccaucauc aacggccuga gcgaccugua 540
ccaccccauc cagauccugg ccgacuaccu gacccugcag gagcacuaca gcagccugaa 600
gggccugacc cugagcugga ucggcgacgg caacaacauc cugcacagca ucaugaugag 660
cgccgccaag uucggcaugc accugcaggc cgccaccccc aagggcuacg agcccgacgc 720
cagcgugacc aagcuggccg agcaguacgc caaggagaac ggcaccaagc ugcugcugac 780
caacgacccc cuggaggccg cccacggcgg caacgugcug aucaccgaca ccuggaucag 840
caugggccag gaggaggaga agaagaagcg ccugcaggcc uuccagggcu accaggugac 900
caugaagacc gccaaggugg ccgccagcga cuggaccuuc cugcacugcc ugccccgcaa 960
gcccgaggag guggacgacg agguguucua cagcccccgc agccuggugu uccccgaggc 1020
cgagaaccgc aaguggacca ucauggccgu gauggugagc cugcugaccg acuacagccc 1080
ccagcugcag aagcccaagu ucugagcugg agccucggua gccguuccuc cugcccgcug 1140
ggccucccaa cgggcccucc uccccuccuu gcaccggccc uuccuggucu uugaauaaag 1200
ucugaguggg cagcaaaaaa aaaaaaaaaa aaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa aaaaa 1335

<210> SEQ ID NO 69
<211> LENGTH: 1335
<212> TYPE: RNA
<213> ORGANISM: Artificial Sequence
<220> FEATURE:
<223> OTHER INFORMATION: Synthetic construct

<400> SEQUENCE: 69
aggaaacuua agauuauuac aucaaaacaa aaagccgcca augcuuuuca accugagaau 60
ccucuugaac aaugcugcuu uucggaaugg ccacaacuuu augguucgga acuuccguug 120
cggccagccu uuacaaaaca agguccagcu gaagggccgg gauuugcuca cacuaaagaa 180
cuuuacugga gaagagauca aguacaugcu auggcugucg gccgaccuga aguuccguau 240
caagcagaag ggagaauacc uuccgcugcu ucaaggaaag agccucggca ugaucuuuga 300
gaagcgcuca accaggaccc gccuuucuac ugaaacuggg uucgcgcugc ucgguggcca 360
ccccugcuuc cugacgaccc aggacaucca ccucggagug aacgaauccc ucaccgauac 420
cgcccgggug uuaucgagca uggcagaugc cgugcuggcc aggguguaca aacaguccga 480
ucucgauacc uuggcaaagg aggcuuccau ucccaucauc aacggccuga gcgaccugua 540
ccacccaauc caaauccugg cugacuaccu gacccugcaa gagcacuaca gcagccugaa 600
gggucugacc cugucaugga uuggcgaugg aaacaauauu cugcacucca ucaugauguc 660
cgccgcgaag uucggaaugc aucugcaagc cgccacucca aaaggauacg aaccggaugc 720
auccgugacc aaguuggcgg aacaguacgc gaaggagaac ggaaccaagc uccugcugac 780
uaacgacccg cucgaggcug cgcauggggg uaacgugcug auuacggaca ccuggaucuc 840

```
caugggggcag gaggaagaga agaagaagag acugcaggca uuccaggggu accaggucac    900

caugaaaacc gcaaaagugg cagcuucgga cuggacuuuc cugcauugcc ugccgaggaa    960

gccggaggaa gucgacgacg aaguguucua cucgccucgg ucccuggugu uccccgaggc   1020

cgaaaaccgg aaguggacca ucauggccgu gauggugucc uugcugacug acuauagccc   1080

gcagcugcag aagccuaagu ucuaggcugg agccucggua gccguuccuc cugcccgcug   1140

ggccucccaa cgggcccucc uccccuccuu gcaccggccc uuccuggucu uugaauaaag   1200

ucugaguggg cagcaaaaaa aaaaaaaaaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaa                                                    1335
```

<210> SEQ ID NO 70
<211> LENGTH: 1346
<212> TYPE: RNA
<213> ORGANISM: Artificial Sequence
<220> FEATURE:
<223> OTHER INFORMATION: Synthetic construct

<400> SEQUENCE: 70

```
aggaaacuua agaauuauug guuaaagaag uauauuagug cuaauuuccc uccguuuguc     60

cuagcuuuuc ucuucuguca accccacacg ccuuuggcac aaugcuuuuc aaucuccgca    120

uccuccuuaa caacgccgcg uuuagaaacg gccacaacuu caugguccgg aacuucagau    180

guggccagcc gcuucaaaac aagguccagc ugaagggccg ggaucuucug acccugaaga    240

acuuuacugg cgaagagauc aaguacaugc ucuggcucuc cgcggacuug aaguuccgca    300

uuaagcagaa gggggaauac cuuccgcugc uucaaggaaa gagccucggc augaucuuug    360

agaagcgcuc aaccaggacc cgccuuucua cugaaacugg guucgcgcug cucgguggcc    420

accccugcuu ccugacgacc caggacaucc accucggagu gaacgaaucc cucaccgaua    480

ccgcccgggu guuaucgagc auggcagaug ccgugcuggc cagggguguac aaacaguccg    540

aucuggacac ucuggccaag gaggcgucaa uuccuauuau caacggccuu agugaccucu    600

accauccgau ucagauccug gccgauuacc ucacccugca agaacacuac agcucccuga    660

agggucugac auuguccugg aucggcgacg gcaacaacau ucuccauucc aucaugaugu    720

ccgccgcaaa auucggcaug caucuucaag ccgccacgcc gaaggguuac gagcccgacg    780

cuuccgugac uaagcucgcc gagcaguacg cuaaggagaa cggaaccaag cuucugcuga    840

cuaacgaccc acuagaagca gcccacgggg gcaacgugcu uauuacugac accuggaucu    900

ccaugggcca ggaagaagag aaaaagaagc ggcugcaggc guuccaggga uaucagguca    960

ccaugaaaac cgccaagguc gcugccuccg acuggaccuu ccugcacugc cugccucgca   1020

agccugaaga aguggacgac gagguguucu acucgccacg gagccucgug uuccccgagg   1080

ccgagaauag aaaguggacc aucauggccg ugauggugc acugcucacc gacuacagcc   1140

cgcagcuuca gaagcccaag uucuagcucg agacacauca caaccacaac cuucucaggc   1200

uacccugaga aaaaaagaca ugaagacuca ggacucaucu uuucuguugg uguaaaauca   1260

acacccuaag gaacacaaau uucuuuaaac auuugacuuc uugucucugu gcugcaauua   1320

auaaaaaaug gaaagaaucu aucuag                                        1346
```

<210> SEQ ID NO 71
<211> LENGTH: 1346
<212> TYPE: RNA

<213> ORGANISM: Artificial Sequence
<220> FEATURE:
<223> OTHER INFORMATION: Synthetic construct

<400> SEQUENCE: 71
aggaaacuua agaauuauug guuaaagaag uauauuagug cuaauuuccc uccguuuguc 60
cuagcuuuuc ucuucuguca accccacacg ccuuuggcac aaugcuguuc aaccugcgca 120
uccugcugaa caacgccgcc uuccgcaacg gccacaacuu cauggugcgc aacuuccgcu 180
gcggccagcc ccugcagaac aaggugcagc ugaagggccg cgaccugcug acccugaaga 240
acuucaccgg cgaggagauc aaguacaugc uguggcugag cgccgaccug aaguuccgca 300
ucaagcagaa gggcgaguac cugccccugc ugcagggcaa gagccugggc augaucuucg 360
agaagcgcag cacccgcacc cgccugagca ccgagacagg ccuggcccug cugggcggcc 420
accccugcuu ccugaccacc caggacaucc accugggcgu gaacgagagc cugaccgaca 480
ccgcccgcgu gcugagcagc auggccgacg ccgugcuggc ccgcguguac aagcagagcg 540
accuggacac ccuggccaag gaggccagca uccccaucau caacggccug agcgaccugu 600
accaccccau ccagauccug gccgacuacc ugacccugca ggagcacuac agcagccuga 660
agggccugac ccugagcugg aucggcgacg gcaacaacau ccugcacagc aucaugauga 720
gcgccgccaa guucggcaug caccugcagg ccgccacccc caagggcuac gagcccgacg 780
ccagcgugac caagcuggcc gagcaguacg ccaaggagaa cggcaccaag cugcugcuga 840
ccaacgaccc ccuggaggcc gcccacggcg gcaacgugcu gaucaccgac accuggauca 900
gcaugggcca ggaggaggag aagaagaagc gccugcaggc cuuccagggc uaccagguga 960
ccaugaagac cgccaaggug gccgccagcg acuggaccuu ccugcacugc cugccccgca 1020
agcccgagga gguggacgac gagguguucu acagcccccg cagccuggug uuccccgagg 1080
ccgagaaccg caaguggacc aucauggccg ugauggugag ccugcugacc gacuacagcc 1140
cccagcugca gaagcccaag uucugacucg agacacauca caaccacaac cuucucaggc 1200
uacccugaga aaaaaagaca ugaagacuca ggacucaucu uuucuguugg uguaaaauca 1260
acacccuaag gaacacaaau uucuuuaaac auuugacuuc uugucucugu gcugcaauua 1320
auaaaaaaug gaaagaaucu aucuag 1346

<210> SEQ ID NO 72
<211> LENGTH: 1346
<212> TYPE: RNA
<213> ORGANISM: Artificial Sequence
<220> FEATURE:
<223> OTHER INFORMATION: Synthetic construct

<400> SEQUENCE: 72
aggaaacuua agaauuauug guuaaagaag uauauuagug cuaauuuccc uccguuuguc 60
cuagcuuuuc ucuucuguca accccacacg ccuuuggcac aaugcuuuuc aaccugagaa 120
uccucuugaa caaugcugcu uuucggaaug gccacaacuu uaugguucgg aacuuccguu 180
gcggccagcc uuuacaaaac aagguccagc ugaagggccg ggauuugcuc acacuaaaga 240
acuuuacugg agaagagauc aaguacaugc uauggcuguc ggccgaccug aaguuccgua 300
ucaagcagaa gggagaauac cuuccgcugc uucaaggaaa gagccucggc augaucuuug 360
agaagcgcuc aaccaggacc cgccuuucua cugaaacugg guucgcgcug cucgguggcc 420
accccugcuu ccugacgacc caggacaucc accucggagu gaacgaaucc cucaccgaua 480
ccgcccgggu guuaucgagc auggcagaug ccgugcuggc cagggugua c aaacaguccg 540 aucucgauac cuuggcaaag gaggcuucca uucccaucau caacggccug agcgaccugu 600
accacccaau ccaaauccug gcugacuacc ugacccugca agagcacuac agcagccuga 660
agggucugac ccugucaugg auuggcgaug gaaacaauau ucugcacucc aucaugaugu 720
ccgccgcgaa guucggaaug caucugcaag ccgccacucc aaaaggauac gaaccggaug 780
cauccgugac caaguuggcg gaacaguacg cgaaggagaa cggaaccaag cuccugcuga 840
cuaacgaccc gcucgaggcu gcgcaugggg guaacgugcu gauuacggac accuggaucu 900
ccauggggca ggaggaagag aagaagaaga gacugcaggc auuccagggg uaccagguca 960
ccaugaaaac cgcaaaagug gcagcuucgg acuggacuuu ccugcauugc cugccgagga 1020
agccggagga agucgacgac gaaguguucu acucgccucg gucccuggug uuccccgagg 1080
ccgaaaaccg gaaguggacc aucauggccg ugaugguguc cuugcugacu gacuauagcc 1140
cgcagcugca gaagccuaag uucuagcucg agacacauca caaccacaac cuucucaggc 1200
uacccugaga aaaaaagaca ugaagacuca ggacucaucu uuucuguugg uguaaaauca 1260
acacccuaag gaacacaaau uucuuuaaac auuugacuuc uugucucugu gcugcaauua 1320
auaaaaaaug gaaagaaucu aucuag 1346

<210> SEQ ID NO 73
<211> LENGTH: 1222
<212> TYPE: RNA
<213> ORGANISM: Artificial Sequence
<220> FEATURE:
<223> OTHER INFORMATION: Synthetic construct

<400> SEQUENCE: 73
auuauuacau caaaacaaaa agccgccacc augcuguuca accugcgcau ccugcugaac 60
aacgccgccu uccgcaacgg ccacaacuuc auggugcgca acuuccgcug cggccagccc 120
cugcagaaca aggugcagcu gaagggccgc gaccugcuga cccugaagaa cuucaccggc 180
gaggagauca aguacaugcu guggcugagc gccgaccuga aguuccgcau caagcagaag 240
ggcgaguacc ugccccugcu gcagggcaag agccugggca ugaucuucga gaagcgcagc 300
acccgcaccc gccugagcac cgagacaggc uucgcccugc ugggcggcca ccccugcuuc 360
cugaccaccc aggacaucca ccugggcgug aacgagagcc ugaccgacac cgcccgcgug 420
cugagcagca uggccgacgc cgugcuggcc cgcguguaca agcagagcga ccuggacacc 480
cuggccaagg aggccagcau ccccaucauc aacggccuga gcgaccugua ccaccccauc 540
cagauccugg ccgacuaccu gacccugcag gagcacuaca gcagccugaa gggccugacc 600
cugagcugga ucggcgacgg caacaacauc cugcacagca ucaugaugag cgccgccaag 660
uucggcaugc accugcaggc cgccaccccc aagggcuacg agcccgacgc cagcgugacc 720
aagcuggccg agcaguacgc caaggagaac ggcaccaagc ugcugcugac caacgacccc 780
cuggaggccg cccacggcgg caacgugcug aucaccgaca ccuggaucag caugggccag 840
gaggaggaga agaagaagcg ccugcaggcc uuccagggcu accaggugac caugaagacc 900
gccaaggugg ccgccagcga cuggaccuuc cugcacugcc ugccccgcaa gcccgaggag 960
guggacgacg agguguucua cagcccccgc agccuggugu uccccgaggc cgagaaccgc 1020
aaguggacca ucauggccgu gauggugagc cugcugaccg acuacagccc ccagcugcag 1080
aagcccaagu ucugaggucu cuaguaauga gcuggagccu cgguagccgu uccuccugcc 1140
cgcugggccu cccaacgggc ccuccucccc uccuugcacc ggcccuuccu ggucuuugaa 1200
uaaagucuga gugggcaucu ag 1222

<210> SEQ ID NO 74
<211> LENGTH: 1346
<212> TYPE: RNA
<213> ORGANISM: Artificial Sequence
<220> FEATURE:
<223> OTHER INFORMATION: Synthetic construct

<400> SEQUENCE: 74
aggaaacuua agaauuauug guuaaagaag uauauuagug cuaauuuccc uccguuuguc 60
cuagcuuuuc ucuucuguca accccacacg ccuuuggcac aaugcuguuc aaccugcgca 120
uccugcugaa caacgccgcc uuccgcaacg gccacaacuu cauggugcgc aacuuccgcu 180
gcggccagcc ccugcagaac aaggugcagc ugaagggccg cgaccugcug acccugaaga 240
acuucaccgg cgaggagauc aaguacaugc uguggcugag cgccgaccug aaguuccgca 300
ucaagcagaa gggcgaguac cugccccugc ugcagggcaa gagccugggc augaucuucg 360
agaagcgcag cacccgcacc cgccugagca ccgagacagg cuucgcccug cugggcggcc 420
accccugcuu ccugaccacc caggacaucc accugggcgu gaacgagagc cugaccgaca 480
ccgcccgcgu gcugagcagc auggccgacg ccgugcuggc ccgcguguac aagcagagcg 540
accuggacac ccuggccaag gaggccagca uccccaucau caacggccug agcgaccugu 600
accaccccau ccagauccug gccgacuacc ugacccugca ggagcacuac agcagccuga 660
agggccugac ccugagcugg aucggcgacg gcaacaacau ccugcacagc aucaugauga 720
gcgccgccaa guucggcaug caccugcagg ccgccacccc caagggcuac gagcccgacg 780
ccagcgugac caagcuggcc gagcaguacg ccaaggagaa cggcaccaag cugcugcuga 840
ccaacgaccc ccuggaggcc gcccacggcg gcaacgugcu gaucaccgac accuggauca 900
gcaugggcca ggaggaggag aagaagaagc gccugcaggc cuuccagggc uaccagguga 960
ccaugaagac cgccaaggug gccgccagcg acuggaccuu ccugcacugc cugccccgca 1020
agcccgagga gguggacgac gagguguucu acagccccg cagccuggug uuccccgagg 1080
ccgagaaccg caaguggacc aucauggccg ugauggugag ccugcugacc gacuacagcc 1140
cccagcugca gaagcccaag uucugacucg agacacauca caaccacaac cuucucaggc 1200
uacccugaga aaaaaagaca ugaagacuca ggacucaucu uuucuguugg uguaaaauca 1260
acacccuaag gaacacaaau uucuuuaaac auuugacuuc uugucucugu gcugcaauua 1320
auaaaaaaug gaaagaaucu aucuag 1346

<210> SEQ ID NO 75
<211> LENGTH: 1368
<212> TYPE: RNA
<213> ORGANISM: Artificial Sequence
<220> FEATURE:
<223> OTHER INFORMATION: Synthetic construct

<400> SEQUENCE: 75
aggaaacuua agauuauuac aucaaaacaa aaagccgcca augcuguuca accugcgcau 60
ccugcugaac aacgccgccu uccgcaacgg ccacaacuuc auggugcgca acuuccgcug 120
cggccagccc cugcagaaca aggugcagcu gaagggccgc gaccugcuga cccugaagaa 180
cuucaccggc gaggagauca aguacaugcu guggcugagc gccgaccuga aguuccgcau 240
caagcagaag ggcgaguacc ugccccugcu gcagggcaag agccugggca ugaucuucga 300
gaagcgcagc acccgcaccc gccugagcac cgagacaggc uucgcccugc ugggcggcca 360

```
ccccugcuuc cugaccaccc aggacaucca ccugggcgug aacgagagcc ugaccgacac    420

cgcccgcgug cugagcagca uggccgacgc cgugcuggcc cgcguguaca agcagagcga    480

ccuggacacc cuggccaagg aggccagcau ccccaucauc aacggccuga gcgaccugua    540

ccaccccauc cagauccugg ccgacuaccu gacccugcag gagcacuaca gcagccugaa    600

gggccugacc cugagcugga ucggcgacgg caacaacauc cugcacagca ucaugaugag    660

cgccgccaag uucggcaugc accugcaggc cgccaccccc aagggcuacg agcccgacgc    720

cagcgugacc aagcuggccg agcaguacgc caaggagaac ggcaccaagc ugcugcugac    780

caacgacccc cuggaggccg cccacggcgg caacgugcug aucaccgaca ccuggaucag    840

caugggccag gaggaggaga agaagaagcg ccugcaggcc uuccagggcu accaggugac    900

caugaagacc gccaaggugg ccgccagcga cuggaccuuc cugcacugcc ugccccgcaa    960

gcccgaggag guggacgacg agguguucua cagcccccgc agccuggugu uccccgaggc   1020

cgagaaccgc aaguggacca ucauggccgu gauggugagc cugcugaccg acuacagccc   1080

ccagcugcag aagcccaagu ucugaacgcc gaagccugca gccaugcgac cccacgccac   1140

cccgugccuc cugccuccgc gcagccugca gcgggagacc cuguccccgc cccagccguc   1200

cuccuggggu ggacccuagu uuaauaaaga uucaccaagu uucacgcaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa aaaaaaaaaa aaaaaaaaaa aaaaaaaaaa aaaaaaaa                1368
```

<210> SEQ ID NO 76
<211> LENGTH: 1496
<212> TYPE: RNA
<213> ORGANISM: Artificial Sequence
<220> FEATURE:
<223> OTHER INFORMATION: Synthetic construct

<400> SEQUENCE: 76

```
cuuaaggggg cgcugccuac ggagguggca gccaucuccu ucucggcauc aagcuuacca     60

uggugcccca ggcccugcuc uugguccegc ugcugguguu cccccucugc uucggcaagu    120

uccccaucua caccaucccc gacaagcugg ggccguggag ccccaucgac auccaccacc    180

uguccugccc caacaaccuc gugguucgagg acgagggcug caccaaccug agcggguucu    240

ccuacaugcu guucaaccug cgcauccugc ugaacaacgc cgccuuccgc aacggccaca    300

acuucauggu gcgcaacuuc cgcugcggcc agccccugca gaacaaggug cagcugaagg    360

gccgcgaccu gcugacccug aagaacuuca ccggcgagga gaucaaguac augcuguggc    420

ugagcgccga ccugaaguuc cgcaucaagc agaagggcga guaccugccc cugcugcagg    480

gcaagagccu gggcaugauc uucgagaagc gcagcacccg cacccgccug agcaccgaga    540

caggcuucgc ccugcugggc ggccaccccu gcuuccugac cacccaggac auccaccugg    600

gcgugaacga gagccugacc gacaccgccc gcgugcugag cagcauggcc gacgccgugc    660

uggcccgcgu guacaagcag agcgaccugg acacccuggc caaggaggcc agcaucccca    720

ucaucaacgg ccugagcgac cuguaccacc ccauccagau ccuggccgac uaccugaccc    780

ugcaggagca cuacagcagc cugaagggcc ugacccugag cuggaucggc gacggcaaca    840

acauccugca cagcaucaug augagcgccg ccaaguucgg caugcaccug caggccgcca    900

cccccaaggg cuacgagccc gacgccagcg ugaccaagcu ggccgagcag uacgccaagg    960

agaacggcac caagcugcug cugaccaacg acccccugga ggccgcccac ggcggcaacg   1020
```

ugcugaucac cgacaccugg aucagcaugg gccaggagga ggagaagaag aagcgccugc 1080
aggccuucca gggcuaccag gugaccauga agaccgccaa gguggccgcc agcgacugga 1140
ccuuccugca cugccugccc cgcaagcccg aggaggugga cgacgaggug uucuacagcc 1200
cccgcagccu gguguucccc gaggccgaga accgcaagug gaccaucaug gccgugaugg 1260
ugagccugcu gaccgacuac agcccccagc ugcagaagcc caaguucuga auaagugaau 1320
gcaaggcugg ccggaagccc uugccugaaa gcaagauuuc agccuggaag agggcaaagu 1380
ggacgggagu ggacaggagu ggaugcgaua agaugugguu ugaagcugau gggugccagc 1440
ccugcauugc ugagucaauc aauaaaagagc uuucuuuuga cccauucuag aucuag 1496

<210> SEQ ID NO 77
<211> LENGTH: 1380
<212> TYPE: RNA
<213> ORGANISM: Artificial Sequence
<220> FEATURE:
<223> OTHER INFORMATION: Synthetic construct

<400> SEQUENCE: 77
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugggc gucuucaacc ugcggauccu gcugaacaac gccgccuucc 180
ggaacggcca caacuucaug guccgcaacu ucagaugcgg ccagccccug cagaacaagg 240
ugcagcugaa gggccgggac cugcugaccc ugaagaacuu caccggcgaa gagaucaagu 300
acaugcugug gcugagcgcc gaccugaagu uccggaucaa gcagaagggc gaguaccugc 360
cccugcugca aggcaagagc cugggcauga ucuucgagaa gcggagcacc cggacccggc 420
ugagcaccga gacaggcuuu gcccugcugg gaggccaccc cugcuuucug accacccagg 480
acauccaccu gggcgugaac gagagccuga ccgacaccgc cagagugcug agcagcaugg 540
ccgacgccgu gcuggcccgg guguacaagc agagcgaccu ggacacccug gccaaagagg 600
ccagcauccc caucaucaac ggccugagcg accuguacca ccccauccag auccuggccg 660
acuaccugac ccugcaggaa cacuacagcu cccugaaggg ccugacccug agcuggaucg 720
gcgacggcaa caacauccug cacagcauca ugaugagcgc cgccaaguuc ggcaugcauc 780
ugcaggccgc cacccccaag ggcuacgagc cugaugccag cgugaccaag cuggccgagc 840
aguacgccaa agagaacggc accaagcugc ugcugaccaa cgacccccug gaagccgccc 900
acggcggcaa cgugcugauc accgacaccu ggaucagcau gggccaggaa gaggaaaaga 960
agaagcggcu gcaggccuuc cagggcuacc aggucacaau gaagaccgcc aagguggccg 1020
ccagcgacug gaccuuccug cacugccugc cccggaagcc cgaagaggug gacgacgagg 1080
uguucuacag cccccggucc cuggguuucc ccgaggccga gaaccggaag uggaccauua 1140
uggccgugau gguguccug cugaccgacu acucccccca gcugcagaag cccaaguucu 1200
agauaaguga acucgagcua gugacugacu aggaucuggu uaccacuaaa ccagccucaa 1260
gaacacccga auggagucuc uaagcuacau aauaccaacu uacacuuaca aaauguuguc 1320
ccccaaaaug uagccauucg uaucugcucc uaauaaaaag aaaguuucuu cacauucuag 1380

<210> SEQ ID NO 78
<211> LENGTH: 1380
<212> TYPE: RNA
<213> ORGANISM: Artificial Sequence
<220> FEATURE:
<223> OTHER INFORMATION: Synthetic construct

<400> SEQUENCE: 78
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugggc gucuucaacc ugcggauccu gcugaacaac gccgccuucc 180
ggaacggcca caacuucaug guccgcaacu ucagaugcgg ccagccccug cagaacaggg 240
ugcagcugaa gggccgggac cugcugaccc ugaagaacuu caccggcgaa gagaucaggu 300
acaugcugug gcugagcgcc gaccugaagu uccggaucaa gcagaagggc gaguaccugc 360
cccugcugca aggcaagagc cugggcauga ucuucgagaa gcggagcacc cggacccggc 420
ugagcaccga gacaggcuuu gcccugcugg gaggccaccc cugcuuucug accacccagg 480
acauccaccu gggcgugaac gagagccuga ccgacaccgc cagagugcug agcagcaugg 540
ccgacgccgu gcuggcccgg guguacaagc agagcgaccu ggacacccug gccaaagagg 600
ccagcauccc caucaucaac ggccugagcg accuguacca ccccauccag auccuggccg 660
acuaccugac ccugcaggaa cacuacagcu cccugaaggg ccugacccug agcuggaucg 720
gcgacggcaa caacauccug cacagcauca ugaugagcgc cgccaaguuc ggcaugcauc 780
ugcaggccgc cacccccaag ggcuacgagc cugaugccag cgugaccaag cuggccgagc 840
aguacgccaa agagaacggc accaagcugc ugcugaccaa cgacccccug gaagccgccc 900
acggcggcaa cgugcugauc accgacaccu ggaucagcau gggccaggaa gaggaaaaga 960
agaagcggcu gcaggccuuc cagggcuacc aggucacaau gaagaccgcc aagguggccg 1020
ccagcgacug gaccuuccug cacugccugc ccggaagcc cgaagaggug gacgacgagg 1080
uguucuacag cccccggucc cuggcguuucc ccgaggccga gaaccggaag uggaccauua 1140
uggccgugau ggugucccug cugaccgacu acucccccca gcugcagaag cccaaguucu 1200
agauaaguga acucgagcua gugacugacu aggaucuggu uaccacuaaa ccagccucaa 1260
gaacacccga auggagucuc uaagcuacau aauaccaacu uacacuuaca aaauguuguc 1320
ccccaaaaug uagccauucg uaucugcucc uaauaaaaag aaaguuucuu cacauucuag 1380

<210> SEQ ID NO 79
<211> LENGTH: 1380
<212> TYPE: RNA
<213> ORGANISM: Artificial Sequence
<220> FEATURE:
<223> OTHER INFORMATION: Synthetic construct

<400> SEQUENCE: 79
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug gucuucaacc ugcggauccu gcugaacaac gccgccuucc 180
ggaacggcca caacuucaug guccgcaacu ucagaugcgg ccagccccug cagaacaggg 240
ugcagcugaa gggccgggac cugcugaccc ugaagaacuu caccggcgaa gagaucaggu 300
acaugcugug gcugagcgcc gaccugaagu uccggaucaa gcagaagggc gaguaccugc 360
cccugcugca aggcaagagc cugggcauga ucuucgagaa gcggagcacc cggacccggc 420
ugagcaccga gacaggcuuu gcccugcugg gaggccaccc cugcuuucug accacccagg 480
acauccaccu gggcgugaac gagagccuga ccgacaccgc cagagugcug agcagcaugg 540
ccgacgccgu gcuggcccgg guguacaagc agagcgaccu ggacacccug gccaaagagg 600

-continued ccagcauccc caucaucaac ggccugagcg accuguacca ccccauccag auccuggccg 660
acuaccugac ccugcaggaa cacuacagcu cccugaaggg ccugacccug agcuggaucg 720
gcgacggcaa caacauccug cacagcauca ugaugagcgc cgccaaguuc ggcaugcauc 780
ugcaggccgc cacccccaag ggcuacgagc cugaugccag cgugaccaag cuggccgagc 840
aguacgccaa agagaacggc accaagcugc ugcugaccaa cgacccccug gaagccgccc 900
acggcggcaa cgugcugauc accgacaccu ggaucagcau gggccaggaa gaggaaaaga 960
agaagcggcu gcaggccuuc cagggcuacc aggucacaau gaagaccgcc aagguggccg 1020
ccagcgacug gaccuuccug cacugccugc cccggaagcc cgaagaggug gacgacgagg 1080
uguucuacag cccccggucc cuggguguucc ccgaggccga gaaccggaag uggaccauua 1140
uggccgugau gguguccug cugaccgacu acuccccca gcugcagaag cccaaguucu 1200
agauaaguga acucgagcua gugacugacu aggaucuggu uaccacuaaa ccagccucaa 1260
gaacacccga auggagucuc uaagcuacau aauaccaacu uacacuuaca aaauguuguc 1320
ccccaaaaug uagccauucg uaucugcucc uaauaaaaag aaaguuucuu cacauucuag 1380

<210> SEQ ID NO 80
<211> LENGTH: 1377
<212> TYPE: RNA
<213> ORGANISM: Artificial Sequence
<220> FEATURE:
<223> OTHER INFORMATION: Synthetic construct

<400> SEQUENCE: 80
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccuga ggauccugcu gaacaacgca gcuuucagga 180
acggccacaa cuucauggug aggaacuucc ggugcggcca gccccugcag aacaaggugc 240
agcugaaggg cagggaccug cugacccuga agaacuucac cggagaggag aucaaguaca 300
ugcuguggcu gagcgcagac cugaaguuca ggaucaagca gaagggagag uaccugcccc 360
ugcugcaggg gaagucccug ggcaugaucu ucgagaagag gaguaccagg accaggcuga 420
gcaccgaaac cggcuucgcc cugcugggag gacaccccug cuuccugacc acccaggaca 480
uccaccuggg cgugaacgag agucugaccg acaccgccag ggugcugucu agcauggccg 540
acgccgugcu ggccagggug uacaagcagu cagaccugga cacccuggcu aaggaggcca 600
gcauccccau caucaacggc cugagcgacc uguaccaccc cauccagauc cuggcugacu 660
accugacccu gcaggagcac uacagcucuc ugaagggccu gacccugagc uggaucggcg 720
acgggaacaa cauccugcac agcaucauga ugagcgccgc caaguucggc augcaccugc 780
aggccgcuac ccccaagggu uacgagcccg acgccagcgu gaccaagcug gcagagcagu 840
acgccaagga gaacggcacc aagcugcugc ugaccaacga cccccuggag gccgcccacg 900
gaggcaacgu gcugaucacc gacaccugga ucagcauggg acaggaggag gagaagaaga 960
agcggcugca ggcuuuccag gguuaccagg ugaccaugaa gaccgccaag guggcugcca 1020
gcgacuggac cuuccugcac ugccugccca ggaagcccga ggagguggac gacgaggugu 1080
ucuacucucc caggagccug guguuccccg aggccgagaa caggaagugg accaucaugg 1140
cugugauggu gucccugcug accgacuaca gcccccagcu gcagaagccc aaguucugaa 1200
uaagugaacu cgagcuagug acugacuagg aucugguuac cacuaaacca gccucaagaa 1260
cacccgaaug gagucucuaa gcuacauaau accaacuuac acuuacaaaa uguuguccccc 1320 caaaauguag ccauucguau cugcuccuaa uaaaaagaaa guuucuucac auucuag 1377

<210> SEQ ID NO 81
<211> LENGTH: 1377
<212> TYPE: RNA
<213> ORGANISM: Artificial Sequence
<220> FEATURE:
<223> OTHER INFORMATION: Synthetic construct

<400> SEQUENCE: 81
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccuga ggauccugcu gaacaacgca gcuuucagga 180
acggccacaa cuucauggug aggaacuucc ggugcggcca gccccugcag aacaaggugc 240
agcugaaggg cagggaccug cugacccuga agaacuucac cggagaggag aucaaguaca 300
ugcuguggcu gagcgcagac cugaaguuca ggaucaagca gaagggagag uaccugcccc 360
ugcugcaggg gaagucccug ggcaugaucu ucgagaagag gaguaccagg accaggcuga 420
gcaccgaaac cggcuucgcc cugcugggag gacaccccug cuuccugacg acccaggaca 480
uccaccucgg agugaacgaa ucccucaccg auaccgcccg gguguuauca agcauggcag 540
augccgugcu ggccagggug uacaaacagu ccgaucugga cacucuggcu aaggaggcca 600
gcauccccau caucaacggc cugagcgacc uguaccaccc cauccagauc cuggcugacu 660
accugacccu gcaggagcac uacagcucuc ugaagggccu gacccugagc uggaucggcg 720
acgggaacaa cauccugcac uccaucauga uguccgccgc gaaguucgga augcaucugc 780
aagccgccac gccaaaagga uacgaaccgg augcgcccgu gacaaaguug gcggaacagu 840
acgcuaagga gaacggaacc aagcugcugc ugaccaacga cccccuggag gccgcccacg 900
gaggcaacgu gcugaucacc gacaccugga ucagcauggg acaggaggag gagaagaaga 960
agcggcugca ggcuuuccag gguuaccagg ugaccaugaa gaccgccaag guggcugcca 1020
gcgacuggac cuuccugcac ugccugccca ggaagcccga ggagguggac gacgaggugu 1080
ucuacucucc caggagccug guguuccccg aggccgagaa caggaagugg accaucaugg 1140
cugugauggu gucccugcug accgacuaca gcccccagcu gcagaagccc aaguucugaa 1200
uaagugaacu cgagcuagug acugacuagg aucugguuac cacuaaacca gccucaagaa 1260
cacccgaaug gagucucuaa gcuacauaau accaacuuac acuuacaaaa uguuguccccc 1320 caaaauguag ccauucguau cugcuccuaa uaaaaagaaa guuucuucac auucuag 1377

<210> SEQ ID NO 82
<211> LENGTH: 1477
<212> TYPE: RNA
<213> ORGANISM: Artificial Sequence
<220> FEATURE:
<223> OTHER INFORMATION: Synthetic construct

<400> SEQUENCE: 82
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccugc gcauccugcu gaacaacgcc gccuuccgca 180
acggccacaa cuucauggug cgcaacuucc gcugcggcca gccccugcag aacaaggugc 240
agcugaaggg ccgcgaccug cugacccuga agaacuucac cggcgaggag aucaaguaca 300

```
ugcuguggcu gagcgccgac cugaaguucc gcaucaagca gaagggcgag uaccugcccc    360

ugcugcaggg caagagccug ggcaugaucu ucgagaagcg cagcacccgc acccgccuga    420

gcaccgagac aggcuucgcc cugcugggcg gccaccccug cuuccugacc acccaggaca    480

uccaccuggg cgugaacgag agccugaccg acaccgcccg cgugcugagc agcauggccg    540

acgccgugcu ggcccgcgug uacaagcaga gcgaccugga cacccuggcc aaggaggcca    600

gcauccccau caucaacggc cugagcgacc uguaccaccc cauccagauc cuggccgacu    660

accugacccu gcaggagcac uacagcagcc ugaagggccu gacccugagc uggaucggcg    720

acggcaacaa cauccugcac agcaucauga ugagcgccgc caaguucggc augcaccugc    780

aggccgccac ccccaagggc uacgagcccg acgccagcgu gaccaagcug gccgagcagu    840

acgccaagga gaacggcacc aagcugcugc ugaccaacga cccccuggag gccgcccacg    900

gcggcaacgu gcugaucacc gacaccugga ucagcauggg ccaggaggag gagaagaaga    960

agcgccugca ggccuuccag ggcuaccagg ugaccaugaa gaccgccaag guggccgcca   1020

gcgacuggac cuuccugcac ugccugcccc gcaagcccga ggagguggac gacgaggugu   1080

ucuacagccc ccgcagccug guguuccccg aggccgagaa ccgcaagugg accaucaugg   1140

ccgugauggu gagccugcug accgacuaca gcccccagcu gcagaagccc aaguucugaa   1200

uaagugaacu cgagcuagug acugacuagg aucugguuac cacuaaacca gccucaagaa   1260

cacccgaaug gagucucuaa gcuacauaau accaacuuac acuuacaaaa uguuguccc    1320

caaaauguag ccauucguau cugcuccuaa uaaaaagaaa guuucuucac auucuagaaa   1380

aaaaaaaaaa aaaaaaaaaa aaaaaaaaaa aaaaaaaaaa aaaaaaaaaa aaaaaaaaaa   1440

aaaaaaaaaa aaaaaaaaaa aaaaaaaaaa aaaaaaa                            1477


<210> SEQ ID NO 83
<211> LENGTH: 1371
<212> TYPE: RNA
<213> ORGANISM: Artificial Sequence
<220> FEATURE:
<223> OTHER INFORMATION: Synthetic construct

<400> SEQUENCE: 83

aggaaacuua agucaacaca acauauacaa aacaaacgaa ucucaagcaa ucaagcauuc     60

uacuucuauu gcagcaauuu aaaucauuuc uuuuaaagca aaagcaauuu ucugaaaauu    120

uucaccauuu acgaacgaua gccaugcugu ucaaccugcg cauccugcug aacaacgccg    180

ccuuccgcaa cggccacaac uucaugggugc gcaacuuccg cugcggccag ccccugcaga   240

acaaggugca gcugaagggc cgcgaccugc ugacccugaa gaacuucacc ggcgaggaga    300

ucaaguacau gcuguggcug agcgccgacc ugaaguuccg caucaagcag aagggcgagu    360

accugccccu gcugcagggc aagagccugg gcaugaucuu cgagaagcgc agcacccgca    420

cccgccugag caccgagaca ggcuucgccc ugcugggcgg ccaccccugc uuccugacca    480

cccaggacau ccaccugggc gugaacgaga gccugaccga caccgcccgc gugcugagca    540

gcauggccga cgccgugcug gcccgcgugu acaagcagag cgaccuggac acccuggcca    600

aggaggccag cauccccauc aucaacggcc ugagcgaccu guaccacccc auccagaucc    660

uggccgacua ccugacccug caggagcacu acagcagccu gaagggccug acccugagcu    720

ggaucggcga cggcaacaac auccugcaca gcaucaugau gagcgccgcc aaguucggca    780

ugcaccugca ggccgccacc cccaagggcu acgagcccga cgccagcgug accaagcugg    840

ccgagcagua cgccaaggag aacggcacca agcugcugcu gaccaacgac ccccuggagg    900
```

```
ccgcccacgg cggcaacgug cugaucaccg acaccuggau cagcaugggc caggaggagg    960

agaagaagaa gcgccugcag gccuuccagg gcuaccaggu gaccaugaag accgccaagg   1020

uggccgccag cgacuggacc uuccugcacu gccugccccg caagcccgag gagguggacg   1080

acgaggugu cuacagcccc cgcagccugg uguuccccga ggccgagaac cgcaagugga    1140

ccaucauggc cgugauggug agccugcuga ccgacuacag cccccagcug cagaagccca   1200

aguucugacu agugacugac uaggaucugg uuaccacuaa accagccuca agaacacccg   1260

aauggagucu cuaagcuaca uaauaccaac uuacacuuac aaaauguugu cccccaaaau   1320

guagccauuc guaucugcuc cuaauaaaaa gaaaguuucu ucacauucua g            1371
```

<210> SEQ ID NO 84
<211> LENGTH: 1371
<212> TYPE: RNA
<213> ORGANISM: Artificial Sequence
<220> FEATURE:
<223> OTHER INFORMATION: Synthetic construct

<400> SEQUENCE: 84

```
ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc caccaugcuu uucaacuuga gaauccugcu gaacaacgcc gccuuucgca    180

acggucacaa uuuuaugguc agaaacuuca gaugcggaca gccccuccaa aacaaggucc    240

agcugaaggg ccgcgaucuc cucacccuga agaacuucac gggggaggag aucaaguaca    300

ugcuguggcu cuccgcugac cugaaguuca ggaucaagca gaagggagaa uaucugccgc    360

ugcugcaagg gaagucccug ggaugauuu ucgagaagcg gagcacccgg acucggcucu     420

ccacugaaac ugguuucgcc cuucugggcg gucaccccug cuuccugacc acucaagaca    480

uucaccucgg agugaacgag uccuugacug acaccgcccg ggugcugucg agcauggcag    540

acgccgugcu agcccgcgug uacaagcagu cagaccucga uacccuggcc aaggaggcuu    600

cgaucccgau caucaacggg uuguccgacc uguaccaccc gauucagauu cucgccgacu    660

accucacccu gcaagagcau uacagcuccc ugaaggggcu uacccugucc uggauuggcg    720

acggaaacaa cauccugcac uccauuauga ugucggcggc caaguucggc augcaccucc    780

aagccgcgac cccuaagggu uacgaaccag acgcgucagu gacuaagcug gccgaacagu    840

acgcaaagga aaauggcacg aagcugcucc ugaccaacga uccguuggaa gccgcccaug    900

gcggaaaugu gcucaucacc gacaccugga ucucgauggg acaggaggaa gagaagaaga    960

agcggcugca ggcguuccag ggcuaccagg ucaccaugaa aacugccaag guggccgcca   1020

gcgacuggac cuuccugcac ugccuucccgc gcaagccuga ggagguggac gaugaagugu   1080

ucuacucucc acggucccug guguuccccg aggcggagaa ccgcaaaugg accaucaugg   1140

cugugauggu cagccugcug accgauuaca gcccucaguu gcaaaagccg aaguuuugau   1200

aacucgagcu agugacugac uaggaucugg uuaccacuaa accagccuca agaacacccg   1260

aauggagucu cuaagcuaca uaauaccaac uuacacuuac aaaauguugu cccccaaaau   1320

guagccauuc guaucugcuc cuaauaaaaa gaaaguuucu ucacauucua g            1371
```

<210> SEQ ID NO 85
<211> LENGTH: 1471
<212> TYPE: RNA
<213> ORGANISM: Artificial Sequence
<220> FEATURE:

<223> OTHER INFORMATION: Synthetic construct

<400> SEQUENCE: 85
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug uucaaccucc gcauccuccu caacaacgcc gcauucagaa 180
acgggcacaa cuucaugguc agaaacuucc gcugcgggca accccuacaa aacaaggucc 240
agcucaaggg gcgggaccuc cugacccuga agaacuucac cggcgaagag aucaaguaca 300
ugcuguggcu cuccgccgac cugaaguucc gcaucaagca gaagggagag uaccuccccgc 360 ugcugcaagg gaagucgcug gggaugaucu ucgagaagcg gucaaccaga acccggcugu 420
caaccgaaac cggguucgca cugcuggggg gacacccgug cuuccugacc acccaagaca 480
uccaccuggg agugaacgaa ucgcugaccg acaccgcccg cgugcugagc ucaauggcgg 540
acgccgugcu ggcccgcgug uacaagcagu ccgaccugga cacccuggcc aaggaagcgu 600
ccaucccgau caucaacgga cuguccgacc uguaccaccc gauccagauc cuggcagacu 660
accugacccu gcaagaacac uacagcuccc ugaagggccu gacccuguca uggaucgggg 720
acgggaacaa cauccugcac uccauaauga ugucagccgc caaguucgga augcaccucc 780
aagccgcaac cccgaagggc uacgaaccgg acgcaucagu gaccaaacug gccgagcagu 840
acgccaagga aaacggcacc aagcuccugc ugaccaacga cccgcuggag gccgcacacg 900
gggggaacgu gcugaucacc gacaccugga ucuccauggg acaggaggag gaaaagaaga 960
agcggcugca ggcguuccag ggguaccagg ucaccaugaa aaccgcgaag gucgcggcau 1020
cagacuggac cuuccugcac ugccugcccc ggaagccgga agagguggac gacgaggugu 1080
ucuacucgcc gcgcucgcug guguuccccg aggcggagaa caggaagugg accaucaugg 1140
cggugauggu cagccuccug accgacuacu cgccgcagcu gcagaagccg aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua gaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa a 1471

<210> SEQ ID NO 86
<211> LENGTH: 1771
<212> TYPE: RNA
<213> ORGANISM: Artificial Sequence
<220> FEATURE:
<223> OTHER INFORMATION: Synthetic construct

<400> SEQUENCE: 86
cucccucccc ccccccuaac guuacuggcc gaagccgcuu ggaauaaggc cggugugcgu 60
uugucuauau guuauuuucc accauauugc cgucuuuugg caaugugagg gcccggaaac 120
cuggcccugu cuucuugacg agcauuccua ggggucuuuc cccucucgcc aaaggaaugc 180
aaggucuguu gaaugucgug aaggaagcag uuccucugga agcuucuuga agacaaacaa 240
cgucuguagc gacccuuugc aggcagcgga accccccacc uggcgacagg ugccucugcg 300
gccaaaagcc acguguauaa gauacaccug caaaggcggc acaaccccag ugccacguug 360
ugaguuggau aguuguggaa agagucaaau ggcucuccuc aagcguauuc aacaaggggc 420
ugaaggaugc ccagaaggua ccccauugua ugggaucuga ucuggggccu cggugcacau 480
gcuuuacgug uguuuagucg agguuaaaaa acgucuaggc cccccgaacc acggggacgu 540
gguuuuccuu ugaaaaacac gaugauaaua ugcuuuucaa ucuccgcauc cuccuuaaca 600
acgccgcguu uagaaacggc cacaacuuca ugguccggaa cuucagaugu ggccagccgc 660
uucaaaacaa gguccagcug aagggccggg aucuucugac ccugaagaac uuuacuggcg 720
aagagaucaa guacaugcuc uggcucuccg cggacuugaa guuccgcauu aagcagaagg 780
gggaauaccu uccgcugcuu caaggaaaga gccucggcau gaucuuugag aagcgcucaa 840
ccaggacccg ccuuucuacu gaaacugggu ucgcgcugcu cgguggccac cccugcuucc 900
ugacgaccca ggacauccac cucggaguga acgaaucccu caccgauacc gcccgggugu 960
uaucgagcau ggcagaugcc gugcuggcca ggguguacaa acaguccgau cuggacacuc 1020
uggccaagga ggcgucaauu ccuauuauca acggccuuag ugaccucuac cauccgauuc 1080
agauccuggc cgauuaccuc acccugcaag aacacuacag cucccugaag ggucugacau 1140
uguccuggau cggcgacggc aacaacauuc uccauuccau caugaugucc gccgcaaaau 1200
ucggcaugca ucuucaagcc gccacgccga aggguuacga gcccgacgcu uccgugacua 1260
agcucgccga gcaguacgcu aaggagaacg gaaccaagcu ucugcugacu aacgacccac 1320
uagaagcagc ccacgggggc aacgugcuua uuacugacac cuggaucucc augggccagg 1380
aagaagagaa aaagaagcgg cugcaggcgu uccagggaua ucaggucacc augaaaaccg 1440
ccaaggucgc ugccuccgac uggaccuucc ugcacugccu gccucgcaag ccugaagaag 1500
uggacgacga gguguucuac ucgccacgga gccucguguu ccccgaggcc gagaauagaa 1560
aguggaccau cauggccgug auggugucac ugcucaccga cuacagcccg cagcuucaga 1620
agcccaaguu cugaauaagu agauagugca gucacuggca caacgcguug cccgguaagc 1680
caaucgggua uacacggucg ucauacugca gacaggguuc uucuacuuug caagauaguc 1740
uagaguagua aaauaaauag uauaagucua g 1771

<210> SEQ ID NO 87
<211> LENGTH: 1771
<212> TYPE: RNA
<213> ORGANISM: Artificial Sequence
<220> FEATURE:
<223> OTHER INFORMATION: Synthetic construct

<400> SEQUENCE: 87
cucccucccc cccccccuaac guuacuggcc gaagccgcuu ggaauaaggc cggugugcgu 60
uugucuauau guuauuuucc accauauugc cgucuuuugg caaugugagg gcccggaaac 120
cuggcccugu cuucuugacg agcauuccua ggggucuuuc cccucucgcc aaaggaaugc 180
aaggucuguu gaaugucgug aaggaagcag uuccucugga agcuucuuga agacaaacaa 240
cgucuguagc gacccuuugc aggcagcgga acccccccacc uggcgacagg ugccucugcg 300
gccaaaagcc acguguauaa gauacaccug caaaggcggc acaaccccag ugccacguug 360
ugaguuggau aguuguggaa agagucaaau ggcucuccuc aagcguauuc aacaaggggc 420
ugaaggaugc ccagaaggua ccccauugua ugggaucuga ucuggggccu cggugcacau 480
gcuuuacgug uguuuagucg agguuaaaaa acgucuaggc cccccgaacc acggggacgu 540
gguuuuccuu ugaaaaacac gaugauaaua ugcuuuucaa ccugagaauc cucuugaaca 600
augcugcuuu ucggaauggc cacaacuuua ugguucggaa cuuccguugc ggccagccuu 660
uacaaaacaa gguccagcug aagggccggg auuugcucac acuaaagaac uuuacuggag 720
aagagaucaa guacaugcua uggcugucgg ccgaccugaa guuccguauc aagcagaagg 780
gagaauaccu uccgcugcuu caaggaaaga gccucggcau gaucuuugag aagcgcucaa 840
ccaggacccg ccuuucuacu gaaacugggu ucgcgcugcu cgguggccac cccugcuucc 900
ugacgaccca ggacauccac cucggaguga acgaaucccu caccgauacc gcccgggugu 960
uaucgagcau ggcagaugcc gugcuggcca ggguguacaa acaguccgau cucgauaccu 1020
uggcaaagga ggcuuccauu cccaucauca acggccugag cgaccuguac cacccaaucc 1080
aaauccuggc ugacuaccug acccugcaag agcacuacag cagccugaag ggucugaccc 1140
ugucauggau uggcgaugga aacaauauuc ugcacuccau caugaugucc gccgcgaagu 1200
ucggaaugca ucugcaagcc gccacuccaa aaggauacga accggaugca uccgugacca 1260
aguuggcgga acaguacgcg aaggagaacg gaaccaagcu ccugcugacu aacgacccgc 1320
ucgaggcugc gcaugggggu aacgugcuga uuacggacac cuggaucucc auggggcagg 1380
aggaagagaa gaagaagaga cugcaggcau uccaggggua ccaggucacc augaaaaccg 1440 caaaagugge agcuucggac uggacuuucc ugcauugccu gccgaggaag ccggaggaag 1500
ucgacgacga aguguucuac ucgccucggu cccuggugau ccccgaggcc gaaaaccgga 1560
aguggaccau cauggccgug augguguccu ugcugacuga cuauagcccg cagcugcaga 1620
agccuaaguu cugaauaagu agauagugca gucacuggca caacgcguug cccgguaagc 1680
caaucgggua uacacggucg ucauacugca gacaggguuc uucuacuuug caagauaguc 1740
uagaguagua aaauaaauag uauaagucua g 1771

<210> SEQ ID NO 88
<211> LENGTH: 1771
<212> TYPE: RNA
<213> ORGANISM: Artificial Sequence
<220> FEATURE:
<223> OTHER INFORMATION: Synthetic construct

<400> SEQUENCE: 88
cucccucccc cccccccuaac guuacuggcc gaagccgcuu ggaauaaggc cggugugcgu 60
uugucuauau guuauuuucc accauauugc cgucuuuugg caaugugagg gcccggaaac 120
cuggcccugu cuucuugacg agcauuccua ggggucuuuc cccucucgcc aaaggaaugc 180
aaggucuguu gaaugucgug aaggaagcag uuccucugga agcuucuuga agacaaacaa 240
cgucuguagc gacccuuugc aggcagcgga acccccacc uggcgacagg ugccucugcg 300
gccaaaagcc acguguauaa gauacaccug caaaggcggc acaaccccag ugccacguug 360
ugaguuggau aguuguggaa agagucaaau ggcucuccuc aagcguauuc aacaaggggc 420
ugaaggaugc ccagaaggua ccccauugua ugggaucuga ucuggggccu cggugcacau 480
gcuuuacgug uguuuagucg agguuaaaaa acgucuaggc cccccgaacc acggggacgu 540
gguuuuccuu ugaaaaacac gaugauaaua ugcuguucaa ccugcgcauc cugcugaaca 600
acgccgccuu ccgcaacggc cacaacuuca uggugcgcaa cuuccgcugc ggccagcccc 660
ugcagaacaa ggugcagcug aagggccgcg accugcugac ccugaagaac uucaccggcg 720
aggagaucaa guacaugcug uggcugagcg ccgaccugaa guuccgcauc aagcagaagg 780
gcgaguaccu gccccugcug cagggcaaga gccugggcau gaucuucgag aagcgcagca 840
cccgcacccg ccugagcacc gagacaggcc uggcccugcu gggcggccac cccugcuucc 900
ugaccaccca ggacauccac cugggcguga acgagagccu gaccgacacc gcccgcgugc 960
ugagcagcau ggccgacgcc gugcuggccc gcguguacaa gcagagcgac cuggacaccc 1020

```
uggccaagga ggccagcauc cccaucauca acggccugag cgaccuguac caccccaucc   1080

agauccuggc cgacuaccug acccugcagg agcacuacag cagccugaag ggccugaccc   1140

ugagcuggau cggcgacggc aacaacaucc ugcacagcau caugaugagc gccgccaagu   1200

ucggcaugca ccugcaggcc gccaccccca agggcuacga gcccgacgcc agcgugacca   1260

agcuggccga gcaguacgcc aaggagaacg gcaccaagcu gcugcugacc aacgaccccc   1320

uggaggccgc ccacggcggc aacgugcuga ucaccgacac cuggaucagc augggccagg   1380

aggaggagaa gaagaagcgc cugcaggccu uccagggcua ccaggugacc augaagaccg   1440

ccaagguggc cgccagcgac uggaccuucc ugcacugccu gccccgcaag cccgaggagg   1500

uggacgacga gguguucuac agcccccgca gccugguguu ccccgaggcc gagaaccgca   1560

aguggaccau cauggccgug auggugagcc ugcugaccga cuacagcccc cagcugcaga   1620

agcccaaguu cugaauaagu agauagugca gucacuggca caacgcguug cccgguaagc   1680

caaucgggua uacacggucg ucauacugca gacaggguuc uucuacuuug caagauaguc   1740

uagaguagua aaauaaauag uauaagucua g                                  1771
```

<210> SEQ ID NO 89
<211> LENGTH: 1368
<212> TYPE: RNA
<213> ORGANISM: Artificial Sequence
<220> FEATURE:
<223> OTHER INFORMATION: Synthetic construct

<400> SEQUENCE: 89

```
ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc caccaugcuu uucaaucucc gcauccuccu uaacaacgcc gcguuuagaa    180

acggccacaa cuucaugguc cggaacuuca gauguggcca gccgcuucaa aacaaggucc    240

agcugaaggg ccgggaucuu cugacccuga agaacuuuac uggcgaagag aucaaguaca    300

ugcucuggcu cuccgcggac uugaaguucc gcauuaagca gaagggggaa uaccuuccgc    360

ugcuucaagg aaagagccuc ggcaugaucu uugagaagcg cucaaccagg acccgccuuu    420

cuacugaaac uggguucgcg cugcucggug gccacccug cuuccugacg acccaggaca    480

uccaccucgg agugaacgaa ucccucaccg auaccgcccg gguguuaucg agcauggcag    540

augccgugcu ggccagggug uacaaacagu ccgaucugga cacucuggcc aaggaggcgu    600

caauuccuau uaucaacggc cuuagugacc ucuaccaucc gauucagauc cuggccgauu    660

accucacccu gcaagaacac uacagcuccc ugaagggucu gacauugucc uggaucggcg    720

acggcaacaa cauucuccau uccaucauga uguccgccgc aaaauucggc augcaucuuc    780

aagccgccac gccgaagggu uacgagcccg acgcuuccgu gacuaagcuc gccgagcagu    840

acgcuaagga gaacggaacc aagcuucugc ugacuaacga cccacuagaa gcagcccacg    900

ggggcaacgu gcuuauuacu gacaccugga ucuccauggg ccaggaagaa gagaaaaaga    960

agcggcugca ggcguuccag ggauaucagg ucaccaugaa aaccgccaag gucgcugccu   1020

ccgacuggac cuuccugcac ugccugccuc gcaagccuga agaaguggac gacgaggugu   1080

ucuacucgcc acggagccuc guguuccccg aggccgagaa uagaaagugg accaucaugg   1140

ccgugauggu gucacugcuc accgacuaca gcccgcagcu ucagaagccc aaguucuagc   1200

ucgagcuagu gacugacuag gaucugguua ccacuaaacc agccucaaga acacccgaau   1260
```

ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 90
<211> LENGTH: 1368
<212> TYPE: RNA
<213> ORGANISM: Artificial Sequence
<220> FEATURE:
<223> OTHER INFORMATION: Synthetic construct

<400> SEQUENCE: 90
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggccacaa cuucaugguc cggaacuuca gauguggcca gccgcuucaa aacaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 91
<211> LENGTH: 1368
<212> TYPE: RNA
<213> ORGANISM: Artificial Sequence
<220> FEATURE:
<223> OTHER INFORMATION: Synthetic construct

<400> SEQUENCE: 91
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggccacaa cuucaugguc cggaacuuca gauguggcca gccgcuucaa aacaaggucc 240
agcugaaggg ccgggaucuu cugacccuga agaacuuuac uggcgaagag aucaaguaca 300

```
ugcucuggcu cuccgcggac uugaaguucc gcauuaagca gaagggggaa uaccuuccgc    360

ugcuucaagg aaagagccuc ggcaugaucu uugagaagcg cucaaccagg acccgccuuu    420

cuacugaaac uggguucgcg cugcucggug gccaccccug cuuccugacg acccaggaca    480

uccaccucgg agugaacgaa ucccucaccg auaccgcccg gguguuaucg agcauggcag    540

augccgugcu ggccagggug uacaaacagu ccgaucugga cacucuggcc aaggaggcgu    600

caauuccuau uaucaacggc cuuagugacc ucuaccaucc gauucagauc cuggccgauu    660

accucacccu gcaagaacac uacagcuccc ugaagggucu gacauugucc uggaucggcg    720

acggcaacaa cauucuccau uccaucauga uguccgccgc aaaauucggc augcaucuuc    780

aagccgccac gccgaagggu uacgagcccg acgcuuccgu gacuaagcuc gccgagcagu    840

acgcuaagga gaacggaacc aagcuucugc ugacuaacga cccacuagaa gcagcccacg    900

ggggcaacgu gcuuauuacu gacaccugga ucuccauggg ccaggaagaa gagaaaaaga    960

agcggcugca ggcguuccag ggauaucagg ucaccaugaa aaccgccaag gucgcugccu   1020

ccgacuggac cuuccugcac ugccugccuc gcaagccuga agaaguggac gacgaggugu   1080

ucuacucgcc acggagccuc guguuccccg aggccgagaa uagaaagugg accaucaugg   1140

ccgugauggu gucacugcuc accgacuaca gcccgcagcu ucagaagccc aaguucuagc   1200

ucgagcuagu gacugacuag gaucugguua ccacuaaacc agccucaaga acacccgaau   1260

ggagucucua agcuacauaa uaccaacuua cacuuacaaa auguuguccc ccaaaaugua   1320

gccauucgua ucugcuccua auaaaaagaa aguuucuuca cauucuag                 1368
```

```
<210> SEQ ID NO 92
<211> LENGTH: 1368
<212> TYPE: RNA
<213> ORGANISM: Artificial Sequence
<220> FEATURE:
<223> OTHER INFORMATION: Synthetic construct

<400> SEQUENCE: 92

ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc caccaugcuu uucaaucucc gcauccuccu uaacaacgcc gcguuuagaa    180

acggccacaa cuucaugguc cggaacuuca gauguggcca gccgcuucaa aacaaggucc    240

agcugaaggg ccgggaucuu cugacccuga agaacuuuac uggcgaagag aucaaguaca    300

ugcucuggcu cuccgcggac uugaaguucc gcauuaagca gaagggggaa uaccuuccgc    360

ugcuucaagg aaagagccuc ggcaugaucu uugagaagcg cucaaccagg acccgccuuu    420

cuacugaaac uggguucgcg cugcucggug gccaccccug cuuccugacg acccaggaca    480

uccaccucgg agugaacgaa ucccucaccg auaccgcccg gguguuaucg agcauggcag    540

augccgugcu ggccagggug uacaaacagu ccgaucugga cacucuggcc aaggaggcgu    600

caauuccuau uaucaacggc cuuagugacc ucuaccaucc gauucagauc cuggccgauu    660

accucacccu gcaagaacac uacagcuccc ugaagggucu gacauugucc uggaucggcg    720

acggcaacaa cauucuccau uccaucauga uguccgccgc aaaauucggc augcaucuuc    780

aagccgccac gccgaagggu uacgagcccg acgcuuccgu gacuaagcuc gccgagcagu    840

acgcuaagga gaacggaacc aagcuucugc ugacuaacga cccacuagaa gcagcccacg    900

ggggcaacgu gcuuauuacu gacaccugga ucuccauggg ccaggaagaa gagaaaaaga    960
```

agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 93
<211> LENGTH: 1368
<212> TYPE: RNA
<213> ORGANISM: Artificial Sequence
<220> FEATURE:
<223> OTHER INFORMATION: Synthetic construct

<400> SEQUENCE: 93
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu uucaaucucc gcauccuccu uaacaacgcc gcguuuagaa 180
acggccacaa cuucaugguc cggaacuuca gauguggcca gccgcuucaa aacaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 94
<211> LENGTH: 1371
<212> TYPE: RNA
<213> ORGANISM: Artificial Sequence
<220> FEATURE:
<223> OTHER INFORMATION: Synthetic construct

<400> SEQUENCE: 94
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccauggug uucaaccucc gcauccuccu caacaacgcc gcauucagaa 180
acgggcacaa cuucaugguc agaaacuucc gcugcgggca accccuacaa aacaaggucc 240
agcucaaggg gcgggaccuc cugacccuga agaacuucac cggcgaagag aucaaguaca 300
ugcuguggcu cuccgccgac cugaaguucc gcaucaagca gaagggagag uaccucccgc 360
ugcugcaagg gaagucgcug gggaugaucu ucgagaagcg gucaaccaga acccggcugu 420
caaccgaaac cggguucgca cugcuggggg gacacccgug cuuccugacc acccaagaca 480
uccaccuggg agugaacgaa ucgcugaccg acaccgcccg cgugcugagc ucaauggcgg 540
acgccgugcu ggcccgcgug uacaagcagu ccgaccugga cacccuggcc aaggaagcgu 600
ccaucccgau caucaacgga cuguccgacc uguaccaccc gauccagauc cuggcagacu 660
accugacccu gcaagaacac uacagcuccc ugaagggccu gacccuguca uggaucgggg 720
acgggaacaa cauccugcac uccauaauga ugucagccgc caaguucgga augcaccucc 780
aagccgcaac cccgaagggc uacgaaccgg acgcaucagu gaccaaacug gccgagcagu 840
acgccaagga aaacggcacc aagcuccugc ugaccaacga cccgcuggag gccgcacacg 900
gggggaacgu gcugaucacc gacaccugga ucuccauggg acaggaggag gaaaagaaga 960
agcggcugca ggcguuccag ggguaccagg ucaccaugaa aaccgcgaag gucgcggcau 1020
cagacuggac cuuccugcac ugccugcccc ggaagccgga agagguggac gacgaggugu 1080
ucuacucgcc gcgcucgcug guguuccccg aggcggagaa caggaagugg accaucaugg 1140
cggugauggu cagccuccug accgacuacu cgccgcagcu gcagaagccg aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 95
<211> LENGTH: 1371
<212> TYPE: RNA
<213> ORGANISM: Artificial Sequence
<220> FEATURE:
<223> OTHER INFORMATION: Synthetic construct

<400> SEQUENCE: 95
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccauggug uucaaccucc gcauccuccu caacaacgcc gcauucagaa 180
acgggcacaa cuucaugguc agaaacuucc gcugcgggca accccuacaa aaccgggucc 240
agcucaaggg gcgggaccuc cugacccuga agaacuucac cggcgaagag aucaaguaca 300
ugcuguggcu cuccgccgac cugaaguucc gcaucaagca gaagggagag uaccucccgc 360
ugcugcaagg gaagucgcug gggaugaucu ucgagaagcg gucaaccaga acccggcugu 420
caaccgaaac cggguucgca cugcuggggg gacacccgug cuuccugacc acccaagaca 480
uccaccuggg agugaacgaa ucgcugaccg acaccgcccg cgugcugagc ucaauggcgg 540
acgccgugcu ggcccgcgug uacaagcagu ccgaccugga cacccuggcc aaggaagcgu 600
ccaucccgau caucaacgga cuguccgacc uguaccaccc gauccagauc cuggcagacu 660

```
accugacccu gcaagaacac uacagcuccc ugaagggccu gacccuguca uggaucgggg    720

acgggaacaa cauccugcac uccauaauga ugucagccgc caaguucgga augcaccucc    780

aagccgcaac cccgaagggc uacgaaccgg acgcaucagu gaccaaacug gccgagcagu    840

acgccaagga aaacggcacc aagcuccugc ugaccaacga cccgcuggag gccgcacacg    900

gggggaacgu gcugaucacc gacaccugga ucuccauggg acaggaggag gaaaagaaga    960

agcggcugca ggcguuccag ggguaccagg ucaccaugaa aaccgcgaag gucgcggcau   1020

cagacuggac cuuccugcac ugccugcccc ggaagccgga agagguggac gacgaggugu   1080

ucuacucgcc gcgcucgcug guguuccccg aggcggagaa caggaagugg accaucaugg   1140

cggugauggu cagccuccug accgacuacu cgccgcagcu gcagaagccg aaguucugau   1200

aacucgagcu agugacugac uaggaucugg uuaccacuaa accagccuca agaacacccg   1260

aauggagucu cuaagcuaca uaauaccaac uuacacuuac aaaauguugu cccccaaaau   1320

guagccauuc guaucugcuc cuaauaaaaa gaaaguuucu ucacauucua g            1371
```

<210> SEQ ID NO 96
<211> LENGTH: 1371
<212> TYPE: RNA
<213> ORGANISM: Artificial Sequence
<220> FEATURE:
<223> OTHER INFORMATION: Synthetic construct

<400> SEQUENCE: 96

```
ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc caccauggug uucaaccucc gcauccuccu caacaacgcc gcauucagaa    180

acgggcacaa cuucaugguc agaaacuucc gcugcgggca accccuacaa aaccgggucc    240

agcucaaggg gcgggaccuc cugacccuga agaacuucac cggcgaagag auccgguaca    300

ugcuguggcu cuccgccgac cugaaguucc gcaucaagca gaagggagag uaccucccgc    360

ugcugcaagg gaagucgcug gggaugaucu ucgagaagcg gucaaccaga acccggcugu    420

caaccgaaac cggguucgca cugcuggggg gacacccgug cuuccugacc acccaagaca    480

uccaccuggg agugaacgaa ucgcugaccg acaccgcccg cgugcugagc ucaauggcgg    540

acgccgugcu ggcccgcgug uacaagcagu ccgaccugga cacccuggcc aaggaagcgu    600

ccaucccgau caucaacgga cuguccgacc uguaccaccc gauccagauc cuggcagacu    660

accugacccu gcaagaacac uacagcuccc ugaagggccu gacccuguca uggaucgggg    720

acgggaacaa cauccugcac uccauaauga ugucagccgc caaguucgga augcaccucc    780

aagccgcaac cccgaagggc uacgaaccgg acgcaucagu gaccaaacug gccgagcagu    840

acgccaagga aaacggcacc aagcuccugc ugaccaacga cccgcuggag gccgcacacg    900

gggggaacgu gcugaucacc gacaccugga ucuccauggg acaggaggag gaaaagaaga    960

agcggcugca ggcguuccag ggguaccagg ucaccaugaa aaccgcgaag gucgcggcau   1020

cagacuggac cuuccugcac ugccugcccc ggaagccgga agagguggac gacgaggugu   1080

ucuacucgcc gcgcucgcug guguuccccg aggcggagaa caggaagugg accaucaugg   1140

cggugauggu cagccuccug accgacuacu cgccgcagcu gcagaagccg aaguucugau   1200

aacucgagcu agugacugac uaggaucugg uuaccacuaa accagccuca agaacacccg   1260

aauggagucu cuaagcuaca uaauaccaac uuacacuuac aaaauguugu cccccaaaau   1320

guagccauuc guaucugcuc cuaauaaaaa gaaaguuucu ucacauucua g            1371
```

<210> SEQ ID NO 97
<211> LENGTH: 1371
<212> TYPE: RNA
<213> ORGANISM: Artificial Sequence
<220> FEATURE:
<223> OTHER INFORMATION: Synthetic construct

<400> SEQUENCE: 97
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug gucaaccucc gcauccuccu caacaacgcc gcauucagaa 180
acgggcacaa cuucaugguc agaaacuucc gcugcgggca accccuacaa aacaaggucc 240
agcucaaggg gcgggaccuc cugacccuga agaacuucac cggcgaagag aucaaguaca 300
ugcuguggcu cuccgccgac cugaaguucc gcaucaagca gaagggagag uaccucccgc 360
ugcugcaagg gaagucgcug gggaugaucu ucgagaagcg gucaaccaga acccggcugu 420
caaccgaaac cggguucgca cugcuggggg gacacccgug cuuccugacc acccaagaca 480
uccaccuggg agugaacgaa ucgcugaccg acaccgcccg cgugcugagc ucaauggcgg 540
acgccgugcu ggcccgcgug uacaagcagu ccgaccugga cacccuggcc aaggaagcgu 600
ccaucccgau caucaacgga cuguccgacc uguaccaccc gauccagauc cuggcagacu 660
accugacccu gcaagaacac uacagcuccc ugaagggccu gacccuguca uggaucgggg 720
acgggaacaa cauccugcac uccauaauga ugucagccgc caaguucgga augcaccucc 780
aagccgcaac cccgaagggc uacgaaccgg acgcaucagu gaccaaacug gccgagcagu 840
acgccaagga aaacggcacc aagcuccugc ugaccaacga cccgcuggag gccgcacacg 900
gggggaacgu gcugaucacc gacaccugga ucuccauggg acaggaggag gaaaagaaga 960
agcggcugca ggcguuccag ggguaccagg ucaccaugaa aaccgcgaag gucgcggcau 1020
cagacuggac cuuccugcac ugccugcccc ggaagccgga agagguggac gacgaggugu 1080
ucuacucgcc gcgcucgcug guguuccccg aggcggagaa caggaagugg accaucaugg 1140
cggugauggu cagccuccug accgacuacu cgccgcagcu gcagaagccg aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 98
<211> LENGTH: 1471
<212> TYPE: RNA
<213> ORGANISM: Artificial Sequence
<220> FEATURE:
<223> OTHER INFORMATION: Synthetic construct

<400> SEQUENCE: 98
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug gucaaccucc gcauccuccu caacaacgcc gcauucagaa 180
acgggcacaa cuucaugguc agaaacuucc gcugcgggca accccuacaa aaccgggucc 240
agcucaaggg gcgggaccuc cugacccuga agaacuucac cggcgaagag aucaaguaca 300
ugcuguggcu cuccgccgac cugaaguucc gcaucaagca gaagggagag uaccucccgc 360
ugcugcaagg gaagucgcug gggaugaucu ucgagaagcg gucaaccaga acccggcugu 420
caaccgaaac cggguucgca cugcuggggg gacacccgug cuuccugacc acccaagaca 480
uccaccuggg agugaacgaa ucgcugaccg acaccgcccg cgugcugagc ucaauggcgg 540
acgccgugcu ggcccgcgug uacaagcagu ccgaccugga cacccuggcc aaggaagcgu 600
ccaucccgau caucaacgga cuguccgacc uguaccaccc gauccagauc cuggcagacu 660
accugacccu gcaagaacac uacagcuccc ugaagggccu gacccuguca uggaucgggg 720
acgggaacaa cauccugcac uccauaauga ugucagccgc caaguucgga augcaccucc 780
aagccgcaac cccgaagggc uacgaaccgg acgcaucagu gaccaaacug gccgagcagu 840
acgccaagga aaacggcacc aagcuccugc ugaccaacga cccgcuggag gccgcacacg 900
gggggaacgu gcugaucacc gacaccugga ucuccauggg acaggaggag gaaaagaaga 960
agcggcugca ggcguuccag ggguaccagg ucaccaugaa aaccgcgaag gucgcggcau 1020
cagacuggac cuuccugcac ugccugcccc ggaagccgga agagguggac gacgaggugu 1080
ucuacucgcc gcgcucgcug guguuccccg aggcggagaa caggaagugg accaucaugg 1140
cggugauggu cagccuccug accgacuacu cgccgcagcu gcagaagccg aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua gaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa a 1471

<210> SEQ ID NO 99
<211> LENGTH: 1371
<212> TYPE: RNA
<213> ORGANISM: Artificial Sequence
<220> FEATURE:
<223> OTHER INFORMATION: Synthetic construct

<400> SEQUENCE: 99
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug gucaaccucc gcauccuccu caacaacgcc gcauucagaa 180
acgggcacaa cuucaugguc agaaacuucc gcugcgggca accccuacaa aaccgggucc 240
agcucaaggg gcgggaccuc cugacccuga agaacuucac cggcgaagag auccgguaca 300
ugcuguggcu cuccgccgac cugaaguucc gcaucaagca gaagggagag uaccucccgc 360
ugcugcaagg gaagucgcug gggaugaucu ucgagaagcg gucaaccaga acccggcugu 420
caaccgaaac cggguucgca cugcuggggg gacacccgug cuuccugacc acccaagaca 480
uccaccuggg agugaacgaa ucgcugaccg acaccgcccg cgugcugagc ucaauggcgg 540
acgccgugcu ggcccgcgug uacaagcagu ccgaccugga cacccuggcc aaggaagcgu 600
ccaucccgau caucaacgga cuguccgacc uguaccaccc gauccagauc cuggcagacu 660
accugacccu gcaagaacac uacagcuccc ugaagggccu gacccuguca uggaucgggg 720
acgggaacaa cauccugcac uccauaauga ugucagccgc caaguucgga augcaccucc 780
aagccgcaac cccgaagggc uacgaaccgg acgcaucagu gaccaaacug gccgagcagu 840
acgccaagga aaacggcacc aagcuccugc ugaccaacga cccgcuggag gccgcacacg 900
gggggaacgu gcugaucacc gacaccugga ucuccauggg acaggaggag gaaaagaaga 960
agcggcugca ggcguuccag ggguaccagg ucaccaugaa aaccgcgaag gucgcggcau 1020
cagacuggac cuuccugcac ugccugcccc ggaagccgga agagguggac gacgaggugu 1080
ucuacucgcc gcgcucgcug guguuccccg aggcggagaa caggaagugg accaucaugg 1140
cggugauggu cagccuccug accgacuacu cgccgcagcu gcagaagccg aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 100
<211> LENGTH: 1471
<212> TYPE: RNA
<213> ORGANISM: Artificial Sequence
<220> FEATURE:
<223> OTHER INFORMATION: Synthetic construct

<400> SEQUENCE: 100
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug gucaaccugc gcauccugcu gaacaacgcc gccuuccgca 180
acggccacaa cuucauggug cgcaacuucc gcugcggcca gccccugcag aacaaggugc 240
agcugaaggg ccgcgaccug cugacccuga agaacuucac cggcgaggag aucaaguaca 300
ugcuguggcu gagcgccgac cugaaguucc gcaucaagca gaagggcgag uaccugcccc 360
ugcugcaggg caagagccug ggcaugaucu ucgagaagcg cagcacccgc acccgccuga 420
gcaccgagac aggcuucgcc cugcugggcg gccaccccug cuuccugacc acccaggaca 480
uccaccuggg cgugaacgag agccugaccg acaccgcccg cgugcugagc agcauggccg 540
acgccgugcu ggcccgcgug uacaagcaga gcgaccugga cacccuggcc aaggaggcca 600
gcauccccau caucaacggc cugagcgacc uguaccaccc cauccagauc cuggccgacu 660
accugacccu gcaggagcac uacagcagcc ugaagggccu gacccugagc uggaucggcg 720
acggcaacaa cauccugcac agcaucauga ugagcgccgc caaguucggc augcaccugc 780
aggccgccac ccccaagggc uacgagcccg acgccagcgu gaccaagcug gccgagcagu 840
acgccaagga gaacggcacc aagcugcugc ugaccaacga cccccuggag gccgcccacg 900
gcggcaacgu gcugaucacc gacaccugga ucagcauggg ccaggaggag gagaagaaga 960
agcgccugca ggccuuccag ggcuaccagg ugaccaugaa gaccgccaag guggccgcca 1020
gcgacuggac cuuccugcac ugccugcccc gcaagcccga ggagguggac gacgaggugu 1080
ucuacagccc ccgcagccug guguuccccg aggccgagaa ccgcaagugg accaucaugg 1140
ccgugauggu gagccugcug accgacuaca gcccccagcu gcagaagccc aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua gaaaaaaaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa a 1471

<210> SEQ ID NO 101
<211> LENGTH: 1371
<212> TYPE: RNA

<213> ORGANISM: Artificial Sequence
<220> FEATURE:
<223> OTHER INFORMATION: Synthetic construct

<400> SEQUENCE: 101
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcug gucaaccugc gcauccugcu gaacaacgcc gccuuccgca 180
acggccacaa cuucauggug cgcaacuucc gcugcggcca gccccugcag aaccgggugc 240
agcugaaggg ccgcgaccug cugacccuga agaacuucac cggcgaggag aucaaguaca 300
ugcuguggcu gagcgccgac cugaaguucc gcaucaagca gaagggcgag uaccugcccc 360
ugcugcaggg caagagccug ggcaugaucu ucgagaagcg cagcacccgc acccgccuga 420
gcaccgagac aggcuucgcc cugcugggcg gccaccccug cuuccugacc acccaggaca 480
uccaccuggg cgugaacgag agccugaccg acaccgcccg cgugcugagc agcauggccg 540
acgccgugcu ggcccgcgug uacaagcaga gcgaccugga cacccuggcc aaggaggcca 600
gcauccccau caucaacggc cugagcgacc uguaccaccc cauccagauc cuggccgacu 660
accugacccu gcaggagcac uacagcagcc ugaagggccu gacccugagc uggaucggcg 720
acggcaacaa cauccugcac agcaucauga ugagcgccgc caaguucggc augcaccugc 780
aggccgccac ccccaagggc uacgagcccg acgccagcgu gaccaagcug gccgagcagu 840
acgccaagga gaacggcacc aagcugcugc ugaccaacga cccccuggag gccgcccacg 900
gcggcaacgu gcugaucacc gacaccugga ucagcauggg ccaggaggag gagaagaaga 960
agcgccugca ggccuuccag ggcuaccagg ugaccaugaa gaccgccaag guggccgcca 1020
gcgacuggac cuuccugcac ugccugcccc gcaagcccga ggagguggac gacgaggugu 1080
ucuacagccc ccgcagccug guguuccccg aggccgagaa ccgcaagugg accaucaugg 1140
ccgugauggu gagccugcug accgacuaca gcccccagcu gcagaagccc aaguucugau 1200
aacucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 102
<211> LENGTH: 1368
<212> TYPE: RNA
<213> ORGANISM: Artificial Sequence
<220> FEATURE:
<223> OTHER INFORMATION: Synthetic construct

<400> SEQUENCE: 102
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu gucaaucucc gcauccuccu uaacaacgcc gcguuuagaa 180
acggccacaa cuucaugguc cggaacuuca gauguggcca gccgcuucaa aacaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 103
<211> LENGTH: 1368
<212> TYPE: RNA
<213> ORGANISM: Artificial Sequence
<220> FEATURE:
<223> OTHER INFORMATION: Synthetic construct

<400> SEQUENCE: 103
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugcuu gucaaucucc gcauccuccu uaacaacgcc gcguuuagaa 180
acggccacaa cuucaugguc cggaacuuca gauguggcca gccgcuucaa aaccgggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuagc 1200
ucgagcuagu gacugacuag gaucugguua ccacuaaacc agccucaaga acacccgaau 1260
ggagucucua agcuacauaa uaccaacuua cacuuacaaa auguuguccc ccaaaaugua 1320
gccauucgua ucugcuccua auaaaaagaa aguuucuuca cauucuag 1368

<210> SEQ ID NO 104
<211> LENGTH: 1371
<212> TYPE: RNA
<213> ORGANISM: Artificial Sequence
<220> FEATURE:
<223> OTHER INFORMATION: Synthetic construct

<400> SEQUENCE: 104
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugggc cuugucaauc uccgcauccu ccuuaacaac gccgcguuua 180
gaaacggcca caacuucaug guccggaacu ucagaugugg ccagccgcuu caaaacaagg 240
uccagcugaa gggccgggau cuucugaccc ugaagaacuu uacuggcgaa gagaucaagu 300
acaugcucug gcucuccgcg gacuugaagu uccgcauuaa gcagaagggg gaauaccuuc 360
cgcugcuuca aggaaagagc cucggcauga ucuuugagaa gcgcucaacc aggacccgcc 420
uuucuacuga aacuggguuc gcgcugcucg guggccaccc cugcuuccug acgacccagg 480
acauccaccu cggagugaac gaaucccuca ccgauaccgc ccgggguguua ucgagcaugg 540 cagaugccgu gcuggccagg guguacaaac aguccgaucu ggacacucug gccaaggagg 600
cgucaauucc uauuaucaac ggccuuagug accucuacca uccgauucag auccuggccg 660
auuaccucac ccugcaagaa cacuacagcu cccugaaggg ucugacauug uccuggaucg 720
gcgacggcaa caacauucuc cauuccauca ugauguccgc cgcaaaauuc ggcaugcauc 780
uucaagccgc cacgccgaag gguuacgagc ccgacgcuuc cgugacuaag cucgccgagc 840
aguacgcuaa ggagaacgga accaagcuuc ugcugacuaa cgacccacua gaagcagccc 900
acgggggcaa cgugcuuauu acugacaccu ggaucuccau gggccaggaa gaagagaaaa 960
agaagcggcu gcaggcguuc cagggauauc aggucaccau gaaaaccgcc aaggucgcug 1020
ccuccgacug gaccuuccug cacugccugc cucgcaagcc ugaagaagug gacgacgagg 1080
uguucuacuc gccacggagc cucguguucc ccgaggccga gaauagaaag uggaccauca 1140
uggccgugau ggugucacug cucaccgacu acagcccgca gcuucagaag cccaaguucu 1200
agcucgagcu agugacugac uaggaucugg uuaccacuaa accagccuca agaacacccg 1260
aauggagucu cuaagcuaca uaauaccaac uuacacuuac aaaauguugu cccccaaaau 1320
guagccauuc guaucugcuc cuaauaaaaa gaaaguuucu ucacauucua g 1371

<210> SEQ ID NO 105
<211> LENGTH: 1485
<212> TYPE: RNA
<213> ORGANISM: Artificial Sequence
<220> FEATURE:
<223> OTHER INFORMATION: Synthetic construct

<400> SEQUENCE: 105
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccaugggc cuugucaauc uccgcauccu ccuuaacaac gccgcguuua 180
gaaacggcca caacuucaug guccggaacu ucagaugugg ccagccgcuu caaaaccggg 240

```
uccagcugaa gggccgggau cuucugaccc ugaagaacuu uacuggcgaa gagaucaagu     300
acaugcucug gcucuccgcg gacuugaagu uccgcauuaa gcagaagggg gaauaccuuc     360
cgcugcuuca aggaaagagc cucggcauga ucuuugagaa gcgcucaacc aggacccgcc     420
uuucuacuga aacuggguuc gcgcugcucg guggccaccc cugcuuccug acgacccagg     480
acauccaccu cggagugaac gaaucccuca ccgauaccgc ccggguguua ucgagcaugg     540
cagaugccgu gcuggccagg guguacaaac aguccgaucu ggacacucug gccaaggagg     600
cgucaauucc uauuaucaac ggccuuagug accucuacca uccgauucag auccuggccg     660
auuaccucac ccugcaagaa cacuacagcu cccugaaggg ucugacauug uccuggaucg     720
gcgacggcaa caacauucuc cauuccauca ugauguccgc cgcaaaauuc ggcaugcauc     780
uucaagccgc cacgccgaag gguuacgagc ccgacgcuuc cgugacuaag cucgccgagc     840
aguacgcuaa ggagaacgga accaagcuuc ugcugacuaa cgacccacua gaagcagccc     900
acgggggcaa cgugcuuauu acugacaccu ggaucuccau gggccaggaa gaagagaaaa     960
agaagcggcu gcaggcguuc cagggauauc aggucaccau gaaaaccgcc aaggucgcug    1020
ccuccgacug gaccuuccug cacugccugc cucgcaagcc ugaagaagug gacgacgagg    1080
uguucuacuc gccacggagc cucguguucc ccgaggccga gaauagaaag uggaccauca    1140
uggccgugau ggugucacug cucaccgacu acagcccgca gcuucagaag cccaaguucu    1200
agcucgagcu agugacugac uaggaucugg uuaccacuaa accagccuca agaacacccg    1260
aauggagucu cuaagcuaca uaauaccaac uuacacuuac aaaauguugu cccccaaaau    1320
guagccauuc guaucugcuc cuaauaaaaa gaaaguuucu ucacauucua gaaaaaaaaa    1380
aaaaaaaaaa aaaaaaaaaa aaaaaaaaaa aaaaaaaaaa aaaaaaaaaa aaaaaaaaaa    1440
aaaaaaaaaa aaaaaaaaaa aaaaaaaaaa aaaaaaaaaa aaaaa                    1485
```

```
<210> SEQ ID NO 106
<211> LENGTH: 1374
<212> TYPE: RNA
<213> ORGANISM: Artificial Sequence
<220> FEATURE:
<223> OTHER INFORMATION: Synthetic construct

<400> SEQUENCE: 106

ucaacacaac auauacaaaa caaacgaauc ucaagcaauc aagcauucua cuucuauugc      60
agcaauuuaa aucauuucuu uuaaagcaaa agcaauuuuc ugaaaauuuu caccauuuac     120
gaacgauagc caccaugggc ggacuuguca aucuccgcau ccuccuuaac aacgccgcgu     180
uuagaaacgg ccacaacuuc augguccgga acuucagaug uggccagccg cuucaaaaca     240
agguccagcu gaagggccgg gaucuucuga cccugaagaa cuuuacuggc gaagagauca     300
aguacaugcu cuggcucucc gcggacuuga aguuccgcau uaagcagaag gggggaauacc    360
uuccgcugcu ucaaggaaag agccucggca ugaucuuuga gaagcgcuca accaggaccc     420
gccuuucuac ugaaacuggg uucgcgcugc ucgguggcca ccccugcuuc cugacgaccc     480
aggacaucca ccucggagug aacgaauccc ucaccgauac cgcccgggug uuaucgagca     540
uggcagaugc cgugcuggcc agggguguaca aacaguccga ucuggacacu cuggccaagg    600
aggcgucaau uccuauuauc aacggccuua gugaccucua ccauccgauu cagauccugg     660
ccgauuaccu cacccugcaa gaacacuaca gcucccugaa gggucugaca uuguccugga     720
ucggcgacgg caacaacauu cuccauucca ucaugauguc cgccgcaaaa uucggcaugc     780
```

aucuucaagc cgccacgccg aagggguuacg agcccgacgc uuccgugacu aagcucgccg 840
agcaguacgc uaaggagaac ggaaccaagc uucugcugac uaacgaccca cuagaagcag 900
cccacggggg caacgugcuu auuacugaca ccuggaucuc caugggccag gaagaagaga 960
aaaagaagcg gcugcaggcg uuccagggau aucaggucac caugaaaacc gccaaggucg 1020
cugccuccga cuggaccuuc cugcacugcc ugccucgcaa gccugaagaa guggacgacg 1080
agguguucua cucgccacgg agccucgugu uccccgaggc cgagaauaga aaguggacca 1140
ucauggccgu gaugguguca cugcucaccg acuacagccc gcagcuucag aagcccaagu 1200
ucuagcucga gcuagugacu gacuaggauc ugguuaccac uaaaccagcc ucaagaacac 1260
ccgaauggag ucucuaagcu acauaauacc aacuuacacu uacaaaaugu uguccccaa 1320 aauguagcca uucguaucug cuccuaauaa aaagaaaguu ucuucacauu cuag 1374

<210> SEQ ID NO 107
<211> LENGTH: 1377
<212> TYPE: RNA
<213> ORGANISM: Artificial Sequence
<220> FEATURE:
<223> OTHER INFORMATION: Synthetic construct

<400> SEQUENCE: 107
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc cauggcccuu uucaaucucc gcauccuccu uaacaacgcc gcguuuagaa 180
acggccacaa cuucauggguc cggaacuuca gauguggcca gccgcuucaa ggcaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac ugguucgcg cugcucggug gccaccccug cuuccugacg acccaggaca 480
uccaccucgg agugaacgaa ucccucaccg auaccgcccg ggugguuaucg agcauggcag 540 augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuaga 1200
uaagugaacu cgagcuagug acugacuagg aucugguuac cacuaaacca gccucaagaa 1260
cacccgaaug gagucucuaa gcuacauaau accaacuuac acuuacaaaa uguuguccccc 1320 caaaauguag ccauucguau cugcuccuaa uaaaaagaaa guuucuucac auucuag 1377

<210> SEQ ID NO 108
<211> LENGTH: 1377

<212> TYPE: RNA
<213> ORGANISM: Artificial Sequence
<220> FEATURE:
<223> OTHER INFORMATION: Synthetic construct

<400> SEQUENCE: 108
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc cauggcccuu uucaaucucc gcauccuccu uaacaacgcc gcguuuagaa 180
acggccacaa cuucaugguc cggaacuuca gauguggcca gccgcuucaa ggccgggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuaga 1200
uaagugaacu cgagcuagug acugacuagg aucugguuac cacuaaacca gccucaagaa 1260
cacccgaaug gagucucuaa gcuacauaau accaacuuac acuuacaaaa uguuguccc c 1320 caaaauguag ccauucguau cugcuccuaa uaaaaagaaa guuucuucac auucuag 1377

<210> SEQ ID NO 109
<211> LENGTH: 1377
<212> TYPE: RNA
<213> ORGANISM: Artificial Sequence
<220> FEATURE:
<223> OTHER INFORMATION: Synthetic construct

<400> SEQUENCE: 109
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc cauggcccuu uucaaucucc gcauccuccu uaacaacgcc gcguuuagaa 180
acggccacaa cuucaugguc cggaacuuca gauguggcca gccgcuucaa ggccgggucc 240
agcugaaggg ccgggaucuu cugacccuga agaacuuuac uggcgaagag aucagguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480

-continued

```
uccaccucgg agugaacgaa ucccucaccg auaccgcccg gguguuaucg agcauggcag    540

augccgugcu ggccagggug uacaaacagu ccgaucugga cacucuggcc aaggaggcgu    600

caauuccuau uaucaacggc cuuagugacc ucuaccaucc gauucagauc cuggccgauu    660

accucacccu gcaagaacac uacagcuccc ugaagggucu gacauugucc uggaucggcg    720

acggcaacaa cauucuccau uccaucauga uguccgccgc aaaauucggc augcaucuuc    780

aagccgccac gccgaagggu uacgagcccg acgcuuccgu gacuaagcuc gccgagcagu    840

acgcuaagga gaacggaacc aagcuucugc ugacuaacga cccacuagaa gcagcccacg    900

ggggcaacgu gcuuauuacu gacaccugga ucuccauggg ccaggaagaa gagaaaaaga    960

agcggcugca ggcguuccag ggauaucagg ucaccaugaa aaccgccaag gucgcugccu   1020

ccgacuggac cuuccugcac ugccugccuc gcaagccuga agaaguggac gacgaggugu   1080

ucuacucgcc acggagccuc guguuccccg aggccgagaa uagaaagugg accaucaugg   1140

ccgugauggu gucacugcuc accgacuaca gcccgcagcu ucagaagccc aaguucuaga   1200

uaagugaacu cgagcuagug acugacuagg aucugguuac cacuaaacca gccucaagaa   1260

cacccgaaug gagucucuaa gcuacauaau accaacuuac acuuacaaaa uguuguccccc   1320

caaaauguag ccauucguau cugcuccuaa uaaaaagaaa guuucuucac auucuag      1377
```

<210> SEQ ID NO 110
<211> LENGTH: 1377
<212> TYPE: RNA
<213> ORGANISM: Artificial Sequence
<220> FEATURE:
<223> OTHER INFORMATION: Synthetic construct

<400> SEQUENCE: 110

```
ucaacacaac auauacaaaa caaacgaauc ucaagcaauc aagcauucua cuucuauugc     60

agcaauuuaa aucauuucuu uuaaagcaaa agcaauuuuc ugaaaauuuu caccauuuac    120

gaacgauagc cauggcccuu gucaaucucc gcauccuccu uaacaacgcc gcguuuagaa    180

acggccacaa cuucaugguc cggaacuuca gauguggcca gccgcuucaa ggcagggucc    240

agcugaaggg ccgggaucuu cugacccuga agaacuuuac uggcgaagag aucaaguaca    300

ugcucuggcu cuccgcggac uugaaguucc gcauuaagca gaaggggaa uaccuuccgc    360

ugcuucaagg aaagagccuc ggcaugaucu uugagaagcg cucaaccagg acccgccuuu    420

cuacugaaac uggguucgcg cugcucggug gccaccccug cuuccugacg acccaggaca    480

uccaccucgg agugaacgaa ucccucaccg auaccgcccg gguguuaucg agcauggcag    540

augccgugcu ggccagggug uacaaacagu ccgaucugga cacucuggcc aaggaggcgu    600

caauuccuau uaucaacggc cuuagugacc ucuaccaucc gauucagauc cuggccgauu    660

accucacccu gcaagaacac uacagcuccc ugaagggucu gacauugucc uggaucggcg    720

acggcaacaa cauucuccau uccaucauga uguccgccgc aaaauucggc augcaucuuc    780

aagccgccac gccgaagggu uacgagcccg acgcuuccgu gacuaagcuc gccgagcagu    840

acgcuaagga gaacggaacc aagcuucugc ugacuaacga cccacuagaa gcagcccacg    900

ggggcaacgu gcuuauuacu gacaccugga ucuccauggg ccaggaagaa gagaaaaaga    960

agcggcugca ggcguuccag ggauaucagg ucaccaugaa aaccgccaag gucgcugccu   1020

ccgacuggac cuuccugcac ugccugccuc gcaagccuga agaaguggac gacgaggugu   1080

ucuacucgcc acggagccuc guguuccccg aggccgagaa uagaaagugg accaucaugg   1140

ccgugauggu gucacugcuc accgacuaca gcccgcagcu ucagaagccc aaguucuaag   1200
```

ugaauagacu cgagcuagug acugacuagg aucugguuac cacuaaacca gccucaagaa 1260
cacccgaaug gagucucuaa gcuacauaau accaacuuac acuuacaaaa uguugucccc 1320
caaaauguag ccauucguau cugcuccuaa uaaaaagaaa guuucuucac auucuag 1377

<210> SEQ ID NO 111
<211> LENGTH: 1496
<212> TYPE: RNA
<213> ORGANISM: Artificial Sequence
<220> FEATURE:
<223> OTHER INFORMATION: Synthetic construct

<400> SEQUENCE: 111
ucaacacaac auauacaaaa caaacgaauc ucaagcaauc aagcauucua cuucuauugc 60
agcaauuuaa aucauuucuu uuaaaagcaaa agcaauuuuc ugaaaauuuu caccauuuac 120
gaacgauagc cauggcccuu uucaaucucc gcauccuccu uaacaacgcc gcguuuagaa 180
acggccacaa cuucaugguc cggaacuuca gauguggcca gccgcuucaa gucaaggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac ugguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagccccacg 900 ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuaga 1200
uaagugaacu cgagcuagug acugacuagg aucugguuac cacuaaacca gccucaagaa 1260
cacccgaaug gagucucuaa gcuacauaau accaacuuac acuuacaaaa uguugucccc 1320
caaaauguag ccauucguau cugcuccuaa uaaaaagaaa guuucuucac auucuagaaa 1380
aaaaaaaaaa aaaaaaaaaa aaaaaaaaaa aaaaaaaaaa aaaaaaaaaa aaaaaaaaaa 1440
aaaaaaaaaa aaaaaaaaaa aaaaaaaaaa aaaaaaaaaa aaaaaaaaaa aaaaaa 1496

<210> SEQ ID NO 112
<211> LENGTH: 1377
<212> TYPE: RNA
<213> ORGANISM: Artificial Sequence
<220> FEATURE:
<223> OTHER INFORMATION: Synthetic construct

<400> SEQUENCE: 112
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc cauggcccuu uucaaucucc gcauccuccu uaacaacgcc gcguuuagaa 180
acggccacaa cuucaugguc cggaacuuca gauguggcca gccgcuucaa gucagggucc 240
agcugaaggg ccgggaucuu cugacccuga agaacuuuac uggcgaagag aucaaguaca 300
ugcucuggcu cuccgcggac uugaaguucc gcauuaagca gaagggggaa uaccuuccgc 360
ugcuucaagg aaagagccuc ggcaugaucu uugagaagcg cucaaccagg acccgccuuu 420
cuacugaaac uggguucgcg cugcucggug gccaccccug cuuccugacg acccaggaca 480
uccaccucgg agugaacgaa ucccucaccg auaccgcccg gguguuaucg agcauggcag 540
augccgugcu ggccagggug uacaaacagu ccgaucugga cacucuggcc aaggaggcgu 600
caauuccuau uaucaacggc cuuagugacc ucuaccaucc gauucagauc cuggccgauu 660
accucacccu gcaagaacac uacagcuccc ugaagggucu gacauugucc uggaucggcg 720
acggcaacaa cauucuccau uccaucauga uguccgccgc aaaauucggc augcaucuuc 780
aagccgccac gccgaagggu uacgagcccg acgcuuccgu gacuaagcuc gccgagcagu 840
acgcuaagga gaacggaacc aagcuucugc ugacuaacga cccacuagaa gcagcccacg 900
ggggcaacgu gcuuauuacu gacaccugga ucuccauggg ccaggaagaa gagaaaaaga 960
agcggcugca ggcguuccag ggauaucagg ucaccaugaa aaccgccaag gucgcugccu 1020
ccgacuggac cuuccugcac ugccugccuc gcaagccuga agaaguggac gacgaggugu 1080
ucuacucgcc acggagccuc guguuccccg aggccgagaa uagaaagugg accaucaugg 1140
ccgugauggu gucacugcuc accgacuaca gcccgcagcu ucagaagccc aaguucuaga 1200
uaagugaacu cgagcuagug acugacuagg aucugguuac cacuaaacca gccucaagaa 1260
cacccgaaug gagucucuaa gcuacauaau accaacuuac acuuacaaaa uguuguccccc 1320 caaaauguag ccauucguau cugcuccuaa uaaaaagaaa guuucuucac auucuag 1377

<210> SEQ ID NO 113
<211> LENGTH: 1282
<212> TYPE: RNA
<213> ORGANISM: Artificial Sequence
<220> FEATURE:
<223> OTHER INFORMATION: Synthetic construct

<400> SEQUENCE: 113
ggcagaaaaa uuugcuacau uguuucacaa acuucaaaua uuauucauuu auuuagaucu 60
auuauuacau caaaacaaaa agccgccacc augcuguuca accugcgcau ccugcugaac 120
aacgccgccu uccgcaacgg ccacaacuuc auggugcgca acuuccgcug cggccagccc 180
cugcagaaca aggugcagcu gaagggccgc gaccugcuga cccugaagaa cuucaccggc 240
gaggagauca aguacaugcu guggcugagc gccgaccuga aguuccgcau caagcagaag 300
ggcgaguacc ugccccugcu gcagggcaag agccugggca ugaucuucga gaagcgcagc 360
acccgcaccc gccugagcac cgagacaggc uucgcccugc ugggcggcca ccccugcuuc 420
cugaccaccc aggacaucca ccugggcgug aacgagagcc ugaccgacac cgcccgcgug 480
cugagcagca uggccgacgc cgugcuggcc cgcguguaca agcagagcga ccuggacacc 540
cuggccaagg aggccagcau ccccaucauc aacggccuga gcgaccugua ccaccccauc 600
cagauccugg ccgacuaccu gacccugcag gagcacuaca gcagccugaa gggccugacc 660
cugagcugga ucggcgacgg caacaacauc cugcacagca ucaugaugag cgccgccaag 720
uucggcaugc accugcaggc cgccaccccc aagggcuacg agcccgacgc cagcgugacc 780
aagcuggccg agcaguacgc caaggagaac ggcaccaagc ugcugcugac caacgacccc 840
cuggaggccg cccacggcgg caacgugcug aucaccgaca ccuggaucag caugggccag 900
gaggaggaga agaagaagcg ccugcaggcc uuccagggcu accaggugac caugaagacc 960
gccaaggugg ccgccagcga cuggaccuuc cugcacugcc ugccccgcaa gcccgaggag 1020
guggacgacg agguguucua cagcccccgc agccuggugu uccccgaggc cgagaaccgc 1080
aaguggacca ucauggccgu gauggugagc cugcugaccg acuacagccc ccagcugcag 1140
aagcccaagu ucugaggucu cuaguaauga gcuggagccu cgguagccgu uccuccugcc 1200
cgcugggccu cccaacgggc ccuccucccc uccuugcacc ggcccuuccu ggucuuugaa 1260
uaaagucuga gugggcaucu ag 1282

<210> SEQ ID NO 114
<211> LENGTH: 1285
<212> TYPE: RNA
<213> ORGANISM: Artificial Sequence
<220> FEATURE:
<223> OTHER INFORMATION: Synthetic construct

<400> SEQUENCE: 114
ggcagaaaaa uuugcuacau uguuucacaa acuucaaaua uuauucauuu auuuagaucu 60
auuauuacau caaaacaaaa agccgccacc augggaguau ucaaccugcg cauccugcug 120
aacaacgccg ccuuccgcaa cggccacaac uucauggugc gcaacuuccg cugcggccag 180
ccccugcaga acaaggugca gcugaagggc cgcgaccugc ugacccugaa gaacuucacc 240
ggcgaggaga ucaaguacau gcuguggcug agcgccgacc ugaaguuccg caucaagcag 300
aagggcgagu accugcccu gcugcagggc aagagccugg gcaugaucuu cgagaagcgc 360
agcacccgca cccgccugag caccgagaca ggcuucgccc ugcugggcgg ccaccccugc 420
uuccugacca cccaggacau ccaccugggc gugaacgaga gccugaccga caccgcccgc 480
gugcugagca gcauggccga cgccgugcug gcccgcgugu acaagcagag cgaccuggac 540
acccuggcca aggaggccag caucccauc aucaacggcc ugagcgaccu guaccacccc 600
auccagaucc uggccgacua ccugacccug caggagcacu acagcagccu gaagggccug 660
acccugagcu ggaucggcga cggcaacaac auccugcaca gcaucaugau gagcgccgcc 720
aaguucggca ugcaccugca ggccgccacc cccaagggcu acgagcccga cgccagcgug 780
accaagcugg ccgagcagua cgccaaggag aacggcacca agcugcugcu gaccaacgac 840
ccccuggagg ccgcccacgg cggcaacgug cugaucaccg acaccuggau cagcaugggc 900
caggaggagg agaagaagaa gcgccugcag gccuuccagg gcuaccaggu gaccaugaag 960
accgccaagg uggccgccag cgacuggacc uuccugcacu gccugccccg caagcccgag 1020
gagguggacg acgagguguu cuacagcccc cgcagccugg uguuccccga ggccgagaac 1080
cgcaagugga ccaucauggc cgugauggug agccugcuga ccgacuacag cccccagcug 1140
cagaagccca aguucugagg ucucuaguaa ugagcuggag ccucgguagc cguuccuccu 1200
gcccgcuggg ccucccaacg ggcccuccuc cccuccuugc accggcccuu ccuggucuuu 1260
gaauaaaguc ugagugggca ucuag 1285

<210> SEQ ID NO 115
<211> LENGTH: 1285
<212> TYPE: RNA
<213> ORGANISM: Artificial Sequence
<220> FEATURE:

<223> OTHER INFORMATION: Synthetic construct

<400> SEQUENCE: 115

```
ggcagaaaaa uuugcuacau uguuucacaa acuucaaaua uuauucauuu auuuagaucu     60
auuauuacau caaaacaaaa agccgccacc augggaguau ucaaccugcg cauccugcug    120
aacaacgccg ccuuccgcaa cggccacaac uucauggugc gcaacuuccg cugcggccag    180
ccccugcaga accgggugca gcugaagggc cgcgaccugc ugacccugaa gaacuucacc    240
ggcgaggaga uccgguacau gcuguggcug agcgccgacc ugaaguuccg caucaagcag    300
aagggcgagu accugcccu gcugcagggc aagagccugg gcaugaucuu cgagaagcgc    360
agcacccgca cccgccugag caccgagaca ggcuucgccc ugcugggcgg ccaccccugc    420
uuccugacca cccaggacau ccaccugggc gugaacgaga gccugaccga caccgcccgc    480
gugcugagca gcauggccga cgccgugcug gcccgcgugu acaagcagag cgaccuggac    540
acccuggcca aggaggccag cauccccauc aucaacggcc ugagcgaccu guaccacccc    600
auccagaucc uggccgacua ccugacccug caggagcacu acagcagccu gaagggccug    660
acccugagcu ggaucggcga cggcaacaac auccugcaca gcaucaugau gagcgccgcc    720
aaguucggca ugcaccugca ggccgccacc cccaagggcu acgagcccga cgccagcgug    780
accaagcugg ccgagcagua cgccaaggag aacggcacca agcugcugcu gaccaacgac    840
ccccuggagg ccgcccacgg cggcaacgug cugaucaccg acaccuggau cagcaugggc    900
caggaggagg agaagaagaa gcgccugcag gccuuccagg gcuaccaggu gaccaugaag    960
accgccaagg uggccgccag cgacuggacc uuccugcacu gccugccccg caagcccgag   1020
gagguggacg acgaggguuu cuacagcccc cgcagccugg uguuccccga ggccgagaac   1080
cgcaagugga ccaucauggc cgugauggug agccugcuga ccgacuacag cccccagcug   1140
cagaagccca aguucugagg ucucuaguaa ugagcuggag ccucgguagc cguuccuccu   1200
gcccgcuggg ccucccaacg ggcccuccuc cccuccuugc accggcccuu ccuggucuuu   1260
gaauaaaguc ugagugggca ucuag                                         1285
```

<210> SEQ ID NO 116
<211> LENGTH: 1285
<212> TYPE: RNA
<213> ORGANISM: Artificial Sequence
<220> FEATURE:
<223> OTHER INFORMATION: Synthetic construct

<400> SEQUENCE: 116

```
ggcagaaaaa uuugcuacau uguuucacaa acuucaaaua uuauucauuu auuuagaucu     60
auuauuacau caaaacaaaa agccgccacc augcugguau ucaaccugcg cauccugcug    120
aacaacgccg ccuuccgcaa cggccacaac uucauggugc gcaacuuccg cugcggccag    180
ccccugcaga accgggugca gcugaagggc cgcgaccugc ugacccugaa gaacuucacc    240
ggcgaggaga uccgguacau gcuguggcug agcgccgacc ugaaguuccg caucaagcag    300
aagggcgagu accugcccu gcugcagggc aagagccugg gcaugaucuu cgagaagcgc    360
agcacccgca cccgccugag caccgagaca ggcuucgccc ugcugggcgg ccaccccugc    420
uuccugacca cccaggacau ccaccugggc gugaacgaga gccugaccga caccgcccgc    480
gugcugagca gcauggccga cgccgugcug gcccgcgugu acaagcagag cgaccuggac    540
acccuggcca aggaggccag cauccccauc aucaacggcc ugagcgaccu guaccacccc    600
auccagaucc uggccgacua ccugacccug caggagcacu acagcagccu gaagggccug    660
```

acccugagcu ggaucggcga cggcaacaac auccugcaca gcaucaugau gagcgccgcc 720
aaguucggca ugcaccugca ggccgccacc cccaagggcu acgagcccga cgccagcgug 780
accaagcugg ccgagcagua cgccaaggag aacggcacca agcugcugcu gaccaacgac 840
ccccuggagg ccgcccacgg cggcaacgug cugaucaccg acaccuggau cagcaugggc 900
caggaggagg agaagaagaa gcgccugcag gccuuccagg gcuaccaggu gaccaugaag 960
accgccaagg uggccgccag cgacuggacc uuccugcacu gccugccccg caagcccgag 1020
gagguggacg acgaggugtu cuacagcccc cgcagccugg uguuccccga ggccgagaac 1080
cgcaagugga ccaucauggc cgugauggug agccugcuga ccgacuacag cccccagcug 1140
cagaagccca aguucugagg ucucuaguaa ugagcuggag ccucgguagc cguuccuccu 1200
gcccgcuggg ccucccaacg ggcccuccuc cccuccuugc accggcccuu ccuggucuuu 1260
gaauaaaguc ugagugggca ucuag 1285

<210> SEQ ID NO 117
<211> LENGTH: 1225
<212> TYPE: RNA
<213> ORGANISM: Artificial Sequence
<220> FEATURE:
<223> OTHER INFORMATION: Synthetic construct

<400> SEQUENCE: 117
auuauuacau caaaacaaaa agccgccacc augggaguau ucaaccugcg cauccugcug 60
aacaacgccg ccuuccgcaa cggccacaac uucauggugc gcaacuuccg cugcggccag 120
ccccugcaga acaaggugca gcugaagggc cgcgaccugc ugacccugaa gaacuucacc 180
ggcgaggaga ucaaguacau gcuguggcug agcgccgacc ugaaguuccg caucaagcag 240
aagggcgagu accugcccu gcugcagggc aagagccugg gcaugaucuu cgagaagcgc 300
agcacccgca cccgccugag caccgagaca ggcuucgccc ugcugggcgg ccaccccugc 360
uuccugacca cccaggacau ccaccugggc gugaacgaga gccugaccga caccgcccgc 420
gugcugagca gcauggccga cgccgugcug gcccgcgugu acaagcagag cgaccuggac 480
acccuggcca aggaggccag cauccccauc aucaacggcc ugagcgaccu guaccacccc 540
auccagaucc uggccgacua ccugacccug caggagcacu acagcagccu gaagggccug 600
acccugagcu ggaucggcga cggcaacaac auccugcaca gcaucaugau gagcgccgcc 660
aaguucggca ugcaccugca ggccgccacc cccaagggcu acgagcccga cgccagcgug 720
accaagcugg ccgagcagua cgccaaggag aacggcacca agcugcugcu gaccaacgac 780
ccccuggagg ccgcccacgg cggcaacgug cugaucaccg acaccuggau cagcaugggc 840
caggaggagg agaagaagaa gcgccugcag gccuuccagg gcuaccaggu gaccaugaag 900
accgccaagg uggccgccag cgacuggacc uuccugcacu gccugccccg caagcccgag 960
gagguggacg acgaggugtu cuacagcccc cgcagccugg uguuccccga ggccgagaac 1020
cgcaagugga ccaucauggc cgugauggug agccugcuga ccgacuacag cccccagcug 1080
cagaagccca aguucugagg ucucuaguaa ugagcuggag ccucgguagc cguuccuccu 1140
gcccgcuggg ccucccaacg ggcccuccuc cccuccuugc accggcccuu ccuggucuuu 1200
gaauaaaguc ugagugggca ucuag 1225

<210> SEQ ID NO 118
<211> LENGTH: 1225
<212> TYPE: RNA

<213> ORGANISM: Artificial Sequence
<220> FEATURE:
<223> OTHER INFORMATION: Synthetic construct

<400> SEQUENCE: 118
auuauuacau caaaacaaaa agccgccacc augggaguau ucaaccugcg cauccugcug 60
aacaacgccg ccuuccgcaa cggccacaac uucauggugc gcaacuuccg cugcggccag 120
ccccugcaga accgggugca gcugaagggc cgcgaccugc ugacccugaa gaacuucacc 180
ggcgaggaga uccgguacau gcuguggcug agcgccgacc ugaaguuccg caucaagcag 240
aagggcgagu accugcccu gcugcagggc aagagccugg gcaugaucuu cgagaagcgc 300
agcacccgca cccgccugag caccgagaca ggcuucgccc ugcugggcgg ccaccccugc 360
uuccugacca cccaggacau ccaccugggc gugaacgaga gccugaccga caccgcccgc 420
gugcugagca gcauggccga cgccgugcug gcccgcgugu acaagcagag cgaccuggac 480
acccuggcca aggaggccag caucccauc aucaacggcc ugagcgaccu guaccacccc 540
auccagaucc uggccgacua ccugacccug caggagcacu acagcagccu gaagggccug 600
acccugagcu ggaucggcga cggcaacaac auccugcaca gcaucaugau gagcgccgcc 660
aaguucggca ugcaccugca ggccgccacc cccaagggcu acgagcccga cgccagcgug 720
accaagcugg ccgagcagua cgccaaggag aacggcacca agcugcugcu gaccaacgac 780
ccccuggagg ccgcccacgg cggcaacgug cugaucaccg acaccuggau cagcaugggc 840
caggaggagg agaagaagaa gcgccugcag gccuuccagg gcuaccaggu gaccaugaag 900
accgccaagg uggccgccag cgacuggacc uuccugcacu gccugccccg caagcccgag 960
gagguggacg acgaggugu cuacagcccc cgcagccugg uguuccccga ggccgagaac 1020
cgcaagugga ccaucauggc cgugauggug agccugcuga ccgacuacag cccccagcug 1080
cagaagccca aguucugagg ucucuaguaa ugagcuggag ccucgguagc cguuccuccu 1140
gcccgcuggg ccucccaacg ggcccuccuc cccuccuugc accggcccuu ccuggucuuu 1200
gaauaaaguc ugagugggca ucuag 1225

<210> SEQ ID NO 119
<211> LENGTH: 1228
<212> TYPE: RNA
<213> ORGANISM: Artificial Sequence
<220> FEATURE:
<223> OTHER INFORMATION: Synthetic construct

<400> SEQUENCE: 119
auuauuacau caaaacaaaa agccgccacc augcugguau ucaaccugcg cauccugcug 60
aacaacgccg ccuuccgcaa cggccacaac uucauggugc gcaacuuccg cugcggccag 120
ccccugcaga accgggugca gcugaagggc cgcgaccugc ugacccugaa gaacuucacc 180
ggcgaggaga uccgguacau gcuguggcug agcgccgacc ugaaguuccg caucaagcag 240
aagggcgagu accugcccu gcugcagggc aagagccugg gcaugaucuu cgagaagcgc 300
agcacccgca cccgccugag caccgagaca ggcuucgccc ugcugggcgg ccaccccugc 360
uuccugacca cccaggacau ccaccugggc gugaacgaga gccugaccga caccgcccgc 420
gugcugagca gcauggccga cgccgugcug gcccgcgugu acaagcagag cgaccuggac 480
acccuggcca aggaggccag caucccauc aucaacggcc ugagcgaccu guaccacccc 540
auccagaucc uggccgacua ccugacccug caggagcacu acagcagccu gaagggccug 600
acccugagcu ggaucggcga cggcaacaac auccugcaca gcaucaugau gagcgccgcc 660
aaguucggca ugcaccugca ggccgccacc cccaagggcu acgagcccga cgccagcgug 720
accaagcugg ccgagcagua cgccaaggag aacggcacca agcugcugcu gaccaacgac 780
ccccuggagg ccgcccacgg cggcaacgug cugaucaccg acaccuggau cagcaugggc 840
caggaggagg agaagaagaa gcgccugcag gccuuccagg gcuaccaggu gaccaugaag 900
accgccaagg uggccgccag cgacuggacc uuccugcacu gccugccccg caagcccgag 960
gagguggacg acgagguguu cuacagcccc cgcagccugg uguuccccga ggccgagaac 1020
cgcaagugga ccaucauggc cgugauggug agccugcuga ccgacuacag cccccagcug 1080
cagaagccca aguucugagg ucucuaguaa ugagcuggag ccucgguagc cguuccuccu 1140
gcccgcuggg ccucccaacg ggcccuccuc cccuccuugc accggcccuu ccuggucuuu 1200
gaauaaaguc ugagugggca gcaucuag 1228

<210> SEQ ID NO 120
<211> LENGTH: 1376
<212> TYPE: RNA
<213> ORGANISM: Artificial Sequence
<220> FEATURE:
<223> OTHER INFORMATION: Synthetic construct

<400> SEQUENCE: 120
ucaacacaac auauacaaaa caaacgaauc ucaagcaauc aagcauucua cuucuauugc 60
agcaauuuaa aucauuucuu uuaaagcaaa agcaauuuuc ugaaaauuuu caccauuuac 120
gaacgauagc caccauguug uucaacuuga ggaucuuguu gaacaacgcc gccuucagga 180
acggacacaa cuucauggua aggaacuuca ggugcggaca gcccuugcag aacaaaguac 240
aguugaaagg aagggacuug uugacauuga aaaacuucac aggagaagaa aucaaauaca 300
uguugugguu gucggccgac uugaaauuca ggaucaaaca gaaaggagaa uacuugcccu 360
uguugcaggg aaaaucguug ggaaugaucu ucgaaaaaag gucgacaagg acaagguugu 420
cgacagaaac aggauucgcc uuguugggag gacaccccug cuucuugaca acacaggaca 480
uccacuuggg aguaaacgaa ucguugacag acacagccag gguauugucg ucgauggccg 540
acgccguauu ggccagggua uacaaacagu cggacuugga cacauuggcc aaagaagccu 600
cgauccccau caucaacgga uugucggacu uguaccaccc cauccagauc uuggccgacu 660
acuugacauu gcaggaacac uacucgucgu ugaaaggauu gacauugucg uggaucggag 720
acggaaacaa caucuugcac ucgaucauga ugucggccgc caaauucgga augcacuugc 780
aggccgccac acccaaagga uacgaacccg acgccucggu aacaaaauug gccgaacagu 840
acgccaaaga aaacggaaca aaauuguugu ugacaaacga ccccuuggaa gccgcccacg 900
gaggaaacgu auugaucaca gacacaugga ucucgauggg acaggaagaa gaaaaaaaaa 960
aaagguugca ggccuuccag ggauaccagg uaacaaugaa aacagccaaa guagccgccu 1020
cggacuggac auucuugcac ugcuugccca ggaaacccga agaaguagac gacgaaguau 1080
ucuacucgcc caggucguug guauuccccg aagccgaaaa caggaaaugg acaaucaugg 1140
ccguaauggu aucguuguug acagacuacu cgccccaguu gcagaaaccc aaauucugaa 1200
uagugaacuc gagcuaguga cugacuagga ucugguuacc acuaaaccag ccucaagaac 1260
acccgaaugg agucucuaag cuacauaaua ccaacuuaca cuuacaaaau guuguccccc 1320
aaaauguagc cauucguauc ugcuccuaau aaaaagaaag uuucuucaca uucuag 1376

<210> SEQ ID NO 121

<211> LENGTH: 1222
<212> TYPE: RNA
<213> ORGANISM: Artificial Sequence
<220> FEATURE:
<223> OTHER INFORMATION: Synthetic construct

<400> SEQUENCE: 121
auuauuacau caaaacaaaa agccgccacc augcuguuca accugcgcau ccugcugaac 60
aacgccgccu uccgcaacgg ccacaacuuc auggugcgca acuuccgcug cggccagccc 120
cugcagggca aggugcagcu gaagggccgc gaccugcuga cccugaagaa cuucaccggc 180
gaggagauca aguacaugcu guggcugagc gccgaccuga aguuccgcau caagcagaag 240
ggcgaguacc ugccccugcu gcagggcaag agccugggca ugaucuucga gaagcgcagc 300
acccgcaccc gccugagcac cgagacaggc uucgcccugc ugggcggcca ccccugcuuc 360
cugaccaccc aggacaucca ccugggcgug aacgagagcc ugaccgacac cgcccgcgug 420
cugagcagca uggccgacgc cgugcuggcc cgcguguaca agcagagcga ccuggacacc 480
cuggccaagg aggccagcau ccccaucauc aacggccuga gcgaccugua ccaccccauc 540
cagauccugg ccgacuaccu gacccugcag gagcacuaca gcagccugaa gggccugacc 600
cugagcugga ucggcgacgg caacaacauc cugcacagca ucaugaugag cgccgccaag 660
uucggcaugc accugcaggc cgccaccccc aagggcuacg agcccgacgc cagcgugacc 720
aagcuggccg agcaguacgc caaggagaac ggcaccaagc ugcugcugac caacgacccc 780
cuggaggccg cccacggcgg caacgugcug aucaccgaca ccuggaucag caugggccag 840
gaggaggaga agaagaagcg ccugcaggcc uuccagggcu accaggugac caugaagacc 900
gccaaggugg ccgccagcga cuggaccuuc cugcacugcc ugccccgcaa gcccgaggag 960
guggacgacg agguguucua cagcccccgc agccuggugu uccccgaggc cgagaaccgc 1020
aaguggacca ucauggccgu gauggugagc cugcugaccg acuacagccc ccagcugcag 1080
aagcccaagu ucugaggucu cuaguaauga gcuggagccu cgguagccgu uccuccugcc 1140
cgcugggccu cccaacgggc ccuccucccc uccuugcacc ggcccuuccu ggucuuugaa 1200
uaaagucuga gugggcaucu ag 1222

<210> SEQ ID NO 122
<211> LENGTH: 1222
<212> TYPE: RNA
<213> ORGANISM: Artificial Sequence
<220> FEATURE:
<223> OTHER INFORMATION: Synthetic construct

<400> SEQUENCE: 122
auuauuacau caaaacaaaa agccgccacc augcuguuca accugcgcau ccugcugaac 60
aacgccgccu uccgcaacgg ccacaacuuc auggugcgca acuuccgcug cggccagccc 120
cugcagggcc gggugcagcu gaagggccgc gaccugcuga cccugaagaa cuucaccggc 180
gaggagauca aguacaugcu guggcugagc gccgaccuga aguuccgcau caagcagaag 240
ggcgaguacc ugccccugcu gcagggcaag agccugggca ugaucuucga gaagcgcagc 300
acccgcaccc gccugagcac cgagacaggc uucgcccugc ugggcggcca ccccugcuuc 360
cugaccaccc aggacaucca ccugggcgug aacgagagcc ugaccgacac cgcccgcgug 420
cugagcagca uggccgacgc cgugcuggcc cgcguguaca agcagagcga ccuggacacc 480
cuggccaagg aggccagcau ccccaucauc aacggccuga gcgaccugua ccaccccauc 540
cagauccugg ccgacuaccu gacccugcag gagcacuaca gcagccugaa gggccugacc 600
cugagcugga ucggcgacgg caacaacauc cugcacagca ucaugaugag cgccgccaag 660
uucggcaugc accugcaggc cgccaccccc aagggcuacg agcccgacgc cagcgugacc 720
aagcuggccg agcaguacgc caaggagaac ggcaccaagc ugcugcugac caacgacccc 780
cuggaggccg cccacggcgg caacgugcug aucaccgaca ccuggaucag caugggccag 840
gaggaggaga agaagaagcg ccugcaggcc uuccagggcu accaggugac caugaagacc 900
gccaaggugg ccgccagcga cuggaccuuc cugcacugcc ugccccgcaa gcccgaggag 960
guggacgacg agguguucua cagcccccgc agccuggugu uccccgaggc cgagaaccgc 1020
aaguggacca ucauggccgu gauggugagc cugcugaccg acuacagccc ccagcugcag 1080
aagcccaagu ucugaggucu cuaguaauga gcuggagccu cgguagccgu uccuccugcc 1140
cgcugggccu cccaacgggc ccuccucccc uccuugcacc ggcccuuccu ggucuuugaa 1200
uaaagucuga gugggcaucu ag 1222

<210> SEQ ID NO 123
<211> LENGTH: 1222
<212> TYPE: RNA
<213> ORGANISM: Artificial Sequence
<220> FEATURE:
<223> OTHER INFORMATION: Synthetic construct

<400> SEQUENCE: 123
auuauuacau caaaacaaaa agccgccacc augcuguuca accugcgcau ccugcugaac 60
aacgccgccu uccgcaacgg ccacaacuuc auggugcgca acuuccgcug cggccagccc 120
cugcagggcc gggugcagcu gaagggccgc gaccugcuga cccugaagaa cuucaccggc 180
gaggagaucc gguacaugcu guggcugagc gccgaccuga aguuccgcau caagcagaag 240
ggcgaguacc ugccccugcu gcagggcaag agccugggca ugaucuucga gaagcgcagc 300
acccgcaccc gccugagcac cgagacaggc uucgcccugc ugggcggcca ccccugcuuc 360
cugaccaccc aggacaucca ccugggcgug aacgagagcc ugaccgacac cgcccgcgug 420
cugagcagca uggccgacgc cgugcuggcc cgcguguaca agcagagcga ccuggacacc 480
cuggccaagg aggccagcau ccccaucauc aacggccuga gcgaccugua ccaccccauc 540
cagauccugg ccgacuaccu gacccugcag gagcacuaca gcagccugaa gggccugacc 600
cugagcugga ucggcgacgg caacaacauc cugcacagca ucaugaugag cgccgccaag 660
uucggcaugc accugcaggc cgccaccccc aagggcuacg agcccgacgc cagcgugacc 720
aagcuggccg agcaguacgc caaggagaac ggcaccaagc ugcugcugac caacgacccc 780
cuggaggccg cccacggcgg caacgugcug aucaccgaca ccuggaucag caugggccag 840
gaggaggaga agaagaagcg ccugcaggcc uuccagggcu accaggugac caugaagacc 900
gccaaggugg ccgccagcga cuggaccuuc cugcacugcc ugccccgcaa gcccgaggag 960
guggacgacg agguguucua cagcccccgc agccuggugu uccccgaggc cgagaaccgc 1020
aaguggacca ucauggccgu gauggugagc cugcugaccg acuacagccc ccagcugcag 1080
aagcccaagu ucugaggucu cuaguaauga gcuggagccu cgguagccgu uccuccugcc 1140
cgcugggccu cccaacgggc ccuccucccc uccuugcacc ggcccuuccu ggucuuugaa 1200
uaaagucuga gugggcaucu ag 1222

<210> SEQ ID NO 124
<211> LENGTH: 1282
<212> TYPE: RNA

<213> ORGANISM: Artificial Sequence
<220> FEATURE:
<223> OTHER INFORMATION: Synthetic construct

<400> SEQUENCE: 124
ggcagaaaaa uuugcuacau uguuucacaa acuucaaaua uuauucauuu auuuagaucu 60
auuauuacau caaaacaaaa agccgccacc augcuguuca accugcgcau ccugcugaac 120
aacgccgccu uccgcaacgg ccacaacuuc auggugcgca acuuccgcug cggccagccc 180
cugcagggca aggugcagcu gaagggccgc gaccugcuga cccugaagaa cuucaccggc 240
gaggagauca aguacaugcu guggcugagc gccgaccuga aguuccgcau caagcagaag 300
ggcgaguacc ugccccugcu gcagggcaag agccugggca ugaucuucga gaagcgcagc 360
acccgcaccc gccugagcac cgagacaggc uucgcccugc ugggcggcca ccccugcuuc 420
cugaccaccc aggacaucca ccugggcgug aacgagagcc ugaccgacac cgcccgcgug 480
cugagcagca uggccgacgc cgugcuggcc cgcguguaca agcagagcga ccuggacacc 540
cuggccaagg aggccagcau ccccaucauc aacggccuga gcgaccugua ccaccccauc 600
cagauccugg ccgacuaccu gacccugcag gagcacuaca gcagccugaa gggccugacc 660
cugagcugga ucggcgacgg caacaacauc cugcacagca ucaugaugag cgccgccaag 720
uucggcaugc accugcaggc cgccaccccc aagggcuacg agcccgacgc cagcgugacc 780
aagcuggccg agcaguacgc caaggagaac ggcaccaagc ugcugcugac caacgacccc 840
cuggaggccg cccacggcgg caacgugcug aucaccgaca ccuggaucag caugggccag 900
gaggaggaga agaagaagcg ccugcaggcc uuccagggcu accaggugac caugaagacc 960
gccaaggugg ccgccagcga cuggaccuuc cugcacugcc ugccccgcaa gcccgaggag 1020
guggacgacg agguguucua cagcccccgc agccuggugu uccccgaggc cgagaaccgc 1080
aaguggacca ucauggccgu gauggugagc cugcugaccg acuacagccc ccagcugcag 1140
aagcccaagu ucugaggucu cuaguaauga gcuggagccu cgguagccgu uccuccugcc 1200
cgcugggccu cccaacgggc ccuccucccc uccuugcacc ggcccuuccu ggucuuugaa 1260
uaaagucuga gugggcaucu ag 1282

<210> SEQ ID NO 125
<211> LENGTH: 21
<212> TYPE: RNA
<213> ORGANISM: Artificial Sequence
<220> FEATURE:
<223> OTHER INFORMATION: Synthetic construct

<400> SEQUENCE: 125
cacaaagagu aaagaagaac a 21

<210> SEQ ID NO 126
<211> LENGTH: 21
<212> TYPE: RNA
<213> ORGANISM: Artificial Sequence
<220> FEATURE:
<223> OTHER INFORMATION: Synthetic construct

<400> SEQUENCE: 126
aacacuaaaa guagaagaaa a 21

<210> SEQ ID NO 127
<211> LENGTH: 21
<212> TYPE: RNA
<213> ORGANISM: Artificial Sequence
<220> FEATURE:
<223> OTHER INFORMATION: Synthetic construct

<400> SEQUENCE: 127
cucagaaaga uaagaucagc c 21

<210> SEQ ID NO 128
<211> LENGTH: 1065
<212> TYPE: DNA
<213> ORGANISM: Artificial Sequence
<220> FEATURE:
<223> OTHER INFORMATION: Synthetic construct

<400> SEQUENCE: 128
atgctgttta atctgaggat cctgttaaac aatgcagctt ttagaaatgg tcacaacttc 60
atggttcgaa attttcggtg tggacaacca ctacaaaata aagtgcagct gaagggccgt 120
gaccttctca ctctaaaaaa ctttaccgga gaagaaatta aatatatgct atggctatca 180
gcagatctga aatttaggat aaaacagaaa ggagagtatt tgcctttatt gcaagggaag 240
tccttaggca tgatttttga gaaaagaagt actcgaacaa gattgtctac agaaacaggc 300
tttgcacttc tgggaggaca tccttgtttt cttaccacac aagatattca tttgggtgtg 360
aatgaaagtc tcacggacac ggcccgtgta ttgtctagca tggcagatgc agtattggct 420
cgagtgtata aacaatcaga tttggacacc ctggctaaag aagcatccat cccaattatc 480
aatgggctgt cagatttgta ccatcctatc cagatcctgg ctgattacct cacgctccag 540
gaacactata gctctctgaa aggtcttacc ctcagctgga tcggggatgg gaacaatatc 600
ctgcactcca tcatgatgag cgcagcgaaa ttcggaatgc accttcaggc agctactcca 660
aagggttatg agccggatgc tagtgtaacc aagttggcag agcagtatgc caaagagaat 720
ggtaccaagc tgttgctgac aaatgatcca ttggaagcag cgcatggagg caatgtatta 780
attacagaca cttggataag catgggacaa gaagaggaga agaaaaagcg gctccaggct 840
ttccaaggtt accaggttac aatgaagact gctaaagttg ctgcctctga ctggacattt 900
ttacactgct tgcccagaaa gccagaagaa gtggatgatg aagtctttta ttctcctcga 960
tcactagtgt tcccagaggc agaaaacaga aagtggacaa tcatggctgt catggtgtcc 1020
ctgctgacag attactcacc tcagctccag aagcctaaat tttga 1065

<210> SEQ ID NO 129
<211> LENGTH: 1065
<212> TYPE: DNA
<213> ORGANISM: Artificial Sequence
<220> FEATURE:
<223> OTHER INFORMATION: Synthetic construct

<400> SEQUENCE: 129
atgctcttta atctgcgcat cttactgaac aacgccgcat tccggaacgg tcacaacttc 60
atggtccgca atttccgctg tggccagccg cttcaaaaca aggtccagct gaagggacgg 120
gatctgctga cactgaagaa cttcaccgga gaagagatca agtacatgct gtggctcagc 180
gcagacttga agttccggat caagcagaag ggagaatact tgcccctgct gcaaggaaag 240
tcgctgggaa tgatttttga gaagcggtca actcgcacca gactctccac cgaaactggt 300
ttcgcactgc ttggcgggca cccttgcttc ctgacgactc aggacatcca cctcggcgtg 360
aacgaatcgc taaccgatac cgccagagtg ctttcttcca tggccgacgc ggtgctggcc 420
agggtgtaca agcagtccga cctcgatacc ttggcaaagg aggcttccat tcccatcatc 480
aacggcctga gcgacctgta ccacccaatc caaatcctgg ctgactacct gaccctgcaa 540
gagcactaca gcagcctgaa gggtctgacc ctgtcatgga ttggcgatgg aaacaatatt 600
ctgcactcca tcatgatgtc cgccgcgaag ttcggaatgc atctgcaagc cgccactcca 660
aaaggatacg aaccggatgc gtccgtgacc aagttggcgg aacagtacgc gaaggagaac 720
ggaaccaagc ttctgctgac taacgacccc ctcgaggctg cgcatggggg caacgtgctg 780
attaccgaca cctggatctc catggggcag gaggaagaga agaagaagag actgcaggca 840
ttccaggggt accaggtcac catgaaaacc gcaaaagtgg cagcttcgga ctggactttc 900
ctgcattgcc tgccgaggaa gccggaggaa gtcgacgacg aagtgttcta ctcgcctcgg 960
tccctggtgt tccccgaggc cgaaaaccgg aagtggacca tcatggccgt gatggtgtcc 1020
ttgctgactg actatagccc gcagctgcag aagcctaagt tctag 1065

<210> SEQ ID NO 130
<211> LENGTH: 1065
<212> TYPE: DNA
<213> ORGANISM: Artificial Sequence
<220> FEATURE:
<223> OTHER INFORMATION: Synthetic construct

<400> SEQUENCE: 130
atgctgttta acctacgtat tttgctcaac aatgcagcct ttagaaacgg acataacttt 60
atggttcgaa actttcgctg cgggcagcca ctgcagaaca aggtccagct gaaagggaga 120
gatttgctca cgctgaagaa ctttactggc gaagaaatca agtatatgct gtggttgtcc 180
gcggacctca agtttcggat taagcagaaa ggggagtatc tgccactgct gcaaggaaag 240
agcctcggca tgatcttcga gaagcggagc actcggacca ggctgagtac cgaaactggc 300
ttcgcattgt tgggtggaca tccatgtttt ctgacaacgc aggacattca tctgggcgtg 360
aacgagagtc tgacggacac agctcgcgtt ctgtcctcta tggctgatgc ggtgttggcc 420
cgggtctata agcagtccga tttggacacc ttggctaagg aagctagcat accgattatc 480
aatgggctgt ccgacctgta tcaccctatt caaatcctgg ccgactacct cacactgcaa 540
gaacactata gctcattgaa gggactgacc ctgagctgga taggggacgg aaacaacatc 600
ctacatagca ttatgatgtc cgctgccaag tttggcatgc atcttcaagc cgccacgcca 660
aagggttatg agcccgacgc gtcagtgaca aagctggccg agcagtacgc taaggagaat 720
ggtaccaaat tactgctgac taatgatcca ctggaggctg cacatggcgg caatgtactg 780
atcaccgaca catggatctc gatgggccag gaggaagaaa agaagaagag gcttcaggcc 840
ttccaaggct accaggtcac catgaaaaca gctaaggttg cagcatctga ttggaccttt 900
ctgcactgtc tgccaaggaa gcccgaagag gtggacgatg aagtattcta tagcccacgg 960
agtttggtgt tccctgaggc tgaaaatagg aagtggacaa ttatggccgt aatggtgtcc 1020
ctgttaaccg actactctcc gcaactgcag aaacctaagt tttag 1065

<210> SEQ ID NO 131
<211> LENGTH: 1065
<212> TYPE: DNA
<213> ORGANISM: Artificial Sequence
<220> FEATURE:
<223> OTHER INFORMATION: Synthetic construct

<400> SEQUENCE: 131
atgctgttta acttaaggat cctgctgaac aacgccgctt ttcgtaacgg tcataacttt 60
atggtccgga actttagatg tggccagccg ctgcagaaca aggttcagct gaaggggagg 120
gatctgctga ccttgaagaa ctttaccggc gaagagatca agtacatgtt gtggctgagc 180
gccgatctga agtttaggat taagcagaag ggggagtatt tgccactgct gcaaggaaaa 240
tccttgggga tgatcttcga gaagcgctcc actagaaccc ggctaagcac agaaaccggc 300
ttcgcacttc tgggtggaca tccctgtttt ctgacgacgc aggatataca cctgggcgtg 360
aatgagagtc tgacggacac agctagggtg ttgagcagca tggccgatgc agtactggcc 420
cgcgtttata agcagagcga cttggacaca ctggccaagg aagcgtcaat tccgattatc 480
aatgggctgt cagacctgta tcatcccatt caaatcttgg ctgactatct gaccctgcaa 540
gaacattaca gctccctgaa gggcctcacg ttgtcctgga ttggcgacgg aaacaacatt 600
ctgcattcga tcatgatgag cgctgctaag tttggcatgc acctccaagc cgctacacct 660
aagggatatg agcctgatgc cagcgtaacc aagctggccg aacagtacgc gaaggagaat 720
ggcacgaaac tgctgttgac aaatgaccca ctggaggcag ctcacggtgg caacgtgctg 780
atcaccgaca cgtggatatc tatgggacag gaagaagaga agaagaagcg gctgcaggca 840
ttccaagggt atcaggtcac catgaaaacg gccaaggttg ctgcatccga ctggacattt 900
ctgcattgct tgccccgcaa accagaagaa gtagacgacg aagtctttta ttccccacgg 960
tcgctggtgt tccccgaggc ggagaatcga aagtggacga ttatggccgt gatggtgtcc 1020
ctgctgactg attactctcc ccaactgcaa aagcctaagt tttag 1065

<210> SEQ ID NO 132
<211> LENGTH: 1065
<212> TYPE: DNA
<213> ORGANISM: Artificial Sequence
<220> FEATURE:
<223> OTHER INFORMATION: Synthetic construct

<400> SEQUENCE: 132
atgcttttca acctgaggat cctcctgaac aacgccgcct ttcgcaatgg tcacaacttt 60
atggtccgga acttcagatg cggccagccg ctgcagaaca aggtccagct gaagggacgg 120
gatctgctga ctctgaagaa cttcaccgga gaagagatca agtacatgct gtggctgtcg 180
gccgacctga agttcaggat caagcagaag ggagaatacc tcccgctgct gcaaggaaag 240
tccctgggca tgattttcga gaagcgctcg accagaactc ggttgtccac cgaaaccggg 300
tttgcgctgc tgggcggaca tccttgcttc ctgacgactc aggatattca cctgggagtg 360
aacgagtcgc tgaccgacac cgccagagtg ctgagctcga tggccgacgc cgtgttggca 420
cgcgtgtaca agcagtccga tctggatacc ctggccaaag aagcttccat cccgatcatt 480
aacgggctga gcgacctcta ccaccccatt caaatcctgg ccgactacct gactctgcaa 540
gaacactaca gctcgctgaa ggggttgact ctgtcctgga tcggcgacgg aaacaacatc 600
ctgcactcca tcatgatgtc ggccgcaaag ttcggcatgc atttgcaagc cgccaccccca 660 aagggctacg aaccagacgc gagcgtcacc aagctggccg aacagtacgc gaaggaaaat 720
ggtactaagc tgctgctgac caacgaccca ttggaagctg cccatggtgg aaacgtgctg 780
atcaccgaca cctggatctc gatgggccag gaagaggaga agaagaagcg gctgcaggcg 840
ttccaggggt atcaggtcac catgaaaaca gccaaagtgg cagcgtcaga ctggaccttc 900
ctccactgtc tgcctcgcaa gccagaggag gtggacgacg aggtgttcta ctcccctcgg 960
tccctcgtgt tccctgaggc tgagaaccgg aagtggacca ttatggccgt gatggtgtca 1020
ctcctgactg attactcccc gcaactgcag aagcccaagt tctag 1065

<210> SEQ ID NO 133
<211> LENGTH: 1065
<212> TYPE: DNA
<213> ORGANISM: Artificial Sequence
<220> FEATURE:
<223> OTHER INFORMATION: Synthetic construct

<400> SEQUENCE: 133
atgctgttta acctgaggat cctattgaac aatgctgctt ttcgtaatgg ccataacttt 60
atggttcgga actttagatg cgggcagcca ctgcagaaca aggtccagtt gaaaggccgc 120
gatctgttga cattgaagaa ctttaccggc gaagagatta agtatatgct gtggctgtct 180
gctgacctca agtttcgaat caagcagaag ggcgaatatc tccccctgct gcaaggaaag 240
tctctcggca tgatctttga gaagcggagt acccgaacac ggctgagcac cgaaacgggc 300
ttcgcactgc tgggggggcca tccctgtttt ctgacaacgc aggacatcca cttgggggtt 360
aacgaatcat tgactgatac cgcccgcgta ctgtcatcca tggccgacgc tgtgctggct 420
agggtgtaca agcagtcaga tctggataca ctggccaagg aagctagcat accaatcatc 480
aatggactga gtgaccttta tcacccgatt caaatactag ccgattatct gaccctgcaa 540
gagcattact cctcgctgaa aggcctcacg ctgtcctgga tcggcgacgg caacaacatt 600
ctgcatagta ttatgatgtc tgctgccaaa ttcggcatgc atctgcaagc tgctacgccg 660
aagggttatg aacccgacgc gtcagttacg aagctcgctg agcagtatgc aaaggagaat 720
ggcacaaagc tgttgcttac caacgatccc ctggaagctg ctcatggcgg caatgtgctg 780
attactgaca cctggatttc aatgggccag gaggaggaga agaagaagag gttacaggct 840
tttcaaggtt accaagtcac gatgaaaacc gctaaggtcg cagccagcga ctggacattc 900
ctgcactgtc tgccaagaaa gccggaagaa gtggacgacg aggtgttcta ttccccgcgg 960
tctttggtgt ttccggaggc cgaaaacagg aaatggacca ttatggccgt gatggtatcg 1020
ttgctgacgg actacagccc tcagttgcaa aagcccaagt tctag 1065

<210> SEQ ID NO 134
<211> LENGTH: 1065
<212> TYPE: DNA
<213> ORGANISM: Artificial Sequence
<220> FEATURE:
<223> OTHER INFORMATION: Synthetic construct

<400> SEQUENCE: 134
atgctcttta acctccgcat cctcctcaac aacgccgcct tccggaatgg gcataacttc 60
atggtccgga acttcagatg cggccagccc ctgcaaaaca aggtccagtt gaagggacgg 120
gacctcctta cgctgaagaa ctttaccgga gaagagatta agtacatgct gtggttgtcc 180
gctgacctca agttccgcat taagcagaag ggagaatatc tgccgctgct gcaaggaaag 240
agcctgggca tgatcttcga aaagcgctcc actagaaccc ggctgtcgac tgagactgga 300
ttcgccttgc tcggtggaca cccgtgcttc ctgacgaccc aggacatcca cctgggagtg 360
aacgagtcac ttacggatac cgcgagggtg ctgtcctcaa tggccgacgc agtgctcgcg 420
cgcgtgtaca agcagtcaga tctggatacc ctggccaagg aagccagcat tcccatcatc 480
aacggactga gcgaccttta ccacccaatc cagatcctcg ccgactactt aaccctgcaa 540
gagcactaca gctccctgaa gggactgact ctgtcctgga tcggggatgg aaacaacatc 600
ctgcactcca tcatgatgtc tgccgctaag tttgggatgc atctgcaagc cgcaacccct 660
aagggatacg agcccgacgc ctcggtgacc aaacttgcgg aacagtacgc caaggaaaac 720
ggtaccaagc tgctgctgac caacgaccct ctggaagcgg cccacggagg aaatgtgctg 780
attaccgaca cctggatttc gatgggccag gaggaggaga agaagaagag actgcaggcg 840
ttccagggat atcaggtcac catgaaaacc gccaaggtcg ccgccagcga ctggaccttc 900
ctgcactgtc tccctcggaa accggaagaa gtggatgacg aggtgttcta ctccccgcgc 960
tcgctggtgt tcccggaggc tgaaaacagg aagtggacaa tcatggccgt gatggtgtcc 1020
ctgttgaccg actactcccc acaactgcag aagcccaagt tctag 1065

<210> SEQ ID NO 135
<211> LENGTH: 1065
<212> TYPE: DNA
<213> ORGANISM: Artificial Sequence
<220> FEATURE:
<223> OTHER INFORMATION: Synthetic construct

<400> SEQUENCE: 135
atgcttttca atctgcgcat cctcctgaac aacgccgcct tccgcaatgg acacaacttt 60
atggtccgca acttccgctg tgggcagccg ctgcagaaca aggtccagct caaggggaga 120
gatctcctga ccctgaagaa cttcactgga gaggagatca agtacatgct gtggctgtcc 180
gccgacctga aatttcggat taagcagaag ggcgaatacc tcccactgct gcaaggaaag 240
tctttgggca tgatcttcga aaagagaagc acccggaccc ggttgagcac cgaaactggg 300
ttcgcgctcc tcggtggaca cccgtgcttc ctgaccaccc aagatattca tctgggtgtc 360
aacgaaagcc tgaccgacac cgccagggtg ctgtcatcca tggctgacgc agtgctcgcc 420
cgggtgtaca agcagtcaga cctggacacc ctcgccaagg aagcttcgat ccctatcatc 480
aacggacttt ccgacctgta ccaccccatc caaattctgg ccgactacct gactctgcaa 540
gaacactata gctcgctgaa aggacttact ctgtcctgga tcggggacgg caacaacatt 600
ctccattcca tcatgatgtc cgctgccaag ttcggaatgc accttcaagc agcgactccc 660
aagggatacg aacctgatgc ctccgtgact aagctggcag agcagtacgc caaggagaac 720
ggtacaaagc tgctgctcac gaacgacccc ctggaggcgg cccacggcgg aaacgtgctg 780
attaccgata cctggatctc aatgggccag gaagaggaga agaagaagcg gctccaggcg 840
tttcaaggct accaggtcac catgaaaacc gcgaaggtcg ccgcctccga ctggactttc 900
ttgcactgcc tgccgcggaa gcccgaggaa gtggatgacg aagtgttcta ctcgccgaga 960
tcgttggtgt tccctgaggc cgaaaacagg aagtggacca tcatggccgt gatggtgtcc 1020
ctgctgactg attacagccc acagctgcag aagcctaagt tctag 1065

<210> SEQ ID NO 136
<211> LENGTH: 1065
<212> TYPE: DNA
<213> ORGANISM: Artificial Sequence
<220> FEATURE:
<223> OTHER INFORMATION: Synthetic construct

<400> SEQUENCE: 136
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag ggggaatacc ttccgctgct tcaaggaaag 240
agcctcggca tgatctttga gaagcgctca accaggaccc gcctttctac tgaaactggg 300

```
ttcgcgctgc tcggtggcca cccctgcttc ctgacgaccc aggacatcca cctcggagtg    360

aacgaatccc tcaccgatac cgcccgggtg ttatcgagca tggcagatgc cgtgctggcc    420

agggtgtaca aacagtccga tctggacact ctggccaagg aggcgtcaat tcctattatc    480

aacggcctta gtgacctcta ccatccgatt cagatcctgg ccgattacct caccctgcaa    540

gaacactaca gctccctgaa gggtctgaca ttgtcctgga tcggcgacgg caacaacatt    600

ctccattcca tcatgatgtc cgccgcaaaa ttcggcatgc atcttcaagc cgccacgccg    660

aagggttacg agcccgacgc ttccgtgact aagctcgccg agcagtacgc taaggagaac    720

ggaaccaagc ttctgctgac taacgaccca ctagaagcag cccacggggg caacgtgctt    780

attactgaca cctggatctc catgggccag gaagaagaga aaaagaagcg gctgcaggcg    840

ttccagggat atcaggtcac catgaaaacc gccaaggtcg ctgcctccga ctggaccttc    900

ctgcactgcc tgcctcgcaa gcctgaagaa gtggacgacg aggtgttcta ctcgccacgg    960

agcctcgtgt tccccgaggc cgagaataga aagtggacca tcatggccgt gatggtgtca   1020

ctgctcaccg actacagccc gcagcttcag aagcccaagt tctag                   1065
```

<210> SEQ ID NO 137
<211> LENGTH: 1065
<212> TYPE: DNA
<213> ORGANISM: Artificial Sequence
<220> FEATURE:
<223> OTHER INFORMATION: Synthetic construct

<400> SEQUENCE: 137

```
atgcttttca acctgagaat cctcctgaac aacgccgcct tccgcaatgg tcataacttc     60

atggtccgca actttcgctg cggacagcct ctccaaaaca aggtccagct caaggggcgc    120

gacctcctca cactgaagaa cttcactgga gaagaaatca agtacatgct gtggctgagc    180

gccgatctga agttccggat caagcagaag ggagagtacc ttcctctgct gcaagggaag    240

tccttgggaa tgattttcga gaagcggtcc acccggacca ggctgagcac tgaaactggc    300

ttcgccctgc tgggaggcca cccttgtttc ctgaccactc aggacatcca cctgggcgtg    360

aacgagtccc tgaccgatac tgccagagtg ctgtcctcca tggccgacgc cgtgctcgcc    420

cgggtgtaca agcagtcaga cctcgatacg ctggccaagg aagcctccat tcccattatc    480

aatggtctgt cggacctcta ccatccaatc caaatcctcg ccgactacct gactctgcaa    540

gaacactaca gctcactcaa gggcctcacc ctctcctgga tcggcgacgg aaacaacatc    600

cttcactcga ttatgatgtc ggccgcgaag ttcgggatgc acctccaagc tgccactcca    660

aaaggctacg agccggatgc ctcagtgact aagttggcgg aacagtatgc gaaggagaac    720

ggtaccaagc tcctgctgac taacgacccg ctggaggccg cccacggggg aaacgtgctc    780

atcaccgata cttggatttc catgggacag gaggaagaga agaagaagcg gttgcaggca    840

tttcagggct accaggtcac catgaaaact gccaaagtcg ccgccagcga ctggaccttc    900

ctgcactgcc tgccccgcaa gcctgaagaa gtggacgacg aggtgttcta ctctccccgg    960

tccctcgtgt tccctgaggc cgaaaacagg aagtggacca tcatggctgt gatggtgtcc   1020

ctcctgaccg actacagccc tcagctccaa aaacccaagt tttag                   1065
```

<210> SEQ ID NO 138
<211> LENGTH: 1065
<212> TYPE: DNA
<213> ORGANISM: Artificial Sequence
<220> FEATURE:
<223> OTHER INFORMATION: Synthetic construct

<400> SEQUENCE: 138
atgcttttca acctgagaat cctcttgaac aatgctgctt ttcggaatgg ccacaacttt 60
atggttcgga acttccgttg cggccagcct ttacaaaaca aggtccagct gaagggccgg 120
gatttgctca cactgaagaa ctttactggg gaggagatta agtatatgct gtggctgtcc 180
gctgacctga agtttaggat caagcagaag ggcgaatatc tgccgctgct gcaagggaaa 240
agtctgggca tgatttttga aaagcgctct acccggacca gactgtctac ggaaacaggc 300
tttgccctgc tgggcggcca cccctgtttt ctgacaacgc aggacatcca tctgggcgtg 360
aacgaatcac tgaccgatac tgctcgggta ctcagttcta tggctgacgc agtgctggct 420
agggtgtaca agcagagcga cttggacaca ctggctaagg aggccagcat ccccattatc 480
aatggcctgt ctgatttgta ccatcccatt caaatcctgg ctgattatct gacactacaa 540
gagcattact caagtctgaa gggtttgact ctctcctgga tcggcgacgg caacaacatt 600
ttacattcca ttatgatgag tgctgctaag tttggcatgc atttgcaagc tgctacccca 660
aagggctatg aacctgacgc tagcgtaacc aagttggccg aacagtatgc taaagagaat 720
ggcaccaagc tgctcctgac gaatgacccc ctggaagctg ctcatggcgg aaacgtactt 780
ataactgata catggattag catgggccag gaagaggaga agaagaagag actgcaggcc 840
ttccaaggct atcaggtcac catgaaaact gccaaggttg cagctagcga ctggaccttc 900
ctgcactgtt tgccgaggaa acccgaggag gtggacgatg aagtctttta ttctccccgc 960
tccttggtgt ttcccgaggc tgaaaatcga aagtggacga taatggcagt gatggtgtcc 1020
ctactgaccg actattctcc acaactgcag aagcctaaat tctag 1065

<210> SEQ ID NO 139
<211> LENGTH: 1065
<212> TYPE: DNA
<213> ORGANISM: Artificial Sequence
<220> FEATURE:
<223> OTHER INFORMATION: Synthetic construct

<400> SEQUENCE: 139
atgcttttca atctgaggat cctgctgaac aacgctgctt ttcgcaacgg tcataacttt 60
atggttcgca attttcgttg tggccagccg ctgcagaaca aggttcagct gaagggcaga 120
gatctgctga ctctgaagaa cttcactggg gaagaaatca agtatatgtt atggctgtcc 180
gcggatctga aatttcgaat caagcagaag ggcgaatatc ttccccctgct gcaagggaaa 240
tccttgggca tgatttttga gaagaggagc actaggacta gattgtcaac agaaacaggc 300
tttgctttgt tgggcggaca tccctgcttt ctgacgacac aggatatcca cctcggcgta 360
aacgagtccc tcaccgacac tgctagggta ctgagcagca tggccgacgc tgtgctagcc 420
cgggtttaca agcagtcaga cctggacacc cttgccaagg aagcttctat tccaattatc 480
aacggcctga gtgacctgta tcaccctatt caaatactcg ccgactattt gacgcttcaa 540
gaacattaca gcagcctcaa gggcttaacc ttgagttgga taggcgacgg caacaatatc 600
ctgcattcca ttatgatgtc tgccgctaag tttggcatgc atctacaagc cgcaacaccc 660
aagggctatg aacccgacgc tagcgtgacc aagctggccg agcagtatgc taaggaaaat 720
ggcacaaagc tccttcttac caacgatccc ctggaggctg ctcacggcgg caacgtgctg 780
attaccgata catggattag catgggccag gaggaggaga aaaagaagcg gctccaggct 840
tttcaaggct atcaggtcac catgaaaact gcaaaggtcg ctgcctccga ctggactttc 900
ctgcattgtc taccccgcaa gcctgaggaa gtggacgatg aggtgttcta ctccccacgg 960
agtctggtgt tcccggaagc agagaatcgg aagtggacca tcatggctgt catggtgtcg 1020
ctcttgactg actattctcc ccaactgcaa aaacccaagt tttag 1065

<210> SEQ ID NO 140
<211> LENGTH: 1065
<212> TYPE: DNA
<213> ORGANISM: Artificial Sequence
<220> FEATURE:
<223> OTHER INFORMATION: Synthetic construct

<400> SEQUENCE: 140
atgcttttca atctgaggat cctgctgaac aacgctgctt ttcgcaacgg tcataacttt 60
atggttcgca attttcgttg tggccagccg ctgcagaaca aggttcagct gaagggcaga 120
gatctgctga ctctgaagaa cttcactggg gaagaaatca agtatatgtt atggctgtcc 180
gcggatctga aatttcgaat caagcagaag ggcgaatatc ttcccctgct gcaagggaaa 240
tccttgggca tgatttttga gaagaggagc actaggacta gattgtcaac agaaacaggc 300
tttgctttgt tgggcggaca tccctgcttt ctgacgacac aggatatcca cctcggcgta 360
aacgagtccc tcaccgacac tgctagggta ctgagcagca tggccgacgc tgtgctagcc 420
cgggtttaca agcagtcaga cctggacacc cttgccaagg aagcttctat tccaattatc 480
aacggcctga gtgacctgta tcaccctatt caaatactcg ccgactattt gacgcttcaa 540
gaacattaca gcagcctcaa gggcttaacc ttgagttgga taggcgacgg caacaatatc 600
ctgcattcca ttatgatgtc tgccgctaag tttggcatgc atctacaagc cgcaacaccc 660
aagggctatg aacccgacgc tagcgtgacc aagctggccg agcagtatgc taaggaaaat 720
ggcacaaagc tccttcttac caacgatccc ctggaggctg ctcacggcgg caacgtgctg 780
attaccgata catggattag catgggccag gaggaggaga aaaagaagcg gctccaggct 840
tttcaaggct atcaggtcac catgaaaact gcaaaggtcg ctgcctccga ctggactttc 900
ctgcattgtc taccccgcaa gcctgaggaa gtggacgatg aggtgttcta ctccccacgg 960
agtctggtgt tcccggaagc agagaatcgg aagtggacca tcatggctgt catggtgtcg 1020
ctcttgactg actattctcc ccaactgcaa aaacccaagt tttag 1065

<210> SEQ ID NO 141
<211> LENGTH: 1065
<212> TYPE: DNA
<213> ORGANISM: Artificial Sequence
<220> FEATURE:
<223> OTHER INFORMATION: Synthetic construct

<400> SEQUENCE: 141
atgcttttta atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcccatcatc 480
aacggcctga gcgacctgta ccacccaatc caaatcctgg ctgactacct gaccctgcaa 540
gagcactaca gcagcctgaa gggtctgacc ctgtcatgga ttggcgatgg aaacaatatt 600
ctgcactcca tcatgatgtc cgccgcgaag ttcggaatgc atctgcaagc cgccacgcca 660
aaaggatacg aaccggatgc gtccgtgacg aagttggcgg aacagtacgc gaaggagaac 720
ggaaccaagc ttctgctgac taacgacccc ctcgaggctg cgcatggggg caacgtgctg 780
attaccgaca cctggatctc catggggcag gaggaagaga agaagaagag actgcaggca 840
ttccaggggt accaggtcac catgaaaacc gcaaaagtgg cagcttcgga ctggactttc 900
ctgcattgcc tgccgaggaa gccggaggaa gtcgacgacg aagtgttcta ctcgcctcgg 960
tccctggtgt tccccgaggc cgaaaaccgg aagtggacca tcatggccgt gatggtgtcc 1020
ttgctgactg actatagccc gcagctgcag aagcctaagt tctag 1065

<210> SEQ ID NO 142
<211> LENGTH: 1065
<212> TYPE: DNA
<213> ORGANISM: Artificial Sequence
<220> FEATURE:
<223> OTHER INFORMATION: Synthetic construct

<400> SEQUENCE: 142
atgcttttca acctgagaat cctcttgaac aatgctgctt ttcggaatgg ccacaacttt 60
atggttcgga acttccgttg cggccagcct ttacaaaaca aggtccagct gaagggccgg 120
gatttgctca cactgaagaa ctttactgga gaagagatca agtacatgct gtggctgtcg 180
gccgacctga agttcaggat caagcagaag ggagaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctcgatacc ttggcaaagg aggcttccat tcccatcatc 480
aacggcctga gcgacctgta ccacccaatc caaatcctgg ctgactacct gaccctgcaa 540
gagcactaca gcagcctgaa gggtctgacc ctgtcatgga ttggcgatgg aaacaatatt 600
ctgcactcca tcatgatgtc cgccgcgaag ttcggaatgc atctgcaagc cgccactcca 660
aaaggatacg aaccggatgc gtccgtgacc aagttggcgg aacagtacgc gaaggagaac 720
ggaaccaagc ttctgctgac taacgacccc ctcgaggctg cgcatggggg caacgtgctg 780
attaccgaca cctggatctc catggggcag gaggaagaga agaagaagag actgcaggca 840
ttccaggggt accaggtcac catgaaaacc gcaaaagtgg cagcttcgga ctggactttc 900
ctgcattgcc tgccgaggaa gccggaggaa gtcgacgacg aagtgttcta ctcgcctcgg 960
tccctggtgt tccccgaggc cgaaaaccgg aagtggacca tcatggccgt gatggtgtcc 1020
ttgctgactg actatagccc gcagctgcag aagcctaagt tctag 1065

<210> SEQ ID NO 143
<211> LENGTH: 1065
<212> TYPE: DNA
<213> ORGANISM: Artificial Sequence
<220> FEATURE:
<223> OTHER INFORMATION: Synthetic construct

<400> SEQUENCE: 143
atgcttttca acctgagaat cctcttgaac aatgctgctt ttcggaatgg ccacaacttt 60
atggttcgga acttccgttg cggccagcct ttacaaaaca aggtccagct gaagggccgg 120

```
gatttgctca cactaaagaa ctttactgga gaagagatca agtacatgct atggctgtcg    180

gccgacctga agttccgtat caagcagaag ggagaatacc ttccgctgct tcaaggaaag    240

agcctcggca tgatctttga gaagcgctca accaggaccc gcctttctac tgaaactggg    300

ttcgcgctgc tcggtggcca cccctgcttc ctgacgaccc aggacatcca cctcggagtg    360

aacgaatccc tcaccgatac cgcccgggtg ttatcgagca tggcagatgc cgtgctggcc    420

agggtgtaca aacagtccga tctcgatacc ttggcaaagg aggcttccat tcccatcatc    480

aacggcctga gcgacctgta ccacccaatc caaatcctgg ctgactacct gaccctgcaa    540

gagcactaca gcagcctgaa gggtctgacc ctgtcatgga ttggcgatgg aaacaatatt    600

ctgcactcca tcatgatgtc cgccgcgaag ttcggaatgc atctgcaagc cgccactcca    660

aaaggatacg aaccggatgc atccgtgacc aagttggcgg aacagtacgc gaaggagaac    720

ggaaccaagc tcctgctgac taacgacccg ctcgaggctg cgcatggggg taacgtgctg    780

attacggaca cctggatctc catggggcag gaggaagaga agaagaagag actgcaggca    840

ttccaggggt accaggtcac catgaaaacc gcaaaagtgg cagcttcgga ctggactttc    900

ctgcattgcc tgccgaggaa gccggaggaa gtcgacgacg aagtgttcta ctcgcctcgg    960

tccctggtgt tccccgaggc cgaaaaccgg aagtggacca tcatggccgt gatggtgtcc   1020

ttgctgactg actatagccc gcagctgcag aagcctaagt tctag                   1065


<210> SEQ ID NO 144
<211> LENGTH: 1065
<212> TYPE: DNA
<213> ORGANISM: Artificial Sequence
<220> FEATURE:
<223> OTHER INFORMATION: Synthetic construct

<400> SEQUENCE: 144

atgcttttca acctgagaat cctcttgaac aatgctgctt ttcggaatgg ccacaacttt     60

atggttcgga acttccgttg cggccagcct ttacaaaaca aggtccagct gaagggccgg    120

gatttgctca cactaaagaa ctttactgga gaagagatca agtacatgct atggctgtcg    180

gccgacctga agttccgtat caagcagaag ggagaatacc ttccgctgct tcaaggaaag    240

agcctcggca tgatctttga gaagcgctca accaggaccc gcctttctac tgaaactggg    300

ttcgcgctgc tcggtggcca cccctgcttc ctgacgaccc aggacatcca cctcggagtg    360

aacgaatccc tcaccgatac cgcccgggtg ttatcgagca tggcagatgc cgtgctggcc    420

agggtgtaca aacagtccga tctcgatacc ttggcaaagg aggcttccat tcccatcatc    480

aacggcctga gcgacctgta ccacccaatc caaatcctgg ctgactacct gaccctgcaa    540

gagcactaca gcagcctgaa gggtctgacc ctgtcatgga ttggcgatgg aaacaatatt    600

ctgcactcca tcatgatgtc cgccgcgaag ttcggaatgc atctgcaagc cgccactcca    660

aaaggatacg aaccggatgc gtccgtgacc aagttggcgg aacagtacgc gaaggagaac    720

ggaaccaagc ttctgctgac taacgacccc ctcgaggctg cgcatggggg caacgtgctg    780

attaccgaca cctggatctc catggggcag gaggaagaga agaagaagag actgcaggca    840

ttccaggggt accaggtcac catgaaaacc gcaaaagtgg cagcttcgga ctggactttc    900

ctgcattgcc tgccgaggaa gccggaggaa gtcgacgacg aagtgttcta ctcgcctcgg    960

tccctggtgt tccccgaggc cgaaaaccgg aagtggacca tcatggccgt gatggtgtcc   1020

ttgctgactg actatagccc gcagctgcag aagcctaagt tctag                   1065
```

<210> SEQ ID NO 145
<211> LENGTH: 1065
<212> TYPE: DNA
<213> ORGANISM: Artificial Sequence
<220> FEATURE:
<223> OTHER INFORMATION: Synthetic construct

<400> SEQUENCE: 145
atgctgttca acctgcgaat cctgctgaac aacgccgctt ttcggaacgg gcacaacttt 60
atggtgagga actttcgctg cggacagccc ctccagaata aggtccagct gaagggcagg 120
gacctgctga ccctgaaaaa tttcacaggg gaggaaatca agtatatgct gtggctgtca 180
gctgatctga agttccggat caagcagaag ggcgaatatc tgcctctgct ccagggcaaa 240
agcctgggga tgatcttcga aaagcgcagt actcggacca gactgtcaac cgagactgga 300
ttcgctctgc tgggaggaca cccttgtttt ctgaccactc aggacattca cctgggagtg 360
aacgagtccc tgaccgacac tgctcgcgtc ctgagctcta tggccgacgc tgtgctggct 420
cgagtctaca aacagtccga cctggatacc ctggccaagg aagcttctat cccaattatt 480
aacggcctgt cagacctgta tcaccccatc cagattctgg ccgattacct gaccctccag 540
gagcactatt ctagtctgaa agggctgaca ctgagttgga ttggggacgg aaacaatatc 600
ctgcactcta ttatgatgtc agccgccaag tttggaatgc acctccaggc tgcaacccca 660
aaaggctacg aacccgatgc ctcagtgaca aagctggctg aacagtacgc caaagagaac 720
ggcactaagc tgctgctgac caacgaccct ctggaggccg ctcacggagg caacgtgctg 780
atcaccgata cctggattag tatgggacag gaggaagaga agaagaagcg gctccaggcc 840
ttccagggct accaggtgac aatgaaaacc gctaaggtcg cagccagcga ttggaccttt 900
ctgcactgcc tgcccagaaa gcccgaagag gtggacgacg aggtcttcta ctctcccaga 960
agcctggtgt ttcccgaagc tgagaatagg aagtggacaa ttatggcagt gatggtcagc 1020
ctgctgactg attattcacc tcagctccag aaaccaaagt tctga 1065

<210> SEQ ID NO 146
<211> LENGTH: 1065
<212> TYPE: DNA
<213> ORGANISM: Artificial Sequence
<220> FEATURE:
<223> OTHER INFORMATION: Synthetic construct

<400> SEQUENCE: 146
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ctggccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720

```
ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctga                  1065
```

<210> SEQ ID NO 147
<211> LENGTH: 1065
<212> TYPE: DNA
<213> ORGANISM: Artificial Sequence
<220> FEATURE:
<223> OTHER INFORMATION: Synthetic construct

<400> SEQUENCE: 147

```
atgctgttca acctgcgaat cctgctgaac aacgccgctt ttcggaacgg gcacaacttt     60

atggtgagga actttcgctg cggacagccc ctccagaata aggtccagct gaagggcagg    120

gacctgctga ccctgaaaaa tttcacaggg gaggaaatca agtatatgct gtggctgtca    180

gctgatctga agttccggat caagcagaag ggcgaatatc tgcctctgct ccagggcaaa    240

agcctgggga tgatcttcga aaagcgcagt actcggacca gactgtcaac cgagactgga    300

ttcgctctgc tgggaggaca ccccttgttt ctgaccactc aggacattca cctgggagtg    360

aacgagtccc tgaccgacac tgctcgcgtc ctgagctcta tggccgacgc tgtgctagct    420

cgagtctaca aacagtccga cctggatacc ctggccaagg aagcttctat cccaattatt    480

aacggcctgt cagacctgta tcaccccatc cagattctgg ccgattacct gaccctccag    540

gagcactatt ctagtctgaa agggctgaca ctgagttgga ttggggacgg aaacaatatc    600

ctgcactcta ttatgatgtc agccgccaag tttggaatgc acctccaggc tgcaacccca    660

aaaggctacg aacccgatgc ctcagtgaca aagctggctg aacagtacgc caaagagaac    720

ggcactaagc tgctgctgac caacgaccct ctggaggccg ctcacggagg caacgtgctg    780

atcaccgata cctggattag tatgggacag gaggaagaga agaagaagcg gctccaggcc    840

ttccagggct accaggtgac aatgaaaacc gctaaggtcg cagccagcga ttggaccttt    900

ctgcactgcc tgcccagaaa gcccgaagag gtggacgacg aggtcttcta ctctcccaga    960

agcctggtgt ttcccgaagc tgagaatagg aagtggacaa ttatggcagt gatggtcagc   1020

ctgctgactg attattcacc tcagctccag aaaccaaagt tctga                  1065
```

<210> SEQ ID NO 148
<211> LENGTH: 1065
<212> TYPE: DNA
<213> ORGANISM: Artificial Sequence
<220> FEATURE:
<223> OTHER INFORMATION: Synthetic construct

<400> SEQUENCE: 148

```
atgctgttca acctgcgaat cctgctgaac aatgccgctt ttcggaacgg gcacaatttc     60

atggtgagga actttcgctg cggacagccc ctccagaaca aggtccagct gaagggcagg    120

gacctgctga ccctgaaaaa tttcacaggg gaggaaatca agtacatgct gtggctgtca    180

gccgatctga agttccggat caagcagaag ggcgaatatc tgcctctgct ccagggcaaa    240

agcctgggga tgatcttcga aaagcgcagt actcggacca gactgtcaac agagactgga    300

ttcgcactgc tgggaggaca cccatgtttt ctgaccacac aggacattca tctgggagtg    360
```

```
aacgagtccc tgaccgacac agcacgcgtc ctgagctcca tggctgatgc agtgctggct    420

cgagtctaca aacagtctga cctggatacc ctggccaagg aagcttctat cccaatcatt    480

aatggcctga gtgacctgta tcacccccatc cagattctgg ccgattacct gaccctccag    540

gagcattatt ctagtctgaa agggctgaca ctgagctgga ttggggacgg aaacaatatc    600

ctgcactcca ttatgatgag cgccgccaag tttggaatgc acctccaggc tgcaacccca    660

aaaggctacg aacccgatgc ctccgtgaca aagctggcag aacagtatgc caaagagaac    720

ggcactaagc tgctgctgac caatgaccct ctggaggccg ctcacggagg caacgtgctg    780

atcactgata cctggattag tatgggacag gaggaagaga agaagaagcg gctccaggcc    840

ttccagggct accaggtgac aatgaaaact gctaaggtcg cagccagcga ctggaccttt    900

ctgcattgcc tgcccagaaa gcctgaagag gtggacgatg aggtcttcta ctcacccaga    960

agcctggtgt ttcctgaagc tgagaatagg aagtggacaa tcatggcagt gatggtcagc   1020

ctgctgactg attattcccc tcagctccag aaaccaaagt tctga                   1065
```

```
<210> SEQ ID NO 149
<211> LENGTH: 1065
<212> TYPE: DNA
<213> ORGANISM: Artificial Sequence
<220> FEATURE:
<223> OTHER INFORMATION: Synthetic construct

<400> SEQUENCE: 149

atgcttttca accttcgcat tctcctcaac aacgccgcgt ttagaaacgg acacaacttc     60

atggtccgca acttccgctg cggacagccg ctgcagaaca aggtccagct caagggtcgg    120

gatctcctga cgctgaagaa ctttaccggc gaagagatta agtacatgct gtggctgtcc    180

gccgacctta agttccggat caagcagaag ggcgaatacc ttcccctgct gcaaggaaag    240

tccctgggca tgatcttcga gaagcgcagt accagaacca gactctccac tgaaaccggg    300

ttcgcgctgc ttggcggcca cccgtgtttc ctcactacgc aagacatcca tcttggcgtg    360

aacgagtccc ttaccgacac cgccagggtg ctgtcaagca tggccgacgc cgtccttgcg    420

cgcgtgtaca agcagtcaga ccttgatact ctggccaagg aagcctccat ccctattatc    480

aacggcctat ccgaccttta ccacccgatc cagatcctcg ctgactacct gaccctgcaa    540

gaacactaca gcagcctcaa gggactgact ctgtcctgga tcggcgacgg gaacaacatc    600

ctgcactcaa tcatgatgag cgcagccaag ttcggcatgc atctccaagc cgctacaccc    660

aagggttatg aaccggacgc ctctgtgacc aagttggcag aacagtacgc caaggagaac    720

ggtactaagc tccttttaac caacgacccc ctcgaagcag cccatggcgg gaatgtgctc    780

attaccgata cctggatttc gatgggccag gaggaggaga agaagaagcg gctgcaggcg    840

ttccagggct accaggtcac catgaaaact gccaaagtgg ccgcctcgga ttggaccttt    900

ctccactgcc tgcctcggaa gcctgaggag gtggacgacg aagtgttcta ctccccacgg    960

tccctcgtgt tccccgaggc cgaaaatagg aagtggacca tcatggccgt gatggtgtcc   1020

ctcttgaccg attacagccc gcagcttcag aagcctaaat tctag                   1065
```

```
<210> SEQ ID NO 150
<211> LENGTH: 1065
<212> TYPE: DNA
<213> ORGANISM: Artificial Sequence
<220> FEATURE:
<223> OTHER INFORMATION: Synthetic construct
```

<400> SEQUENCE: 150

```
atgcttttca atcttcgcat cctgttgaac aacgccgcct tccgcaatgg tcacaacttc     60
atggtccgga acttcagatg tggacagcct ctccaaaaca aggtccagct gaagggaagg    120
gacctcttaa ccctcaaaaa ctttactgga gaggagatca agtacatgct gtggcttagc    180
gccgacctta agttccggat caagcagaag ggagagtacc tcccgctgct gcaaggaaag    240
agtcttggaa tgatcttcga gaagcggtcc accagaactc gcctctccac tgaaaccgga    300
ttcgcactcc tgggtggaca cccgtgcttt ctgaccaccc aagacatcca cctcggagtg    360
aacgagagcc tcacggacac cgcgagagtg ctgtcatcca tggccgacgc cgtgcttgca    420
cgggtctaca agcagtccga tctggacact cttgccaagg aagcctccat tcctatcatt    480
aacggtctgt cggatctgta ccacccgatt cagatccttg cggactacct cacacttcaa    540
gaacactatt caagcctaaa gggtctgacc ctgtcctgga tcggagatgg aaacaacatt    600
ctccattcca tcatgatgag cgctgccaag ttcggaatgc atctccaagc agcgactcct    660
aagggttacg agccggacgc ctcagtgact aagctggccg agcagtacgc caaggagaac    720
ggtaccaaac tgttgcttac taacgacccg cttgaagcgg cccatggagg aaacgtgctg    780
attaccgaca cctggatttc gatgggacag gaagaggaga agaagaagcg gctccaggcg    840
ttccagggat accaggtcac catgaaaacg gccaaagtgg ccgctagcga ttggaccttt    900
ctgcactgcc tcccgcgcaa gcctgaagaa gtggacgacg aagtgttcta ctcccctcgc    960
tctcttgtgt tcccggaagc cgaaaacagg aagtggacca tcatggccgt gatggtgtcc   1020
ctcctgaccg attacagccc gcagctgcag aagcctaagt tctag                   1065
```

<210> SEQ ID NO 151
<211> LENGTH: 1065
<212> TYPE: DNA
<213> ORGANISM: Artificial Sequence
<220> FEATURE:
<223> OTHER INFORMATION: Synthetic construct

<400> SEQUENCE: 151

```
atgcttttca atctccgcat cctcctcaac aacgccgcgt ttagaaacgg ccacaacttc     60
atggtccgga acttcagatg tggccagccg cttcagaaca aggtccagct caagggccgg    120
gatcttctga ccctgaagaa ctttactggc gaagaaatca agtacatgct ctggctctcc    180
gccgacttga agttccgcat taagcagaag gggggaatacc ttccgctgct gcaaggaaag    240
tcgctcggca tgatctttga gaagcgctca acccgcacca ggctgtccac tgaaaccggg    300
ttcgcgctgc ttggtggcca cccctgcttc ctgaccaccc aagacattca cctcggagtg    360
aacgaatcgc tcactgatac tgcccgggtg ctgtcgtcga tggccgatgc agtgctggcc    420
agggtgtaca aacagtccga tctggacact ctggccaagg aggcgtccat ccctattatc    480
aacggccttt ccgacctcta ccacccgatt cagatccttg ccgattacct caccctgcaa    540
gaacactact cgtcactgaa gggtctgacc ttgtcctgga tcggcgacgg caacaacatc    600
ctccattcca ttatgatgtc cgccgccaaa ttcggcatgc atcttcaagc cgcaacccct    660
aagggttacg agccggacgc ttccgtgacc aagctcgccg agcagtacgc taaggagaac    720
ggaaccaagc ttctgctgac taacgacccc ctagaggcag cccacggggg caacgtgctt    780
attactgaca cctggatctc catgggacag gaagaagaga agaagaagcg gttacaggcg    840
ttccagggct atcaggtcac catgaaaacc gccaaggtcg ctgcctcgga ctggaccttc    900
ctgcattgcc tgcctcgcaa gcccgaagaa gtggacgacg aggtgttcta ctcgccacgg    960
```

tcccttgtgt tccctgaggc cgagaataga aagtggacca ttatggccgt gatggtgtcc 1020
cttctcaccg actactcgcc gcaactgcag aaacccaagt tctag 1065

<210> SEQ ID NO 152
<211> LENGTH: 1065
<212> TYPE: DNA
<213> ORGANISM: Artificial Sequence
<220> FEATURE:
<223> OTHER INFORMATION: Synthetic construct

<400> SEQUENCE: 152
atgcttttca atcttcgcat cctcctcaac aacgccgcct tccggaacgg tcacaacttc 60
atggtccgga acttccgctg cggccagccg ctccaaaaca aagtgcagct taagggccgc 120
gatctcctga ccctgaagaa cttcaccgga gaggaaatca agtacatgct gtggctctcg 180
gcggacctga agtttaggat taagcagaag gggagtatc tgccgctgct ccaagggaag 240
tcccttggca tgatcttcga aaagaggtcc acccggactc ggctcagcac cgaaacaggt 300
tttgcacttc tgggggcca cccgtgcttc ctgacgaccc aggacatcca tctgggtgtc 360
aacgagagtt tgaccgacac tgccagagtg ctgtcatcca tggcggacgc ggtgctcgcg 420
agagtgtaca agcagtccga tcttgacacc ctggcaaaag aggcttcaat cccgatcatt 480
aacggactct cggatctgta ccaccctatc caaatcttgg ccgactacct gaccctgcaa 540
gaacactaca gctccctgaa gggcctgact ctttcctgga ttggcgatgg aaacaacatt 600
ctccattcta ttatgatgtc cgccgccaag ttcggcatgc accttcaagc cgccaccccg 660
aagggctacg aacctgacgc ctccgtgact aagctagccg aacagtacgc taaggagaac 720
ggcactaagc ttctccttac caacgatccg ctggaggcgg cccatggcgg aaatgtgctt 780
atcaccgaca cctggattag catggggcag gaagaagaga agaagaaacg gctccaggca 840
ttccagggct accaggtcac catgaaaact gccaaggtcg ccgctagcga ctggaccttc 900
ctccactgtc tgcctcgcaa gcctgaagaa gtggacgacg aggtgttcta ctccccgcgc 960
tccctcgtgt ttcctgaggc cgagaacaga aagtggacca tcatggccgt gatggtgtca 1020
ttacttacgg actacagccc gcagctgcag aagccgaagt tctag 1065

<210> SEQ ID NO 153
<211> LENGTH: 1065
<212> TYPE: DNA
<213> ORGANISM: Artificial Sequence
<220> FEATURE:
<223> OTHER INFORMATION: Synthetic construct

<400> SEQUENCE: 153
atgcttttta acttgagaat ccttctgaac aacgccgctt tccgcaacgg tcataacttc 60
atggtccgga acttcagatg tggccagccc ctccaaaaca aagtgcagct gaagggccgg 120
gaccttctta cgctgaagaa tttcaccggc gaagaaatca agtacatgct ctggctgtcc 180
gccgatctta agttccgcat taagcagaag gggaatacc tcccgctgct gcaagggaag 240
tcgctgggca tgatttttga gaagcggtca actcgcaccc gcctgtccac tgaaactgga 300
ttcgcactgc tcggtggcca tccctgcttc ctgaccaccc aagacatcca cctcggcgtg 360
aacgagtccc tgactgacac cgcccgggtc ttatcctcga tggccgatgc tgtgcttgcg 420
agggtgtaca agcagtccga cctcgacaca ctcgcgaagg aggcctccat ccccatcatc 480
aacggcctgt ccgaccttta ccacccaatt cagatcctcg ccgattacct gaccctgcaa 540

```
gagcactact cgtcgctcaa ggggcttacc ctctcgtgga ttggcgacgg caacaacatc    600

cttcactcca tcatgatgtc ggcagcgaag ttcggcatgc atctgcaagc cgccacgcct    660

aagggttatg aaccggatgc ctcagtgacc aagctcgccg aacagtacgc gaaagagaat    720

ggaaccaagc tacttctgac caacgacccc ctggaggccg ctcacggcgg caacgtcctc    780

attaccgata cttggatttc gatgggacag gaagaggaaa agaagaagag actgcaggcg    840

ttccagggat accaggtcac catgaaaact gccaaagtgg cagcctccga ctggaccttc    900

cttcactgcc tgccgaggaa gcctgaagag gtggacgacg aggtgttcta ctccccgcgc    960

tccttggtgt ttcctgaggc cgaaaaccgg aagtggacta tcatggccgt gatggtgtcc   1020

ctcctcaccg actactcgcc gcaactgcag aagcctaagt tctag                   1065
```

```
<210> SEQ ID NO 154
<211> LENGTH: 1065
<212> TYPE: DNA
<213> ORGANISM: Artificial Sequence
<220> FEATURE:
<223> OTHER INFORMATION: Synthetic construct

<400> SEQUENCE: 154

atgttattca accttagaat tctccttaac aacgccgcct tccggaatgg gcataacttt     60

atggtccgca atttccgctg tggacagcct ctgcaaaaca aggtccagct caagggccgg    120

gatctgctga ctctcaagaa cttcactggg gaagaaatca agtacatgct ctggctgagc    180

gccgacctca agttccgcat caagcagaag ggagagtacc tcccgctgct ccaagggaag    240

tccctgggca tgatcttcga gaagagatcc acccgcacca gactttccac tgagactggc    300

ttcgccttgc tgggaggcca cccatgcttc ctgacgaccc aggacattca ccttggcgtg    360

aacgagtccc tgactgacac cgcaagggtg ttgtcctcga tggccgacgc cgtgcttgcc    420

cgggtgtaca agcagagcga tcttgacacc ctggctaagg aagcttccat tcccatcatc    480

aacggtctga gcgacctgta ccacccgatt cagatcctgg cggactacct aaccctgcaa    540

gagcactata gctccctgaa gggcctcaca ctttcatgga tcggcgacgg caacaacatc    600

ctgcactcta ttatgatgag cgctgccaaa ttcggcatgc acctccaagc cgccacgcct    660

aaaggctacg agcccgacgc ctcggtgacc aagcttgcgg agcagtacgc gaaggaaaac    720

ggcaccaagc tgcttctcac caacgatcct ctggaagcgg cccatggtgg caacgtgctc    780

attaccgaca cttggatctc catgggacag gaggaggaaa agaagaagcg gctccaggcg    840

tttcagggtt accaggtcac catgaaaacc gccaaggtcg cagcctccga ctggaccttc    900

cttcattgcc ttccgcgcaa gcccgaagaa gtggacgatg aagtgtttta ctcacctcgg    960

tcactcgtgt tcccggaagc agagaacagg aaatggacca ttatggccgt gatggtgtcc   1020

ctgctcaccg attacagtcc gcaactgcag aagcccaagt tctag                   1065
```

```
<210> SEQ ID NO 155
<211> LENGTH: 1065
<212> TYPE: DNA
<213> ORGANISM: Artificial Sequence
<220> FEATURE:
<223> OTHER INFORMATION: Synthetic construct

<400> SEQUENCE: 155

atgcttttca atctccgcat cctccttaac aacgccgcgt ttagaaacgg ccacaacttc     60

atggtccgga acttcagatg tggccagccg cttcaaaaca aggtccagct gaagggccgg    120

gatcttctga ccctgaagaa ctttactggc gaagagatca agtacatgct ctggctctcc    180
```

gcggacttga agttccgcat taagcagaag ggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt caaatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgcct 660
aagggttacg aacccgacgc ttccgtgact aagctcgccg agcagtacgc taaggagaac 720
ggaaccaagc tgctgctgac taacgacccg ctagaagcag cccacggggg caacgtgctt 780
attactgaca cctggatctc catgggccag gaggaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
cttctcaccg actacagccc gcagcttcag aagcccaagt tctag 1065

<210> SEQ ID NO 156
<211> LENGTH: 1065
<212> TYPE: DNA
<213> ORGANISM: Artificial Sequence
<220> FEATURE:
<223> OTHER INFORMATION: Synthetic construct

<400> SEQUENCE: 156
atgcttttca atctccgcat cctccttaac aacgccgcgt ttagaaacgg ccacaacttc 60
atggtccgga acttcagatg tggccagccg cttcaaaaca aggtccagct taagggccgg 120
gatctcctca cccttaaaaa cttcaccggc gaagagatca agtacatgct ctggctctcc 180
gcggacctta agttccgcat taagcagaag ggggaatacc ttccgctgct tcaaggaaag 240
agcctcggca tgatctttga gaagcgctca accaggacca ggctttctac tgaaactggg 300
ttcgcgcttc tcggcggtca tccctgcttc ctcacgaccc aagacatcca cctcggagtg 360
aacgaatccc tcacggatac tgcccgcgtg ctttcgagca tggcagacgc cgtgctcgcc 420
cgggtgtaca aacagtccga tctcgacact ctcgccaagg aggcgtcaat tcctattatc 480
aacggtctta gtgaccttta ccacccgatc cagatcctcg ccgattacct cacactccaa 540
gaacactaca gctcccttaa gggtcttacc ctctcctgga tcggcgacgg caacaacatt 600
ctccactcca tcatgatgtc cgccgcaaag ttcggcatgc atcttcaagc cgccaccccg 660
aagggctacg agcctgatgc ttccgtgact aagctcgccg agcagtacgc taaggagaac 720
ggaaccaagc ttcttctcac taacgaccca ctcgaagcag cccatggggg caacgtgctt 780
atcactgaca cctggatctc catgggccag gaagaagaga agaagaagcg gctccaggcg 840
ttccagggat atcaggtcac catgaaaacc gccaaggtcg ctgcctccga ctggaccttt 900
ctccactgcc tccctcgcaa acctgaagaa gtggacgacg aggtgttcta ctcgccccgg 960
agcctcgtgt tccccgaggc cgagaataga aagtggacca ttatggccgt gatggtgtca 1020
ctcctcaccg actacagccc gcagcttcag aagcccaagt tctag 1065

<210> SEQ ID NO 157

<211> LENGTH: 1065
<212> TYPE: DNA
<213> ORGANISM: Artificial Sequence
<220> FEATURE:
<223> OTHER INFORMATION: Synthetic construct

<400> SEQUENCE: 157
atgcttttca atctccgcat cctccttaac aacgccgcgt ttagaaacgg acataacttc 60
atggtccgga acttcagatg tggacagccg cttcaaaaca aggtccagct gaagggtcgg 120
gatcttctga ccctgaagaa ctttaccgga gaagagatca agtacatgct ctggctctcc 180
gcggacttga agttccgcat taagcagaag ggagaatacc tcccgctgct tcaaggaaag 240
agcctcggaa tgatttttga gaagcgctca accaggaccc gcctttctac tgaaactgga 300
ttcgcgctgc tgggtggaca cccctgcttc ctgacgaccc aggacatcca cctcggagtg 360
aacgaatccc tcactgatac cgcccgggtg ttatcgagca tggcagatgc cgtgctggcc 420
agggtgtaca aacagtccga tctggacact ctggccaagg aggcgtcaat tcctatcatc 480
aacggactta gtgacctcta ccatccgatt caaatcctgg ccgactacct caccctgcaa 540
gaacactaca gctccctgaa gggtctgaca ttgtcctgga tcggagatgg aaacaacatt 600
ctccactcca tcatgatgtc cgccgcaaaa ttcggaatgc atcttcaagc cgccacgcct 660
aagggttacg aacccgacgc ttccgtgact aagctcgccg agcagtacgc taaggagaac 720
ggtaccaagc ttctcctgac caacgaccca ctagaagcag cccacggtgg aaacgtgctt 780
attactgaca cttggatctc catgggacag gaggaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccgcgg 960
agcctcgtgt tccccgaggc cgagaataga aagtggacca tcatggccgt gatggtgtca 1020
ctgctcaccg actacagccc gcagcttcag aagcccaagt tctag 1065

<210> SEQ ID NO 158
<211> LENGTH: 1065
<212> TYPE: DNA
<213> ORGANISM: Artificial Sequence
<220> FEATURE:
<223> OTHER INFORMATION: Synthetic construct

<400> SEQUENCE: 158
atgcttttca acctccgcat tctcctcaac aacgctgcct tccggaatgg acataacttc 60
atggtccgga acttcagatg cggacagccg cttcagaaca aggtccagct taaggggaga 120
gatctcctta ccctcaaaaa cttcactggc gaagaaatca agtacatgct ctggcttagt 180
gcggatctca agttccgcat caagcagaag ggagaatacc tcccgctcct tcaaggaaag 240
agcctcggca tgatttttga gaagaggtcc accagaactc gcctttcaac cgagactggg 300
ttcgccctgc ttggcggtca cccctgcttc ctcactaccc aagacatcca cctcggcgtg 360
aacgagagcc ttaccgacac cgcccgcgtg ctctcctcaa tggccgacgc tgtgctcgcc 420
cgggtgtaca agcagtccga ccttgatact ctcgccaagg aggcctccat cccaattatc 480
aacgggctct ctgatctcta ccaccctatc caaatcctcg cggactacct caccctccaa 540
gagcactata gctcgctcaa gggcctcacc ctttcctgga ttggcgacgg caacaacatt 600
cttcactcga tcatgatgtc cgccgccaag ttcggcatgc atctccaagc cgcgaccccc 660
aagggctacg agcctgacgc atccgtgacc aagctcgccg agcagtacgc gaaggaaaat 720
ggcaccaagc ttcttctcac caacgacccc cttgaggccg ctcatggcgg caacgtgctc 780
atcactgaca cttggatcag catgggccag gaggaggaaa agaagaagcg ccttcaggca 840
ttccagggtt accaggtcac catgaaaacc gccaaagtgg ccgcctccga ctggaccttt 900
cttcactgtc tcccgcggaa gcctgaagaa gtggatgacg aagtgtttta ctcccctcgg 960
tcactcgtgt tcccggaagc agaaaacagg aagtggacca ttatggcggt catggtgtcc 1020
ctcctcaccg actacagccc gcagcttcag aaacccaagt tctag 1065

<210> SEQ ID NO 159
<211> LENGTH: 1065
<212> TYPE: DNA
<213> ORGANISM: Artificial Sequence
<220> FEATURE:
<223> OTHER INFORMATION: Synthetic construct

<400> SEQUENCE: 159
atgcttttca atctccgcat cctccttaac aacgcagcgt ttagaaacgg tcacaacttc 60
atggtccgga acttccgctg tggacagccg cttcaaaaca aggtccagct gaagggtcgg 120
gaccttctga ccctgaagaa ctttactgga gaagagatca agtacatgct ttggctgtcc 180
gcggacttga agttccgcat taagcagaag ggagaatacc ttccgctgct ccaaggaaag 240
agcctgggaa tgatctttga gaagcgctca accaggaccc gcctttctac tgaaactgga 300
ttcgcgctgc tgggtggtca cccttgcttc ctgacgaccc aggacattca cctcggagtg 360
aacgagtccc tcactgatac cgccagagtg ttatcgagca tggcagatgc cgtgctggct 420
agggtgtaca aacagtccga tctggacacc ctggccaagg aggcatcaat tcctattatc 480
aacggactta gtgacctcta ccatccgatt caaatcctgg ccgattacct caccctgcaa 540
gaacactaca gctccctgaa gggtctgaca ttgtcctgga tcggagatgg aaacaacatt 600
ctccattcca tcatgatgtc cgcggccaag ttcggaatgc atctccaagc cgccacgccg 660
aaaggatacg agccggacgc ttccgtgact aagctcgccg agcagtacgc taaggagaac 720
ggaaccaagc ttctgctgac taacgacccg ctagaagccg cccacggtgg aaacgtgctt 780
attactgaca cctggatctc catgggacag gaagaagaga aaaagaagcg gctgcaggcg 840
ttccagggat atcaggtcac catgaaaacc gccaaggtcg ccgcctccga ctggaccttc 900
cttcactgcc tgcctcggaa gcctgaagaa gtggacgacg aggtgttcta ctcgccgcgg 960
agcctcgtgt tccctgaggc cgagaataga aagtggacca tcatggccgt gatggtgtca 1020
ctcctcaccg actacagccc gcagcttcag aagcctaagt tctag 1065

<210> SEQ ID NO 160
<211> LENGTH: 1065
<212> TYPE: DNA
<213> ORGANISM: Artificial Sequence
<220> FEATURE:
<223> OTHER INFORMATION: Synthetic construct

<400> SEQUENCE: 160
atgcttttca atctccgcat tctcctcaac aacgcagcct ttagaaacgg ccacaacttc 60
atggtccgga acttcagatg tggccagccg cttcagaaca aggtccagct caagggccgg 120
gacctcctca ccctcaaaaa ctttaccggc gaagagatca agtacatgct ctggctttcg 180
gccgacctta agttccgcat caagcagaag gggg aatacc ttccgctgct tcaaggaaag 240
tccctcggca tgatctttga aaagcgctcg accaggaccc gcctttccac tgaaaccggg 300
ttcgcgcttc tcggtggcca cccctgcttc ctcaccaccc aagacattca cctcggagtg 360

-continued

```
aacgaatccc ttaccgatac cgcaagagtg ctttcgtcga tggccgatgc cgtgcttgcg    420

cgggtgtaca agcagtcaga tctcgacact ctcgccaagg aggcgtccat tcctattatc    480

aacggccttt ccgaccttta ccacccgatt cagatcctcg ccgattacct caccctgcaa    540

gagcactact cgtcactcaa gggtcttacc ctctcctgga tcggcgacgg aaacaacatc    600

ctccattcga tcatgatgtc cgccgccaaa ttcggcatgc acctccaagc cgcgaccccg    660

aagggttacg agcccgacgc ttccgtgacc aagctcgccg aacagtacgc taaggaaaac    720

ggcaccaagc tcctcctcac taacgaccct ctcgaagcag cccatggggg caacgtgctc    780

attactgaca cttggatctc gatgggccag gaagaggaga aaaagaagcg gcttcaggcg    840

ttccagggat atcaggtcac catgaaaacc gccaaggtcg ctgcctcgga ctggaccttc    900

cttcactgcc ttccgcgcaa gcctgaagag gtggacgatg aggtgttcta ctccccacgg    960

tcccttgtgt tccccgaggc cgagaatagg aagtggacca tcatggccgt gatggtgtcg   1020

ctcctcactg actactcccc gcaacttcag aagcctaagt tctag                   1065
```

<210> SEQ ID NO 161
<211> LENGTH: 1065
<212> TYPE: DNA
<213> ORGANISM: Artificial Sequence
<220> FEATURE:
<223> OTHER INFORMATION: Synthetic construct

<400> SEQUENCE: 161

```
atgctgttta atctgagaat acttctaaac aacgccgcct tccggaatgg ccataacttt     60

atggttcgga atttccgctg cggccagccg ctgcagaaca aggtccagct gaagggaaga    120

gacttgctga ccctcaagaa cttcaccgga gaagaaatca agtatatgct gtggctgtcc    180

gccgacctga aattccgcat caagcagaag ggcgaatatc tgccgctgtt gcaagggaag    240

tccctgggga tgatcttcga gaagaggtcc accagaacac ggctttcaac cgaaaccggg    300

tttgcactgc tgggtggaca cccctgtttt ctgaccactc aagatatcca cctgggcgtg    360

aacgagtccc ttaccgacac tgctagggtg ttgtccagca tggccgatgc cgtcctggct    420

cgcgtgtaca agcagtccga cctggatacc ctggcaaagg aagcgtccat tcccattatc    480

aacgggctgt ccgacctgta ccatccgatt caaatcctgg cggactacct gactctgcaa    540

gagcattaca gcagcttgaa ggggcttact ctctcgtgga tcggcgacgg gaacaacatc    600

ctgcactcca tcatgatgtc cgccgccaag ttcgggatgc atttgcaagc tgcgaccccg    660

aaaggttacg agcccgatgc tagcgtaact aagcttgccg aacagtacgc caaagagaat    720

ggtacaaaac tgcttctgac taacgacccg ctggaagcag cccacggcgg gaacgtgctg    780

ataaccgaca cctggatttc aatggggcag gaggaagaga agaagaagcg actgcaggcg    840

ttccaaggct atcaggttac catgaaaacc gccaaagtgg cagccagcga ttggactttc    900

ctgcactgtc tgccgcggaa gcccgaggaa gttgatgacg aagtattcta ctcaccccgg    960

agcctcgtgt tccccgaggc cgaaaaccgg aagtggacta ttatggccgt gatggtgtcg   1020

ctgttgaccg actacagccc gcaactgcag aagccgaagt tttag                   1065
```

<210> SEQ ID NO 162
<211> LENGTH: 1065
<212> TYPE: DNA
<213> ORGANISM: Artificial Sequence
<220> FEATURE:
<223> OTHER INFORMATION: Synthetic construct

<400> SEQUENCE: 162
atgcttttca acctgaggat ccttttgaac aacgccgcct ttcgcaacgg ccacaacttt 60
atggtccgca atttccgctg cgggcagccg ctgcagaaca aggtccagct gaagggccgg 120
gatctgctga ccctgaagaa cttcaccggg gaggaaatca agtacatgct ttggctctcc 180
gccgatctga agttcagaat caagcagaag ggagagtacc tcccgttgct gcaaggaaag 240
tcactcggaa tgattttcga aaagagaagc actaggaccc gcctctcaac tgaaaccggg 300
ttcgcgctgc tcgggggcca tccgtgtttc ctgactaccc aagacatcca cctgggagtg 360
aacgagtcgc tgaccgacac cgcacgcgtg ctgtcatcca tggcggacgc agtgcttgcc 420
cgggtgtaca agcagtcgga cctggacact cttgccaagg aggcatcaat ccccatcatt 480
aacggactgt ccgatctcta ccacccgatt cagatcctgg ctgactacct aaccctgcaa 540
gagcactact caagcctgaa ggggctgacc ctgtcgtgga tcggggacgg caacaacatt 600
ctgcactcca tcatgatgtc ggcggctaag ttcgggatgc atttgcaagc ggcaactccg 660
aagggttatg aacccgacgc ctccgtgacc aagctggccg aacagtacgc caaggaaaac 720
ggaaccaagt tgctgctgac taatgatccc ctggaggcgg cccacggggg gaacgtgctg 780
ataaccgata cctggatctc catggggcag gaagaagaga agaaaaagcg gctgcaggca 840
ttccagggat accaggtcac catgaaaacc gcaaaagtgg cagccagcga ctggactttc 900
ctccattgcc tgccgcgaaa gccggaggag gtcgatgacg aggtgttcta ctccccgcgg 960
tcgctggtgt tcccggaggc ggaaaaccgg aagtggacca ttatggccgt gatggtgtca 1020
ctcctgactg actacagccc gcaactgcag aagccgaagt tctag 1065

<210> SEQ ID NO 163
<211> LENGTH: 1074
<212> TYPE: DNA
<213> ORGANISM: Artificial Sequence
<220> FEATURE:
<223> OTHER INFORMATION: Synthetic construct

<400> SEQUENCE: 163
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960

-continued agcctcgtgt tccccgaggc cgagaataga aagtggacca tcatggccgt gatggtgtca 1020
ctgctcaccg actacagccc gcagcttcag aagcccaagt tctagataag tgaa 1074

<210> SEQ ID NO 164
<211> LENGTH: 1073
<212> TYPE: DNA
<213> ORGANISM: Artificial Sequence
<220> FEATURE:
<223> OTHER INFORMATION: Synthetic construct

<400> SEQUENCE: 164
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ctggccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag tga 1073

<210> SEQ ID NO 165
<211> LENGTH: 1073
<212> TYPE: DNA
<213> ORGANISM: Artificial Sequence
<220> FEATURE:
<223> OTHER INFORMATION: Synthetic construct

<400> SEQUENCE: 165
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ctggccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag tga 1073

<210> SEQ ID NO 166
<211> LENGTH: 1074
<212> TYPE: DNA
<213> ORGANISM: Artificial Sequence
<220> FEATURE:
<223> OTHER INFORMATION: Synthetic construct

<400> SEQUENCE: 166
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctagataag tgaa 1074

<210> SEQ ID NO 167
<211> LENGTH: 1073
<212> TYPE: DNA
<213> ORGANISM: Artificial Sequence
<220> FEATURE:
<223> OTHER INFORMATION: Synthetic construct

<400> SEQUENCE: 167
atgcttttca acctgagaat cctcttgaac aatgctgctt ttcggaatgg ccacaacttt 60
atggttcgga acttccgttg cggccagcct ttacaaaaca aggtccagct gaagggccgg 120
gatttgctca cactaaagaa ctttactgga gaagagatca agtacatgct atggctgtcg 180

```
gccgacctga agttccgtat caagcagaag ggagaatacc ttccgctgct tcaaggaaag    240

agcctcggca tgatctttga gaagcgctca accaggaccc gcctttctac tgaaactggg    300

ttcgcgctgc tcggtggcca cccctgcttc ctgacgaccc aggacatcca cctcggagtg    360

aacgaatccc tcaccgatac cgcccgggtg ttatcgagca tggcagatgc cgtgctggcc    420

agggtgtaca aacagtccga tctcgatacc ttggcaaagg aggcttccat tcccatcatc    480

aacggcctga gcgacctgta ccacccaatc caaatcctgg ctgactacct gaccctgcaa    540

gagcactaca gcagcctgaa gggtctgacc ctgtcatgga ttggcgatgg aaacaatatt    600

ctgcactcca tcatgatgtc cgccgcgaag ttcggaatgc atctgcaagc cgccactcca    660

aaaggatacg aaccggatgc atccgtgacc aagttggcgg aacagtacgc gaaggagaac    720

ggaaccaagc tcctgctgac taacgacccg ctcgaggctg cgcatggggg taacgtgctg    780

attacggaca cctggatctc catggggcag gaggaagaga agaagaagag actgcaggca    840

ttccaggggt accaggtcac catgaaaacc gcaaaagtgg cagcttcgga ctggactttc    900

ctgcattgcc tgccgaggaa gccggaggaa gtcgacgacg aagtgttcta ctcgcctcgg    960

tccctggtgt tccccgaggc cgaaaaccgg aagtggacca tcatggccgt gatggtgtcc   1020

ttgctgactg actatagccc gcagctgcag aagcctaagt tctagataag tga          1073


<210> SEQ ID NO 168
<211> LENGTH: 1073
<212> TYPE: DNA
<213> ORGANISM: Artificial Sequence
<220> FEATURE:
<223> OTHER INFORMATION: Synthetic construct

<400> SEQUENCE: 168

atgctgttca acctgcgcat cctgctgaac aacgccgcct tccgcaacgg ccacaacttc     60

atggtgcgca acttccgctg cggccagccc ctgcagaaca aggtgcagct gaagggccgc    120

gacctgctga ccctgaagaa cttcaccggc gaggagatca agtacatgct gtggctgagc    180

gccgacctga agttccgcat caagcagaag ggcgagtacc tgcccctgct gcagggcaag    240

agcctgggca tgatcttcga gaagcgcagc acccgcaccc gcctgagcac cgagacaggc    300

ctggccctgc tgggcggcca cccctgcttc ctgaccaccc aggacatcca cctgggcgtg    360

aacgagagcc tgaccgacac cgcccgcgtg ctgagcagca tggccgacgc cgtgctggcc    420

cgcgtgtaca agcagagcga cctggacacc ctggccaagg aggccagcat ccccatcatc    480

aacggcctga gcgacctgta ccaccccatc cagatcctgg ccgactacct gaccctgcag    540

gagcactaca gcagcctgaa gggcctgacc ctgagctgga tcggcgacgg caacaacatc    600

ctgcacagca tcatgatgag cgccgccaag ttcggcatgc acctgcaggc cgccaccccc    660

aagggctacg agcccgacgc cagcgtgacc aagctggccg agcagtacgc caaggagaac    720

ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctgaataag tga          1073


<210> SEQ ID NO 169
<211> LENGTH: 1074
```

<212> TYPE: DNA
<213> ORGANISM: Artificial Sequence
<220> FEATURE:
<223> OTHER INFORMATION: Synthetic construct

<400> SEQUENCE: 169
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctagataag tgaa 1074

<210> SEQ ID NO 170
<211> LENGTH: 1073
<212> TYPE: DNA
<213> ORGANISM: Artificial Sequence
<220> FEATURE:
<223> OTHER INFORMATION: Synthetic construct

<400> SEQUENCE: 170
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ctggccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780

-continued atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag tga 1073

<210> SEQ ID NO 171
<211> LENGTH: 1073
<212> TYPE: DNA
<213> ORGANISM: Artificial Sequence
<220> FEATURE:
<223> OTHER INFORMATION: Synthetic construct

<400> SEQUENCE: 171
atgcttttca acctgagaat cctcttgaac aatgctgctt ttcggaatgg ccacaacttt 60
atggttcgga acttccgttg cggccagcct ttacaaaaca aggtccagct gaagggccgg 120
gatttgctca cactaaagaa ctttactgga gaagagatca agtacatgct atggctgtcg 180
gccgacctga agttccgtat caagcagaag ggagaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctcgatacc ttggcaaagg aggcttccat tcccatcatc 480
aacggcctga gcgacctgta ccacccaatc caaatcctgg ctgactacct gaccctgcaa 540
gagcactaca gcagcctgaa gggtctgacc ctgtcatgga ttggcgatgg aaacaatatt 600
ctgcactcca tcatgatgtc cgccgcgaag ttcggaatgc atctgcaagc cgccactcca 660
aaaggatacg aaccggatgc atccgtgacc aagttggcgg aacagtacgc gaaggagaac 720
ggaaccaagc tcctgctgac taacgacccg ctcgaggctg cgcatggggg taacgtgctg 780
attacggaca cctggatctc catggggcag gaggaagaga agaagaagag actgcaggca 840
ttccaggggt accaggtcac catgaaaacc gcaaaagtgg cagcttcgga ctggactttc 900
ctgcattgcc tgccgaggaa gccggaggaa gtcgacgacg aagtgttcta ctcgcctcgg 960
tccctggtgt tccccgaggc cgaaaaccgg aagtggacca tcatggccgt gatggtgtcc 1020
ttgctgactg actatagccc gcagctgcag aagcctaagt tctagataag tga 1073

<210> SEQ ID NO 172
<211> LENGTH: 1074
<212> TYPE: DNA
<213> ORGANISM: Artificial Sequence
<220> FEATURE:
<223> OTHER INFORMATION: Synthetic construct

<400> SEQUENCE: 172
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctagataag tgaa 1074

<210> SEQ ID NO 173
<211> LENGTH: 1073
<212> TYPE: DNA
<213> ORGANISM: Artificial Sequence
<220> FEATURE:
<223> OTHER INFORMATION: Synthetic construct

<400> SEQUENCE: 173
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ctggccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag tga 1073

<210> SEQ ID NO 174
<211> LENGTH: 1073
<212> TYPE: DNA
<213> ORGANISM: Artificial Sequence
<220> FEATURE:
<223> OTHER INFORMATION: Synthetic construct

<400> SEQUENCE: 174
atgcttttca acctgagaat cctcttgaac aatgctgctt ttcggaatgg ccacaacttt 60
atggttcgga acttccgttg cggccagcct ttacaaaaca aggtccagct gaagggccgg 120
gatttgctca cactaaagaa ctttactgga gaagagatca agtacatgct atggctgtcg 180
gccgacctga agttccgtat caagcagaag ggagaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctcgatacc ttggcaaagg aggcttccat tcccatcatc 480
aacggcctga gcgacctgta ccacccaatc caaatcctgg ctgactacct gaccctgcaa 540
gagcactaca gcagcctgaa gggtctgacc ctgtcatgga ttggcgatgg aaacaatatt 600
ctgcactcca tcatgatgtc cgccgcgaag ttcggaatgc atctgcaagc cgccactcca 660
aaaggatacg aaccggatgc atccgtgacc aagttggcgg aacagtacgc gaaggagaac 720
ggaaccaagc tcctgctgac taacgacccg ctcgaggctg cgcatggggg taacgtgctg 780
attacggaca cctggatctc catggggcag gaggaagaga agaagaagag actgcaggca 840
ttccaggggt accaggtcac catgaaaacc gcaaaagtgg cagcttcgga ctggactttc 900
ctgcattgcc tgccgaggaa gccggaggaa gtcgacgacg aagtgttcta ctcgcctcgg 960
tccctggtgt tccccgaggc cgaaaaccgg aagtggacca tcatggccgt gatggtgtcc 1020
ttgctgactg actatagccc gcagctgcag aagcctaagt tctagataag tga 1073

<210> SEQ ID NO 175
<211> LENGTH: 1065
<212> TYPE: DNA
<213> ORGANISM: Artificial Sequence
<220> FEATURE:
<223> OTHER INFORMATION: Synthetic construct

<400> SEQUENCE: 175
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 176
<211> LENGTH: 1065
<212> TYPE: DNA
<213> ORGANISM: Artificial Sequence
<220> FEATURE:
<223> OTHER INFORMATION: Synthetic construct

<400> SEQUENCE: 176
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 177
<211> LENGTH: 1065
<212> TYPE: DNA
<213> ORGANISM: Artificial Sequence
<220> FEATURE:
<223> OTHER INFORMATION: Synthetic construct

<400> SEQUENCE: 177
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600

```
ctgcacagca tcatgatgag cgccgccaag ttcggcatgc acctgcaggc cgccaccccc    660

aagggctacg agcccgacgc cagcgtgacc aagctggccg agcagtacgc caaggagaac    720

ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctga                   1065
```

<210> SEQ ID NO 178
<211> LENGTH: 1074
<212> TYPE: DNA
<213> ORGANISM: Artificial Sequence
<220> FEATURE:
<223> OTHER INFORMATION: Synthetic construct

<400> SEQUENCE: 178

```
atgctgttca acctgcgcat cctgctgaac aacgccgcct tccgcaacgg ccacaacttc     60

atggtgcgca acttccgctg cggccagccc ctgcagaaca aggtgcagct gaagggccgc    120

gacctgctga ccctgaagaa cttcaccggc gaggagatca agtacatgct gtggctgagc    180

gccgacctga agttccgcat caagcagaag ggcgagtacc tgcccctgct gcagggcaag    240

agcctgggca tgatcttcga gaagcgcagc acccgcaccc gcctgagcac cgagacaggc    300

ttcgccctgc tgggcggcca cccctgcttc ctgaccaccc aggacatcca cctgggcgtg    360

aacgagagcc tgaccgacac cgcccgcgtg ctgagcagca tggccgacgc cgtgctggcc    420

cgcgtgtaca agcagagcga cctggacacc ctggccaagg aggccagcat ccccatcatc    480

aacggcctga gcgacctgta ccaccccatc cagatcctgg ccgactacct gaccctgcag    540

gagcactaca gcagcctgaa gggcctgacc ctgagctgga tcggcgacgg caacaacatc    600

ctgcacagca tcatgatgag cgccgccaag ttcggcatgc acctgcaggc cgccaccccc    660

aagggctacg agcccgacgc cagcgtgacc aagctggccg agcagtacgc caaggagaac    720

ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctgaataag tgaa         1074
```

<210> SEQ ID NO 179
<211> LENGTH: 1077
<212> TYPE: DNA
<213> ORGANISM: Artificial Sequence
<220> FEATURE:
<223> OTHER INFORMATION: Synthetic construct

<400> SEQUENCE: 179

```
atgggcgtct tcaacctgcg gatcctgctg aacaacgccg ccttccggaa cggccacaac     60

ttcatggtcc gcaacttcag atgcggccag cccctgcaga acaaggtgca gctgaagggc    120

cgggacctgc tgaccctgaa gaacttcacc ggcgaagaga tcaagtacat gctgtggctg    180

agcgccgacc tgaagttccg gatcaagcag aagggcgagt acctgcccct gctgcaaggc    240
```

-continued

```
aagagcctgg gcatgatctt cgagaagcgg agcacccgga cccggctgag caccgagaca    300

ggctttgccc tgctgggagg ccacccctgc tttctgacca cccaggacat ccacctgggc    360

gtgaacgaga gcctgaccga caccgccaga gtgctgagca gcatggccga cgccgtgctg    420

gcccgggtgt acaagcagag cgacctggac accctggcca aagaggccag catccccatc    480

atcaacggcc tgagcgacct gtaccacccc atccagatcc tggccgacta cctgaccctg    540

caggaacact acagctccct gaagggcctg accctgagct ggatcggcga cggcaacaac    600

atcctgcaca gcatcatgat gagcgccgcc aagttcggca tgcatctgca ggccgccacc    660

cccaagggct acgagcctga tgccagcgtg accaagctgg ccgagcagta cgccaaagag    720

aacggcacca agctgctgct gaccaacgac cccctggaag ccgcccacgg cggcaacgtg    780

ctgatcaccg acacctggat cagcatgggc caggaagagg aaaagaagaa gcggctgcag    840

gccttccagg gctaccaggt cacaatgaag accgccaagg tggccgccag cgactggacc    900

ttcctgcact gcctgccccg gaagcccgaa gaggtggacg acgaggtgtt ctacagcccc    960

cggtccctgg tgttccccga ggccgagaac cggaagtgga ccattatggc cgtgatggtg   1020

tccctgctga ccgactactc cccccagctg cagaagccca agttctagat aagtgaa      1077
```

<210> SEQ ID NO 180
<211> LENGTH: 1077
<212> TYPE: DNA
<213> ORGANISM: Artificial Sequence
<220> FEATURE:
<223> OTHER INFORMATION: Synthetic construct

<400> SEQUENCE: 180

```
atgggcgtct tcaacctgcg gatcctgctg aacaacgccg ccttccggaa cggccacaac     60

ttcatggtcc gcaacttcag atgcggccag cccctgcaga acagggtgca gctgaagggc    120

cgggacctgc tgaccctgaa gaacttcacc ggcgaagaga tcaggtacat gctgtggctg    180

agcgccgacc tgaagttccg gatcaagcag aagggcgagt acctgcccct gctgcaaggc    240

aagagcctgg gcatgatctt cgagaagcgg agcacccgga cccggctgag caccgagaca    300

ggctttgccc tgctgggagg ccacccctgc tttctgacca cccaggacat ccacctgggc    360

gtgaacgaga gcctgaccga caccgccaga gtgctgagca gcatggccga cgccgtgctg    420

gcccgggtgt acaagcagag cgacctggac accctggcca aagaggccag catccccatc    480

atcaacggcc tgagcgacct gtaccacccc atccagatcc tggccgacta cctgaccctg    540

caggaacact acagctccct gaagggcctg accctgagct ggatcggcga cggcaacaac    600

atcctgcaca gcatcatgat gagcgccgcc aagttcggca tgcatctgca ggccgccacc    660

cccaagggct acgagcctga tgccagcgtg accaagctgg ccgagcagta cgccaaagag    720

aacggcacca agctgctgct gaccaacgac cccctggaag ccgcccacgg cggcaacgtg    780

ctgatcaccg acacctggat cagcatgggc caggaagagg aaaagaagaa gcggctgcag    840

gccttccagg gctaccaggt cacaatgaag accgccaagg tggccgccag cgactggacc    900

ttcctgcact gcctgccccg gaagcccgaa gaggtggacg acgaggtgtt ctacagcccc    960

cggtccctgg tgttccccga ggccgagaac cggaagtgga ccattatggc cgtgatggtg   1020

tccctgctga ccgactactc cccccagctg cagaagccca agttctagat aagtgaa      1077
```

<210> SEQ ID NO 181
<211> LENGTH: 1077
<212> TYPE: DNA

<213> ORGANISM: Artificial Sequence
<220> FEATURE:
<223> OTHER INFORMATION: Synthetic construct

<400> SEQUENCE: 181
atgctggtct tcaacctgcg gatcctgctg aacaacgccg ccttccggaa cggccacaac 60
ttcatggtcc gcaacttcag atgcggccag cccctgcaga acagggtgca gctgaagggc 120
cgggacctgc tgaccctgaa gaacttcacc ggcgaagaga tcaggtacat gctgtggctg 180
agcgccgacc tgaagttccg gatcaagcag aagggcgagt acctgcccct gctgcaaggc 240
aagagcctgg gcatgatctt cgagaagcgg agcacccgga cccggctgag caccgagaca 300
ggctttgccc tgctgggagg ccacccctgc tttctgacca cccaggacat ccacctgggc 360
gtgaacgaga gcctgaccga caccgccaga gtgctgagca gcatggccga cgccgtgctg 420
gcccgggtgt acaagcagag cgacctggac accctggcca aagaggccag catccccatc 480
atcaacggcc tgagcgacct gtaccacccc atccagatcc tggccgacta cctgaccctg 540
caggaacact acagctccct gaagggcctg accctgagct ggatcggcga cggcaacaac 600
atcctgcaca gcatcatgat gagcgccgcc aagttcggca tgcatctgca ggccgccacc 660
cccaagggct acgagcctga tgccagcgtg accaagctgg ccgagcagta cgccaaagag 720
aacggcacca agctgctgct gaccaacgac cccctggaag ccgcccacgg cggcaacgtg 780
ctgatcaccg acacctggat cagcatgggc caggaagagg aaaagaagaa gcggctgcag 840
gccttccagg gctaccaggt cacaatgaag accgccaagg tggccgccag cgactggacc 900
ttcctgcact gcctgccccg gaagcccgaa gaggtggacg acgaggtgtt ctacagcccc 960
cggtccctgg tgttccccga ggccgagaac cggaagtgga ccattatggc cgtgatggtg 1020
tccctgctga ccgactactc cccccagctg cagaagccca agttctagat aagtgaa 1077

<210> SEQ ID NO 182
<211> LENGTH: 1074
<212> TYPE: DNA
<213> ORGANISM: Artificial Sequence
<220> FEATURE:
<223> OTHER INFORMATION: Synthetic construct

<400> SEQUENCE: 182
atgctgttca acctgaggat cctgctgaac aacgcagctt tcaggaacgg ccacaacttc 60
atggtgagga acttccggtg cggccagccc ctgcagaaca aggtgcagct gaagggcagg 120
gacctgctga ccctgaagaa cttcaccgga gaggagatca agtacatgct gtggctgagc 180
gcagacctga agttcaggat caagcagaag ggagagtacc tgcccctgct gcaggggaag 240
tccctgggca tgatcttcga gaagaggagt accaggacca ggctgagcac cgaaaccggc 300
ttcgccctgc tgggaggaca cccctgcttc ctgaccaccc aggacatcca cctgggcgtg 360
aacgagagtc tgaccgacac cgccagggtg ctgtctagca tggccgacgc cgtgctggcc 420
agggtgtaca agcagtcaga cctggacacc ctggctaagg aggccagcat ccccatcatc 480
aacggcctga gcgacctgta ccaccccatc cagatcctgg ctgactacct gaccctgcag 540
gagcactaca gctctctgaa gggcctgacc ctgagctgga tcggcgacgg gaacaacatc 600
ctgcacagca tcatgatgag cgccgccaag ttcggcatgc acctgcaggc cgctaccccc 660
aagggttacg agcccgacgc cagcgtgacc aagctggcag agcagtacgc caaggagaac 720
ggcaccaagc tgctgctgac caacgacccc ctggaggccg cccacggagg caacgtgctg 780
atcaccgaca cctggatcag catgggacag gaggaggaga agaagaagcg gctgcaggct 840
ttccagggtt accaggtgac catgaagacc gccaaggtgg ctgccagcga ctggaccttc 900
ctgcactgcc tgcccaggaa gcccgaggag gtggacgacg aggtgttcta ctctcccagg 960
agcctggtgt tccccgaggc cgagaacagg aagtggacca tcatggctgt gatggtgtcc 1020
ctgctgaccg actacagccc ccagctgcag aagcccaagt tctgaataag tgaa 1074

<210> SEQ ID NO 183
<211> LENGTH: 1074
<212> TYPE: DNA
<213> ORGANISM: Artificial Sequence
<220> FEATURE:
<223> OTHER INFORMATION: Synthetic construct

<400> SEQUENCE: 183
atgctgttca acctgaggat cctgctgaac aacgcagctt tcaggaacgg ccacaacttc 60
atggtgagga acttccggtg cggccagccc ctgcagaaca aggtgcagct gaagggcagg 120
gacctgctga ccctgaagaa cttcaccgga gaggagatca agtacatgct gtggctgagc 180
gcagacctga agttcaggat caagcagaag ggagagtacc tgcccctgct gcaggggaag 240
tccctgggca tgatcttcga gaagaggagt accaggacca ggctgagcac cgaaaccggc 300
ttcgccctgc tgggaggaca cccctgcttc ctgacgaccc aggacatcca cctcggagtg 360
aacgaatccc tcaccgatac cgcccgggtg ttatcaagca tggcagatgc cgtgctggcc 420
agggtgtaca aacagtccga tctggacact ctggctaagg aggccagcat ccccatcatc 480
aacggcctga gcgacctgta ccaccccatc cagatcctgg ctgactacct gaccctgcag 540
gagcactaca gctctctgaa gggcctgacc ctgagctgga tcggcgacgg gaacaacatc 600
ctgcactcca tcatgatgtc cgccgcgaag ttcggaatgc atctgcaagc cgccacgcca 660
aaaggatacg aaccggatgc gcccgtgaca aagttggcgg aacagtacgc taaggagaac 720
ggaaccaagc tgctgctgac caacgacccc ctggaggccg cccacggagg caacgtgctg 780
atcaccgaca cctggatcag catgggacag gaggaggaga agaagaagcg gctgcaggct 840
ttccagggtt accaggtgac catgaagacc gccaaggtgg ctgccagcga ctggaccttc 900
ctgcactgcc tgcccaggaa gcccgaggag gtggacgacg aggtgttcta ctctcccagg 960
agcctggtgt tccccgaggc cgagaacagg aagtggacca tcatggctgt gatggtgtcc 1020
ctgctgaccg actacagccc ccagctgcag aagcccaagt tctgaataag tgaa 1074

<210> SEQ ID NO 184
<211> LENGTH: 1074
<212> TYPE: DNA
<213> ORGANISM: Artificial Sequence
<220> FEATURE:
<223> OTHER INFORMATION: Synthetic construct

<400> SEQUENCE: 184
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag tgaa 1074

<210> SEQ ID NO 185
<211> LENGTH: 1074
<212> TYPE: DNA
<213> ORGANISM: Artificial Sequence
<220> FEATURE:
<223> OTHER INFORMATION: Synthetic construct

<400> SEQUENCE: 185
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag tgaa 1074

<210> SEQ ID NO 186
<211> LENGTH: 1065
<212> TYPE: DNA
<213> ORGANISM: Artificial Sequence
<220> FEATURE:
<223> OTHER INFORMATION: Synthetic construct

<400> SEQUENCE: 186
atgcttttca acttgagaat cctgctgaac aacgccgcct ttcgcaacgg tcacaatttt 60
atggtcagaa acttcagatg cggacagccc ctccaaaaca aggtccagct gaagggccgc 120
gatctcctca ccctgaagaa cttcacgggg gaggagatca agtacatgct gtggctctcc 180
gctgacctga agttcaggat caagcagaag ggagaatatc tgccgctgct gcaagggaag 240
tccctgggga tgattttcga gaagcggagc acccggactc ggctctccac tgaaactggt 300
ttcgcccttc tgggcggtca cccctgcttc ctgaccactc aagacattca cctcggagtg 360
aacgagtcct tgactgacac cgcccgggtg ctgtcgagca tggcagacgc cgtgctagcc 420
cgcgtgtaca agcagtcaga cctcgatacc ctggccaagg aggcttcgat cccgatcatc 480
aacgggttgt ccgacctgta ccacccgatt cagattctcg ccgactacct caccctgcaa 540
gagcattaca gctccctgaa ggggcttacc ctgtcctgga ttggcgacgg aaacaacatc 600
ctgcactcca ttatgatgtc ggcggccaag ttcggcatgc acctccaagc cgcgacccct 660
aagggttacg aaccagacgc gtcagtgact aagctggccg aacagtacgc aaaggaaaat 720
ggcacgaagc tgctcctgac caacgatccg ttggaagccg cccatggcgg aaatgtgctc 780
atcaccgaca cctggatctc gatgggacag gaggaagaga agaagaagcg gctgcaggcg 840
ttccagggct accaggtcac catgaaaact gccaaggtgg ccgccagcga ctggaccttc 900
ctgcactgcc ttccgcgcaa gcctgaggag gtggacgatg aagtgttcta ctctccacgg 960
tccctggtgt tccccgaggc ggagaaccgc aaatggacca tcatggctgt gatggtcagc 1020
ctgctgaccg attacagccc tcagttgcaa aagccgaagt tttga 1065

<210> SEQ ID NO 187
<211> LENGTH: 1065
<212> TYPE: DNA
<213> ORGANISM: Artificial Sequence
<220> FEATURE:
<223> OTHER INFORMATION: Synthetic construct

<400> SEQUENCE: 187
atgctgttca acctccgcat cctcctcaac aacgccgcat tcagaaacgg gcacaacttc 60
atggtcagaa acttccgctg cgggcaaccc ctacaaaaca aggtccagct caaggggcgg 120
gacctcctga ccctgaagaa cttcaccggc gaagagatca agtacatgct gtggctctcc 180
gccgacctga agttccgcat caagcagaag ggagagtacc tcccgctgct gcaagggaag 240
tcgctgggga tgatcttcga gaagcggtca accagaaccc ggctgtcaac cgaaaccggg 300
ttcgcactgc tggggggaca cccgtgcttc ctgaccaccc aagacatcca cctgggagtg 360
aacgaatcgc tgaccgacac cgcccgcgtg ctgagctcaa tggcggacgc cgtgctggcc 420
cgcgtgtaca agcagtccga cctggacacc ctggccaagg aagcgtccat cccgatcatc 480
aacggactgt ccgacctgta ccacccgatc cagatcctgg cagactacct gaccctgcaa 540
gaacactaca gctccctgaa gggcctgacc ctgtcatgga tcggggacgg gaacaacatc 600
ctgcactcca taatgatgtc agccgccaag ttcggaatgc acctccaagc cgcaaccccg 660
aagggctacg aaccggacgc atcagtgacc aaactggccg agcagtacgc caaggaaaac 720
ggcaccaagc tcctgctgac caacgacccg ctggaggccg cacacggggg gaacgtgctg 780
atcaccgaca cctggatctc catgggacag gaggaggaaa agaagaagcg gctgcaggcg 840
ttccaggggt accaggtcac catgaaaacc gcgaaggtcg cggcatcaga ctggaccttc 900
ctgcactgcc tgccccggaa gccggaagag gtggacgacg aggtgttcta ctcgccgcgc 960
tcgctggtgt tccccgaggc ggagaacagg aagtggacca tcatggcggt gatggtcagc 1020
ctcctgaccg actactcgcc gcagctgcag aagccgaagt tctga 1065

<210> SEQ ID NO 188
<211> LENGTH: 1074
<212> TYPE: DNA
<213> ORGANISM: Artificial Sequence
<220> FEATURE:
<223> OTHER INFORMATION: Synthetic construct

<400> SEQUENCE: 188
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag ggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctgaataag taga 1074

<210> SEQ ID NO 189
<211> LENGTH: 1074
<212> TYPE: DNA
<213> ORGANISM: Artificial Sequence
<220> FEATURE:
<223> OTHER INFORMATION: Synthetic construct

<400> SEQUENCE: 189
atgcttttca acctgagaat cctcttgaac aatgctgctt ttcggaatgg ccacaacttt 60
atggttcgga acttccgttg cggccagcct ttacaaaaca aggtccagct gaagggccgg 120
gatttgctca cactaaagaa ctttactgga gaagagatca agtacatgct atggctgtcg 180
gccgacctga agttccgtat caagcagaag ggagaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctcgatacc ttggcaaagg aggcttccat tcccatcatc 480
aacggcctga gcgacctgta ccacccaatc caaatcctgg ctgactacct gaccctgcaa 540
gagcactaca gcagcctgaa gggtctgacc ctgtcatgga ttggcgatgg aaacaatatt 600
ctgcactcca tcatgatgtc cgccgcgaag ttcggaatgc atctgcaagc cgccactcca 660
aaaggatacg aaccggatgc atccgtgacc aagttggcgg aacagtacgc gaaggagaac 720
ggaaccaagc tcctgctgac taacgacccg ctcgaggctg cgcatggggg taacgtgctg 780
attacggaca cctggatctc catggggcag gaggaagaga agaagaagag actgcaggca 840
ttccaggggt accaggtcac catgaaaacc gcaaaagtgg cagcttcgga ctggactttc 900
ctgcattgcc tgccgaggaa gccggaggaa gtcgacgacg aagtgttcta ctcgcctcgg 960
tccctggtgt tccccgaggc cgaaaaccgg aagtggacca tcatggccgt gatggtgtcc 1020
ttgctgactg actatagccc gcagctgcag aagcctaagt tctgaataag taga 1074

<210> SEQ ID NO 190
<211> LENGTH: 1074
<212> TYPE: DNA
<213> ORGANISM: Artificial Sequence
<220> FEATURE:
<223> OTHER INFORMATION: Synthetic construct

<400> SEQUENCE: 190
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ctggccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctgaataag taga 1074

<210> SEQ ID NO 191
<211> LENGTH: 1065
<212> TYPE: DNA
<213> ORGANISM: Artificial Sequence
<220> FEATURE:
<223> OTHER INFORMATION: Synthetic construct

<400> SEQUENCE: 191
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggggaatacc ttccgctgct tcaaggaaag 240

```
agcctcggca tgatctttga gaagcgctca accaggaccc gcctttctac tgaaactggg    300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca aacagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                   1065
```

<210> SEQ ID NO 192
<211> LENGTH: 1065
<212> TYPE: DNA
<213> ORGANISM: Artificial Sequence
<220> FEATURE:
<223> OTHER INFORMATION: Synthetic construct

<400> SEQUENCE: 192

```
atgcttttca atctccgcat cctccttaac aacgccgcgt ttagaaacgg ccacaacttc     60
atggtccgga acttcagatg tggccagccg cttcaaaaca aggtccagct gaagggccgg    120
gatcttctga ccctgaagaa ctttactggc gaagagatca agtacatgct ctggctctcc    180
gcggacttga agttccgcat taagcagaag gggggaatacc ttccgctgct tcaaggaaag    240
agcctcggca tgatctttga gaagcgctca accaggaccc gcctttctac tgaaactggg    300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca aacagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                   1065
```

<210> SEQ ID NO 193
<211> LENGTH: 1065
<212> TYPE: DNA
<213> ORGANISM: Artificial Sequence
<220> FEATURE:
<223> OTHER INFORMATION: Synthetic construct

<400> SEQUENCE: 193
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctag 1065

<210> SEQ ID NO 194
<211> LENGTH: 1065
<212> TYPE: DNA
<213> ORGANISM: Artificial Sequence
<220> FEATURE:
<223> OTHER INFORMATION: Synthetic construct

<400> SEQUENCE: 194
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctag 1065

<210> SEQ ID NO 195
<211> LENGTH: 1065
<212> TYPE: DNA
<213> ORGANISM: Artificial Sequence
<220> FEATURE:
<223> OTHER INFORMATION: Synthetic construct

<400> SEQUENCE: 195
atgcttttca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag ggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctag 1065

<210> SEQ ID NO 196
<211> LENGTH: 1065
<212> TYPE: DNA
<213> ORGANISM: Artificial Sequence
<220> FEATURE:
<223> OTHER INFORMATION: Synthetic construct

<400> SEQUENCE: 196
atggtgttca acctccgcat cctcctcaac aacgccgcat tcagaaacgg gcacaacttc 60
atggtcagaa acttccgctg cgggcaaccc ctacaaaaca aggtccagct caaggggcgg 120
gacctcctga ccctgaagaa cttcaccggc gaagagatca agtacatgct gtggctctcc 180
gccgacctga agttccgcat caagcagaag ggagagtacc tcccgctgct gcaagggaag 240
tcgctgggga tgatcttcga gaagcggtca accagaaccc ggctgtcaac cgaaaccggg 300
ttcgcactgc tggggggaca cccgtgcttc ctgaccaccc aagacatcca cctgggagtg 360
aacgaatcgc tgaccgacac cgcccgcgtg ctgagctcaa tggcggacgc cgtgctggcc 420
cgcgtgtaca agcagtccga cctggacacc ctggccaagg aagcgtccat cccgatcatc 480
aacggactgt ccgacctgta ccacccgatc cagatcctgg cagactacct gaccctgcaa 540
gaacactaca gctccctgaa gggcctgacc ctgtcatgga tcggggacgg gaacaacatc 600
ctgcactcca taatgatgtc agccgccaag ttcggaatgc acctccaagc cgcaaccccg 660
aagggctacg aaccggacgc atcagtgacc aaactggccg agcagtacgc caaggaaaac 720
ggcaccaagc tcctgctgac caacgacccg ctggaggccg cacacggggg gaacgtgctg 780
atcaccgaca cctggatctc catgggacag gaggaggaaa agaagaagcg gctgcaggcg 840
ttccaggggt accaggtcac catgaaaacc gcgaaggtcg cggcatcaga ctggaccttc 900
ctgcactgcc tgccccggaa gccggaagag gtggacgacg aggtgttcta ctcgccgcgc 960
tcgctggtgt tccccgaggc ggagaacagg aagtggacca tcatggcggt gatggtcagc 1020
ctcctgaccg actactcgcc gcagctgcag aagccgaagt tctga 1065

<210> SEQ ID NO 197
<211> LENGTH: 1065
<212> TYPE: DNA
<213> ORGANISM: Artificial Sequence
<220> FEATURE:
<223> OTHER INFORMATION: Synthetic construct

<400> SEQUENCE: 197
atggtgttca acctccgcat cctcctcaac aacgccgcat tcagaaacgg gcacaacttc 60
atggtcagaa acttccgctg cgggcaaccc ctacaaaacc gggtccagct caaggggcgg 120
gacctcctga ccctgaagaa cttcaccggc gaagagatca agtacatgct gtggctctcc 180
gccgacctga agttccgcat caagcagaag ggagagtacc tcccgctgct gcaagggaag 240
tcgctgggga tgatcttcga gaagcggtca accagaaccc ggctgtcaac cgaaaccggg 300
ttcgcactgc tgggggggaca cccgtgcttc ctgaccaccc aagacatcca cctgggagtg 360
aacgaatcgc tgaccgacac cgcccgcgtg ctgagctcaa tggcggacgc cgtgctggcc 420
cgcgtgtaca agcagtccga cctggacacc ctggccaagg aagcgtccat cccgatcatc 480
aacggactgt ccgacctgta ccacccgatc cagatcctgg cagactacct gaccctgcaa 540
gaacactaca gctccctgaa gggcctgacc ctgtcatgga tcggggacgg gaacaacatc 600
ctgcactcca taatgatgtc agccgccaag ttcggaatgc acctccaagc cgcaaccccg 660
aagggctacg aaccggacgc atcagtgacc aaactggccg agcagtacgc caaggaaaac 720
ggcaccaagc tcctgctgac caacgacccg ctggaggccg cacacggggg gaacgtgctg 780
atcaccgaca cctggatctc catgggacag gaggaggaaa agaagaagcg gctgcaggcg 840
ttccaggggt accaggtcac catgaaaacc gcgaaggtcg cggcatcaga ctggaccttc 900
ctgcactgcc tgccccggaa gccggaagag gtggacgacg aggtgttcta ctcgccgcgc 960
tcgctggtgt tccccgaggc ggagaacagg aagtggacca tcatggcggt gatggtcagc 1020
ctcctgaccg actactcgcc gcagctgcag aagccgaagt tctga 1065

<210> SEQ ID NO 198
<211> LENGTH: 1065
<212> TYPE: DNA
<213> ORGANISM: Artificial Sequence
<220> FEATURE:
<223> OTHER INFORMATION: Synthetic construct

<400> SEQUENCE: 198
atggtgttca acctccgcat cctcctcaac aacgccgcat tcagaaacgg gcacaacttc 60

```
atggtcagaa acttccgctg cgggcaaccc ctacaaaacc gggtccagct caaggggcgg    120

gacctcctga ccctgaagaa cttcaccggc gaagagatcc ggtacatgct gtggctctcc    180

gccgacctga agttccgcat caagcagaag ggagagtacc tcccgctgct gcaagggaag    240

tcgctgggga tgatcttcga gaagcggtca accagaaccc ggctgtcaac cgaaaccggg    300

ttcgcactgc tggggggaca cccgtgcttc ctgaccaccc aagacatcca cctgggagtg    360

aacgaatcgc tgaccgacac cgcccgcgtg ctgagctcaa tggcggacgc cgtgctggcc    420

cgcgtgtaca agcagtccga cctggacacc ctggccaagg aagcgtccat cccgatcatc    480

aacggactgt ccgacctgta ccacccgatc cagatcctgg cagactacct gaccctgcaa    540

gaacactaca gctccctgaa gggcctgacc ctgtcatgga tcggggacgg gaacaacatc    600

ctgcactcca taatgatgtc agccgccaag ttcggaatgc acctccaagc cgcaaccccg    660

aagggctacg aaccggacgc atcagtgacc aaactggccg agcagtacgc caaggaaaac    720

ggcaccaagc tcctgctgac caacgacccg ctggaggccg cacacggggg gaacgtgctg    780

atcaccgaca cctggatctc catgggacag gaggaggaaa agaagaagcg gctgcaggcg    840

ttccaggggt accaggtcac catgaaaacc gcgaaggtcg cggcatcaga ctggaccttc    900

ctgcactgcc tgccccggaa gccggaagag gtggacgacg aggtgttcta ctcgccgcgc    960

tcgctggtgt tccccgaggc ggagaacagg aagtggacca tcatggcggt gatggtcagc   1020

ctcctgaccg actactcgcc gcagctgcag aagccgaagt tctga                  1065
```

```
<210> SEQ ID NO 199
<211> LENGTH: 1065
<212> TYPE: DNA
<213> ORGANISM: Artificial Sequence
<220> FEATURE:
<223> OTHER INFORMATION: Synthetic construct

<400> SEQUENCE: 199

atgctggtca acctccgcat cctcctcaac aacgccgcat tcagaaacgg gcacaacttc     60

atggtcagaa acttccgctg cgggcaaccc ctacaaaaca aggtccagct caaggggcgg    120

gacctcctga ccctgaagaa cttcaccggc gaagagatca agtacatgct gtggctctcc    180

gccgacctga agttccgcat caagcagaag ggagagtacc tcccgctgct gcaagggaag    240

tcgctgggga tgatcttcga gaagcggtca accagaaccc ggctgtcaac cgaaaccggg    300

ttcgcactgc tggggggaca cccgtgcttc ctgaccaccc aagacatcca cctgggagtg    360

aacgaatcgc tgaccgacac cgcccgcgtg ctgagctcaa tggcggacgc cgtgctggcc    420

cgcgtgtaca agcagtccga cctggacacc ctggccaagg aagcgtccat cccgatcatc    480

aacggactgt ccgacctgta ccacccgatc cagatcctgg cagactacct gaccctgcaa    540

gaacactaca gctccctgaa gggcctgacc ctgtcatgga tcggggacgg gaacaacatc    600

ctgcactcca taatgatgtc agccgccaag ttcggaatgc acctccaagc cgcaaccccg    660

aagggctacg aaccggacgc atcagtgacc aaactggccg agcagtacgc caaggaaaac    720

ggcaccaagc tcctgctgac caacgacccg ctggaggccg cacacggggg gaacgtgctg    780

atcaccgaca cctggatctc catgggacag gaggaggaaa agaagaagcg gctgcaggcg    840

ttccaggggt accaggtcac catgaaaacc gcgaaggtcg cggcatcaga ctggaccttc    900

ctgcactgcc tgccccggaa gccggaagag gtggacgacg aggtgttcta ctcgccgcgc    960

tcgctggtgt tccccgaggc ggagaacagg aagtggacca tcatggcggt gatggtcagc   1020

ctcctgaccg actactcgcc gcagctgcag aagccgaagt tctga                  1065
```

<210> SEQ ID NO 200
<211> LENGTH: 1065
<212> TYPE: DNA
<213> ORGANISM: Artificial Sequence
<220> FEATURE:
<223> OTHER INFORMATION: Synthetic construct

<400> SEQUENCE: 200
atgctggtca acctccgcat cctcctcaac aacgccgcat tcagaaacgg gcacaacttc 60
atggtcagaa acttccgctg cgggcaaccc ctacaaaacc gggtccagct caaggggcgg 120
gacctcctga ccctgaagaa cttcaccggc gaagagatca agtacatgct gtggctctcc 180
gccgacctga agttccgcat caagcagaag ggagagtacc tcccgctgct gcaagggaag 240
tcgctgggga tgatcttcga gaagcggtca accagaaccc ggctgtcaac cgaaaccggg 300
ttcgcactgc tgggggggaca cccgtgcttc ctgaccaccc aagacatcca cctgggagtg 360
aacgaatcgc tgaccgacac cgcccgcgtg ctgagctcaa tggcggacgc cgtgctggcc 420
cgcgtgtaca agcagtccga cctggacacc ctggccaagg aagcgtccat cccgatcatc 480
aacggactgt ccgacctgta ccacccgatc cagatcctgg cagactacct gaccctgcaa 540
gaacactaca gctccctgaa gggcctgacc ctgtcatgga tcggggacgg gaacaacatc 600
ctgcactcca taatgatgtc agccgccaag ttcggaatgc acctccaagc cgcaaccccg 660
aagggctacg aaccggacgc atcagtgacc aaactggccg agcagtacgc caaggaaaac 720
ggcaccaagc tcctgctgac caacgacccg ctggaggccg cacacggggg gaacgtgctg 780
atcaccgaca cctggatctc catgggacag gaggaggaaa agaagaagcg gctgcaggcg 840
ttccaggggt accaggtcac catgaaaacc gcgaaggtcg cggcatcaga ctggaccttc 900
ctgcactgcc tgccccggaa gccggaagag gtggacgacg aggtgttcta ctcgccgcgc 960
tcgctggtgt tccccgaggc ggagaacagg aagtggacca tcatggcggt gatggtcagc 1020
ctcctgaccg actactcgcc gcagctgcag aagccgaagt tctga 1065

<210> SEQ ID NO 201
<211> LENGTH: 1065
<212> TYPE: DNA
<213> ORGANISM: Artificial Sequence
<220> FEATURE:
<223> OTHER INFORMATION: Synthetic construct

<400> SEQUENCE: 201
atgctggtca acctccgcat cctcctcaac aacgccgcat tcagaaacgg gcacaacttc 60
atggtcagaa acttccgctg cgggcaaccc ctacaaaacc gggtccagct caaggggcgg 120
gacctcctga ccctgaagaa cttcaccggc gaagagatcc ggtacatgct gtggctctcc 180
gccgacctga agttccgcat caagcagaag ggagagtacc tcccgctgct gcaagggaag 240
tcgctgggga tgatcttcga gaagcggtca accagaaccc ggctgtcaac cgaaaccggg 300
ttcgcactgc tgggggggaca cccgtgcttc ctgaccaccc aagacatcca cctgggagtg 360
aacgaatcgc tgaccgacac cgcccgcgtg ctgagctcaa tggcggacgc cgtgctggcc 420
cgcgtgtaca agcagtccga cctggacacc ctggccaagg aagcgtccat cccgatcatc 480
aacggactgt ccgacctgta ccacccgatc cagatcctgg cagactacct gaccctgcaa 540
gaacactaca gctccctgaa gggcctgacc ctgtcatgga tcggggacgg gaacaacatc 600
ctgcactcca taatgatgtc agccgccaag ttcggaatgc acctccaagc cgcaaccccg 660

```
aagggctacg aaccggacgc atcagtgacc aaactggccg agcagtacgc caaggaaaac    720

ggcaccaagc tcctgctgac caacgacccg ctggaggccg cacacggggg gaacgtgctg    780

atcaccgaca cctggatctc catgggacag gaggaggaaa agaagaagcg gctgcaggcg    840

ttccaggggt accaggtcac catgaaaacc gcgaaggtcg cggcatcaga ctggaccttc    900

ctgcactgcc tgccccggaa gccggaagag gtggacgacg aggtgttcta ctcgccgcgc    960

tcgctggtgt tccccgaggc ggagaacagg aagtggacca tcatggcggt gatggtcagc   1020

ctcctgaccg actactcgcc gcagctgcag aagccgaagt tctga                   1065
```

```
<210> SEQ ID NO 202
<211> LENGTH: 1065
<212> TYPE: DNA
<213> ORGANISM: Artificial Sequence
<220> FEATURE:
<223> OTHER INFORMATION: Synthetic construct

<400> SEQUENCE: 202

atgctggtca acctgcgcat cctgctgaac aacgccgcct tccgcaacgg ccacaacttc     60

atggtgcgca acttccgctg cggccagccc ctgcagaaca aggtgcagct gaagggccgc    120

gacctgctga ccctgaagaa cttcaccggc gaggagatca agtacatgct gtggctgagc    180

gccgacctga agttccgcat caagcagaag ggcgagtacc tgcccctgct gcagggcaag    240

agcctgggca tgatcttcga gaagcgcagc acccgcaccc gcctgagcac cgagacaggc    300

ttcgccctgc tgggcggcca cccctgcttc ctgaccaccc aggacatcca cctgggcgtg    360

aacgagagcc tgaccgacac cgcccgcgtg ctgagcagca tggccgacgc cgtgctggcc    420

cgcgtgtaca agcagagcga cctggacacc ctggccaagg aggccagcat ccccatcatc    480

aacggcctga gcgacctgta ccaccccatc cagatcctgg ccgactacct gaccctgcag    540

gagcactaca gcagcctgaa gggcctgacc ctgagctgga tcggcgacgg caacaacatc    600

ctgcacagca tcatgatgag cgccgccaag ttcggcatgc acctgcaggc cgccaccccc    660

aagggctacg agcccgacgc cagcgtgacc aagctggccg agcagtacgc caaggagaac    720

ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctga                   1065
```

```
<210> SEQ ID NO 203
<211> LENGTH: 1065
<212> TYPE: DNA
<213> ORGANISM: Artificial Sequence
<220> FEATURE:
<223> OTHER INFORMATION: Synthetic construct

<400> SEQUENCE: 203

atgctggtca acctgcgcat cctgctgaac aacgccgcct tccgcaacgg ccacaacttc     60

atggtgcgca acttccgctg cggccagccc ctgcagaacc gggtgcagct gaagggccgc    120

gacctgctga ccctgaagaa cttcaccggc gaggagatca agtacatgct gtggctgagc    180

gccgacctga agttccgcat caagcagaag ggcgagtacc tgcccctgct gcagggcaag    240

agcctgggca tgatcttcga gaagcgcagc acccgcaccc gcctgagcac cgagacaggc    300
```

ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccacccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 204
<211> LENGTH: 1065
<212> TYPE: DNA
<213> ORGANISM: Artificial Sequence
<220> FEATURE:
<223> OTHER INFORMATION: Synthetic construct

<400> SEQUENCE: 204
atgcttgtca atctccgcat cctccttaac aacgccgcgt ttagaaacgg ccacaacttc 60
atggtccgga acttcagatg tggccagccg cttcaaaaca aggtccagct gaagggccgg 120
gatcttctga ccctgaagaa ctttactggc gaagagatca agtacatgct ctggctctcc 180
gcggacttga agttccgcat taagcagaag gggggaatacc ttccgctgct tcaaggaaag 240
agcctcggca tgatctttga gaagcgctca accaggaccc gcctttctac tgaaactggg 300
ttcgcgctgc tcggtggcca cccctgcttc ctgacgaccc aggacatcca cctcggagtg 360
aacgaatccc tcaccgatac cgcccgggtg ttatcgagca tggcagatgc cgtgctggcc 420
agggtgtaca aacagtccga tctggacact ctggccaagg aggcgtcaat tcctattatc 480
aacggcctta gtgacctcta ccatccgatt cagatcctgg ccgattacct caccctgcaa 540
gaacactaca gctccctgaa gggtctgaca ttgtcctgga tcggcgacgg caacaacatt 600
ctccattcca tcatgatgtc cgccgcaaaa ttcggcatgc atcttcaagc cgccacgccg 660
aagggttacg agcccgacgc ttccgtgact aagctcgccg agcagtacgc taaggagaac 720
ggaaccaagc ttctgctgac taacgaccca ctagaagcag cccacggggg caacgtgctt 780
attactgaca cctggatctc catgggccag gaagaagaga aaaagaagcg gctgcaggcg 840
ttccagggat atcaggtcac catgaaaacc gccaaggtcg ctgcctccga ctggaccttc 900
ctgcactgcc tgcctcgcaa gcctgaagaa gtggacgacg aggtgttcta ctcgccacgg 960
agcctcgtgt tccccgaggc cgagaataga aagtggacca tcatggccgt gatggtgtca 1020
ctgctcaccg actacagccc gcagcttcag aagcccaagt tctag 1065

<210> SEQ ID NO 205
<211> LENGTH: 1065
<212> TYPE: DNA
<213> ORGANISM: Artificial Sequence
<220> FEATURE:

<223> OTHER INFORMATION: Synthetic construct

<400> SEQUENCE: 205

```
atgcttgtca atctccgcat cctccttaac aacgccgcgt ttagaaacgg ccacaacttc     60
atggtccgga acttcagatg tggccagccg cttcaaaacc gggtccagct gaagggccgg    120
gatcttctga ccctgaagaa ctttactggc gaagagatca agtacatgct ctggctctcc    180
gcggacttga agttccgcat taagcagaag gggaatacc ttccgctgct tcaaggaaag     240
agcctcggca tgatctttga gaagcgctca accaggaccc gcctttctac tgaaactggg    300
ttcgcgctgc tcggtggcca cccctgcttc ctgacgaccc aggacatcca cctcggagtg    360
aacgaatccc tcaccgatac cgcccgggtg ttatcgagca tggcagatgc cgtgctggcc    420
agggtgtaca aacagtccga tctggacact ctggccaagg aggcgtcaat tcctattatc    480
aacggcctta gtgacctcta ccatccgatt cagatcctgg ccgattacct caccctgcaa    540
gaacactaca gctccctgaa gggtctgaca ttgtcctgga tcggcgacgg caacaacatt    600
ctccattcca tcatgatgtc cgccgcaaaa ttcggcatgc atcttcaagc cgccacgccg    660
aagggttacg agcccgacgc ttccgtgact aagctcgccg agcagtacgc taaggagaac    720
ggaaccaagc ttctgctgac taacgaccca ctagaagcag cccacggggg caacgtgctt    780
attactgaca cctggatctc catgggccag gaagaagaga aaaagaagcg gctgcaggcg    840
ttccagggat atcaggtcac catgaaaacc gccaaggtcg ctgcctccga ctggaccttc    900
ctgcactgcc tgcctcgcaa gcctgaagaa gtggacgacg aggtgttcta ctcgccacgg    960
agcctcgtgt tccccgaggc cgagaataga aagtggacca tcatggccgt gatggtgtca   1020
ctgctcaccg actacagccc gcagcttcag aagcccaagt tctag                   1065
```

<210> SEQ ID NO 206
<211> LENGTH: 1068
<212> TYPE: DNA
<213> ORGANISM: Artificial Sequence
<220> FEATURE:
<223> OTHER INFORMATION: Synthetic construct

<400> SEQUENCE: 206

```
atgggccttg tcaatctccg catcctcctt aacaacgccg cgtttagaaa cggccacaac     60
ttcatggtcc ggaacttcag atgtggccag ccgcttcaaa acaaggtcca gctgaagggc    120
cgggatcttc tgaccctgaa gaactttact ggcgaagaga tcaagtacat gctctggctc    180
tccgcggact tgaagttccg cattaagcag aagggggaat accttccgct gcttcaagga    240
aagagcctcg gcatgatctt tgagaagcgc tcaaccagga cccgcctttc tactgaaact    300
gggttcgcgc tgctcggtgg ccacccctgc ttcctgacga cccaggacat ccacctcgga    360
gtgaacgaat ccctcaccga taccgcccgg gtgttatcga gcatggcaga tgccgtgctg    420
gccagggtgt acaaacagtc cgatctggac actctggcca aggaggcgtc aattcctatt    480
atcaacggcc ttagtgacct ctaccatccg attcagatcc tggccgatta cctcaccctg    540
caagaacact acagctccct gaagggtctg acattgtcct ggatcggcga cggcaacaac    600
attctccatt ccatcatgat gtccgccgca aaattcggca tgcatcttca agccgccacg    660
ccgaagggtt acgagcccga cgcttccgtg actaagctcg ccgagcagta cgctaaggag    720
aacggaacca agcttctgct gactaacgac ccactagaag cagcccacgg gggcaacgtg    780
cttattactg acacctggat ctccatgggc caggaagaag agaaaaagaa gcggctgcag    840
gcgttccagg gatatcaggt caccatgaaa accgccaagg tcgctgcctc cgactggacc    900
```

ttcctgcact gcctgcctcg caagcctgaa gaagtggacg acgaggtgtt ctactcgcca 960
cggagcctcg tgttccccga ggccgagaat agaaagtgga ccatcatggc cgtgatggtg 1020
tcactgctca ccgactacag cccgcagctt cagaagccca agttctag 1068

<210> SEQ ID NO 207
<211> LENGTH: 1068
<212> TYPE: DNA
<213> ORGANISM: Artificial Sequence
<220> FEATURE:
<223> OTHER INFORMATION: Synthetic construct

<400> SEQUENCE: 207
atgggccttg tcaatctccg catcctcctt aacaacgccg cgtttagaaa cggccacaac 60
ttcatggtcc ggaacttcag atgtggccag ccgcttcaaa accgggtcca gctgaagggc 120
cgggatcttc tgaccctgaa gaactttact ggcgaagaga tcaagtacat gctctggctc 180
tccgcggact tgaagttccg cattaagcag aagggggaat accttccgct gcttcaagga 240
aagagcctcg gcatgatctt tgagaagcgc tcaaccagga cccgcctttc tactgaaact 300
gggttcgcgc tgctcggtgg ccacccctgc ttcctgacga cccaggacat ccacctcgga 360
gtgaacgaat ccctcaccga taccgcccgg gtgttatcga gcatggcaga tgccgtgctg 420
gccagggtgt acaaacagtc cgatctggac actctggcca aggaggcgtc aattcctatt 480
atcaacggcc ttagtgacct ctaccatccg attcagatcc tggccgatta cctcaccctg 540
caagaacact acagctccct gaagggtctg acattgtcct ggatcggcga cggcaacaac 600
attctccatt ccatcatgat gtccgccgca aaattcggca tgcatcttca agccgccacg 660
ccgaagggtt acgagcccga cgcttccgtg actaagctcg ccgagcagta cgctaaggag 720
aacggaacca agcttctgct gactaacgac ccactagaag cagcccacgg gggcaacgtg 780
cttattactg acacctggat ctccatgggc caggaagaag agaaaaagaa gcggctgcag 840
gcgttccagg gatatcaggt caccatgaaa accgccaagg tcgctgcctc cgactggacc 900
ttcctgcact gcctgcctcg caagcctgaa gaagtggacg acgaggtgtt ctactcgcca 960
cggagcctcg tgttccccga ggccgagaat agaaagtgga ccatcatggc cgtgatggtg 1020
tcactgctca ccgactacag cccgcagctt cagaagccca agttctag 1068

<210> SEQ ID NO 208
<211> LENGTH: 1071
<212> TYPE: DNA
<213> ORGANISM: Artificial Sequence
<220> FEATURE:
<223> OTHER INFORMATION: Synthetic construct

<400> SEQUENCE: 208
atgggcggac ttgtcaatct ccgcatcctc cttaacaacg ccgcgtttag aaacggccac 60
aacttcatgg tccggaactt cagatgtggc cagccgcttc aaaacaaggt ccagctgaag 120
ggccgggatc ttctgaccct gaagaacttt actggcgaag agatcaagta catgctctgg 180
ctctccgcgg acttgaagtt ccgcattaag cagaaggggg aataccttcc gctgcttcaa 240
ggaaagagcc tcggcatgat ctttgagaag cgctcaacca ggacccgcct ttctactgaa 300
actgggttcg cgctgctcgg tggccacccc tgcttcctga cgacccagga catccacctc 360
ggagtgaacg aatccctcac cgataccgcc cgggtgttat cgagcatggc agatgccgtg 420
ctggccaggg tgtacaaaca gtccgatctg gacactctgg ccaaggaggc gtcaattcct 480
attatcaacg gccttagtga cctctaccat ccgattcaga tcctggccga ttacctcacc 540
ctgcaagaac actacagctc cctgaagggt ctgacattgt cctggatcgg cgacggcaac 600
aacattctcc attccatcat gatgtccgcc gcaaaattcg gcatgcatct tcaagccgcc 660
acgccgaagg gttacgagcc cgacgcttcc gtgactaagc tcgccgagca gtacgctaag 720
gagaacggaa ccaagcttct gctgactaac gacccactag aagcagccca cgggggcaac 780
gtgcttatta ctgacacctg gatctccatg ggccaggaag aagagaaaaa gaagcggctg 840
caggcgttcc agggatatca ggtcaccatg aaaaccgcca aggtcgctgc ctccgactgg 900
accttcctgc actgcctgcc tcgcaagcct gaagaagtgg acgacgaggt gttctactcg 960
ccacggagcc tcgtgttccc cgaggccgag aatagaaagt ggaccatcat ggccgtgatg 1020
gtgtcactgc tcaccgacta cagcccgcag cttcagaagc ccaagttcta g 1071

<210> SEQ ID NO 209
<211> LENGTH: 1077
<212> TYPE: DNA
<213> ORGANISM: Artificial Sequence
<220> FEATURE:
<223> OTHER INFORMATION: Synthetic construct

<400> SEQUENCE: 209
atggcccttt tcaatctccg catcctcctt aacaacgccg cgtttagaaa cggccacaac 60
ttcatggtcc ggaacttcag atgtggccag ccgcttcaag gcaaggtcca gctgaagggc 120
cgggatcttc tgaccctgaa gaactttact ggcgaagaga tcaagtacat gctctggctc 180
tccgcggact tgaagttccg cattaagcag aagggggaat accttccgct gcttcaagga 240
aagagcctcg gcatgatctt tgagaagcgc tcaaccagga cccgcctttc tactgaaact 300
gggttcgcgc tgctcggtgg ccacccctgc ttcctgacga cccaggacat ccacctcgga 360
gtgaacgaat ccctcaccga taccgcccgg gtgttatcga gcatggcaga tgccgtgctg 420
gccagggtgt acaaacagtc cgatctggac actctggcca aggaggcgtc aattcctatt 480
atcaacggcc ttagtgacct ctaccatccg attcagatcc tggccgatta cctcaccctg 540
caagaacact acagctccct gaagggtctg acattgtcct ggatcggcga cggcaacaac 600
attctccatt ccatcatgat gtccgccgca aaattcggca tgcatcttca agccgccacg 660
ccgaagggtt acgagcccga cgcttccgtg actaagctcg ccgagcagta cgctaaggag 720
aacggaacca agcttctgct gactaacgac ccactagaag cagcccacgg gggcaacgtg 780
cttattactg acacctggat ctccatgggc caggaagaag agaaaaagaa gcggctgcag 840
gcgttccagg gatatcaggt caccatgaaa accgccaagg tcgctgcctc cgactggacc 900
ttcctgcact gcctgcctcg caagcctgaa gaagtggacg acgaggtgtt ctactcgcca 960
cggagcctcg tgttccccga ggccgagaat agaaagtgga ccatcatggc cgtgatggtg 1020
tcactgctca ccgactacag cccgcagctt cagaagccca agttctagat aagtgaa 1077

<210> SEQ ID NO 210
<211> LENGTH: 1077
<212> TYPE: DNA
<213> ORGANISM: Artificial Sequence
<220> FEATURE:
<223> OTHER INFORMATION: Synthetic construct

<400> SEQUENCE: 210
atggcccttt tcaatctccg catcctcctt aacaacgccg cgtttagaaa cggccacaac 60
ttcatggtcc ggaacttcag atgtggccag ccgcttcaag gccgggtcca gctgaagggc 120

```
cgggatcttc tgaccctgaa gaactttact ggcgaagaga tcaagtacat gctctggctc    180

tccgcggact tgaagttccg cattaagcag aaggggggaat accttccgct gcttcaagga    240

aagagcctcg gcatgatctt tgagaagcgc tcaaccagga cccgcctttc tactgaaact    300

gggttcgcgc tgctcggtgg ccacccctgc ttcctgacga cccaggacat ccacctcgga    360

gtgaacgaat ccctcaccga taccgcccgg gtgttatcga gcatggcaga tgccgtgctg    420

gccagggtgt acaaacagtc cgatctggac actctggcca aggaggcgtc aattcctatt    480

atcaacggcc ttagtgacct ctaccatccg attcagatcc tggccgatta cctcaccctg    540

caagaacact acagctccct gaagggtctg acattgtcct ggatcggcga cggcaacaac    600

attctccatt ccatcatgat gtccgccgca aaattcggca tgcatcttca agccgccacg    660

ccgaagggtt acgagcccga cgcttccgtg actaagctcg ccgagcagta cgctaaggag    720

aacggaacca agcttctgct gactaacgac ccactagaag cagcccacgg gggcaacgtg    780

cttattactg acacctggat ctccatgggc caggaagaag agaaaaagaa gcggctgcag    840

gcgttccagg gatatcaggt caccatgaaa accgccaagg tcgctgcctc cgactggacc    900

ttcctgcact gcctgcctcg caagcctgaa gaagtggacg acgaggtgtt ctactcgcca    960

cggagcctcg tgttccccga ggccgagaat agaaagtgga ccatcatggc cgtgatggtg   1020

tcactgctca ccgactacag cccgcagctt cagaagccca agttctagat aagtgaa      1077
```

```
<210> SEQ ID NO 211
<211> LENGTH: 1077
<212> TYPE: DNA
<213> ORGANISM: Artificial Sequence
<220> FEATURE:
<223> OTHER INFORMATION: Synthetic construct

<400> SEQUENCE: 211

atggcccttt tcaatctccg catcctcctt aacaacgccg cgtttagaaa cggccacaac     60

ttcatggtcc ggaacttcag atgtggccag ccgcttcaag gccgggtcca gctgaagggc    120

cgggatcttc tgaccctgaa gaactttact ggcgaagaga tcaggtacat gctctggctc    180

tccgcggact tgaagttccg cattaagcag aaggggggaat accttccgct gcttcaagga    240

aagagcctcg gcatgatctt tgagaagcgc tcaaccagga cccgcctttc tactgaaact    300

gggttcgcgc tgctcggtgg ccacccctgc ttcctgacga cccaggacat ccacctcgga    360

gtgaacgaat ccctcaccga taccgcccgg gtgttatcga gcatggcaga tgccgtgctg    420

gccagggtgt acaaacagtc cgatctggac actctggcca aggaggcgtc aattcctatt    480

atcaacggcc ttagtgacct ctaccatccg attcagatcc tggccgatta cctcaccctg    540

caagaacact acagctccct gaagggtctg acattgtcct ggatcggcga cggcaacaac    600

attctccatt ccatcatgat gtccgccgca aaattcggca tgcatcttca agccgccacg    660

ccgaagggtt acgagcccga cgcttccgtg actaagctcg ccgagcagta cgctaaggag    720

aacggaacca agcttctgct gactaacgac ccactagaag cagcccacgg gggcaacgtg    780

cttattactg acacctggat ctccatgggc caggaagaag agaaaaagaa gcggctgcag    840

gcgttccagg gatatcaggt caccatgaaa accgccaagg tcgctgcctc cgactggacc    900

ttcctgcact gcctgcctcg caagcctgaa gaagtggacg acgaggtgtt ctactcgcca    960

cggagcctcg tgttccccga ggccgagaat agaaagtgga ccatcatggc cgtgatggtg   1020

tcactgctca ccgactacag cccgcagctt cagaagccca agttctagat aagtgaa      1077
```

<210> SEQ ID NO 212
<211> LENGTH: 1077
<212> TYPE: DNA
<213> ORGANISM: Artificial Sequence
<220> FEATURE:
<223> OTHER INFORMATION: Synthetic construct

<400> SEQUENCE: 212
atggcccttg tcaatctccg catcctcctt aacaacgccg cgtttagaaa cggccacaac 60
ttcatggtcc ggaacttcag atgtggccag ccgcttcaag gcagggtcca gctgaagggc 120
cgggatcttc tgaccctgaa gaactttact ggcgaagaga tcaagtacat gctctggctc 180
tccgcggact tgaagttccg cattaagcag aagggggaat accttccgct gcttcaagga 240
aagagcctcg gcatgatctt tgagaagcgc tcaaccagga cccgcctttc tactgaaact 300
gggttcgcgc tgctcggtgg ccacccctgc ttcctgacga cccaggacat ccacctcgga 360
gtgaacgaat ccctcaccga taccgcccgg gtgttatcga gcatggcaga tgccgtgctg 420
gccagggtgt acaaacagtc cgatctggac actctggcca aggaggcgtc aattcctatt 480
atcaacggcc ttagtgacct ctaccatccg attcagatcc tggccgatta cctcaccctg 540
caagaacact acagctccct gaagggtctg acattgtcct ggatcggcga cggcaacaac 600
attctccatt ccatcatgat gtccgccgca aaattcggca tgcatcttca agccgccacg 660
ccgaagggtt acgagcccga cgcttccgtg actaagctcg ccgagcagta cgctaaggag 720
aacggaacca agcttctgct gactaacgac ccactagaag cagcccacgg gggcaacgtg 780
cttattactg acacctggat ctccatgggc caggaagaag agaaaaagaa gcggctgcag 840
gcgttccagg gatatcaggt caccatgaaa accgccaagg tcgctgcctc cgactggacc 900
ttcctgcact gcctgcctcg caagcctgaa gaagtggacg acgaggtgtt ctactcgcca 960
cggagcctcg tgttccccga ggccgagaat agaaagtgga ccatcatggc cgtgatggtg 1020
tcactgctca ccgactacag cccgcagctt cagaagccca agttctaagt gaataga 1077

<210> SEQ ID NO 213
<211> LENGTH: 1077
<212> TYPE: DNA
<213> ORGANISM: Artificial Sequence
<220> FEATURE:
<223> OTHER INFORMATION: Synthetic construct

<400> SEQUENCE: 213
atggcccttt tcaatctccg catcctcctt aacaacgccg cgtttagaaa cggccacaac 60
ttcatggtcc ggaacttcag atgtggccag ccgcttcaag tcaaggtcca gctgaagggc 120
cgggatcttc tgaccctgaa gaactttact ggcgaagaga tcaagtacat gctctggctc 180
tccgcggact tgaagttccg cattaagcag aagggggaat accttccgct gcttcaagga 240
aagagcctcg gcatgatctt tgagaagcgc tcaaccagga cccgcctttc tactgaaact 300
gggttcgcgc tgctcggtgg ccacccctgc ttcctgacga cccaggacat ccacctcgga 360
gtgaacgaat ccctcaccga taccgcccgg gtgttatcga gcatggcaga tgccgtgctg 420
gccagggtgt acaaacagtc cgatctggac actctggcca aggaggcgtc aattcctatt 480
atcaacggcc ttagtgacct ctaccatccg attcagatcc tggccgatta cctcaccctg 540
caagaacact acagctccct gaagggtctg acattgtcct ggatcggcga cggcaacaac 600
attctccatt ccatcatgat gtccgccgca aaattcggca tgcatcttca agccgccacg 660
ccgaagggtt acgagcccga cgcttccgtg actaagctcg ccgagcagta cgctaaggag 720
aacggaacca agcttctgct gactaacgac ccactagaag cagcccacgg gggcaacgtg 780
cttattactg acacctggat ctccatgggc caggaagaag agaaaaagaa gcggctgcag 840
gcgttccagg gatatcaggt caccatgaaa accgccaagg tcgctgcctc cgactggacc 900
ttcctgcact gcctgcctcg caagcctgaa gaagtggacg acgaggtgtt ctactcgcca 960
cggagcctcg tgttccccga ggccgagaat agaaagtgga ccatcatggc cgtgatggtg 1020
tcactgctca ccgactacag cccgcagctt cagaagccca agttctagat aagtgaa 1077

<210> SEQ ID NO 214
<211> LENGTH: 1077
<212> TYPE: DNA
<213> ORGANISM: Artificial Sequence
<220> FEATURE:
<223> OTHER INFORMATION: Synthetic construct

<400> SEQUENCE: 214
atggcccttt tcaatctccg catcctcctt aacaacgccg cgtttagaaa cggccacaac 60
ttcatggtcc ggaacttcag atgtggccag ccgcttcaag tcagggtcca gctgaagggc 120
cgggatcttc tgaccctgaa gaactttact ggcgaagaga tcaagtacat gctctggctc 180
tccgcggact tgaagttccg cattaagcag aagggggaat accttccgct gcttcaagga 240
aagagcctcg gcatgatctt tgagaagcgc tcaaccagga cccgcctttc tactgaaact 300
gggttcgcgc tgctcggtgg ccacccctgc ttcctgacga cccaggacat ccacctcgga 360
gtgaacgaat ccctcaccga taccgcccgg gtgttatcga gcatggcaga tgccgtgctg 420
gccagggtgt acaaacagtc cgatctggac actctggcca aggaggcgtc aattcctatt 480
atcaacggcc ttagtgacct ctaccatccg attcagatcc tggccgatta cctcaccctg 540
caagaacact acagctccct gaagggtctg acattgtcct ggatcggcga cggcaacaac 600
attctccatt ccatcatgat gtccgccgca aaattcggca tgcatcttca agccgccacg 660
ccgaagggtt acgagcccga cgcttccgtg actaagctcg ccgagcagta cgctaaggag 720
aacggaacca agcttctgct gactaacgac ccactagaag cagcccacgg gggcaacgtg 780
cttattactg acacctggat ctccatgggc caggaagaag agaaaaagaa gcggctgcag 840
gcgttccagg gatatcaggt caccatgaaa accgccaagg tcgctgcctc cgactggacc 900
ttcctgcact gcctgcctcg caagcctgaa gaagtggacg acgaggtgtt ctactcgcca 960
cggagcctcg tgttccccga ggccgagaat agaaagtgga ccatcatggc cgtgatggtg 1020
tcactgctca ccgactacag cccgcagctt cagaagccca agttctagat aagtgaa 1077

<210> SEQ ID NO 215
<211> LENGTH: 1065
<212> TYPE: DNA
<213> ORGANISM: Artificial Sequence
<220> FEATURE:
<223> OTHER INFORMATION: Synthetic construct

<400> SEQUENCE: 215
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300

-continued

```
ttcgccctgc tgggcggcca cccctgcttc ctgaccaccc aggacatcca cctgggcgtg    360

aacgagagcc tgaccgacac cgcccgcgtg ctgagcagca tggccgacgc cgtgctggcc    420

cgcgtgtaca agcagagcga cctggacacc ctggccaagg aggccagcat ccccatcatc    480

aacggcctga gcgacctgta ccaccccatc cagatcctgg ccgactacct gaccctgcag    540

gagcactaca gcagcctgaa gggcctgacc ctgagctgga tcggcgacgg caacaacatc    600

ctgcacagca tcatgatgag cgccgccaag ttcggcatgc acctgcaggc cgccaccccc    660

aagggctacg agcccgacgc cagcgtgacc aagctggccg agcagtacgc caaggagaac    720

ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctga                   1065
```

<210> SEQ ID NO 216
<211> LENGTH: 1068
<212> TYPE: DNA
<213> ORGANISM: Artificial Sequence
<220> FEATURE:
<223> OTHER INFORMATION: Synthetic construct

<400> SEQUENCE: 216

```
atgggagtat tcaacctgcg catcctgctg aacaacgccg ccttccgcaa cggccacaac     60

ttcatggtgc gcaacttccg ctgcggccag cccctgcaga acaaggtgca gctgaagggc    120

cgcgacctgc tgaccctgaa gaacttcacc ggcgaggaga tcaagtacat gctgtggctg    180

agcgccgacc tgaagttccg catcaagcag aagggcgagt acctgcccct gctgcagggc    240

aagagcctgg gcatgatctt cgagaagcgc agcacccgca cccgcctgag caccgagaca    300

ggcttcgccc tgctgggcgg ccacccctgc ttcctgacca cccaggacat ccacctgggc    360

gtgaacgaga gcctgaccga caccgcccgc gtgctgagca gcatggccga cgccgtgctg    420

gcccgcgtgt acaagcagag cgacctggac accctggcca aggaggccag catccccatc    480

atcaacggcc tgagcgacct gtaccacccc atccagatcc tggccgacta cctgaccctg    540

caggagcact acagcagcct gaagggcctg accctgagct ggatcggcga cggcaacaac    600

atcctgcaca gcatcatgat gagcgccgcc aagttcggca tgcacctgca ggccgccacc    660

cccaagggct acgagcccga cgccagcgtg accaagctgg ccgagcagta cgccaaggag    720

aacggcacca agctgctgct gaccaacgac cccctggagg ccgcccacgg cggcaacgtg    780

ctgatcaccg acacctggat cagcatgggc caggaggagg agaagaagaa gcgcctgcag    840

gccttccagg gctaccaggt gaccatgaag accgccaagg tggccgccag cgactggacc    900

ttcctgcact gcctgccccg caagcccgag gaggtggacg acgaggtgtt ctacagcccc    960

cgcagcctgg tgttccccga ggccgagaac cgcaagtgga ccatcatggc cgtgatggtg   1020

agcctgctga ccgactacag cccccagctg cagaagccca agttctga                1068
```

<210> SEQ ID NO 217
<211> LENGTH: 1068
<212> TYPE: DNA
<213> ORGANISM: Artificial Sequence
<220> FEATURE:
<223> OTHER INFORMATION: Synthetic construct

<400> SEQUENCE: 217

```
atgggagtat tcaacctgcg catcctgctg aacaacgccg ccttccgcaa cggccacaac     60
ttcatggtgc gcaacttccg ctgcggccag cccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccacccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca agctgctgct gaccaacgac cccctggagg ccgcccacgg cggcaacgtg    780
ctgatcaccg acacctggat cagcatgggc caggaggagg agaagaagaa gcgcctgcag    840
gccttccagg gctaccaggt gaccatgaag accgccaagg tggccgccag cgactggacc    900
ttcctgcact gcctgccccg caagcccgag gaggtggacg acgaggtgtt ctacagcccc    960
cgcagcctgg tgttccccga ggccgagaac cgcaagtgga ccatcatggc cgtgatggtg   1020
agcctgctga ccgactacag cccccagctg cagaagccca agttctga                1068
```

<210> SEQ ID NO 218
<211> LENGTH: 1068
<212> TYPE: DNA
<213> ORGANISM: Artificial Sequence
<220> FEATURE:
<223> OTHER INFORMATION: Synthetic construct

<400> SEQUENCE: 218

```
atgctggtat tcaacctgcg catcctgctg aacaacgccg ccttccgcaa cggccacaac     60
ttcatggtgc gcaacttccg ctgcggccag cccctgcaga accgggtgca gctgaagggc    120
cgcgacctgc tgaccctgaa gaacttcacc ggcgaggaga tccggtacat gctgtggctg    180
agcgccgacc tgaagttccg catcaagcag aagggcgagt acctgcccct gctgcagggc    240
aagagcctgg gcatgatctt cgagaagcgc agcacccgca cccgcctgag caccgagaca    300
ggcttcgccc tgctgggcgg ccacccctgc ttcctgacca cccaggacat ccacctgggc    360
gtgaacgaga gcctgaccga caccgcccgc gtgctgagca gcatggccga cgccgtgctg    420
gcccgcgtgt acaagcagag cgacctggac accctggcca aggaggccag catccccatc    480
atcaacggcc tgagcgacct gtaccacccc atccagatcc tggccgacta cctgaccctg    540
caggagcact acagcagcct gaagggcctg accctgagct ggatcggcga cggcaacaac    600
atcctgcaca gcatcatgat gagcgccgcc aagttcggca tgcacctgca ggccgccacc    660
cccaagggct acgagcccga cgccagcgtg accaagctgg ccgagcagta cgccaaggag    720
aacggcacca agctgctgct gaccaacgac cccctggagg ccgcccacgg cggcaacgtg    780
ctgatcaccg acacctggat cagcatgggc caggaggagg agaagaagaa gcgcctgcag    840
gccttccagg gctaccaggt gaccatgaag accgccaagg tggccgccag cgactggacc    900
```

ttcctgcact gcctgccccg caagcccgag gaggtggacg acgaggtgtt ctacagcccc 960
cgcagcctgg tgttccccga ggccgagaac cgcaagtgga ccatcatggc cgtgatggtg 1020
agcctgctga ccgactacag cccccagctg cagaagccca agttctga 1068

<210> SEQ ID NO 219
<211> LENGTH: 1068
<212> TYPE: DNA
<213> ORGANISM: Artificial Sequence
<220> FEATURE:
<223> OTHER INFORMATION: Synthetic construct

<400> SEQUENCE: 219
atgggagtat tcaacctgcg catcctgctg aacaacgccg ccttccgcaa cggccacaac 60
ttcatggtgc gcaacttccg ctgcggccag cccctgcaga acaaggtgca gctgaagggc 120
cgcgacctgc tgaccctgaa gaacttcacc ggcgaggaga tcaagtacat gctgtggctg 180
agcgccgacc tgaagttccg catcaagcag aagggcgagt acctgcccct gctgcagggc 240
aagagcctgg gcatgatctt cgagaagcgc agcacccgca cccgcctgag caccgagaca 300
ggcttcgccc tgctgggcgg ccacccctgc ttcctgacca cccaggacat ccacctgggc 360
gtgaacgaga gcctgaccga caccgcccgc gtgctgagca gcatggccga cgccgtgctg 420
gcccgcgtgt acaagcagag cgacctggac accctggcca aggaggccag catccccatc 480
atcaacggcc tgagcgacct gtaccacccc atccagatcc tggccgacta cctgaccctg 540
caggagcact acagcagcct gaagggcctg accctgagct ggatcggcga cggcaacaac 600
atcctgcaca gcatcatgat gagcgccgcc aagttcggca tgcacctgca ggccgccacc 660
cccaagggct acgagcccga cgccagcgtg accaagctgg ccgagcagta cgccaaggag 720
aacggcacca agctgctgct gaccaacgac cccctggagg ccgcccacgg cggcaacgtg 780
ctgatcaccg acacctggat cagcatgggc caggaggagg agaagaagaa gcgcctgcag 840
gccttccagg gctaccaggt gaccatgaag accgccaagg tggccgccag cgactggacc 900
ttcctgcact gcctgccccg caagcccgag gaggtggacg acgaggtgtt ctacagcccc 960
cgcagcctgg tgttccccga ggccgagaac cgcaagtgga ccatcatggc cgtgatggtg 1020
agcctgctga ccgactacag cccccagctg cagaagccca agttctga 1068

<210> SEQ ID NO 220
<211> LENGTH: 1068
<212> TYPE: DNA
<213> ORGANISM: Artificial Sequence
<220> FEATURE:
<223> OTHER INFORMATION: Synthetic construct

<400> SEQUENCE: 220
atgggagtat tcaacctgcg catcctgctg aacaacgccg ccttccgcaa cggccacaac 60
ttcatggtgc gcaacttccg ctgcggccag cccctgcaga accgggtgca gctgaagggc 120
cgcgacctgc tgaccctgaa gaacttcacc ggcgaggaga tccggtacat gctgtggctg 180
agcgccgacc tgaagttccg catcaagcag aagggcgagt acctgcccct gctgcagggc 240
aagagcctgg gcatgatctt cgagaagcgc agcacccgca cccgcctgag caccgagaca 300
ggcttcgccc tgctgggcgg ccacccctgc ttcctgacca cccaggacat ccacctgggc 360
gtgaacgaga gcctgaccga caccgcccgc gtgctgagca gcatggccga cgccgtgctg 420
gcccgcgtgt acaagcagag cgacctggac accctggcca aggaggccag catccccatc 480
atcaacggcc tgagcgacct gtaccacccc atccagatcc tggccgacta cctgaccctg 540
caggagcact acagcagcct gaagggcctg accctgagct ggatcggcga cggcaacaac 600
atcctgcaca gcatcatgat gagcgccgcc aagttcggca tgcacctgca ggccgccacc 660
cccaagggct acgagcccga cgccagcgtg accaagctgg ccgagcagta cgccaaggag 720
aacggcacca agctgctgct gaccaacgac cccctggagg ccgcccacgg cggcaacgtg 780
ctgatcaccg acacctggat cagcatgggc caggaggagg agaagaagaa gcgcctgcag 840
gccttccagg gctaccaggt gaccatgaag accgccaagg tggccgccag cgactggacc 900
ttcctgcact gcctgccccg caagcccgag gaggtggacg acgaggtgtt ctacagcccc 960
cgcagcctgg tgttccccga ggccgagaac cgcaagtgga ccatcatggc cgtgatggtg 1020
agcctgctga ccgactacag cccccagctg cagaagccca agttctga 1068

<210> SEQ ID NO 221
<211> LENGTH: 1068
<212> TYPE: DNA
<213> ORGANISM: Artificial Sequence
<220> FEATURE:
<223> OTHER INFORMATION: Synthetic construct

<400> SEQUENCE: 221
atgctggtat tcaacctgcg catcctgctg aacaacgccg ccttccgcaa cggccacaac 60
ttcatggtgc gcaacttccg ctgcggccag cccctgcaga accgggtgca gctgaagggc 120
cgcgacctgc tgaccctgaa gaacttcacc ggcgaggaga tccggtacat gctgtggctg 180
agcgccgacc tgaagttccg catcaagcag aagggcgagt acctgcccct gctgcagggc 240
aagagcctgg gcatgatctt cgagaagcgc agcacccgca cccgcctgag caccgagaca 300
ggcttcgccc tgctgggcgg ccacccctgc ttcctgacca cccaggacat ccacctgggc 360
gtgaacgaga gcctgaccga caccgcccgc gtgctgagca gcatggccga cgccgtgctg 420
gcccgcgtgt acaagcagag cgacctggac accctggcca aggaggccag catccccatc 480
atcaacggcc tgagcgacct gtaccacccc atccagatcc tggccgacta cctgaccctg 540
caggagcact acagcagcct gaagggcctg accctgagct ggatcggcga cggcaacaac 600
atcctgcaca gcatcatgat gagcgccgcc aagttcggca tgcacctgca ggccgccacc 660
cccaagggct acgagcccga cgccagcgtg accaagctgg ccgagcagta cgccaaggag 720
aacggcacca agctgctgct gaccaacgac cccctggagg ccgcccacgg cggcaacgtg 780
ctgatcaccg acacctggat cagcatgggc caggaggagg agaagaagaa gcgcctgcag 840
gccttccagg gctaccaggt gaccatgaag accgccaagg tggccgccag cgactggacc 900
ttcctgcact gcctgccccg caagcccgag gaggtggacg acgaggtgtt ctacagcccc 960
cgcagcctgg tgttccccga ggccgagaac cgcaagtgga ccatcatggc cgtgatggtg 1020
agcctgctga ccgactacag cccccagctg cagaagccca agttctga 1068

<210> SEQ ID NO 222
<211> LENGTH: 1073
<212> TYPE: DNA
<213> ORGANISM: Artificial Sequence
<220> FEATURE:
<223> OTHER INFORMATION: Synthetic construct

<400> SEQUENCE: 222
atgttgttca acttgaggat cttgttgaac aacgccgcct tcaggaacgg acacaacttc 60
atggtaagga acttcaggtg cggacagccc ttgcagaaca aagtacagtt gaaaggaagg 120

```
gacttgttga cattgaaaaa cttcacagga gaagaaatca aatacatgtt gtggttgtcg    180

gccgacttga aattcaggat caaacagaaa ggagaatact tgcccttgtt gcagggaaaa    240

tcgttgggaa tgatcttcga aaaaaggtcg acaaggacaa ggttgtcgac agaaacagga    300

ttcgccttgt tgggaggaca cccctgcttc ttgacaacac aggacatcca cttgggagta    360

aacgaatcgt tgacagacac agccagggta ttgtcgtcga tggccgacgc cgtattggcc    420

agggtataca aacagtcgga cttggacaca ttggccaaag aagcctcgat ccccatcatc    480

aacggattgt cggacttgta ccaccccatc cagatcttgg ccgactactt gacattgcag    540

gaacactact cgtcgttgaa aggattgaca ttgtcgtgga tcggagacgg aaacaacatc    600

ttgcactcga tcatgatgtc ggccgccaaa ttcggaatgc acttgcaggc cgccacaccc    660

aaaggatacg aacccgacgc ctcggtaaca aaattggccg aacagtacgc caaagaaaac    720

ggaacaaaat tgttgttgac aaacgacccc ttggaagccg cccacggagg aaacgtattg    780

atcacagaca catggatctc gatgggacag gaagaagaaa aaaaaaaaag gttgcaggcc    840

ttccagggat accaggtaac aatgaaaaca gccaaagtag ccgcctcgga ctggacattc    900

ttgcactgct tgcccaggaa acccgaagaa gtagacgacg aagtattcta ctcgcccagg    960

tcgttggtat tccccgaagc cgaaaacagg aaatggacaa tcatggccgt aatggtatcg   1020

ttgttgacag actactcgcc ccagttgcag aaacccaaat tctgaatagt gaa          1073
```

<210> SEQ ID NO 223
<211> LENGTH: 1065
<212> TYPE: DNA
<213> ORGANISM: Artificial Sequence
<220> FEATURE:
<223> OTHER INFORMATION: Synthetic construct

<400> SEQUENCE: 223

```
atgctgttca acctgcgcat cctgctgaac aacgccgcct tccgcaacgg ccacaacttc     60

atggtgcgca acttccgctg cggccagccc ctgcagggca aggtgcagct gaagggccgc    120

gacctgctga ccctgaagaa cttcaccggc gaggagatca agtacatgct gtggctgagc    180

gccgacctga agttccgcat caagcagaag ggcgagtacc tgcccctgct gcagggcaag    240

agcctgggca tgatcttcga gaagcgcagc acccgcaccc gcctgagcac cgagacaggc    300

ttcgccctgc tgggcggcca cccctgcttc ctgaccaccc aggacatcca cctgggcgtg    360

aacgagagcc tgaccgacac cgcccgcgtg ctgagcagca tggccgacgc cgtgctggcc    420

cgcgtgtaca agcagagcga cctggacacc ctggccaagg aggccagcat ccccatcatc    480

aacggcctga gcgacctgta ccaccccatc cagatcctgg ccgactacct gaccctgcag    540

gagcactaca gcagcctgaa gggcctgacc ctgagctgga tcggcgacgg caacaacatc    600

ctgcacagca tcatgatgag cgccgccaag ttcggcatgc acctgcaggc cgccaccccc    660

aagggctacg agcccgacgc cagcgtgacc aagctggccg agcagtacgc caaggagaac    720

ggcaccaagc tgctgctgac caacgacccc ctggaggccg cccacggcgg caacgtgctg    780

atcaccgaca cctggatcag catgggccag gaggaggaga agaagaagcg cctgcaggcc    840

ttccagggct accaggtgac catgaagacc gccaaggtgg ccgccagcga ctggaccttc    900

ctgcactgcc tgccccgcaa gcccgaggag gtggacgacg aggtgttcta cagcccccgc    960

agcctggtgt tccccgaggc cgagaaccgc aagtggacca tcatggccgt gatggtgagc   1020

ctgctgaccg actacagccc ccagctgcag aagcccaagt tctga                   1065
```

<210> SEQ ID NO 224
<211> LENGTH: 1065
<212> TYPE: DNA
<213> ORGANISM: Artificial Sequence
<220> FEATURE:
<223> OTHER INFORMATION: Synthetic construct

<400> SEQUENCE: 224
atgctgttca acctgcgcat cctgctgaac aacgccgcct tccgcaacgg ccacaacttc 60
atggtgcgca acttccgctg cggccagccc ctgcagggcc gggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 225
<211> LENGTH: 1065
<212> TYPE: DNA
<213> ORGANISM: Artificial Sequence
<220> FEATURE:
<223> OTHER INFORMATION: Synthetic construct

<400> SEQUENCE: 225
atgctgttca acctgcgcat cctgctgaac aacgccgcct tccgcaacgg ccacaacttc 60
atggtgcgca acttccgctg cggccagccc ctgcagggcc gggtgcagct gaagggccgc 120
gacctgctga ccctgaagaa cttcaccggc gaggagatcc ggtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 226
<211> LENGTH: 1065
<212> TYPE: DNA
<213> ORGANISM: Artificial Sequence
<220> FEATURE:
<223> OTHER INFORMATION: Synthetic construct

<400> SEQUENCE: 226
atgctgttca acctgcgcat cctgctgaac aacgccgcct tccgcaacgg ccacaacttc 60
atggtgcgca acttccgctg cggccagccc ctgcagggca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccaccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 227
<211> LENGTH: 1065
<212> TYPE: DNA
<213> ORGANISM: Artificial Sequence
<220> FEATURE:
<223> OTHER INFORMATION: Synthetic construct

<400> SEQUENCE: 227
atgctgttca acctgcgcat cctgctgaac aacgccgcct tccgcaacgg ccacaacttc 60
atggtgcgca acttccgctg cggccagccc ctgcagaaca aggtgcagct gaagggccgc 120
gacctgctga ccctgaagaa cttcaccggc gaggagatca agtacatgct gtggctgagc 180
gccgacctga agttccgcat caagcagaag ggcgagtacc tgcccctgct gcagggcaag 240
agcctgggca tgatcttcga gaagcgcagc acccgcaccc gcctgagcac cgagacaggc 300
ttcgccctgc tgggcggcca cccctgcttc ctgaccaccc aggacatcca cctgggcgtg 360
aacgagagcc tgaccgacac cgcccgcgtg ctgagcagca tggccgacgc cgtgctggcc 420
cgcgtgtaca agcagagcga cctggacacc ctggccaagg aggccagcat ccccatcatc 480
aacggcctga gcgacctgta ccacccccatc cagatcctgg ccgactacct gaccctgcag 540
gagcactaca gcagcctgaa gggcctgacc ctgagctgga tcggcgacgg caacaacatc 600
ctgcacagca tcatgatgag cgccgccaag ttcggcatgc acctgcaggc cgccaccccc 660
aagggctacg agcccgacgc cagcgtgacc aagctggccg agcagtacgc caaggagaac 720
ggcaccaagc tgctgctgac caacgacccc ctggaggccg cccacggcgg caacgtgctg 780
atcaccgaca cctggatcag catgggccag gaggaggaga agaagaagcg cctgcaggcc 840
ttccagggct accaggtgac catgaagacc gccaaggtgg ccgccagcga ctggaccttc 900
ctgcactgcc tgccccgcaa gcccgaggag gtggacgacg aggtgttcta cagcccccgc 960
agcctggtgt tccccgaggc cgagaaccgc aagtggacca tcatggccgt gatggtgagc 1020
ctgctgaccg actacagccc ccagctgcag aagcccaagt tctga 1065

<210> SEQ ID NO 228
<211> LENGTH: 1068
<212> TYPE: DNA
<213> ORGANISM: Artificial Sequence
<220> FEATURE:
<223> OTHER INFORMATION: Synthetic construct

<400> SEQUENCE: 228
atgctggtat tcaacctgcg catcctgctg aacaacgccg ccttccgcaa cggccacaac 60
ttcatggtgc gcaacttccg ctgcggccag cccctgcaga accgggtgca gctgaagggc 120
cgcgacctgc tgaccctgaa gaacttcacc ggcgaggaga tccggtacat gctgtggctg 180
agcgccgacc tgaagttccg catcaagcag aagggcgagt acctgcccct gctgcagggc 240
aagagcctgg gcatgatctt cgagaagcgc agcacccgca cccgcctgag caccgagaca 300
ggcttcgccc tgctgggcgg ccacccctgc ttcctgacca cccaggacat ccacctgggc 360
gtgaacgaga gcctgaccga caccgcccgc gtgctgagca gcatggccga cgccgtgctg 420
gcccgcgtgt acaagcagag cgacctggac accctggcca aggaggccag catccccatc 480
atcaacggcc tgagcgacct gtaccacccc atccagatcc tggccgacta cctgaccctg 540
caggagcact acagcagcct gaagggcctg accctgagct ggatcggcga cggcaacaac 600
atcctgcaca gcatcatgat gagcgccgcc aagttcggca tgcacctgca ggccgccacc 660
cccaagggct acgagcccga cgccagcgtg accaagctgg ccgagcagta cgccaaggag 720
aacggcacca agctgctgct gaccaacgac cccctggagg ccgcccacgg cggcaacgtg 780
ctgatcaccg acacctggat cagcatgggc caggaggagg agaagaagaa gcgcctgcag 840
gccttccagg gctaccaggt gaccatgaag accgccaagg tggccgccag cgactggacc 900
ttcctgcact gcctgccccg caagcccgag gaggtggacg acgaggtgtt ctacagcccc 960
cgcagcctgg tgttccccga ggccgagaac cgcaagtgga ccatcatggc cgtgatggtg 1020
agcctgctga ccgactacag cccccagctg cagaagccca agttctga 1068

<210> SEQ ID NO 229
<211> LENGTH: 1068
<212> TYPE: DNA
<213> ORGANISM: Artificial Sequence
<220> FEATURE:
<223> OTHER INFORMATION: Synthetic construct

<400> SEQUENCE: 229
atgctggtat tcaacctgcg catcctgctg aacaacgccg ccttccgcaa cggccacaac 60
ttcatggtgc gcaacttccg ctgcggccag cccctgcaga accgggtgca gctgaagggc 120
cgcgacctgc tgaccctgaa gaacttcacc ggcgaggaga tccggtacat gctgtggctg 180
agcgccgacc tgaagttccg catcaagcag aagggcgagt acctgcccct gctgcagggc 240
aagagcctgg gcatgatctt cgagaagcgc agcacccgca cccgcctgag caccgagaca 300
ggcttcgccc tgctgggcgg ccacccctgc ttcctgacca cccaggacat ccacctgggc 360
gtgaacgaga gcctgaccga caccgcccgc gtgctgagca gcatggccga cgccgtgctg 420
gcccgcgtgt acaagcagag cgacctggac accctggcca aggaggccag catccccatc 480
atcaacggcc tgagcgacct gtaccacccc atccagatcc tggccgacta cctgaccctg 540
caggagcact acagcagcct gaagggcctg accctgagct ggatcggcga cggcaacaac 600
atcctgcaca gcatcatgat gagcgccgcc aagttcggca tgcacctgca ggccgccacc 660
cccaagggct acgagcccga cgccagcgtg accaagctgg ccgagcagta cgccaaggag 720
aacggcacca agctgctgct gaccaacgac cccctggagg ccgcccacgg cggcaacgtg 780
ctgatcaccg acacctggat cagcatgggc caggaggagg agaagaagaa gcgcctgcag 840
gccttccagg gctaccaggt gaccatgaag accgccaagg tggccgccag cgactggacc 900
ttcctgcact gcctgccccg caagcccgag gaggtggacg acgaggtgtt ctacagcccc 960
cgcagcctgg tgttccccga ggccgagaac cgcaagtgga ccatcatggc cgtgatggtg 1020
agcctgctga ccgactacag cccccagctg cagaagccca agttctga 1068

<210> SEQ ID NO 230
<211> LENGTH: 21
<212> TYPE: RNA
<213> ORGANISM: Artificial Sequence
<220> FEATURE:
<223> OTHER INFORMATION: Synthetic construct

<400> SEQUENCE: 230
aaccaaucga aagaaaccaa a 21

<210> SEQ ID NO 231
<211> LENGTH: 21
<212> TYPE: RNA
<213> ORGANISM: Artificial Sequence
<220> FEATURE:
<223> OTHER INFORMATION: Synthetic construct

<400> SEQUENCE: 231
cucuaaucac caggaguaaa a 21

<210> SEQ ID NO 232
<211> LENGTH: 21
<212> TYPE: RNA
<213> ORGANISM: Artificial Sequence
<220> FEATURE:
<223> OTHER INFORMATION: Synthetic construct

<400> SEQUENCE: 232
gagagagauc uuaacaaaaa a 21

<210> SEQ ID NO 233
<211> LENGTH: 21
<212> TYPE: RNA
<213> ORGANISM: Artificial Sequence
<220> FEATURE:
<223> OTHER INFORMATION: Synthetic construct

<400> SEQUENCE: 233
uguguaacaa caacaacaac a 21

<210> SEQ ID NO 234
<211> LENGTH: 21
<212> TYPE: RNA
<213> ORGANISM: Artificial Sequence
<220> FEATURE:
<223> OTHER INFORMATION: Synthetic construct

<400> SEQUENCE: 234
ccgcaguagg aagagaaagc c 21

<210> SEQ ID NO 235
<211> LENGTH: 21
<212> TYPE: RNA
<213> ORGANISM: Artificial Sequence
<220> FEATURE:
<223> OTHER INFORMATION: Synthetic construct

<400> SEQUENCE: 235
aaaaaaaaaa gaaaucauaa a 21

<210> SEQ ID NO 236
<211> LENGTH: 21
<212> TYPE: RNA
<213> ORGANISM: Artificial Sequence
<220> FEATURE:
<223> OTHER INFORMATION: Synthetic construct

<400> SEQUENCE: 236
gagagaagaa agaagaagac g 21

<210> SEQ ID NO 237
<211> LENGTH: 21
<212> TYPE: RNA
<213> ORGANISM: Artificial Sequence
<220> FEATURE:
<223> OTHER INFORMATION: Synthetic construct

<400> SEQUENCE: 237
caauuaaaaa uacuuaccaa a 21

<210> SEQ ID NO 238
<211> LENGTH: 21
<212> TYPE: RNA
<213> ORGANISM: Artificial Sequence
<220> FEATURE:
<223> OTHER INFORMATION: Synthetic construct

<400> SEQUENCE: 238
gcaaacagag uaagcgaaac g 21

<210> SEQ ID NO 239
<211> LENGTH: 21
<212> TYPE: RNA
<213> ORGANISM: Artificial Sequence
<220> FEATURE:
<223> OTHER INFORMATION: Synthetic construct

<400> SEQUENCE: 239
gcgaagaaga cgaacgcaaa g 21

```
<210> SEQ ID NO 240
<211> LENGTH: 21
<212> TYPE: RNA
<213> ORGANISM: Artificial Sequence
<220> FEATURE:
<223> OTHER INFORMATION: Synthetic construct

<400> SEQUENCE: 240

uuaggacugu auugacuggc c                                              21

<210> SEQ ID NO 241
<211> LENGTH: 21
<212> TYPE: RNA
<213> ORGANISM: Artificial Sequence
<220> FEATURE:
<223> OTHER INFORMATION: Synthetic construct

<400> SEQUENCE: 241

aucaucggaa uucggaaaaa g                                              21

<210> SEQ ID NO 242
<211> LENGTH: 21
<212> TYPE: RNA
<213> ORGANISM: Artificial Sequence
<220> FEATURE:
<223> OTHER INFORMATION: Synthetic construct

<400> SEQUENCE: 242

aaaacaaaag uuaaagcaga c                                              21

<210> SEQ ID NO 243
<211> LENGTH: 21
<212> TYPE: RNA
<213> ORGANISM: Artificial Sequence
<220> FEATURE:
<223> OTHER INFORMATION: Synthetic construct

<400> SEQUENCE: 243

uuuaucucaa auaagaaggc a                                              21

<210> SEQ ID NO 244
<211> LENGTH: 21
<212> TYPE: RNA
<213> ORGANISM: Artificial Sequence
<220> FEATURE:
<223> OTHER INFORMATION: Synthetic construct

<400> SEQUENCE: 244

gguggggagg ugagauuucu u                                              21

<210> SEQ ID NO 245
<211> LENGTH: 21
<212> TYPE: RNA
<213> ORGANISM: Artificial Sequence
<220> FEATURE:
<223> OTHER INFORMATION: Synthetic construct

<400> SEQUENCE: 245

ugauuaggaa acuacaaagc c                                              21

<210> SEQ ID NO 246
<211> LENGTH: 21
<212> TYPE: RNA
<213> ORGANISM: Artificial Sequence
<220> FEATURE:
<223> OTHER INFORMATION: Synthetic construct
```

<400> SEQUENCE: 246
cauuuuucaa uuucauaaaa c 21

<210> SEQ ID NO 247
<211> LENGTH: 21
<212> TYPE: RNA
<213> ORGANISM: Artificial Sequence
<220> FEATURE:
<223> OTHER INFORMATION: Synthetic construct

<400> SEQUENCE: 247
uuacuuuuaa gcccaacaaa a 21

<210> SEQ ID NO 248
<211> LENGTH: 21
<212> TYPE: RNA
<213> ORGANISM: Artificial Sequence
<220> FEATURE:
<223> OTHER INFORMATION: Synthetic construct

<400> SEQUENCE: 248
ggcgugugug uguguuguug a 21

<210> SEQ ID NO 249
<211> LENGTH: 21
<212> TYPE: RNA
<213> ORGANISM: Artificial Sequence
<220> FEATURE:
<223> OTHER INFORMATION: Synthetic construct

<400> SEQUENCE: 249
guggugaagg ggaagguuua g 21

<210> SEQ ID NO 250
<211> LENGTH: 21
<212> TYPE: RNA
<213> ORGANISM: Artificial Sequence
<220> FEATURE:
<223> OTHER INFORMATION: Synthetic construct

<400> SEQUENCE: 250
uuguuuuuuu uugguuuggu u 21

<210> SEQ ID NO 251
<211> LENGTH: 1331
<212> TYPE: RNA
<213> ORGANISM: Artificial Sequence
<220> FEATURE:
<223> OTHER INFORMATION: Synthetic construct

<400> SEQUENCE: 251
aggauuauua caucaaaaca aaaagccgcc accaugcugg uauucaaccu gcgcauccug 60
cugaacaacg ccgccuuccg caacggccac aacuucaugg ugcgcaacuu ccgcugcggc 120
cagccccugc agaaccgggu gcagcugaag ggccgcgacc ugcugacccu gaagaacuuc 180
accggcgagg agauccggua caugcugugg cugagcgccg accugaaguu ccgcaucaag 240
cagaagggcg aguaccugcc ccugcugcag ggcaagagcc ugggcaugau cuucgagaag 300
cgcagcaccc gcacccgccu gagcaccgag acaggcuucg cccugcuggg cggccacccc 360
ugcuuccuga ccacccagga cauccaccug ggcgugaacg agagccugac cgacaccgcc 420
cgcgugcuga gcagcauggc cgacgccgug cuggcccgcg uguacaagca gagcgaccug 480
gacacccugg ccaaggaggc cagcaucccc aucaucaacg gccugagcga ccuguaccac 540
cccauccaga uccuggccga cuaccugacc cugcaggagc acuacagcag ccugaagggc 600
cugacccuga gcuggaucgg cgacggcaac aacauccugc acagcaucau gaugagcgcc 660
gccaaguucg gcaugcaccu gcaggccgcc acccccaagg gcuacgagcc cgacgccagc 720
gugaccaagc uggccgagca guacgccaag gagaacggca ccaagcugcu gcugaccaac 780
gacccccugg aggccgccca cggcggcaac gugcugauca ccgacaccug gaucagcaug 840
ggccaggagg aggagaagaa gaagcgccug caggccuucc agggcuacca ggugaccaug 900
aagaccgcca agguggccgc cagcgacugg accuuccugc acugccugcc ccgcaagccc 960
gaggaggugg acgacgaggu guucuacagc ccccgcagcc ugguguuccc cgaggccgag 1020
aaccgcaagu ggaccaucau ggccgugaug gugagccugc ugaccgacua cagcccccag 1080
cugcagaagc ccaaguucug aggucucuag uaaugagcug gagccucggu agccguuccu 1140
ccugcccgcu gggccuccca acgggcccuc cuccccuccu ugcaccggcc cuuccugguc 1200
uuugaauaaa gucugagugg gcagcaucua gaaaaaaaaa aaaaaaaaaa aaaaaaaaaa 1260
aaaaaaaaaa aaaaaaaaaa aaaaaaaaaa aaaaaaaaaa aaaaaaaaaa aaaaaaaaaa 1320
aaaaaaaaaa a 1331

<210> SEQ ID NO 252
<211> LENGTH: 1334
<212> TYPE: RNA
<213> ORGANISM: Artificial Sequence
<220> FEATURE:
<223> OTHER INFORMATION: Synthetic construct

<400> SEQUENCE: 252
aggauuauua caucaaaaca aaaagccgcc accaugcugg uauucaaccu gcgcauccug 60
cugaacaacg ccgccuuccg caacggccac aacuucaugg ugcgcaacuu ccgcugcggc 120
cagccccugc agaaccgggu gcagcugaag ggccgcgacc ugcugacccu gaagaacuuc 180
accggcgagg agauccggua caugcugugg cugagcgccg accugaaguu ccgcaucaag 240
cagaagggcg aguaccugcc ccugcugcag ggcaagagcc ugggcaugau cuucgagaag 300
cgcagcaccc gcacccgccu gagcaccgag acaggcuucg cccugcuggg cggccacccc 360
ugcuuccuga ccacccagga cauccaccug ggcgugaacg agagccugac cgacaccgcc 420
cgcgugcuga gcagcauggc cgacgccgug cuggcccgcg uguacaagca gagcgaccug 480
gacacccugg ccaaggaggc cagcaucccc aucaucaacg gccugagcga ccuguaccac 540
cccauccaga uccuggccga cuaccugacc cugcaggagc acuacagcag ccugaagggc 600
cugacccuga gcuggaucgg cgacggcaac aacauccugc acagcaucau gaugagcgcc 660
gccaaguucg gcaugcaccu gcaggccgcc acccccaagg gcuacgagcc cgacgccagc 720
gugaccaagc uggccgagca guacgccaag gagaacggca ccaagcugcu gcugaccaac 780
gacccccugg aggccgccca cggcggcaac gugcugauca ccgacaccug gaucagcaug 840
ggccaggagg aggagaagaa gaagcgccug caggccuucc agggcuacca ggugaccaug 900
aagaccgcca agguggccgc cagcgacugg accuuccugc acugccugcc ccgcaagccc 960
gaggaggugg acgacgaggu guucuacagc ccccgcagcc ugguguuccc cgaggccgag 1020
aaccgcaagu ggaccaucau ggccgugaug gugagccugc ugaccgacua cagcccccag 1080
cugcagaagc ccaaguucug aggucucuag uaaugagcug gagccucggu agccguuccu 1140
ccugcccgcu gggccuccca acgggcccuc cuccccuccu ugcaccggcc cuuccugguc 1200

-continued

```
uuugaauaaa gucugagugg gcagcaucua gaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaaaa agcu                                                     1334


<210> SEQ ID NO 253
<211> LENGTH: 1328
<212> TYPE: RNA
<213> ORGANISM: Artificial Sequence
<220> FEATURE:
<223> OTHER INFORMATION: Synthetic construct

<400> SEQUENCE: 253

aggauuauua caucaaaaca aaaagccgcc accaugcugu ucaaccugcg cauccugcug     60

aacaacgccg ccuuccgcaa cggccacaac uucauggugc gcaacuuccg cugcggccag    120

ccccugcaga acaaggugca gcugaagggc cgcgaccugc ugacccugaa gaacuucacc    180

ggcgaggaga ucaaguacau gcuguggcug agcgccgacc ugaaguuccg caucaagcag    240

aagggcgagu accugcccu gcugcagggc aagagccugg gcaugaucuu cgagaagcgc    300

agcacccgca cccgccugag caccgagaca ggcuucgccc ugcugggcgg ccaccccugc    360

uuccugacca cccaggacau ccaccugggc gugaacgaga gccugaccga caccgcccgc    420

gugcugagca gcauggccga cgccgugcug gcccgcgugu acaagcagag cgaccuggac    480

acccuggcca aggaggccag cauccccauc aucaacggcc ugagcgaccu guaccacccc    540

auccagaucc uggccgacua ccugacccug caggagcacu acagcagccu gaagggccug    600

acccugagcu ggaucggcga cggcaacaac auccugcaca gcaucaugau gagcgccgcc    660

aaguucggca ugcaccugca ggccgccacc cccaagggcu acgagcccga cgccagcgug    720

accaagcugg ccgagcagua cgccaaggag aacggcacca agcugcugcu gaccaacgac    780

ccccuggagg ccgcccacgg cggcaacgug cugaucaccg acaccuggau cagcaugggc    840

caggaggagg agaagaagaa gcgccugcag gccuuccagg gcuaccaggu gaccaugaag    900

accgccaagg uggccgccag cgacuggacc uuccugcacu gccugccccg caagcccgag    960

gagguggacg acgaggugu cuacagcccc cgcagccugg uguuccccga ggccgagaac   1020

cgcaagugga ccaucauggc cgugauggug agccugcuga ccgacuacag cccccagcug   1080

cagaagccca aguucugagg ucucuaguaa ugagcuggag ccucgguagc cguuccuccu   1140

gcccgcuggg ccucccaacg ggcccuccuc cccuccuugc accggcccuu ccuggucuuu   1200

gaauaaaguc ugagugggca gcaucuagaa aaaaaaaaaa aaaaaaaaaa aaaaaaaaaa   1260

aaaaaaaaaa aaaaaaaaaa aaaaaaaaaa aaaaaaaaaa aaaaaaaaaa aaaaaaaaaa   1320

aaaaaaaa                                                            1328
```

COMPOSITIONS AND METHODS FOR TREATING ORNITHINE TRANSCARBAMYLASE DEFICIENCY

CROSS-REFERENCE TO RELATED APPLICATIONS

This application claims priority to U.S. Provisional Application No. 62/776,302, filed Dec. 6, 2018. The content of the application is incorporated herein by reference in its entirety.

SEQUENCE LISTING

The instant application contains a Sequence Listing which has been submitted electronically in ASCII format and is hereby incorporated by reference in its entirety. Said ASCII copy, created on Nov. 25, 2019 is named 049386_523001WO_SL.txt and is 363 kilobytes in size.

BACKGROUND

Ornithine transcarbamylase (OTC) is a mitochondrial enzyme present in mammals which plays an essential role in detoxifying the organism from toxic ammonia. OTC mRNA has a mitochondrial signaling peptide (MSP) that is critical to redirect the nascent pre-peptide from the cytosol into the mitochondria. OTC protein exist as a precursor in the cytosol, the presence of the MSP redirects the pro-peptide into the mitochondria, where it undergoes excision of the signaling peptide and delivery of the functional protein into the mitochondrial matrix. OTC is one of six enzymes that play a role in the breakdown of proteins and removal of ammonia from the body, a process known as the urea cycle, a metabolic process that occurs in hepatocytes. OTC is responsible for converting carbamoyl phosphate and ornithine into citrulline.

Deficiency of the OTC enzyme results in excessive accumulation of nitrogen, in the form of ammonia (hyperammonemia), in the blood. Excess ammonia, which is a neurotoxin, travels to the central nervous system through the blood, resulting in the symptoms and physical findings associated with OTC deficiency. These symptoms can include vomiting, refusal to eat, progressive lethargy, or coma. If left untreated a hyperammonemic episode may progress to coma and life-threatening complications.

The severity and age of onset of OTC deficiency vary from person to person, even within the same family. A severe form of the disorder affects some infants, typically males, shortly after birth (neonatal period). A milder form of the disorder affects some children later in infancy. Both males and females may develop symptoms of OTC deficiency during childhood. Presently, the treatment of OTC deficiency is aimed at preventing excessive ammonia from being formed or from removing excessive ammonia during a hyperammonemic episode. Long-term therapy for OTC deficiency combines dietary restrictions and the stimulation of alternative methods of converting and excreting nitrogen from the body (alternative pathways therapy).

Dietary restrictions in individuals with OTC deficiency are aimed at limiting the amount of protein intake to avoid the development of excess ammonia. However, enough protein must be taken in by an affected infant to ensure proper growth. Infants with OTC deficiency are placed on a low protein, high calorie diet supplemented by essential amino acids.

In addition to dietary restrictions, individuals with OTC deficiency are treated by medications that stimulate the removal of nitrogen from the body. These medications provide an alternative method to the urea cycle in converting and removing nitrogen waste. These medications are unpalatable to many patients and are often administered via a tube that is placed in the stomach through the abdominal wall (gastrostomy tube) or a narrow tube that reaches the stomach via the nose (nasogastric tube).

In cases where there is no improvement or in cases where hyperammonemic coma develops, the removal of wastes by filtering an affected individual's blood through a machine (hemodialysis) may be necessary. Hemodialysis is also used to treat infants, children, and adults who are first diagnosed with OTC deficiency during hyperammonemic coma.

In some cases, liver transplantation, may be an appropriate treatment option. Liver transplantation can cure the hyperammonemia in OTC deficiency. However, this operation is risky and may result in post-operative complications. Also, after liver transplantation, patients will need to follow a medication regimen throughout their lives for immunosuppression. Novel approaches and therapies are still needed for the treatment of OTC enzyme deficiency. Strategies are needed which overcome the challenges and limitations associated with, for example, gene therapy. Poor stability, getting enough OTC in the mitochondria and efficient delivery to the target cells are still challenges.

SUMMARY

The present disclosure provides a modified human OTC protein of SEQ ID NO: 4 having improved properties for the treatment of OTC deficiency in a patient. SEQ ID NO: 4 has been modified from wild-type OTC to remove one or more predicted ubiquitination sites resulting in a protein that is less susceptible to ubiquitination and degradation by ubiquitin ligases. However, the modified OTC protein of SEQ ID NO: 4 maintains the catalytic enzyme activity of human wild type OTC. The removal of predicted ubiquitination sites preferably comprises replacing N-terminus residues that have been found to support ubiquitination such as asparagine, arginine, leucine, lysine or phenylalanine with N-terminus residues that have been found to be stabilizing against ubiquitination such as alanine, glycine, methionine, serine, threonine, valine and proline. Stabilization of the modified OTC protein of SEQ ID NO: 4 in this manner is particularly advantageous for preserving the stability of the modified OTC protein during its transport from the cytosol to the mitochondria wherein it exerts its enzymatic activity.

Preferably, the protein of SEQ ID NO: 4 described herein is produced from a nucleic acid encoding the protein of SEQ ID NO: 4. The nucleic acid may be RNA or DNA that encodes the protein of SEQ ID NO: 4. Preferably the nucleic acid is a heterologous mRNA construct comprising an open reading frame encoding for the modified protein of SEQ ID NO: 4. Preferably, the open reading frame is a codon-optimized open reading frame. Preferably, the open reading frame sequence is optimized to have a theoretical minimum of uridines possible to encode for the modified protein. Preferably, the heterologous mRNA construct comprises a 5' cap, a 5'UTR, a 3'UTR, an open reading frame encoding a modified protein of SEQ ID NO: 4 and a 3' poly A tail. Preferably, the 5'UTR derived from a gene expressed by *Arabidopsis thaliana*. Preferably the 5" UTR derived from a gene expressed by *Arabidopsis thaliana* is found in Table 2.

The present disclosure also provides mRNA (also referred to herein as mRNA constructs or mRNA sequences) comprising an optimized coding region encoding wild type human ornithine transcarbamylase (OTC) protein of SEQ ID NO: 3 or an OTC protein sequence that is at least 95% identical over the full length of SEQ ID NO: 3 and having OTC protein enzymatic activity wherein the mRNA sequences comprise a 5'UTR derived from a gene expressed by *Arabidopsis thaliana.*

The mRNA constructs described herein provide high-efficiency expression of the OTC proteins described herein. The expression can be in vitro, ex vivo, or in vivo.

The present disclosure also provides pharmaceutical compositions comprising the mRNA sequences described herein and methods of treating ornithine transcarbamylase (OTC) deficiency by administering the pharmaceutical compositions comprising the mRNA sequences described herein to a patient in need thereof wherein the OTC protein of SEQ ID NO: 3 or SEQ ID NO: 4 is expressed in the patient.

DETAILED DESCRIPTION

Definitions

Figure 1:
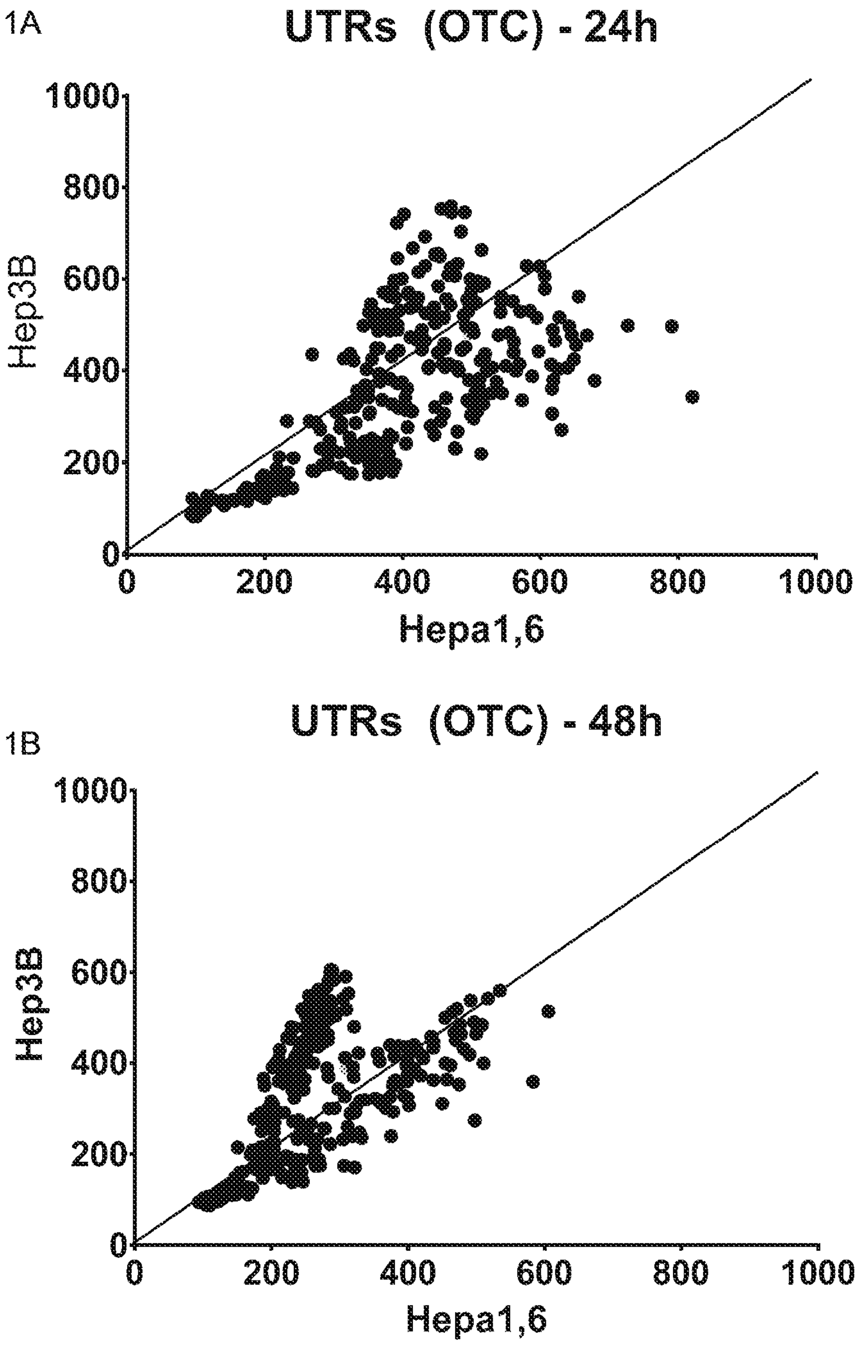
FIGS. 1A-B shows scatter plots illustrating ornithine transcarbamylase (OTC) protein expression in hepatocyte cell lines Hepa1,6 (mouse) and Hep3B (human) at 24 hours (FIG. 1A) and 48 hours (FIG. 1B) using In-Cell Western (ICW) assays.

The term "ornithine transcarbamylase" as used interchangeably herein with "OTC" or "hOTC", or "OTC HUMAN" generally refers to the human protein associated with UniPRotKB-P00480. The amino acid sequence for the wild type human OTC protein is represented herein by SEQ ID NO: 3.

The term "nucleic acid," in its broadest sense, includes any compound and/or substance that comprise a polymer of nucleotides. These polymers are often referred to as polynucleotides. Exemplary nucleic acids or polynucleotides described herein include, but are not limited to, ribonucleic acids (RNAs), deoxyribonucleic acids (DNAs), threose nucleic acids (TNAs), glycol nucleic acids (GNAs), peptide nucleic acids (PNAs), locked nucleic acids (LNAs, including LNA having a β-D-ribo configuration, α-LNA having an α-L-ribo configuration (a diastereomer of LNA), 2'-amino-LNA having a 2'-amino functionalization, and 2'-amino-α-LNA having a 2'-amino functionalization) or hybrids thereof.

As used herein, the term "polynucleotide" is generally used to refer to a nucleic acid (e.g., DNA or RNA). When RNA, such as mRNA, is specifically being referred to, the term polyribonucleotide may be used. The terms polynucleotide, polyribonucleotide, nucleic acid, ribo nucleic acid, DNA, RNA, mRNA, and the like include such molecules that may be comprised of standard or unmodified residues; nonstandard or modified residues (e.g., analogs); and mixtures of standard and nonstandard (e.g., analogs) residues. In certain embodiments a polynucleotide or a polyribonucleotide is a modified polynucleotide or a polyribonucleotide. In the context of the present disclosure, for each RNA (polyribonucleotide) sequence listed herein, the corresponding DNA (polydeoxyribonucleotide or polynucleotide) sequence is contemplated and vice versa. "Polynucleotide" may be used interchangeably with the "oligomer". Polynucleotide sequences shown herein are from left to right, 5' to 3', unless stated otherwise.

As used herein, the term "messenger RNA" (mRNA) refers to any polynucleotide which encodes a protein or polypeptide of interest and which is capable of being translated to produce the encoded protein or polypeptide of interest in vitro, in vivo, in situ or ex vivo.

As used herein, the term "translation" is the process in which ribosomes create polypeptides. In translation, messenger RNA (mRNA) is decoded by transfer RNAS (tRNAs) in a ribosome complex to produce a specific amino acid chain, or polypeptide. The coding region of a polynucleotide sequence (DNA or RNA), also known as the coding sequence or CDS, is capable of being converted to a protein or a fragment thereof by the process of translation.

As used herein, the term "codon-optimized" means a natural (or purposefully designed variant of a natural) coding sequence which has been redesigned by choosing different codons without altering the encoded protein amino acid sequence. Codon optimized sequence can increase the protein expression levels (Gustafsson et al., *Codon bias and heterologous protein expression.* 2004, Trends Biotechnol 22: 346-53) of the encoded proteins amongst providing other advantages. Variables such as high codon adaptation index (CAI), LowU method, mRNA secondary structures, cis-regulatory sequences, GC content and many other similar variables have been shown to somewhat correlate with protein expression levels (Villalobos et al., *Gene Designer: a synthetic biology tool for constructing artificial DNA segments.* 2006, BMC Bioinformatics 7:285). High CAI (codon adaptation index) method picks a most frequently used synonymous codon for an entire protein coding sequence. The most frequently used codon for each amino acid is deduced from 74,218 protein-coding genes from a human genome. The Low U method targets only U-containing codons that can be replaced with a synonymous codon with fewer U moieties. If there are a few choices for the replacement, the more frequently used codon will be selected. The remaining codons in the sequence are not changed by the Low U method. This method may be used in conjunction with the disclosed mRNAs to design coding sequences that are to be synthesized with, for example, 5-methoxyuridine or $N^1$-methylpseudouridine.

As used herein, "modified" refers to a change in the state or structure of a molecule disclosed herein. The molecule may be changed in many ways including chemically, structurally or functionally. Preferably a polynucleotide or polypeptide of the disclosure are modified as compared to the native form of the polynucleotide or polypeptide or as compared to a reference polypeptide sequence or polynucleotide sequence. For example, mRNA disclosed herein may be modified by codon optimization, or by the insertion of non-natural nucleosides or nucleotides. Polypeptides may be modified, for example, by site specific amino acid deletions or substitutions to alter the properties of the polypeptide.

As used herein, the term "homology" refers to the overall relatedness between polymeric molecules, e.g. between nucleic acid molecules (e.g. DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical or similar. The term "homologous" necessarily refers to a comparison between at least two sequences (polynucleotide or polypeptide sequences). In accordance with the present disclosure, two polynucleotide sequences are considered to be homologous if the polypeptides they encode are at least about 50%, 60%, 70%, 80%, 90%, 95%, or even 99% for at least one stretch of at least about 20 amino acids. In some embodiments, homologous polynucleotide sequences are characterized by the ability to encode a stretch of at least 4-5 uniquely specified amino acids. For polynucleotide sequences less than 60 nucleotides in length, homology is determined by the ability to encode a stretch of at least 4-5 uniquely specified amino acids. In accordance with the present disclosure, two protein sequences are considered to be homologous if the proteins are at least about 50%, 60%, 70%, 80%, or 90% identical for at least one stretch of at least about 20 amino acids.

As used herein, the term "identity" refers to the overall relatedness between polymeric molecules, e.g., between oligonucleotide molecules (e.g. DNA molecules and/or RNA molecules) and/or between polypeptide molecules. Calculation of the percent identity of two polynucleotide sequences, for example, can be performed by aligning the two sequences for optimal comparison purposes. In certain embodiments, the length of a sequence aligned for comparison purposes is at least 30%, at least 40%, at least 50%, at least 60%, at least 70%, at least 80%, at least 90%, at least 95%, or 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. Methods commonly employed to determine percent identity between sequences include, but are not limited to those disclosed in Carillo, H., and Lipman, D., SIAM J *Applied Math.,* 48:1073 (1988); incorporated herein by reference. Techniques for determining identity are codified in publicly available computer programs. Exemplary computer software to determine homology between two sequences include, but are not limited to, GCG program package, Devereux, J., et al., *Nucleic Acids Research,* 12(1), 387 (1984), BLASTP, BLASTN, and FASTA Altschul, S. F. et al., *J. Molec. Biol.,* 215, 403 (1990).

An "effective amount" of the mRNA sequence encoding an open reading frame (ORF) protein or a corresponding composition thereof is generally that amount of mRNA that provides efficient ORF protein production in a cell. Preferably protein production using an mRNA composition described herein is more efficient than a composition containing a corresponding wild type mRNA encoding an ORF protein. Increased efficiency may be demonstrated by increased cell transfection (i.e., the percentage of cells transfected with the nucleic acid), increased protein translation from the nucleic acid, decreased nucleic acid degradation (as demonstrated, e.g., by increased duration of protein translation from a modified nucleic acid), or reduced innate immune response of the host cell. When referring to an ORF protein described herein, an effective amount is that amount of ORF protein that overcomes an ORF protein deficiency in a cell.

As used herein, the term "in vitro" refers to events that occur in an artificial environment, e.g., in a test tube or reaction vessel, in cell culture, in a Petri dish, etc., rather than within an organism (e.g., animal, plant, or microbe).

As used herein, the term "in vivo" refers to events that occur within an organism (e.g., animal, plant, or microbe or cell or tissue thereof).

As used herein, the term "isolated" refers to a substance or entity that has been separated from at least some of the components with which it was associated (whether in nature or in an experimental setting). Isolated substances may have varying levels of purity in reference to the substances from which they have been associated. Isolated substances and/or entities may be separated from at least about 10%, about 20%, about 30%, about 40%, about 50%, about 60%, about 70%, about 80%, about 90%, or more of the other components with which they were initially associated. In some embodiments, isolated agents are more than about 80%, about 85%, about 90%, about 91%, about 92%, about 93%, about 94%, about 95%, about 96%, about 97%, about 98%, about 99%, or more than about 99% pure. As used herein, a substance is "pure" if it is substantially free of other components. Substantially isolated: By "substantially isolated" is meant that the compound is substantially separated from the environment in which it was formed or detected. Partial separation can include, for example, a composition enriched in the compound described herein. Substantial separation can include compositions containing at least about 50%, at least about 60%, at least about 70%, at least about 80%, at least about 90%, at least about 95%, at least about 97%, or at least about 99% by weight of the compound described herein, or salt thereof. Methods for isolating compounds and their salts are routine in the art.

As used herein, the term "subject" or "patient" refers to any organism to which a composition in accordance with the present disclosure may be administered, e.g., for experimental, diagnostic, prophylactic, and/or therapeutic purposes. Typical subjects include animals (e.g., mammals such as mice, rats, rabbits, non-human primates, and humans) and/or plants. Preferably "patient" refers to a human subject who may seek or be in need of treatment, requires treatment, is receiving treatment, will receive treatment, or a subject who is under care by a trained professional for a particular disease or condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "preventing" refers to partially or completely delaying onset of an infection, disease, disorder and/or condition; partially or completely delaying onset of one or more symptoms, features, or clinical manifestations of a particular infection, disease, disorder, and/or condition; partially or completely delaying onset of one or more symptoms, features, or manifestations of a particular infection, disease, disorder, and/or condition; partially or completely delaying progression from an infection, a particular disease, disorder and/or condition; and/or decreasing the risk of developing pathology associated with the infection, the disease, disorder, and/or condition.

As used herein, the term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "therapeutically effective amount" means an amount of an agent to be delivered (e.g., nucleic acid, protein or peptide, drug, therapeutic agent, diagnostic agent, prophylactic agent, etc.) that is sufficient, when administered to a subject suffering from or susceptible to an infection, disease, disorder, and/or condition, to treat, improve symptoms of, diagnose, prevent, and/or delay the onset of the infection, disease, disorder, and/or condition.

As used herein, a "total daily dose" is an amount given or prescribed in a 24 hr period. It may be administered as a single unit dose.

As used herein, the term "treating" refers to partially or completely alleviating, ameliorating, improving, relieving, delaying onset of, inhibiting progression of, reducing severity of, and/or reducing incidence of one or more symptoms or features of OTC deficiency. Treatment may be administered to a subject who does not exhibit signs of OTC deficiency and/or to a subject who exhibits only early signs of OTC deficiency for the purpose of decreasing the risk of developing pathology associated with the disease, disorder, and/or condition.

As used herein, the terms "transfect" or "transfection" mean the intracellular introduction of a nucleic acid into a cell, or preferably into a target cell. The introduced nucleic acid may be stably or transiently maintained in the target cell. The term "transfection efficiency" refers to the relative amount of nucleic acid up-taken by the target cell which is subject to transfection. In practice, transfection efficiency is estimated by the amount of a reporter nucleic acid product expressed by the target cells following transfection. Preferred are compositions with high transfection efficacies and in particular those compositions that minimize adverse effects which are mediated by transfection of non-target cells and tissues.

As used herein, the term "target cell" refers to a cell or tissue to which a composition of the disclosure is to be directed or targeted. In some embodiments, the target cells are deficient in a protein or enzyme of interest. For example, where it is desired to deliver a nucleic acid to a hepatocyte, the hepatocyte represents the target cell. In some embodiments, the nucleic acids and compositions of the present disclosure transfect the target cells on a discriminatory basis (i.e., do not transfect non-target cells). The compositions and methods of the present disclosure may be prepared to preferentially target a variety of target cells, which include, but are not limited to, hepatocytes, epithelial cells, hematopoietic cells, epithelial cells, endothelial cells, lung cells, bone cells, stem cells, mesenchymal cells, neural cells (e.g., meninges, astrocytes, motor neurons, cells of the dorsal root ganglia and anterior horn motor neurons), photoreceptor cells (e.g., rods and cones), retinal pigmented epithelial cells, secretory cells, cardiac cells, adipocytes, vascular smooth muscle cells, cardiomyocytes, skeletal muscle cells, beta cells, pituitary cells, synovial lining cells, ovarian cells, testicular cells, fibroblasts, B cells, T cells, reticulocytes, leukocytes, granulocytes and tumor cells.

Following transfection of one or more target cells by the compositions and nucleic acids described herein, expression of the protein encoded by such nucleic acid may be preferably stimulated and the capability of such target cells to express the protein of interest is enhanced. For example, transfection of a target cell with an OTC mRNA will allow expression of the OTC protein product following translation of the nucleic acid. The nucleic acids of the compositions and/or methods provided herein preferably encode a product (e.g., a protein, enzyme, polypeptide, peptide, functional RNA, and/or antisense molecule), and preferably encode a product whose in vivo production is desired.

As used herein "an OTC protein enzymatic activity" refers to enzyme activity that catalyzes the reaction between carbamoyl phosphate and ornithine to form citrulline as part of the urea cycle in mammals.

As used herein, the term "about" or "approximately" as applied to one or more values of interest, refers to a value that is similar to a stated reference value. In certain embodiments, the term "approximately" or "about" refers to a range of values that fall within 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Polynucleotide Sequences

The present disclosure provides improved methods and compositions for the treatment of Ornithine transcarbamylase (OTC) deficiency using, for example, mRNA therapy. The present disclosure provides methods of treating ornithine transcarbamylase (OTC) deficiency, comprising administering to a subject in need of treatment a composition comprising an mRNA sequence described herein encoding a human ornithine transcarbamylase (OTC) protein, modified forms of human OTC protein or active fragments of OTC protein at an effective dose and an administration interval such that at least one symptom or feature of the OTC deficiency is reduced in intensity, severity, or frequency or has delayed onset. The present disclosure also provides modified OTC proteins encoded by the mRNA sequences wherein the modified OTC proteins have improved properties such as enhanced stability and resistance to protein degradation and increased half-life as compared to wild type human OTC proteins.

Preferably, the administration of an mRNA composition described herein results in an increased OTC protein expression or activity of the subject as compared to a control level. Preferably, the control level is a baseline serum OTC protein expression or activity level in the subject prior to the treatment and/or the control level is indicative of the average serum OTC protein expression or activity level in OTC patients without treatment.

Preferably, administration of a mRNA described herein composition results in a reduced urinary orotic acid level in the subject as compared to a control orotic acid level. Preferably, the control orotic acid level is a baseline urinary orotic acid level in the subject prior to the treatment and/or the control orotic acid level is a reference level indicative of the average urinary orotic acid level in OTC patients without treatment.

Preferably, the OTC proteins encoded by the mRNA described herein are produced from a heterologous mRNA construct comprising an open reading frame (ORF) also referred to herein as a "coding sequence" (CDS) encoding for an OTC protein. Preferably, the coding sequence is codon-optimized. Preferably, coding sequence is optimized to have a theoretical minimum of uridines possible to encode for an OTC protein. Preferably, the mRNA constructs described herein comprise one or more of the following features: a 5' cap; a 5'UTR, a 5'UTR enhancer sequence, a Kozak sequence or a partial Kozak sequence, a 3'UTR, an open reading frame encoding an OTC protein and a poly A tail. Preferably, the mRNA constructs described herein can provide high-efficiency expression of an OTC protein. The expression can be in vitro, ex vivo, or in vivo.

Preferably, a human OTC protein encoded by an mRNA described herein comprises a modified human OTC protein of SEQ ID NO: 4 shown in Table 1. SEQ ID NO: 4 has been modified from wild-type OTC of SEQ ID NO: 3 (Table 1) to remove one or more predicted ubiquitination sites resulting in a protein that is less susceptible to ubiquitination and degradation by ubiquitin ligases. The removal of predicted ubiquitination sites preferably comprises replacing N-terminus residues that have been found to support ubiquitination such as asparagine, arginine, leucine, lysine or phenylalanine with N-terminus residues that have been found to be stabilizing against ubiquitination such as alanine, glycine, methionine, serine, threonine, valine and proline. Stabilization of the modified OTC protein of SEQ ID NO: 4 in this manner is particularly advantageous for preserving the stability of the modified OTC protein during its transport from the cytosol to the mitochondria wherein it exerts its enzymatic activity.

Preferably, an OTC protein encoded by an mRNA described herein comprises a protein sequence that is at least 70%, 75%, 80%, 85%, 90%, 95%, 96%, 97%, 98%, 99%, or 100% identical to human wild type OTC protein of SEQ ID NO: 3 as shown in Table 1, while retaining the OTC protein activity of catalyzing the synthesis of citrulline (in the liver and small intestine) from carbamyl phosphate and ornithine.

TABLE 1

Selected OTC Nucleotide and Peptide Sequences

| | |
|---|---|
| mRNA coding sequence for wild type human OTC | **AUGCUGUUUAAUCUGAGGAUCCUGUUAAACAAUGCAGCUUUUAGAAA**<br>**UGGUCACAACUUCAUGGUUCGAAAUUUUCGGUGUGGACAACCACUAC**<br>**AA**AAUAAAGUGCAGCUGAAGGGCCGUGACCUUCUCACUCUAAAAAAC<br>UUUACCGGAGAAGAAAUUAAAUAUAUGCUAUGGCUAUCAGCAGAUCU<br>GAAAUUUAGGAUAAAACAGAAAGGAGAGUAUUUGCCUUUAUUGCAAG<br>GGAAGUCCUUAGGCAUGAUUUUUGAGAAAAGAAGUACUCGAACAAGA<br>UUGUCUACAGAAACAGGCUUUGCACUUCUGGGAGGACAUCCUUGUUU<br>UCUUACCACACAAGAUAUUCAUUUGGGUGUGAAUGAAAGUCUCACGG<br>ACACGGCCCGUGUAUUGUCUAGCAUGGCAGAUGCAGUAUUGGCUCGA<br>GUGUAUAAACAAUCAGAUUUGGACACCCUGGCUAAAGAAGCAUCCAU<br>CCCAAUUAUCAAUGGGCUGUCAGAUUUGUACCAUCCUAUCCAGAUCCU<br>GGCUGAUUACCUCACGCUCCAGGAACACUAUAGCUCUCUGAAAGGUCU<br>UACCCUCAGCUGGAUCGGGGAUGGGAACAAUAUCCUGCACUCCAUCAU<br>GAUGAGCGCAGCGAAAUUCGGAAUGCACCUUCAGGCAGCUACUCCAAA<br>GGGUUAUGAGCCGGAUGCUAGUGUAACCAAGUUGGCAGAGCAGUAUG<br>CCAAAGAGAAUGGUACCAAGCUGUUGCUGACAAAUGAUCCAUUGGAA<br>GCAGCGCAUGGAGGCAAUGUAUUAAUUACAGACACUUGGAUAAGCAU<br>GGGACAAGAAGAGGAGAAGAAAAAGCGGCUCCAGGCUUUCCAAGGUU<br>ACCAGGUUACAAUGAAGACUGCUAAAGUUGCUGCCUCUGACUGGACA<br>UUUUUACACUGCUUGCCCAGAAAGCCAGAAGAAGUGGAUGAUGAAGU<br>CUUUUAUUCUCCUCGAUCACUAGUGUUCCCAGAGGCAGAAAACAGAA<br>AGUGGACAAUCAUGGCUGUCAUGGUGUCCCUGCUGACAGAUUACUCA<br>CCUCAGCUCCAGAAGCCUAAAUUUUGA (SEQ ID NO: 1) |
| DNA coding sequence for wild type human OTC | **ATGCTGTTTAATCTGAGGATCCTGTTAAACAATGCAGCTTTTAGAAATGG**<br>**TCACAACTTCATGGTTCGAAATTTTCGGTGTGGACAACCACTACAA**AATA<br>AAGTGCAGCTGAAGGGCCGTGACCTTCTCACTCTAAAAAACTTTACCGG<br>AGAAGAAATTAAATATATGCTATGGCTATCAGCAGATCTGAAATTTAGG<br>ATAAAACAGAAAGGAGAGTATTTGCCTTTATTGCAAGGGAAGTCCTTAG<br>GCATGATTTTTGAGAAAAGAAGTACTCGAACAAGATTGTCTACAGAAAC |

TABLE 1-continued

| Selected OTC Nucleotide and Peptide Sequences | |
|---|---|
| | AGGCTTTGCACTTCTGGGAGGACATCCTTGTTTTCTTACCACACAAGATA<br>TTCATTTGGGTGTGAATGAAAGTCTCACGGACACGGCCCGTGTATTGTCT<br>AGCATGGCAGATGCAGTATTGGCTCGAGTGTATAAACAATCAGATTTGG<br>ACACCCTGGCTAAAGAAGCATCCATCCCAATTATCAATGGGCTGTCAGA<br>TTTGTACCATCCTATCCAGATCCTGGCTGATTACCTCACGCTCCAGGAAC<br>ACTATAGCTCTCTGAAAGGTCTTACCCTCAGCTGGATCGGGGATGGGAA<br>CAATATCCTGCACTCCATCATGATGAGCGCAGCGAAATTCGGAATGCAC<br>CTTCAGGCAGCTACTCCAAAGGGTTATGAGCCGGATGCTAGTGTAACCA<br>AGTTGGCAGAGCAGTATGCCAAAGAGAATGGTACCAAGCTGTTGCTGAC<br>AAATGATCCATTGGAAGCAGCGCATGGAGGCAATGTATTAATTACAGAC<br>ACTTGGATAAGCATGGGACAAGAAGAGGAGAAGAAAAAGCGGCTCCAG<br>GCTTTCCAAGGTTACCAGGTTACAATGAAGACTGCTAAAGTTGCTGCCTC<br>TGACTGGACATTTTTACACTGCTTGCCCAGAAAGCCAGAAGAAGTGGAT<br>GATGAAGTCTTTTATTCTCCTCGATCACTAGTGTTCCCAGAGGCAGAAAA<br>CAGAAAGTGGACAATCATGGCTGTCATGGTGTCCCTGCTGACAGATTAC<br>TCACCTCAGCTCCAGAAGCCTAAATTTTGA (SEQ ID NO: 2) |
| Human wild type OTC amino acid sequence (The signal peptide for mitochondrial import is underlined*) | **MLFNLRILLNNAAFRNGHNFMVRNFRCGQPLQ**NKVQLKGRDLLTLKNFTG<br>EEIKYMLWLSADLKFRIKQKGEYLPLLQGKSLGMIFEKRSTRTRLSTETGFA<br>LLGGHPCFLTTQDIHLGVNESLTDTARVLSSMADAVLARVYKQSDLDTLAK<br>EASIPIF GLSDLYHPIQILADYLTLQEHYSSLKGLTLSWIGDGNNILHSIMMS<br>AAKFGMHLQAATPKGYEPDASVTKLAEQYAKENGTKLLLTNDPLEAAHGG<br>NVLITDTWISMGQEEEKKKRLQAFQGYQVTMKTAKVAASDWTFLHCLPRK<br>PEEVDDEVFYSPRSLVFPEAENRKWTIMAVMVSLLTDYSPQLQKPKF<br>(SEQ ID NO: 3) |
| Modified OTC amino acid sequence (The signal peptide for mitochondrial import is underlined*) | **MLVFNLRILLNNAAFRNGHNFMVRNFRCGQPLQ**NRVQLKGRDLLTLKNFTGE<br>EIRYMLWLSADLKFRIKQKGEYLPLLQGKSLGMIFEKRSTRTRLSTETGFALLGGH<br>PCFLTTQDIHLGVNESLTDTARVLSSMADAVLARVYKQSDLDTLAKEASIPIINGLS<br>DLYHPIQILADYLTLQEHYSSLKGLTLSWIGDGNNILHSIMMSAAKFGMHLQAAT<br>PKGYEPDASVTKLAEQYAKENGTKLLLTNDPLEAAHGGNVLITDTWISMGQEEEK<br>KKRLQAFQGYQVTMKTAKVAASDWTFLHCLPRKPEEVDDEVFYSPRSLVFPEAEN<br>RKWTIMAVMVSLLTDYSPQLQKPKF (SEQ ID NO: 4) |

*The OTC protein comprises a signal peptide which is translated and which is responsible for translocation to the mitochondria. This signal peptide is represented by the first 32 amino acids as underlined in SEQ ID NO: 3 and SEQ ID NO: 4. The signal sequence of SEQ ID NO: 4 has also been modified as compared to SEQ ID NO: 3. An amino acid, valine is inserted at position 3 of SEQ ID NO: 4. This modification provides better mitochondrial localization of the modified OTC of SEQ ID NO: 4 as compared to wild type human OTC of SEQ ID NO: 3.

Preferably, the open reading frame (ORF) or coding sequence (CDS) of an mRNA sequence described herein encodes an amino acid sequence that is substantially identical to the modified OTC protein of SEQ ID NO: 4.

Preferably, the open reading frame (ORF) or coding sequence (CDS) of an mRNA sequence described herein encodes an amino acid sequence that is substantially identical to wild type human OTC protein of SEQ ID NO: 3. Preferably, an OTC protein encoded by an mRNA described herein comprises a protein sequence that is at least 70%, 75%, 80%, 85%, 90%, 95% 96%, 97%, 98%, 99%, or 100% identical to a modified human OTC protein of SEQ ID NO: 3 shown in Table 1 while retaining the OTC protein activity of catalyzing the synthesis of citrulline (in the liver and small intestine) from carbamyl phosphate and ornithine.

Preferably, the ORF or CDS of an mRNA described herein encodes an amino acid sequence that is substantially identical to modified human OTC protein of SEQ ID NO: 4.

Preferably, the ORF or CDS of an mRNA described herein encoding a human OTC protein comprises a codon optimized polynucleotide sequence at least 70%, 75%, 80%, 85%, 90%, 95%, 96%, 97%, 98%, 99%, or 100% identical to the mRNA coding sequence of SEQ ID NO: 1 of Table 1.

Preferably an mRNA described herein further comprises a sequence immediately downstream (i.e., in the 3' direction from) of the CDS that creates a triple stop codon. The triple stop codon may be incorporated to enhance the efficiency of translation. In some embodiments, the translatable oligomer may comprise the sequence AUAAGUGAA (SEQ ID NO: 25) immediately downstream of an OTC CDS of an mRNA sequence described herein.

Preferably, an mRNA described herein further comprises a 5' untranslated region (UTR) sequence. As is understood in the art, the 5' and/or 3' UTR may affect an mRNA's stability or efficiency of translation. The 5' UTR may be derived from an mRNA molecule known in the art to be relatively stable (e.g., histone, tubulin, globin, glyceraldehyde 1-phosphate dehydrogenase (GAPDH), actin, or citric acid cycle enzymes) to increase the stability of the translatable oligomer. In other embodiments, a 5' UTR sequence may include a partial sequence of a cytomegalovirus (CMV) immediate-early 1 (IE1) gene.

Preferably, the 5' UTR comprises a sequence selected from the 5' UTRs of human IL-6, alanine aminotransferase 1, human apolipoprotein E, human fibrinogen alpha chain, human transthyretin, human haptoglobin, human alpha-1-antichymotrypsin, human antithrombin, human alpha-1-antitrypsin, human albumin, human beta globin, human complement C3, human complement C5, SynK (thylakoid potassium channel protein derived from the cyanobacteria, *Synechocystis* sp.), mouse beta globin, mouse albumin, and a tobacco etch virus, or fragments of any of the foregoing. Preferably, the 5' UTR is derived from a tobacco etch virus (TEV). Preferably, an mRNA described herein comprises a 5' UTR sequence that is derived from a gene expressed by *Arabidopsis thaliana*. Preferably, the 5' UTR sequence of a gene expressed by *Arabidopsis thaliana* is AT1G58420. Preferred 5' UTR sequences comprise SEQ ID NOS: 5-10, 125-127 and 230-250: as shown in Table 2.

TABLE 2

5'UTR sequences

| Name | Sequence | Seq ID No.: |
|---|---|---|
| EV | UCAACACAACAUAUACAAAACAAACGAAUCUCAAGCAAUCAAGCA UUCUACUUCUAUUGCAGCAAUUUAAAUCAUUUCUUUUAAAGCA AAAGCAAUUUUCUGAAAAUUUUCACCAUUUACGAACGAUAG | SEQ ID NO: 5 |
| AT1G58420 | AUUAUUACAUCAAAACAAAAAGCCGCCA | SEQ ID NO: 6 |
| ARC5-2 | CUUAAGGGGGCGCUGCCUACGGAGGUGGCAGCCAUCUCCUUCU CGGCAUCAAGCUUACCAUGGUGCCCCAGGCCCUGCUCUUGGUCC CGCUGCUGGUGUUCCCCUCUGCUUCGGCAAGUUCCCCAUCUAC ACCAUCCCCGACAAGCUGGGGCCGUGGAGCCCCAUCGACAUCCA CCACCUGUCCUGCCCCAACAACCUCGUGGUCGAGGACGAGGGCU GCACCAACCUGAGCGGGUUCUCCUAC | SEQ ID NO: 7 |
| HCV | UGAGUGUCGU ACAGCCUCCA GGCCCCCCCC UCCCGGGAGA GCCAUAGUGG UCUGCGGAACCGGUGAGUAC ACCGGAAUUG CCGGGAAGAC UGGGUCCUUU CUUGGAUAAA CCCACUCUAUGCCCGGCCAU UUGGGCGUGC CCCCGCAAGA CUGCUAGCCG AGUAGUGUUG GGUUGCG | SEQ ID NO: 8 |
| HUMAN ALBUMIN | AAUUAUUGGUUAAAGAAGUAUAUUAGUGCUAAUUUCCCUCCG UUUGUCCUAGCUUUUCUCUUCUGUCAACCCCACACGCCUUUGG CACA | SEQ ID NO: 9 |
| EMCV | CUCCCUCCCC CCCCCCUAAC GUUACUGGCC GAAGCCGCUU GGAAUAAGGC CGGUGUGCGU UUGUCUAUAU GUUAUUUUCC ACCAUAUUGC CGUCUUUUGG CAAUGUGAGG GCCCGGAAAC CUGGCCCUGU CUUCUUGACG AGCAUUCCUA GGGGUCUUUC CCCUCUCGCC AAAGGAAUGC AAGGUCUGUU GAAUGUCGUG AAGGAAGCAG UUCCUCUGGA AGCUUCUUGA AGACAAACAA CGUCUGUAGC GACCCUUUGC AGGCAGCGGA ACCCCCCACC UGGCGACAGG UGCCUCUGCG GCCAAAAGCC ACGUGUAUAA GAUACACCUG CAAAGGCGGC ACAACCCCAG UGCCACGUUG UGAGUUGGAU AGUUGUGGAA AGAGUCAAAU GGCUCUCCUC AAGCGUAUUC AACAAGGGGC UGAAGGAUGC CCAGAAGGUA CCCCAUUGUA UGGGAUCUGA UCUGGGGCCU CGGUGCACAU GCUUUACGUG UGUUUAGUCG AGGUUAAAAA ACGUCUAGGC CCCCCGAACC ACGGGGACGU GGUUUUCCUU UGAAAAACAC GAUGAUAAU | SEQ ID NO: 10 |
| AT1G67090 | CACAAAGAGUAAAGAAGAACA | SEQ ID NO: 125 |
| AT1G35720 | AACACUAAAAGUAGAAGAAAA | SEQ ID NO: 126 |
| AT5G45900 | CUCAGAAAGAUAAGAUCAGCC | SEQ ID NO: 127 |
| AT5G61250 | AACCAAUCGAAAGAAACCAAA | SEQ ID NO: 230 |
| AT5G46430 | CUCUAAUCACCAGGAGUAAAA | SEQ ID NO: 231 |
| AT5G47110 | GAGAGAGAUCUUAACAAAAAA | SEQ ID NO: 232 |
| AT1G03110 | UGUGUAACAACAACAACAACA | SEQ ID NO: 233 |
| AT3G12380 | CCGCAGUAGGAAGAGAAAGCC | SEQ ID NO: 234 |
| AT5G45910 | AAAAAAAAAGAAAUCAUAAA | SEQ ID NO: 235 |
| AT1G07260 | GAGAGAAGAAAGAAGAAGACG | SEQ ID NO: 236 |
| AT3G55500 | CAAUUAAAAAUACUUACCAAA | SEQ ID NO: 237 |
| AT3G46230 | GCAAACAGAGUAAGCGAAACG | SEQ ID NO: 238 |

TABLE 2-continued

| 5'UTR sequences | | |
|---|---|---|
| Name | Sequence | Seq ID No.: |
| AT2G36170 | GCGAAGAAGACGAACGCAAAG | SEQ ID NO: 239 |
| AT1G10660 | UUAGGACUGUAUUGACUGGCC | SEQ ID NO: 240 |
| AT4G14340 | AUCAUCGGAAUUCGGAAAAAG | SEQ ID NO: 241 |
| AT1G49310 | AAAACAAAAGUUAAAGCAGAC | SEQ ID NO: 242 |
| AT4G14360 | UUUAUCUCAAAUAAGAAGGCA | SEQ ID NO: 243 |
| AT1G28520 | GGUGGGGAGGUGAGAUUUCUU | SEQ ID NO: 244 |
| AT1G20160 | UGAUUAGGAAACUACAAAGCC | SEQ ID NO: 245 |
| AT5G37370 | CAUUUUUCAAUUUCAUAAAAC | SEQ ID NO: 246 |
| AT4G11320 | UUACUUUUAAGCCCAACAAAA | SEQ ID NO: 247 |
| AT5G40850 | GGCGUGUGUGUGUGUUGUUGA | SEQ ID NO: 248 |
| AT1G06150 | GUGGUGAAGGGGAAGGUUUAG | SEQ ID NO: 249 |
| AT2G26080 | UUGUUUUUUUUUGGUUUGGUU | SEQ ID NO: 250 |

Preferably the 5'UTR sequence comprises SEQ ID NO: 6 (AT1G58420).

Preferably, an mRNA described herein comprises a translation enhancer sequence. Translation enhancer sequences enhance the translation efficiency of a mRNA described herein and thereby provide increased production of the protein encoded by the mRNA. The translation enhancer region may be located in the 5' or 3' UTR of an mRNA sequence. Examples of translation enhancer regions include naturally-occurring enhancer regions from TEV 5'UTR and *Xenopus* beta-globin 3'UTR. Preferred 5' UTR enhancer sequences include but are not limited to those derived from mRNAs encoding human heat shock proteins (HSP) including HSP70-P2, HSP70-M1 HSP72-M2, HSP17.9 and HSP70-P1. Preferred translation enhancer sequences used in accordance with the embodiments of the present disclosure are represented by SEQ ID NOS 11-15 as shown in Table 3.

TABLE 3

| 5'UTR enhancers | | |
|---|---|---|
| Name | Sequence | Seq ID No.: |
| HSP70-P2 | GUCAGCUUUCAAACUCUUUGUUUCUUGUUUGUUGAUUGAGAAUA | SEQ ID NO: 11 |
| HSP70-M1 | CUCUCGCCUGAGAAAAAAAAUCCACGAACCAAUUUCUCAGCAACCAGCAGCACG | SEQ ID NO: 12 |
| HSP72-M2 | ACCUGUGAGGGUUCGAAGGAAGUAGCAGUGUUUUUUGUUCCUAGAGGAAGAG | SEQ ID NO: 13 |
| HSP17.9 | ACACAGAAACAUUCGCAAAAACAAAAUCCCAGUAUCAAAAUUCUUCUCUUUUUUUCAUAUUUCGCAAAGAC | SEQ ID NO: 14 |
| HSP70-P1 | CAGAAAAAUUUGCUACAUUGUUUCACAAACUUCAAAUAUUAUUCAUUUAUUU | SEQ ID NO: 15 |

Preferably, an mRNA described herein comprises a Kozak sequence. As is understood in the art, a Kozak sequence is a short consensus sequence centered around the translational initiation site of eukaryotic mRNAs that allows for efficient initiation of translation of the mRNA. The ribosomal translation machinery recognizes the AUG initiation codon in the context of the Kozak sequence. A Kozak sequence, may be inserted upstream of the coding sequence for OTC, downstream of a 5' UTR or inserted upstream of the coding sequence for OTC and downstream of a 5' UTR. Preferably, an mRNA described herein comprises a Kozak sequence having the amino acid sequence GCCACC (SEQ ID NO: 23). Preferably an mRNA described herein comprises a partial Kozak sequence "p" having the amino acid sequence GCCA (SEQ ID NO: 24).

Preferably an mRNA described herein comprises a 3'UTR. Preferably, the 3' UTR comprises a sequence selected from the 3' UTRs of alanine aminotransferase 1, human apolipoprotein E, human fibrinogen alpha chain, human haptoglobin, human antithrombin, human alpha globin, human beta globin, human complement C3, human growth factor, human hepcidin, MALAT-1, mouse beta globin, mouse albumin, and *Xenopus* beta globin, or fragments of any of the foregoing. Preferably, the 3' UTR is derived from *Xenopus* beta globin. Preferred 3' UTR sequences include SEQ ID NOS 16-22 as shown in Table 4.

TABLE 4

3'UTR sequences

| Name | Sequence | Seq ID No.: |
|---|---|---|
| XBG | CUAGUGACUGACUAGGAUCUGGUUACCACUAAACCAGCCU CAAGAACACCCGAAUGGAGUCUCUAAGCUACAUAAUACCAA CUUACACUUACAAAAUGUUGUCCCCCAAAAUGUAGCCAUUC GUAUCUGCUCCUAAUAAAAAGAAAGUUUCUUCACAU | SEQ ID NO: 16 |
| HUMAN HAPTOGLOBIN | UGCAAGGCUGGCCGGAAGCCCUUGCCUGAAAGCAAGAUUU CAGCCUGGAAGAGGGCAAAGUGGACGGGAGUGGACAGGAG UGGAUGCGAUAAGAUGUGGUUUGAAGCUGAUGGGUGCCA GCCCUGCAUUGCUGAGUCAAUCAAUAAAGAGCUUUCUUUU GACCCAU | SEQ ID NO: 17 |
| HUMAN APOLIPOPROTEIN E | ACGCCGAAGCCUGCAGCCAUGCGACCCCACGCCACCCCGUGC CUCCUGCCUCCGCGCAGCCUGCAGCGGGAGACCCUGUCCCC GCCCCAGCCGUCCUCCUGGGGUGGACCCUAGUUUAAUAAA GAUUCACCAAGUUUCACGCA | SEQ ID NO: 18 |
| HCV | UAGAGCGGCAAACCCUAGCUACACUCCAUAGCUAGUUUCU UUUUUUUUUGUUUUUUUUUUUUUUUUUUUUUUUUUUU UUUUUUUUUUUUCCUUUCUUUUCCUUCUUUUUUUCCUCU UUUCUUGGUGGCUCCAUCUUAGCCCUAGUCACGGCUAGCU GUGAAAGGUCCGUGAGCCGCAUGACUGCAGAGAGUGCCGU AACUGGUCUCUCUGCAGAUCAUGU | SEQ ID NO: 19 |
| MOUSE ALBUMIN | ACACAUCACAACCACAACCUUCUCAGGCUACCCUGAGAAAA AAAGACAUGAAGACUCAGGACUCAUCUUUUCUGUUGGUGU AAAAUCAACACCCUAAGGAACACAAAUUUCUUUAAACAUUU GACUUCUUGUCUCUGUGCUGCAAUUAAUAAAAAAUGGAAA GAAUCUAC | SEQ ID NO: 20 |
| HUMAN ALPHA GLOBIN | GCUGGAGCCUCGGUAGCCGUUCCUCCUGCCCGCUGGGCCU CCCAACGGGCCCUCCUCCCCUCCUUGCACCGGCCCUUCCUG GUCUUUGAAUAAAGUCUGAGUGGGCAGCA | SEQ ID NO: 21 |
| EMCV | UAGUGCAGUCAC UGGCACAACG CGUUGCCCGG UAAGCCAAUC GGGUAUACAC GGUCGUCAUACUGCAGACAG GGUUCUUCUA CUUUGCAAGA UAGUCUAGAG UAGUAAAAUA AAUAGUAUAAG | SEQ ID NO: 22 |

Preferably, an mRNA described herein comprises a 3' tail region, which can serve to protect the mRNA from exonuclease degradation. The tail region may be a 3'poly(A) and/or 3'poly(C) region. Preferably, the tail region is a 3' poly(A) tail. As used herein a "3' poly(A) tail" is a polymer of sequential adenine nucleotides that can range in size from, for example: 10 to 250 sequential adenine nucleotides; 60-125 sequential adenine nucleotides, 90-125 sequential adenine nucleotides, 95-125 sequential adenine nucleotides, 95-121 sequential adenine nucleotides, 100 to 121 sequential adenine nucleotides, 110-121 sequential adenine nucleotides; sequential adenine nucleotides, 112-121 sequential adenine nucleotides; 114-121 adenine sequential nucleotides; and 115 to 121 sequential adenine nucleotides. Preferably a 3' poly A tail as described herein comprise 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, or 125 sequential adenine nucleotides. 3' Poly(A) tails can be added using a variety of methods known in the art, e.g., using poly(A) polymerase to add tails to synthetic or in vitro transcribed RNA. Other methods include the use of a transcription vector to encode poly A tails or the use of a ligase (e.g., via splint ligation using a T4 RNA ligase and/or T4 DNA ligase), wherein poly(A) may be ligated to the 3' end of a sense RNA. Preferably, a combination of any of the above methods is utilized.

Preferably, an mRNA described herein comprises a 5' cap. 5'-ends capped with various groups and their analogues are known in the art. The 5' cap may be selected from m7GpppA, m7GpppC; unmethylated cap analogs (e.g., GpppG); dimethylated cap analog (e.g., m2,7GpppG), a trimethylated cap analog (e.g., m2,2,7GpppG), dimethylated symmetrical cap analogs (e.g., m7Gpppm7G), or anti reverse cap analogs (e.g., ARCA; m7, 2'OmeGpppG, m72'dGpppG, m7,3'OmeGpppG, m7,3'dGpppG and their tetraphosphate derivatives) (see, e.g., Jemielity, J. et al., RNA 9: 1108-1122 (2003). The 5' cap may be an ARCA cap (3'-OMe-m7G(5')pppG). The 5' cap may be an mCAP (m7G(5')ppp(5')G, $N^7$-Methyl-Guanosine-5'-Triphosphate-5'-Guanosine). The 5' cap may be resistant to hydrolysis. A preferred 5' cap is referred to herein as "m7GpppGm cap" also referred to herein as "Cap1" and has the following core structure:

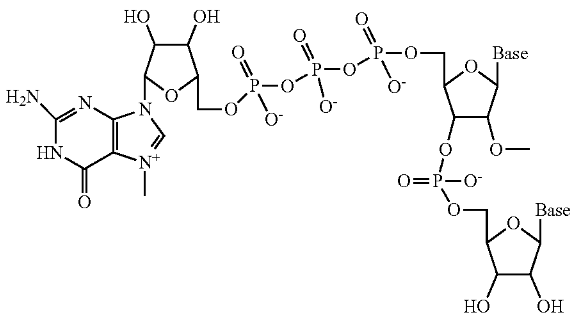

Preferably an mRNA described herein comprises one or more chemically modified nucleotides. Examples of nucleic acid monomers include non-natural, modified, and chemically-modified nucleotides, including any such nucleotides known in the art. mRNA sequences comprising chemically modified nucleotides have been shown to improve mRNA expression, expression rates, half-life and/or expressed protein concentrations. mRNA sequences comprising chemically modified nucleotides have also been useful to optimize protein localization thereby avoiding deleterious bio-responses such as the immune response and/or degradation pathways.

Examples of modified or chemically-modified nucleotides include 5-hydroxycytidines, 5-alkylcytidines, 5-hydroxyalkylcytidines, 5-carboxycytidines, 5-formylcytidines, 5-alkoxycytidines, 5-alkynylcytidines, 5-halocytidines, 2-thiocytidines, $N^4$-alkylcytidines, $N^4$-aminocytidines, $N^4$-acetylcytidines, and $N^4$,$N^4$-dialkylcytidines.

Examples of modified or chemically-modified nucleotides include 5-hydroxycytidine, 5-methylcytidine, 5-hydroxymethylcytidine, 5-carboxycytidine, 5-formylcytidine, 5-methoxycytidine, 5-propynylcytidine, 5-bromocytidine, 5-iodocytidine, 2-thiocytidine; $N^4$-methylcytidine, $N^4$-aminocytidine, $N^4$-acetylcytidine, and $N^4$,$N^4$-dimethylcytidine.

Examples of modified or chemically-modified nucleotides include 5-hydroxyuridines, 5-alkyluridines, 5-hydroxyalkyluridines, 5-carboxyuridines, 5-carboxyalkylesteruridines, 5-formyluridines, 5-alkoxyuridines, 5-alkynyluridines, 5-halouridines, 2-thiouridines, and 6-alkyluridines.

Examples of modified or chemically-modified nucleotides include 5-hydroxyuridine, 5-methyluridine, 5-hydroxymethyluridine, 5-carboxyuridine, 5-carboxymethylesteruridine, 5-formyluridine, 5-methoxyuridine (also referred to herein as "5MeOU"), 5-propynyluridine, 5-bromouridine, 5-fluorouridine, 5-iodouridine, 2-thiouridine, and 6-methyluridine.

Examples of modified or chemically-modified nucleotides include 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

Examples of modified or chemically-modified nucleotides include $N^6$-methyladenosine, 2-aminoadenosine, 3-methyladenosine, 8-azaadenosine, 7-deazaadenosine, 8-oxoadenosine, 8-bromoadenosine, 2-methylthio-$N^6$-methyladenosine, $N^6$-isopentenyladenosine, 2-methylthio-$N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, N6-threonylcarbamoyl-adenosine, $N^6$-methyl-$N^6$-threonylcarbamoyl-adenosine, 2-methylthio-$N^6$-threonylcarbamoyladenosine, $N^6$,$N^6$-dimethyladenosine, N6-hydroxynorvalylcarbamoyladenosine, 2-methylthio-$N^6$-hydroxynorvalylcarbamoyl-adenosine, $N^6$-acetyladenosine, 7-methyl-adenine, 2-methylthio-adenine, 2-methoxy-adenine, alpha-thio-adenosine, 2'-O-methyl-adenosine, $N^6$,2'-O-dimethyl-adenosine, $N^6$,$N^6$,2'-O-trimethyl-adenosine, 1,2'-O-dimethyl-adenosine, 2'-O-ribosyladenosine, 2-amino-$N^6$-methyl-purine, 1-thio-adenosine, 2'-F-ara-adenosine, 2'-F-adenosine, 2'-OH-ara-adenosine, and $N^6$-(19-amino-pentaoxanonadecyl)-adenosine.

Examples of modified or chemically-modified nucleotides include $N^1$-alkylguanosines, $N^2$-alkylguanosines, thienoguanosines, 7-deazaguanosines, 8-oxoguanosines, 8-bromoguanosines, $O^6$-alkylguanosines, xanthosines, inosines, and $N^1$-alkylinosines.

Examples of modified or chemically-modified nucleotides include $N^1$-methylguanosine, $N^2$-methylguanosine, thienoguanosine, 7-deazaguanosine, 8-oxoguanosine, 8-bromoguanosine, $O^6$-methylguanosine, xanthosine, inosine, and $N^1$-methylinosine.

Examples of modified or chemically-modified nucleotides include pseudouridines. Examples of pseudouridines include $N^1$-alkylpseudouridines, $N^1$-cycloalkylpseudouridines, $N^1$-hydroxypseudouridines, $N^1$-hydroxyalkylpseudouridines, $N^1$-phenylpseudouridines, phenylalkylpseudouridines, $N^1$-aminoalkylpseudouridines, $N^3$-alkylpseudouridines, $N^6$-alkylpseudouridines, $N^6$-alkoxypseudouridines, $N^6$-hydroxypseudouridines, $N^6$-hydroxyalkylpseudouridines, $N^6$-morpholinopseudouridines, $N^6$-phenylpseudouridines, and $N^6$-halopseudouridines. Examples of pseudouridines include $N^1$-alkyl-$N^6$-alkylpseudouridines, $N^1$-alkyl-$N^6$-alkoxypseudouridines, $N^1$-alkyl-$N^6$-hydroxypseudouridines, $N^1$-alkyl-$N^6$-hydroxyalkylpseudouridines, $N^1$-alkyl-$N^6$-morpholinopseudouridines, $N^6$-phenylpseudouridines, and $N^1$-alkyl-$N^6$-halopseudouridines. In these examples, the alkyl, cycloalkyl, and phenyl substituents may be unsubstituted, or further substituted with alkyl, halo, haloalkyl, amino, or nitro substituents.

Examples of pseudouridines include $N^1$-methylpseudouridine (also referred to herein as "N1MPU"), $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, and $N^1$-hydroxymethylpseudouridine.

Examples of nucleic acid monomers include modified and chemically-modified nucleotides, including any such nucleotides known in the art.

Examples of modified and chemically-modified nucleotide monomers include any such nucleotides known in the art, for example, 2'-O-methyl ribonucleotides, 2'-O-methyl purine nucleotides, 2'-deoxy-2'-fluoro ribonucleotides, 2'-deoxy-2'-fluoro pyrimidine nucleotides, 2'-deoxy ribonucleotides, 2'-deoxy purine nucleotides, universal base nucleotides, 5-C-methyl-nucleotides, and inverted deoxyabasic monomer residues.

Examples of modified and chemically-modified nucleotide monomers include 3'-end stabilized nucleotides, 3'-glyceryl nucleotides, 3'-inverted abasic nucleotides, and 3'-inverted thymidine.

Examples of modified and chemically-modified nucleotide monomers include locked nucleic acid nucleotides (LNA), 2'-0,4'-C-methylene-(D-ribofuranosyl) nucleotides, 2'-methoxyethoxy (MOE) nucleotides, 2'-methyl-thio-ethyl, 2'-deoxy-2'-fluoro nucleotides, and 2'-O-methyl nucleotides. In an exemplary embodiment, the modified monomer is a locked nucleic acid nucleotide (LNA).

Examples of modified and chemically-modified nucleotide monomers include 2',4'-constrained 2'-O-methoxyethyl (cMOE) and 2'-O-Ethyl (cEt) modified DNAs.

Examples of modified and chemically-modified nucleotide monomers include 2'-amino nucleotides, 2'-O-amino nucleotides, 2'-C-allyl nucleotides, and 2'-O-allyl nucleotides.

Examples of modified and chemically-modified nucleotide monomers include N6-methyladenosine nucleotides.

Examples of modified and chemically-modified nucleotide monomers include nucleotide monomers with modified bases 5-(3-amino)propyluridine, 5-(2-mercapto)ethyluridine, 5-bromouridine; 8-bromoguanosine, or 7-deazaadenosine.

Examples of modified and chemically-modified nucleotide monomers include 2'-O-aminopropyl substituted nucleotides.

Examples of modified and chemically-modified nucleotide monomers include replacing the 2'-OH group of a nucleotide with a 2'-R, a 2'-OR, a 2'-halogen, a 2'-SR, or a 2'-amino, where R can be H, alkyl, alkenyl, or alkynyl.

Example of base modifications described above can be combined with additional modifications of nucleoside or nucleotide structure, including sugar modifications and linkage modifications. Certain modified or chemically-modified nucleotide monomers may be found in nature.

Preferred nucleotide modifications include $N^1$-methylpseudouridine and 5-methoxyuridine.

The constructs for preferred mRNA sequences are provided in Table 5.

TABLE 5

Exemplary mRNA Constructs

| mRNA Construct No. | Cap | 5'UTR | Kozak* | OTC Protein Encoded | 3'UTR | 3' Poly A Tail | mRNA Construct SEQ ID NO: |
|---|---|---|---|---|---|---|---|
| 563 | Cap1 | TEV | Yes | SEQ ID NO: 3 | XBG | Yes | 26 |
| 564 | Cap1 | TEV | Yes | SEQ ID NO: 3 | XBG | Yes | 27 |
| 565 | Cap1 | TEV | Yes | SEQ ID NO: 3 | XBG | Yes | 28 |
| 566 | Cap1 | TEV | Yes | SEQ ID NO: 3 | XBG | Yes | 29 |
| 567 | Cap1 | TEV | Yes | SEQ ID NO: 3 | XBG | Yes | 30 |
| 568 | Cap1 | TEV | Yes | SEQ ID NO: 3 | XBG | Yes | 31 |
| 569 | Cap1 | TEV | Yes | SEQ ID NO: 3 | XBG | Yes | 32 |
| 570 | Cap1 | TEV | Yes | SEQ ID NO: 3 | XBG | Yes | 33 |
| 571 | Cap1 | TEV | Yes | SEQ ID NO: 3 | XBG | Yes | 34 |
| 572 | Cap1 | TEV | Yes | SEQ ID NO: 3 | XBG | Yes | 35 |
| 573 | Cap1 | TEV | Yes | SEQ ID NO: 3 | XBG | Yes | 36 |
| 574 | Cap1 | TEV | Yes | SEQ ID NO: 3 | XBG | Yes | 37 |
| 575 | Cap1 | TEV | P | SEQ ID NO: 3 | XBG | Yes | 38 |
| 708 | Cap1 | TEV | P | SEQ ID NO: 3 | XBG | Yes | 39 |
| 709 | Cap1 | TEV | P | SEQ ID NO: 3 | XBG | Yes | 40 |
| 710 | Cap1 | TEV | P | SEQ ID NO: 3 | XBG | Yes | 41 |
| 711 | Cap1 | TEV | P | SEQ ID NO: 3 | XBG | Yes | 42 |
| 712 | Cap1 | TEV | Yes | SEQ ID NO: 3 | XBG | Yes | 43 |
| 713 | Cap1 | TEV | Yes | SEQ ID NO: 3 | XBG | Yes | 44 |
| 714 | Cap1 | TEV | Yes | SEQ ID NO: 3 | XBG | Yes | 45 |
| 715 | Cap1 | TEV | Yes | SEQ ID NO: 3 | XBG | Yes | 46 |
| 716 | Cap1 | TEV | Yes | SEQ ID NO: 3 | XBG | Yes | 47 |
| 717 | Cap1 | TEV | Yes | SEQ ID NO: 3 | XBG | Yes | 48 |
| 718 | Cap1 | TEV | Yes | SEQ ID NO: 3 | XBG | Yes | 49 |
| 719 | Cap1 | TEV | Yes | SEQ ID NO: 3 | XBG | Yes | 50 |
| 720 | Cap1 | TEV | Yes | SEQ ID NO: 3 | XBG | Yes | 51 |
| 721 | Cap1 | TEV | Yes | SEQ ID NO: 3 | XBG | Yes | 52 |
| 722 | Cap1 | TEV | Yes | SEQ ID NO: 3 | XBG | Yes | 53 |
| 723 | Cap1 | TEV | Yes | SEQ ID NO: 3 | XBG | Yes | 54 |
| 724 | Cap1 | TEV | Yes | SEQ ID NO: 3 | XBG | Yes | 55 |
| 725 | Cap1 | TEV | Yes | SEQ ID NO: 3 | XBG | Yes | 56 |
| 726 | Cap1 | TEV | Yes | SEQ ID NO: 3 | XBG | Yes | 57 |
| 727 | Cap1 | TEV | Yes | SEQ ID NO: 3 | XBG | Yes | 58 |
| 728 | Cap1 | TEV | Yes | SEQ ID NO: 3 | XBG | Yes | 59 |
| 729 | Cap1 | TEV | Yes | SEQ ID NO: 3 | XBG | Yes | 60 |
| 1787 | Cap1 | ARC5-2 | No | SEQ ID NO: 3 | Hu haptoglob | Yes | 61 |
| 1788 | Cap1 | AT1G58420 | P | SEQ ID NO: 3 | Hu ApoE | Yes | 62 |
| 1789 | Cap1 | ARC5-2 | No | SEQ ID NO: 3 | Hu haptoglob | Yes | 63 |
| 1790 | Cap1 | AT1G58420 | P | SEQ ID NO: 3 | Hu ApoE | Yes | 64 |
| 1791 | Cap1 | ARC5-2 | No | SEQ ID NO: 3 | Hu haptoglob | Yes | 65 |
| 1792 | Cap1 | HCV5' | P | SEQ ID NO: 3 | HCV3' | Yes | 66 |
| 1793 | Cap1 | AT1G58420 | P | SEQ ID NO: 3 | Hu a-glob | Yes | 67 |
| 1794 | Cap1 | AT1G58420 | P | SEQ ID NO: 3 | Hu a-glob | Yes | 68 |
| 1795 | Cap1 | AT1G58420 | P | SEQ ID NO: 3 | Hu a-glob | Yes | 69 |
| 1796 | Cap1 | Hu alb | No | SEQ ID NO: 3 | Ms Alb | Yes | 70 |
| 1797 | Cap1 | Hu alb | No | SEQ ID NO: 3 | Ms Alb | Yes | 71 |
| 1798 | Cap1 | Hu alb | No | SEQ ID NO: 3 | Ms Alb | Yes | 72 |

TABLE 5-continued

Exemplary mRNA Constructs

| mRNA Construct No. | Cap | 5'UTR | Kozak* | OTC Protein Encoded | 3'UTR | 3' Poly A Tail | mRNA Construct SEQ ID NO: |
|---|---|---|---|---|---|---|---|
| 1799 | Cap1 | AT1G58420 | Yes | SEQ ID NO: 3 | Hu a-glob | Yes | 73 |
| 1800 | Cap1 | Hu alb | No | SEQ ID NO: 3 | Ms Alb | Yes | 74 |
| 1801 | Cap1 | AT1G58420 | P | SEQ ID NO: 3 | Hu ApoE | Yes | 75 |
| 1802 | Cap1 | ARC5-2 | No | SEQ ID NO: 3 | Hu haptoglob | Yes | 76 |
| 1803 | Cap1 | TEV | Yes | SEQ ID NO: 3 | XBG | Yes | 77 |
| 1804 | Cap1 | TEV | Yes | SEQ ID NO: 3 | XBG | Yes | 78 |
| 1805 | Cap1 | TEV | Yes | SEQ ID NO: 3 | XBG | Yes | 79 |
| 1806 | Cap1 | TEV | Yes | SEQ ID NO: 3 | XBG | Yes | 80 |
| 1808 | Cap1 | TEV | Yes | SEQ ID NO: 3 | XBG | Yes | 81 |
| 1809 | Cap1 | TEV | Yes | SEQ ID NO: 3 | XBG | Yes | 82 |
| 1816 | Cap1 | TEV | P | SEQ ID NO: 3 | XBG | Yes | 83 |
| 1822 | Cap1 | TEV | Yes | SEQ ID NO: 3 | XBG | Yes | 84 |
| 1823 | Cap1 | TEV | Yes | SEQ ID NO: 3 | XBG | Yes | 85 |
| 1840 | Cap1 | EMCV | No | SEQ ID NO: 3 | EMCV | Yes | 86 |
| 1841 | Cap1 | EMCV | No | SEQ ID NO: 3 | EMCV | Yes | 87 |
| 1842 | Cap1 | EMCV | No | SEQ ID NO: 3 | EMCV | Yes | 88 |
| 1843 | Cap1 | HSP70-P2-TEV | Yes | SEQ ID NO: 3 | XBG | Yes | 89 |
| 1844 | Cap1 | HSP70-M1-TEV | Yes | SEQ ID NO: 3 | XBG | Yes | 90 |
| 1845 | Cap1 | HSP70-M2-TEV | Yes | SEQ ID NO: 3 | XBG | Yes | 91 |
| 1846 | Cap1 | HSP17.9-TEV | Yes | SEQ ID NO: 3 | XBG | Yes | 92 |
| 1847 | Cap1 | HSP70-P1-TEV | Yes | SEQ ID NO: 3 | XBG | Yes | 93 |
| 1882 | Cap1 | TEV | Yes | SEQ ID NO: 3 | XBG | Yes | 94 |
| 1883 | Cap1 | TEV | Yes | SEQ ID NO: 3 | XBG | Yes | 95 |
| 1884 | Cap1 | TEV | Yes | SEQ ID NO: 3 | XBG | Yes | 96 |
| 1885 | Cap1 | TEV | Yes | SEQ ID NO: 3 | XBG | Yes | 97 |
| 1886 | Cap1 | TEV | Yes | SEQ ID NO: 3 | XBG | Yes | 98 |
| 1887 | Cap1 | TEV | Yes | SEQ ID NO: 3 | XBG | Yes | 99 |
| 1888 | Cap1 | TEV | Yes | SEQ ID NO: 3 | XBG | Yes | 100 |
| 1889 | Cap1 | TEV | Yes | SEQ ID NO: 3 | XBG | Yes | 101 |
| 1890 | Cap1 | TEV | Yes | SEQ ID NO: 3 | XBG | Yes | 102 |
| 1891 | Cap1 | TEV | Yes | SEQ ID NO: 3 | XBG | Yes | 103 |
| 1898 | Cap1 | TEV | Yes | SEQ ID NO: 3 | XBG | Yes | 104 |
| 1899 | Cap1 | TEV | Yes | SEQ ID NO: 3 | XBG | Yes | 105 |
| 1900 | Cap1 | TEV | Yes | SEQ ID NO: 3 | XBG | Yes | 106 |
| 1903 | Cap1 | TEV | P | SEQ ID NO: 3 | XBG | Yes | 107 |
| 1904 | Cap1 | TEV | P | SEQ ID NO: 3 | XBG | Yes | 108 |
| 1905 | Cap1 | TEV | P | SEQ ID NO: 3 | XBG | Yes | 109 |
| 1906 | Cap1 | TEV | P | SEQ ID NO: 3 | XBG | Yes | 110 |
| 1907 | Cap1 | TEV | P | SEQ ID NO: 3 | XBG | Yes | 111 |
| 1908 | Cap1 | TEV | P | SEQ ID NO: 3 | XBG | Yes | 112 |
| 1915 | Cap1 | HSP70-P1-AT1G58420 | Yes | SEQ ID NO: 3 | Hu a-glob | Yes | 113 |
| 1916 | Cap1 | HSP70-P1-AT1G58420 | Yes | SEQ ID NO: 3 | Hu a-glob | Yes | 114 |
| 1917 | Cap1 | HSP70-P1-AT1G58420 | Yes | SEQ ID NO: 3 | Hu a-glob | Yes | 115 |
| 1918 | Cap1 | HSP70-P1-AT1G58420 | Yes | SEQ ID NO: 3 | Hu a-glob | Yes | 116 |
| 1919 | Cap1 | AT1G58420 | Yes | SEQ ID NO: 3 | Hu a-glob | Yes | 117 |
| 1920 | Cap1 | AT1G58420 | Yes | SEQ ID NO: 3 | Hu a-glob | Yes | 118 |
| 1921 | Cap1 | AT1G58420 | Yes | SEQ ID NO: 4** | Hu a-glob | Yes | 119 |
| 1925 | Cap1 | TEV | Yes | SEQ ID NO: 3 | XBG | Yes | 120 |
| 1926 | Cap1 | AT1G58420 | Yes | SEQ ID NO: 3 | Hu a-glob | Yes | 121 |
| 1927 | Cap1 | AT1G58420 | Yes | SEQ ID NO: 3 | Hu a-glob | Yes | 122 |
| 1928 | Cap1 | AT1G58420 | Yes | SEQ ID NO: 3 | Hu a-glob | Yes | 123 |
| 1929 | Cap1 | HSP70-P1-AT1G58420 | Yes | SEQ ID NO: 3 | Hu a-glob | Yes | 124 |
| 2016 | Cap1 | AT1G58420 | Yes | SEQ ID NO: 3 | Hu a-glob | Yes | 253 |
| 2260 | Cap1 | AT1G58420 | Yes | SEQ ID NO: 4** | Hu a-glob | Yes | 251 |
| 2262 | Cap1 | AT1G58420 | Yes | SEQ IS NO: 4** | Hu a-glob | Yes | 252 |

*Kozak sequence defined as GCCACC (SEQ ID NO: 23). Partial (P) Kozak defined as GCCA (SEQ ID NO: 24).
**Construct encodes modified human OTC protein of SEQ ID NO: 4.

Preferred mRNA sequences include all of the mRNA sequences listed in Table 5. Preferred mRNA sequences include all of the mRNA sequences listed wherein, 0% to 100%, preferably 1% to 100%, preferably 25% to 100%, preferably 50% to 100% and preferably 75% to 100% of the uracil nucleotides of the mRNA sequences are modified. Preferably, 1% to 100% of the uracil nucleotides are $N^1$-methylpseudouridine or 5-methoxyuridine. Preferably 100% of the uracil nucleotides are $N^1$-methylpseudouridine. Preferably 100% of the uracil nucleotides are 5-methoxyuridine.

Preferred mRNA sequences comprise a 5' cap, a 5'UTR that is derived from a gene expressed by *Arabidopsis thaliana*, an optional translation enhancer sequence, an optional Kozak sequence or partial Kozak sequence, a codon optimized coding sequence (CDS/ORF) coding for an OTC protein, a 3' UTR and a poly A tail. Preferably the codon optimized CDS encodes a protein of SEQ ID NO: 3 or SEQ ID NO: 4. Preferably, the 5' UTR that is derived from a gene expressed by *Arabidopsis thaliana* is selected from found in Table 5. Preferably, the 5' UTR that is derived from a gene expressed by *Arabidopsis thaliana* is selected from the group consisting of: SEQ ID NO: 6, SEQ ID NOS: 125-127 and SEQ ID NOS: 230-250. Preferably the 5' UTR sequence is AT1G58420 having the sequence of SEQ ID NO: 6. Preferably, the uracil content of the codon optimized sequence has been reduced with respect to the percentages of uracil content of SEQ ID NO: 1. Preferably, 0% to 100% of the uracil nucleotides of the mRNA sequences are modified. Preferably, 0% to 100% of the uracil nucleotides are $N^1$-methylpseudouridine or 5-methoxyuridine. Preferably 100% of the uracil nucleotides are $N^1$-methylpseudouridine. Preferably 100% of the uracil nucleotides are 5-methoxyuridine.

Preferred mRNA constructs comprise codon optimized coding sequences and a 5' UTR from a gene expressed by *Arabidopsis thaliana* and are selected from: SEQ ID NOS: 62, 67, 68, 69, 73, 113-119, 121-127.

A preferred mRNA construct of the disclosure comprises mRNA construct 1921 (SEQ ID NO: 119) having an optimized ORF encoding the modified human OTC protein of SEQ ID NO: 4 and comprising a 3' Poly A tail of 121 nucleotides. Another preferred mRNA construct comprises construct 2260 (SEQ ID NO: 251) encoding the modified human OTC protein of SEQ ID NO: 4 and comprising a 3' Poly A tail of 100 nucleotides. Another preferred mRNA construct comprises construct 2262 (SEQ ID NO: 252) encoding the modified human OTC protein of SEQ ID NO: 4 and comprising a 3' Poly A tail of 100 nucleotides.

A preferred mRNA sequence of the disclosure includes the mRNA construct 1799 (SEQ ID NO: 73) having a codon optimized ORF encoding wild type human OTC of SEQ ID NO: 3 and having a 3' Poly A tail of 121 nucleotides. Another preferred mRNA construct of the disclosure includes the mRNA construct 2016 (SEQ ID NO: 253) having a codon optimized ORF encoding wild type human OTC of SEQ ID NO: 3 and comprising a 3' Poly A tail of 100 nucleotides.

Preferably 100% of the uridine nucleotides of mRNA constructs 1799, 2016, 1921, 2260 and 2262, are N1-methylpseudouridine. Preferably 100% of the uracil nucleotides of mRNA constructs 1799, 2016, 1921, 2260 and 2262, are 5-methoxyuridine.

The mRNA for use in accordance with this disclosure can exhibit increased translation efficiency. As used herein, translation efficiency refers to a measure of the production of a protein or polypeptide by translation of an mRNA in accordance with the disclosure. Preferably, an mRNA of the disclosure can exhibit at least 2-fold, 3-fold, 5-fold, or 10-fold increased translation efficiency in vivo as compared to mRNA encoding SEQ ID NO: 3 or SEQ ID NO: 4 that is not codon optimized in accordance with the disclosure and/or that does not comprise the preferred UTRs of the disclosure. Preferably an mRNA of the disclosure can provide at least a 2-fold, 3-fold, 5-fold, or 10-fold increased polypeptide or protein level in vivo as compared to mRNA encoding SEQ ID NO: 3 or SEQ ID NO: 4 that is not codon optimized and/or does not comprise the preferred UTRs of the disclosure. Preferably, an mRNA of the disclosure can provide increased levels of a polypeptide or protein in vivo as compared to mRNA encoding SEQ ID NO: 3 or SEQ ID NO: 4 that is not codon optimized in accordance with the disclosure and/or that does not comprise the preferred UTRs of the disclosure. For example, the level of a polypeptide or protein can be increased by 10%, or 20%, or 30%, or 40%, or 50%, or more.

Preferably the mRNA of the disclosure can provide increased functional half-life in the cytoplasm of mammalian cells over mRNA encoding SEQ ID NO: 3 or SEQ ID NO: 4 that is not codon optimized in accordance with the disclosure and/or that does not comprise the preferred UTRs of the disclosure. The inventive translatable molecules can have increased half-life of activity as compared to mRNA encoding SEQ ID NO: 3 or SEQ ID NO: 4 that is not codon optimized in accordance with the disclosure and/or that does not comprise the preferred UTRs of the disclosure.

Preferably, the mRNA of the disclosure can reduce cellular innate immune response as compared to mRNA encoding SEQ ID NO: 3 or SEQ ID NO: 4 that is not codon optimized in accordance with the disclosure and/or that does not comprise the preferred UTRs of the disclosure.

Preferably, the mRNA of the disclosure can reduce the dose levels required for efficacious therapy as compared to mRNA encoding SEQ ID NO: 3 or SEQ ID NO: 4 that is not codon optimized in accordance with the disclosure and/or that does not comprise the preferred UTRs of the disclosure.

Design and Synthesis of the mRNA Sequences mRNA for use in accordance with the disclosure may be prepared according to any available technique including, but not limited to chemical synthesis, in vitro transcription (IVT) or enzymatic or chemical cleavage of a longer precursor, etc. Methods of synthesizing RNAs are known in the art.

In some embodiments, mRNA is produced from a primary complementary DNA (cDNA) construct. The process of design and synthesis of the primary cDNA constructs described herein generally includes the steps of gene construction, mRNA production (either with or without modifications) and purification. In the IVT method, a target polynucleotide sequence encoding an OTC protein is first selected for incorporation into a vector which will be amplified to produce a cDNA template. Optionally, the target polynucleotide sequence and/or any flanking sequences may be codon optimized. The cDNA template is then used to produce mRNA through in vitro transcription (IVT). After production, the mRNA may undergo purification and clean-up processes. The steps of which are provided in more detail below.

The step of gene construction may include, but is not limited to gene synthesis, vector amplification, plasmid purification, plasmid linearization and clean-up, and cDNA template synthesis and clean-up. Once a human OTC protein (e.g. SEQ ID NO: 3 or SEQ ID NO: 4) is selected for production, a primary construct is designed. Within the primary construct, a first region of linked nucleosides encoding the polypeptide of interest may be constructed using an open reading frame (ORF) of a selected nucleic acid (DNA or RNA) transcript. The ORF may comprise the wild type ORF, an isoform, variant or a fragment thereof. As used herein, an "open reading frame" or "ORF" is meant to refer to a nucleic acid sequence (DNA or RNA) which is capable of encoding a polypeptide of interest. ORFs often begin with the start codon, ATG and end with a nonsense or termination codon or signal.

Further, nucleotide sequence of any region of the mRNA or DNA template may be codon optimized. Codon optimization methods are known in the art and may be useful in efforts to achieve one or more of several goals. These goals include to match codon frequencies in target and host organisms to ensure proper folding, to bias GC content to increase mRNA stability or reduce secondary structures, to minimize tandem repeat codons or base runs that may impair gene construction or expression, to customize transcriptional and translational control regions, to insert or remove protein trafficking sequences, to remove/add post translation modification sites in encoded protein (e.g. glycosylation sites), to add, remove or shuffle protein domains, to insert or delete restriction sites, to modify ribosome binding sites and mRNA degradation sites, to adjust translational rates to allow the various domains of the protein to fold properly, or to reduce or eliminate problematic secondary structures within the mRNA. Suitable codon optimization tools, algorithms and services are known in the art.

Preferably, the primary cDNA template may include reducing the occurrence or frequency of appearance of certain nucleotides in the template strand. For example, the occurrence of a nucleotide in a template may be reduced to a level below 25% of nucleotides in the template. In further examples, the occurrence of a nucleotide in a template may be reduced to a level below 20% of nucleotides in the template. In some examples, the occurrence of a nucleotide in a template may be reduced to a level below 16% of nucleotides in the template. Preferably, the occurrence of a nucleotide in a template may be reduced to a level below 15%, and preferably may be reduced to a level below 12% of nucleotides in the template.

For example, the present disclosure provides nucleic acids wherein with altered uracil content at least one codon in the wild-type sequence has been replaced with an alternative codon to generate a uracil-altered sequence. Altered uracil sequences can have at least one of the following properties:

(i) an increase or decrease in global uracil content (i.e., the percentage of uracil of the total nucleotide content in the nucleic acid of a section of the nucleic acid, e.g., the open reading frame); or, (ii) an increase or decrease in local uracil content (i.e., changes in uracil content are limited to specific subsequences); or, (iii) a change in uracil distribution without a change in the global uracil content; or, (iv) a change in uracil clustering (e.g., number of clusters, location of clusters, or distance between clusters); or, (v) combinations thereof.

Preferably, the percentage of uracil nucleobases in the nucleic acid sequence is reduced with respect to the percentage of uracil nucleobases in the wild-type nucleic acid sequence. For example, 30% of nucleobases may be uracil in the wild-type sequence but the nucleobases that are uracil are preferably lower than 15%, preferably lower than 12% and preferably lower than 10% of the nucleobases in the in the nucleic acid sequences of the disclosure. The percentage uracil content can be determined by dividing the number of uracil in a sequence by the total number of nucleotides and multiplying by 100.

Preferably, the percentage of uracil nucleobases in a subsequence of the nucleic acid sequence is reduced with respect to the percentage of uracil nucleobases in the corresponding subsequence of the wild-type sequence. For example, the wild-type sequence may have a 5'-end region (e.g., 30 codons) with a local uracil content of 30%, and the uracil content in that same region could be reduced to preferably 15% or lower, preferably 12% or lower and preferably 10% or lower in the nucleic acid sequences of the disclosure.

Preferably, codons in the nucleic acid sequence of the invention reduce or modify, for example, the number, size, location, or distribution of uracil clusters that could have deleterious effects on protein translation. Although lower uracil content is desirable, in certain aspects, the uracil content, and in particular the local uracil content, of some subsequences of the wild-type sequence can be greater than the wild-type sequence and still maintain beneficial features (e.g., increased expression).

Preferably, the uracil-modified sequence induces a lower Toll-Like Receptor (TLR) response when compared to the wild-type sequence. Several TLRs recognize and respond to nucleic acids. Double-stranded (ds)RNA, a frequent viral constituent, has been shown to activate TLR3. Single-stranded (ss)RNA activates TLR7. RNA oligonucleotides, for example RNA with phosphorothioate internucleotide linkages, are ligands of human TLR8. DNA containing unmethylated CpG motifs, characteristic of bacterial and viral DNA, activate TLR9.

As used herein, the term "TLR response" is defined as the recognition of single-stranded RNA by a TLR7 receptor, and preferably encompasses the degradation of the RNA and/or physiological responses caused by the recognition of the single-stranded RNA by the receptor. Methods to determine and quantify the binding of an RNA to a TLR7 are known in the art. Similarly, methods to determine whether an RNA has triggered a TLR7-mediated physiological response (e.g., cytokine secretion) are well known in the art. Preferably, a TLR response can be mediated by TLR3, TLR8, or TLR9 instead of TLR7. Suppression of TLR7-mediated response can be accomplished via nucleoside modification. RNA undergoes over a hundred different nucleoside modifications in nature. Human rRNA, for example, has ten times more pseudouracil ('P) and 25 times more 2'-O-methylated nucleosides than bacterial rRNA. Bacterial mRNA contains no nucleoside modifications, whereas mammalian mRNAs have modified nucleosides such as 5-methylcytidine (m5C), N6-methyladenosine (m6A), inosine and many 2'-O-methylated nucleosides in addition to N7-methylguanosine (m7G).

Preferably, the uracil content of polynucleotides disclosed herein and preferably polynucleotides encoding the modified OTC protein of SEQ ID NO: 4 is less than 50%, 49%, 48%, 47%, 46%, 45%, 44%, 43%, 42%, 41%, 40%, 39%, 38%, 37%, 36%, 35%, 34%, 33%, 32%, 31%, 30%, 29%, 28%, 27%, 26%, 25%, 24%, 23%, 22%, 21%, 20%, 19%, 18%, 17%, 16%, 15%, 14%, 13%, 12%, 11%, 10%, 90%, 80%, 70%, 60%, 5%, 4%, 3%, 2% or 1% of the total nucleobases in the sequence in the reference sequence. Preferably, the uracil content of polynucleotides disclosed herein and preferably polynucleotides encoding the modified OTC protein of SEQ ID NO: 4, is between about 5% and about 25%. Preferably, the uracil content of polynucleotides disclosed herein and preferably polynucleotides encoding the modified OTC protein of SEQ ID NO: 4 is about 15% and about 25%.

The cDNA templates may be transcribed to produce an mRNA sequence described herein using an in vitro transcription (IVT) system. The system typically comprises a transcription buffer, nucleotide triphosphates (NTPs), an RNase inhibitor and a polymerase. The NTPs may be selected from, but are not limited to, those described herein including natural and unnatural (modified) NTPs. The polymerase may be selected from, but is not limited to, T7 RNA polymerase, T3 RNA polymerase and mutant polymerases such as, but not limited to, polymerases able to incorporate modified nucleic acids.

The primary cDNA template or transcribed mRNA sequence may also undergo capping and/or tailing reactions. A capping reaction may be performed by methods known in the art to add a 5' cap to the 5' end of the primary construct. Methods for capping include, but are not limited to, using a Vaccinia Capping enzyme (New England Biolabs, Ipswich, Mass.) or CLEANCAP® technology (TriLink Biotechnologies). A poly-A tailing reaction may be performed by methods known in the art, such as, but not limited to, 2' O-methyltransferase and by methods as described herein. If the primary construct generated from cDNA does not include a poly-T, it may be beneficial to perform the poly-A-tailing reaction before the primary construct is cleaned.

Codon optimized cDNA constructs encoding an ornithine transcarbamylase (OTC) protein are particularly suitable for generating mRNA sequences described herein. For example, such cDNA constructs may be used as the basis to transcribe, in vitro, a polyribonucleotide encoding an ornithine transcarbamylase (OTC) protein. Table 6 provides a listing of exemplary cDNA ORF templates used for in vitro transcription of the mRNA sequences listed in Table 5.

TABLE 6

Exemplary cDNA Templates

| DNA Construct No***: | SEQ ID NO: | Protein encoded by cDNA template SEQ ID NO: |
|---|---|---|
| p563 | 128 | SEQ ID NO: 3* |
| p564 | 129 | SEQ ID NO: 3* |
| p565 | 130 | SEQ ID NO: 3* |
| p566 | 131 | SEQ ID NO: 3* |
| p567 | 132 | SEQ ID NO: 3* |
| p568 | 133 | SEQ ID NO: 3* |
| p569 | 134 | SEQ ID NO: 3* |
| p570 | 135 | SEQ ID NO: 3* |
| p571 | 136 | SEQ ID NO: 3* |
| p572 | 137 | SEQ ID NO: 3* |
| p573 | 138 | SEQ ID NO: 3* |
| p574 | 139 | SEQ ID NO: 3* |
| p575 | 140 | SEQ ID NO: 3* |
| p708 | 141 | SEQ ID NO: 3* |
| p709 | 142 | SEQ ID NO: 3* |
| p710 | 143 | SEQ ID NO: 3* |
| p711 | 144 | SEQ ID NO: 3* |
| p712 | 145 | SEQ ID NO: 3* |
| p713 | 146 | SEQ ID NO: 3* |
| p714 | 147 | SEQ ID NO: 3* |
| p715 | 148 | SEQ ID NO: 3* |
| p716 | 149 | SEQ ID NO: 3* |
| p717 | 150 | SEQ ID NO: 3* |
| p718 | 151 | SEQ ID NO: 3* |
| p719 | 152 | SEQ ID NO: 3* |
| p720 | 153 | SEQ ID NO: 3* |
| p721 | 154 | SEQ ID NO: 3* |
| p722 | 155 | SEQ ID NO: 3* |
| p723 | 156 | SEQ ID NO: 3* |
| p724 | 157 | SEQ ID NO: 3* |
| p725 | 158 | SEQ ID NO: 3* |
| p726 | 159 | SEQ ID NO: 3* |
| p727 | 160 | SEQ ID NO: 3* |
| p728 | 161 | SEQ ID NO: 3* |
| p729 | 162 | SEQ ID NO: 3* |
| p1787 | 163 | SEQ ID NO: 3* |
| p1788 | 164 | SEQ ID NO: 3* |
| p1789 | 165 | SEQ ID NO: 3* |
| p1790 | 166 | SEQ ID NO: 3* |
| p1791 | 167 | SEQ ID NO: 3* |
| p1792 | 168 | SEQ ID NO: 3* |
| p1793 | 169 | SEQ ID NO: 3* |
| p1794 | 170 | SEQ ID NO: 3* |
| p1795 | 171 | SEQ ID NO: 3* |
| p1796 | 172 | SEQ ID NO: 3* |
| p1797 | 173 | SEQ ID NO: 3* |
| p1798 | 174 | SEQ ID NO: 3* |
| p1799 | 175 | SEQ ID NO: 3* |
| p1800 | 176 | SEQ ID NO: 3* |
| p1801 | 177 | SEQ ID NO: 3* |
| p1802 | 178 | SEQ ID NO: 3* |
| p1803 | 179 | SEQ ID NO: 3* |
| p1804 | 180 | SEQ ID NO: 3* |
| p1805 | 181 | SEQ ID NO: 3* |
| p1806 | 182 | SEQ ID NO: 3* |
| p1808 | 183 | SEQ ID NO: 3* |
| p1809 | 184 | SEQ ID NO: 3* |
| p1816 | 185 | SEQ ID NO: 3* |
| p1822 | 186 | SEQ ID NO: 3* |
| p1823 | 187 | SEQ ID NO: 3* |
| p1840 | 188 | SEQ ID NO: 3* |
| p1841 | 189 | SEQ ID NO: 3* |
| p1842 | 190 | SEQ ID NO: 3* |
| p1843 | 191 | SEQ ID NO: 3* |
| p1844 | 192 | SEQ ID NO: 3* |
| p1845 | 193 | SEQ ID NO: 3* |
| p1846 | 194 | SEQ ID NO: 3* |
| p1847 | 195 | SEQ ID NO: 3* |
| p1882 | 196 | SEQ ID NO: 3* |
| p1883 | 197 | SEQ ID NO: 3* |
| p1884 | 198 | SEQ ID NO: 3* |
| p1885 | 199 | SEQ ID NO: 3* |
| p1886 | 200 | SEQ ID NO: 3* |
| p1887 | 201 | SEQ ID NO: 3* |
| p1888 | 202 | SEQ ID NO: 3* |
| p1889 | 203 | SEQ ID NO: 3* |
| p1890 | 204 | SEQ ID NO: 3* |
| p1891 | 205 | SEQ ID NO: 3* |
| p1898 | 206 | SEQ ID NO: 3* |
| p1899 | 207 | SEQ ID NO: 3* |
| p1900 | 208 | SEQ ID NO: 3* |
| p1903 | 209 | SEQ ID NO: 3* |
| p1904 | 210 | SEQ ID NO: 3* |
| p1905 | 211 | SEQ ID NO: 3* |
| p1906 | 212 | SEQ ID NO: 3* |
| p1907 | 213 | SEQ ID NO: 3* |
| p1908 | 214 | SEQ ID NO: 3* |
| p1915 | 215 | SEQ ID NO: 3* |
| p1916 | 216 | SEQ ID NO: 3* |
| p1917 | 217 | SEQ ID NO: 3* |
| p1918 | 218 | SEQ ID NO: 3* |
| p1919 | 219 | SEQ ID NO: 3* |
| p1920 | 220 | SEQ ID NO: 3* |
| p1921 | 221 | SEQ ID NO: 4** |
| p1925 | 222 | SEQ ID NO: 3* |
| p1926 | 223 | SEQ ID NO: 3* |
| p1927 | 224 | SEQ ID NO: 3* |
| p1928 | 225 | SEQ ID NO: 3* |
| p1929 | 226 | SEQ ID NO: 3* |
| p2016 | 175 | SEQ ID NO: 3* |
| p2260 | 221 | SEQ ID NO: 4** |
| p2262 | 221 | SEQ ID NO: 4** |

*SEQ ID NO: 3 is the amino acid sequence for wild type human OTC.
**SEQ ID NO: 4 is the amino acid sequence for modified human OTC.
***The entire plasmid sequence is not included.

Preferred cDNA template sequences include the DNA sequence of SEQ ID NO: 175 (p1779) having an optimized coding sequence encoding wild type human OTC of SEQ ID NO: 3. Preferred cDNA template sequences also include cDNA sequence of SEQ ID NO: 221 (p1921), having an optimized coding sequence encoding a modified OTC protein of SEQ ID NO: 4.

The present disclosure also provides polynucleotides (e.g. DNA, RNA, cDNA, mRNA) encoding a human OTC protein that may be operably linked to one or more regulatory nucleotide sequences in an expression construct, such as a vector or plasmid. In certain embodiments, such constructs are DNA constructs. Regulatory nucleotide sequences will generally be appropriate for a host cell used for expression. Numerous types of appropriate expression vectors and suitable regulatory sequences are known in the art for a variety of host cells.

Typically, said one or more regulatory nucleotide sequences may include, but are not limited to, promoter sequences, leader or signal sequences, ribosomal binding sites, transcriptional start and termination sequences, translational start and termination sequences, and enhancer or activator sequences. Constitutive or inducible promoters as known in the art are contemplated by the embodiments of the present disclosure. The promoters may be either naturally occurring promoters, or hybrid promoters that combine elements of more than one promoter.

An expression construct may be present in a cell on an episome, such as a plasmid, or the expression construct may be inserted in a chromosome. Preferably, the expression vector contains a selectable marker gene to allow the selection of transformed host cells. Selectable marker genes are well known in the art and will vary with the host cell used.

The present disclosure also provides expression vectors comprising a nucleotide sequence encoding an ornithine transcarbamylase (OTC) protein that is preferably operably linked to at least one regulatory sequence. Regulatory sequences are art-recognized and are selected to direct expression of the encoded polypeptide.

Accordingly, the term regulatory sequence includes promoters, enhancers, and other expression control elements. The design of the expression vector may depend on such factors as the choice of the host cell to be transformed and/or the type of protein desired to be expressed.

The present disclosure also provides a host cell transfected with an mRNA or DNA described herein which encodes an ornithine transcarbamylase (OTC) polypeptide described herein. Preferably, the human OTC polypeptide has the sequence of SEQ ID NO: 4. The host cell may be any prokaryotic or eukaryotic cell. For example, an ornithine transcarbamylase (OTC) polypeptide may be expressed in bacterial cells such as *E. coli*, insect cells (e.g., using a baculovirus expression system), yeast, or mammalian cells. Other suitable host cells are known to those skilled in the art.

The present disclosure also provides a host cell comprising a vector comprising a polynucleotide which encodes an mRNA sequence of any one of SEQ ID NOs: 26-229.

The present disclosure also provides methods of producing a human wild type OTC protein of SEQ ID NO: 3 or a modified human OTC protein SEQ ID NO: 4. Preferably, the OTC protein is SEQ ID NO: 4 and is encoded by mRNA of SEQ ID NO 119. For example, a host cell transfected with an expression vector encoding an OTC protein can be cultured under appropriate conditions to allow expression of the polypeptide to occur. The polypeptide may be secreted and isolated from a mixture of cells and medium containing the polypeptides. Alternatively, the polypeptides may be retained in the cytoplasm or in a membrane fraction and the cells harvested, lysed and the protein isolated. A cell culture includes host cells, media and other byproducts. Suitable media for cell culture are well known in the art.

The expressed OTC proteins described herein can be isolated from cell culture medium, host cells, or both using techniques known in the art for purifying proteins, including ion-exchange chromatography, gel filtration chromatography, ultrafiltration, electrophoresis, and immunoaffinity purification with antibodies specific for particular epitopes of the OTC polypeptide.

Lipid-Based Formulations

Lipid-based formulations have been increasingly recognized as one of the most promising delivery systems (also referred to herein as a delivery vehicle or carrier) for RNA due to their biocompatibility and their ease of large-scale production. Cationic lipids have been widely studied as synthetic materials for delivery of RNA. After mixing together, nucleic acids are condensed by cationic lipids to form lipid/nucleic acid complexes known as lipoplexes. These lipid complexes are able to protect genetic material from the action of nucleases and to deliver it into cells by interacting with the negatively charged cell membrane. Lipoplexes can be prepared by directly mixing positively charged lipids at physiological pH with negatively charged nucleic acids.

Conventional liposomes consist of a lipid bilayer that can be composed of cationic, anionic, or neutral (phospho)lipids and cholesterol, which encloses an aqueous core. Both the lipid bilayer and the aqueous space can incorporate hydrophobic or hydrophilic compounds, respectively. Liposome characteristics and behavior in vivo can be modified by addition of a hydrophilic polymer coating, e.g. polyethylene glycol (PEG), to the liposome surface to confer steric stabilization. Furthermore, liposomes can be used for specific targeting by attaching ligands (e.g., antibodies, peptides, and carbohydrates) to its surface or to the terminal end of the attached PEG chains (Front Pharmacol. 2015 Dec. 1; 6:286).

Liposomes are colloidal lipid-based and surfactant-based delivery systems composed of a phospholipid bilayer surrounding an aqueous compartment. They may present as spherical vesicles and can range in size from 20 nm to a few microns. Cationic lipid-based liposomes are able to complex with negatively charged nucleic acids via electrostatic interactions, resulting in complexes that offer biocompatibility, low toxicity, and the possibility of the large-scale production required for in vivo clinical applications. Liposomes can fuse with the plasma membrane for uptake; once inside the cell, the liposomes are processed via the endocytic pathway and the genetic material is then released from the endosome/carrier into the cytoplasm. Liposomes have long been perceived as drug delivery vehicles because of their superior biocompatibility, given that liposomes are basically analogs of biological membranes, and can be prepared from both natural and synthetic phospholipids (Int J Nanomedicine. 2014; 9: 1833-1843).

Cationic liposomes have been traditionally the most commonly used non-viral delivery systems for oligonucleotides, including plasmid DNA, antisense oligos, and siRNA/small hairpin R A-shRNA). Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids to form nanoparticles by electrostatic interaction, providing high in vitro transfection efficiency. Furthermore, neutral lipid-based nanoliposomes for RNA delivery as e.g. neutral 1,2-dioleoyl-sn-glycero-3-phosphatidylcholine (DOPC)-based nanoliposomes were developed. (Adv Drug Deliv. Rev. 2014 February; 66: 110-116.)

Preferably, the mRNA constructs described herein are lipid formulated. The lipid formulation is preferably selected from, but not limited to, liposomes, lipoplexes, copolymers, such as PLGA, and lipid nanoparticles. Preferably a lipid nanoparticle (LNP) comprises:

(a) a nucleic acid, (b) a cationic lipid, (c) an aggregation reducing agent (such as polyethylene glycol (PEG) lipid or PEG-modified lipid), (d) optionally a non-cationic lipid (such as a neutral lipid), and (e) optionally, a sterol.

Preferably, the lipid nanoparticle formulation consists of (i) at least one cationic lipid; (ii) a neutral lipid; (iii) a sterol, e.g., cholesterol; and (iv) a PEG-lipid, in a molar ratio of about 20-60% cationic lipid: 5-25% neutral lipid: 25-55% sterol; 0.5-15% PEG-lipid.

Some examples of lipids and lipid compositions for delivery of an active molecule of this disclosure are given in WO 2015/074085, U.S. 2018/0169268, WO 2018/119163, WO 20185/118102, U.S. 2018/0222863, WO 2016/081029, WO 2017/023817, WO 2017/117530, each of which is hereby incorporated by reference in its entirety. In certain embodiments, the lipid is a compound of the following Formula I:

Formula I

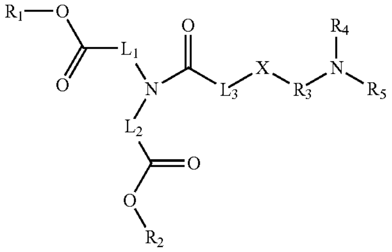

wherein $R_1$ and $R_2$ both consist of a linear alkyl consisting of 1 to 14 carbons, or an alkenyl or alkynyl consisting of 2 to 14 carbons;

$L_1$ and $L_2$ both consist of a linear alkylene or alkenylene consisting of 5 to 18 carbons, or forming a heterocycle with N;

X is S;

$L_3$ consists of a bond or a linear alkylene consisting of 1 to 6 carbons, or forming a heterocycle with N;

$R_3$ consists of a linear or branched alkylene consisting of 1 to 6 carbons; and $R_4$ and $R_5$ are the same or different, each consisting of a hydrogen or a linear or branched alkyl consisting of 1 to 6 carbons;

or a pharmaceutically acceptable salt thereof.

The lipid formulation of may contain one or more ionizable cationic lipids selected from among the following (also referred to herein as "ATX lipids"):

ATX-001

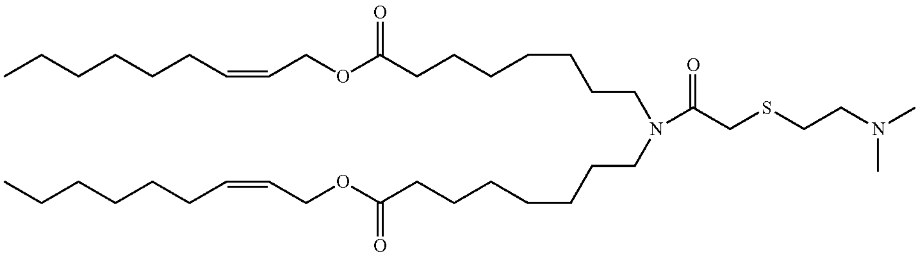

ATX-002

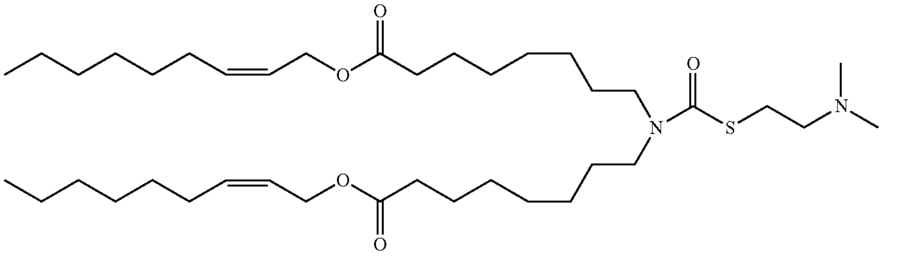

ATX-003

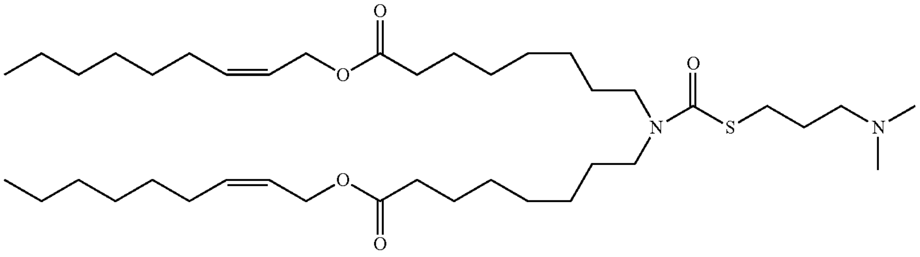

-continued
ATX-004
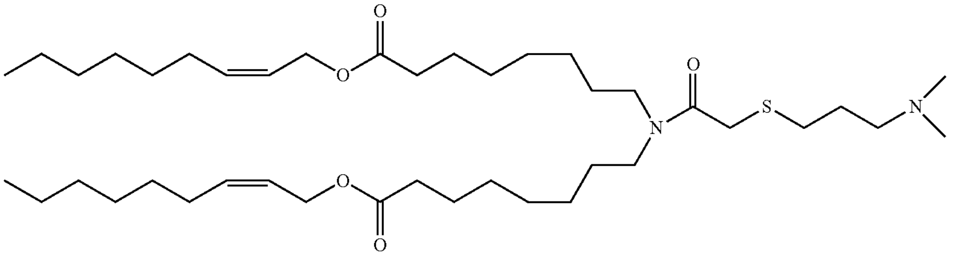
ATX-005
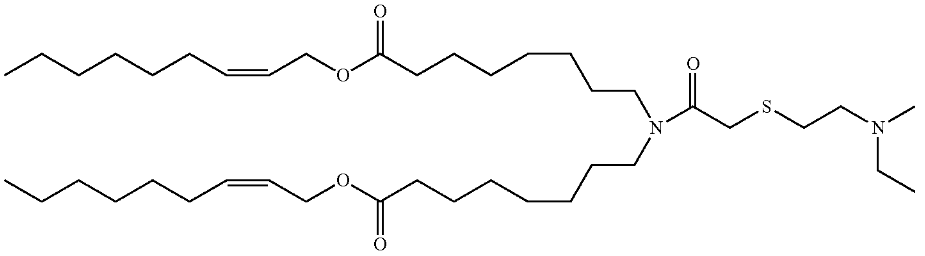
ATX-006
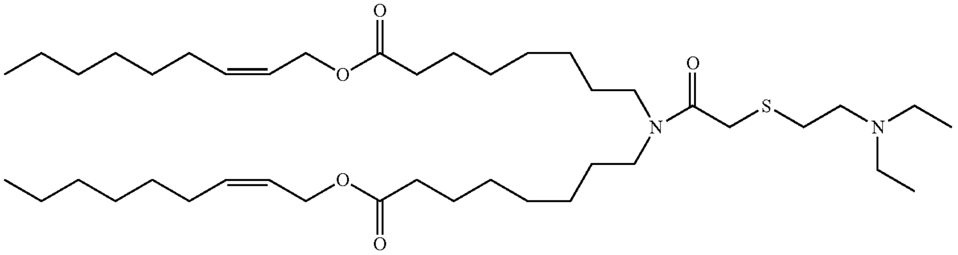
ATX-007
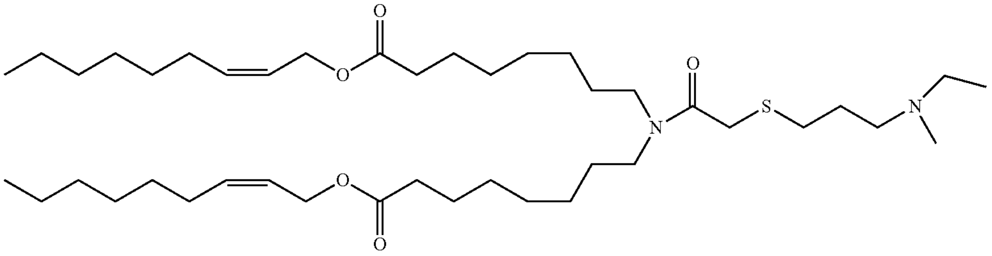
ATX-008
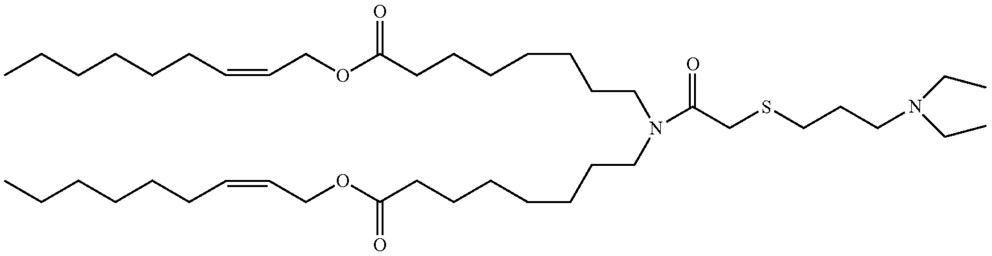
ATX-009
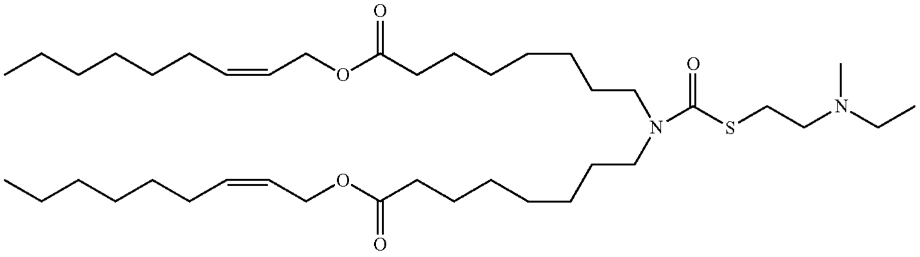

-continued
ATX-010
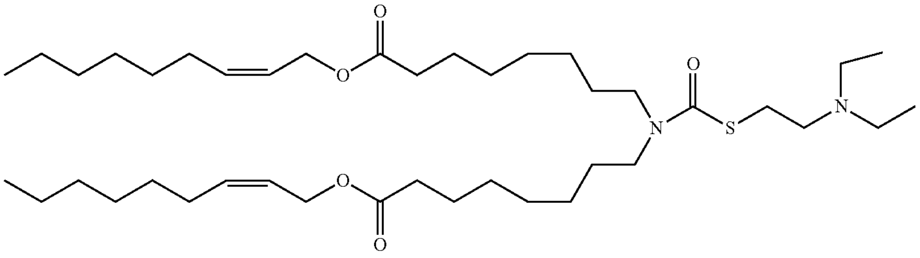
ATX-011
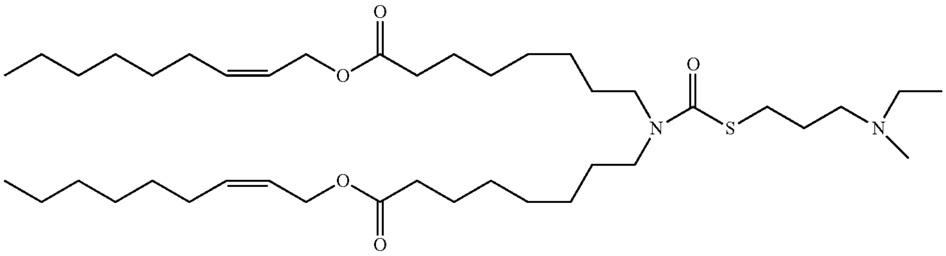
ATX-012
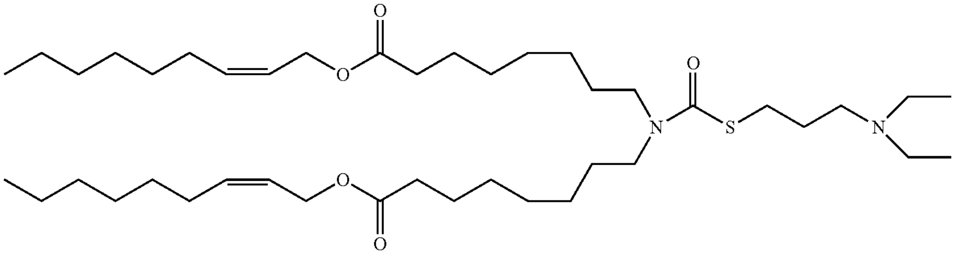
ATX-013
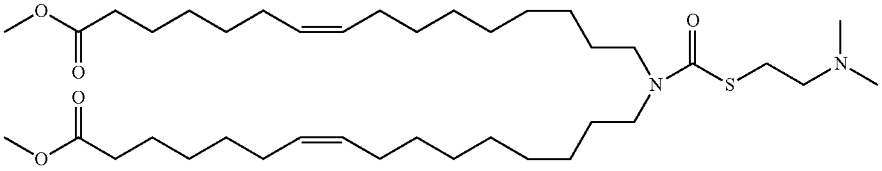
ATX-014
ATX-015
ATX-016
ATX-017
ATX-018
ATX-019
ATX-020
ATX-021
ATX-022
ATX-023
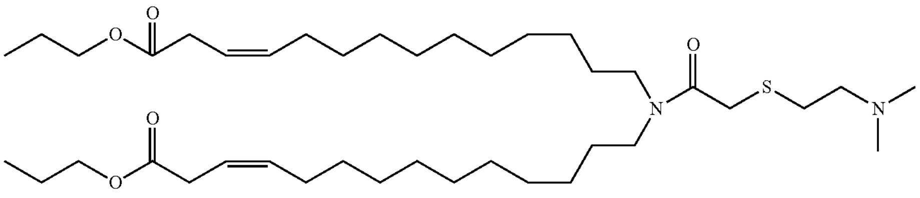

-continued
ATX-024
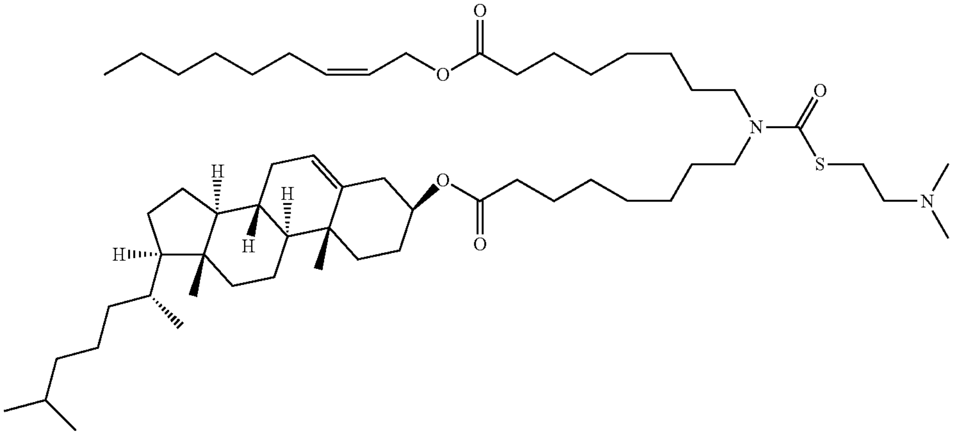
ATX-025
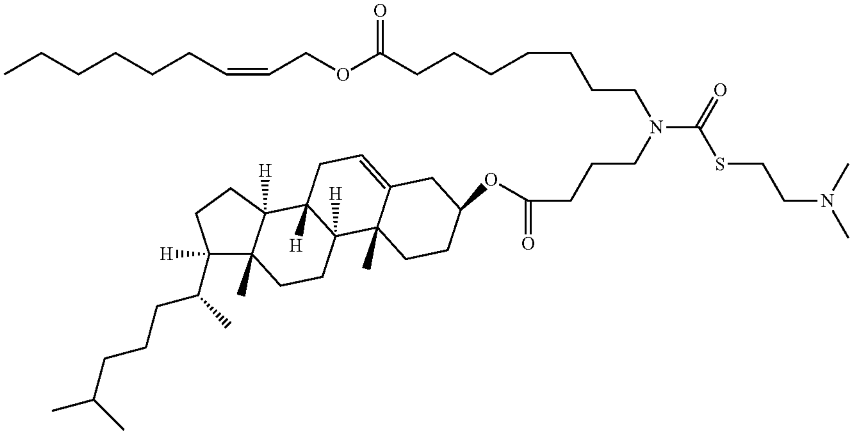
ATX-026
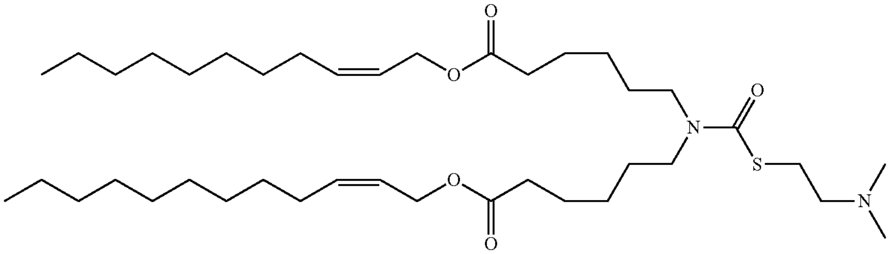
ATX-027
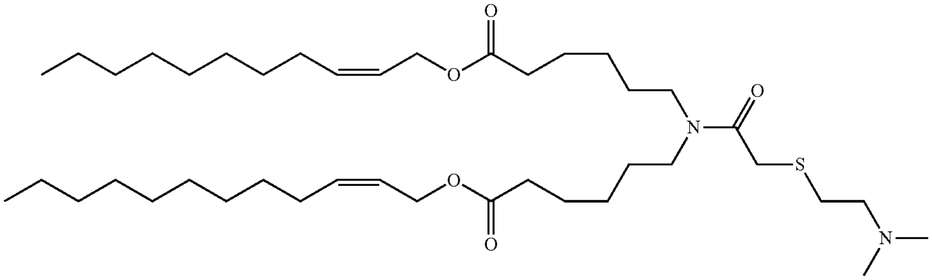
ATX-028
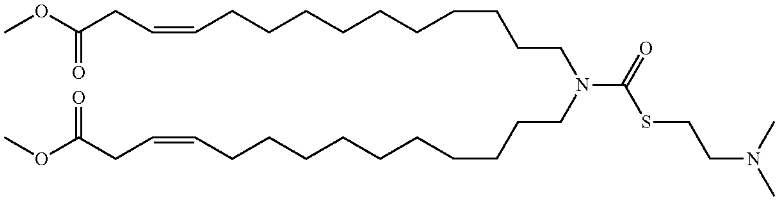

-continued
ATX-031
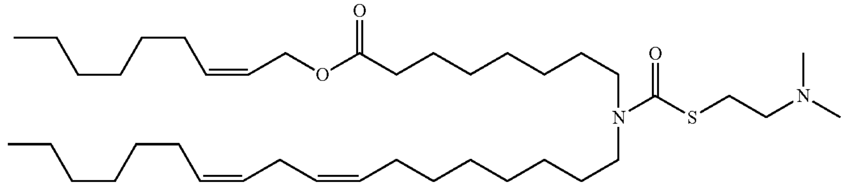
ATX-032
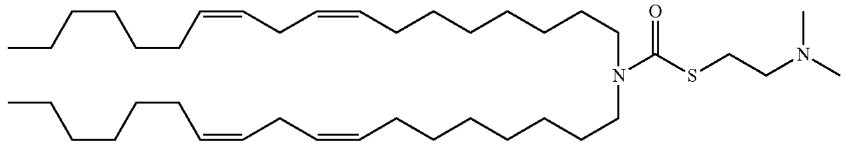
ATX-081
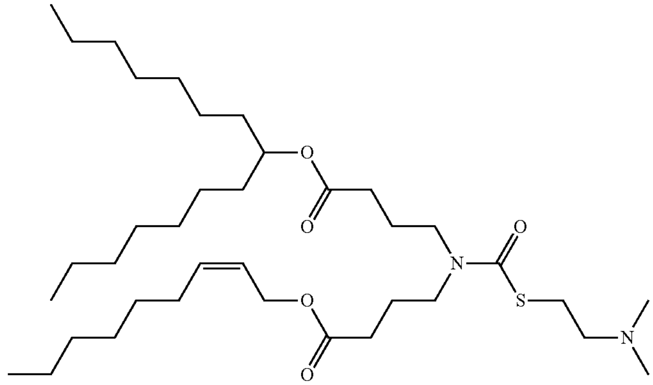
ATX-095
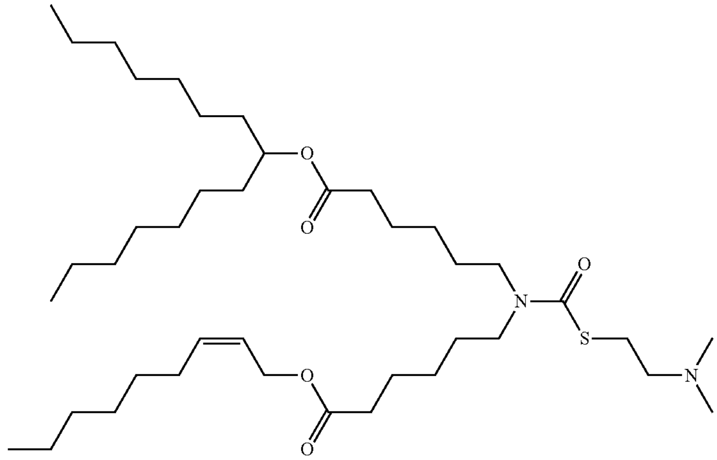

-continued

ATX-0126

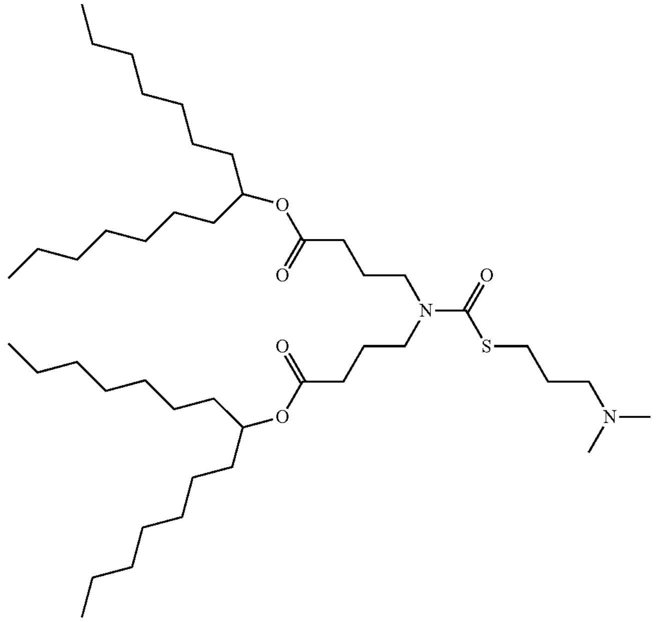

The lipid nanoparticle preferably includes a cationic lipid suitable for forming a lipid nanoparticle. Preferably, the cationic lipid carries a net positive charge at about physiological pH. The cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N-dimethylaminopropane (DLenDMA), 1,2-di-y-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.CI), 1,2-Dilinoleoyl-3-trimethylaminopropane chloride salt (DLin-TAP.CI), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)-N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl) amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)[1,3]-dioxolane (DLin-K-C2-DMA), 2,2-dilinoleyl dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,3 1-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination of any of the foregoing. Other cationic lipids include, but are not limited to, N,N-distearyl-N,N-dimethylammonium bromide (DDAB), 3P—(N—(N',$N^1$-dimethylaminoethane)-carbamoyl)cholesterol (DC-Choi), N-(1-(2,3-dioleyloxy)propyl)-N-2-(sperminecarboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl[1,3]-dioxolane (XTC). Additionally, commercial preparations of cationic lipids can be used, such as, e.g., LIPOFECTIN (including DOTMA and DOPE, available from GIBCO/BRL), and Lipofectamine (comprising DOSPA and DOPE, available from GIBCO/BRL).

Other suitable cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010.

Other suitable amino lipids include those having alternative fatty acid groups and other dialkylamino groups, including those, in which the alkyl substituents are different (e.g., N-ethyl-N-methylamino-, and N-propyl-N-ethylamino-). In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

Preferably, the LNP comprises the cationic lipid with formula (III) according to the patent application PCT/EP2017/064066. In this context, the disclosure of PCT/EP2017/064066 is also incorporated herein by reference.

Preferably, amino or cationic lipids of the disclosure have at least one protonatable or deprotonatable group, such that the lipid is positively charged at a pH at or below physiological pH (e.g. pH 7.4), and neutral at a second pH, preferably at or above physiological pH. It will, of course, be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11, e.g., a pKa of about 5 to about 7.

The cationic lipid can comprise from about 20 mol % to about 70 or 75 mol % or from about 45 to about 65 mol % or about 20, 25, 30, 35, 40, 45, 50, 55, 60, 65, or about 70 mol % of the total lipid present in the particle. In another embodiment, the lipid nanoparticles include from about 25% to about 75% on a molar basis of cationic lipid, e.g., from about 20 to about 70%, from about 35 to about 65%, from about 45 to about 65%, about 60%, about 57.5%, about 57.1%, about 50% or about 40% on a molar basis (based upon 100% total moles of lipid in the lipid nanoparticle). In one embodiment, the ratio of cationic lipid to nucleic acid is from about 3 to about 15, such as from about 5 to about 13 or from about 7 to about 11.

Pharmaceutical Compositions

Preferably, the disclosure provides pharmaceutical compositions containing a codon optimized mRNA encoding a human OTC protein of SEQ ID NO: 3 or SEQ ID NO: 4, preferably formulated in a lipid delivery system or lipid carrier and preferably comprising pharmaceutically acceptable excipients. Pharmaceutical compositions disclosed herein preferably facilitate expression of mRNA in vivo.

Suitable routes of administration include, for example, oral, rectal, vaginal, transmucosal, pulmonary including intratracheal or inhaled, or intestinal administration; parenteral delivery, including intradermal, transdermal (topical), intramuscular, subcutaneous, intramedullary injections, as well as intrathecal, direct intraventricular, intravenous, intraperitoneal, or intranasal.

Preferably, the intramuscular administration is to a muscle selected from the group consisting of skeletal muscle, smooth muscle and cardiac muscle. In some embodiments the administration results in delivery of the mRNA to a muscle cell. In some embodiments the administration results in delivery of the mRNA to a hepatocyte (i.e., liver cell). In a particular embodiment, the intramuscular administration results in delivery of the mRNA to a muscle cell.

Preferably, mRNAs and lipid formulations thereof may be administered in a local rather than systemic manner, for example, via injection of the pharmaceutical composition directly into a targeted tissue, preferably in a sustained release formulation. Local delivery can be affected in various ways, depending on the tissue to be targeted. For example, aerosols containing compositions of the present disclosure can be inhaled (for nasal, tracheal, or bronchial delivery); can be supplied in liquid, tablet or capsule form for administration to the stomach or intestines, can be supplied in suppository form for rectal or vaginal application; or can even be delivered to the eye by use of creams, drops, or even injection. Formulations containing provided compositions complexed with therapeutic molecules or ligands can even be surgically administered, for example in association with a polymer or other structure or substance that can allow the compositions to diffuse from the site of implantation to surrounding cells. Alternatively, they can be applied surgically without the use of polymers or supports.

Pharmaceutical compositions may be administered to any desired tissue. In some embodiments, the OTC mRNA delivered by provided liposomes or compositions is expressed in the tissue in which the liposomes and/or compositions were administered. In some embodiments, the mRNA delivered is expressed in a tissue different from the tissue in which the liposomes and/or compositions were administered. Exemplary tissues in which delivered mRNA may be delivered and/or expressed include, but are not limited to the liver, kidney, heart, spleen, serum, brain, skeletal muscle, lymph nodes, skin, and/or cerebrospinal fluid.

Preferably, a pharmaceutical composition can contain a polynucleotide described herein such as a primary DNA construct or mRNA described herein within a viral or bacterial vector.

Preferably, the primary DNA construct for an mRNA described herein or an mRNA described herein can be formulated using one or more excipients to: (1) increase stability; (2) increase cell transfection; (3) permit a sustained or delayed release (e.g., from a depot formulation of the polynucleotide, primary construct, or mRNA); (4) alter the biodistribution (e.g., target the polynucleotide, primary construct, or mRNA to specific tissues or cell types); (5) increase the translation of encoded protein in vivo; and/or (6) alter the release profile of encoded protein in vivo.

In addition to traditional excipients such as any and all solvents, dispersion media, diluents, or other liquid vehicles, dispersion or suspension aids, surface active agents, isotonic agents, thickening or emulsifying agents, preservatives, excipients of the present disclosure can include, without limitation, liposomes, lipid nanoparticles, polymers, lipoplexes, core-shell nanoparticles, peptides, proteins, cells transfected with primary DNA construct, or mRNA (e.g., for transplantation into a subject), hyaluronidase, nanoparticle mimics and combinations thereof.

Accordingly, the formulations described herein can include one or more excipients, each in an amount that together increases the stability of the primary DNA construct, or mRNA, increases cell transfection by the primary construct, or mRNA, increases the expression of polynucleotide, primary construct, or mRNA encoded protein, and/or alters the release profile of polynucleotide, primary construct, or mRNA encoded proteins. Further, the primary construct and mRNA of the present disclosure may be formulated using self-assembled nucleic acid nanoparticles.

Formulations of the pharmaceutical compositions described herein may be prepared by any method known or hereafter developed in the art of pharmacology. In general, such preparatory methods include the step of associating the active ingredient with an excipient and/or one or more other accessory ingredients.

A pharmaceutical composition in accordance with the present disclosure may be prepared, packaged, and/or sold in bulk, as a single unit dose, and/or as a plurality of single unit doses. As used herein, a "unit dose" refers to a discrete amount of the pharmaceutical composition comprising a predetermined amount of the active ingredient. The amount of the active ingredient may generally be equal to the dosage of the active ingredient which would be administered to a subject and/or a convenient fraction of such a dosage including, but not limited to, one-half or one-third of such a dosage.

Relative amounts of the active ingredient, the pharmaceutically acceptable excipient, and/or any additional ingredients in a pharmaceutical composition in accordance with the present disclosure may vary, depending upon the identity, size, and/or condition of the subject being treated and further depending upon the route by which the composition is to be administered. For example, the composition may comprise between 0.1% and 99% (w/w) of the active ingredient.

Pharmaceutical formulations may additionally comprise a pharmaceutically acceptable excipient, which, as used herein, includes, but is not limited to, any and all solvents, dispersion media, diluents, or other liquid vehicles, dispersion or suspension aids, surface active agents, isotonic agents, thickening or emulsifying agents, preservatives, and the like, as suited to the particular dosage form desired.

Various excipients for formulating pharmaceutical compositions and techniques for preparing the composition are known in the art (see Remington: The Science and Practice of Pharmacy, 21st Edition, A. R. Gennaro, Lippincott, Williams & Wilkins, Baltimore, Md., 2006; incorporated herein by reference in its entirety). The use of a conventional excipient medium may be contemplated within the scope of the embodiments of the present disclosure, except insofar as any conventional excipient medium may be incompatible with a substance or its derivatives, such as by producing any undesirable biological effect or otherwise interacting in a deleterious manner with any other component(s) of the pharmaceutical composition.

Therapeutic Uses

The mRNA sequences, primary DNA constructs that transcribe the mRNA sequences described herein and pharmaceutical compositions thereof provide numerous in vivo and in vitro methods and are useful to treat OTC deficiency. The treatment may comprise treating a human patient with OTC deficiency. Similarly, compositions described herein, may be used in vitro or ex vivo to study OTC deficiency in cell or animal-based models. For example, cells deficient for OTC expression can be used to analyze the ability to restore OTC expression and/or activity, as well as the time period over which expression and/or activity persists. Such cells and animal models are also suitable to identify other factors involved in the pathway, whether binding partners or factors in the same biochemical pathway. In other embodiments, compositions described herein can be used to study or track mitochondrial delivery.

Polynucleotides described herein, such as a DNA construct or template or an mRNA sequence described herein can be delivered to patients or cells experiencing OTC deficiency. Preferably the mRNA sequence comprises SEQ ID NO: 119 encoding a modified OTC protein of SEQ ID NO: 4. Preferably the DNA sequence comprises SEQ ID NO: 221 encoding a modified OTC protein of SEQ ID NO: 4.

Following administration, OTC is expressed in the cells or subject. Preferably, compositions described herein are delivered to mitochondria. Preferably compositions described herein are delivered to liver cells.

Preferably the therapeutic methods described herein decrease ammonia levels in plasma and/or urine in a subject in need thereof or in cells in culture, such as a subject having an OTC deficiency. Preferably, the therapeutic methods described herein decrease orotic acid levels in plasma and/or urine in a subject in need thereof or in cells in culture. Preferably, the therapeutic methods described herein increase citrulline in plasma and/or urine in a subject in need thereof or in cells in culture. Preferably, ammonia levels, orotic acid levels and/or citrulline levels are used as biomarkers to (i) identify subjects in need of treatment and/or (ii) to evaluate efficacy of treatment using the mRNA or DNA templates described herein.

Examples of mRNA sequences for use with these methods include those listed in Table 5. Preferably cDNA templates used to transcribe the mRNA sequences described herein are listed in Table 6. Preferred mRNA sequences for administering to patients for treatment of OTC deficiency are SEQ ID NOS: 1799 and SEQ ID NOS: 1921. Preferably the preferred mRNA sequences of SEQ ID NO: 1799 and SEQ ID NO: 1921.

Dosing

An effective dose of a mRNA, a protein or pharmaceutical formulations thereof of the present disclosure can be an amount that is sufficient to treat ORF protein deficiency in a cell and/or in a patient. A therapeutically effective dose can be an amount of an agent or formulation that is sufficient to cause a therapeutic effect. A therapeutically effective dose can be administered in one or more separate administrations, and by different routes. Generally, a therapeutically effective amount is sufficient to achieve a meaningful benefit to the subject (e.g., treating, modulating, curing, preventing and/or ameliorating phenylketonuria). For example, a therapeutically effective amount may be an amount sufficient to achieve a desired therapeutic and/or prophylactic effect. Generally, the amount of a therapeutic agent administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays may optionally be employed to identify optimal dosage ranges.

Methods provided herein contemplate single as well as multiple administrations of a therapeutically effective amount of an mRNA sequence described herein. Pharmaceutical compositions comprising an mRNA sequence encoding an ORF protein described herein can be administered at regular intervals, depending on the nature, severity and extent of the subject's condition. Preferably, a therapeutically effective amount an mRNA sequence of the present disclosure may be administered periodically at regular intervals (e.g., once every year, once every six months, once every four months, once every three months, once every two months, once a month), biweekly, weekly, daily, twice a day, three times a day, four times a day, five times a day, six times a day, or continuously.

Preferably, the pharmaceutical compositions of the mRNA of the present disclosure are formulated such that they are suitable for extended-release of the translatable compound encoding a modified protein described herein contained therein. Such extended-release compositions may be conveniently administered to a subject at extended dosing intervals. For instance, in one embodiment, the pharmaceutical compositions of the present disclosure are administered to a subject twice a day, daily or every other day. In some embodiments, the pharmaceutical compositions of the present disclosure are administered to a subject twice a week, once a week, every 10 days, every two weeks, every 28 days, every month, every six weeks, every eight weeks, every other month, every three months, every four months, every six months, every nine months or once a year. Also contemplated herein are pharmaceutical compositions which are formulated for depot administration (e.g., subcutaneously, intramuscularly) to either deliver or release an mRNA sequence encoding an OTC protein described herein over extended periods of time. Preferably, the extended-release means employed are combined with modifications made to the translatable compound encoding an OTC protein described herein to enhance stability.

A therapeutically effective dose, upon administration, can result in serum or plasma levels of OTC of 1-1000 pg/ml, or 1-1000 ng/ml, or 1-1000 μg/ml, or more. In some embodiments, administering a therapeutically effective dose of a composition comprising an mRNA sequence described herein can result in increased liver modified protein levels in a treated subject. Preferably, administering a composition comprising a mRNA described herein results in a 5%, 10%, 20%, 30%, 40%, 50%, 60%, 70%, 80%, 90%, or 95% increase in liver modified protein levels relative to a baseline modified protein level in the subject prior to treatment. Preferably, administering a therapeutically effective dose of a composition comprising an mRNA described herein will result an increase in liver OTC levels relative to baseline liver OTC levels in the subject prior to treatment. In some embodiments, the increase in liver OTC levels relative to baseline liver OTC levels will be at least 5%, 10%, 20%, 30%, 40%, 50%, 100%, 200%, or more.

Preferably, a therapeutically effective dose, when administered regularly, results in increased expression of OTC in the liver as compared to baseline levels prior to treatment. Preferably, administering a therapeutically effective dose of a composition comprising an mRNA sequence described herein results in the expression of a modified protein level at or above about 10 ng/mg, about 20 ng/mg, about 50 ng/mg, about 100 ng/mg, about 150 ng/mg, about 200 ng/mg, about 250 ng/mg, about 300 ng/mg, about 350 ng/mg, about 400 ng/mg, about 450 ng/mg, about 500 ng/mg, about 600 ng/mg, about 700 ng/mg, about 800 ng/mg, about 900 ng/mg, about 1000 ng/mg, about 1200 ng/mg or about 1500 ng/mg of the total protein in the liver of a treated subject.

Preferably, a therapeutically effective dose, when administered regularly, results in a reduction of orotic acid levels in a biological sample. In some embodiments, administering a therapeutically effective dose of a composition comprising an mRNA described herein results in a reduction of orotic acid levels in a biological sample (e.g., urine, plasma or serum sample) by at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95% as compared to baseline orotic acid levels before treatment. Preferably, the biological sample is selected from plasma, serum, whole blood, urine, or cerebrospinal fluid. Preferably, administering a therapeutically effective dose of a composition comprising an mRNA described herein results in reduction of orotic acid levels to about 1000 μmol/L or less, about 900 μmol/L or less, about 800 μmol/L or less, about μmol/L or less, about 600 μmol/L or less, about 500 μmol/L or less, about 400 μmol/L or less, about 300 μmol/L or less, about 200 μmol/L or less, about 100 μmol/L or less or about 50 μmol/L or less in serum or plasma. Preferably, a therapeutically effective dose, when administered regularly results in reduction of orotic acid levels to about 600 μmol/L or less in serum or plasma. In another exemplary embodiment, a therapeutically effective dose, when administered regularly results in reduction of orotic acid levels to about 360 μmol/L or less in serum or plasma. Preferably, a therapeutically effective dose, when administered regularly results in reduction of orotic acid levels to about 120 μmol/L or less in serum or plasma.

A therapeutically effective dose of an mRNA described herein in vivo can be a dose of about 0.001 to about 500 mg/kg body weight. For instance, the therapeutically effective dose may be about 0.001-0.01 mg/kg body weight, or 0.01-0.1 mg/kg, or 0.1-1 mg/kg, or 1-10 mg/kg, or 10-100 mg/kg. Preferably, a Lipid-enabled and Unlocked Nucleomonomer Agent modified RNA (LUNAR)-mRNA (see WO 2015/074085 and U.S. 2018/0169268), encoding an OTC protein described herein, is provided at a dose ranging from about 0.1 to about 10 mg/kg body weight.

Combinations

The cDNA primary constructs, mRNA or encoded OTC proteins described herein may be used in combination with one or more other therapeutic, prophylactic, diagnostic, or imaging agents. By "in combination with," it is not intended to imply that the agents must be administered at the same time and/or formulated for delivery together, although these methods of delivery are within the scope of the present disclosure. Compositions can be administered concurrently with, prior to, or subsequent to, one or more other desired therapeutics or medical procedures. In general, each agent will be administered at a dose and/or on a time schedule determined for that agent. Preferably, the methods of treatment of the present disclosure encompass the delivery of pharmaceutical, prophylactic, diagnostic, or imaging compositions in combination with agents that may improve their bioavailability, reduce and/or modify their metabolism, inhibit their excretion, and/or modify their distribution within the body. As a non-limiting example, mRNA disclosed herein and preferably an mRNA sequence comprising SEQ ID NO: 119, encoding a modified OTC protein of SEQ ID NO: 4 may be used in combination with a pharmaceutical agent for the treatment of OTC deficiency. The pharmaceutical agent includes, but is not limited to one or more of: sodium phenylbutyrate, glycerol phenylbutyrate, sodium phenylacetate, sodium benzoate, arginine, citrulline, Multiple vitamins, calcium supplements or combined with low protein/high caloric diet. In general, it is expected that agents utilized in combination with be utilized at levels that do not exceed the levels at which they are utilized individually. In some embodiments, the levels utilized in combination will be lower than those utilized individually. In one embodiment, the combinations, each or together may be administered according to the split dosing regimens as are known in the art.

EXAMPLES

Example 1: Material and Methods

In Vitro Transcription Protocol

The mRNAs were synthesized in vitro using T7RNA polymerase-mediated DNA-dependent RNA transcription where uridine triphosphate (UTP) was substituted and unsubstituted with modified UTPs such as 5 methoxy UTP (5MeOU), N1-methoxy methyl pseudo UTP (N1-MOM), 5-hydroxy methyl UTP, 5-carboxy UTP, and mixture of modifications using linearized template for each UTR combination. The mRNA was purified using column chromatography, the DNA and double stranded mRNA contamination of all mRNAs was removed using an enzymatic reaction, and the mRNA was concentrated, and buffer exchanged.

Preparation of Lipid Encapsulated mRNA

Lipid encapsulated mRNA particles were prepared by mixing lipids (ATX lipid: DSPC: Cholesterol: PEG-DMG) in ethanol with OTC mRNA dissolved in Citrate buffer. The mixed material was instantaneously diluted with Phosphate Buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 50 mM NaCl and 9% sucrose, pH 7.3. The formulation was concentrated followed by 0.2 μm filtration using PES filters. The mRNA concentration in the formulation was then measured by Ribogreen fluorimetric assay following which the concentration was adjusted to a final desired concentration by diluting with HEPES buffer containing 50 mM NaCl, 9% sucrose, pH 7.3 containing glycerol. The final formulation was then filtered through a 0.2 μm filter and filled into glass vials, stoppered, capped and placed at −70±5° C. The frozen formulations were characterized for their mRNA content and percent encapsulation by Ribogreen assay, mRNA integrity by fragment analyzer, lipid content by high performance liquid chromatography (HPLC), particle size by dynamic light scattering on a Malvern Zetasizer Nano ZS, pH and Osmolality.

In-Cell Western (ICW)

96-well collagen plates were used to seed the cells at the appropriate density in Dulbecco's Modified Eagle Media (DMEM)/Fetal Bovine Serum (FBS) culture media. At the optimal confluence, cells were transfected with the targeted mRNAs diluted in the transfection reagent mix (MessengerMax and Opti-MEM). Cells were placed in the $CO_2$ incubator and allowed to grow. At the desire timepoint, media was removed, and cells were fixed in 4% fresh paraformaldehyde (PFA) for 20 min. After that, fixative was removed, and cells were permeabilize in tris buffered saline with TWEEN (TBST) for 5 min several times. When permeabilization washes were complete, cells were incubated with a blocking buffer (ODYSSEY® Blocking Buffer (PBS) (Li-Cor, Lincoln, Nebr.)) for 45 min. Primary antibody was then added and incubated for 1 h at room temperature. Cells were then washed several times in TBST and incubated for 1 h with a secondary antibody diluted in blocking buffer and containing a CellTag 700 stain. To finalize, cells were washed several times in TBST followed by a last wash in tris-buffered saline (TBS). The plate was imaged using the Licor detection system and data was normalized to the total number of cells labeled by the CellTag 700.

Example 2: UTRs Screening in Hepa1,6 and Hep3B—Correlation at 24 h and 48 h

A UTR library was screened in vitro using mRNA construct #571 comprising the sequence of SEQ ID NO: 34 as CDS (coding sequence). In-Cell Western assays as described in Example 1 were used to transfect the different mRNAs into Hepa1,6 and Hep3B using commercially available transfection reagents. OTC protein expression levels were measured by near-infrared fluorescent imaging systems. Commercially available antibodies for OTC were used for detection. Untransfected and reference sequences were used as internal controls. FIG. 1, Panel A is a scatter plot of OTC protein expression levels found in Hepa1,6 and Hep3B cells at 24 hours. FIG. 1, Panel B is a scatter plot of OTC protein expression levels found in Hepa1,6 and Hep3B cells at 48 hours. The aim of the screening was to determine an UTR-specific impact on OTC expression levels in a human (Hep3B) and a mouse (Hepa1,6) liver cell line that will be beneficial to determine which UTRs would work best in both models, in particular, its translatability from mouse-to-human. Top expressing UTRs were used in further profiling studies.

Figure 2:
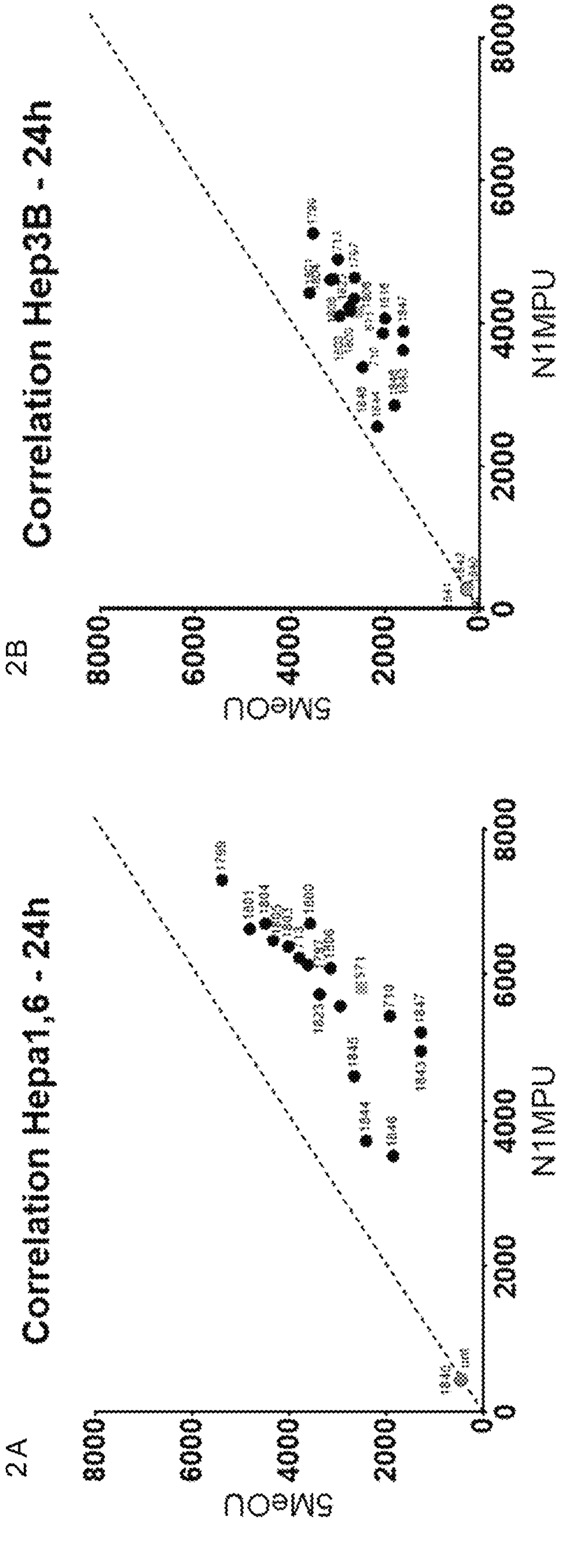
FIGS. 2A-B shows scatter plots illustrating the correlation of protein stability compounds screened in Hepa1,6 cells (FIG. 2A) and Hep3B cells (FIG. 2B) at 24 h in Round 1.

Example 3: Round 1 of Protein Stability Compounds Screened in Hepa1,6 and Hep3B at 24 h—Correlation In vitro screening of certain mRNA constructs of Table 5 that were designed based on a protein-stability approach was performed. The mRNA constructs were tested in two different chemistries $N^1$-methylpseudouridine (N1MPU) and 5-methoxyuridine (5MeOU) meaning that 100% of the uridines in each mRNA were N1MPU only or 5MeOU only (not a combination of 5MeOU or N1MPU). In-Cell Western (ICW) assays as described in Example 1 were used to transfect the different mRNAs into Hepa1,6 and Hep3B using commercially available transfection reagents. OTC protein expression levels were measured by near-infrared fluorescent imaging systems. Commercially available antibodies for OTC were used for detection. Untransfected and reference sequences were used as internal controls. FIG. 2, panel A is a scatter plot showing the correlation of OTC protein expression levels in Hepa1,6 cells at 24 hours as a function of mRNAs tested in N1MPU and 5MeOU chemistries. FIG. 2, panel B is a scatter plot showing the correlation of OTC protein expression levels in Hep3B cells at 24 hours as a function of mRNAs tested in N1MPU and 5MeOU chemistries. These figures exhibit the degree of variability in expression levels when mRNAs from two different chemistries are tested in a mouse and a human liver cell line. It can be seen that that in this experiment, most of the compounds express better when an N1MPU chemistry is used in the mRNA.

Figure 3:
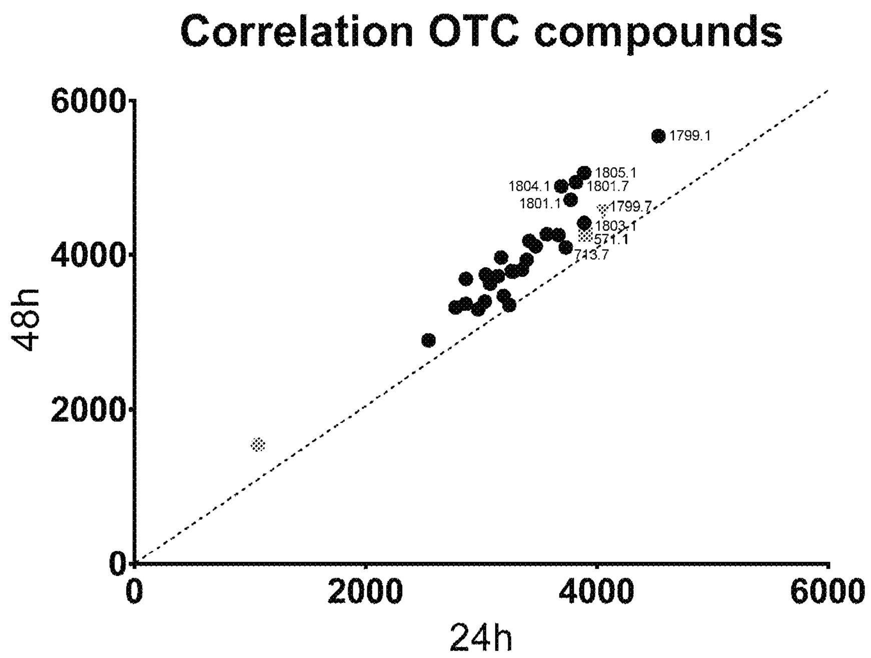
FIGS. 3A-B shows scatter plots illustrating the correlation of protein stability compounds screened in human primary hepatocytes at 24 h and 48 h in Round 2 (newly optimized compounds based on Round 1) as shown with FIG. 3A and FIG. 3B.
Figure 3:
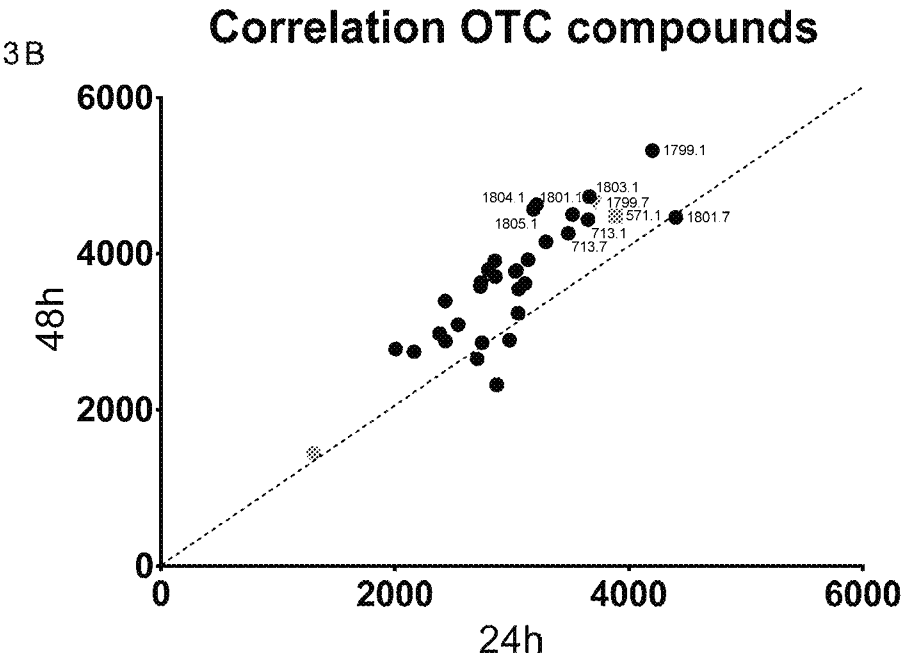

Example 4: Round 2 of Protein Stability Compounds Screened in Human Primary Hepatocytes at 24 h and 48 h—Correlation In vitro screening of certain mRNA constructs of Table 5 that were designed based on a protein stability approach was performed. The mRNAs were tested in two different chemistries, 100% of the Uridines are N1MPU indicated by the name of mRNA constructs followed by "0.1" and 100% of the uridines are 5MeOU indicated by the name of mRNA constructs followed by "0.7". In-Cell Western (ICW) assays as described in Example 1 were used to transfect the different mRNAs into human primary hepatocytes using commercially available transfection reagents. OTC protein expression levels were measured by near-infrared fluorescent imaging systems. Commercially available antibodies for OTC were used for detection. Untransfected and reference sequences were used as internal controls. (FIG. 3, Panels A and B). The results indicate that, in contrast to the experiments conducted in cancer cell lines (Hepa1,6; Hep3B; Example 3, both chemistries express similarly in human primary hepatocytes.

Figure 4:
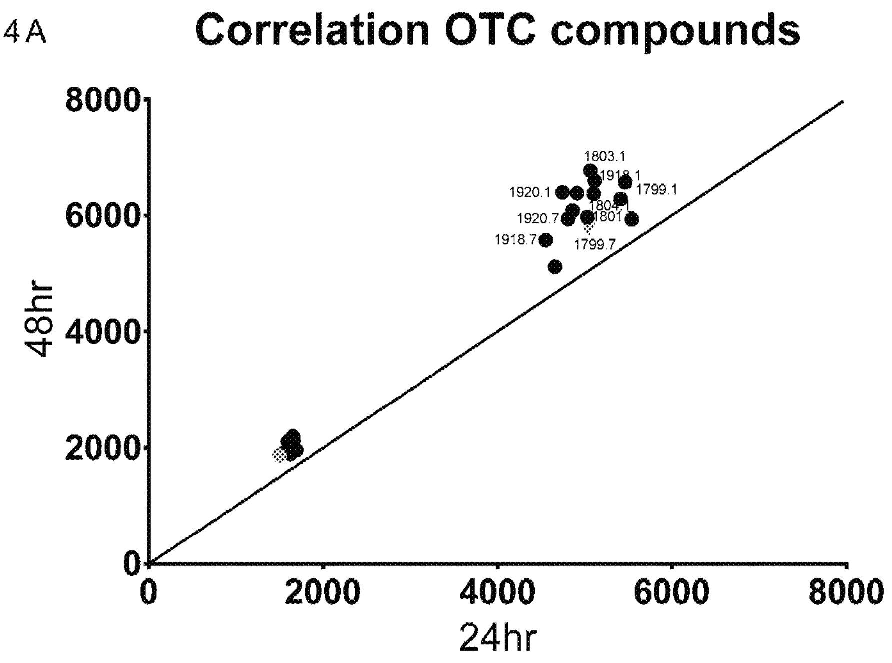
FIGS. 4A-B shows scatter plots illustrating the correlation of protein stability compounds screened in human primary hepatocytes at 24 h and 48 h in Round 3 (newly optimized compounds based on rounds 1 and 2) as shown with FIG. 4A and FIG. 4B.
Figure 4:
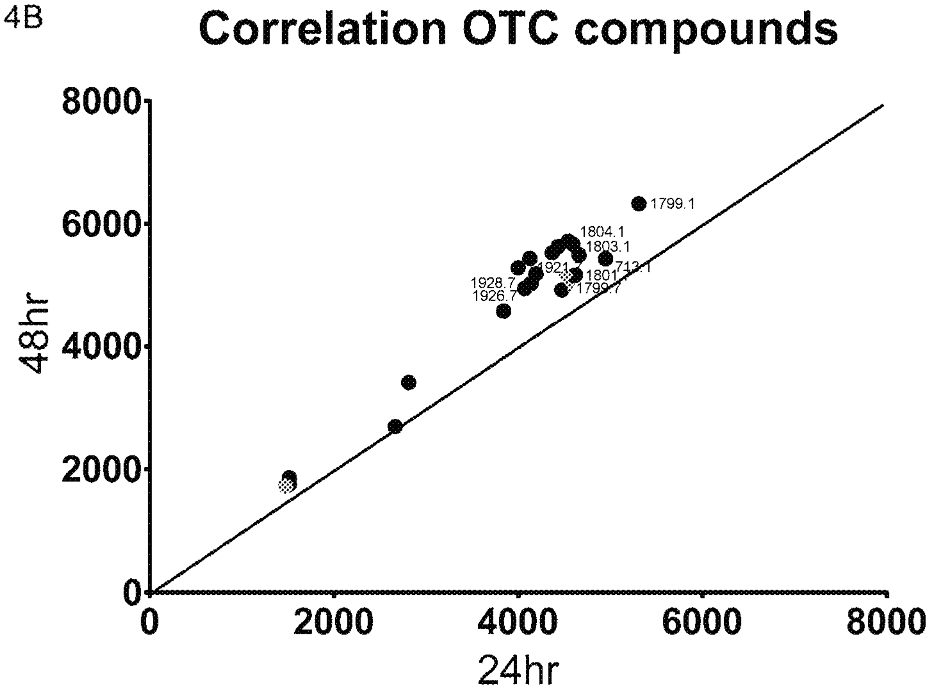

Example 5: Round 3 of Protein Stability Compounds Screening in Human Primary Hepatocytes at 24 h and 48 h—Correlation In vitro screening of novel compounds designed based on a protein stability approach was performed. mRNAs were tested in two different chemistries, N1MPU indicated by the name of mRNA constructs followed by "0.1" and 5MeOU indicated by the name of mRNA constructs followed by "0.7". In-Cell Western (ICW) assays as described in Example 1 were used to transfect the different mRNAs into human primary hepatocytes using commercially-available transfection reagents. OTC protein expression levels were measured by near-infrared fluorescent imaging systems. Commercially available antibodies for OTC protein were used for detection. Untransfected and reference sequences were used as internal controls. (FIG. 4, Panels A and B). The results indicate that, in contrast to the experiments conducted in cancer cell lines (Hepa1,6; Hep3B; Example 3), both chemistries express similarly in human primary hepatocyte.

Example 6: OTC Protein-Expression Levels in Human Primary Cells Transfected with OTC mRNA Constructs 1799.7 (5MeOU Chemistry) Encoding the OTC Protein of SEQ ID NO: 3 and 1921.7 (5MeOU Chemistry) Encoding the Modified OTC Protein of SEQ ID NO: 4

Figure 5:
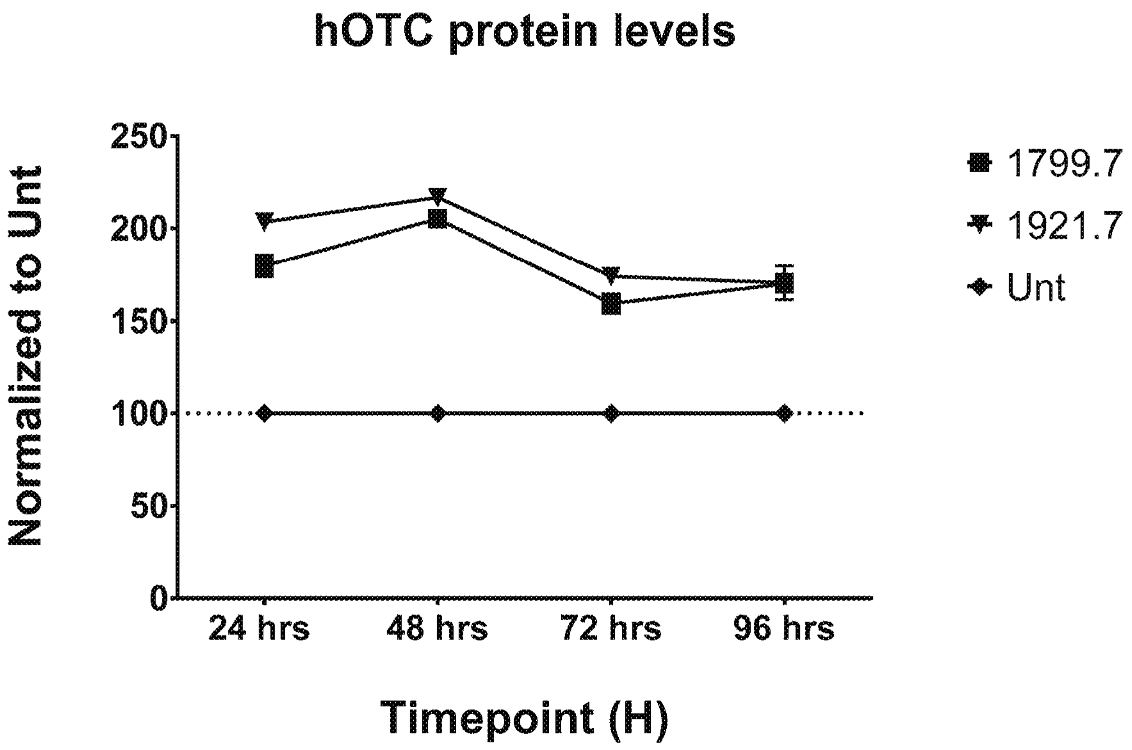
FIG. 5 is a plot illustrating OTC protein expression levels in human primary hepatocytes transfected with lead OTC mRNAs. 1799.1 is an mRNA having the sequence of SEQ ID NO: 175 wherein 100% of the uridines in SEQ ID NO: 175 are $N^1$-methylpseudouridine (N1MPU).

In-Cell Western (ICW) assays as described in Example 1 were used to transfect OTC mRNAs into human primary hepatocytes using commercially available transfection reagents. OTC protein expression levels were measured by near-infrared fluorescent imaging systems during a time course study up to 96 h. Commercially available OTC antibodies were used for detection. Untransfected cells were used as internal control. Plot shows OTC protein levels normalized to untransfected controls. (FIG. 5). The purpose of this study was to evaluate the half-life of the unmodified versus the modified protein sequence (encoded by constructs 1799.7, 1921.7, respectively) under in vitro conditions in transfected human primary hepatocytes. The results indicate that 1921.7 demonstrated more stable expression than 1799.7

Figure 6:
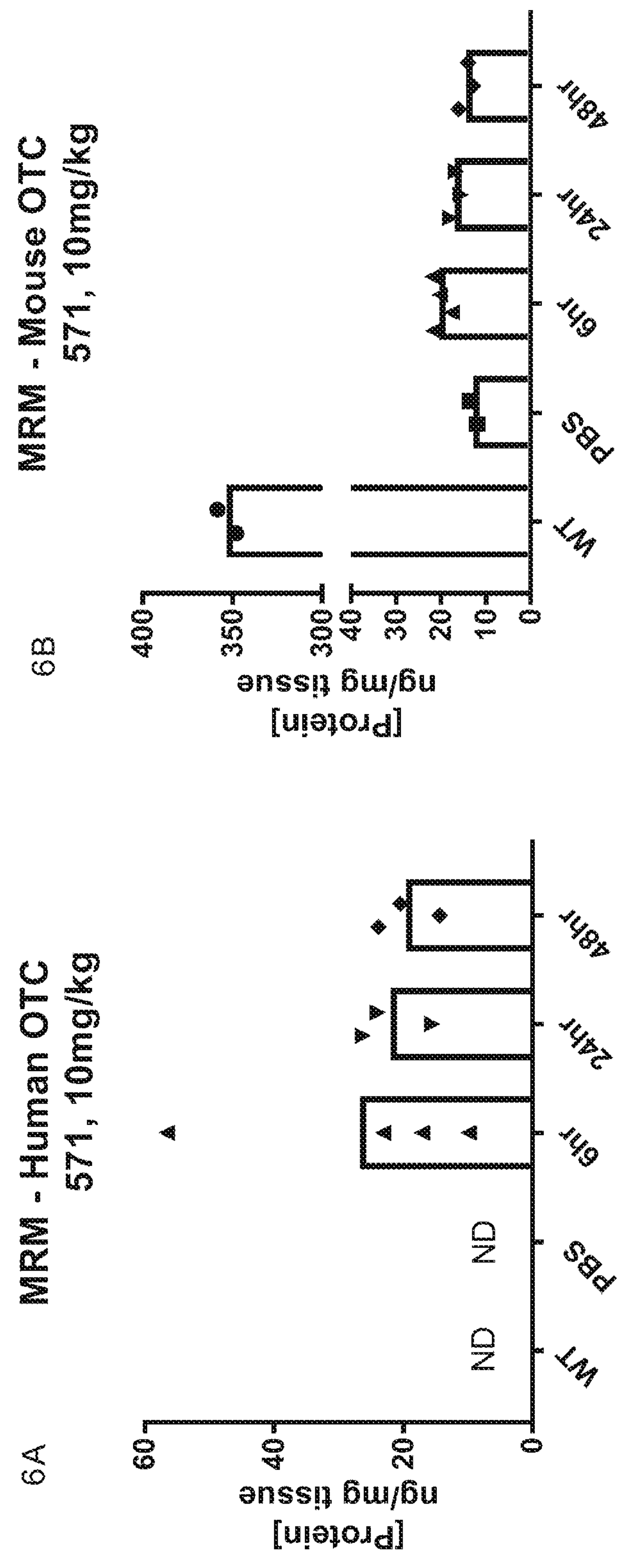
FIGS. 6A-B shows bar graphs depicting time course OTC expression levels in spf/ash mice dosed at 10 mg/kg with human-specific OTC-mRNA epitopes (FIG. 6A) or mouse-specific OTC-mRNA epitopes (FIG. 6B).

Example 7: OTC Expression Levels Measured by Multiple Reaction Monitoring (MRM) Mass Spectrometry in Spf/Ash Mice Dosed at 10 mg/kg Spf/ash mice received an IV injection with either PBS or lipid-formulated (as described in Example 1) OTC-mRNAs at a 10 mg/kg dosing. WT mice were used as internal controls to determine endogenous levels. A time course (6 h, 24 h and 48 h) was performed, and expression levels were measured by MRM using human and mouse specific epitopes for OTC. Graphs were made that represent the amount of protein (ng/mg tissue) detected by MRM specific for human OTC (FIG. 6, Panel A) or mouse (FIG. 6, Panel B). Human- and mouse-specific heavy peptides were designed to measure total levels of OTC in both species. This data set shows quantitative levels of human-specific OTC derived from translation of delivered mRNAs are detected. This expression maintains a high level of stability up to 48 h.

Figure 7:
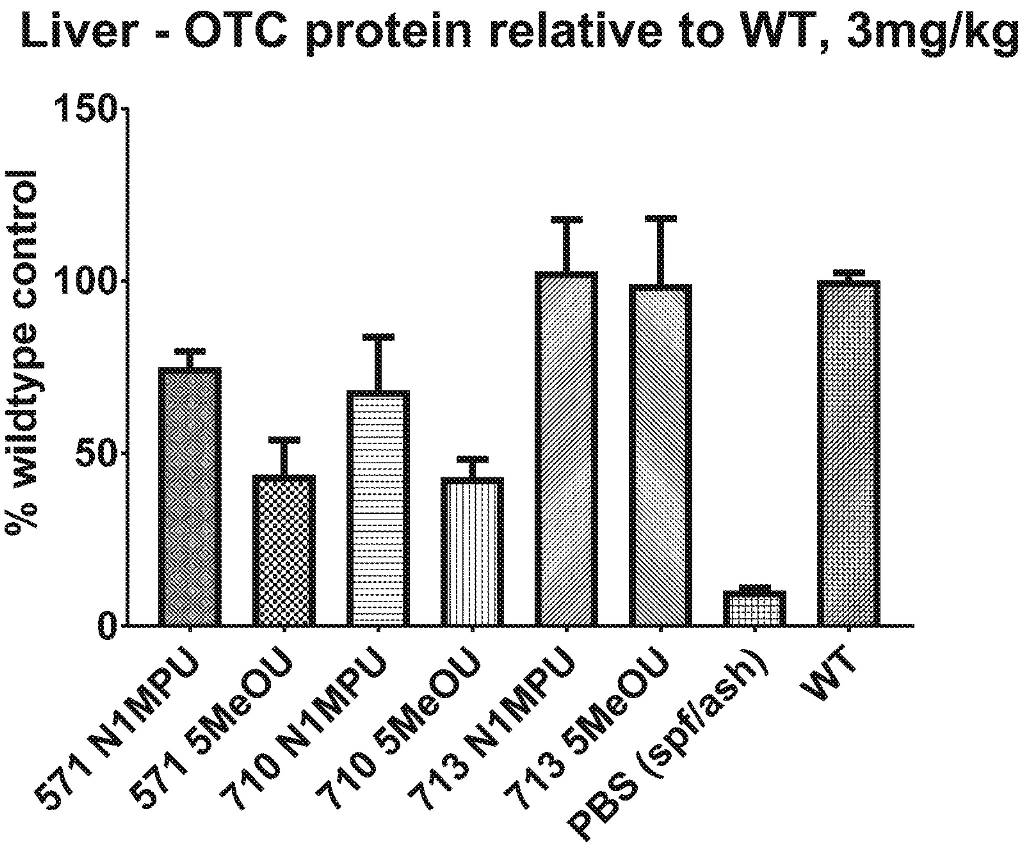
FIG. 7 is a bar graph depicting OTC expression levels in spf/ash mice dosed at 3 mg/kg with OTC-mRNAs using two different chemistries wherein 100% of the uridines are $N^1$-methylpseudouridine (N1MPU) and 100% of the uridines are 5-methoxyuridine (5MeOU).

Example 8: OTC Expression Levels Measured by Western Blot in WT Mice Dosed at 3 mg/kg Spf/ash mice received an IV injection with either phosphate buffered saline (PBS) or lipid-formulated OTC-mRNAs at a 3 mg/kg dosing using two different chemistries (N1MPU and 5MeOU). WT mice were used as internal controls to determine endogenous levels. Animals were sacrificed 24 h post-dose. OTC expression levels were measured by Western Blot (WB) using an OTC specific antibody. In the results provided in FIG. 7, the bars represent the percentage of expression relative to WT levels (100%). The data generated in this figure shows that WT levels of total OTC in a mouse background were achieved for several codon-optimized sequences.

Figure 8:
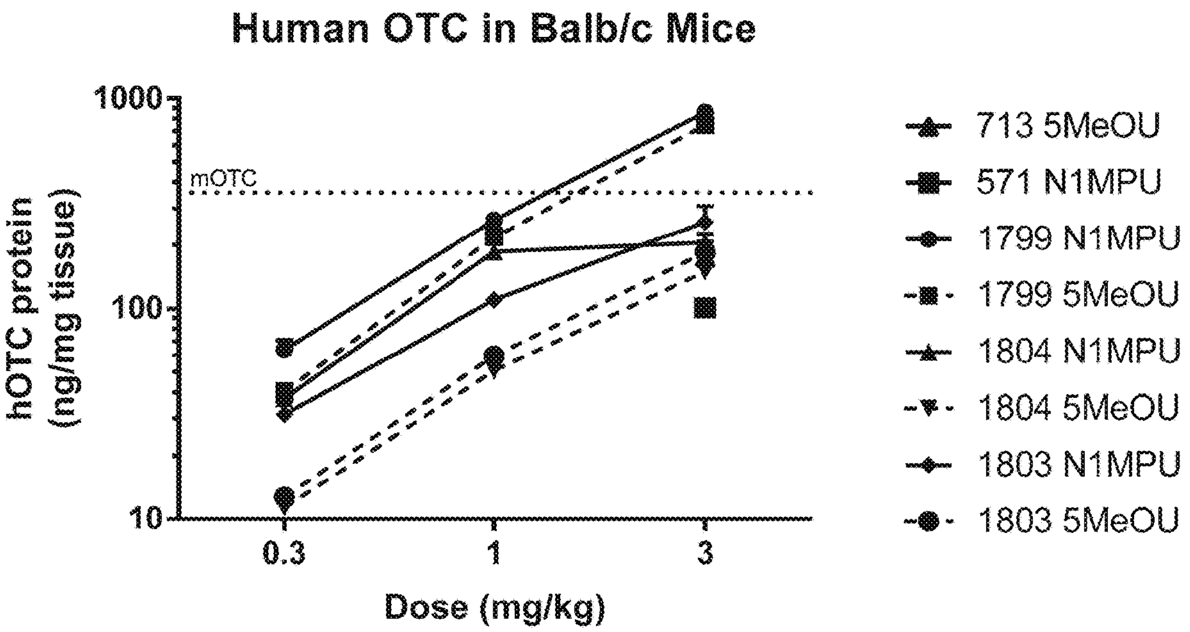
FIG. 8 is a graph depicting OTC expression levels in Balb/c mice dosed with OTC-mRNAs at three different doses and using two different chemistries (N1MPU and 5MeOU).

Example 9: OTC Expression Levels Measured by MRM in a Dose Range Finding Study Balb/c mice received an IV injection with either PBS or lipid-formulated OTC-mRNAs at three different doses: 0.3 mg/kg, 1 mg/kg and 3 mg/kg and using two different chemistries (N1MPU and 5MeOU). Animals were sacrificed 24 h post-dose and expression levels were measured by MRM using human and mouse specific epitopes for OTC. The graph in FIG. 8 represents the percentage of expression of human OTC (ng) per mg of liver tissue in Balb/c mice. The horizontal dotted line represents the relative mouse OTC levels in Balb/c mice. (FIG. 8). Expression levels of hOTC protein for mRNA construct 713 5MeOU and mRNA construct 571 N1MPU are indicated by arrows in FIG. 8. In this figure, the MRM was used to quantitatively determine human-selective and mouse-selective OTC protein levels. The data generated in this figure shows, in a dose dependent manner, that WT levels of human OTC in a mouse background are achieved with the codon-optimized sequences disclosed herein.

Example 10: Urinary Orotate Levels Measured in PBS and Treated Spf/Ash Mice

Figure 9:
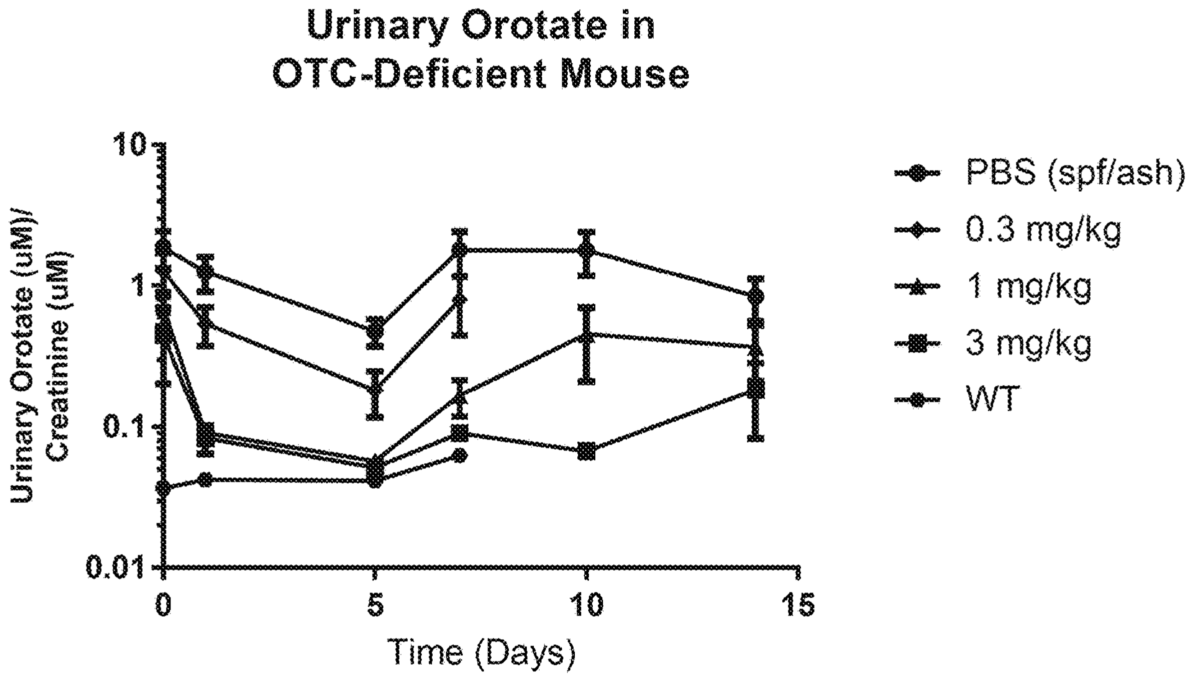
FIG. 9 is a graph depicting urinary orotate levels measured in spf/ash mice dosed with OTC-mRNA 1799.7 at three different doses: 0.3 mg/kg, 1 mg/kg and 3 mg/kg. 1799.1 is an mRNA having the sequence of SEQ ID NO: 175 wherein 100% of the uridines in SEQ ID NO: 175 are 5MeOU.

Spf/ash mice received an IV injection with either PBS or lipid-formulated OTC-mRNA construct 1799.7 (5MeOU chemistry) at three different doses: 0.3 mg/kg, 1 mg/kg and 3 mg/kg. WT and spf/ash mice were used to determine baseline and high urinary orotate levels, respectively. A spf/ash time course was determined, and urinary orotate levels were measured at each timepoint. The results can be seen in FIG. 9. Urinary orotate was normalized to creatinine, which is represented in the graph in the Y axis throughout the time course and serve as a proof-of-concept of functional restoration of OTC activity post-injection. At 3 mg/kg, a sustainable reduction of urinary orotate levels up to 14 days was observed.

Figure 10:
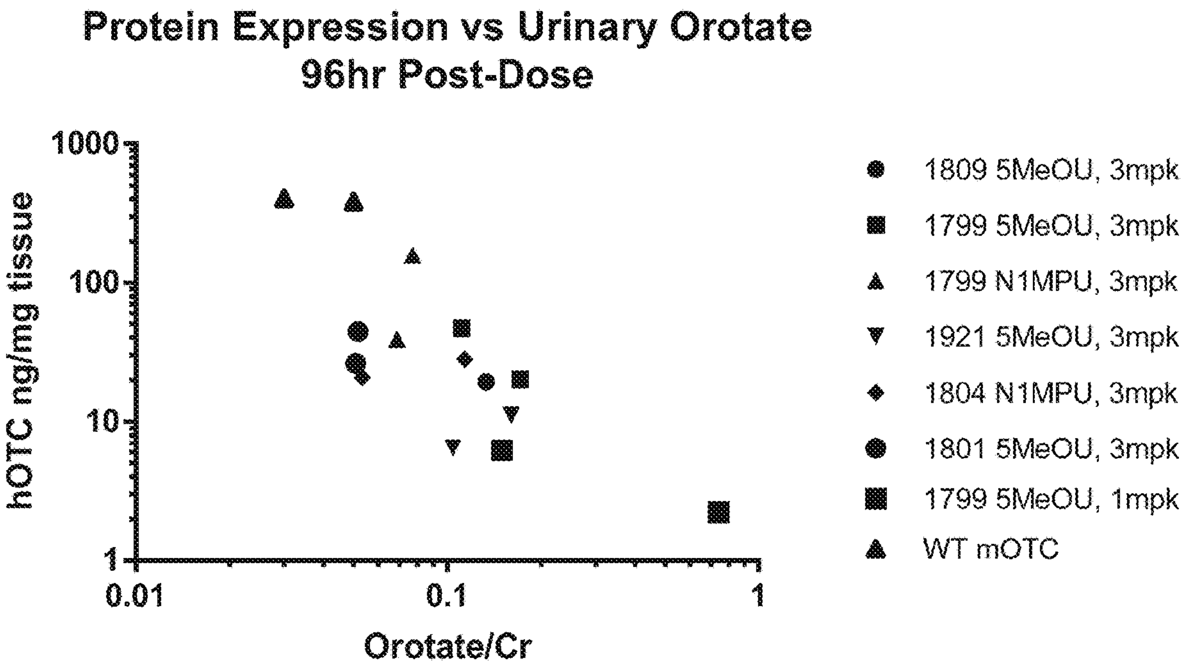
FIG. 10 is a scatter plot comparing human OTC expression levels and Urinary Orotate at 96 h in spf/ash mice dosed with OTC-mRNAs at 1 mg/kg and 3 mg/kg using two different chemistries (N1MPU and 5MeOU).

Example 11: Pharmacokinetic/Pharmacodynamic (PK/PD) Analysis Comparing Human OTC Expression Levels and Urinary Orotate at 96 h Spf/ash mice received an IV injection with either PBS or certain lipid-formulated OTC-mRNAs from Table 5 at 1 mg/kg and 3 mg/kg using two different chemistries (N1MPU and 5MeOU). WT mice were used as internal controls. Human-specific OTC levels were measured by MRM whereas urinary orotate was determined in each sample and normalized to creatinine. PK/PD is plotted in FIG. 10. PK/PD analysis shows the correlation between protein expression levels and reduction of urinary orotate in a compound-specific manner. Construct 1799.7 shows a high PK/PD correlation.

Figure 11:
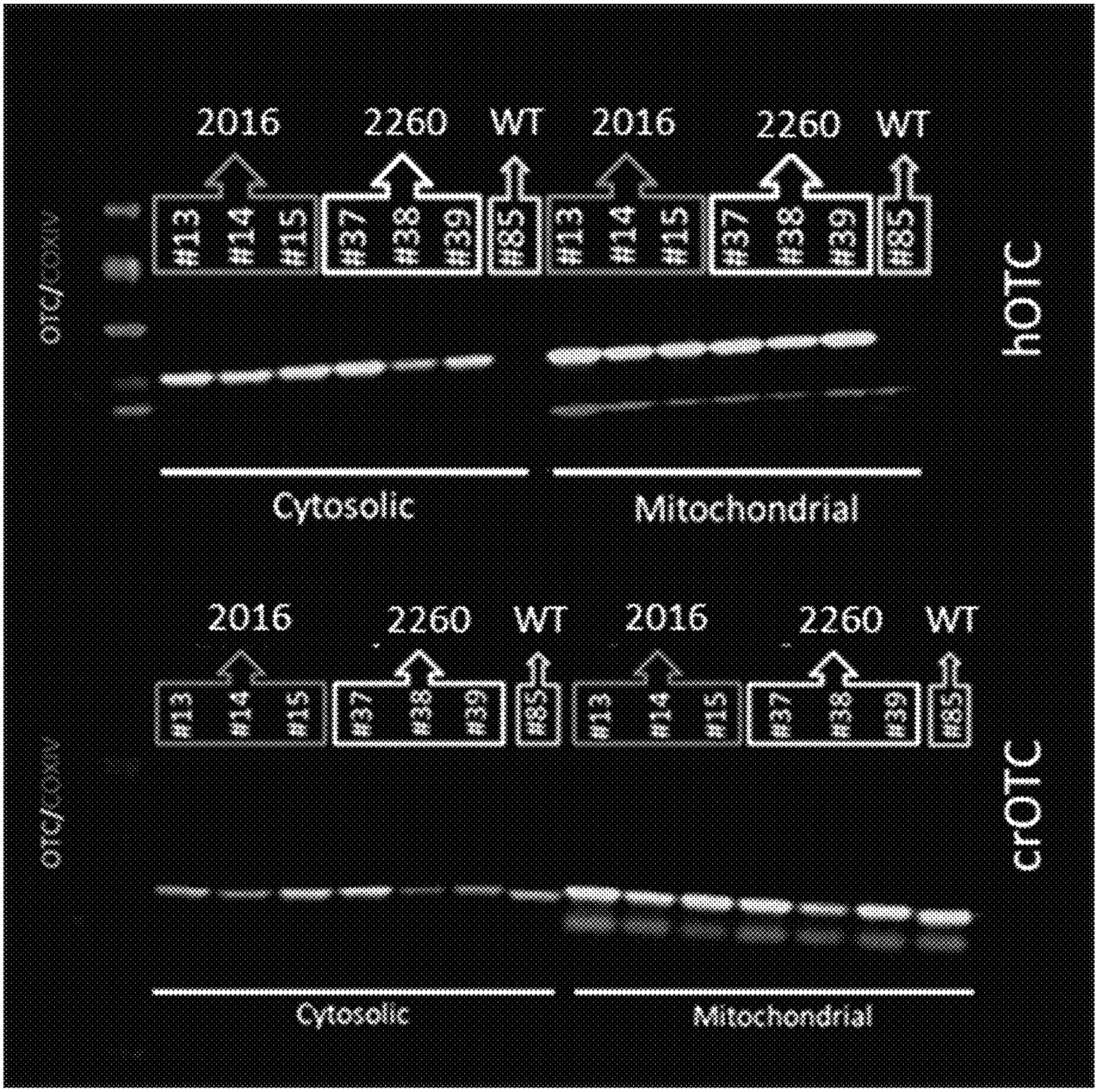
FIG. 11 is a western blot illustrating the protein expression levels of OTC-mRNAs in spf/ash mice dosed at 1 mg/kg and 3 mg/kg with lead OTC-mRNAs.

Example 12: Fractioning of Spf/Ash Mice In Vivo Samples Treated with Selected mRNAs Spf/ash mice received an IV injection with either PBS or lipid-formulated (as described in Example 1) OTC-mRNAs at 1 mg/kg and 3 mg/kg. WT mice were used as internal controls. Sample fractioning was performed on the liver samples, separating a cytosolic and a mitochondrial fraction. OTC levels were measured by WB using human specific (hOTC) and crossreactive (crOTC) antibodies (FIG. 11). Cyclooxygenase IV (CoxIV) was used as a mitochondrial control. OTC protein expression levels were measured by near-infrared fluorescent imaging systems and normalized to total protein. WB indicates differences in OTC expression levels within mitochondrial and cytosolic fractions when 2016 and 2260 mRNAs were delivered in the spf/ash mice. These results indicate that both compounds can efficiently target the mitochondria.

Example 13: Plot of the Mitochondrial Vs Cytosolic Fractions of Spf/Ash Mice Samples Treated with mRNA Constructs 2016 and 2260

Figure 12:
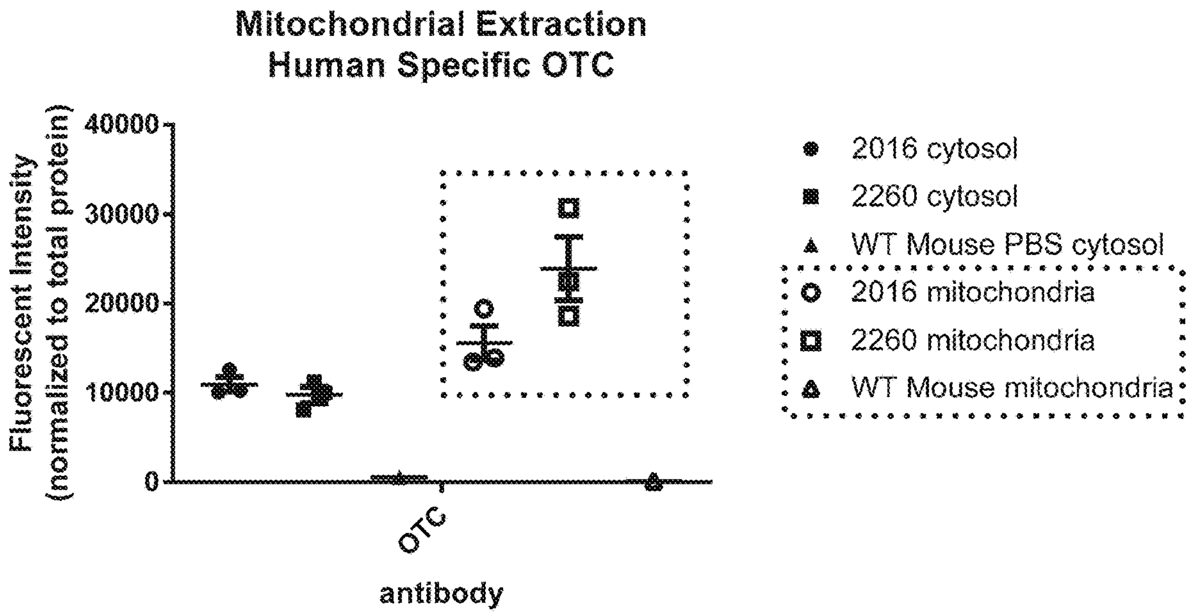
FIG. 12 is a western blot illustrating the protein expression levels in mitochondrial vs cytosolic fractions of spf/ash mice treated with lead OTC-mRNAs.

Spf/ash mice received an IV injection with either PBS or lipid-formulated OTC-mRNAs at 3 mg/kg. WT mice were used as internal controls. Sample fractioning was performed on the liver samples, separating a cytosolic and a mitochondrial fraction. OTC levels were measured by western blot using a human specific antibody. OTC protein expression levels were measured by near-infrared fluorescent imaging systems and both fractions normalized to total protein were plotted (FIG. 12). The plot of protein expression levels shown in FIG. 11 (Example 12), indicate that even though both compounds, 2016 and 2260, deliver similar protein levels in the cytosol, it is in the mitochondria where 2260 delivers more human OTC than 2016. The 2260 includes a modified mitochondrial signaling peptide sequence of the invention.

Example 14: Urinary Orotate Levels in Spf/Ash Mice Treated with mRNA Construct 2260

Figure 13:
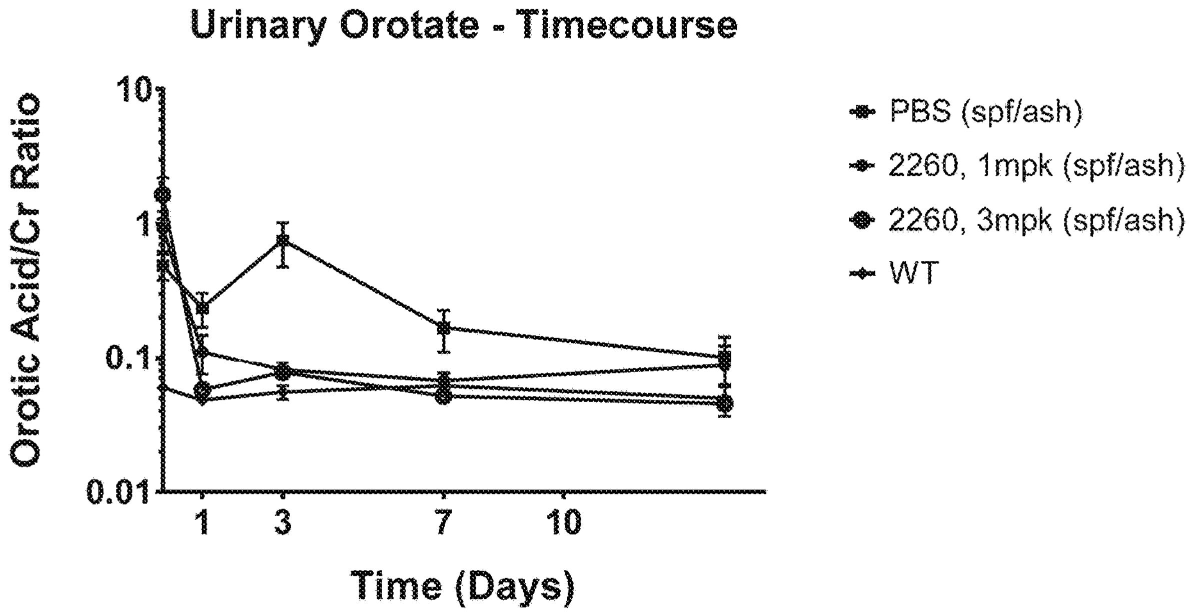
FIG. 13 is a plot illustrating the time course of expression of urinary orotate levels in spf/ash mice treated with lead OTC-mRNA.

Spf/ash mice received an IV injection with either PBS or lipid-formulated (as described in Example 1) OTC-mRNA at 1 mg/kg and 3 mg/kg. WT mice were included as an internal control. Urinary orotate levels were measured at 0, 1, 3, 7 and 14 days, and levels were normalized to creatinine (FIG. 13). The functional read-out of this assay shows that urinary orotate levels are reduced for up to 14 days with compound 2260, in a dose dependent manner.

Example 15: Survival of Spf/Ash Mice on a High Protein Diet During Treatment with OTC-mRNA Construct 1799.7 (5MeOU Chemistry)

Figure 14:
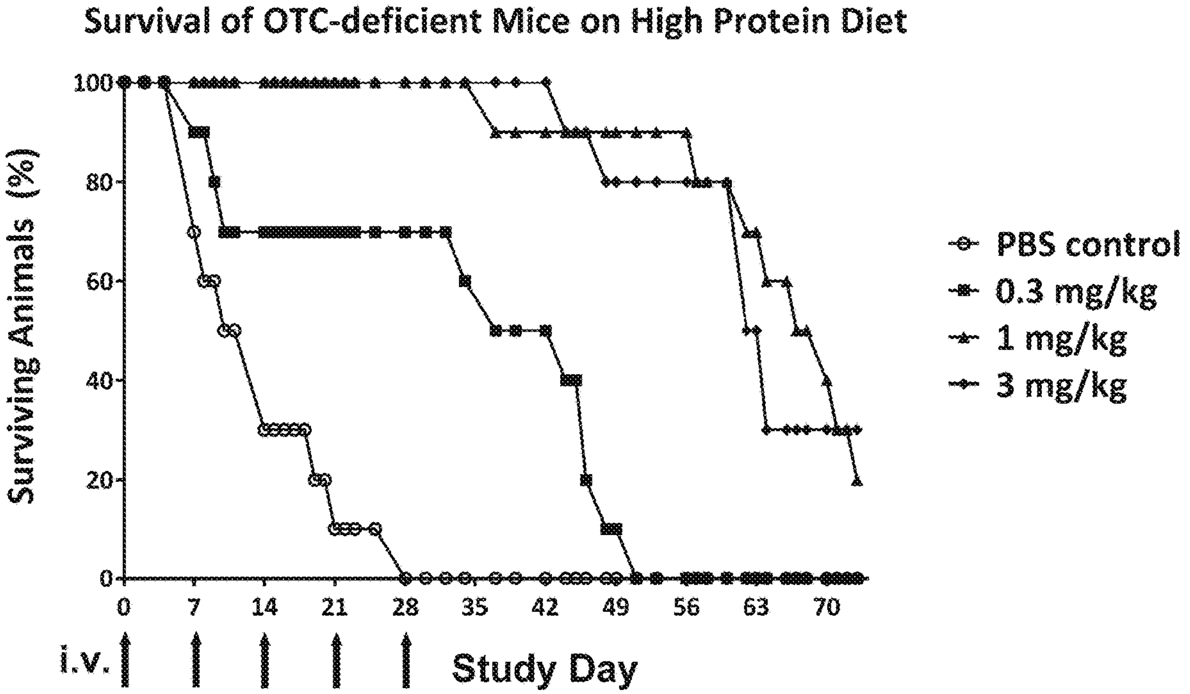
FIG. 14 is a plot illustrating the survival of OTC-deficient mice (spf/ash) on a high protein diet during treatment with three different doses of OTC-mRNA 1799.7.

Spf/ash mice received an IV injection with either PBS or lipid-formulated OTC-mRNA (1799.7) at three doses: 0.3 mg/kg, 1 mg/kg and 3 mg/kg. Mice were under a high protein diet since day 0 to the end of the study. Treated animals were injected by IV on days 0, 7, 14, 21 and 28 (arrows). Survival rates were determined every week. The plot in FIG. 14 summarizes the entire study timeline and the survival rates observed for the different groups. The results show that animals treated with human OTC mRNAs described herein have a higher chance to survive during a hyperammonemic crisis, suggesting the protective role of OTC mRNAs described herein in detoxifying the animals from toxic ammonia. This survival rate was dose-dependent, and animals treated with a 3 mg/kg dose have a higher survival rate than animals treated at 1 mg/kg or 0.3 mg/kg.

Figure 15:
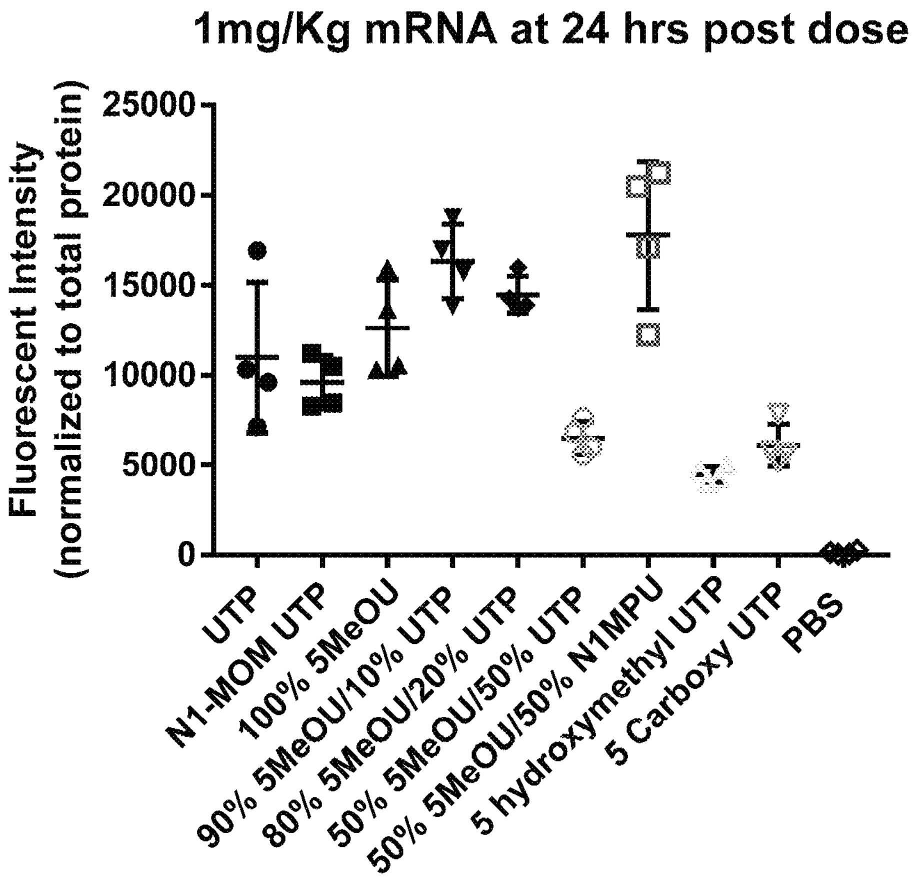
FIG. 15 is a plot illustrating hOTC expression levels in male C57BL/6 mice dosed with OTC-mRNAs (2262) having different modifications.

Example 16: Comparison of hOTC Expression Levels with Different Modifications Lipid-formulated OTC-mRNA construct 2262 doses were injected by IV in 8 week-old male C57BL/6 mice at a dose of 1 mg/kg. Different chemistries were used in this study as indicated in the bottom axis of the chart provided in FIG. 15. The mice livers were harvested at 24 hours post IV-administration, and western blot was performed using a hOTC specific antibody. Levels were normalized to total protein (FIG. 15). Each construct was formulated as a lipid nanoparticle comprising an ATX lipid as described in Example 1. This dataset indicates the impact of different uridine chemistries on the expression levels of our codon-optimized mRNAs.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this disclosure has been particularly shown and described with references to preferred embodiments thereof, it will be understood by those skilled in the art that various changes in form and details may be made therein without departing from the scope of the disclosure encompassed by the appended claims. It should also be understood that the embodiments described herein are not mutually exclusive and that features from the various embodiments may be combined in whole or in part in accordance with the disclosure.

SEQUENCE LISTING mRNA coding sequence for wild type human OTC (SEQ ID NO: 1)

```
AUGCUGUUUAAUCUGAGGAUCCUGUUAAACAAUGCAGCUUUUAGAAAUGGUC
ACAACUUCAUGGUUCGAAAUUUUCGGUGUGGACAACCACUACAAAAUAAAGU
GCAGCUGAAGGGCCGUGACCUUCUCACUCUAAAAAAC
UUUACCGGAGAAGAAAUUAAAUAUAUGCUAUGGCUAUCAGCAGAUCUGAAAU
UUAGGAUAAAACAGAAAGGAGAGUAUUUGCCUUUAUUGCAAGGGAAGUCCUU
AGGCAUGAUUUUUGAGAAAAGAAGUACUCGAACAAGAUUGUCUACAGAAACA
GGCUUUGCACUUCUGGGAGGACAUCCUUGUUUUCUUACCACACAAGAUAUUCA
UUUGGGUGUGAAUGAAAGUCUCACGGACACGGCCCGUGUAUUGUCUAGCAUG
GCAGAUGCAGUAUUGGCCGAGUGUAUAAACAAUCAGAUUUGGACACCCUGG
CUAAAGAAGCAUCCAUCCCAAUUAUCAAUGGGCUGUCAGAUUUGUACCAUCCU
AUCCAGAUCCUGGCUGAUUACCUCACGCUCCAGGAACACUAUAGCUCUCUGAA
AGGUCUUACCCUCAGCUGGAUCGGGGAUGGGAACAAUAUCCUGCACUCCAUCA
```

-continued

| SEQUENCE LISTING |
|---|

UGAUGAGCGCAGCGAAAUUCGGAAUGCACCUUCAGGCAGCUACUCCAAAGGGU
UAUGAGCCGGAUGCUAGUGUAACCAAGUUGGCAGAGCAGUAUGCCAAAGAGA
AUGGUACCAAGCUGUUGCUGACAAAUGAUCCAUUGGAAGCAGCGCAUGGAGG
CAAUGUAUUAAUUACAGACACUUGGAUAAGCAUGGGACAAGAAGAGGAGAAG
AAAAAGCGGCUCCAGGCUUUCCAAGGUUACCAGGUUACAAUGAAGACUGCUA
AAGUUGCUGCCUCUGACUGGACAUUUUUACACUGCUUGCCCAGAAAGCCAGAA
GAAGUGGAUGAUGAAGUCUUUUAUUCUCCUCGAUCACUAGUGUUCCCAGAGG
CAGAAAACAGAAAGUGGACAAUCAUGGCUGUCAUGGUGUCCCUGCUGACAGA
UUACUCACCUCAGCUCCAGAAGCCUAAAUUUUGA

DNA coding sequence for wild type human OTC (SEQ ID NO: 2)
ATGCTGTTTAATCTGAGGATCCTGTTAAACAATGCAGCTTTTAGAAATGGTCACA
ACTTCATGGTTCGAAATTTTCGGTGTGGACAACCACTACAAAATAAAGTGCAGCT
GAAGGGCCGTGACCTTCTCACTCTAAAAAACTTTACCGGAGAAGAAATTAAATA
TATGCTATGGCTATCAGCAGATCTGAAATTTAGGATAAAACAGAAAGGAGAGTA
TTTGCCTTTATTGCAAGGGAAGTCCTTAGGCATGATTTTTGAGAAAAGAAGTACT
CGAACAAGATTGTCTACAGAAACAGGCTTTGCACTTCTGGGAGGACATCCTTGTT
TTCTTACCACACAAGATATTCATTTGGGTGTGAATGAAAGTCTCACGGACACGGC
CCGTGTATTGTCTAGCATGGCAGATGCAGTATTGGCTCGAGTGTATAAACAATCA
GATTTGGACACCCTGGCTAAAGAAGCATCCATCCCAATTATCAATGGGCTGTCAG
ATTTGTACCATCCTATCCAGATCCTGGCTGATTACCTCACGCTCCAGGAACACTA
TAGCTCTCTGAAAGGTCTTACCCTCAGCTGGATCGGGGATGGGAACAATATCCTG
CACTCCATCATGATGAGCGCAGCGAAATTCGGAATGCACCTTCAGGCAGCTACTC
CAAAGGGTTATGAGCCGGATGCTAGTGTAACCAAGTTGGCAGAGCAGTATGCCA
AAGAGAATGGTACCAAGCTGTTGCTGACAAATGATCCATTGGAAGCAGCGCATG
GAGGCAATGTATTAATTACAGACACTTGGATAAGCATGGGACAAGAAGAGGAGA
AGAAAAAGCGGCTCCAGGCTTTCCAAGGTTACCAGGTTACAATGAAGACTGCTA
AAGTTGCTGCCTCTGACTGGACATTTTTACACTGCTTGCCCAGAAAGCCAGAAGA
AGTGGATGATGAAGTCTTTTATTCTCCTCGATCACTAGTGTTCCCAGAGGCAGAA
AACAGAAAGTGGACAATCATGGCTGTCATGGTGTCCCTGCTGACAGATTACTCAC
CTCAGCTCCAGAAGCCTAAATTTTGA Human wild type OTC amino acid sequence
(The signal peptide for mitochondrial import is underlined*)(SEQ ID NO: 3)
MLFNLRILLNNAAFRNGHNFMVRNFRCGQPLQNKVQLKGRDLLTLKNFTGEEIK
YMLWLSADLKFRIKQKGEYLPLLQGKSLGMIFEKRSTRTRLSTETGFALLGGHPCFL
TTQDIHLGVNESLTDTARVLSSMADAVLARVYKQSDLDTLAKEASIPIF
GLSDLYHPIQILADYLTLQEHYSSLKGLTLSWIGDGNNILHSIMMSAAKFGMHLQAA
TPKGYEPDASVTKLAEQYAKENGTKLLLTNDPLEAAHGGNVLITDTWISMGQEEEK
KKRLQAFQGYQVTMKTAKVAASDWTFLHCLPRKPEEVDDEVFYSPRSLVFPEAENR
KWTIMAVMVSLLTDYSPQLQKPKF Modified OTC amino acid sequence
(The signal peptide for mitochondrial import is underlined*)(SEQ ID NO: 4)
MLVFNLRILLNNAAFRNGHNFMVRNFRCGQPLQNRVQLKGRDLLTLKNFTGEEI
RYMLWLSADLKFRIKQKGEYLPLLQGKSLGMIFEKRSTRTRLSTETGFALLGGHPCF
LTTQDIHLGVNESLTDTARVLSSMADAVLARVYKQSDLDTLAKEASIPIINGLSDLYH
PIQILADYLTLQEHYSSLKGLTLSWIGDGNNILHSIMMSAAKFGMHLQAATPKGYEP
DASVTKLAEQYAKENGTKLLLTNDPLEAAHGGNVLITDTWISMGQEEEKKKRLQAF
QGYQVTMKTAKVAASDWTFLHCLPRKPEEVDDEVFYSPRSLVFPEAENRKWTIMA
VMVSLLTDYSPQLQKPKF TEV (SEQ ID NO: 5)
TCAACACAACATATACAAAACAAACGAATCTCAAGCAATCAAGCATTCTACTTCT
ATTGCAGCAATTTAAATCATTTCTTTTAAAGCAAAAGCAATTTTCTGAAAATTTTC
ACCATTTACGAACGATAG

AT1G58420 (SEQ ID NO: 6)
ATTATTACATCAAAACAAAAAGCCGCCA

ARC5-2 (SEQ ID NO: 7)
CTTAAGGGGGCGCTGCCTACGGAGGTGGCAGCCATCTCCTTCTCGGCATCAAGCT
TACCATGGTGCCCCAGGCCCTGCTCTTgGTCCCGCTGCTGGTGTTCCCCCTCTGCT
TCGGCAAGTTCCCCATCTACACCATCCCCGACAAGCTGGGGCCGTGGAGCCCCAT
CGACATCCACCACCTGTCCTGCCCCAACAACCTCGTGGTCGAGGACGAGGGCTG
CACCAACCTGAGCGGGTTCTCCTAC

HCV (SEQ ID NO: 8)
TGAGTGTCGT ACAGCCTCCA GGCCCCCCCC TCCCGGGAGA GCCATAGTGG
TCTGCGGAACCGGTGAGTAC ACCGGAATTG CCGGGAAGAC TGGGTCCTTT
CTTGGATAAA CCCACTCTATGCCCGGCCAT TTGGGCGTGC CCCCGCAAGA
CTGCTAGCCG AGTAGTGTTG GGTTGCG

HUMAN ALBUMIN (SEQ ID NO: 9)
AATTATTGGTTAAAGAAGTATATTAGTGCTAATTTCCCTCCGTTTGTCCTAGCTTT
TCTCTTCTGTCAACCCCACACGCCTTTGGCACA

-continued

SEQUENCE LISTING

EMCV (SEQ ID NO: 10)
CTCCCTCCCC CCCCCCTAAC GTTACTGGC CGAAGCCGCTT GGAATAAGGC
CGGTGTGCGT TTGTCTATAT GTTATTTTC CACCATATTGC CGTCTTTTGG
CAATGTGAGG GCCCGGAAAC CTGGCCCTGT CTTCTTGACG AGCATTCCTA
GGGGTCTTTC CCCTCTCGCC AAAGGAATGC AAGGTCTGTT GAATGTCGTG
AAGGAAGCAG TTCCTCTGGA AGCTTCTTGA AGACAAACAA CGTCTGTAGC
GACCCTTTGC AGGCAGCGGA ACCCCCCACC TGGCGACAGG TGCCTCTGCG
GCCAAAAGCC ACGTGTATAA GATACACCTG CAAAGGCGGC ACAACCCCAG
TGCCACGTTG TGAGTTGGAT AGTTGTGGAA AGAGTCAAAT GGCTCTCCTC
AAGCGTATTC AACAAGGGGC TGAAGGATGC CCAGAAGGTA CCCCATTGTA
TGGGATCTGA TCTGGGGCCT CGGTGCACAT GCTTTACGTG TGTTTAGTCG
AGGTTAAAAA ACGTCTAGGC CCCCCGAACC ACGGGGACGT GGTTTTCCTT
TGAAAAACAC GATGATAAT

HSP70-P2 (SEQ ID NO: 11)
GTCAGCTTTCAAACTCTTTGTTTCTTGTTTGTTGATTGAGAATA

HSP70-M1 (SEQ ID NO: 12)
CTCTCGCCTGAGAAAAAAAATCCACGAACCAATTTCTCAGCAACCAGCAGCACG

HSP72-M2 (SEQ ID NO: 13)
ACCTGTGAGGGTTCGAAGGAAGTAGCAGTGTTTTTTGTTCCTAGAGGAAGAG

HSP17.9 (SEQ ID NO: 14)
ACACAGAAACATTCGCAAAACAAAATCCCAGTATCAAAATTCTTCTCTTTTTTT
CATATTTCGCAAAGAC

HSP70-P1 (SEQ ID NO: 15)
CAGAAAAATTTGCTACATTGTTTCACAAACTTCAAATATTATTCATTTATTT

XBG (SEQ ID NO: 16)
CTAGTGACTGACTAGGATCTGGTTACCACTAAACCAGCCTCAAGAACACCCGAA
TGGAGTCTCTAAGCTACATAATACCAACTTACACTTACAAAATGTTGTCCCCCAA
AATGTAGCCATTCGTATCTGCTCCTAATAAAAAGAAAGTTTCTTCACAT

HUMAN HAPTOGLOBIN (SEQ ID NO: 17)
TGCAAGGCTGGCCGGAAGCCCTTGCCTGAAAGCAAGATTTCAGCCTGGAAGAGG
GCAAAGTGGACGGGAGTGGACAGGAGTGGATGCGATAAGATGTGGTTTGAAGCT
GATGGGTGCCAGCCCTGCATTGCTGAGTCAATCAATAAAGAGCTTTCTTTTGACC
CAT

HUMAN APOLIPOPROTEIN E (SEQ ID NO: 18)
ACGCCGAAGCCTGCAGCCATGCGACCCCACGCCACCCCGTGCCTCCTGCCTCCGC
GCAGCCTGCAGCGGGAGACCCTGTCCCCGCCCCAGCCGTCCTCCTGGGGTGGAC
CCTAGTTTAATAAAGATTCACCAAGTTTCACGCA

HCV (SEQ ID NO: 19)
TAGAGCGGCAAACCCTAGCTACACTCCATAGCTAGTTTCTTTTTTTTTTGTTTTTTT
TTTTTTTTTTTTTTTTTTTTTTTTTTTTTTTTTCCTTTCTTTTCCTTCTTTTTTTCCTCTT
TTCTTGGTGGCTCCATCTTAGCCCTAGTCACGGCTAGCTGTGAAAGGTCCGTGAG
CCGCATGACTGCAGAGAGTGCCGTAACTGGTCTCTCTGCAGATCATGT

MOUSE ALBUMIN (SEQ ID NO: 20)
ACACATCACAACCACAACCTTCTCAGGCTACCCTGAGAAAAAAAGACATGAAGA
CTCAGGACTCATCTTTTCTGTTGGTGTAAAATCAACACCCTAAGGAACACAAATT
TCTTTAAACATTTGACTTCTTGTCTCTGTGCTGCAATTAATAAAAAATGGAAAGA
ATCTAC

HUMAN ALPHA GLOBIN (SEQ ID NO: 21)
GCTGGAGCCTCGGTAGCCGTTCCTCCTGCCCGCTGGGCCTCCCAACGGGCCCTCC
TCCCCTCCTTGCACCGGCCCTTCCTGGTCTTTGAATAAAGTCTGAGTGGGCAGCA

EMCV (SEQ ID NO: 22)
TAGTGCAGTCAC TGGCACAACG CGTTGCCCGG TAAGCCAATC GGGTATACAC
GGTCGTCATACTGCAGACAG GGTTCTTCTA CTTTGCAAGA TAGTCTAGAG
TAGTAAAATA AATAGTATAAG (SEQ ID NO: 23)
GCCACC (SEQ ID NO: 24)
GCCA (SEQ ID NO: 25)
AUAAGUGAA

-continued

SEQUENCE LISTING

>mARM563 (SEQ ID NO: 26)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUUAAUCUGAGGAUCCUG
UUAAACAAUGCAGCUUUUAGAAAUGGUCACAACUUCAUGGUUCGAAAUUUUC
GGUGUGGACAACCACUACAAAAUAAAGUGCAGCUGAAGGGCCGUGACCUUCUC
ACUCUAAAAAACUUUACCGGAGAAGAAAUUAAAUAUAUGCUAUGGCUAUCAG
CAGAUCUGAAAUUUAGGAUAAAACAGAAAGGAGAGUAUUUGCCUUUAUUGCA
AGGGAAGUCCUUAGGCAUGAUUUUUGAGAAAAGAAGUACUCGAACAAGAUUG
UCUACAGAAACAGGCUUUGCACUUCUGGGAGGACAUCCUUGUUUUCUUACCAC
ACAAGAUAUUCAUUUGGGUGUGAAUGAAAGUCUCACGGACACGGCCCGUGUA
UUGUCUAGCAUGGCAGAUGCAGUAUUGGCUCGAGUGUAUAAACAAUCAGAUU
UGGACACCCUGGCUAAAGAAGCAUCCAUCCCAAUUAUCAAUGGGCUGUCAGAU
UUGUACCAUCCUAUCCAGAUCCUGGCUGAUUACCUCACGCUCCAGGAACACUA
UAGCUCUCUGAAAGGUCUUACCCUCAGCUGGAUCGGGGAUGGGAACAAUAUCC
UGCACUCCAUCAUGAUGAGCGCAGCGAAAUUCGGAAUGCACCUUCAGGCAGCU
ACUCCAAAGGGUUAUGAGCCGGAUGCUAGUGUAACCAAGUUGGCAGAGCAGU
AUGCCAAAGAGAAUGGUACCAAGCUGUUGCUGACAAAUGAUCCAUUGGAAGC
AGCGCAUGGAGGCAAUGUAUUAAUUACAGACACUUGGAUAAGCAUGGGACAA
GAAGAGGAGAAGAAAAAGCGGCUCCAGGCUUUCCAAGGUUACCAGGUUACAA
UGAAGACUGCUAAAGUUGCUGCCUCUGACUGGACAUUUUUACACUGCUUGCCC
AGAAAGCCAGAAGAAGUGGAUGAUGAAGUCUUUUAUUCUCCUCGAUCACUAG
UGUUCCCAGAGGCAGAAAACAGAAAGUGGACAAUCAUGGCUGUCAUGGUGUC
CCUGCUGACAGAUUACUCACCUCAGCUCCAGAAGCCUAAAUUUUGACUCGAGC
UAGUGACUGACUAGGAUCUGGUUACCACUAAACCAGCCUCAAGAACACCCGAA
UGGAGUCUCUAAGCUACAUAAUACCAACUUACACUUACAAAAUGUUGUCCCCC
AAAAUGUAGCCAUUCGUAUCUGCUCCUAAUAAAAAGAAAGUUUCUUCACAUU
CUAG

>mARM564 (SEQ ID NO: 27)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUCUUUAAUCUGCGCAUCUUA
CUGAACAACGCCGCAUUCCGGAACGGUCACAACUUCAUGGUCCGCAAUUUCCG
CUGUGGCCAGCCGCUUCAAAACAAGGUCCAGCUGAAGGGACGGGAUCUGCUGA
CACUGAAGAACUUCACCGGAGAAGAGAUCAAGUACAUGCUGUGGCUCAGCGCA
GACUUGAAGUUCCGGAUCAAGCAGAAGGGAGAAUACUUGCCCCUGCUGCAAG
GAAAGUCGCUGGGAAUGAUUUUUGAGAAGCGGUCAACUCGCACCAGACUCUCC
ACCGAAACUGGUUUCGCACUGCUUGGCGGGCACCCUUGCUUCCUGACGACUCA
GGACAUCCACCUCGGCGUGAACGAAUCGCUAACCGAUACCGCCAGAGUGCUUU
CUUCCAUGGCCGACGCGGUGCUGGCCAGGGUGUACAAGCAGUCCGACCUCGAU
ACCUUGGCAAAGGAGGCUUCCAUUCCCAUCAUCAACGGCCUGAGCGACCUGUA
CCACCCAAUCCAAAUCCUGGCUGACUACCUGACCCUGCAAGAGCACUACAGCA
GCCUGAAGGGUCUGACCCUGUCAUGGAUUGGCGAUGGAAACAAUAUUCUGCA
CUCCAUCAUGAUGUCCGCCGCGAAGUUCGGAAUGCAUCUGCAAGCCGCCACUC
CAAAAGGAUACGAACCGGAUGCGUCCGUGACCAAGUUGGCGGAACAGUACGCG
AAGGAGAACGGAACCAAGCUUCUGCUGACUAACGACCCCCUCGAGGCUGCGCA
UGGGGGCAACGUGCUGAUUACCGACACCUGGAUCUCCAUGGGGCAGGAGGAA
GAGAAGAAGAAGAGACUGCAGGCAUUCCAGGGGUACCAGGUCACCAUGAAAA
CCGCAAAAGUGGCAGCUUCGGACUGGACUUUCCUGCAUUGCCUGCCGAGGAAG
CCGGAGGAAGUCGACGACGAAGUGUUCUACUCGCCUCGGUCCCUGGUGUUCCC
CGAGGCCGAAAACCGGAAGUGGACCAUCAUGGCCGUGAUGGUGUCCUUGCUGA
CUGACUAUAGCCCGCAGCUGCAGAAGCCUAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM565 (SEQ ID NO: 28)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUUAACCUACGUAUUUUG
CUCAACAAUGCAGCCUUUAGAAACGGACAUAACUUUAUGGUUCGAAACUUUC
GCUGCGGGCAGCCACUGCAGAACAAGGUCCAGCUGAAAGGGAGAGAUUUGCUC
ACGCUGAAGAACUUUACUGGCGAAGAAAUCAAGUAUAUGCUGUGGUUGUCCG
CGGACCUCAAGUUUCGGAUUAAGCAGAAAGGGGAGUAUCUGCCACUGCUGCA
AGGAAAGAGCCUCGGCAUGAUCUUCGAGAAGCGGAGCACUCGGACCAGGCUGA
GUACCGAAACUGGCUUCGCAUUGUUGGGUGGACAUCCAUGUUUUCUGACAAC
GCAGGACAUUCAUCUGGGCGUGAACGAGAGUCUGACGGACACAGCUCGCGUUC
UGUCCUCUAUGGCUGAUGCGGUGUUGGCCCGGGUCUAUAAGCAGUCCGAUUU
GGACACCUUGGCUAAGGAAGCUAGCAUACCGAUUAUCAAUGGGCUGUCCGACC
UGUAUCACCCUAUUCAAAUCCUGGCCGACUACCUCACACUGCAAGAACACUAU
AGCUCAUUGAAGGGACUGACCCUGAGCUGGAUAGGGGACGGAAACAACAUCC
UACAUAGCAUUAUGAUGUCCGCUGCCAAGUUUGGCAUGCAUCUUCAAGCCGCC
ACGCCAAAGGGUUAUGAGCCCGACGCGUCAGUGACAAAGCUGGCCGAGCAGUA
CGCUAAGGAGAAUGGUACCAAAUUACUGCUGACUAAUGAUCCACUGGAGGCU
GCACAUGGCGGCAAUGUACUGAUCACCGACACAUGGAUCUCGAUGGGCCAGGA
GGAAGAAAAGAAGAAGAGGCUUCAGGCCUUCCAAGGCUACCAGGUCACCAUG

-continued

SEQUENCE LISTING

AAAACAGCUAAGGUUGCAGCAUCUGAUUGGACCUUUCUGCACUGUCUGCCAAG
GAAGCCCGAAGAGGUGGACGAUGAAGUAUUCUAUAGCCCACGGAGUUUGGUG
UUCCCUGAGGCUGAAAAUAGGAAGUGGACAAUUAUGGCCGUAAUGGUGUCCC
UGUUAACCGACUACUCUCCGCAACUGCAGAAACCUAAGUUUUAGCUCGAGCUA
GUGACUGACUAGGAUCUGGUUACCACUAAACCAGCCUCAAGAACACCCGAAUG
GAGUCUCUAAGCUACAUAAUACCAACUUACACUUACAAAAUGUUGUCCCCCAA
AAUGUAGCCAUUCGUAUCUGCUCCUAAUAAAAAGAAAGUUUCUUCACAUUCU
AG

>mARM566 (SEQ ID NO: 29)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUUAACUUAAGGAUCCUG
CUGAACAACGCCGCUUUUCGUAACGGUCAUAACUUUAUGGUCCGGAACUUUAG
AUGUGGCCAGCCGCUGCAGAACAAGGUUCAGCUGAAGGGGAGGGAUCUGCUG
ACCUUGAAGAACUUUACCGGCGAAGAGAUCAAGUACAUGUUGUGGCUGAGCG
CCGAUCUGAAGUUUAGGAUUAAGCAGAAGGGGGAGUAUUUGCCACUGCUGCA
AGGAAAAUCCUUGGGGAUGAUCUUCGAGAAGCGCUCCACUAGAACCCGGCUAA
GCACAGAAACCGGCUUCGCACUUCUGGGUGGACAUCCCUGUUUUCUGACGACG
CAGGAUAUACACCUGGGCGUGAAUGAGAGUCUGACGGACACAGCUAGGGUGU
UGAGCAGCAUGGCCGAUGCAGUACUGGCCCGCGUUUAUAAGCAGAGCGACUUG
GACACACUGGCCAAGGAAGCGUCAAUUCCGAUUAUCAAUGGGCUGUCAGACCU
GUAUCAUCCCAUUCAAAUCUUGGCUGACUAUCUGACCCUGCAAGAACAUUACA
GCUCCCUGAAGGGCCUCACGUUGUCCUGGAUUGGCGACGGAAACAACAUUCUG
CAUUCGAUCAUGAUGAGCGCUGCUAAGUUUGGCAUGCACCUCCAAGCCGCUAC
ACCUAAGGGAUAUGAGCCUGAUGCCAGCGUAACCAAGCUGGCCGAACAGUACG
CGAAGGAGAAUGGCACGAAACUGCUGUUGACAAAUGACCCACUGGAGGCAGC
UCACGGUGGCAACGUGCUGAUCACCGACACGUGGAUAUCUAUGGGACAGGAA
GAAGAGAAGAAGAAGCGGCUGCAGGCAUUCCAAGGGUAUCAGGUCACCAUGA
AAACGGCCAAGGUUGCUGCAUCCGACUGGACAUUUCUGCAUUGCUUGCCCCGC
AAACCAGAAGAAGUAGACGACGAAGUCUUUUAUUCCCCACGGUCGCUGGUGU
UCCCCGAGGCGGAGAAUCGAAAGUGGACGAUUAUGGCCGUGAUGGUGUCCCU
GCUGACUGAUUACUCUCCCCAACUGCAAAAGCCUAAGUUUUAGCUCGAGCUAG
UGACUGACUAGGAUCUGGUUACCACUAAACCAGCCUCAAGAACACCCGAAUGG
AGUCUCUAAGCUACAUAAUACCAACUUACACUUACAAAAUGUUGUCCCCCAAA
AUGUAGCCAUUCGUAUCUGCUCCUAAUAAAAAGAAAGUUUCUUCACAUUCUA
G

>mARM567 (SEQ ID NO: 30)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACCUGAGGAUCCUC
CUGAACAACGCCGCCUUUCGCAAUGGUCACAACUUUAUGGUCCGGAACUUCAG
AUGCGGCCAGCCGCUGCAGAACAAGGUCCAGCUGAAGGGACGGGAUCUGCUGA
CUCUGAAGAACUUCACCGGAGAAGAGAUCAAGUACAUGCUGUGGCUGUCGGCC
GACCUGAAGUUCAGGAUCAAGCAGAAGGGAGAAUACCUCCCGCUGCUGCAAGG
AAAGUCCCUGGGCAUGAUUUUCGAGAAGCGCUCGACCAGAACUCGGUUGUCCA
CCGAAACCGGGUUUGCGCUGCUGGGCGGACAUCCUUGCUUCCUGACGACUCAG
GAUAUUCACCUGGGAGUGAACGAGUCGCUGACCGACACCGCCAGAGUGCUGAG
CUCGAUGGCCGACGCCGUGUUGGCACGCGUGUACAAGCAGUCCGAUCUGGAUA
CCCUGGCCAAAGAAGCUUCCAUCCCGAUCAUUAACGGGCUGAGCGACCUCUAC
CACCCCAUUCAAAUCCUGGCCGACUACCUGACUCUGCAAGAACACUACAGCUC
GCUGAAGGGGUUGACUCUGUCCUGGAUCGGCGACGGAAACAACAUCCUGCACU
CCAUCAUGAUGUCGGCCGCAAAGUUCGGCAUGCAUUUGCAAGCCGCCACCCCA
AAGGGCUACGAACCAGACGCGAGCGUCACCAAGCUGGCCGAACAGUACGCGAA
GGAAAAUGGUACUAAGCUGCUGCUGACCAACGACCCAUUGGAAGCUGCCCAUG
GUGGAAACGUGCUGAUCACCGACACCUGGAUCUCGAUGGGCCAGGAAGAGGA
GAAGAAGAAGCGGCUGCAGGCGUUCCAGGGGUAUCAGGUCACCAUGAAAACA
GCCAAAGUGGCAGCGUCAGACUGGACCUUCCUCCACUGUCUGCCUCGCAAGCC
AGAGGAGGUGGACGACGAGGUGUUCUACUCCCCUCGGUCCCUCGUGUUCCCUG
AGGCUGAGAACCGGAAGUGGACCAUUAUGGCCGUGAUGGUGUCACUCCUGAC
UGAUUACUCCCCGCAACUGCAGAAGCCCAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM568 (SEQ ID NO: 31)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUUAACCUGAGGAUCCUA
UUGAACAAUGCUGCUUUUCGUAAUGGCCAUAACUUUAUGGUUCGGAACUUUA
GAUGCGGGCAGCCACUGCAGAACAAGGUCCAGUUGAAAGGCCGCGAUCUGUUG
ACAUUGAAGAACUUUACCGGCGAAGAGAUUAAGUAUAUGCUGUGGCUGUCUG
CUGACCUCAAGUUUCGAAUCAAGCAGAAGGGCGAAUAUCUCCCCCUGCUGCAA
GGAAAGUCUCUCGGCAUGAUCUUUGAGAAGCGGAGUACCCGAACACGGCUGA
GCACCGAAACGGGCUUCGCACUGCUGGGGGGCCAUCCCUGUUUUCUGACAACG
CAGGACAUCCACUUGGGGGUUAACGAAUCAUUGACUGAUACCGCCCGCGUACU

-continued

SEQUENCE LISTING

GUCAUCCAUGGCCGACGCUGUGCUGGCUAGGGUGUACAAGCAGUCAGAUCUGG
AUACACUGGCCAAGGAAGCUAGCAUACCAAUCAUCAAUGGACUGAGUGACCUU
UAUCACCCGAUUCAAAUACUAGCCGAUUAUCUGACCCUGCAAGAGCAUUACUC
CUCGCUGAAAGGCCUCACGCUGUCCUGGAUCGGCGACGGCAACAACAUUCUGC
AUAGUAUUAUGAUGUCUGCUGCCAAAUUCGGCAUGCAUCUGCAAGCUGCUAC
GCCGAAGGGUUAUGAACCCGACGCGUCAGUUACGAAGCUCGCUGAGCAGUAUG
CAAAGGAGAAUGGCACAAAGCUGUUGCUUACCAACGAUCCCCUGGAAGCUGCU
CAUGGCGGCAAUGUGCUGAUUACUGACACCUGGAUUUCAAUGGGCCAGGAGG
AGGAGAAGAAGAAGAGGUUACAGGCUUUUCAAGGUUACCAAGUCACGAUGAA
AACCGCUAAGGUCGCAGCCAGCGACUGGACAUUCCUGCACUGUCUGCCAAGAA
AGCCGGAAGAAGUGGACGACGAGGUGUUCUAUUCCCCGCGGUCUUUGGUGUU
UCCGGAGGCCGAAAACAGGAAAUGGACCAUUAUGGCCGUGAUGGUAUCGUUG
CUGACGGACUACAGCCCUCAGUUGCAAAAGCCCAAGUUCUAGCUCGAGCUAGU
GACUGACUAGGAUCUGGUUACCACUAAACCAGCCUCAAGAACACCCGAAUGGA
GUCUCUAAGCUACAUAAUACCAACUUACACUUACAAAAUGUUGUCCCCCAAAA
UGUAGCCAUUCGUAUCUGCUCCUAAUAAAAAGAAAGUUUCUUCACAUUCUAG

>mARM569 (SEQ ID NO: 32)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUCUUUAACCUCCGCAUCCUC
CUCAACAACGCCGCCUUCCGGAAUGGGCAUAACUUCAUGGUCCGGAACUUCAG
AUGCGGCCAGCCCCUGCAAAACAAGGUCCAGUUGAAGGGACGGGACCUCCUUA
CGCUGAAGAACUUUACCGGAGAAGAGAUUAAGUACAUGCUGUGGUUGUCCGC
UGACCUCAAGUUCCGCAUUAAGCAGAAGGGAGAAUAUCUGCCGCUGCUGCAAG
GAAAGAGCCUGGGCAUGAUCUUCGAAAAGCGCUCCACUAGAACCCGGCUGUCG
ACUGAGACUGGAUUCGCCUUGCUCGGUGGACACCCGUGCUUCCUGACGACCCA
GGACAUCCACCUGGGAGUGAACGAGUCACUUACGGAUACCGCGAGGGUGCUGU
CCUCAAUGGCCGACGCAGUGCUCGCGCGCGUGUACAAGCAGUCAGAUCUGGAU
ACCCUGGCCAAGGAAGCCAGCAUUCCCAUCAUCAACGGACUGAGCGACCUUUA
CCACCCAAUCCAGAUCCUCGCCGACUACUUAACCCUGCAAGAGCACUACAGCU
CCCUGAAGGGACUGACUCUGUCCUGGAUCGGGGAUGGAAACAACAUCCUGCAC
UCCAUCAUGAUGUCUGCCGCUAAGUUUGGGAUGCAUCUGCAAGCCGCAACCCC
UAAGGGAUACGAGCCCGACGCCUCGGUGACCAAACUUGCGGAACAGUACGCCA
AGGAAAACGGUACCAAGCUGCUGCUGACCAACGACCCUCUGGAAGCGGCCCAC
GGAGGAAAUGUGCUGAUUACCGACACCUGGAUUUCGAUGGGCCAGGAGGAGG
AGAAGAAGAAGAGACUGCAGGCGUUCCAGGGAUAUCAGGUCACCAUGAAAAC
CGCCAAGGUCGCCGCCAGCGACUGGACCUUCCUGCACUGUCUCCCUCGGAAAC
CGGAAGAAGUGGAUGACGAGGUGUUCUACUCCCCGCGCUCGCUGGUGUUCCCG
GAGGCUGAAAACAGGAAGUGGACAAUCAUGGCCGUGAUGGUGUCCCUGUUGA
CCGACUACUCCCCACAACUGCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM570 (SEQ ID NO: 33)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUGCGCAUCCUC
CUGAACAACGCCGCCUUCCGCAAUGGACACAACUUUAUGGUCCGCAACUUCCG
CUGUGGGCAGCCGCUGCAGAACAAGGUCCAGCUCAAGGGGAGAGAUCUCCUGA
CCCUGAAGAACUUCACUGGAGAGGAGAUCAAGUACAUGCUGUGGCUGUCCGCC
GACCUGAAAUUUCGGAUUAAGCAGAAGGGCGAAUACCUCCCACUGCUGCAAGG
AAAGUCUUUGGGCAUGAUCUUCGAAAAGAGAAGCACCCGGACCCGGUUGAGC
ACCGAAACUGGGUUCGCGCUCCUCGGUGGACACCCGUGCUUCCUGACCACCCA
AGAUAUUCAUCUGGGUGUCAACGAAAGCCUGACCGACACCGCCAGGGUGCUGU
CAUCCAUGGCUGACGCAGUGCUCGCCCGGGUGUACAAGCAGUCAGACCUGGAC
ACCCUCGCCAAGGAAGCUUCGAUCCCUAUCAUCAACGGACUUUCCGACCUGUA
CCACCCCAUCCAAAUUCUGGCCGACUACCUGACUCUGCAAGAACACUAUAGCU
CGCUGAAAGGACUUACUCUGUCCUGGAUCGGGGACGGCAACAACAUUCUCCAU
UCCAUCAUGAUGUCCGCUGCCAAGUUCGGAAUGCACCUUCAAGCAGCGACUCC
CAAGGGAUACGAACCUGAUGCCUCCGUGACUAAGCUGGCAGAGCAGUACGCCA
AGGAGAACGGUACAAAGCUGCUGCUCACGAACGACCCCCUGGAGGCGGCCCAC
GGCGGAAACGUGCUGAUUACCGAUACCUGGAUCUCAAUGGGCCAGGAAGAGG
AGAAGAAGAAGCGGCUCCAGGCGUUUCAAGGCUACCAGGUCACCAUGAAAACC
GCGAAGGUCGCCGCCUCCGACUGGACUUUCUUGCACUGCCUGCCGCGGAAGCC
CGAGGAAGUGGAUGACGAAGUGUUCUACUCGCCGAGAUCGUUGGUGUUCCCU
GAGGCCGAAAACAGGAAGUGGACCAUCAUGGCCGUGAUGGUGUCCCUGCUGAC
UGAUUACAGCCCACAGCUGCAGAAGCCUAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM571 (SEQ ID NO: 34)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC

-continued

SEQUENCE LISTING

CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM572 (SEQ ID NO: 35)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACCUGAGAAUCCUC
CUGAACAACGCCGCCUUCCGCAAUGGUCAUAACUUCAUGGUCCGCAACUUUCG
CUGCGGACAGCCUCUCCAAAACAAGGUCCAGCUCAAGGGGCGCGACCUCCUCA
CACUGAAGAACUUCACUGGAGAAGAAAUCAAGUACAUGCUGUGGCUGAGCGC
CGAUCUGAAGUUCCGGAUCAAGCAGAAGGGAGAGUACCUUCCUCUGCUGCAAG
GGAAGUCCUUGGGAAUGAUUUUCGAGAAGCGGUCCACCCGGACCAGGCUGAGC
ACUGAAACUGGCUUCGCCCUGCUGGGAGGCCACCCUUGUUUCCUGACCACUCA
GGACAUCCACCUGGGCGUGAACGAGUCCCUGACCGAUACUGCCAGAGUGCUGU
CCUCCAUGGCCGACGCCGUGCUCGCCCGGGUGUACAAGCAGUCAGACCUCGAU
ACGCUGGCCAAGGAAGCCUCCAUUCCCAUUAUCAAUGGUCUGUCGGACCUCUA
CCAUCCAAUCCAAAUCCUCGCCGACUACCUGACUCUGCAAGAACACUACAGCU
CACUCAAGGGCCUCACCCUCUCCUGGAUCGGCGACGGAAACAACAUCCUUCAC
UCGAUUAUGAUGUCGGCCGCGAAGUUCGGGAUGCACCUCCAAGCUGCCACUCC
AAAAGGCUACGAGCCGGAUGCCUCAGUGACUAAGUUGGCGGAACAGUAUGCG
AAGGAGAACGGUACCAAGCUCCUGCUGACUAACGACCCGCUGGAGGCCGCCCA
CGGGGGAAACGUGCUCAUCACCGAUACUUGGAUUUCCAUGGGACAGGAGGAA
GAGAAGAAGAAGCGGUUGCAGGCAUUUCAGGGCUACCAGGUCACCAUGAAAA
CUGCCAAAGUCGCCGCCAGCGACUGGACCUUCCUGCACUGCCUGCCCCGCAAG
CCUGAAGAAGUGGACGACGAGGUGUUCUACUCUCCCCGGUCCCUCGUGUUCCC
UGAGGCCGAAAACAGGAAGUGGACCAUCAUGGCUGUGAUGGUGUCCCUCCUG
ACCGACUACAGCCCUCAGCUCCAAAAACCCAAGUUUUAGCUCGAGCUAGUGAC
UGACUAGGAUCUGGUUACCACUAAACCAGCCUCAAGAACACCCGAAUGGAGUC
UCUAAGCUACAUAAUACCAACUUACACUUACAAAAUGUUGUCCCCCAAAAUGU
AGCCAUUCGUAUCUGCUCCUAAUAAAAAGAAAGUUUCUUCACAUUCUAG

>mARM573 (SEQ ID NO: 36)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACCUGAGAAUCCUC
UUGAACAAUGCUGCUUUUCGGAAUGGCCACAACUUUAUGGUUCGGAACUUCC
GUUGCGGCCAGCCUUUACAAAACAAGGUCCAGCUGAAGGGCCGGGAUUUGCUC
ACACUGAAGAACUUUACUGGGGAGGAGAUUAAGUAUAUGCUGUGGCUGUCCG
CUGACCUGAAGUUUAGGAUCAAGCAGAAGGGCGAAUAUCUGCCGCUGCUGCA
AGGGAAAAGUCUGGGCAUGAUUUUUGAAAAGCGCUCUACCCGGACCAGACUG
UCUACGGAAACAGGCUUUGCCCUGCUGGGCGGCCACCCCUGUUUUCUGACAAC
GCAGGACAUCCAUCUGGGCGUGAACGAAUCACUGACCGAUACUGCUCGGGUAC
UCAGUUCUAUGGCUGACGCAGUGCUGGCUAGGGUGUACAAGCAGAGCGACUU
GGACACACUGGCUAAGGAGGCCAGCAUCCCCAUUAUCAAUGGCCUGUCUGAUU
UGUACCAUCCCAUUCAAAUCCUGGCUGAUUAUCUGACACUACAAGAGCAUUAC
UCAAGUCUGAAGGGUUUGACUCUCUCCUGGAUCGGCGACGGCAACAACAUUUU
ACAUUCCAUUAUGAUGAGUGCUGCUAAGUUUGGCAUGCAUUUGCAAGCUGCU
ACCCCAAAGGGCUAUGAACCUGACGCUAGCGUAACCAAGUUGGCCGAACAGUA
UGCUAAAGAGAAUGGCACCAAGCUGCUCCUGACGAAUGACCCCCUGGAAGCUG
CUCAUGGCGGAAACGUACUUAUAACUGAUACAUGGAUUAGCAUGGGCCAGGA
AGAGGAGAAGAAGAAGAGACUGCAGGCCUUCCAAGGCUAUCAGGUCACCAUG
AAAACUGCCAAGGUUGCAGCUAGCGACUGGACCUUCCUGCACUGUUUGCCGAG
GAAACCCGAGGAGGUGGACGAUGAAGUCUUUUAUUCUCCCCGCUCCUUGGUGU
UUCCCGAGGCUGAAAAUCGAAAGUGGACGAUAAUGGCAGUGAUGGUGUCCCU
ACUGACCGACUAUUCUCCACAACUGCAGAAGCCUAAAUUCUAGCUCGAGCUAG
UGACUGACUAGGAUCUGGUUACCACUAAACCAGCCUCAAGAACACCCGAAUGG

-continued

SEQUENCE LISTING

AGUCUCUAAGCUACAUAAUACCAACUUACACUUACAAAAUGUUGUCCCCCAAA
AUGUAGCCAUUCGUAUCUGCUCCUAAUAAAAAGAAAGUUUCUUCACAUUCUA
G

>mARM574 (SEQ ID NO: 37)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUGAGGAUCCUG
CUGAACAACGCUGCUUUUCGCAACGGUCAUAACUUUAUGGUUCGCAAUUUUCG
UUGUGGCCAGCCGCUGCAGAACAAGGUUCAGCUGAAGGGCAGAGAUCUGCUG
ACUCUGAAGAACUUCACUGGGGAAGAAAUCAAGUAUAUGUUAUGGCUGUCCG
CGGAUCUGAAAUUUCGAAUCAAGCAGAAGGGCGAAUAUCUUCCCCUGCUGCAA
GGGAAAUCCUUGGGCAUGAUUUUUGAGAAGAGGAGCACUAGGACUAGAUUGU
CAACAGAAACAGGCUUUGCUUUGUUGGGCGGACAUCCCUGCUUUCUGACGACA
CAGGAUAUCCACCUCGGCGUAAACGAGUCCCUCACCGACACUGCUAGGGUACU
GAGCAGCAUGGCCGACGCUGUGCUAGCCCGGGUUUACAAGCAGUCAGACCUGG
ACACCCUUGCCAAGGAAGCUUCUAUUCCAAUUAUCAACGGCCUGAGUGACCUG
UAUCACCCUAUUCAAAUACUCGCCGACUAUUUGACGCUUCAAGAACAUUACAG
CAGCCUCAAGGGCUUAACCUUGAGUUGGAUAGGCGACGGCAACAAUAUCCUGC
AUUCCAUUAUGAUGUCUGCCGCUAAGUUUGGCAUGCAUCUACAAGCCGCAACA
CCCAAGGGCUAUGAACCCGACGCUAGCGUGACCAAGCUGGCCGAGCAGUAUGC
UAAGGAAAAUGGCACAAAGCUCCUUCUUACCAACGAUCCCCUGGAGGCUGCUC
ACGGCGGCAACGUGCUGAUUACCGAUACAUGGAUUAGCAUGGGCCAGGAGGA
GGAGAAAAAGAAGCGGCUCCAGGCUUUUCAAGGCUAUCAGGUCACCAUGAAA
ACUGCAAAGGUCGCUGCCUCCGACUGGACUUUCCUGCAUUGUCUACCCCGCAA
GCCUGAGGAAGUGGACGAUGAGGUGUUCUACUCCCCACGGAGUCUGGUGUUCC
CGGAAGCAGAGAAUCGGAAGUGGACCAUCAUGGCUGUCAUGGUGUCGCUCUU
GACUGACUAUUCUCCCCAACUGCAAAAACCCAAGUUUUAGCUCGAGCUAGUGA
CUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUG
UAGCCAUUCGUAUCUGCUCCUAAUAAAAAGAAAGUUUCUUCACAUUCUAG

>mARM575 (SEQ ID NO: 38)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGUUAUUCAACCUUCGUAUCCUG
CUAAACAAUGCUGCUUUUCGCAAUGGCCAUAACUUUAUGGUUCGCAACUUUA
GAUGCGGCCAGCCGCUGCAGAACAAGGUUCAGCUGAAGGGCCGGGACUUGCUG
ACGCUGAAAAACUUUACCGGGGAAGAGAUUAAGUAUAUGCUGUGGCUAAGCG
CUGAUCUGAAGUUUAGGAUCAAGCAGAAGGGCGAAUAUCUGCCACUGCUGCA
AGGGAAGAGUCUUGGCAUGAUUUUUGAAAAGCGGUCUACCAGAACCCGGCUG
UCGACCGAGACAGGUUUUGCUCUGCUGGGGGGCCAUCCCUGUUUUCUGACAAC
UCAGGACAUUCACCUGGGCGUGAAUGAGUCCCUGACCGAUACUGCUAGGGUGU
UGAGUAGCAUGGCCGACGCUGUACUCGCUCGAGUGUAUAAGCAGUCUGAUCU
GGACACUCUGGCUAAGGAAGCUUCCAUUCCUAUUAUCAACGGCUUGAGCGACC
UGUACCACCCCAUUCAAAUCCUCGCUGAUUACUUGACUUUGCAAGAACAUUAC
AGCAGCUUGAAGGGCUUAACACUGAGCUGGAUAGGCGACGGAAACAACAUCU
UGCAUUCCAUAAUGAUGUCCGCCGCUAAGUUCGGGAUGCACCUCCAAGCAGCC
ACACCCAAGGGCUAUGAACCGGAUGCUUCCGUGACAAAACUGGCUGAGCAGUA
UGCUAAGGAGAAUGGCACGAAACUGCUGCUCACCAACGACCCAUUGGAAGCUG
CACAUGGUGGCAACGUACUGAUCACUGACACUUGGAUCUCAAUGGGCCAGGAG
GAAGAGAAGAAGAAAAGGCUGCAGGCAUUUCAGGGAUACCAAGUCACUAUGA
AAACUGCCAAGGUCGCUGCCUCCGACUGGACAUUCCUGCAUUGUCUGCCACGG
AAGCCUGAGGAAGUCGAUGACGAAGUGUUCUAUAGCCCACGAAGCUUGGUGU
UUCCCGAGGCUGAGAAUAGGAAGUGGACCAUUAUGGCUGUUAUGGUGUCCCU
GCUCACCGACUAUUCCCCUCAACUGCAAAAACCCAAGUUUUAGCUCGAGCUAG
UGACUGACUAGGAUCUGGUUACCACUAAACCAGCCUCAAGAACACCCGAAUGG
AGUCUCUAAGCUACAUAAUACCAACUUACACUUACAAAAUGUUGUCCCCCAAA
AUGUAGCCAUUCGUAUCUGCUCCUAAUAAAAAGAAAGUUUCUUCACAUUCUA
G

>mARM708 (SEQ ID NO: 39)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGCUUUUUAAUCUCCGCAUCCUCCUU
AACAACGCCGCGUUUAGAAACGGCCACAACUUCAUGGUCCGGAACUUCAGAUG
UGGCCAGCCGCUUCAAAACAAGGUCCAGCUGAAGGGCCGGGAUCUUCUGACCC
UGAAGAACUUUACUGGCGAAGAGAUCAAGUACAUGCUCUGGCUCUCCGCGGAC
UUGAAGUUCCGCAUUAAGCAGAAGGGGGAAUACCUUCCGCUGCUUCAAGGAA
AGAGCCUCGGCAUGAUCUUUGAGAAGCGCUCAACCAGGACCCGCCUUUCUACU
GAAACUGGGUUCGCGCUGCUCGGUGGCCACCCCUGCUUCCUGACGACCCAGGA
CAUCCACCUCGGAGUGAACGAAUCCCUCACCGAUACCGCCCGGGUGUUAUCGA
GCAUGGCAGAUGCCGUGCUGGCCAGGGUGUACAAACAGUCCGAUCUGGACACU
CUGGCCAAGGAGGCGUCAAUUCCCAUCAUCAACGGCCUGAGCGACCUGUACCA
CCCAAUCCAAAUCCUGGCUGACUACCUGACCCUGCAAGAGCACUACAGCAGCC
UGAAGGGUCUGACCCUGUCAUGGAUUGGCGAUGGAAACAAUAUUCUGCACUC
CAUCAUGAUGUCCGCCGCGAAGUUCGGAAUGCAUCUGCAAGCCGCCACGCCAA

-continued

SEQUENCE LISTING

AAGGAUACGAACCGGAUGCGUCCGUGACGAAGUUGGCGGAACAGUACGCGAA
GGAGAACGGAACCAAGCUUCUGCUGACUAACGACCCCCUCGAGGCUGCGCAUG
GGGGCAACGUGCUGAUUACCGACACCUGGAUCUCCAUGGGGCAGGAGGAAGA
GAAGAAGAAGAGACUGCAGGCAUUCCAGGGGUACCAGGUCACCAUGAAAACC
GCAAAAGUGGCAGCUUCGGACUGGACUUUCCUGCAUUGCCUGCCGAGGAAGCC
GGAGGAAGUCGACGACGAAGUGUUCUACUCGCCUCGGUCCCUGGUGUUCCCCG
AGGCCGAAAACCGGAAGUGGACCAUCAUGGCCGUGAUGGUGUCCUUGCUGACU
GACUAUAGCCCGCAGCUGCAGAAGCCUAAGUUCUAGCUCGAGCUAGUGACUGA
CUAGGAUCUGGUUACCACUAAACCAGCCUCAAGAACACCCGAAUGGAGUCUCU
AAGCUACAUAAUACCAACUUACACUUACAAAAUGUUGUCCCCCAAAAUGUAGC
CAUUCGUAUCUGCUCCUAAUAAAAAGAAAGUUUCUUCACAUUCUAG

>mARM709 (SEQ ID NO: 40)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGCUUUUCAACCUGAGAAUCCUCUUG
AACAAUGCUGCUUUUCGGAAUGGCCACAACUUUAUGGUUCGGAACUUCCGUU
GCGGCCAGCCUUUACAAAACAAGGUCCAGCUGAAGGGCCGGGAUUUGCUCACA
CUGAAGAACUUUACUGGAGAAGAGAUCAAGUACAUGCUGUGGCUGUCGGCCG
ACCUGAAGUUCAGGAUCAAGCAGAAGGGAGAAUACCUUCCGCUGCUUCAAGG
AAAGAGCCUCGGCAUGAUCUUUGAGAAGCGCUCAACCAGGACCCGCCUUUCUA
CUGAAACUGGGUUCGCGCUGCUCGGUGGCCACCCCUGCUUCCUGACGACCCAG
GACAUCCACCUCGGAGUGAACGAAUCCCUCACCGAUACCGCCCGGGUGUUAUC
GAGCAUGGCAGAUGCCGUGCUGGCCAGGGUGUACAAACAGUCCGAUCUCGAUA
CCUUGGCAAAGGAGGCUUCCAUUCCCAUCAUCAACGGCCUGAGCGACCUGUAC
CACCCAAUCCAAAUCCUGGCUGACUACCUGACCCUGCAAGAGCACUACAGCAG
CCUGAAGGGUCUGACCCUGUCAUGGAUUGGCGAUGGAAACAAUAUUCUGCAC
UCCAUCAUGAUGUCCGCCGCGAAGUUCGGAAUGCAUCUGCAAGCCGCCACUCC
AAAAGGAUACGAACCGGAUGCGUCCGUGACCAAGUUGGCGGAACAGUACGCG
AAGGAGAACGGAACCAAGCUUCUGCUGACUAACGACCCCCUCGAGGCUGCGCA
UGGGGGCAACGUGCUGAUUACCGACACCUGGAUCUCCAUGGGGCAGGAGGAA
GAGAAGAAGAAGAGACUGCAGGCAUUCCAGGGGUACCAGGUCACCAUGAAAA
CCGCAAAAGUGGCAGCUUCGGACUGGACUUUCCUGCAUUGCCUGCCGAGGAAG
CCGGAGGAAGUCGACGACGAAGUGUUCUACUCGCCUCGGUCCCUGGUGUUCCC
CGAGGCCGAAAACCGGAAGUGGACCAUCAUGGCCGUGAUGGUGUCCUUGCUGA
CUGACUAUAGCCCGCAGCUGCAGAAGCCUAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM710 (SEQ ID NO: 41)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGCUUUUCAACCUGAGAAUCCUCUUG
AACAAUGCUGCUUUUCGGAAUGGCCACAACUUUAUGGUUCGGAACUUCCGUU
GCGGCCAGCCUUUACAAAACAAGGUCCAGCUGAAGGGCCGGGAUUUGCUCACA
CUAAAGAACUUUACUGGAGAAGAGAUCAAGUACAUGCUAUGGCUGUCGGCCG
ACCUGAAGUUCCGUAUCAAGCAGAAGGGAGAAUACCUUCCGCUGCUUCAAGGA
AAGAGCCUCGGCAUGAUCUUUGAGAAGCGCUCAACCAGGACCCGCCUUUCUAC
UGAAACUGGGUUCGCGCUGCUCGGUGGCCACCCCUGCUUCCUGACGACCCAGG
ACAUCCACCUCGGAGUGAACGAAUCCCUCACCGAUACCGCCCGGGUGUUAUCG
AGCAUGGCAGAUGCCGUGCUGGCCAGGGUGUACAAACAGUCCGAUCUCGAUAC
CUUGGCAAAGGAGGCUUCCAUUCCCAUCAUCAACGGCCUGAGCGACCUGUACC
ACCCAAUCCAAAUCCUGGCUGACUACCUGACCCUGCAAGAGCACUACAGCAGC
CUGAAGGGUCUGACCCUGUCAUGGAUUGGCGAUGGAAACAAUAUUCUGCACU
CCAUCAUGAUGUCCGCCGCGAAGUUCGGAAUGCAUCUGCAAGCCGCCACUCCA
AAAGGAUACGAACCGGAUGCAUCCGUGACCAAGUUGGCGGAACAGUACGCGA
AGGAGAACGGAACCAAGCUCCUGCUGACUAACGACCCGCUCGAGGCUGCGCAU
GGGGGUAACGUGCUGAUUACGGACACCUGGAUCUCCAUGGGGCAGGAGGAAG
AGAAGAAGAAGAGACUGCAGGCAUUCCAGGGGUACCAGGUCACCAUGAAAAC
CGCAAAAGUGGCAGCUUCGGACUGGACUUUCCUGCAUUGCCUGCCGAGGAAGC
CGGAGGAAGUCGACGACGAAGUGUUCUACUCGCCUCGGUCCCUGGUGUUCCCC
GAGGCCGAAAACCGGAAGUGGACCAUCAUGGCCGUGAUGGUGUCCUUGCUGAC
UGACUAUAGCCCGCAGCUGCAGAAGCCUAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM711 (SEQ ID NO: 42)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGCUUUUCAACCUGAGAAUCCUCUUG
AACAAUGCUGCUUUUCGGAAUGGCCACAACUUUAUGGUUCGGAACUUCCGUU
GCGGCCAGCCUUUACAAAACAAGGUCCAGCUGAAGGGCCGGGAUUUGCUCACA
CUAAAGAACUUUACUGGAGAAGAGAUCAAGUACAUGCUAUGGCUGUCGGCCG
ACCUGAAGUUCCGUAUCAAGCAGAAGGGAGAAUACCUUCCGCUGCUUCAAGGA
AAGAGCCUCGGCAUGAUCUUUGAGAAGCGCUCAACCAGGACCCGCCUUUCUAC

-continued

SEQUENCE LISTING

UGAAACUGGGUUCGCGCUGCUCGGUGGCCACCCCUGCUUCCUGACGACCCAGG
ACAUCCACCUCGGAGUGAACGAAUCCCUCACCGAUACCGCCCGGGUGUUAUCG
AGCAUGGCAGAUGCCGUGCUGGCCAGGGUGUACAAACAGUCCGAUCUCGAUAC
CUUGGCAAAGGAGGCUUCCAUUCCCAUCAUCAACGGCCUGAGCGACCUGUACC
ACCCAAUCCAAAUCCUGGCUGACUACCUGACCCUGCAAGAGCACUACAGCAGC
CUGAAGGGUCUGACCCUGUCAUGGAUUGGCGAUGGAAACAAUAUUCUGCACU
CCAUCAUGAUGUCCGCCGCGAAGUUCGGAAUGCAUCUGCAAGCCGCCACUCCA
AAAGGAUACGAACCGGAUGCGUCCGUGACCAAGUUGGCGGAACAGUACGCGA
AGGAGAACGGAACCAAGCUUCUGCUGACUAACGACCCCCUCGAGGCUGCGCAU
GGGGGCAACGUGCUGAUUACCGACACCUGGAUCUCCAUGGGGCAGGAGGAAG
AGAAGAAGAAGAGACUGCAGGCAUUCCAGGGGUACCAGGUCACCAUGAAAAC
CGCAAAAGUGGCAGCUUCGGACUGGACUUUCCUGCAUUGCCUGCCGAGGAAGC
CGGAGGAAGUCGACGACGAAGUGUUCUACUCGCCUCGGUCCCUGGUGUUCCCC
GAGGCCGAAAACCGGAAGUGGACCAUCAUGGCCGUGAUGGUGUCCUUGCUGAC
UGACUAUAGCCCGCAGCUGCAGAAGCCUAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM712 (SEQ ID NO: 43)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUGCGAAUCCUG
CUGAACAACGCCGCUUUUCGGAACGGGCACAACUUUAUGGUGAGGAACUUUCG
CUGCGGACAGCCCCUCCAGAAUAAGGUCCAGCUGAAGGGCAGGGACCUGCUGA
CCCUGAAAAAUUUCACAGGGGAGGAAAUCAAGUAUAUGCUGUGGCUGUCAGC
UGAUCUGAAGUUCCGGAUCAAGCAGAAGGGCGAAUAUCUGCCUCUGCUCCAGG
GCAAAAGCCUGGGGAUGAUCUUCGAAAAGCGCAGUACUCGGACCAGACUGUCA
ACCGAGACUGGAUUCGCUCUGCUGGGAGGACACCCUUGUUUUCUGACCACUCA
GGACAUUCACCUGGGAGUGAACGAGUCCCUGACCGACACUGCUCGCGUCCUGA
GCUCUAUGGCCGACGCUGUGCUGGCUCGAGUCUACAAACAGUCCGACCUGGAU
ACCCUGGCCAAGGAAGCUUCUAUCCCAAUUAUUAACGGCCUGUCAGACCUGUA
UCACCCCAUCCAGAUUCUGGCCGAUUACCUGACCCUCCAGGAGCACUAUUCUA
GUCUGAAAGGGCUGACACUGAGUUGGAUUGGGGACGGAAACAAUAUCCUGCA
CUCUAUUAUGAUGUCAGCCGCCAAGUUUGGAAUGCACCUCCAGGCUGCAACCC
CAAAAGGCUACGAACCCGAUGCCUCAGUGACAAAGCUGGCUGAACAGUACGCC
AAAGAGAACGGCACUAAGCUGCUGCUGACCAACGACCCUCUGGAGGCCGCUCA
CGGAGGCAACGUGCUGAUCACCGAUACCUGGAUUAGUAUGGGACAGGAGGAA
GAGAAGAAGAAGCGGCUCCAGGCCUUCCAGGGCUACCAGGUGACAAUGAAAAC
CGCUAAGGUCGCAGCCAGCGAUUGGACCUUUCUGCACUGCCUGCCCAGAAAGC
CCGAAGAGGUGGACGACGAGGUCUUCUACUCUCCCAGAAGCCUGGUGUUUCCC
GAAGCUGAGAAUAGGAAGUGGACAAUUAUGGCAGUGAUGGUCAGCCUGCUGA
CUGAUUAUUCACCUCAGCUCCAGAAACCAAAGUUCUGAUAACUCGAGCUAGUG
ACUGACUAGGAUCUGGUUACCACUAAACCAGCCUCAAGAACACCCGAAUGGAG
UCUCUAAGCUACAUAAUACCAACUUACACUUACAAAAUGUUGUCCCCCAAAAU
GUAGCCAUUCGUAUCUGCUCCUAAUAAAAAGAAAGUUUCUUCACAUUCUAG

>mARM713 (SEQ ID NO: 44)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUGCGCAUCCUG
CUGAACAACGCCGCCUUCCGCAACGGCCACAACUUCAUGGUGCGCAACUUCCG
CUGCGGCCAGCCCCUGCAGAACAAGGUGCAGCUGAAGGGCCGCGACCUGCUGA
CCCUGAAGAACUUCACCGGCGAGGAGAUCAAGUACAUGCUGUGGCUGAGCGCC
GACCUGAAGUUCCGCAUCAAGCAGAAGGGCGAGUACCUGCCCCUGCUGCAGGG
CAAGAGCCUGGGCAUGAUCUUCGAGAAGCGCAGCACCCGCACCCGCCUGAGCA
CCGAGACAGGCCUGGCCCUGCUGGGCGGCCACCCCUGCUUCCUGACCACCCAG
GACAUCCACCUGGGCGUGAACGAGAGCCUGACCGACACCGCCCGCGUGCUGAG
CAGCAUGGCCGACGCCGUGCUGGCCCGCGUGUACAAGCAGAGCGACCUGGACA
CCCUGGCCAAGGAGGCCAGCAUCCCCAUCAUCAACGGCCUGAGCGACCUGUAC
CACCCCAUCCAGAUCCUGGCCGACUACCUGACCCUGCAGGAGCACUACAGCAG
CCUGAAGGGCCUGACCCUGAGCUGGAUCGGCGACGGCAACAACAUCCUGCACA
GCAUCAUGAUGAGCGCCGCCAAGUUCGGCAUGCACCUGCAGGCCGCCACCCCC
AAGGGCUACGAGCCCGACGCCAGCGUGACCAAGCUGGCCGAGCAGUACGCCAA
GGAGAACGGCACCAAGCUGCUGCUGACCAACGACCCCCUGGAGGCCGCCCACG
GCGGCAACGUGCUGAUCACCGACACCUGGAUCAGCAUGGGCCAGGAGGAGGAG
AAGAAGAAGCGCCUGCAGGCCUUCCAGGGCUACCAGGUGACCAUGAAGACCGC
CAAGGUGGCCGCCAGCGACUGGACCUUCCUGCACUGCCUGCCCCGCAAGCCCG
AGGAGGUGGACGACGAGGUGUUCUACAGCCCCCGCAGCCUGGUGUUCCCCGAG
GCCGAGAACCGCAAGUGGACCAUCAUGGCCGUGAUGGUGAGCCUGCUGACCGA
CUACAGCCCCCAGCUGCAGAAGCCCAAGUUCUGAUAACUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

-continued

SEQUENCE LISTING

>mARM714 (SEQ ID NO: 45)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUGCGAAUCCUG
CUGAACAACGCCGCUUUUCGGAACGGGCACAACUUUAUGGUGAGGAACUUUCG
CUGCGGACAGCCCCUCCAGAAUAAGGUCCAGCUGAAGGGCAGGGACCUGCUGA
CCCUGAAAAAUUUCACAGGGGAGGAAAUCAAGUAUAUGCUGUGGCUGUCAGC
UGAUCUGAAGUUCCGGAUCAAGCAGAAGGGCGAAUAUCUGCCCUCUGCUCCAGG
GCAAAAGCCUGGGGAUGAUCUUCGAAAAGCGCAGUACUCGGACCAGACUGUCA
ACCGAGACUGGAUUCGCUCUGCUGGGAGGACACCCUUGUUUUCUGACCACUCA
GGACAUUCACCUGGGAGUGAACGAGUCCCUGACCGACACUGCUCGCGUCCUGA
GCUCUAUGGCCGACGCUGUGCUAGCUCGAGUCUACAAACAGUCCGACCUGGAU
ACCCUGGCCAAGGAAGCUUCUAUCCCAAUUAUUAACGGCCUGUCAGACCUGUA
UCACCCCAUCCAGAUUCUGGCCGAUUACCUGACCCUCCAGGAGCACUAUUCUA
GUCUGAAAGGGCUGACACUGAGUUGGAUUGGGGACGGAAACAAUAUCCUGCA
CUCUAUUAUGAUGUCAGCCGCCAAGUUUGGAAUGCACCUCCAGGCUGCAACCC
CAAAAGGCUACGAACCCGAUGCCUCAGUGACAAAGCUGGCUGAACAGUACGCC
AAAGAGAACGGCACUAAGCUGCUGCUGACCAACGACCCUCUGGAGGCCGCUCA
CGGAGGCAACGUGCUGAUCACCGAUACCUGGAUUAGUAUGGGACAGGAGGAA
GAGAAGAAGAAGCGGCUCCAGGCCUUCCAGGGCUACCAGGUGACAAUGAAAAC
CGCUAAGGUCGCAGCCAGCGAUUGGACCUUUCUGCACUGCCUGCCCAGAAAGC
CCGAAGAGGUGGACGACGAGGUCUUCUACUCUCCCAGAAGCCUGGUGUUUCCC
GAAGCUGAGAAUAGGAAGUGGACAAUUAUGGCAGUGAUGGUCAGCCUGCUGA
CUGAUUAUUCACCUCAGCUCCAGAAACCAAAGUUCUGAUAACUCGAGCUAGUG
ACUGACUAGGAUCUGGUUACCACUAAACCAGCCUCAAGAACACCCGAAUGGAG
UCUCUAAGCUACAUAAUACCAACUUACACUUACAAAAUGUUGUCCCCCAAAAU
GUAGCCAUUCGUAUCUGCUCCUAAUAAAAGAAAGUUUCUUCACAUUCUAG

>mARM715 (SEQ ID NO: 46)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUGCGAAUCCUG
CUGAACAAUGCCGCUUUUCGGAACGGGCACAAUUUCAUGGUGAGGAACUUUC
GCUGCGGACAGCCCCUCCAGAACAAGGUCCAGCUGAAGGGCAGGGACCUGCUG
ACCCUGAAAAAUUUCACAGGGGAGGAAAUCAAGUACAUGCUGUGGCUGUCAG
CCGAUCUGAAGUUCCGGAUCAAGCAGAAGGGCGAAUAUCUGCCCUCUGCUCCAG
GGCAAAAGCCUGGGGAUGAUCUUCGAAAAGCGCAGUACUCGGACCAGACUGUC
AACAGAGACUGGAUUCGCACUGCUGGGAGGACACCCAUGUUUUCUGACCACAC
AGGACAUUCAUCUGGGAGUGAACGAGUCCCUGACCGACACAGCACGCGUCCUG
AGCUCCAUGGCUGAUGCAGUGCUGGCUCGAGUCUACAAACAGUCUGACCUGGA
UACCCUGGCCAAGGAAGCUUCUAUCCCAAUCAUUAAUGGCCUGAGUGACCUGU
AUCACCCCAUCCAGAUUCUGGCCGAUUACCUGACCCUCCAGGAGCAUUAUUCU
AGUCUGAAAGGGCUGACACUGAGCUGGAUUGGGGACGGAAACAAUAUCCUGC
ACUCCAUUAUGAUGAGCGCCGCCAAGUUUGGAAUGCACCUCCAGGCUGCAACC
CCAAAAGGCUACGAACCCGAUGCCUCCGUGACAAAGCUGGCAGAACAGUAUGC
CAAAGAGAACGGCACUAAGCUGCUGCUGACCAAUGACCCUCUGGAGGCCGCUC
ACGGAGGCAACGUGCUGAUCACUGAUACCUGGAUUAGUAUGGGACAGGAGGA
AGAGAAGAAGAAGCGGCUCCAGGCCUUCCAGGGCUACCAGGUGACAAUGAAA
ACUGCUAAGGUCGCAGCCAGCGACUGGACCUUUCUGCAUUGCCUGCCCAGAAA
GCCUGAAGAGGUGGACGAUGAGGUCUUCUACUCACCCAGAAGCCUGGUGUUUC
CUGAAGCUGAGAAUAGGAAGUGGACAAUCAUGGCAGUGAUGGUCAGCCUGCU
GACUGAUUAUUCCCCUCAGCUCCAGAAACCAAAGUUCUGAUAACUCGAGCUAG
UGACUGACUAGGAUCUGGUUACCACUAAACCAGCCUCAAGAACACCCGAAUGG
AGUCUCUAAGCUACAUAAUACCAACUUACACUUACAAAAUGUUGUCCCCCAAA
AUGUAGCCAUUCGUAUCUGCUCCUAAUAAAAGAAAGUUUCUUCACAUUCUA
G

>mARM716 (SEQ ID NO: 47)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACCUUCGCAUUCUC
CUCAACAACGCCGCGUUUAGAAACGGACACAACUUCAUGGUCCGCAACUUCCG
CUGCGGACAGCCGCUGCAGAACAAGGUCCAGCUCAAGGGUCGGGAUCUCCUGA
CGCUGAAGAACUUUACCGGCGAAGAGAUUAAGUACAUGCUGUGGCUGUCCGCC
GACCUUAAGUUCCGGAUCAAGCAGAAGGGCGAAUACCUUCCCCUGCUGCAAGG
AAAGUCCCUGGGCAUGAUCUUCGAGAAGCGCAGUACCAGAACCAGACUCUCCA
CUGAAACCGGGUUCGCGCUGCUUGGCGGCCACCCGUGUUUCCUCACUACGCAA
GACAUCCAUCUUGGCGUGAACGAGUCCCUUACCGACACCGCCAGGGUGCUGUC
AAGCAUGGCCGACGCCGUCCUUGCGCGCGUGUACAAGCAGUCAGACCUUGAUA
CUCUGGCCAAGGAAGCCUCCAUCCCUAUUAUCAACGGCCUAUCCGACCUUUAC
CACCCGAUCCAGAUCCUCGCUGACUACCUGACCCUGCAAGAACACUACAGCAG
CCUCAAGGGACUGACUCUGUCCUGGAUCGGCGACGGGAACAACAUCCUGCACU
CAAUCAUGAUGAGCGCAGCCAAGUUCGGCAUGCAUCUCCAAGCCGCUACACCC
AAGGGUUAUGAACCGGACGCCUCUGUGACCAAGUUGGCAGAACAGUACGCCAA
GGAGAACGGUACUAAGCUCCUUUUAACCAACGACCCCCUCGAAGCAGCCCAUG
GCGGGAAUGUGCUCAUUACCGAUACCUGGAUUUCGAUGGGCCAGGAGGAGGA
GAAGAAGAAGCGGCUGCAGGCGUUCCAGGGCUACCAGGUCACCAUGAAAACUG

-continued

SEQUENCE LISTING

CCAAAGUGGCCGCCUCGGAUUGGACCUUUCUCCACUGCCUGCCUCGGAAGCCU
GAGGAGGUGGACGACGAAGUGUUCUACUCCCCACGGUCCCUCGUGUUCCCCGA
GGCCGAAAAUAGGAAGUGGACCAUCAUGGCCGUGAUGGUGUCCCUCUUGACCG
AUUACAGCCCGCAGCUUCAGAAGCCUAAAUUCUAGCUCGAGCUAGUGACUGAC
UAGGAUCUGGUUACCACUAAACCAGCCUCAAGAACACCCGAAUGGAGUCUCUA
AGCUACAUAAUACCAACUUACACUUACAAAAUGUUGUCCCCCAAAAUGUAGCC
AUUCGUAUCUGCUCCUAAUAAAAAGAAAGUUUCUUCACAUUCUAG

>mARM717 (SEQ ID NO: 48)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUUCGCAUCCUG
UUGAACAACGCCGCCUUCCGCAAUGGUCACAACUUCAUGGUCCGGAACUUCAG
AUGUGGACAGCCUCUCCAAAACAAGGUCCAGCUGAAGGGAAGGGACCUCUUAA
CCCUCAAAAACUUUACUGGAGAGGAGAUCAAGUACAUGCUGUGGCUUAGCGCC
GACCUUAAGUUCCGGAUCAAGCAGAAGGGAGAGUACCUCCCGCUGCUGCAAGG
AAAGAGUCUUGGAAUGAUCUUCGAGAAGCGGUCCACCAGAACUCGCCUCUCCA
CUGAAACCGGAUUCGCACUCCUGGGUGGACACCCGUGCUUUCUGACCACCCAA
GACAUCCACCUCGGAGUGAACGAGAGCCUCACGGACACCGCGAGAGUGCUGUC
AUCCAUGGCCGACGCCGUGCUUGCACGGGUCUACAAGCAGUCCGAUCUGGACA
CUCUUGCCAAGGAAGCCUCCAUUCCUAUCAUUAACGGUCUGUCGGAUCUGUAC
CACCCGAUUCAGAUCCUUGCGGACUACCUCACACUUCAAGAACACUAUUCAAG
CCUAAAGGGUCUGACCCUGUCCUGGAUCGGAGAUGGAAACAACAUUCUCCAUU
CCAUCAUGAUGAGCGCUGCCAAGUUCGGAAUGCAUCUCCAAGCAGCGACUCCU
AAGGGUUACGAGCCGGACGCCUCAGUGACUAAGCUGGCCGAGCAGUACGCCAA
GGAGAACGGUACCAAACUGUUGCUUACUAACGACCCGCUUGAAGCGGCCCAUG
GAGGAAACGUGCUGAUUACCGACACCUGGAUUUCGAUGGGACAGGAAGAGGA
GAAGAAGAAGCGGCUCCAGGCGUUCCAGGGAUACCAGGUCACCAUGAAAACGG
CCAAAGUGGCCGCUAGCGAUUGGACCUUUCUGCACUGCCUCCCGCGCAAGCCU
GAAGAAGUGGACGACGAAGUGUUCUACUCCCCUCGCUCUCUUGUGUUCCCGGA
AGCCGAAAACAGGAAGUGGACCAUCAUGGCCGUGAUGGUGUCCCUCCUGACCG
AUUACAGCCCGCAGCUGCAGAAGCCUAAGUUCUAGCUCGAGCUAGUGACUGAC
UAGGAUCUGGUUACCACUAAACCAGCCUCAAGAACACCCGAAUGGAGUCUCUA
AGCUACAUAAUACCAACUUACACUUACAAAAUGUUGUCCCCCAAAAUGUAGCC
AUUCGUAUCUGCUCCUAAUAAAAAGAAAGUUUCUUCACAUUCUAG

>mARM718 (SEQ ID NO: 49)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUCAACAACGCCGCGUUUAGAAACGGCCACAACUUCAUGGUCCGGAACUUCAG
AUGUGGCCAGCCGCUUCAGAACAAGGUCCAGCUCAAGGGCCGGGAUCUUCUGA
CCCUGAAGAACUUUACUGGCGAAGAAAUCAAGUACAUGCUCUGGCUCUCCGCC
GACUUGAAGUUCCGCAUUAAGCAGAAGGGGGAAUACCUUCCGCUGCUGCAAG
GAAAGUCGCUCGGCAUGAUCUUUGAGAAGCGCUCAACCCGCACCAGGCUGUCC
ACUGAAACCGGGUUCGCGCUGCUUGGUGGCCACCCCUGCUUCCUGACCACCCA
AGACAUUCACCUCGGAGUGAACGAAUCGCUCACUGAUACUGCCCGGGUGCUGU
CGUCGAUGGCCGAUGCAGUGCUGGCCAGGGUGUACAAACAGUCCGAUCUGGAC
ACUCUGGCCAAGGAGGCGUCCAUCCCUAUUAUCAACGGCCUUUCCGACCUCUA
CCACCCGAUUCAGAUCCUUGCCGAUUACCUCACCCUGCAAGAACACUACUCGU
CACUGAAGGGUCUGACCUUGUCCUGGAUCGGCGACGGCAACAACAUCCUCCAU
UCCAUUAUGAUGUCCGCCGCCAAAUUCGGCAUGCAUCUUCAAGCCGCAACCCC
UAAGGGUUACGAGCCGGACGCUUCCGUGACCAAGCUCGCCGAGCAGUACGCUA
AGGAGAACGGAACCAAGCUUCUGCUGACUAACGACCCCCUAGAGGCAGCCCAC
GGGGGCAACGUGCUUAUUACUGACACCUGGAUCUCCAUGGGACAGGAAGAAG
AGAAGAAGAAGCGGUUACAGGCGUUCCAGGGCUAUCAGGUCACCAUGAAAAC
CGCCAAGGUCGCUGCCUCGGACUGGACCUUCCUGCAUUGCCUGCCUCGCAAGC
CCGAAGAAGUGGACGACGAGGUGUUCUACUCGCCACGGUCCCUUGUGUUCCCU
GAGGCCGAGAAUAGAAAGUGGACCAUUAUGGCCGUGAUGGUGUCCCUUCUCA
CCGACUACUCGCCGCAACUGCAGAAACCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM719 (SEQ ID NO: 50)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUUCGCAUCCUC
CUCAACAACGCCGCCUUCCGGAACGGUCACAACUUCAUGGUCCGGAACUUCCG
CUGCGGCCAGCCGCUCCAAAACAAAGUGCAGCUUAAGGGCCGCGAUCUCCUGA
CCCUGAAGAACUUCACCGGAGAGGAAAUCAAGUACAUGCUGUGGCUCUCGGCG
GACCUGAAGUUUAGGAUUAAGCAGAAGGGGGAGUAUCUGCCGCUGCUCCAAG
GGAAGUCCCUUGGCAUGAUCUUCGAAAAGAGGUCCACCCGGACUCGGCUCAGC
ACCGAAACAGGUUUUGCACUUCUGGGGGGCCACCCGUGCUUCCUGACGACCCA
GGACAUCCAUCUGGGUGUCAACGAGAGUUUGACCGACACUGCCAGAGUGCUGU
CAUCCAUGGCGGACGCGGUGCUCGCGAGAGUGUACAAGCAGUCCGAUCUUGAC
ACCCUGGCAAAAGAGGCUUCAAUCCCGAUCAUUAACGGACUCUCGGAUCUGUA

-continued

SEQUENCE LISTING

CCACCCUAUCCAAAUCUUGGCCGACUACCUGACCCUGCAAGAACACUACAGCU
CCCUGAAGGGCCUGACUCUUUCCUGGAUUGGCGAUGGAAACAACAUUCUCCAU
UCUAUUAUGAUGUCCGCCGCCAAGUUCGGCAUGCACCUUCAAGCCGCCACCCC
GAAGGGCUACGAACCUGACGCCUCCGUGACUAAGCUAGCCGAACAGUACGCUA
AGGAGAACGGCACUAAGCUUCUCCUUACCAACGAUCCGCUGGAGGCGGCCCAU
GGCGGAAAUGUGCUUAUCACCGACACCUGGAUUAGCAUGGGGCAGGAAGAAG
AGAAGAAGAAACGGCUCCAGGCAUUCCAGGGCUACCAGGUCACCAUGAAAACU
GCCAAGGUCGCCGCUAGCGACUGGACCUUCCUCCACUGUCUGCCUCGCAAGCC
UGAAGAAGUGGACGACGAGGUGUUCUACUCCCCGCGCUCCCUCGUGUUUCCUG
AGGCCGAGAACAGAAAGUGGACCAUCAUGGCCGUGAUGGUGUCAUUACUUAC
GGACUACAGCCCGCAGCUGCAGAAGCCGAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM720 (SEQ ID NO: 51)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUUAACUUGAGAAUCCUU
CUGAACAACGCCGCUUUCCGCAACGGUCAUAACUUCAUGGUCCGGAACUUCAG
AUGUGGCCAGCCCCUCCAAAACAAAGUGCAGCUGAAGGGCCGGGACCUUCUUA
CGCUGAAGAAUUUCACCGGCGAAGAAAUCAAGUACAUGCUCUGGCUGUCCGCC
GAUCUUAAGUUCCGCAUUAAGCAGAAGGGGGAAUACCUCCCGCUGCUGCAAGG
GAAGUCGCUGGGCAUGAUUUUUGAGAAGCGGUCAACUCGCACCCGCCUGUCCA
CUGAAACUGGAUUCGCACUGCUCGGUGGCCAUCCCUGCUUCCUGACCACCCAA
GACAUCCACCUCGGCGUGAACGAGUCCCUGACUGACACCGCCCGGGUCUUAUC
CUCGAUGGCCGAUGCUGUGCUUGCGAGGGUGUACAAGCAGUCCGACCUCGACA
CACUCGCGAAGGAGGCCUCCAUCCCCAUCAUCAACGGCCUGUCCGACCUUUAC
CACCCAAUUCAGAUCCUCGCCGAUUACCUGACCCUGCAAGAGCACUACUCGUC
GCUCAAGGGGCUUACCCUCUCGUGGAUUGGCGACGGCAACAACAUCCUUCACU
CCAUCAUGAUGUCGGCAGCGAAGUUCGGCAUGCAUCUGCAAGCCGCCACGCCU
AAGGGUUAUGAACCGGAUGCCUCAGUGACCAAGCUCGCCGAACAGUACGCGAA
AGAGAAUGGAACCAAGCUACUUCUGACCAACGACCCCCUGGAGGCCGCUCACG
GCGGCAACGUCCUCAUUACCGAUACUUGGAUUUCGAUGGGACAGGAAGAGGA
AAAGAAGAAGAGACUGCAGGCGUUCCAGGGAUACCAGGUCACCAUGAAAACU
GCCAAAGUGGCAGCCUCCGACUGGACCUUCCUUCACUGCCUGCCGAGGAAGCC
UGAAGAGGUGGACGACGAGGUGUUCUACUCCCCGCGCUCCUUGGUGUUUCCUG
AGGCCGAAAACCGGAAGUGGACUAUCAUGGCCGUGAUGGUGUCCCUCCUCACC
GACUACUCGCCGCAACUGCAGAAGCCUAAGUUCUAGCUCGAGCUAGUGACUGA
CUAGGAUCUGGUUACCACUAAACCAGCCUCAAGAACACCCGAAUGGAGUCUCU
AAGCUACAUAAUACCAACUUACACUUACAAAAUGUUGUCCCCCAAAAUGUAGC
CAUUCGUAUCUGCUCCUAAUAAAAAGAAAGUUUCUUCACAUUCUAG

>mARM721 (SEQ ID NO: 52)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGUUAUUCAACCUUAGAAUUCUC
CUUAACAACGCCGCCUUCCGGAAUGGGCAUAACUUUAUGGUCCGCAAUUUCCG
CUGUGGACAGCCUCUGCAAAACAAGGUCCAGCUCAAGGGCCGGGAUCUGCUGA
CUCUCAAGAACUUCACUGGGGAAGAAAUCAAGUACAUGCUCUGGCUGAGCGCC
GACCUCAAGUUCCGCAUCAAGCAGAAGGGAGAGUACCUCCCGCUGCUCCAAGG
GAAGUCCCUGGGCAUGAUCUUCGAGAAGAGAUCCACCCGCACCAGACUUUCCA
CUGAGACUGGCUUCGCCUUGCUGGGAGGCCACCCAUGCUUCCUGACGACCCAG
GACAUUCACCUUGGCGUGAACGAGUCCCUGACUGACACCGCAAGGGUGUUGUC
CUCGAUGGCCGACGCCGUGCUUGCCCGGGUGUACAAGCAGAGCGAUCUUGACA
CCCUGGCUAAGGAAGCUUCCAUUCCCAUCAUCAACGGUCUGAGCGACCUGUAC
CACCCGAUUCAGAUCCUGGCGGACUACCUAACCCUGCAAGAGCACUAUAGCUC
CCUGAAGGGCCUCACACUUUCAUGGAUCGGCGACGGCAACAACAUCCUGCACU
CUAUUAUGAUGAGCGCUGCCAAAUUCGGCAUGCACCUCCAAGCCGCCACGCCU
AAAGGCUACGAGCCCGACGCCUCGGUGACCAAGCUUGCGGAGCAGUACGCGAA
GGAAAACGGCACCAAGCUGCUUCUCACCAACGAUCCUCUGGAAGCGGCCCAUG
GUGGCAACGUGCUCAUUACCGACACUUGGAUCUCCAUGGGACAGGAGGAGGA
AAAGAAGAAGCGGCUCCAGGCGUUUCAGGGUUACCAGGUCACCAUGAAAACCG
CCAAGGUCGCAGCCUCCGACUGGACCUUCCUUCAUUGCCUUCCGCGCAAGCCC
GAAGAAGUGGACGAUGAAGUGUUUUACUCACCUCGGUCACUCGUGUUCCCGG
AAGCAGAGAACAGGAAAUGGACCAUUAUGGCCGUGAUGGUGUCCCUGCUCACC
GAUUACAGUCCGCAACUGCAGAAGCCCAAGUUCUAGCUCGAGCUAGUGACUGA
CUAGGAUCUGGUUACCACUAAACCAGCCUCAAGAACACCCGAAUGGAGUCUCU
AAGCUACAUAAUACCAACUUACACUUACAAAAUGUUGUCCCCCAAAAUGUAGC
CAUUCGUAUCUGCUCCUAAUAAAAAGAAAGUUUCUUCACAUUCUAG

>mARM722 (SEQ ID NO: 53)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA

-continued

SEQUENCE LISTING

CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAAAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
UAAGGGUUACGAACCCGACGCUUCCGUGACUAAGCUCGCCGAGCAGUACGCUA
AGGAGAACGGAACCAAGCUGCUGCUGACUAACGACCCGCUAGAAGCAGCCCAC
GGGGGCAACGUGCUUAUUACUGACACCUGGAUCUCCAUGGGCCAGGAGGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUUCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM723 (SEQ ID NO: 54)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUUAAGGGCCGGGAUCUCCUCA
CCCUUAAAAACUUCACCGGCGAAGAGAUCAAGUACAUGCUCUGGCUCUCCGCG
GACCUUAAGUUCCGCAUUAAGCAGAAGGGGGAAUACCUUCCGCUGCUUCAAGG
AAAGAGCCUCGGCAUGAUCUUUGAGAAGCGCUCAACCAGGACCAGGCUUUCUA
CUGAAACUGGGUUCGCGCUUCUCGGCGGUCAUCCCUGCUUCCUCACGACCCAA
GACAUCCACCUCGGAGUGAACGAAUCCCUCACGGAUACUGCCCGCGUGCUUUC
GAGCAUGGCAGACGCCGUGCUCGCCCGGGUGUACAAACAGUCCGAUCUCGACA
CUCUCGCCAAGGAGGCGUCAAUUCCUAUUAUCAACGGUCUUAGUGACCUUUAC
CACCCGAUCCAGAUCCUCGCCGAUUACCUCACACUCCAAGAACACUACAGCUC
CCUUAAGGGUCUUACCCUCUCCUGGAUCGGCGACGGCAACAACAUUCUCCACU
CCAUCAUGAUGUCCGCCGCAAAGUUCGGCAUGCAUCUUCAAGCCGCCACCCCG
AAGGGCUACGAGCCUGAUGCUUCCGUGACUAAGCUCGCCGAGCAGUACGCUAA
GGAGAACGGAACCAAGCUUCUUCUCACUAACGACCCACUCGAAGCAGCCCAUG
GGGGCAACGUGCUUAUCACUGACACCUGGAUCUCCAUGGGCCAGGAAGAAGAG
AAGAAGAAGCGGCUCCAGGCGUUCCAGGGAUAUCAGGUCACCAUGAAAACCGC
CAAGGUCGCUGCCUCCGACUGGACCUUUCUCCACUGCCUCCCUCGCAAACCUG
AAGAAGUGGACGACGAGGUGUUCUACUCGCCCCGGAGCCUCGUGUUCCCCGAG
GCCGAGAAUAGAAAGUGGACCAUUAUGGCCGUGAUGGUGUCACUCCUCACCGA
CUACAGCCCGCAGCUUCAGAAGCCCAAGUUCUAGCUCGAGCUAGUGACUGACU
AGGAUCUGGUUACCACUAAACCAGCCUCAAGAACACCCGAAUGGAGUCUCUAA
GCUACAUAAUACCAACUUACACUUACAAAAUGUUGUCCCCCAAAAUGUAGCCA
UUCGUAUCUGCUCCUAAUAAAAAGAAAGUUUCUUCACAUUCUAG

>mARM724 (SEQ ID NO: 55)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGACAUAACUUCAUGGUCCGGAACUUCAG
AUGUGGACAGCCGCUUCAAAACAAGGUCCAGCUGAAGGGUCGGGAUCUUCUG
ACCCUGAAGAACUUUACCGGAGAAGAGAUCAAGUACAUGCUCUGGCUCUCCGC
GGACUUGAAGUUCCGCAUUAAGCAGAAGGGAGAAUACCUCCCGCUGCUUCAAG
GAAAGAGCCUCGGAAUGAUUUUUGAGAAGCGCUCAACCAGGACCCGCCUUUCU
ACUGAAACUGGAUUCGCGCUGCUGGGUGGACACCCCUGCUUCCUGACGACCCA
GGACAUCCACCUCGGAGUGAACGAAUCCCUCACUGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUCAUCAACGGACUUAGUGACCUCUA
CCAUCCGAUUCAAAUCCUGGCCGACUACCUCACCCUGCAAGAACACUACAGCU
CCCUGAAGGGUCUGACAUUGUCCUGGAUCGGAGAUGGAAACAACAUUCUCCAC
UCCAUCAUGAUGUCCGCCGCAAAAUUCGGAAUGCAUCUUCAAGCCGCCACGCC
UAAGGGUUACGAACCCGACGCUUCCGUGACUAAGCUCGCCGAGCAGUACGCUA
AGGAGAACGGUACCAAGCUUCUCCUGACCAACGACCCACUAGAAGCAGCCCAC
GGUGGAAACGUGCUUAUUACUGACACUUGGAUCUCCAUGGGACAGGAGGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCGCGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

-continued

SEQUENCE LISTING

>mARM725 (SEQ ID NO: 56)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACCUCCGCAUUCUC
CUCAACAACGCUGCCUUCCGGAAUGGACAUAACUUCAUGGUCCGGAACUUCAG
AUGCGGACAGCCGCUUCAGAACAAGGUCCAGCUUAAGGGGAGAGAUCUCCUUA
CCCUCAAAAACUUCACUGGCGAAGAAAUCAAGUACAUGCUCUGGCUUAGUGCG
GAUCUCAAGUUCCGCAUCAAGCAGAAGGGAGAAUACCUCCCGCUCCUUCAAGG
AAAGAGCCUCGGCAUGAUUUUUGAGAAGAGGUCCACCAGAACUCGCCUUUCAA
CCGAGACUGGGUUCGCCCUGCUUGGCGGUCACCCCUGCUUCCUCACUACCCAA
GACAUCCACCUCGGCGUGAACGAGAGCCUUACCGACACCGCCCGCGUGCUCUC
CUCAAUGGCCGACGCUGUGCUCGCCCGGGUGUACAAGCAGUCCGACCUUGAUA
CUCUCGCCAAGGAGGCCUCCAUCCCAAUUAUCAACGGGCUCUCUGAUCUCUAC
CACCCUAUCCAAAUCCUCGCGGACUACCUCACCCUCCAAGAGCACUAUAGCUC
GCUCAAGGGCCUCACCCUUUCCUGGAUUGGCGACGGCAACAACAUUCUUCACU
CGAUCAUGAUGUCCGCCGCCAAGUUCGGCAUGCAUCUCCAAGCCGCGACCCCC
AAGGGCUACGAGCCUGACGCAUCCGUGACCAAGCUCGCCGAGCAGUACGCGAA
GGAAAAUGGCACCAAGCUUCUUCUCACCAACGACCCCCUUGAGGCCGCUCAUG
GCGGCAACGUGCUCAUCACUGACACUUGGAUCAGCAUGGGCCAGGAGGAGGAA
AAGAAGAAGCGCCUUCAGGCAUUCCAGGGUUACCAGGUCACCAUGAAAACCGC
CAAAGUGGCCGCCUCCGACUGGACCUUUCUUCACUGUCUCCCGCGGAAGCCUG
AAGAAGUGGAUGACGAAGUGUUUUACUCCCCUCGGUCACUCGUGUUCCCGGAA
GCAGAAAACAGGAAGUGGACCAUUAUGGCGGUCAUGGUGUCCCUCCUCACCGA
CUACAGCCCGCAGCUUCAGAAACCCAAGUUCUAGCUCGAGCUAGUGACUGACU
AGGAUCUGGUUACCACUAAACCAGCCUCAAGAACACCCGAAUGGAGUCUCUAA
GCUACAUAAUACCAACUUACACUUACAAAAUGUUGUCCCCCAAAAUGUAGCCA
UUCGUAUCUGCUCCUAAUAAAAAGAAAGUUUCUUCACAUUCUAG

>mARM726 (SEQ ID NO: 57)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCAGCGUUUAGAAACGGUCACAACUUCAUGGUCCGGAACUUCCG
CUGUGGACAGCCGCUUCAAAACAAGGUCCAGCUGAAGGGUCGGGACCUUCUGA
CCCUGAAGAACUUUACUGGAGAAGAGAUCAAGUACAUGCUUUGGCUGUCCGC
GGACUUGAAGUUCCGCAUUAAGCAGAAGGGAGAAUACCUUCCGCUGCUCCAAG
GAAAGAGCCUGGGAAUGAUCUUUGAGAAGCGCUCAACCAGGACCCGCCUUUCU
ACUGAAACUGGAUUCGCGCUGCUGGGUGGUCACCCUUGCUUCCUGACGACCCA
GGACAUUCACCUCGGAGUGAACGAGUCCCUCACUGAUACCGCCAGAGUGUUAU
CGAGCAUGGCAGAUGCCGUGCUGGCUAGGGUGUACAAACAGUCCGAUCUGGAC
ACCCUGGCCAAGGAGGCAUCAAUUCCUAUUAUCAACGGACUUAGUGACCUCUA
CCAUCCGAUUCAAAUCCUGGCCGAUUACCUCACCCUGCAAGAACACUACAGCU
CCCUGAAGGGUCUGACAUUGUCCUGGAUCGGAGAUGGAAACAACAUUCUCCAU
UCCAUCAUGAUGUCCGCGGCCAAGUUCGGAAUGCAUCUCCAAGCCGCCACGCC
GAAAGGAUACGAGCCGGACGCUUCCGUGACUAAGCUCGCCGAGCAGUACGCUA
AGGAGAACGGAACCAAGCUUCUGCUGACUAACGACCCGCUAGAAGCCGCCCAC
GGUGGAAACGUGCUUAUUACUGACACCUGGAUCUCCAUGGGACAGGAAGAAG
AGAAAAAGAAGCGGCUGCAGGCGUUCCAGGGAUAUCAGGUCACCAUGAAAAC
CGCCAAGGUCGCCGCCUCCGACUGGACCUUCCUUCACUGCCUGCCUCGGAAGC
CUGAAGAAGUGGACGACGAGGUGUUCUACUCGCCGCGGAGCCUCGUGUUCCCU
GAGGCCGAGAAUAGAAAGUGGACCAUCAUGGCCGUGAUGGUGUCACUCCUCAC
CGACUACAGCCCGCAGCUUCAGAAGCCUAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM727 (SEQ ID NO: 58)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUUCUC
CUCAACAACGCAGCCUUUAGAAACGGCCACAACUUCAUGGUCCGGAACUUCAG
AUGUGGCCAGCCGCUUCAGAACAAGGUCCAGCUCAAGGGCCGGGACCUCCUCA
CCCUCAAAAACUUUACCGGCGAAGAGAUCAAGUACAUGCUCUGGCUUUCGGCC
GACCUUAAGUUCCGCAUCAAGCAGAAGGGGGAAUACCUUCCGCUGCUUCAAGG
AAAGUCCCUCGGCAUGAUCUUUGAAAAGCGCUCGACCAGGACCCGCCUUUCCA
CUGAAACCGGGUUCGCGCUUCUCGGUGGCCACCCCUGCUUCCUCACCACCCAA
GACAUUCACCUCGGAGUGAACGAAUCCCUUACCGAUACCGCAAGAGUGCUUUC
GUCGAUGGCCGAUGCCGUGCUUGCGCGGGUGUACAAGCAGUCAGAUCUCGACA
CUCUCGCCAAGGAGGCGUCCAUUCCUAUUAUCAACGGCCUUUCCGACCUUUAC
CACCCGAUUCAGAUCCUCGCCGAUUACCUCACCCUGCAAGAGCACUACUCGUC
ACUCAAGGGUCUUACCCUCUCCUGGAUCGGCGACGGAAACAACAUCCUCCAUU
CGAUCAUGAUGUCCGCCGCCAAAUUCGGCAUGCACCUCCAAGCCGCGACCCCG
AAGGGUUACGAGCCCGACGCUUCCGUGACCAAGCUCGCCGAACAGUACGCUAA
GGAAAACGGCACCAAGCUCCUCCUCACUAACGACCCUCUCGAAGCAGCCCAUG
GGGGCAACGUGCUCAUUACUGACACUUGGAUCUCGAUGGGCCAGGAAGAGGA
GAAAAAGAAGCGGCUUCAGGCGUUCCAGGGAUAUCAGGUCACCAUGAAAACC
GCCAAGGUCGCUGCCUCGGACUGGACCUUCCUUCACUGCCUUCCGCGCAAGCC

-continued

SEQUENCE LISTING

UGAAGAGGUGGACGAUGAGGUGUUCUACUCCCCACGGUCCCUUGUGUUCCCCG
AGGCCGAGAAUAGGAAGUGGACCAUCAUGGCCGUGAUGGUGUCGCUCCUCACU
GACUACUCCCCGCAACUUCAGAAGCCUAAGUUCUAGCUCGAGCUAGUGACUGA
CUAGGAUCUGGUUACCACUAAACCAGCCUCAAGAACACCCGAAUGGAGUCUCU
AAGCUACAUAAUACCAACUUACACUUACAAAAUGUUGUCCCCCAAAAUGUAGC
CAUUCGUAUCUGCUCCUAAUAAAAAGAAAGUUUCUUCACAUUCUAG

>mARM728 (SEQ ID NO: 59)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUUAAUCUGAGAAUACU
UCUAAACAACGCCGCCUUCCGGAAUGGCCAUAACUUUAUGGUUCGGAAUUUCC
GCUGCGGCCAGCCGCUGCAGAACAAGGUCCAGCUGAAGGGAAGAGACUUGCUG
ACCCUCAAGAACUUCACCGGAGAAGAAAUCAAGUAUAUGCUGUGGCUGUCCGC
CGACCUGAAAUUCCGCAUCAAGCAGAAGGGCGAAUAUCUGCCGCUGUUGCAAG
GGAAGUCCCUGGGGAUGAUCUUCGAGAAGAGGUCCACCAGAACACGGCUUUCA
ACCGAAACCGGGUUUGCACUGCUGGGUGGACACCCCUGUUUUCUGACCACUCA
AGAUAUCCACCUGGGCGUGAACGAGUCCCUUACCGACACUGCUAGGGUGUUGU
CCAGCAUGGCCGAUGCCGUCCUGGCUCGCGUGUACAAGCAGUCCGACCUGGAU
ACCCUGGCAAAGGAAGCGUCCAUUCCCAUUAUCAACGGGCUGUCCGACCUGUA
CCAUCCGAUUCAAAUCCUGGCGGACUACCUGACUCUGCAAGAGCAUUACAGCA
GCUUGAAGGGGCUUACUCUCUCGUGGAUCGGCGACGGGAACAACAUCCUGCAC
UCCAUCAUGAUGUCCGCCGCCAAGUUCGGGAUGCAUUUGCAAGCUGCGACCCC
GAAAGGUUACGAGCCCGAUGCUAGCGUAACUAAGCUUGCCGAACAGUACGCCA
AAGAGAAUGGUACAAAACUGCUUCUGACUAACGACCCGCUGGAAGCAGCCCAC
GGCGGGAACGUGCUGAUAACCGACACCUGGAUUUCAAUGGGGCAGGAGGAAG
AGAAGAAGAAGCGACUGCAGGCGUUCCAAGGCUAUCAGGUUACCAUGAAAAC
CGCCAAAGUGGCAGCCAGCGAUUGGACUUUCCUGCACUGUCUGCCGCGGAAGC
CCGAGGAAGUUGAUGACGAAGUAUUCUACUCACCCCGGAGCCUCGUGUUCCCC
GAGGCCGAAAACCGGAAGUGGACUAUUAUGGCCGUGAUGGUGUCGCUGUUGA
CCGACUACAGCCCGCAACUGCAGAAGCCGAAGUUUUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM729 (SEQ ID NO: 60)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACCUGAGGAUCCUU
UUGAACAACGCCGCCUUUCGCAACGGCCACAACUUUAUGGUCCGCAAUUUCCG
CUGCGGGCAGCCGCUGCAGAACAAGGUCCAGCUGAAGGGCCGGGAUCUGCUGA
CCCUGAAGAACUUCACCGGGGAGGAAAUCAAGUACAUGCUUUGGCUCUCCGCC
GAUCUGAAGUUCAGAAUCAAGCAGAAGGGAGAGUACCUCCCGUUGCUGCAAG
GAAAGUCACUCGGAAUGAUUUUCGAAAAGAGAAGCACUAGGACCCGCCUCUCA
ACUGAAACCGGGUUCGCGCUGCUCGGGGCCAUCCGUGUUUCCUGACUACCCA
AGACAUCCACCUGGGAGUGAACGAGUCGCUGACCGACACCGCACGCGUGCUGU
CAUCCAUGGCGGACGCAGUGCUUGCCCGGGUGUACAAGCAGUCGGACCUGGAC
ACUCUUGCCAAGGAGGCAUCAAUCCCCAUCAUUAACGGACUGUCCGAUCUCUA
CCACCCGAUUCAGAUCCUGGCUGACUACCUAACCCUGCAAGAGCACUACUCAA
GCCUGAAGGGGCUGACCCUGUCGUGGAUCGGGGACGGCAACAACAUUCUGCAC
UCCAUCAUGAUGUCGGCGGCUAAGUUCGGGAUGCAUUUGCAAGCGGCAACUCC
GAAGGGUUAUGAACCCGACGCCUCCGUGACCAAGCUGGCCGAACAGUACGCCA
AGGAAAACGGAACCAAGUUGCUGCUGACUAAUGAUCCCCUGGAGGCGGCCCAC
GGGGGGAACGUGCUGAUAACCGAUACCUGGAUCUCCAUGGGGCAGGAAGAAG
AGAAGAAAAAGCGGCUGCAGGCAUUCCAGGGAUACCAGGUCACCAUGAAAACC
GCAAAAGUGGCAGCCAGCGACUGGACUUUCCUCCAUUGCCUGCCGCGAAAGCC
GGAGGAGGUCGAUGACGAGGUGUUCUACUCCCCGCGGUCGCUGGUGUUCCCGG
AGGCGGAAAACCGGAAGUGGACCAUUAUGGCCGUGAUGGUGUCACUCCUGAC
UGACUACAGCCCGCAACUGCAGAAGCCGAAGUUCUAGCUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM1787 (SEQ ID NO: 61)
CUUAAGGGGGCGCUGCCUACGGAGGUGGCAGCCAUCUCCUUCUCGGCAUCAAG
CUUACCAUGGUGCCCCAGGCCCUGCUCUUGGUCCCGCUGCUGGUGUUCCCCCU
CUGCUUCGGCAAGUUCCCCAUCUACACCAUCCCCGACAAGCUGGGGCCGUGGA
GCCCCAUCGACAUCCACCACCUGUCCUGCCCCAACAACCUCGUGGUCGAGGAC
GAGGGCUGCACCAACCUGAGCGGGUUCUCCUACAUGCUUUUCAAUCUCCGCAU
CCUCCUUAACAACGCCGCGUUUAGAAACGGCCACAACUUCAUGGUCCGGAACU
UCAGAUGUGGCCAGCCGCUUCAAAACAAGGUCCAGCUGAAGGGCCGGGAUCUU
CUGACCCUGAAGAACUUUACUGGCGAAGAGAUCAAGUACAUGCUCUGGCUCUC
CGCGGACUUGAAGUUCCGCAUUAAGCAGAAGGGGGAAUACCUUCCGCUGCUUC
AAGGAAAGAGCCUCGGCAUGAUCUUUGAGAAGCGCUCAACCAGGACCCGCCUU
UCUACUGAAACUGGGUUCGCGCUGCUCGGUGGCCACCCCUGCUUCCUGACGAC
CCAGGACAUCCACCUCGGAGUGAACGAAUCCCUCACCGAUACCGCCCGGGUGU
UAUCGAGCAUGGCAGAUGCCGUGCUGGCCAGGGUGUACAAACAGUCCGAUCUG

-continued

SEQUENCE LISTING

```
GACACUCUGGCCAAGGAGGCGUCAAUUCCUAUUAUCAACGGCCUUAGUGACCU
CUACCAUCCGAUUCAGAUCCUGGCCGAUUACCUCACCCUGCAAGAACACUACA
GCUCCCUGAAGGGUCUGACAUUGUCCUGGAUCGGCGACGGCAACAACAUUCUC
CAUUCCAUCAUGAUGUCCGCCGCAAAAUUCGGCAUGCAUCUUCAAGCCGCCAC
GCCGAAGGGUUACGAGCCCGACGCUUCCGUGACUAAGCUCGCCGAGCAGUACG
CUAAGGAGAACGGAACCAAGCUUCUGCUGACUAACGACCCACUAGAAGCAGCC
CACGGGGGCAACGUGCUUAUUACUGACACCUGGAUCUCCAUGGGCCAGGAAGA
AGAGAAAAAGAAGCGGCUGCAGGCGUUCCAGGGAUAUCAGGUCACCAUGAAA
ACCGCCAAGGUCGCUGCCUCCGACUGGACCUUCCUGCACUGCCUGCCUCGCAA
GCCUGAAGAAGUGGACGACGAGGUGUUCUACUCGCCACGGAGCCUCGUGUUCC
CCGAGGCCGAGAAUAGAAAGUGGACCAUCAUGGCCGUGAUGGUGUCACUGCUC
ACCGACUACAGCCCGCAGCUUCAGAAGCCCAAGUUCUAGAUAAGUGAAUGCAA
GGCUGGCCGGAAGCCCUUGCCUGAAAGCAAGAUUUCAGCCUGGAAGAGGGCAA
AGUGGACGGGAGUGGACAGGAGUGGAUGCGAUAAGAUGUGGUUUGAAGCUGA
UGGGUGCCAGCCCUGCAUUGCUGAGUCAAUCAAUAAAGAGCUUUCUUUUGACC
CAUUCUAGAUCUAG

>mARM1788 (SEQ ID NO: 62)
AGGAAACUUAAGAUUAUUACAUCAAAACAAAAAGCCGCCAAUGCUGUUCAAC
CUGCGCAUCCUGCUGAACAACGCCGCCUUCCGCAACGGCCACAACUUCAUGGU
GCGCAACUUCCGCUGCGGCCAGCCCCUGCAGAACAAGGUGCAGCUGAAGGGCC
GCGACCUGCUGACCCUGAAGAACUUCACCGGCGAGGAGAUCAAGUACAUGCUG
UGGCUGAGCGCCGACCUGAAGUUCCGCAUCAAGCAGAAGGGCGAGUACCUGCC
CCUGCUGCAGGGCAAGAGCCUGGGCAUGAUCUUCGAGAAGCGCAGCACCCGCA
CCCGCCUGAGCACCGAGACAGGCCUGGCCCUGCUGGGCGGCCACCCCUGCUUC
CUGACCACCCAGGACAUCCACCUGGGCGUGAACGAGAGCCUGACCGACACCGC
CCGCGUGCUGAGCAGCAUGGCCGACGCCGUGCUGGCCCGCGUGUACAAGCAGA
GCGACCUGGACACCCUGGCCAAGGAGGCCAGCAUCCCCAUCAUCAACGGCCUG
AGCGACCUGUACCACCCCAUCCAGAUCCUGGCCGACUACCUGACCCUGCAGGA
GCACUACAGCAGCCUGAAGGGCCUGACCCUGAGCUGGAUCGGCGACGGCAACA
ACAUCCUGCACAGCAUCAUGAUGAGCGCCGCCAAGUUCGGCAUGCACCUGCAG
GCCGCCACCCCCAAGGGCUACGAGCCCGACGCCAGCGUGACCAAGCUGGCCGA
GCAGUACGCCAAGGAGAACGGCACCAAGCUGCUGCUGACCAACGACCCCCUGG
AGGCCGCCCACGGCGGCAACGUGCUGAUCACCGACACCUGGAUCAGCAUGGGC
CAGGAGGAGGAGAAGAAGAAGCGCCUGCAGGCCUUCCAGGGCUACCAGGUGAC
CAUGAAGACCGCCAAGGUGGCCGCCAGCGACUGGACCUUCCUGCACUGCCUGC
CCCGCAAGCCCGAGGAGGUGGACGACGAGGUGUUCUACAGCCCCCGCAGCCUG
GUGUUCCCCGAGGCCGAGAACCGCAAGUGGACCAUCAUGGCCGUGAUGGUGAG
CCUGCUGACCGACUACAGCCCCCAGCUGCAGAAGCCCAAGUUCUGAACGCCGA
AGCCUGCAGCCAUGCGACCCCACGCCACCCCGUGCCUCCUGCCUCCGCGCAGCC
UGCAGCGGGAGACCCUGUCCCCGCCCCAGCCGUCCUCCUGGGGUGGACCCUAG
UUUAAUAAAGAUUCACCAAGUUUCACGCAAAAAAAAAAAAAAAAAAAAA
AAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA

>mARM1789 (SEQ ID NO: 63)
CUUAAGGGGGCGCUGCCUACGGAGGUGGCAGCCAUCUCCUUCUCGGCAUCAAG
CUUACCAUGGUGCCCCAGGCCCUGCUCUUGGUCCCGCUGCUGGUGUUCCCCCU
CUGCUUCGGCAAGUUCCCCAUCUACACCAUCCCCGACAAGCUGGGGCCGUGGA
GCCCCAUCGACAUCCACCACCUGUCCUGCCCCAACAACCUCGUGGUCGAGGAC
GAGGGCUGCACCAACCUGAGCGGGUUCUCCUACAUGCUGUUCAACCUGCGCAU
CCUGCUGAACAACGCCGCCUUCCGCAACGGCCACAACUUCAUGGUGCGCAACU
UCCGCUGCGGCCAGCCCCUGCAGAACAAGGUGCAGCUGAAGGGCCGCGACCUG
CUGACCCUGAAGAACUUCACCGGCGAGGAGAUCAAGUACAUGCUGUGGCUGAG
CGCCGACCUGAAGUUCCGCAUCAAGCAGAAGGGCGAGUACCUGCCCCUGCUGC
AGGGCAAGAGCCUGGGCAUGAUCUUCGAGAAGCGCAGCACCCGCACCCGCCUG
AGCACCGAGACAGGCCUGGCCCUGCUGGGCGGCCACCCCUGCUUCCUGACCAC
CCAGGACAUCCACCUGGGCGUGAACGAGAGCCUGACCGACACCGCCCGCGUGC
UGAGCAGCAUGGCCGACGCCGUGCUGGCCCGCGUGUACAAGCAGAGCGACCUG
GACACCCUGGCCAAGGAGGCCAGCAUCCCCAUCAUCAACGGCCUGAGCGACCU
GUACCACCCCAUCCAGAUCCUGGCCGACUACCUGACCCUGCAGGAGCACUACA
GCAGCCUGAAGGGCCUGACCCUGAGCUGGAUCGGCGACGGCAACAACAUCCUG
CACAGCAUCAUGAUGAGCGCCGCCAAGUUCGGCAUGCACCUGCAGGCCGCCAC
CCCCAAGGGCUACGAGCCCGACGCCAGCGUGACCAAGCUGGCCGAGCAGUACG
CCAAGGAGAACGGCACCAAGCUGCUGCUGACCAACGACCCCCUGGAGGCCGCC
CACGGCGGCAACGUGCUGAUCACCGACACCUGGAUCAGCAUGGGCCAGGAGGA
GGAGAAGAAGAAGCGCCUGCAGGCCUUCCAGGGCUACCAGGUGACCAUGAAGA
CCGCCAAGGUGGCCGCCAGCGACUGGACCUUCCUGCACUGCCUGCCCCGCAAG
CCCGAGGAGGUGGACGACGAGGUGUUCUACAGCCCCCGCAGCCUGGUGUUCCC
CGAGGCCGAGAACCGCAAGUGGACCAUCAUGGCCGUGAUGGUGAGCCUGCUGA
CCGACUACAGCCCCCAGCUGCAGAAGCCCAAGUUCUGAAUAAGUGAUGCAAGG
CUGGCCGGAAGCCCUUGCCUGAAAGCAAGAUUUCAGCCUGGAAGAGGGCAAAG
UGGACGGGAGUGGACAGGAGUGGAUGCGAUAAGAUGUGGUUUGAAGCUGAUG
GGUGCCAGCCCUGCAUUGCUGAGUCAAUCAAUAAAGAGCUUUCUUUUGACCCA
UUCUAGAUCUAG
```

-continued

SEQUENCE LISTING

>mARM1790 (SEQ ID NO: 64)
AGGAAACUUAAGAUUAUUACAUCAAAACAAAAAGCCGCCAAUGCUUUUCAAU
CUCCGCAUCCUCCUUAACAACGCCGCGUUUAGAAACGGCCACAACUUCAUGGU
CCGGAACUUCAGAUGUGGCCAGCCGCUUCAAAACAAGGUCCAGCUGAAGGGCC
GGGAUCUUCUGACCCUGAAGAACUUUACUGGCGAAGAGAUCAAGUACAUGCU
CUGGCUCUCCGCGGACUUGAAGUUCCGCAUUAAGCAGAAGGGGGAAUACCUUC
CGCUGCUUCAAGGAAAGAGCCUCGGCAUGAUCUUUGAGAAGCGCUCAACCAGG
ACCCGCCUUUCUACUGAAACUGGGUUCGCGCUGCUCGGUGGCCACCCCUGCUU
CCUGACGACCCAGGACAUCCACCUCGGAGUGAACGAAUCCCUCACCGAUACCG
CCCGGGUGUUAUCGAGCAUGGCAGAUGCCGUGCUGGCCAGGGUGUACAAACAG
UCCGAUCUGGACACUCUGGCCAAGGAGGCGUCAAUUCCUAUUAUCAACGGCCU
UAGUGACCUCUACCAUCCGAUUCAGAUCCUGGCCGAUUACCUCACCCUGCAAG
AACACUACAGCUCCCUGAAGGGUCUGACAUUGUCCUGGAUCGGCGACGGCAAC
AACAUUCUCCAUUCCAUCAUGAUGUCCGCCGCAAAAUUCGGCAUGCAUCUUCA
AGCCGCCACGCCGAAGGGUUACGAGCCCGACGCUUCCGUGACUAAGCUCGCCG
AGCAGUACGCUAAGGAGAACGGAACCAAGCUUCUGCUGACUAACGACCCACUA
GAAGCAGCCCACGGGGGCAACGUGCUUAUUACUGACACCUGGAUCUCCAUGGG
CCAGGAAGAAGAGAAAAAGAAGCGGCUGCAGGCGUUCCAGGGAUAUCAGGUC
ACCAUGAAAACCGCCAAGGUCGCUGCCUCCGACUGGACCUUCCUGCACUGCCU
GCCUCGCAAGCCUGAAGAAGUGGACGACGAGGUGUUCUACUCGCCACGGAGCC
UCGUGUUCCCCGAGGCCGAGAAUAGAAAGUGGACCAUCAUGGCCGUGAUGGU
GUCACUGCUCACCGACUACAGCCCGCAGCUUCAGAAGCCCAAGUUCUAGACGC
CGAAGCCUGCAGCCAUGCGACCCCACGCCACCCCGUGCCUCCUGCCUCCGCGCA
GCCUGCAGCGGGAGACCCUGUCCCCGCCCCAGCCGUCCUCCUGGGGUGGACCC
UAGUUUAAUAAAGAUUCACCAAGUUUCACGCAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAA

>mARM1791 (SEQ ID NO: 65)
CUUAAGGGGGCGCUGCCUACGGAGGUGGCAGCCAUCUCCUUCUCGGCAUCAAG
CUUACCAUGGUGCCCCAGGCCCUGCUCUUGGUCCCGCUGCUGGUGUUCCCCCU
CUGCUUCGGCAAGUUCCCCAUCUACACCAUCCCCGACAAGCUGGGGCCGUGGA
GCCCCAUCGACAUCCACCACCUGUCCUGCCCCAACAACCUCGUGGUCGAGGAC
GAGGGCUGCACCAACCUGAGCGGGUUCUCCUACAUGCUUUUCAACCUGAGAAU
CCUCUUGAACAAUGCUGCUUUUCGGAAUGGCCACAACUUUAUGGUUCGGAACU
UCCGUUGCGGCCAGCCUUUACAAAACAAGGUCCAGCUGAAGGGCCGGGAUUUG
CUCACACUAAAGAACUUUACUGGAGAAGAGAUCAAGUACAUGCUAUGGCUGU
CGGCCGACCUGAAGUUCCGUAUCAAGCAGAAGGGAGAAUACCUUCCGCUGCUU
CAAGGAAAGAGCCUCGGCAUGAUCUUUGAGAAGCGCUCAACCAGGACCCGCCU
UUCUACUGAAACUGGGUUCGCGCUGCUCGGUGGCCACCCCUGCUUCCUGACGA
CCCAGGACAUCCACCUCGGAGUGAACGAAUCCCUCACCGAUACCGCCCGGGUG
UUAUCGAGCAUGGCAGAUGCCGUGCUGGCCAGGGUGUACAAACAGUCCGAUCU
CGAUACCUUGGCAAAGGAGGCUUCCAUUCCCAUCAUCAACGGCCUGAGCGACC
UGUACCACCCAAUCCAAAUCCUGGCUGACUACCUGACCCUGCAAGAGCACUAC
AGCAGCCUGAAGGGUCUGACCCUGUCAUGGAUUGGCGAUGGAAACAAUAUUC
UGCACUCCAUCAUGAUGUCCGCCGCGAAGUUCGGAAUGCAUCUGCAAGCCGCC
ACUCCAAAAGGAUACGAACCGGAUGCAUCCGUGACCAAGUUGGCGGAACAGUA
CGCGAAGGAGAACGGAACCAAGCUCCUGCUGACUAACGACCCGCUCGAGGCUG
CGCAUGGGGGUAACGUGCUGAUUACGGACACCUGGAUCUCCAUGGGGCAGGA
GGAAGAGAAGAAGAAGAGACUGCAGGCAUUCCAGGGGUACCAGGUCACCAUG
AAAACCGCAAAAGUGGCAGCUUCGGACUGGACUUUCCUGCAUUGCCUGCCGAG
GAAGCCGGAGGAAGUCGACGACGAAGUGUUCUACUCGCCUCGGUCCCUGGUGU
UCCCCGAGGCCGAAAACCGGAAGUGGACCAUCAUGGCCGUGAUGGUGUCCUUG
CUGACUGACUAUAGCCCGCAGCUGCAGAAGCCUAAGUUCUAGAUAAGUGAUGC
AAGGCUGGCCGGAAGCCCUUGCCUGAAAGCAAGAUUUCAGCCUGGAAGAGGGC
AAAGUGGACGGGAGUGGACAGGAGUGGAUGCGAUAAGAUGUGGUUUGAAGCU
GAUGGGUGCCAGCCCUGCAUUGCUGAGUCAAUCAAUAAAGAGCUUUCUUUUG
ACCCAUUCUAGAUCUAG

>mARM1792 (SEQ ID NO: 66)
UGAGUGUCGUACAGCCUCCAGGCCCCCCCCUCCCGGGAGAGCCAUAGUGGUCU
GCGGAACCGGUGAGUACACCGGAAUUGCCGGGAAGACUGGGUCCUUUCUUGG
AUAAACCCACUCUAUGCCCGGCCAUUUGGGCGUGCCCCCGCAAGACUGCUAGC
CGAGUAGUGUUGGGUUGCGAUGCUGUUCAACCUGCGCAUCCUGCUGAACAACG
CCGCCUUCCGCAACGGCCACAACUUCAUGGUGCGCAACUUCCGCUGCGGCCAG
CCCCUGCAGAACAAGGUGCAGCUGAAGGGCCGCGACCUGCUGACCCUGAAGAA
CUUCACCGGCGAGGAGAUCAAGUACAUGCUGUGGCUGAGCGCCGACCUGAAGU
UCCGCAUCAAGCAGAAGGGCGAGUACCUGCCCCUGCUGCAGGGCAAGAGCCUG
GGCAUGAUCUUCGAGAAGCGCAGCACCCGCACCCGCCUGAGCACCGAGACAGG
CCUGGCCCUGCUGGGCGGCCACCCCUGCUUCCUGACCACCCAGGACAUCCACCU
GGGCGUGAACGAGAGCCUGACCGACACCGCCCGCGUGCUGAGCAGCAUGGCCG
ACGCCGUGCUGGCCCGCGUGUACAAGCAGAGCGACCUGGACACCCUGGCCAAG
GAGGCCAGCAUCCCCAUCAUCAACGGCCUGAGCGACCUGUACCACCCCAUCCA
GAUCCUGGCCGACUACCUGACCCUGCAGGAGCACUACAGCAGCCUGAAGGGCC
UGACCCUGAGCUGGAUCGGCGACGGCAACAACAUCCUGCACAGCAUCAUGAUG
AGCGCCGCCAAGUUCGGCAUGCACCUGCAGGCCGCCACCCCCAAGGGCUACGA
GCCCGACGCCAGCGUGACCAAGCUGGCCGAGCAGUACGCCAAGGAGAACGGCA

-continued

| SEQUENCE LISTING |
|---|

CCAAGCUGCUGCUGACCAACGACCCCCUGGAGGCCGCCCACGGCGGCAACGUG
CUGAUCACCGACACCUGGAUCAGCAUGGGCCAGGAGGAGGAGAAGAAGAAGC
GCCUGCAGGCCUUCCAGGGCUACCAGGUGACCAUGAAGACCGCCAAGGUGGCC
GCCAGCGACUGGACCUUCCUGCACUGCCUGCCCCGCAAGCCCGAGGAGGUGGA
CGACGAGGUGUUCUACAGCCCCCGCAGCCUGGUGUUCCCCGAGGCCGAGAACC
GCAAGUGGACCAUCAUGGCCGUGAUGGUGAGCCUGCUGACCGACUACAGCCCC
CAGCUGCAGAAGCCCAAGUUCUGAAUAAGUGAUAGAGCGGCAAACCCUAGCUA
CACUCCAUAGCUAGUUUCUUUUUUUUUUGUUUUUUUUUUUUUUUUUUUUUUU
UUUUUUUUUUUUUUUUCCUUUCUUUUCCUUCUUUUUUUCCUCUUUUCUUGGU
GGCUCCAUCUUAGCCCUAGUCACGGCUAGCUGUGAAAGGUCCGUGAGCCGCAU
GACUGCAGAGAGUGCCGUAACUGGCCUCUCUGCAGAUCAUGUUCUAG

>mARM1793 (SEQ ID NO: 67)
AGGAAACUUAAGAUUAUUACAUCAAAACAAAAAGCCGCCAAUGCUUUUCAAU
CUCCGCAUCCUCCUUAACAACGCCGCGUUUAGAAACGGCCACAACUUCAUGGU
CCGGAACUUCAGAUGUGGCCAGCCGCUUCAAAACAAGGUCCAGCUGAAGGGCC
GGGAUCUUCUGACCCUGAAGAACUUUACUGGCGAAGAGAUCAAGUACAUGCU
CUGGCUCUCCGCGGACUUGAAGUUCCGCAUUAAGCAGAAGGGGGAAUACCUUC
CGCUGCUUCAAGGAAAGAGCCUCGGCAUGAUCUUUGAGAAGCGCUCAACCAGG
ACCCGCCUUUCUACUGAAACUGGGUUCGCGCUGCUCGGUGGCCACCCCUGCUU
CCUGACGACCCAGGACAUCCACCUCGGAGUGAACGAAUCCCUCACCGAUACCG
CCCGGGUGUUAUCGAGCAUGGCAGAUGCCGUGCUGGCCAGGGUGUACAAACAG
UCCGAUCUGGACACUCUGGCCAAGGAGGCGUCAAUUCCUAUUAUCAACGGCCU
UAGUGACCUCUACCAUCCGAUUCAGAUCCUGGCCGAUUACCUCACCCUGCAAG
AACACUACAGCUCCCUGAAGGGUCUGACAUUGUCCUGGAUCGGCGACGGCAAC
AACAUUCUCCAUUCCAUCAUGAUGUCCGCCGCAAAAUUCGGCAUGCAUCUUCA
AGCCGCCACGCCGAAGGGUUACGAGCCCGACGCUUCCGUGACUAAGCUCGCCG
AGCAGUACGCUAAGGAGAACGGAACCAAGCUUCUGCUGACUAACGACCCACUA
GAAGCAGCCCACGGGGGCAACGUGCUUAUUACUGACACCUGGAUCUCCAUGGG
CCAGGAAGAAGAGAAAAAGAAGCGGCUGCAGGCGUUCCAGGGAUAUCAGGUC
ACCAUGAAAACCGCCAAGGUCGCUGCCUCCGACUGGACCUUCCUGCACUGCCU
GCCUCGCAAGCCUGAAGAAGUGGACGACGAGGUGUUCUACUCGCCACGGAGCC
UCGUGUUCCCCGAGGCCGAGAAUAGAAAGUGGACCAUCAUGGCCGUGAUGGU
GUCACUGCUCACCGACUACAGCCCGCAGCUUCAGAAGCCCAAGUUCUAGGCUG
GAGCCUCGGUAGCCGUUCCUCCUGCCCGCUGGGCCUCCCAACGGGCCCUCCUCC
CCUCCUUGCACCGGCCCUUCCUGGUCUUUGAAUAAAGUCUGAGUGGGCAGCAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAA

>mARM1794 (SEQ ID NO: 68)
AGGAAACUUAAGAUUAUUACAUCAAAACAAAAAGCCGCCAAUGCUGUUCAAC
CUGCGCAUCCUGCUGAACAACGCCGCCUUCCGCAACGGCCACAACUUCAUGGU
GCGCAACUUCCGCUGCGGCCAGCCCCUGCAGAACAAGGUGCAGCUGAAGGGCC
GCGACCUGCUGACCCUGAAGAACUUCACCGGCGAGGAGAUCAAGUACAUGCUG
UGGCUGAGCGCCGACCUGAAGUUCCGCAUCAAGCAGAAGGGCGAGUACCUGCC
CCUGCUGCAGGGCAAGAGCCUGGGCAUGAUCUUCGAGAAGCGCAGCACCCGCA
CCCGCCUGAGCACCGAGACAGGCCUGGCCCUGCUGGGCGGCCACCCCUGCUUC
CUGACCACCCAGGACAUCCACCUGGGCGUGAACGAGAGCCUGACCGACACCGC
CCGCGUGCUGAGCAGCAUGGCCGACGCCGUGCUGGCCCGCGUGUACAAGCAGA
GCGACCUGGACACCCUGGCCAAGGAGGCCAGCAUCCCCAUCAUCAACGGCCUG
AGCGACCUGUACCACCCCAUCCAGAUCCUGGCCGACUACCUGACCCUGCAGGA
GCACUACAGCAGCCUGAAGGGCCUGACCCUGAGCUGGAUCGGCGACGGCAACA
ACAUCCUGCACAGCAUCAUGAUGAGCGCCGCCAAGUUCGGCAUGCACCUGCAG
GCCGCCACCCCCAAGGGCUACGAGCCCGACGCCAGCGUGACCAAGCUGGCCGA
GCAGUACGCCAAGGAGAACGGCACCAAGCUGCUGCUGACCAACGACCCCCUGG
AGGCCGCCCACGGCGGCAACGUGCUGAUCACCGACACCUGGAUCAGCAUGGGC
CAGGAGGAGGAGAAGAAGAAGCGCCUGCAGGCCUUCCAGGGCUACCAGGUGAC
CAUGAAGACCGCCAAGGUGGCCGCCAGCGACUGGACCUUCCUGCACUGCCUGC
CCCGCAAGCCCGAGGAGGUGGACGACGAGGUGUUCUACAGCCCCCGCAGCCUG
GUGUUCCCCGAGGCCGAGAACCGCAAGUGGACCAUCAUGGCCGUGAUGGUGAG
CCUGCUGACCGACUACAGCCCCCAGCUGCAGAAGCCCAAGUUCUGAGCUGGAG
CCUCGGUAGCCGUUCCUCCUGCCCGCUGGGCCUCCCAACGGGCCCUCCUCCCCU
CCUUGCACCGGCCCUUCCUGGUCUUUGAAUAAAGUCUGAGUGGGCAGCAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAA

>mARM1795 (SEQ ID NO: 69)
AGGAAACUUAAGAUUAUUACAUCAAAACAAAAAGCCGCCAAUGCUUUUCAAC
CUGAGAAUCCUCUUGAACAAUGCUGCUUUUCGGAAUGGCCACAACUUUAUGG
UUCGGAACUUCCGUUGCGGCCAGCCUUUACAAAACAAGGUCCAGCUGAAGGGC
CGGGAUUUGCUCACACUAAAGAACUUUACUGGAGAAGAGAUCAAGUACAUGC
UAUGGCUGUCGGCCGACCUGAAGUUCCGUAUCAAGCAGAAGGGAGAAUACCU
UCCGCUGCUUCAAGGAAAGAGCCUCGGCAUGAUCUUUGAGAAGCGCUCAACCA
GGACCCGCCUUUCUACUGAAACUGGGUUCGCGCUGCUCGGUGGCCACCCCUGC
UUCCUGACGACCCAGGACAUCCACCUCGGAGUGAACGAAUCCCUCACCGAUAC

-continued

SEQUENCE LISTING

CGCCCGGGUGUUAUCGAGCAUGGCAGAUGCCGUGCUGGCCAGGGUGUACAAAC
AGUCCGAUCUCGAUACCUUGGCAAAGGAGGCUUCCAUUCCCAUCAUCAACGGC
CUGAGCGACCUGUACCACCCAAUCCAAAUCCUGGCUGACUACCUGACCCUGCA
AGAGCACUACAGCAGCCUGAAGGGUCUGACCCUGUCAUGGAUUGGCGAUGGA
AACAAUAUUCUGCACUCCAUCAUGAUGUCCGCCGCGAAGUUCGGAAUGCAUCU
GCAAGCCGCCACUCCAAAAGGAUACGAACCGGAUGCAUCCGUGACCAAGUUGG
CGGAACAGUACGCGAAGGAGAACGGAACCAAGCUCCUGCUGACUAACGACCCG
CUCGAGGCUGCGCAUGGGGGUAACGUGCUGAUUACGGACACCUGGAUCUCCAU
GGGGCAGGAGGAAGAGAAGAAGAAGAGACUGCAGGCAUUCCAGGGGUACCAG
GUCACCAUGAAAACCGCAAAAGUGGCAGCUUCGGACUGGACUUUCCUGCAUUG
CCUGCCGAGGAAGCCGGAGGAAGUCGACGACGAAGUGUUCUACUCGCCUCGGU
CCCUGGUGUUCCCCGAGGCCGAAAACCGGAAGUGGACCAUCAUGGCCGUGAUG
GUGUCCUUGCUGACUGACUAUAGCCCGCAGCUGCAGAAGCCUAAGUUCUAGGC
UGGAGCCUCGGUAGCCGUUCCUCCUGCCCGCUGGGCCUCCCAACGGGCCCUCC
UCCCCUCCUUGCACCGGCCCUUCCUGGUCUUUGAAUAAAGUCUGAGUGGGCAG
CAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAAAAAAAAAAAAA

>mARM1796 (SEQ ID NO: 70)
AGGAAACUUAAGAAUUAUUGGUUAAAGAAGUAUAUUAGUGCUAAUUUCCCUC
CGUUUGUCCUAGCUUUUCUCUUCUGUCAACCCCACACGCCUUUGGCACAAUGC
UUUUCAAUCUCCGCAUCCUCCUUAACAACGCCGCGUUUAGAAACGGCCACAAC
UUCAUGGUCCGGAACUUCAGAUGUGGCCAGCCGCUUCAAAACAAGGUCCAGCU
GAAGGGCCGGGAUCUUCUGACCCUGAAGAACUUUACUGGCGAAGAGAUCAAG
UACAUGCUCUGGCUCUCCGCGGACUUGAAGUUCCGCAUUAAGCAGAAGGGGGA
AUACCUUCCGCUGCUUCAAGGAAAGAGCCUCGGCAUGAUCUUUGAGAAGCGCU
CAACCAGGACCCGCCUUUCUACUGAAACUGGGUUCGCGCUGCUCGGUGGCCAC
CCCUGCUUCCUGACGACCCAGGACAUCCACCUCGGAGUGAACGAAUCCCUCAC
CGAUACCGCCCGGGUGUUAUCGAGCAUGGCAGAUGCCGUGCUGGCCAGGGUGU
ACAAACAGUCCGAUCUGGACACUCUGGCCAAGGAGGCGUCAAUUCCUAUUAUC
AACGGCCUUAGUGACCUCUACCAUCCGAUUCAGAUCCUGGCCGAUUACCUCAC
CCUGCAAGAACACUACAGCUCCCUGAAGGGUCUGACAUUGUCCUGGAUCGGCG
ACGGCAACAACAUUCUCCAUUCCAUCAUGAUGUCCGCCGCAAAAUUCGGCAUG
CAUCUUCAAGCCGCCACGCCGAAGGGUUACGAGCCCGACGCUUCCGUGACUAA
GCUCGCCGAGCAGUACGCUAAGGAGAACGGAACCAAGCUUCUGCUGACUAACG
ACCCACUAGAAGCAGCCCACGGGGGCAACGUGCUUAUUACUGACACCUGGAUC
UCCAUGGGCCAGGAAGAAGAGAAAAAGAAGCGGCUGCAGGCGUUCCAGGGAU
AUCAGGUCACCAUGAAAACCGCCAAGGUCGCUGCCUCCGACUGGACCUUCCUG
CACUGCCUGCCUCGCAAGCCUGAAGAAGUGGACGACGAGGUGUUCUACUCGCC
ACGGAGCCUCGUGUUCCCCGAGGCCGAGAAUAGAAAGUGGACCAUCAUGGCCG
UGAUGGUGUCACUGCUCACCGACUACAGCCCGCAGCUUCAGAAGCCCAAGUUC
UAGCUCGAGACACAUCACAACCACAACCUUCUCAGGCUACCCUGAGAAAAAAA
GACAUGAAGACUCAGGACUCAUCUUUUCUGUUGGUGUAAAAUCAACACCCUA
AGGAACACAAAUUUCUUUAAACAUUUGACUUCUUGUCUCUGUGCUGCAAUUA
AUAAAAAAUGGAAAGAAUCUAUCUAG

>mARM1797 (SEQ ID NO: 71)
AGGAAACUUAAGAAUUAUUGGUUAAAGAAGUAUAUUAGUGCUAAUUUCCCUC
CGUUUGUCCUAGCUUUUCUCUUCUGUCAACCCCACACGCCUUUGGCACAAUGC
UGUUCAACCUGCGCAUCCUGCUGAACAACGCCGCCUUCCGCAACGGCCACAAC
UUCAUGGUGCGCAACUUCCGCUGCGGCCAGCCCCUGCAGAACAAGGUGCAGCU
GAAGGGCCGCGACCUGCUGACCCUGAAGAACUUCACCGGCGAGGAGAUCAAGU
ACAUGCUGUGGCUGAGCGCCGACCUGAAGUUCCGCAUCAAGCAGAAGGGCGAG
UACCUGCCCCUGCUGCAGGGCAAGAGCCUGGGCAUGAUCUUCGAGAAGCGCAG
CACCCGCACCCGCCUGAGCACCGAGACAGGCCUGGCCCUGCUGGGCGGCCACCC
CUGCUUCCUGACCACCCAGGACAUCCACCUGGGCGUGAACGAGAGCCUGACCG
ACACCGCCCGCGUGCUGAGCAGCAUGGCCGACGCCGUGCUGGCCCGCGUGUAC
AAGCAGAGCGACCUGGACACCCUGGCCAAGGAGGCCAGCAUCCCCAUCAUCAA
CGGCCUGAGCGACCUGUACCACCCCAUCCAGAUCCUGGCCGACUACCUGACCC
UGCAGGAGCACUACAGCAGCCUGAAGGGCCUGACCCUGAGCUGGAUCGGCGAC
GGCAACAACAUCCUGCACAGCAUCAUGAUGAGCGCCGCCAAGUUCGGCAUGCA
CCUGCAGGCCGCCACCCCCAAGGGCUACGAGCCCGACGCCAGCGUGACCAAGC
UGGCCGAGCAGUACGCCAAGGAGAACGGCACCAAGCUGCUGCUGACCAACGAC
CCCCUGGAGGCCGCCCACGGCGGCAACGUGCUGAUCACCGACACCUGGAUCAG
CAUGGGCCAGGAGGAGGAGAAGAAGAAGCGCCUGCAGGCCUUCCAGGGCUACC
AGGUGACCAUGAAGACCGCCAAGGUGGCCGCCAGCGACUGGACCUUCCUGCAC
UGCCUGCCCCGCAAGCCCGAGGAGGUGGACGACGAGGUGUUCUACAGCCCCCG
CAGCCUGGUGUUCCCCGAGGCCGAGAACCGCAAGUGGACCAUCAUGGCCGUGA
UGGUGAGCCUGCUGACCGACUACAGCCCCCAGCUGCAGAAGCCCAAGUUCUGA
CUCGAGACACAUCACAACCACAACCUUCUCAGGCUACCCUGAGAAAAAAAGAC
AUGAAGACUCAGGACUCAUCUUUUCUGUUGGUGUAAAAUCAACACCCUAAGG
AACACAAAUUUCUUUAAACAUUUGACUUCUUGUCUCUGUGCUGCAAUUAAUA
AAAAAUGGAAAGAAUCUAUCUAG

-continued

SEQUENCE LISTING

>mARM1798 (SEQ ID NO: 72)
AGGAAACUUAAGAAUUAUUGGUUAAAGAAGUAUAUUAGUGCUAAUUUCCCUC
CGUUUGUCCUAGCUUUUCUCUUCUGUCAACCCCACACGCCUUUGGCACAAUGC
UUUUCAACCUGAGAAUCCUCUUGAACAAUGCUGCUUUUCGGAAUGGCCACAAC
UUUAUGGUUCGGAACUUCCGUUGCGGCCAGCCUUUACAAAACAAGGUCCAGCU
GAAGGGCCGGGAUUUGCUCACACUAAAGAACUUUACUGGAGAAGAGAUCAAG
UACAUGCUAUGGCUGUCGGCCGACCUGAAGUUCCGUAUCAAGCAGAAGGGAG
AAUACCUUCCGCUGCUUCAAGGAAAGAGCCUCGGCAUGAUCUUUGAGAAGCGC
UCAACCAGGACCCGCCUUUCUACUGAAACUGGGUUCGCGCUGCUCGGUGGCCA
CCCCUGCUUCCUGACGACCCAGGACAUCCACCUCGGAGUGAACGAAUCCCUCA
CCGAUACCGCCCGGGUGUUAUCGAGCAUGGCAGAUGCCGUGCUGGCCAGGGUG
UACAAACAGUCCGAUCUCGAUACCUUGGCAAAGGAGGCUUCCAUUCCCAUCAU
CAACGGCCUGAGCGACCUGUACCACCCAAUCCAAAUCCUGGCUGACUACCUGA
CCCUGCAAGAGCACUACAGCAGCCUGAAGGGUCUGACCCUGUCAUGGAUUGGC
GAUGGAAACAAUAUUCUGCACUCCAUCAUGAUGUCCGCCGCGAAGUUCGGAAU
GCAUCUGCAAGCCGCCACUCCAAAAGGAUACGAACCGGAUGCAUCCGUGACCA
AGUUGGCGGAACAGUACGCGAAGGAGAACGGAACCAAGCUCCUGCUGACUAAC
GACCCGCUCGAGGCUGCGCAUGGGGGUAACGUGCUGAUUACGGACACCUGGAU
CUCCAUGGGGCAGGAGGAAGAGAAGAAGAAGAGACUGCAGGCAUUCCAGGGG
UACCAGGUCACCAUGAAAACCGCAAAAGUGGCAGCUUCGGACUGGACUUUCCU
GCAUUGCCUGCCGAGGAAGCCGGAGGAAGUCGACGACGAAGUGUUCUACUCGC
CUCGGUCCCUGGUGUUCCCCGAGGCCGAAAACCGGAAGUGGACCAUCAUGGCC
GUGAUGGUGUCCUUGCUGACUGACUAUAGCCCGCAGCUGCAGAAGCCUAAGUU
CUAGCUCGAGACACAUCACAACCACAACCUUCUCAGGCUACCCUGAGAAAAAA
AGACAUGAAGACUCAGGACUCAUCUUUUCUGUUGGUGUAAAAUCAACACCCU
AAGGAACACAAAUUUCUUUAAACAUUUGACUUCUUGUCUCUGUGCUGCAAUU
AAUAAAAAAUGGAAAGAAUCUAUCUAG

>mARM1799 (SEQ ID NO: 73)
AUUAUUACAUCAAAACAAAAAGCCGCCACCAUGCUGUUCAACCUGCGCAUCCU
GCUGAACAACGCCGCCUUCCGCAACGGCCACAACUUCAUGGUGCGCAACUUCC
GCUGCGGCCAGCCCCUGCAGAACAAGGUGCAGCUGAAGGGCCGCGACCUGCUG
ACCCUGAAGAACUUCACCGGCGAGGAGAUCAAGUACAUGCUGUGGCUGAGCGC
CGACCUGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCCUGAGC
ACCGAGACAGGCUUCGCCCUGCUGGGCGGCCACCCCUGCUUCCUGACCACCCA
GGACAUCCACCUGGGCGUGAACGAGAGCCUGACCGACACCGCCCGCGUGCUGA
GCAGCAUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGACCUGUA
CCACCCCAUCCAGAUCCUGGCCGACUACCUGACCCUGCAGGAGCACUACAGCA
GCCUGAAGGGCCUGACCCUGAGCUGGAUCGGCGACGGCAACAACAUCCUGCAC
AGCAUCAUGAUGAGCGCCGCCAAGUUCGGCAUGCACCUGCAGGCCGCCACCCC
CAAGGGCUACGAGCCCGACGCCAGCGUGACCAAGCUGGCCGAGCAGUACGCCA
AGGAGAACGGCACCAAGCUGCUGCUGACCAACGACCCCCUGGAGGCCGCCCAC
GGCGGCAACGUGCUGAUCACCGACACCUGGAUCAGCAUGGGCCAGGAGGAGGA
GAAGAAGAAGCGCCUGCAGGCCUUCCAGGGCUACCAGGUGACCAUGAAGACCG
CCAAGGUGGCCGCCAGCGACUGGACCUUCCUGCACUGCCUGCCCCGCAAGCCC
GAGGAGGUGGACGACGAGGUGUUCUACAGCCCCCGCAGCCUGGUGUUCCCCGA
GGCCGAGAACCGCAAGUGGACCAUCAUGGCCGUGAUGGUGAGCCUGCUGACCG
ACUACAGCCCCCAGCUGCAGAAGCCCAAGUUCUGAGGUCUCUAGUAAUGAGCU
GGAGCCUCGGUAGCCGUUCCUCCUGCCCGCUGGGCCUCCCAACGGGCCCUCCU
CCCCUCCUUGCACCGGCCCUUCCUGGUCUUUGAAUAAAGUCUGAGUGGGCAUC
UAG

>mARM1800 (SEQ ID NO: 74)
AGGAAACUUAAGAAUUAUUGGUUAAAGAAGUAUAUUAGUGCUAAUUUCCCUC
CGUUUGUCCUAGCUUUUCUCUUCUGUCAACCCCACACGCCUUUGGCACAAUGC
UGUUCAACCUGCGCAUCCUGCUGAACAACGCCGCCUUCCGCAACGGCCACAAC
UUCAUGGUGCGCAACUUCCGCUGCGGCCAGCCCCUGCAGAACAAGGUGCAGCU
GAAGGGCCGCGACCUGCUGACCCUGAAGAACUUCACCGGCGAGGAGAUCAAGU
ACAUGCUGUGGCUGAGCGCCGACCUGAAGUUCCGCAUCAAGCAGAAGGGCGAG
UACCUGCCCCUGCUGCAGGGCAAGAGCCUGGGCAUGAUCUUCGAGAAGCGCAG
CACCCGCACCCGCCUGAGCACCGAGACAGGCUUCGCCCUGCUGGGCGGCCACCC
CUGCUUCCUGACCACCCAGGACAUCCACCUGGGCGUGAACGAGAGCCUGACCG
ACACCGCCCGCGUGCUGAGCAGCAUGGCCGACGCCGUGCUGGCCCGCGUGUAC
AAGCAGAGCGACCUGGACACCCUGGCCAAGGAGGCCAGCAUCCCCAUCAUCAA
CGGCCUGAGCGACCUGUACCACCCCAUCCAGAUCCUGGCCGACUACCUGACCC
UGCAGGAGCACUACAGCAGCCUGAAGGGCCUGACCCUGAGCUGGAUCGGCGAC
GGCAACAACAUCCUGCACAGCAUCAUGAUGAGCGCCGCCAAGUUCGGCAUGCA
CCUGCAGGCCGCCACCCCCAAGGGCUACGAGCCCGACGCCAGCGUGACCAAGC
UGGCCGAGCAGUACGCCAAGGAGAACGGCACCAAGCUGCUGCUGACCAACGAC
CCCCUGGAGGCCGCCCACGGCGGCAACGUGCUGAUCACCGACACCUGGAUCAG
CAUGGGCCAGGAGGAGGAGAAGAAGAAGCGCCUGCAGGCCUUCCAGGGCUACC
AGGUGACCAUGAAGACCGCCAAGGUGGCCGCCAGCGACUGGACCUUCCUGCAC
UGCCUGCCCCGCAAGCCCGAGGAGGUGGACGACGAGGUGUUCUACAGCCCCCG
CAGCCUGGUGUUCCCCGAGGCCGAGAACCGCAAGUGGACCAUCAUGGCCGUGA
UGGUGAGCCUGCUGACCGACUACAGCCCCCAGCUGCAGAAGCCCAAGUUCUGA

-continued

SEQUENCE LISTING

CUCGAGACACAUCACAACCACAACCUUCUCAGGCUACCCUGAGAAAAAAAGAC
AUGAAGACUCAGGACUCAUCUUUUCUGUUGGUGUAAAAUCAACACCCUAAGG
AACACAAAUUUCUUUAAACAUUUGACUUCUUGUCUCUGUGCUGCAAUUAAUA
AAAAAUGGAAAGAAUCUAUCUAG

>mARM1801 (SEQ ID NO: 75)
AGGAAACUUAAGAUUAUUACAUCAAAACAAAAAGCCGCCAAUGCUGUUCAAC
CUGCGCAUCCUGCUGAACAACGCCGCCUUCCGCAACGGCCACAACUUCAUGGU
GCGCAACUUCCGCUGCGGCCAGCCCCUGCAGAACAAGGUGCAGCUGAAGGGCC
GCGACCUGCUGACCCUGAAGAACUUCACCGGCGAGGAGAUCAAGUACAUGCUG
UGGCUGAGCGCCGACCUGAAGUUCCGCAUCAAGCAGAAGGGCGAGUACCUGCC
CCUGCUGCAGGGCAAGAGCCUGGGCAUGAUCUUCGAGAAGCGCAGCACCCGCA
CCCGCCUGAGCACCGAGACAGGCUUCGCCCUGCUGGGCGGCCACCCCUGCUUC
CUGACCACCCAGGACAUCCACCUGGGCGUGAACGAGAGCCUGACCGACACCGC
CCGCGUGCUGAGCAGCAUGGCCGACGCCGUGCUGGCCCGCGUGUACAAGCAGA
GCGACCUGGACACCCUGGCCAAGGAGGCCAGCAUCCCCAUCAUCAACGGCCUG
AGCGACCUGUACCACCCCAUCCAGAUCCUGGCCGACUACCUGACCCUGCAGGA
GCACUACAGCAGCCUGAAGGGCCUGACCCUGAGCUGGAUCGGCGACGGCAACA
ACAUCCUGCACAGCAUCAUGAUGAGCGCCGCCAAGUUCGGCAUGCACCUGCAG
GCCGCCACCCCCAAGGGCUACGAGCCCGACGCCAGCGUGACCAAGCUGGCCGA
GCAGUACGCCAAGGAGAACGGCACCAAGCUGCUGCUGACCAACGACCCCCUGG
AGGCCGCCCACGGCGGCAACGUGCUGAUCACCGACACCUGGAUCAGCAUGGGC
CAGGAGGAGGAGAAGAAGAAGCGCCUGCAGGCCUUCCAGGGCUACCAGGUGAC
CAUGAAGACCGCCAAGGUGGCCGCCAGCGACUGGACCUUCCUGCACUGCCUGC
CCCGCAAGCCCGAGGAGGUGGACGACGAGGUGUUCUACAGCCCCCGCAGCCUG
GUGUUCCCCGAGGCCGAGAACCGCAAGUGGACCAUCAUGGCCGUGAUGGUGAG
CCUGCUGACCGACUACAGCCCCCAGCUGCAGAAGCCCAAGUUCUGAACGCCGA
AGCCUGCAGCCAUGCGACCCCACGCCACCCCGUGCCUCCUGCCUCCGCGCAGCC
UGCAGCGGGAGACCCUGUCCCCGCCCCAGCCGUCCUCCUGGGGUGGACCCUAG
UUUAAUAAAGAUUCACCAAGUUUCACGCAAAAAAAAAAAAAAAAAAAAA
AAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAA

>mARM1802 (SEQ ID NO: 76)
CUUAAGGGGGCGCUGCCUACGGAGGUGGCAGCCAUCUCCUUCUCGGCAUCAAG
CUUACCAUGGUGCCCCAGGCCCUGCUCUUGGUCCCGCUGCUGGUGUUCCCCCU
CUGCUUCGGCAAGUUCCCCAUCUACACCAUCCCCGACAAGCUGGGGCCGUGGA
GCCCCAUCGACAUCCACCACCUGUCCUGCCCCAACAACCUCGUGGUCGAGGAC
GAGGGCUGCACCAACCUGAGCGGGUUCUCCUACAUGCUGUUCAACCUGCGCAU
CCUGCUGAACAACGCCGCCUUCCGCAACGGCCACAACUUCAUGGUGCGCAACU
UCCGCUGCGGCCAGCCCCUGCAGAACAAGGUGCAGCUGAAGGGCCGCGACCUG
CUGACCCUGAAGAACUUCACCGGCGAGGAGAUCAAGUACAUGCUGUGGCUGAG
CGCCGACCUGAAGUUCCGCAUCAAGCAGAAGGGCGAGUACCUGCCCCUGCUGC
AGGGCAAGAGCCUGGGCAUGAUCUUCGAGAAGCGCAGCACCCGCACCCGCCUG
AGCACCGAGACAGGCUUCGCCCUGCUGGGCGGCCACCCCUGCUUCCUGACCAC
CCAGGACAUCCACCUGGGCGUGAACGAGAGCCUGACCGACACCGCCCGCGUGC
UGAGCAGCAUGGCCGACGCCGUGCUGGCCCGCGUGUACAAGCAGAGCGACCUG
GACACCCUGGCCAAGGAGGCCAGCAUCCCCAUCAUCAACGGCCUGAGCGACCU
GUACCACCCCAUCCAGAUCCUGGCCGACUACCUGACCCUGCAGGAGCACUACA
GCAGCCUGAAGGGCCUGACCCUGAGCUGGAUCGGCGACGGCAACAACAUCCUG
CACAGCAUCAUGAUGAGCGCCGCCAAGUUCGGCAUGCACCUGCAGGCCGCCAC
CCCCAAGGGCUACGAGCCCGACGCCAGCGUGACCAAGCUGGCCGAGCAGUACG
CCAAGGAGAACGGCACCAAGCUGCUGCUGACCAACGACCCCCUGGAGGCCGCC
CACGGCGGCAACGUGCUGAUCACCGACACCUGGAUCAGCAUGGGCCAGGAGGA
GGAGAAGAAGAAGCGCCUGCAGGCCUUCCAGGGCUACCAGGUGACCAUGAAGA
CCGCCAAGGUGGCCGCCAGCGACUGGACCUUCCUGCACUGCCUGCCCCGCAAG
CCCGAGGAGGUGGACGACGAGGUGUUCUACAGCCCCCGCAGCCUGGUGUUCCC
CGAGGCCGAGAACCGCAAGUGGACCAUCAUGGCCGUGAUGGUGAGCCUGCUGA
CCGACUACAGCCCCCAGCUGCAGAAGCCCAAGUUCUGAAUAAGUGAAUGCAAG
GCUGGCCGGAAGCCCUUGCCUGAAAGCAAGAUUUCAGCCUGGAAGAGGGCAAA
GUGGACGGGAGUGGACAGGAGUGGAUGCGAUAAGAUGUGGUUUGAAGCUGAU
GGGUGCCAGCCCUGCAUUGCUGAGUCAAUCAAUAAAGAGCUUUCUUUUGACCC
AUUCUAGAUCUAG

>mARM1803 (SEQ ID NO: 77)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGGCGUCUUCAACCUGCGGAUC
CUGCUGAACAACGCCGCCUUCCGGAACGGCCACAACUUCAUGGUCCGCAACUU
CAGAUGCGGCCAGCCCCUGCAGAACAAGGUGCAGCUGAAGGGCCGGGACCUGC
UGACCCUGAAGAACUUCACCGGCGAAGAGAUCAAGUACAUGCUGUGGCUGAGC
GCCGACCUGAAGUUCCGGAUCAAGCAGAAGGGCGAGUACCUGCCCCUGCUGCA
AGGCAAGAGCCUGGGCAUGAUCUUCGAGAAGCGGAGCACCCGGACCCGGCUGA
GCACCGAGACAGGCUUUGCCCUGCUGGGAGGCCACCCCUGCUUUCUGACCACC
CAGGACAUCCACCUGGGCGUGAACGAGAGCCUGACCGACACCGCCAGAGUGCU
GAGCAGCAUGGCCGACGCCGUGCUGGCCCGGGUGUACAAGCAGAGCGACCUGG
ACACCCUGGCCAAAGAGGCCAGCAUCCCCAUCAUCAACGGCCUGAGCGACCUG

-continued

SEQUENCE LISTING

UACCACCCCAUCCAGAUCCUGGCCGACUACCUGACCCUGCAGGAACACUACAG
CUCCCUGAAGGGCCUGACCCUGAGCUGGAUCGGCGACGGCAACAACAUCCUGC
ACAGCAUCAUGAUGAGCGCCGCCAAGUUCGGCAUGCAUCUGCAGGCCGCCACC
CCCAAGGGCUACGAGCCUGAUGCCAGCGUGACCAAGCUGGCCGAGCAGUACGC
CAAAGAGAACGGCACCAAGCUGCUGCUGACCAACGACCCCCUGGAAGCCGCCC
ACGGCGGCAACGUGCUGAUCACCGACACCUGGAUCAGCAUGGGCCAGGAAGAG
GAAAAGAAGAAGCGGCUGCAGGCCUUCCAGGGCUACCAGGUCACAAUGAAGAC
CGCCAAGGUGGCCGCCAGCGACUGGACCUUCCUGCACUGCCUGCCCCGGAAGC
CCGAAGAGGUGGACGACGAGGUGUUCUACAGCCCCCGGUCCCUGGUGUUCCCC
GAGGCCGAGAACCGGAAGUGGACCAUUAUGGCCGUGAUGGUGUCCCUGCUGAC
CGACUACUCCCCCCAGCUGCAGAAGCCCAAGUUCUAGAUAAGUGAACUCGAGC
UAGUGACUGACUAGGAUCUGGUUACCACUAAACCAGCCUCAAGAACACCCGAA
UGGAGUCUCUAAGCUACAUAAUACCAACUUACACUUACAAAAUGUUGUCCCCC
AAAAUGUAGCCAUUCGUAUCUGCUCCUAAUAAAAAGAAAGUUUCUUCACAUU
CUAG

>mARM1804 (SEQ ID NO: 78)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGGCGUCUUCAACCUGCGGAUC
CUGCUGAACAACGCCGCCUUCCGGAACGGCCACAACUUCAUGGUCCGCAACUU
CAGAUGCGGCCAGCCCCUGCAGAACAGGGUGCAGCUGAAGGGCCGGGACCUGC
UGACCCUGAAGAACUUCACCGGCGAAGAGAUCAGGUACAUGCUGUGGCUGAGC
GCCGACCUGAAGUUCCGGAUCAAGCAGAAGGGCGAGUACCUGCCCCUGCUGCA
AGGCAAGAGCCUGGGCAUGAUCUUCGAGAAGCGGAGCACCCGGACCCGGCUGA
GCACCGAGACAGGCUUUGCCCUGCUGGGAGGCCACCCCUGCUUUCUGACCACC
CAGGACAUCCACCUGGGCGUGAACGAGAGCCUGACCGACACCGCCAGAGUGCU
GAGCAGCAUGGCCGACGCCGUGCUGGCCCGGGUGUACAAGCAGAGCGACCUGG
ACACCCUGGCCAAAGAGGCCAGCAUCCCCAUCAUCAACGGCCUGAGCGACCUG
UACCACCCCAUCCAGAUCCUGGCCGACUACCUGACCCUGCAGGAACACUACAG
CUCCCUGAAGGGCCUGACCCUGAGCUGGAUCGGCGACGGCAACAACAUCCUGC
ACAGCAUCAUGAUGAGCGCCGCCAAGUUCGGCAUGCAUCUGCAGGCCGCCACC
CCCAAGGGCUACGAGCCUGAUGCCAGCGUGACCAAGCUGGCCGAGCAGUACGC
CAAAGAGAACGGCACCAAGCUGCUGCUGACCAACGACCCCCUGGAAGCCGCCC
ACGGCGGCAACGUGCUGAUCACCGACACCUGGAUCAGCAUGGGCCAGGAAGAG
GAAAAGAAGAAGCGGCUGCAGGCCUUCCAGGGCUACCAGGUCACAAUGAAGAC
CGCCAAGGUGGCCGCCAGCGACUGGACCUUCCUGCACUGCCUGCCCCGGAAGC
CCGAAGAGGUGGACGACGAGGUGUUCUACAGCCCCCGGUCCCUGGUGUUCCCC
GAGGCCGAGAACCGGAAGUGGACCAUUAUGGCCGUGAUGGUGUCCCUGCUGAC
CGACUACUCCCCCCAGCUGCAGAAGCCCAAGUUCUAGAUAAGUGAACUCGAGC
UAGUGACUGACUAGGAUCUGGUUACCACUAAACCAGCCUCAAGAACACCCGAA
UGGAGUCUCUAAGCUACAUAAUACCAACUUACACUUACAAAAUGUUGUCCCCC
AAAAUGUAGCCAUUCGUAUCUGCUCCUAAUAAAAAGAAAGUUUCUUCACAUU
CUAG

>mARM1805 (SEQ ID NO: 79)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGGUCUUCAACCUGCGGAUC
CUGCUGAACAACGCCGCCUUCCGGAACGGCCACAACUUCAUGGUCCGCAACUU
CAGAUGCGGCCAGCCCCUGCAGAACAGGGUGCAGCUGAAGGGCCGGGACCUGC
UGACCCUGAAGAACUUCACCGGCGAAGAGAUCAGGUACAUGCUGUGGCUGAGC
GCCGACCUGAAGUUCCGGAUCAAGCAGAAGGGCGAGUACCUGCCCCUGCUGCA
AGGCAAGAGCCUGGGCAUGAUCUUCGAGAAGCGGAGCACCCGGACCCGGCUGA
GCACCGAGACAGGCUUUGCCCUGCUGGGAGGCCACCCCUGCUUUCUGACCACC
CAGGACAUCCACCUGGGCGUGAACGAGAGCCUGACCGACACCGCCAGAGUGCU
GAGCAGCAUGGCCGACGCCGUGCUGGCCCGGGUGUACAAGCAGAGCGACCUGG
ACACCCUGGCCAAAGAGGCCAGCAUCCCCAUCAUCAACGGCCUGAGCGACCUG
UACCACCCCAUCCAGAUCCUGGCCGACUACCUGACCCUGCAGGAACACUACAG
CUCCCUGAAGGGCCUGACCCUGAGCUGGAUCGGCGACGGCAACAACAUCCUGC
ACAGCAUCAUGAUGAGCGCCGCCAAGUUCGGCAUGCAUCUGCAGGCCGCCACC
CCCAAGGGCUACGAGCCUGAUGCCAGCGUGACCAAGCUGGCCGAGCAGUACGC
CAAAGAGAACGGCACCAAGCUGCUGCUGACCAACGACCCCCUGGAAGCCGCCC
ACGGCGGCAACGUGCUGAUCACCGACACCUGGAUCAGCAUGGGCCAGGAAGAG
GAAAAGAAGAAGCGGCUGCAGGCCUUCCAGGGCUACCAGGUCACAAUGAAGAC
CGCCAAGGUGGCCGCCAGCGACUGGACCUUCCUGCACUGCCUGCCCCGGAAGC
CCGAAGAGGUGGACGACGAGGUGUUCUACAGCCCCCGGUCCCUGGUGUUCCCC
GAGGCCGAGAACCGGAAGUGGACCAUUAUGGCCGUGAUGGUGUCCCUGCUGAC
CGACUACUCCCCCCAGCUGCAGAAGCCCAAGUUCUAGAUAAGUGAACUCGAGC
UAGUGACUGACUAGGAUCUGGUUACCACUAAACCAGCCUCAAGAACACCCGAA
UGGAGUCUCUAAGCUACAUAAUACCAACUUACACUUACAAAAUGUUGUCCCCC
AAAAUGUAGCCAUUCGUAUCUGCUCCUAAUAAAAAGAAAGUUUCUUCACAUU
CUAG

>mARM1806 (SEQ ID NO: 80)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA

-continued

SEQUENCE LISTING

AUUUUCACCAUUUACGAACGAUAGCCACCAUGCUGUUCAACCUGAGGAUCCUG
CUGAACAACGCAGCUUUCAGGAACGGCCACAACUUCAUGGUGAGGAACUUCCG
GUGCGGCCAGCCCCUGCAGAACAAGGUGCAGCUGAAGGGCAGGGACCUGCUGA
CCCUGAAGAACUUCACCGGAGAGGAGAUCAAGUACAUGCUGUGGCUGAGCGCA
GACCUGAAGUUCAGGAUCAAGCAGAAGGGAGAGUACCUGCCCCUGCUGCAGGG
GAAGUCCCUGGGCAUGAUCUUCGAGAAGAGGAGUACCAGGACCAGGCUGAGC
ACCGAAACCGGCUUCGCCCUGCUGGGAGGACACCCCUGCUUCCUGACCACCCA
GGACAUCCACCUGGGCGUGAACGAGAGUCUGACCGACACCGCCAGGGUGCUGU
CUAGCAUGGCCGACGCCGUGCUGGCCAGGGUGUACAAGCAGUCAGACCUGGAC
ACCCUGGCUAAGGAGGCCAGCAUCCCCAUCAUCAACGGCCUGAGCGACCUGUA
CCACCCCAUCCAGAUCCUGGCUGACUACCUGACCCUGCAGGAGCACUACAGCU
CUCUGAAGGGCCUGACCCUGAGCUGGAUCGGCGACGGGAACAACAUCCUGCAC
AGCAUCAUGAUGAGCGCCGCCAAGUUCGGCAUGCACCUGCAGGCCGCUACCCC
CAAGGGUUACGAGCCCGACGCCAGCGUGACCAAGCUGGCAGAGCAGUACGCCA
AGGAGAACGGCACCAAGCUGCUGCUGACCAACGACCCCCUGGAGGCCGCCCAC
GGAGGCAACGUGCUGAUCACCGACACCUGGAUCAGCAUGGGACAGGAGGAGG
AGAAGAAGAAGCGGCUGCAGGCUUUCCAGGGUUACCAGGUGACCAUGAAGAC
CGCCAAGGUGGCUGCCAGCGACUGGACCUUCCUGCACUGCCUGCCCAGGAAGC
CCGAGGAGGUGGACGACGAGGUGUUCUACUCUCCCAGGAGCCUGGUGUUCCCC
GAGGCCGAGAACAGGAAGUGGACCAUCAUGGCUGUGAUGGUGUCCCUGCUGA
CCGACUACAGCCCCCAGCUGCAGAAGCCCAAGUUCUGAAUAAGUGAACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1808 (SEQ ID NO: 81)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUGAGGAUCCUG
CUGAACAACGCAGCUUUCAGGAACGGCCACAACUUCAUGGUGAGGAACUUCCG
GUGCGGCCAGCCCCUGCAGAACAAGGUGCAGCUGAAGGGCAGGGACCUGCUGA
CCCUGAAGAACUUCACCGGAGAGGAGAUCAAGUACAUGCUGUGGCUGAGCGCA
GACCUGAAGUUCAGGAUCAAGCAGAAGGGAGAGUACCUGCCCCUGCUGCAGGG
GAAGUCCCUGGGCAUGAUCUUCGAGAAGAGGAGUACCAGGACCAGGCUGAGC
ACCGAAACCGGCUUCGCCCUGCUGGGAGGACACCCCUGCUUCCUGACGACCCA
GGACAUCCACCUCGGAGUGAACGAAUCCCUCACCGAUACCGCCCGGGUGUUAU
CAAGCAUGGCAGAUGCCGUGCUGGCCAGGGUGUACAAACAGUCCGAUCUGGAC
ACUCUGGCUAAGGAGGCCAGCAUCCCCAUCAUCAACGGCCUGAGCGACCUGUA
CCACCCCAUCCAGAUCCUGGCUGACUACCUGACCCUGCAGGAGCACUACAGCU
CUCUGAAGGGCCUGACCCUGAGCUGGAUCGGCGACGGGAACAACAUCCUGCAC
UCCAUCAUGAUGUCCGCCGCGAAGUUCGGAAUGCAUCUGCAAGCCGCCACGCC
AAAAGGAUACGAACCGGAUGCGCCCGUGACAAAGUUGGCGGAACAGUACGCU
AAGGAGAACGGAACCAAGCUGCUGCUGACCAACGACCCCCUGGAGGCCGCCCA
CGGAGGCAACGUGCUGAUCACCGACACCUGGAUCAGCAUGGGACAGGAGGAGG
AGAAGAAGAAGCGGCUGCAGGCUUUCCAGGGUUACCAGGUGACCAUGAAGAC
CGCCAAGGUGGCUGCCAGCGACUGGACCUUCCUGCACUGCCUGCCCAGGAAGC
CCGAGGAGGUGGACGACGAGGUGUUCUACUCUCCCAGGAGCCUGGUGUUCCCC
GAGGCCGAGAACAGGAAGUGGACCAUCAUGGCUGUGAUGGUGUCCCUGCUGA
CCGACUACAGCCCCCAGCUGCAGAAGCCCAAGUUCUGAAUAAGUGAACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1809 (SEQ ID NO: 82)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUGCGCAUCCUG
CUGAACAACGCCGCCUUCCGCAACGGCCACAACUUCAUGGUGCGCAACUUCCG
CUGCGGCCAGCCCCUGCAGAACAAGGUGCAGCUGAAGGGCCGCGACCUGCUGA
CCCUGAAGAACUUCACCGGCGAGGAGAUCAAGUACAUGCUGUGGCUGAGCGCC
GACCUGAAGUUCCGCAUCAAGCAGAAGGGCGAGUACCUGCCCCUGCUGCAGGG
CAAGAGCCUGGGCAUGAUCUUCGAGAAGCGCAGCACCCGCACCCGCCUGAGCA
CCGAGACAGGCUUCGCCCUGCUGGGCGGCCACCCCUGCUUCCUGACCACCCAG
GACAUCCACCUGGGCGUGAACGAGAGCCUGACCGACACCGCCCGCGUGCUGAG
CAGCAUGGCCGACGCCGUGCUGGCCCGCGUGUACAAGCAGAGCGACCUGGACA
CCCUGGCCAAGGAGGCCAGCAUCCCCAUCAUCAACGGCCUGAGCGACCUGUAC
CACCCCAUCCAGAUCCUGGCCGACUACCUGACCCUGCAGGAGCACUACAGCAG
CCUGAAGGGCCUGACCCUGAGCUGGAUCGGCGACGGCAACAACAUCCUGCACA
GCAUCAUGAUGAGCGCCGCCAAGUUCGGCAUGCACCUGCAGGCCGCCACCCCC
AAGGGCUACGAGCCCGACGCCAGCGUGACCAAGCUGGCCGAGCAGUACGCCAA
GGAGAACGGCACCAAGCUGCUGCUGACCAACGACCCCCUGGAGGCCGCCCACG
GCGGCAACGUGCUGAUCACCGACACCUGGAUCAGCAUGGGCCAGGAGGAGGAG
AAGAAGAAGCGCCUGCAGGCCUUCCAGGGCUACCAGGUGACCAUGAAGACCGC
CAAGGUGGCCGCCAGCGACUGGACCUUCCUGCACUGCCUGCCCCGCAAGCCCG
AGGAGGUGGACGACGAGGUGUUCUACAGCCCCCGCAGCCUGGUGUUCCCCGAG

-continued

SEQUENCE LISTING

GCCGAGAACCGCAAGUGGACCAUCAUGGCCGUGAUGGUGAGCCUGCUGACCGA
CUACAGCCCCCAGCUGCAGAAGCCCAAGUUCUGAAUAAGUGAACUCGAGCUAG
UGACUGACUAGGAUCUGGUUACCACUAAACCAGCCUCAAGAACACCCGAAUGG
AGUCUCUAAGCUACAUAAUACCAACUUACACUUACAAAAUGUUGUCCCCCAAA
AUGUAGCCAUUCGUAUCUGCUCCUAAUAAAAAGAAAGUUUCUUCACAUUCUA
GAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAA

>mARM1816 (SEQ ID NO: 83)
AGGAAACUUAAGUCAACACAACAUAUACAAAACAAACGAAUCUCAAGCAAUC
AAGCAUUCUACUUCUAUUGCAGCAAUUUAAAUCAUUUCUUUUAAAGCAAAAG
CAAUUUUCUGAAAAUUUUCACCAUUUACGAACGAUAGCCAUGCUGUUCAACCU
GCGCAUCCUGCUGAACAACGCCGCCUUCCGCAACGGCCACAACUUCAUGGUGC
GCAACUUCCGCUGCGGCCAGCCCCUGCAGAACAAGGUGCAGCUGAAGGGCCGC
GACCUGCUGACCCUGAAGAACUUCACCGGCGAGGAGAUCAAGUACAUGCUGUG
GCUGAGCGCCGACCUGAAGUUCCGCAUCAAGCAGAAGGGCGAGUACCUGCCCC
UGCUGCAGGGCAAGAGCCUGGGCAUGAUCUUCGAGAAGCGCAGCACCCGCACC
CGCCUGAGCACCGAGACAGGCUUCGCCCUGCUGGGCGGCCACCCCUGCUUCCU
GACCACCCAGGACAUCCACCUGGGCGUGAACGAGAGCCUGACCGACACCGCCC
GCGUGCUGAGCAGCAUGGCCGACGCCGUGCUGGCCCGCGUGUACAAGCAGAGC
GACCUGGACACCCUGGCCAAGGAGGCCAGCAUCCCCAUCAUCAACGGCCUGAG
CGACCUGUACCACCCCAUCCAGAUCCUGGCCGACUACCUGACCCUGCAGGAGC
ACUACAGCAGCCUGAAGGGCCUGACCCUGAGCUGGAUCGGCGACGGCAACAAC
AUCCUGCACAGCAUCAUGAUGAGCGCCGCCAAGUUCGGCAUGCACCUGCAGGC
CGCCACCCCCAAGGGCUACGAGCCCGACGCCAGCGUGACCAAGCUGGCCGAGC
AGUACGCCAAGGAGAACGGCACCAAGCUGCUGCUGACCAACGACCCCCUGGAG
GCCGCCCACGGCGGCAACGUGCUGAUCACCGACACCUGGAUCAGCAUGGGCCA
GGAGGAGGAGAAGAAGAAGCGCCUGCAGGCCUUCCAGGGCUACCAGGUGACCA
UGAAGACCGCCAAGGUGGCCGCCAGCGACUGGACCUUCCUGCACUGCCUGCCC
CGCAAGCCCGAGGAGGUGGACGACGAGGUGUUCUACAGCCCCCGCAGCCUGGU
GUUCCCCGAGGCCGAGAACCGCAAGUGGACCAUCAUGGCCGUGAUGGUGAGCC
UGCUGACCGACUACAGCCCCCAGCUGCAGAAGCCCAAGUUCUGACUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1822 (SEQ ID NO: 84)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAACUUGAGAAUCCUG
CUGAACAACGCCGCCUUUCGCAACGGUCACAAUUUUAUGGUCAGAAACUUCAG
AUGCGGACAGCCCCUCCAAAACAAGGUCCAGCUGAAGGGCCGCGAUCUCCUCA
CCCUGAAGAACUUCACGGGGGAGGAGAUCAAGUACAUGCUGUGGCUCUCCGCU
GACCUGAAGUUCAGGAUCAAGCAGAAGGGAGAAUAUCUGCCGCUGCUGCAAG
GGAAGUCCCUGGGGAUGAUUUUCGAGAAGCGGAGCACCCGGACUCGGCUCUCC
ACUGAAACUGGUUUCGCCCUUCUGGGCGGUCACCCCUGCUUCCUGACCACUCA
AGACAUUCACCUCGGAGUGAACGAGUCCUUGACUGACACCGCCCGGGUGCUGU
CGAGCAUGGCAGACGCCGUGCUAGCCCGCGUGUACAAGCAGUCAGACCUCGAU
ACCCUGGCCAAGGAGGCUUCGAUCCCGAUCAUCAACGGGUUGUCCGACCUGUA
CCACCCGAUUCAGAUUCUCGCCGACUACCUCACCCUGCAAGAGCAUUACAGCU
CCCUGAAGGGGCUUACCCUGUCCUGGAUUGGCGACGGAAACAACAUCCUGCAC
UCCAUUAUGAUGUCGGCGGCCAAGUUCGGCAUGCACCUCCAAGCCGCGACCCC
UAAGGGUUACGAACCAGACGCGUCAGUGACUAAGCUGGCCGAACAGUACGCAA
AGGAAAAUGGCACGAAGCUGCUCCUGACCAACGAUCCGUUGGAAGCCGCCCAU
GGCGGAAAUGUGCUCAUCACCGACACCUGGAUCUCGAUGGGACAGGAGGAAG
AGAAGAAGAAGCGGCUGCAGGCGUUCCAGGGCUACCAGGUCACCAUGAAAACU
GCCAAGGUGGCCGCCAGCGACUGGACCUUCCUGCACUGCCUUCCGCGCAAGCC
UGAGGAGGUGGACGAUGAAGUGUUCUACUCUCCACGGUCCCUGGUGUUCCCCG
AGGCGGAGAACCGCAAAUGGACCAUCAUGGCUGUGAUGGUCAGCCUGCUGACC
GAUUACAGCCCUCAGUUGCAAAAGCCGAAGUUUUGAUAACUCGAGCUAGUGA
CUGACUAGGAUCUGGUUACCACUAAACCAGCCUCAAGAACACCCGAAUGGAGU
CUCUAAGCUACAUAAUACCAACUUACACUUACAAAAUGUUGUCCCCCAAAAUG
UAGCCAUUCGUAUCUGCUCCUAAUAAAAAGAAAGUUUCUUCACAUUCUAG

>mARM1823 (SEQ ID NO: 85)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGUUCAACCUCCGCAUCCUC
CUCAACAACGCCGCAUUCAGAAACGGGCACAACUUCAUGGUCAGAAACUUCCG
CUGCGGGCAACCCCUACAAAACAAGGUCCAGCUCAAGGGGCGGGACCUCCUGA
CCCUGAAGAACUUCACCGGCGAAGAGAUCAAGUACAUGCUGUGGCUCUCCGCC
GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC

-continued

SEQUENCE LISTING

CACCCGAUCCAGAUCCUGGCAGACUACCUGACCCUGCAAGAACACUACAGCUC
CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAGAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAA

>mARM1840 (SEQ ID NO: 86)
CUCCCUCCCCCCCCCCUAACGUUACUGGCCGAAGCCGCUUGGAAUAAGGCCGG
UGUGCGUUUGUCUAUAUGUUAUUUUCCACCAUAUUGCCGUCUUUUGGCAAUG
UGAGGGCCCGGAAACCUGGCCCUGUCUUCUUGACGAGCAUUCCUAGGGGUCUU
UCCCCUCUCGCCAAAGGAAUGCAAGGUCUGUUGAAUGUCGUGAAGGAAGCAG
UUCCUCUGGAAGCUUCUUGAAGACAAACAACGUCUGUAGCGACCCUUUGCAGG
CAGCGGAACCCCCCACCUGGCGACAGGUGCCUCUGCGGCCAAAAGCCACGUGU
AUAAGAUACACCUGCAAAGGCGGCACAACCCCAGUGCCACGUUGUGAGUUGGA
UAGUUGUGGAAAGAGUCAAAUGGCUCUCCUCAAGCGUAUUCAACAAGGGGCU
GAAGGAUGCCCAGAAGGUACCCCAUUGUAUGGGAUCUGAUCUGGGGCCUCGG
UGCACAUGCUUUACGUGUGUUUAGUCGAGGUUAAAAAACGUCUAGGCCCCCCG
AACCACGGGGACGUGGUUUUCCUUUGAAAAACACGAUGAUAAUAUGCUUUUC
AAUCUCCGCAUCCUCCUUAACAACGCCGCGUUUAGAAACGGCCACAACUUCAU
GGUCCGGAACUUCAGAUGUGGCCAGCCGCUUCAAAACAAGGUCCAGCUGAAGG
GCCGGGAUCUUCUGACCCUGAAGAACUUUACUGGCGAAGAGAUCAAGUACAU
GCUCUGGCUCUCCGCGGACUUGAAGUUCCGCAUUAAGCAGAAGGGGGAAUACC
UUCCGCUGCUUCAAGGAAAGAGCCUCGGCAUGAUCUUUGAGAAGCGCUCAACC
AGGACCCGCCUUUCUACUGAAACUGGGUUCGCGCUGCUCGGUGGCCACCCCUG
CUUCCUGACGACCCAGGACAUCCACCUCGGAGUGAACGAAUCCCUCACCGAUA
CCGCCCGGGUGUUAUCGAGCAUGGCAGAUGCCGUGCUGGCCAGGGUGUACAAA
CAGUCCGAUCUGGACACUCUGGCCAAGGAGGCGUCAAUUCCUAUUAUCAACGG
CCUUAGUGACCUCUACCAUCCGAUUCAGAUCCUGGCCGAUUACCUCACCCUGC
AAGAACACUACAGCUCCCUGAAGGGUCUGACAUUGUCCUGGAUCGGCGACGGC
AACAACAUUCUCCAUUCCAUCAUGAUGUCCGCCGCAAAAUUCGGCAUGCAUCU
UCAAGCCGCCACGCCGAAGGGUUACGAGCCCGACGCUUCCGUGACUAAGCUCG
CCGAGCAGUACGCUAAGGAGAACGGAACCAAGCUUCUGCUGACUAACGACCCA
CUAGAAGCAGCCCACGGGGGCAACGUGCUUAUUACUGACACCUGGAUCUCCAU
GGGCCAGGAAGAAGAGAAAAAGAAGCGGCUGCAGGCGUUCCAGGGAUAUCAG
GUCACCAUGAAAACCGCCAAGGUCGCUGCCUCCGACUGGACCUUCCUGCACUG
CCUGCCUCGCAAGCCUGAAGAAGUGGACGACGAGGUGUUCUACUCGCCACGGA
GCCUCGUGUUCCCCGAGGCCGAGAAUAGAAAGUGGACCAUCAUGGCCGUGAUG
GUGUCACUGCUCACCGACUACAGCCCGCAGCUUCAGAAGCCCAAGUUCUGAAU
AAGUAGAUAGUGCAGUCACUGGCACAACGCGUUGCCCGGUAAGCCAAUCGGGU
AUACACGGUCGUCAUACUGCAGACAGGGUUCUUCUACUUUGCAAGAUAGUCU
AGAGUAGUAAAAUAAAUAGUAUAAGUCUAG

>mARM1841 (SEQ ID NO: 87)
CUCCCUCCCCCCCCCCUAACGUUACUGGCCGAAGCCGCUUGGAAUAAGGCCGG
UGUGCGUUUGUCUAUAUGUUAUUUUCCACCAUAUUGCCGUCUUUUGGCAAUG
UGAGGGCCCGGAAACCUGGCCCUGUCUUCUUGACGAGCAUUCCUAGGGGUCUU
UCCCCUCUCGCCAAAGGAAUGCAAGGUCUGUUGAAUGUCGUGAAGGAAGCAG
UUCCUCUGGAAGCUUCUUGAAGACAAACAACGUCUGUAGCGACCCUUUGCAGG
CAGCGGAACCCCCCACCUGGCGACAGGUGCCUCUGCGGCCAAAAGCCACGUGU
AUAAGAUACACCUGCAAAGGCGGCACAACCCCAGUGCCACGUUGUGAGUUGGA
UAGUUGUGGAAAGAGUCAAAUGGCUCUCCUCAAGCGUAUUCAACAAGGGGCU
GAAGGAUGCCCAGAAGGUACCCCAUUGUAUGGGAUCUGAUCUGGGGCCUCGG
UGCACAUGCUUUACGUGUGUUUAGUCGAGGUUAAAAAACGUCUAGGCCCCCCG
AACCACGGGGACGUGGUUUUCCUUUGAAAAACACGAUGAUAAUAUGCUUUUC
AACCUGAGAAUCCUCUUGAACAAUGCUGCUUUUCGGAAUGGCCACAACUUUAU
GGUUCGGAACUUCCGUUGCGGCCAGCCUUUACAAAACAAGGUCCAGCUGAAGG
GCCGGGAUUUGCUCACACUAAAGAACUUUACUGGAGAAGAGAUCAAGUACAU
GCUAUGGCUGUCGGCCGACCUGAAGUUCCGUAUCAAGCAGAAGGGAGAAUACC
UUCCGCUGCUUCAAGGAAAGAGCCUCGGCAUGAUCUUUGAGAAGCGCUCAACC
AGGACCCGCCUUUCUACUGAAACUGGGUUCGCGCUGCUCGGUGGCCACCCCUG
CUUCCUGACGACCCAGGACAUCCACCUCGGAGUGAACGAAUCCCUCACCGAUA
CCGCCCGGGUGUUAUCGAGCAUGGCAGAUGCCGUGCUGGCCAGGGUGUACAAA
CAGUCCGAUCUCGAUACCUUGGCAAAGGAGGCUUCCAUUCCCAUCAUCAACGG
CCUGAGCGACCUGUACCACCCAAUCCAAAUCCUGGCUGACUACCUGACCCUGC
AAGAGCACUACAGCAGCCUGAAGGGUCUGACCCUGUCAUGGAUUGGCGAUGG
AAACAAUAUUCUGCACUCCAUCAUGAUGUCCGCCGCGAAGUUCGGAAUGCAUC

-continued

SEQUENCE LISTING

UGCAAGCCGCCACUCCAAAAGGAUACGAACCGGAUGCAUCCGUGACCAAGUUG
GCGGAACAGUACGCGAAGGAGAACGGAACCAAGCUCCUGCUGACUAACGACCC
GCUCGAGGCUGCGCAUGGGGGUAACGUGCUGAUUACGGACACCUGGAUCUCCA
UGGGGCAGGAGGAAGAGAAGAAGAAGAGACUGCAGGCAUUCCAGGGGUACCA
GGUCACCAUGAAAACCGCAAAAGUGGCAGCUUCGGACUGGACUUUCCUGCAUU
GCCUGCCGAGGAAGCCGGAGGAAGUCGACGACGAAGUGUUCUACUCGCCUCGG
UCCCUGGUGUUCCCCGAGGCCGAAAACCGGAAGUGGACCAUCAUGGCCGUGAU
GGUGUCCUUGCUGACUGACUAUAGCCCGCAGCUGCAGAAGCCUAAGUUCUGAA
UAAGUAGAUAGUGCAGUCACUGGCACAACGCGUUGCCCGGUAAGCCAAUCGGG
UAUACACGGUCGUCAUACUGCAGACAGGGUUCUUCUACUUUGCAAGAUAGUC
UAGAGUAGUAAAAUAAAUAGUAUAAGUCUAG

>mARM1842 (SEQ ID NO: 88)
CUCCCUCCCCCCCCCUAACGUUACUGGCCGAAGCCGCUUGGAAUAAGGCCGG
UGUGCGUUUGUCUAUAUGUUAUUUUCCACCAUAUUGCCGUCUUUUGGCAAUG
UGAGGGCCCGGAAACCUGGCCCUGUCUUCUUGACGAGCAUUCCUAGGGGUCUU
UCCCCUCUCGCCAAAGGAAUGCAAGGUCUGUUGAAUGUCGUGAAGGAAGCAG
UUCCUCUGGAAGCUUCUUGAAGACAAACAACGUCUGUAGCGACCCUUUGCAGG
CAGCGGAACCCCCCACCUGGCGACAGGUGCCUCUGCGGCCAAAAGCCACGUGU
AUAAGAUACACCUGCAAAGGCGGCACAACCCCAGUGCCACGUUGUGAGUUGGA
UAGUUGUGGAAAGAGUCAAAUGGCUCUCCUCAAGCGUAUUCAACAAGGGGCU
GAAGGAUGCCCAGAAGGUACCCCAUUGUAUGGGAUCUGAUCUGGGGCCUCGG
UGCACAUGCUUUACGUGUGUUUAGUCGAGGUUAAAAAACGUCUAGGCCCCCCG
AACCACGGGGACGUGGUUUUCCUUUGAAAAACACGAUGAUAAUAUGCUGUUC
AACCUGCGCAUCCUGCUGAACAACGCCGCCUUCCGCAACGGCCACAACUUCAU
GGUGCGCAACUUCCGCUGCGGCCAGCCCCUGCAGAACAAGGUGCAGCUGAAGG
GCCGCGACCUGCUGACCCUGAAGAACUUCACCGGCGAGGAGAUCAAGUACAUG
CUGUGGCUGAGCGCCGACCUGAAGUUCCGCAUCAAGCAGAAGGGCGAGUACCU
GCCCCUGCUGCAGGGCAAGAGCCUGGGCAUGAUCUUCGAGAAGCGCAGCACCC
GCACCCGCCUGAGCACCGAGACAGGCCUGGCCCUGCUGGGCGGCCACCCCUGC
UUCCUGACCACCCAGGACAUCCACCUGGGCGUGAACGAGAGCCUGACCGACAC
CGCCCGCGUGCUGAGCAGCAUGGCCGACGCCGUGCUGGCCCGCGUGUACAAGC
AGAGCGACCUGGACACCCUGGCCAAGGAGGCCAGCAUCCCCAUCAUCAACGGC
CUGAGCGACCUGUACCACCCCAUCCAGAUCCUGGCCGACUACCUGACCCUGCA
GGAGCACUACAGCAGCCUGAAGGGCCUGACCCUGAGCUGGAUCGGCGACGGCA
ACAACAUCCUGCACAGCAUCAUGAUGAGCGCCGCCAAGUUCGGCAUGCACCUG
CAGGCCGCCACCCCCAAGGGCUACGAGCCCGACGCCAGCGUGACCAAGCUGGC
CGAGCAGUACGCCAAGGAGAACGGCACCAAGCUGCUGCUGACCAACGACCCCC
UGGAGGCCGCCCACGGCGGCAACGUGCUGAUCACCGACACCUGGAUCAGCAUG
GGCCAGGAGGAGGAGAAGAAGAAGCGCCUGCAGGCCUUCCAGGGCUACCAGGU
GACCAUGAAGACCGCCAAGGUGGCCGCCAGCGACUGGACCUUCCUGCACUGCC
UGCCCCGCAAGCCCGAGGAGGUGGACGACGAGGUGUUCUACAGCCCCCGCAGC
CUGGUGUUCCCCGAGGCCGAGAACCGCAAGUGGACCAUCAUGGCCGUGAUGGU
GAGCCUGCUGACCGACUACAGCCCCCAGCUGCAGAAGCCCAAGUUCUGAAUAA
GUAGAUAGUGCAGUCACUGGCACAACGCGUUGCCCGGUAAGCCAAUCGGGUAU
ACACGGUCGUCAUACUGCAGACAGGGUUCUUCUACUUUGCAAGAUAGUCUAG
AGUAGUAAAAUAAAUAGUAUAAGUCUAG

>mARM1843 (SEQ ID NO: 89)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

-continued

SEQUENCE LISTING

```
>mARM1844 (SEQ ID NO: 90)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1845 (SEQ ID NO: 91)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1846 (SEQ ID NO: 92)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
```

-continued

SEQUENCE LISTING

CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1847 (SEQ ID NO: 93)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUUUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1882 (SEQ ID NO: 94)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGUGUUCAACCUCCGCAUCCUC
CUCAACAACGCCGCAUUCAGAAACGGGCACAACUUCAUGGUCAGAAACUUCCG
CUGCGGGCAACCCCUACAAAACAAGGUCCAGCUCAAGGGGCGGGACCUCCUGA
CCCUGAAGAACUUCACCGGCGAAGAGAUCAAGUACAUGCUGUGGCUCUCCGCC
GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC
CACCCGAUCCAGAUCCUGGCAGACUACCUGACCCUGCAAGAACACUACAGCUC
CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1883 (SEQ ID NO: 95)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGUGUUCAACCUCCGCAUCCUC
CUCAACAACGCCGCAUUCAGAAACGGGCACAACUUCAUGGUCAGAAACUUCCG
CUGCGGGCAACCCCUACAAAACCGGGUCCAGCUCAAGGGGCGGGACCUCCUGA
CCCUGAAGAACUUCACCGGCGAAGAGAUCAAGUACAUGCUGUGGCUCUCCGCC
GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC
CACCCGAUCCAGAUCCUGGCAGACUACCUGACCCUGCAAGAACACUACAGCUC

-continued

SEQUENCE LISTING

CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1884 (SEQ ID NO: 96)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGUGUUCAACCUCCGCAUCCUC
CUCAACAACGCCGCAUUCAGAAACGGGCACAACUUCAUGGUCAGAAACUUCCG
CUGCGGGCAACCCCUACAAAACCGGGUCCAGCUCAAGGGGCGGGACCUCCUGA
CCCUGAAGAACUUCACCGGCGAAGAGAUCCGGUACAUGCUGUGGCUCUCCGCC
GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC
CACCCGAUCCAGAUCCUGGCAGACUACCUGACCCUGCAAGAACACUACAGCUC
CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1885 (SEQ ID NO: 97)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGGUCAACCUCCGCAUCCUC
CUCAACAACGCCGCAUUCAGAAACGGGCACAACUUCAUGGUCAGAAACUUCCG
CUGCGGGCAACCCCUACAAAACAAGGUCCAGCUCAAGGGGCGGGACCUCCUGA
CCCUGAAGAACUUCACCGGCGAAGAGAUCAAGUACAUGCUGUGGCUCUCCGCC
GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC
CACCCGAUCCAGAUCCUGGCAGACUACCUGACCCUGCAAGAACACUACAGCUC
CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1886 (SEQ ID NO: 98)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGGUCAACCUCCGCAUCCUC
CUCAACAACGCCGCAUUCAGAAACGGGCACAACUUCAUGGUCAGAAACUUCCG
CUGCGGGCAACCCCUACAAAACCGGGUCCAGCUCAAGGGGCGGGACCUCCUGA
CCCUGAAGAACUUCACCGGCGAAGAGAUCAAGUACAUGCUGUGGCUCUCCGCC

-continued

SEQUENCE LISTING

GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC
CACCCGAUCCAGAUCCUGGCAGACUACCUGACCCUGCAAGAACACUACAGCUC
CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAGAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAA

>mARM1887 (SEQ ID NO: 99)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGGUCAACCUCCGCAUCCUC
CUCAACAACGCCGCAUUCAGAAACGGGCACAACUUCAUGGUCAGAAACUUCCG
CUGCGGGCAACCCCUACAAAACCGGGUCCAGCUCAAGGGGCGGGACCUCCUGA
CCCUGAAGAACUUCACCGGCGAAGAGAUCCGGUACAUGCUGUGGCUCUCCGCC
GACCUGAAGUUCCGCAUCAAGCAGAAGGGAGAGUACCUCCCGCUGCUGCAAGG
GAAGUCGCUGGGGAUGAUCUUCGAGAAGCGGUCAACCAGAACCCGGCUGUCAA
CCGAAACCGGGUUCGCACUGCUGGGGGGACACCCGUGCUUCCUGACCACCCAA
GACAUCCACCUGGGAGUGAACGAAUCGCUGACCGACACCGCCCGCGUGCUGAG
CUCAAUGGCGGACGCCGUGCUGGCCCGCGUGUACAAGCAGUCCGACCUGGACA
CCCUGGCCAAGGAAGCGUCCAUCCCGAUCAUCAACGGACUGUCCGACCUGUAC
CACCCGAUCCAGAUCCUGGCAGACUACCUGACCCUGCAAGAACACUACAGCUC
CCUGAAGGGCCUGACCCUGUCAUGGAUCGGGGACGGGAACAACAUCCUGCACU
CCAUAAUGAUGUCAGCCGCCAAGUUCGGAAUGCACCUCCAAGCCGCAACCCCG
AAGGGCUACGAACCGGACGCAUCAGUGACCAAACUGGCCGAGCAGUACGCCAA
GGAAAACGGCACCAAGCUCCUGCUGACCAACGACCCGCUGGAGGCCGCACACG
GGGGGAACGUGCUGAUCACCGACACCUGGAUCUCCAUGGGACAGGAGGAGGA
AAAGAAGAAGCGGCUGCAGGCGUUCCAGGGGUACCAGGUCACCAUGAAAACCG
CGAAGGUCGCGGCAUCAGACUGGACCUUCCUGCACUGCCUGCCCCGGAAGCCG
GAAGAGGUGGACGACGAGGUGUUCUACUCGCCGCGCUCGCUGGUGUUCCCCGA
GGCGGAGAACAGGAAGUGGACCAUCAUGGCGGUGAUGGUCAGCCUCCUGACCG
ACUACUCGCCGCAGCUGCAGAAGCCGAAGUUCUGAUAACUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1888 (SEQ ID NO: 100)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGGUCAACCUGCGCAUCCUG
CUGAACAACGCCGCCUUCCGCAACGGCCACAACUUCAUGGUGCGCAACUUCCG
CUGCGGCCAGCCCCUGCAGAACAAGGUGCAGCUGAAGGGCCGCGACCUGCUGA
CCCUGAAGAACUUCACCGGCGAGGAGAUCAAGUACAUGCUGUGGCUGAGCGCC
GACCUGAAGUUCCGCAUCAAGCAGAAGGGCGAGUACCUGCCCCUGCUGCAGGG
CAAGAGCCUGGGCAUGAUCUUCGAGAAGCGCAGCACCCGCACCCGCCUGAGCA
CCGAGACAGGCUUCGCCCUGCUGGGCGGCCACCCCUGCUUCCUGACCACCCAG
GACAUCCACCUGGGCGUGAACGAGAGCCUGACCGACACCGCCCGCGUGCUGAG
CAGCAUGGCCGACGCCGUGCUGGCCCGCGUGUACAAGCAGAGCGACCUGGACA
CCCUGGCCAAGGAGGCCAGCAUCCCCAUCAUCAACGGCCUGAGCGACCUGUAC
CACCCCAUCCAGAUCCUGGCCGACUACCUGACCCUGCAGGAGCACUACAGCAG
CCUGAAGGGCCUGACCCUGAGCUGGAUCGGCGACGGCAACAACAUCCUGCACA
GCAUCAUGAUGAGCGCCGCCAAGUUCGGCAUGCACCUGCAGGCCGCCACCCCC
AAGGGCUACGAGCCCGACGCCAGCGUGACCAAGCUGGCCGAGCAGUACGCCAA
GGAGAACGGCACCAAGCUGCUGCUGACCAACGACCCCCUGGAGGCCGCCCACG
GCGGCAACGUGCUGAUCACCGACACCUGGAUCAGCAUGGGCCAGGAGGAGGAG
AAGAAGAAGCGCCUGCAGGCCUUCCAGGGCUACCAGGUGACCAUGAAGACCGC
CAAGGUGGCCGCCAGCGACUGGACCUUCCUGCACUGCCUGCCCCGCAAGCCCG
AGGAGGUGGACGACGAGGUGUUCUACAGCCCCCGCAGCCUGGUGUUCCCCGAG
GCCGAGAACCGCAAGUGGACCAUCAUGGCCGUGAUGGUGAGCCUGCUGACCGA
CUACAGCCCCCAGCUGCAGAAGCCCAAGUUCUGAUAACUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG

-continued

SEQUENCE LISTING

CCAUUCGUAUCUGCUCCUAAUAAAAAGAAAGUUUCUUCACAUUCUAGAAAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAA

>mARM1889 (SEQ ID NO: 101)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUGGUCAACCUGCGCAUCCUG
CUGAACAACGCCGCCUUCCGCAACGGCCACAACUUCAUGGUGCGCAACUUCCG
CUGCGGCCAGCCCCUGCAGAACCGGGUGCAGCUGAAGGGCCGCGACCUGCUGA
CCCUGAAGAACUUCACCGGCGAGGAGAUCAAGUACAUGCUGUGGCUGAGCGCC
GACCUGAAGUUCCGCAUCAAGCAGAAGGGCGAGUACCUGCCCCUGCUGCAGGG
CAAGAGCCUGGGCAUGAUCUUCGAGAAGCGCAGCACCCGCACCCGCCUGAGCA
CCGAGACAGGCUUCGCCCUGCUGGGCGGCCACCCCUGCUUCCUGACCACCCAG
GACAUCCACCUGGGCGUGAACGAGAGCCUGACCGACACCGCCCGCGUGCUGAG
CAGCAUGGCCGACGCCGUGCUGGCCCGCGUGUACAAGCAGAGCGACCUGGACA
CCCUGGCCAAGGAGGCCAGCAUCCCCAUCAUCAACGGCCUGAGCGACCUGUAC
CACCCCAUCCAGAUCCUGGCCGACUACCUGACCCUGCAGGAGCACUACAGCAG
CCUGAAGGGCCUGACCCUGAGCUGGAUCGGCGACGGCAACAACAUCCUGCACA
GCAUCAUGAUGAGCGCCGCCAAGUUCGGCAUGCACCUGCAGGCCGCCACCCCC
AAGGGCUACGAGCCCGACGCCAGCGUGACCAAGCUGGCCGAGCAGUACGCCAA
GGAGAACGGCACCAAGCUGCUGCUGACCAACGACCCCCUGGAGGCCGCCCACG
GCGGCAACGUGCUGAUCACCGACACCUGGAUCAGCAUGGGCCAGGAGGAGGAG
AAGAAGAAGCGCCUGCAGGCCUUCCAGGGCUACCAGGUGACCAUGAAGACCGC
CAAGGUGGCCGCCAGCGACUGGACCUUCCUGCACUGCCUGCCCCGCAAGCCCG
AGGAGGUGGACGACGAGGUGUUCUACAGCCCCCGCAGCCUGGUGUUCCCCGAG
GCCGAGAACCGCAAGUGGACCAUCAUGGCCGUGAUGGUGAGCCUGCUGACCGA
CUACAGCCCCCAGCUGCAGAAGCCCAAGUUCUGAUAACUCGAGCUAGUGACUG
ACUAGGAUCUGGUUACCACUAAACCAGCCUCAAGAACACCCGAAUGGAGUCUC
UAAGCUACAUAAUACCAACUUACACUUACAAAAUGUUGUCCCCCAAAAUGUAG
CCAUUCGUAUCUGCUCCUAAUAAAAAGAAAGUUUCUUCACAUUCUAG

>mARM1890 (SEQ ID NO: 102)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUGUCAAUCUCCGCAUCCUC
CUUAACAACGCCGCGUUUAGAAACGGCCACAACUUCAUGGUCCGGAACUUCAG
AUGUGGCCAGCCGCUUCAAAACAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1891 (SEQ ID NO: 103)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGCUUGUCAAUCUCCGCAUCCUC
CUUAACAACGCCGCGUUUAGAAACGGCCACAACUUCAUGGUCCGGAACUUCAG
AUGUGGCCAGCCGCUUCAAAACCGGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA

-continued

SEQUENCE LISTING

AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGCUCGAGCUAGUGACU
GACUAGGAUCUGGUUACCACUAAACCAGCCUCAAGAACACCCGAAUGGAGUCU
CUAAGCUACAUAAUACCAACUUACACUUACAAAAUGUUGUCCCCCAAAAUGUA
GCCAUUCGUAUCUGCUCCUAAUAAAAAGAAAGUUUCUUCACAUUCUAG

>mARM1898 (SEQ ID NO: 104)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGGCCUUGUCAAUCUCCGCAUC
CUCCUUAACAACGCCGCGUUUAGAAACGGCCACAACUUCAUGGUCCGGAACUU
CAGAUGUGGCCAGCCGCUUCAAAACAAGGUCCAGCUGAAGGGCCGGGAUCUUC
UGACCCUGAAGAACUUUACUGGCGAAGAGAUCAAGUACAUGCUCUGGCUCUCC
GCGGACUUGAAGUUCCGCAUUAAGCAGAAGGGGGAAUACCUUCCGCUGCUUCA
AGGAAAGAGCCUCGGCAUGAUCUUUGAGAAGCGCUCAACCAGGACCCGCCUUU
CUACUGAAACUGGGUUCGCGCUGCUCGGUGGCCACCCCUGCUUCCUGACGACC
CAGGACAUCCACCUCGGAGUGAACGAAUCCCUCACCGAUACCGCCCGGGUGUU
AUCGAGCAUGGCAGAUGCCGUGCUGGCCAGGGUGUACAAACAGUCCGAUCUGG
ACACUCUGGCCAAGGAGGCGUCAAUUCCUAUUAUCAACGGCCUUAGUGACCUC
UACCAUCCGAUUCAGAUCCUGGCCGAUUACCUCACCCUGCAAGAACACUACAG
CUCCCUGAAGGGUCUGACAUUGUCCUGGAUCGGCGACGGCAACAACAUUCUCC
AUUCCAUCAUGAUGUCCGCCGCAAAAUUCGGCAUGCAUCUUCAAGCCGCCACG
CCGAAGGGUUACGAGCCCGACGCUUCCGUGACUAAGCUCGCCGAGCAGUACGC
UAAGGAGAACGGAACCAAGCUUCUGCUGACUAACGACCCACUAGAAGCAGCCC
ACGGGGGCAACGUGCUUAUUACUGACACCUGGAUCUCCAUGGGCCAGGAAGAA
GAGAAAAAGAAGCGGCUGCAGGCGUUCCAGGGAUAUCAGGUCACCAUGAAAA
CCGCCAAGGUCGCUGCCUCCGACUGGACCUUCCUGCACUGCCUGCCUCGCAAG
CCUGAAGAAGUGGACGACGAGGUGUUCUACUCGCCACGGAGCCUCGUGUUCCC
CGAGGCCGAGAAUAGAAAGUGGACCAUCAUGGCCGUGAUGGUGUCACUGCUC
ACCGACUACAGCCCGCAGCUUCAGAAGCCCAAGUUCUAGCUCGAGCUAGUGAC
UGACUAGGAUCUGGUUACCACUAAACCAGCCUCAAGAACACCCGAAUGGAGUC
UCUAAGCUACAUAAUACCAACUUACACUUACAAAAUGUUGUCCCCCAAAAUGU
AGCCAUUCGUAUCUGCUCCUAAUAAAAAGAAAGUUUCUUCACAUUCUAG

>mARM1899 (SEQ ID NO: 105)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGGCCUUGUCAAUCUCCGCAUC
CUCCUUAACAACGCCGCGUUUAGAAACGGCCACAACUUCAUGGUCCGGAACUU
CAGAUGUGGCCAGCCGCUUCAAAACCGGGUCCAGCUGAAGGGCCGGGAUCUUC
UGACCCUGAAGAACUUUACUGGCGAAGAGAUCAAGUACAUGCUCUGGCUCUCC
GCGGACUUGAAGUUCCGCAUUAAGCAGAAGGGGGAAUACCUUCCGCUGCUUCA
AGGAAAGAGCCUCGGCAUGAUCUUUGAGAAGCGCUCAACCAGGACCCGCCUUU
CUACUGAAACUGGGUUCGCGCUGCUCGGUGGCCACCCCUGCUUCCUGACGACC
CAGGACAUCCACCUCGGAGUGAACGAAUCCCUCACCGAUACCGCCCGGGUGUU
AUCGAGCAUGGCAGAUGCCGUGCUGGCCAGGGUGUACAAACAGUCCGAUCUGG
ACACUCUGGCCAAGGAGGCGUCAAUUCCUAUUAUCAACGGCCUUAGUGACCUC
UACCAUCCGAUUCAGAUCCUGGCCGAUUACCUCACCCUGCAAGAACACUACAG
CUCCCUGAAGGGUCUGACAUUGUCCUGGAUCGGCGACGGCAACAACAUUCUCC
AUUCCAUCAUGAUGUCCGCCGCAAAAUUCGGCAUGCAUCUUCAAGCCGCCACG
CCGAAGGGUUACGAGCCCGACGCUUCCGUGACUAAGCUCGCCGAGCAGUACGC
UAAGGAGAACGGAACCAAGCUUCUGCUGACUAACGACCCACUAGAAGCAGCCC
ACGGGGGCAACGUGCUUAUUACUGACACCUGGAUCUCCAUGGGCCAGGAAGAA
GAGAAAAAGAAGCGGCUGCAGGCGUUCCAGGGAUAUCAGGUCACCAUGAAAA
CCGCCAAGGUCGCUGCCUCCGACUGGACCUUCCUGCACUGCCUGCCUCGCAAG
CCUGAAGAAGUGGACGACGAGGUGUUCUACUCGCCACGGAGCCUCGUGUUCCC
CGAGGCCGAGAAUAGAAAGUGGACCAUCAUGGCCGUGAUGGUGUCACUGCUC
ACCGACUACAGCCCGCAGCUUCAGAAGCCCAAGUUCUAGCUCGAGCUAGUGAC
UGACUAGGAUCUGGUUACCACUAAACCAGCCUCAAGAACACCCGAAUGGAGUC
UCUAAGCUACAUAAUACCAACUUACACUUACAAAAUGUUGUCCCCCAAAAUGU
AGCCAUUCGUAUCUGCUCCUAAUAAAAAGAAAGUUUCUUCACAUUCUAGAAA
AAAAAAAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAA
AAAAAAA

>mARM1900 (SEQ ID NO: 106)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGGGCGGACUUGUCAAUCUCCGC
AUCCUCCUUAACAACGCCGCGUUUAGAAACGGCCACAACUUCAUGGUCCGGAA
CUUCAGAUGUGGCCAGCCGCUUCAAAACAAGGUCCAGCUGAAGGGCCGGGAUC
UUCUGACCCUGAAGAACUUUACUGGCGAAGAGAUCAAGUACAUGCUCUGGCUC

-continued

SEQUENCE LISTING

UCCGCGGACUUGAAGUUCCGCAUUAAGCAGAAGGGGGAAUACCUUCCGCUGCU
UCAAGGAAAGAGCCUCGGCAUGAUCUUUGAGAAGCGCUCAACCAGGACCCGCC
UUUCUACUGAAACUGGGUUCGCGCUGCUCGGUGGCCACCCCUGCUUCCUGACG
ACCCAGGACAUCCACCUCGGAGUGAACGAAUCCCUCACCGAUACCGCCCGGGU
GUUAUCGAGCAUGGCAGAUGCCGUGCUGGCCAGGGUGUACAAACAGUCCGAUC
UGGACACUCUGGCCAAGGAGGCGUCAAUUCCUAUUAUCAACGGCCUUAGUGAC
CUCUACCAUCCGAUUCAGAUCCUGGCCGAUUACCUCACCCUGCAAGAACACUA
CAGCUCCCUGAAGGGUCUGACAUUGUCCUGGAUCGGCGACGGCAACAACAUUC
UCCAUUCCAUCAUGAUGUCCGCCGCAAAAUUCGGCAUGCAUCUUCAAGCCGCC
ACGCCGAAGGGUUACGAGCCCGACGCUUCCGUGACUAAGCUCGCCGAGCAGUA
CGCUAAGGAGAACGGAACCAAGCUUCUGCUGACUAACGACCCACUAGAAGCAG
CCCACGGGGGCAACGUGCUUAUUACUGACACCUGGAUCUCCAUGGGCCAGGAA
GAAGAGAAAAAGAAGCGGCUGCAGGCGUUCCAGGGAUAUCAGGUCACCAUGA
AAACCGCCAAGGUCGCUGCCUCCGACUGGACCUUCCUGCACUGCCUGCCUCGC
AAGCCUGAAGAAGUGGACGACGAGGUGUUCUACUCGCCACGGAGCCUCGUGUU
CCCCGAGGCCGAGAAUAGAAAGUGGACCAUCAUGGCCGUGAUGGUGUCACUGC
UCACCGACUACAGCCCGCAGCUUCAGAAGCCCAAGUUCUAGCUCGAGCUAGUG
ACUGACUAGGAUCUGGUUACCACUAAACCAGCCUCAAGAACACCCGAAUGGAG
UCUCUAAGCUACAUAAUACCAACUUACACUUACAAAAUGUUGUCCCCCAAAAU
GUAGCCAUUCGUAUCUGCUCCUAAUAAAAAGAAAGUUUCUUCACAUUCUAG

>mARM1903 (SEQ ID NO: 107)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGGCCCUUUUCAAUCUCCGCAUCCUC
CUUAACAACGCCGCGUUUAGAAACGGCCACAACUUCAUGGUCCGGAACUUCAG
AUGUGGCCAGCCGCUUCAAGGCAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGAUAAGUGAACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1904 (SEQ ID NO: 108)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGGCCCUUUUCAAUCUCCGCAUCCUC
CUUAACAACGCCGCGUUUAGAAACGGCCACAACUUCAUGGUCCGGAACUUCAG
AUGUGGCCAGCCGCUUCAAGGCCGGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGAUAAGUGAACUCGAG
CUAGUGACUGACUAGGAUCUGGUUACCACUAAACCAGCCUCAAGAACACCCGA

-continued

SEQUENCE LISTING

AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1905 (SEQ ID NO: 109)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGGCCCUUUUCAAUCUCCGCAUCCUC
CUUAACAACGCCGCGUUUAGAAACGGCCACAACUUCAUGGUCCGGAACUUCAG
AUGUGGCCAGCCGCUUCAAGGCCGGGUCCAGCUGAAGGGCCGGGAUCUUCUGA
CCCUGAAGAACUUUACUGGCGAAGAGAUCAGGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGAUAAGUGAACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1906 (SEQ ID NO: 110)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGGCCCUUGUCAAUCUCCGCAUCCUC
CUUAACAACGCCGCGUUUAGAAACGGCCACAACUUCAUGGUCCGGAACUUCAG
AUGUGGCCAGCCGCUUCAAGGCAGGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAAGUGAAUAGACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1907 (SEQ ID NO: 111)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGGCCCUUUUCAAUCUCCGCAUCCUC
CUUAACAACGCCGCGUUUAGAAACGGCCACAACUUCAUGGUCCGGAACUUCAG
AUGUGGCCAGCCGCUUCAAGUCAAGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU

-continued

SEQUENCE LISTING

UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGAUAAGUGAACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAGAAAAAAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAAAAAAAAAAAAAA

>mARM1908 (SEQ ID NO: 112)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCAUGGCCCUUUUCAAUCUCCGCAUCCUC
CUUAACAACGCCGCGUUUAGAAACGGCCACAACUUCAUGGUCCGGAACUUCAG
AUGUGGCCAGCCGCUUCAAGUCAGGGUCCAGCUGAAGGGCCGGGAUCUUCUGA
CCCUGAAGAACUUUACUGGCGAAGAGAUCAAGUACAUGCUCUGGCUCUCCGCG
GACUUGAAGUUCCGCAUUAAGCAGAAGGGGGAAUACCUUCCGCUGCUUCAAG
GAAAGAGCCUCGGCAUGAUCUUUGAGAAGCGCUCAACCAGGACCCGCCUUUCU
ACUGAAACUGGGUUCGCGCUGCUCGGUGGCCACCCCUGCUUCCUGACGACCCA
GGACAUCCACCUCGGAGUGAACGAAUCCCUCACCGAUACCGCCCGGGUGUUAU
CGAGCAUGGCAGAUGCCGUGCUGGCCAGGGUGUACAAACAGUCCGAUCUGGAC
ACUCUGGCCAAGGAGGCGUCAAUUCCUAUUAUCAACGGCCUUAGUGACCUCUA
CCAUCCGAUUCAGAUCCUGGCCGAUUACCUCACCCUGCAAGAACACUACAGCU
CCCUGAAGGGUCUGACAUUGUCCUGGAUCGGCGACGGCAACAACAUUCUCCAU
UCCAUCAUGAUGUCCGCCGCAAAAUUCGGCAUGCAUCUUCAAGCCGCCACGCC
GAAGGGUUACGAGCCCGACGCUUCCGUGACUAAGCUCGCCGAGCAGUACGCUA
AGGAGAACGGAACCAAGCUUCUGCUGACUAACGACCCACUAGAAGCAGCCCAC
GGGGGCAACGUGCUUAUUACUGACACCUGGAUCUCCAUGGGCCAGGAAGAAG
AGAAAAAGAAGCGGCUGCAGGCGUUCCAGGGAUAUCAGGUCACCAUGAAAAC
CGCCAAGGUCGCUGCCUCCGACUGGACCUUCCUGCACUGCCUGCCUCGCAAGC
CUGAAGAAGUGGACGACGAGGUGUUCUACUCGCCACGGAGCCUCGUGUUCCCC
GAGGCCGAGAAUAGAAAGUGGACCAUCAUGGCCGUGAUGGUGUCACUGCUCA
CCGACUACAGCCCGCAGCUUCAGAAGCCCAAGUUCUAGAUAAGUGAACUCGAG
CUAGUGACUGACUAGGAUCUGGUUACCACUAAACCAGCCUCAAGAACACCCGA
AUGGAGUCUCUAAGCUACAUAAUACCAACUUACACUUACAAAAUGUUGUCCCC
CAAAAUGUAGCCAUUCGUAUCUGCUCCUAAUAAAAAGAAAGUUUCUUCACAU
UCUAG

>mARM1915 (SEQ ID NO: 113)
GGCAGAAAAAUUUGCUACAUUGUUUCACAAACUUCAAAUAUUAUUCAUUUAU
UUAGAUCUAUUAUUACAUCAAAACAAAAAGCCGCCACCAUGCUGUUCAACCUG
CGCAUCCUGCUGAACAACGCCGCCUUCCGCAACGGCCACAACUUCAUGGUGCG
CAACUUCCGCUGCGGCCAGCCCCUGCAGAACAAGGUGCAGCUGAAGGGCCGCG
ACCUGCUGACCCUGAAGAACUUCACCGGCGAGGAGAUCAAGUACAUGCUGUGG
CUGAGCGCCGACCUGAAGUUCCGCAUCAAGCAGAAGGGCGAGUACCUGCCCCU
GCUGCAGGGCAAGAGCCUGGGCAUGAUCUUCGAGAAGCGCAGCACCCGCACCC
GCCUGAGCACCGAGACAGGCUUCGCCCUGCUGGGCGGCCACCCCUGCUUCCUG
ACCACCCAGGACAUCCACCUGGGCGUGAACGAGAGCCUGACCGACACCGCCCG
CGUGCUGAGCAGCAUGGCCGACGCCGUGCUGGCCCGCGUGUACAAGCAGAGCG
ACCUGGACACCCUGGCCAAGGAGGCCAGCAUCCCCAUCAUCAACGGCCUGAGC
GACCUGUACCACCCCAUCCAGAUCCUGGCCGACUACCUGACCCUGCAGGAGCA
CUACAGCAGCCUGAAGGGCCUGACCCUGAGCUGGAUCGGCGACGGCAACAACA
UCCUGCACAGCAUCAUGAUGAGCGCCGCCAAGUUCGGCAUGCACCUGCAGGCC
GCCACCCCCAAGGGCUACGAGCCCGACGCCAGCGUGACCAAGCUGGCCGAGCA
GUACGCCAAGGAGAACGGCACCAAGCUGCUGCUGACCAACGACCCCCUGGAGG
CCGCCCACGGCGGCAACGUGCUGAUCACCGACACCUGGAUCAGCAUGGGCCAG
GAGGAGGAGAAGAAGAAGCGCCUGCAGGCCUUCCAGGGCUACCAGGUGACCAU
GAAGACCGCCAAGGUGGCCGCCAGCGACUGGACCUUCCUGCACUGCCUGCCCC
GCAAGCCCGAGGAGGUGGACGACGAGGUGUUCUACAGCCCCCGCAGCCUGGUG
UUCCCCGAGGCCGAGAACCGCAAGUGGACCAUCAUGGCCGUGAUGGUGAGCCU
GCUGACCGACUACAGCCCCCAGCUGCAGAAGCCCAAGUUCUGAGGUCUCUAGU
AAUGAGCUGGAGCCUCGGUAGCCGUUCCUCCUGCCCGCUGGGCCUCCCAACGG
GCCCUCCUCCCCUCCUUGCACCGGCCCUUCCUGGUCUUUGAAUAAAGUCUGAG
UGGGCAUCUAG

>mARM1916 (SEQ ID NO: 114)
GGCAGAAAAAUUUGCUACAUUGUUUCACAAACUUCAAAUAUUAUUCAUUUAU
UUAGAUCUAUUAUUACAUCAAAACAAAAAGCCGCCACCAUGGGAGUAUUCAA
CCUGCGCAUCCUGCUGAACAACGCCGCCUUCCGCAACGGCCACAACUUCAUGG
UGCGCAACUUCCGCUGCGGCCAGCCCCUGCAGAACAAGGUGCAGCUGAAGGGC

-continued

SEQUENCE LISTING

CGCGACCUGCUGACCCUGAAGAACUUCACCGGCGAGGAGAUCAAGUACAUGCU
GUGGCUGAGCGCCGACCUGAAGUUCCGCAUCAAGCAGAAGGGCGAGUACCUGC
CCCUGCUGCAGGGCAAGAGCCUGGGCAUGAUCUUCGAGAAGCGCAGCACCCGC
ACCCGCCUGAGCACCGAGACAGGCUUCGCCCUGCUGGGCGGCCACCCCUGCUU
CCUGACCACCCAGGACAUCCACCUGGGCGUGAACGAGAGCCUGACCGACACCG
CCCGCGUGCUGAGCAGCAUGGCCGACGCCGUGCUGGCCCGCGUGUACAAGCAG
AGCGACCUGGACACCCUGGCCAAGGAGGCCAGCAUCCCCAUCAUCAACGGCCU
GAGCGACCUGUACCACCCCAUCCAGAUCCUGGCCGACUACCUGACCCUGCAGG
AGCACUACAGCAGCCUGAAGGGCCUGACCCUGAGCUGGAUCGGCGACGGCAAC
AACAUCCUGCACAGCAUCAUGAUGAGCGCCGCCAAGUUCGGCAUGCACCUGCA
GGCCGCCACCCCCAAGGGCUACGAGCCCGACGCCAGCGUGACCAAGCUGGCCG
AGCAGUACGCCAAGGAGAACGGCACCAAGCUGCUGCUGACCAACGACCCCCUG
GAGGCCGCCCACGGCGGCAACGUGCUGAUCACCGACACCUGGAUCAGCAUGGG
CCAGGAGGAGGAGAAGAAGAAGCGCCUGCAGGCCUUCCAGGGCUACCAGGUGA
CCAUGAAGACCGCCAAGGUGGCCGCCAGCGACUGGACCUUCCUGCACUGCCUG
CCCCGCAAGCCCGAGGAGGUGGACGACGAGGUGUUCUACAGCCCCCGCAGCCU
GGUGUUCCCCGAGGCCGAGAACCGCAAGUGGACCAUCAUGGCCGUGAUGGUGA
GCCUGCUGACCGACUACAGCCCCCAGCUGCAGAAGCCCAAGUUCUGAGGUCUC
UAGUAAUGAGCUGGAGCCUCGGUAGCCGUUCCUCCUGCCCGCUGGGCCUCCCA
ACGGGCCCUCCUCCCCUCCUUGCACCGGCCCUUCCUGGUCUUUGAAUAAAGUC
UGAGUGGGCAUCUAG

>mARM1917 (SEQ ID NO: 115)
GGCAGAAAAAUUUGCUACAUUGUUUCACAAACUUCAAAUAUUAUUCAUUUAU
UUAGAUCUAUUAUUACAUCAAAACAAAAAGCCGCCACCAUGGGAGUAUUCAA
CCUGCGCAUCCUGCUGAACAACGCCGCCUUCCGCAACGGCCACAACUUCAUGG
UGCGCAACUUCCGCUGCGGCCAGCCCCUGCAGAACCGGGUGCAGCUGAAGGGC
CGCGACCUGCUGACCCUGAAGAACUUCACCGGCGAGGAGAUCCGGUACAUGCU
GUGGCUGAGCGCCGACCUGAAGUUCCGCAUCAAGCAGAAGGGCGAGUACCUGC
CCCUGCUGCAGGGCAAGAGCCUGGGCAUGAUCUUCGAGAAGCGCAGCACCCGC
ACCCGCCUGAGCACCGAGACAGGCUUCGCCCUGCUGGGCGGCCACCCCUGCUU
CCUGACCACCCAGGACAUCCACCUGGGCGUGAACGAGAGCCUGACCGACACCG
CCCGCGUGCUGAGCAGCAUGGCCGACGCCGUGCUGGCCCGCGUGUACAAGCAG
AGCGACCUGGACACCCUGGCCAAGGAGGCCAGCAUCCCCAUCAUCAACGGCCU
GAGCGACCUGUACCACCCCAUCCAGAUCCUGGCCGACUACCUGACCCUGCAGG
AGCACUACAGCAGCCUGAAGGGCCUGACCCUGAGCUGGAUCGGCGACGGCAAC
AACAUCCUGCACAGCAUCAUGAUGAGCGCCGCCAAGUUCGGCAUGCACCUGCA
GGCCGCCACCCCCAAGGGCUACGAGCCCGACGCCAGCGUGACCAAGCUGGCCG
AGCAGUACGCCAAGGAGAACGGCACCAAGCUGCUGCUGACCAACGACCCCCUG
GAGGCCGCCCACGGCGGCAACGUGCUGAUCACCGACACCUGGAUCAGCAUGGG
CCAGGAGGAGGAGAAGAAGAAGCGCCUGCAGGCCUUCCAGGGCUACCAGGUGA
CCAUGAAGACCGCCAAGGUGGCCGCCAGCGACUGGACCUUCCUGCACUGCCUG
CCCCGCAAGCCCGAGGAGGUGGACGACGAGGUGUUCUACAGCCCCCGCAGCCU
GGUGUUCCCCGAGGCCGAGAACCGCAAGUGGACCAUCAUGGCCGUGAUGGUGA
GCCUGCUGACCGACUACAGCCCCCAGCUGCAGAAGCCCAAGUUCUGAGGUCUC
UAGUAAUGAGCUGGAGCCUCGGUAGCCGUUCCUCCUGCCCGCUGGGCCUCCCA
ACGGGCCCUCCUCCCCUCCUUGCACCGGCCCUUCCUGGUCUUUGAAUAAAGUC
UGAGUGGGCAUCUAG

>mARM1918 (SEQ ID NO: 116)
GGCAGAAAAAUUUGCUACAUUGUUUCACAAACUUCAAAUAUUAUUCAUUUAU
UUAGAUCUAUUAUUACAUCAAAACAAAAAGCCGCCACCAUGCUGGUAUUCAAC
CUGCGCAUCCUGCUGAACAACGCCGCCUUCCGCAACGGCCACAACUUCAUGGU
GCGCAACUUCCGCUGCGGCCAGCCCCUGCAGAACCGGGUGCAGCUGAAGGGCC
GCGACCUGCUGACCCUGAAGAACUUCACCGGCGAGGAGAUCCGGUACAUGCUG
UGGCUGAGCGCCGACCUGAAGUUCCGCAUCAAGCAGAAGGGCGAGUACCUGCC
CCUGCUGCAGGGCAAGAGCCUGGGCAUGAUCUUCGAGAAGCGCAGCACCCGCA
CCCGCCUGAGCACCGAGACAGGCUUCGCCCUGCUGGGCGGCCACCCCUGCUUC
CUGACCACCCAGGACAUCCACCUGGGCGUGAACGAGAGCCUGACCGACACCGC
CCGCGUGCUGAGCAGCAUGGCCGACGCCGUGCUGGCCCGCGUGUACAAGCAGA
GCGACCUGGACACCCUGGCCAAGGAGGCCAGCAUCCCCAUCAUCAACGGCCUG
AGCGACCUGUACCACCCCAUCCAGAUCCUGGCCGACUACCUGACCCUGCAGGA
GCACUACAGCAGCCUGAAGGGCCUGACCCUGAGCUGGAUCGGCGACGGCAACA
ACAUCCUGCACAGCAUCAUGAUGAGCGCCGCCAAGUUCGGCAUGCACCUGCAG
GCCGCCACCCCCAAGGGCUACGAGCCCGACGCCAGCGUGACCAAGCUGGCCGA
GCAGUACGCCAAGGAGAACGGCACCAAGCUGCUGCUGACCAACGACCCCCUGG
AGGCCGCCCACGGCGGCAACGUGCUGAUCACCGACACCUGGAUCAGCAUGGGC
CAGGAGGAGGAGAAGAAGAAGCGCCUGCAGGCCUUCCAGGGCUACCAGGUGAC
CAUGAAGACCGCCAAGGUGGCCGCCAGCGACUGGACCUUCCUGCACUGCCUGC
CCCGCAAGCCCGAGGAGGUGGACGACGAGGUGUUCUACAGCCCCCGCAGCCUG
GUGUUCCCCGAGGCCGAGAACCGCAAGUGGACCAUCAUGGCCGUGAUGGUGAG
CCUGCUGACCGACUACAGCCCCCAGCUGCAGAAGCCCAAGUUCUGAGGUCUCU
AGUAAUGAGCUGGAGCCUCGGUAGCCGUUCCUCCUGCCCGCUGGGCCUCCCAA
CGGGCCCUCCUCCCCUCCUUGCACCGGCCCUUCCUGGUCUUUGAAUAAAGUCU
GAGUGGGCAUCUAG

-continued

| SEQUENCE LISTING |
| --- |

>mARM1919 (SEQ ID NO: 117)
AUUAUUACAUCAAAACAAAAAGCCGCCACCAUGGGAGUAUUCAACCUGCGCAU
CCUGCUGAACAACGCCGCCUUCCGCAACGGCCACAACUUCAUGGUGCGCAACU
UCCGCUGCGGCCAGCCCCUGCAGAACAAGGUGCAGCUGAAGGGCCGCGACCUG
CUGACCCUGAAGAACUUCACCGGCGAGGAGAUCAAGUACAUGCUGUGGCUGAG
CGCCGACCUGAAGUUCCGCAUCAAGCAGAAGGGCGAGUACCUGCCCCUGCUGC
AGGGCAAGAGCCUGGGCAUGAUCUUCGAGAAGCGCAGCACCCGCACCCGCCUG
AGCACCGAGACAGGCUUCGCCCUGCUGGGCGGCCACCCCUGCUUCCUGACCAC
CCAGGACAUCCACCUGGGCGUGAACGAGAGCCUGACCGACACCGCCCGCGUGC
UGAGCAGCAUGGCCGACGCCGUGCUGGCCCGCGUGUACAAGCAGAGCGACCUG
GACACCCUGGCCAAGGAGGCCAGCAUCCCCAUCAUCAACGGCCUGAGCGACCU
GUACCACCCCAUCCAGAUCCUGGCCGACUACCUGACCCUGCAGGAGCACUACA
GCAGCCUGAAGGGCCUGACCCUGAGCUGGAUCGGCGACGGCAACAACAUCCUG
CACAGCAUCAUGAUGAGCGCCGCCAAGUUCGGCAUGCACCUGCAGGCCGCCAC
CCCCAAGGGCUACGAGCCCGACGCCAGCGUGACCAAGCUGGCCGAGCAGUACG
CCAAGGAGAACGGCACCAAGCUGCUGCUGACCAACGACCCCCUGGAGGCCGCC
CACGGCGGCAACGUGCUGAUCACCGACACCUGGAUCAGCAUGGGCCAGGAGGA
GGAGAAGAAGAAGCGCCUGCAGGCCUUCCAGGGCUACCAGGUGACCAUGAAGA
CCGCCAAGGUGGCCGCCAGCGACUGGACCUUCCUGCACUGCCUGCCCCGCAAG
CCCGAGGAGGUGGACGACGAGGUGUUCUACAGCCCCCGCAGCCUGGUGUUCCC
CGAGGCCGAGAACCGCAAGUGGACCAUCAUGGCCGUGAUGGUGAGCCUGCUGA
CCGACUACAGCCCCCAGCUGCAGAAGCCCAAGUUCUGAGGUCUCUAGUAAUGA
GCUGGAGCCUCGGUAGCCGUUCCUCCUGCCCGCUGGGCCUCCCAACGGGCCCU
CCUCCCCUCCUUGCACCGGCCCUUCCUGGUCUUUGAAUAAAGUCUGAGUGGGC
AUCUAG

>mARM1920 (SEQ ID NO: 118)
AUUAUUACAUCAAAACAAAAAGCCGCCACCAUGGGAGUAUUCAACCUGCGCAU
CCUGCUGAACAACGCCGCCUUCCGCAACGGCCACAACUUCAUGGUGCGCAACU
UCCGCUGCGGCCAGCCCCUGCAGAACCGGGUGCAGCUGAAGGGCCGCGACCUG
CUGACCCUGAAGAACUUCACCGGCGAGGAGAUCCGGUACAUGCUGUGGCUGAG
CGCCGACCUGAAGUUCCGCAUCAAGCAGAAGGGCGAGUACCUGCCCCUGCUGC
AGGGCAAGAGCCUGGGCAUGAUCUUCGAGAAGCGCAGCACCCGCACCCGCCUG
AGCACCGAGACAGGCUUCGCCCUGCUGGGCGGCCACCCCUGCUUCCUGACCAC
CCAGGACAUCCACCUGGGCGUGAACGAGAGCCUGACCGACACCGCCCGCGUGC
UGAGCAGCAUGGCCGACGCCGUGCUGGCCCGCGUGUACAAGCAGAGCGACCUG
GACACCCUGGCCAAGGAGGCCAGCAUCCCCAUCAUCAACGGCCUGAGCGACCU
GUACCACCCCAUCCAGAUCCUGGCCGACUACCUGACCCUGCAGGAGCACUACA
GCAGCCUGAAGGGCCUGACCCUGAGCUGGAUCGGCGACGGCAACAACAUCCUG
CACAGCAUCAUGAUGAGCGCCGCCAAGUUCGGCAUGCACCUGCAGGCCGCCAC
CCCCAAGGGCUACGAGCCCGACGCCAGCGUGACCAAGCUGGCCGAGCAGUACG
CCAAGGAGAACGGCACCAAGCUGCUGCUGACCAACGACCCCCUGGAGGCCGCC
CACGGCGGCAACGUGCUGAUCACCGACACCUGGAUCAGCAUGGGCCAGGAGGA
GGAGAAGAAGAAGCGCCUGCAGGCCUUCCAGGGCUACCAGGUGACCAUGAAGA
CCGCCAAGGUGGCCGCCAGCGACUGGACCUUCCUGCACUGCCUGCCCCGCAAG
CCCGAGGAGGUGGACGACGAGGUGUUCUACAGCCCCCGCAGCCUGGUGUUCCC
CGAGGCCGAGAACCGCAAGUGGACCAUCAUGGCCGUGAUGGUGAGCCUGCUGA
CCGACUACAGCCCCCAGCUGCAGAAGCCCAAGUUCUGAGGUCUCUAGUAAUGA
GCUGGAGCCUCGGUAGCCGUUCCUCCUGCCCGCUGGGCCUCCCAACGGGCCCU
CCUCCCCUCCUUGCACCGGCCCUUCCUGGUCUUUGAAUAAAGUCUGAGUGGGC
AUCUAG

>mARM1921 (SEQ ID NO: 119)
AUUAUUACAUCAAAACAAAAAGCCGCCACCAUGCUGGUAUUCAACCUGCGCAU
CCUGCUGAACAACGCCGCCUUCCGCAACGGCCACAACUUCAUGGUGCGCAACU
UCCGCUGCGGCCAGCCCCUGCAGAACCGGGUGCAGCUGAAGGGCCGCGACCUG
CUGACCCUGAAGAACUUCACCGGCGAGGAGAUCCGGUACAUGCUGUGGCUGAG
CGCCGACCUGAAGUUCCGCAUCAAGCAGAAGGGCGAGUACCUGCCCCUGCUGC
AGGGCAAGAGCCUGGGCAUGAUCUUCGAGAAGCGCAGCACCCGCACCCGCCUG
AGCACCGAGACAGGCUUCGCCCUGCUGGGCGGCCACCCCUGCUUCCUGACCAC
CCAGGACAUCCACCUGGGCGUGAACGAGAGCCUGACCGACACCGCCCGCGUGC
UGAGCAGCAUGGCCGACGCCGUGCUGGCCCGCGUGUACAAGCAGAGCGACCUG
GACACCCUGGCCAAGGAGGCCAGCAUCCCCAUCAUCAACGGCCUGAGCGACCU
GUACCACCCCAUCCAGAUCCUGGCCGACUACCUGACCCUGCAGGAGCACUACA
GCAGCCUGAAGGGCCUGACCCUGAGCUGGAUCGGCGACGGCAACAACAUCCUG
CACAGCAUCAUGAUGAGCGCCGCCAAGUUCGGCAUGCACCUGCAGGCCGCCAC
CCCCAAGGGCUACGAGCCCGACGCCAGCGUGACCAAGCUGGCCGAGCAGUACG
CCAAGGAGAACGGCACCAAGCUGCUGCUGACCAACGACCCCCUGGAGGCCGCC
CACGGCGGCAACGUGCUGAUCACCGACACCUGGAUCAGCAUGGGCCAGGAGGA
GGAGAAGAAGAAGCGCCUGCAGGCCUUCCAGGGCUACCAGGUGACCAUGAAGA
CCGCCAAGGUGGCCGCCAGCGACUGGACCUUCCUGCACUGCCUGCCCCGCAAG
CCCGAGGAGGUGGACGACGAGGUGUUCUACAGCCCCCGCAGCCUGGUGUUCCC
CGAGGCCGAGAACCGCAAGUGGACCAUCAUGGCCGUGAUGGUGAGCCUGCUGA
CCGACUACAGCCCCCAGCUGCAGAAGCCCAAGUUCUGAGGUCUCUAGUAAUGA
GCUGGAGCCUCGGUAGCCGUUCCUCCUGCCCGCUGGGCCUCCCAACGGGCCCU
CCUCCCCUCCUUGCACCGGCCCUUCCUGGUCUUUGAAUAAAGUCUGAGUGGGC
AUCUAG

-continued

SEQUENCE LISTING

>mARM1925 (SEQ ID NO: 120)
UCAACACAACAUAUACAAAACAAACGAAUCUCAAGCAAUCAAGCAUUCUACUU
CUAUUGCAGCAAUUUAAAUCAUUUCUUUUAAAGCAAAAGCAAUUUUCUGAAA
AUUUUCACCAUUUACGAACGAUAGCCACCAUGUUGUUCAACUUGAGGAUCUU
GUUGAACAACGCCGCCUUCAGGAACGGACACAACUUCAUGGUAAGGAACUUCA
GGUGCGGACAGCCCUUGCAGAACAAAGUACAGUUGAAAGGAAGGGACUUGUU
GACAUUGAAAAACUUCACAGGAGAAGAAAUCAAAUACAUGUUGUGGUUGUCG
GCCGACUUGAAAUUCAGGAUCAAACAGAAAGGAGAAUACUUGCCCUUGUUGC
AGGGAAAAUCGUUGGGAAUGAUCUUCGAAAAAAGGUCGACAAGGACAAGGUU
GUCGACAGAAACAGGAUUCGCCUUGUUGGGAGGACACCCCUGCUUCUUGACAA
CACAGGACAUCCACUUGGGAGUAAACGAAUCGUUGACAGACACAGCCAGGGUA
UUGUCGUCGAUGGCCGACGCCGUAUUGGCCAGGGUAUACAAACAGUCGGACUU
GGACACAUUGGCCAAAGAAGCCUCGAUCCCCAUCAUCAACGGAUUGUCGGACU
UGUACCACCCCAUCCAGAUCUUGGCCGACUACUUGACAUUGCAGGAACACUAC
UCGUCGUUGAAAGGAUUGACAUUGUCGUGGAUCGGAGACGGAAACAACAUCU
UGCACUCGAUCAUGAUGUCGGCCGCCAAAUUCGGAAUGCACUUGCAGGCCGCC
ACACCCAAAGGAUACGAACCCGACGCCUCGGUAACAAAAUUGGCCGAACAGUA
CGCCAAAGAAAACGGAACAAAAUUGUUGUUGACAAACGACCCCUUGGAAGCCG
CCCACGGAGGAAACGUAUUGAUCACAGACACAUGGAUCUCGAUGGGACAGGA
AGAAGAAAAAAAAAAAAAGGUUGCAGGCCUUCCAGGGAUACCAGGUAACAAUG
AAAACAGCCAAAGUAGCCGCCUCGGACUGGACAUUCUUGCACUGCUUGCCCAG
GAAACCCGAAGAAGUAGACGACGAAGUAUUCUACUCGCCCAGGUCGUUGGUA
UUCCCCGAAGCCGAAAACAGGAAAUGGACAAUCAUGGCCGUAAUGGUAUCGU
UGUUGACAGACUACUCGCCCCAGUUGCAGAAACCCAAAUUCUGAAUAGUGAAC
UCGAGCUAGUGACUGACUAGGAUCUGGUUACCACUAAACCAGCCUCAAGAACA
CCCGAAUGGAGUCUCUAAGCUACAUAAUACCAACUUACACUUACAAAAUGUUG
UCCCCCAAAAUGUAGCCAUUCGUAUCUGCUCCUAAUAAAAAGAAAGUUUCUUC
ACAUUCUAG

>mARM1926 (SEQ ID NO: 121)
AUUAUUACAUCAAAACAAAAAGCCGCCACCAUGCUGUUCAACCUGCGCAUCCU
GCUGAACAACGCCGCCUUCCGCAACGGCCACAACUUCAUGGUGCGCAACUUCC
GCUGCGGCCAGCCCCUGCAGGGCAAGGUGCAGCUGAAGGGCCGCGACCUGCUG
ACCCUGAAGAACUUCACCGGCGAGGAGAUCAAGUACAUGCUGUGGCUGAGCGC
CGACCUGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCCUGAGC
ACCGAGACAGGCUUCGCCCUGCUGGGCGGCCACCCCUGCUUCCUGACCACCCA
GGACAUCCACCUGGGCGUGAACGAGAGCCUGACCGACACCGCCCGCGUGCUGA
GCAGCAUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGACCUGUA
CCACCCCAUCCAGAUCCUGGCCGACUACCUGACCCUGCAGGAGCACUACAGCA
GCCUGAAGGGCCUGACCCUGAGCUGGAUCGGCGACGGCAACAACAUCCUGCAC
AGCAUCAUGAUGAGCGCCGCCAAGUUCGGCAUGCACCUGCAGGCCGCCACCCC
CAAGGGCUACGAGCCCGACGCCAGCGUGACCAAGCUGGCCGAGCAGUACGCCA
AGGAGAACGGCACCAAGCUGCUGCUGACCAACGACCCCCUGGAGGCCGCCCAC
GGCGGCAACGUGCUGAUCACCGACACCUGGAUCAGCAUGGGCCAGGAGGAGGA
GAAGAAGAAGCGCCUGCAGGCCUUCCAGGGCUACCAGGUGACCAUGAAGACCG
CCAAGGUGGCCGCCAGCGACUGGACCUUCCUGCACUGCCUGCCCCGCAAGCCC
GAGGAGGUGGACGACGAGGUGUUCUACAGCCCCCGCAGCCUGGUGUUCCCCGA
GGCCGAGAACCGCAAGUGGACCAUCAUGGCCGUGAUGGUGAGCCUGCUGACCG
ACUACAGCCCCCAGCUGCAGAAGCCCAAGUUCUGAGGUCUCUAGUAAUGAGCU
GGAGCCUCGGUAGCCGUUCCUCCUGCCCGCUGGGCCUCCCAACGGGCCCUCCU
CCCCUCCUUGCACCGGCCCUUCCUGGUCUUUGAAUAAAGUCUGAGUGGGCAUC
UAG

>mARM1927 (SEQ ID NO: 122)
AUUAUUACAUCAAAACAAAAAGCCGCCACCAUGCUGUUCAACCUGCGCAUCCU
GCUGAACAACGCCGCCUUCCGCAACGGCCACAACUUCAUGGUGCGCAACUUCC
GCUGCGGCCAGCCCCUGCAGGGCCGGGUGCAGCUGAAGGGCCGCGACCUGCUG
ACCCUGAAGAACUUCACCGGCGAGGAGAUCAAGUACAUGCUGUGGCUGAGCGC
CGACCUGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCCUGAGC
ACCGAGACAGGCUUCGCCCUGCUGGGCGGCCACCCCUGCUUCCUGACCACCCA
GGACAUCCACCUGGGCGUGAACGAGAGCCUGACCGACACCGCCCGCGUGCUGA
GCAGCAUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGACCUGUA
CCACCCCAUCCAGAUCCUGGCCGACUACCUGACCCUGCAGGAGCACUACAGCA
GCCUGAAGGGCCUGACCCUGAGCUGGAUCGGCGACGGCAACAACAUCCUGCAC
AGCAUCAUGAUGAGCGCCGCCAAGUUCGGCAUGCACCUGCAGGCCGCCACCCC
CAAGGGCUACGAGCCCGACGCCAGCGUGACCAAGCUGGCCGAGCAGUACGCCA
AGGAGAACGGCACCAAGCUGCUGCUGACCAACGACCCCCUGGAGGCCGCCCAC
GGCGGCAACGUGCUGAUCACCGACACCUGGAUCAGCAUGGGCCAGGAGGAGGA
GAAGAAGAAGCGCCUGCAGGCCUUCCAGGGCUACCAGGUGACCAUGAAGACCG
CCAAGGUGGCCGCCAGCGACUGGACCUUCCUGCACUGCCUGCCCCGCAAGCCC
GAGGAGGUGGACGACGAGGUGUUCUACAGCCCCCGCAGCCUGGUGUUCCCCGA
GGCCGAGAACCGCAAGUGGACCAUCAUGGCCGUGAUGGUGAGCCUGCUGACCG
ACUACAGCCCCCAGCUGCAGAAGCCCAAGUUCUGAGGUCUCUAGUAAUGAGCU

-continued

SEQUENCE LISTING

GGAGCCUCGGUAGCCGUUCCUCCUGCCCGCUGGGCCUCCCAACGGGCCCUCCU
CCCCUCCUUGCACCGGCCCUUCCUGGUCUUUGAAUAAAGUCUGAGUGGGCAUC
UAG

>mARM1928 (SEQ ID NO: 123)
AUUAUUACAUCAAAACAAAAAGCCGCCACCAUGCUGUUCAACCUGCGCAUCCU
GCUGAACAACGCCGCCUUCCGCAACGGCCACAACUUCAUGGUGCGCAACUUCC
GCUGCGGCCAGCCCCUGCAGGGCCGGGUGCAGCUGAAGGGCCGCGACCUGCUG
ACCCUGAAGAACUUCACCGGCGAGGAGAUCCGGUACAUGCUGUGGCUGAGCGC
CGACCUGAAGUUCCGCAUCAAGCAGAAGGGCGAGUACCUGCCCCUGCUGCAGG
GCAAGAGCCUGGGCAUGAUCUUCGAGAAGCGCAGCACCCGCACCCGCCUGAGC
ACCGAGACAGGCUUCGCCCUGCUGGGCGGCCACCCCUGCUUCCUGACCACCCA
GGACAUCCACCUGGGCGUGAACGAGAGCCUGACCGACACCGCCCGCGUGCUGA
GCAGCAUGGCCGACGCCGUGCUGGCCCGCGUGUACAAGCAGAGCGACCUGGAC
ACCCUGGCCAAGGAGGCCAGCAUCCCCAUCAUCAACGGCCUGAGCGACCUGUA
CCACCCCAUCCAGAUCCUGGCCGACUACCUGACCCUGCAGGAGCACUACAGCA
GCCUGAAGGGCCUGACCCUGAGCUGGAUCGGCGACGGCAACAACAUCCUGCAC
AGCAUCAUGAUGAGCGCCGCCAAGUUCGGCAUGCACCUGCAGGCCGCCACCCC
CAAGGGCUACGAGCCCGACGCCAGCGUGACCAAGCUGGCCGAGCAGUACGCCA
AGGAGAACGGCACCAAGCUGCUGCUGACCAACGACCCCCUGGAGGCCGCCCAC
GGCGGCAACGUGCUGAUCACCGACACCUGGAUCAGCAUGGGCCAGGAGGAGGA
GAAGAAGAAGCGCCUGCAGGCCUUCCAGGGCUACCAGGUGACCAUGAAGACCG
CCAAGGUGGCCGCCAGCGACUGGACCUUCCUGCACUGCCUGCCCCGCAAGCCC
GAGGAGGUGGACGACGAGGUGUUCUACAGCCCCCGCAGCCUGGUGUUCCCCGA
GGCCGAGAACCGCAAGUGGACCAUCAUGGCCGUGAUGGUGAGCCUGCUGACCG
ACUACAGCCCCCAGCUGCAGAAGCCCAAGUUCUGAGGUCUCUAGUAAUGAGCU
GGAGCCUCGGUAGCCGUUCCUCCUGCCCGCUGGGCCUCCCAACGGGCCCUCCU
CCCCUCCUUGCACCGGCCCUUCCUGGUCUUUGAAUAAAGUCUGAGUGGGCAUC
UAG

>mARM1929 (SEQ ID NO: 124)
GGCAGAAAAAUUUGCUACAUUGUUUCACAAACUUCAAAUAUUAUUCAUUUAU
UUAGAUCUAUUAUUACAUCAAAACAAAAAGCCGCCACCAUGCUGUUCAACCUG
CGCAUCCUGCUGAACAACGCCGCCUUCCGCAACGGCCACAACUUCAUGGUGCG
CAACUUCCGCUGCGGCCAGCCCCUGCAGGGCAAGGUGCAGCUGAAGGGCCGCG
ACCUGCUGACCCUGAAGAACUUCACCGGCGAGGAGAUCAAGUACAUGCUGUGG
CUGAGCGCCGACCUGAAGUUCCGCAUCAAGCAGAAGGGCGAGUACCUGCCCCU
GCUGCAGGGCAAGAGCCUGGGCAUGAUCUUCGAGAAGCGCAGCACCCGCACCC
GCCUGAGCACCGAGACAGGCUUCGCCCUGCUGGGCGGCCACCCCUGCUUCCUG
ACCACCCAGGACAUCCACCUGGGCGUGAACGAGAGCCUGACCGACACCGCCCG
CGUGCUGAGCAGCAUGGCCGACGCCGUGCUGGCCCGCGUGUACAAGCAGAGCG
ACCUGGACACCCUGGCCAAGGAGGCCAGCAUCCCCAUCAUCAACGGCCUGAGC
GACCUGUACCACCCCAUCCAGAUCCUGGCCGACUACCUGACCCUGCAGGAGCA
CUACAGCAGCCUGAAGGGCCUGACCCUGAGCUGGAUCGGCGACGGCAACAACA
UCCUGCACAGCAUCAUGAUGAGCGCCGCCAAGUUCGGCAUGCACCUGCAGGCC
GCCACCCCCAAGGGCUACGAGCCCGACGCCAGCGUGACCAAGCUGGCCGAGCA
GUACGCCAAGGAGAACGGCACCAAGCUGCUGCUGACCAACGACCCCCUGGAGG
CCGCCCACGGCGGCAACGUGCUGAUCACCGACACCUGGAUCAGCAUGGGCCAG
GAGGAGGAGAAGAAGAAGCGCCUGCAGGCCUUCCAGGGCUACCAGGUGACCAU
GAAGACCGCCAAGGUGGCCGCCAGCGACUGGACCUUCCUGCACUGCCUGCCCC
GCAAGCCCGAGGAGGUGGACGACGAGGUGUUCUACAGCCCCCGCAGCCUGGUG
UUCCCCGAGGCCGAGAACCGCAAGUGGACCAUCAUGGCCGUGAUGGUGAGCCU
GCUGACCGACUACAGCCCCCAGCUGCAGAAGCCCAAGUUCUGAGGUCUCUAGU
AAUGAGCUGGAGCCUCGGUAGCCGUUCCUCCUGCCCGCUGGGCCUCCCAACGG
GCCCUCCUCCCCUCCUUGCACCGGCCCUUCCUGGUCUUUGAAUAAAGUCUGAG
UGGGCAUCUAG

AT1G67090> (SEQ ID NO: 125)
CACAAAGAGUAAAGAAGAACA

AT1G35720> (SEQ ID NO: 126)
AACACUAAAAGUAGAAGAAAA

AT5G45900> (SEQ ID NO: 127)
CUCAGAAAGAUAAGAUCAGCC

>pARM563 (SEQ ID NO: 128)
ATGCTGTTTAATCTGAGGATCCTGTTAAACAATGCAGCTTTTAGAAATGGTCACA
ACTTCATGGTTCGAAATTTTCGGTGTGGACAACCACTACAAAATAAAGTGCAGCT
GAAGGGCCGTGACCTTCTCACTCTAAAAAACTTTACCGGAGAAGAAATTAAATA
TATGCTATGGCTATCAGCAGATCTGAAATTTAGGATAAAACAGAAAGGAGAGTA
TTTGCCTTTATTGCAAGGGAAGTCCTTAGGCATGATTTTTGAGAAAAGAAGTACT
CGAACAAGATTGTCTACAGAAACAGGCTTTGCACTTCTGGGAGGACATCCTTGTT
TTCTTACCACACAAGATATTCATTTGGGTGTGAATGAAAGTCTCACGGACACGGC
CCGTGTATTGTCTAGCATGGCAGATGCAGTATTGGCTCGAGTGTATAAACAATCA
GATTTGGACACCCTGGCTAAAGAAGCATCCATCCCAATTATCAATGGGCTGTCAG
ATTTGTACCATCCTATCCAGATCCTGGCTGATTACCTCACGCTCCAGGAACACTA

-continued

SEQUENCE LISTING

TAGCTCTCTGAAAGGTCTTACCCTCAGCTGGATCGGGGATGGGAACAATATCCTG
CACTCCATCATGATGAGCGCAGCGAAATTCGGAATGCACCTTCAGGCAGCTACTC
CAAAGGGTTATGAGCCGGATGCTAGTGTAACCAAGTTGGCAGAGCAGTATGCCA
AAGAGAATGGTACCAAGCTGTTGCTGACAAATGATCCATTGGAAGCAGCGCATG
GAGGCAATGTATTAATTACAGACACTTGGATAAGCATGGGACAAGAAGAGGAGA
AGAAAAAGCGGCTCCAGGCTTTCCAAGGTTACCAGGTTACAATGAAGACTGCTA
AAGTTGCTGCCTCTGACTGGACATTTTTACACTGCTTGCCCAGAAAGCCAGAAGA
AGTGGATGATGAAGTCTTTTATTCTCCTCGATCACTAGTGTTCCCAGAGGCAGAA
AACAGAAAGTGGACAATCATGGCTGTCATGGTGTCCCTGCTGACAGATTACTCAC
CTCAGCTCCAGAAGCCTAAATTTTGA

>pARM564 (SEQ ID NO: 129)
ATGCTCTTTAATCTGCGCATCTTACTGAACAACGCCGCATTCCGGAACGGTCACA
ACTTCATGGTCCGCAATTTCCGCTGTGGCCAGCCGCTTCAAAACAAGGTCCAGCT
GAAGGGACGGGATCTGCTGACACTGAAGAACTTCACCGGAGAAGAGATCAAGTA
CATGCTGTGGCTCAGCGCAGACTTGAAGTTCCGGATCAAGCAGAAGGGAGAATA
CTTGCCCCTGCTGCAAGGAAAGTCGCTGGGAATGATTTTTGAGAAGCGGTCAACT
CGCACCAGACTCTCCACCGAAACTGGTTTCGCACTGCTTGGCGGGCACCCTTGCT
TCCTGACGACTCAGGACATCCACCTCGGCGTGAACGAATCGCTAACCGATACCG
CCAGAGTGCTTTCTTCCATGGCCGACGCGGTGCTGGCCAGGGTGTACAAGCAGTC
CGACCTCGATACCTTGGCAAAGGAGGCTTCCATTCCCATCATCAACGGCCTGAGC
GACCTGTACCACCCAATCCAAATCCTGGCTGACTACCTGACCCTGCAAGAGCACT
ACAGCAGCCTGAAGGGTCTGACCCTGTCATGGATTGGCGATGGAAACAATATTC
TGCACTCCATCATGATGTCCGCCGCGAAGTTCGGAATGCATCTGCAAGCCGCCAC
TCCAAAAGGATACGAACCGGATGCGTCCGTGACCAAGTTGGCGGAACAGTACGC
GAAGGAGAACGGAACCAAGCTTCTGCTGACTAACGACCCCCTCGAGGCTGCGCA
TGGGGGCAACGTGCTGATTACCGACACCTGGATCTCCATGGGGCAGGAGGAAGA
GAAGAAGAAGAGACTGCAGGCATTCCAGGGGTACCAGGTCACCATGAAAACCG
CAAAAGTGGCAGCTTCGGACTGGACTTTCCTGCATTGCCTGCCGAGGAAGCCGG
AGGAAGTCGACGACGAAGTGTTCTACTCGCCTCGGTCCCTGGTGTTCCCCGAGGC
CGAAAACCGGAAGTGGACCATCATGGCCGTGATGGTGTCCTTGCTGACTGACTAT
AGCCCGCAGCTGCAGAAGCCTAAGTTCTAG

>pARM565 (SEQ ID NO: 130)
ATGCTGTTTAACCTACGTATTTTGCTCAACAATGCAGCCTTTAGAAACGGACATA
ACTTTATGGTTCGAAACTTTCGCTGCGGGCAGCCACTGCAGAACAAGGTCCAGCT
GAAAGGGAGAGATTTGCTCACGCTGAAGAACTTTACTGGCGAAGAAATCAAGTA
TATGCTGTGGTTGTCCGCGGACCTCAAGTTTCGGATTAAGCAGAAAGGGGAGTAT
CTGCCACTGCTGCAAGGAAAGAGCCTCGGCATGATCTTCGAGAAGCGGAGCACT
CGGACCAGGCTGAGTACCGAAACTGGCTTCGCATTGTTGGGTGGACATCCATGTT
TTCTGACAACGCAGGACATTCATCTGGGCGTGAACGAGAGTCTGACGGACACAG
CTCGCGTTCTGTCCTCTATGGCTGATGCGGTGTTGGCCCGGGTCTATAAGCAGTC
CGATTTGGACACCTTGGCTAAGGAAGCTAGCATACCGATTATCAATGGGCTGTCC
GACCTGTATCACCCTATTCAAATCCTGGCCGACTACCTCACACTGCAAGAACACT
ATAGCTCATTGAAGGGACTGACCCTGAGCTGGATAGGGGACGGAAACAACATCC
TACATAGCATTATGATGTCCGCTGCCAAGTTTGGCATGCATCTTCAAGCCGCCAC
GCCAAAGGGTTATGAGCCCGACGCGTCAGTGACAAAGCTGGCCGAGCAGTACGC
TAAGGAGAATGGTACCAAATTACTGCTGACTAATGATCCACTGGAGGCTGCACA
TGGCGGCAATGTACTGATCACCGACACATGGATCTCGATGGGCCAGGAGGAAGA
AAAGAAGAAGAGGCTTCAGGCCTTCCAAGGCTACCAGGTCACCATGAAAACAGC
TAAGGTTGCAGCATCTGATTGGACCTTTCTGCACTGTCTGCCAAGGAAGCCCGAA
GAGGTGGACGATGAAGTATTCTATAGCCCACGGAGTTTGGTGTTCCCTGAGGCTG
AAAATAGGAAGTGGACAATTATGGCCGTAATGGTGTCCCTGTTAACCGACTACTC
TCCGCAACTGCAGAAACCTAAGTTTTAG

>pARM566 (SEQ ID NO: 131)
ATGCTGTTTAACTTAAGGATCCTGCTGAACAACGCCGCTTTTCGTAACGGTCATA
ACTTTATGGTCCGGAACTTTAGATGTGGCCAGCCGCTGCAGAACAAGGTTCAGCT
GAAGGGGAGGGATCTGCTGACCTTGAAGAACTTTACCGGCGAAGAGATCAAGTA
CATGTTGTGGCTGAGCGCCGATCTGAAGTTTAGGATTAAGCAGAAGGGGGAGTA
TTTGCCACTGCTGCAAGGAAAATCCTTGGGGATGATCTTCGAGAAGCGCTCCACT
AGAACCCGGCTAAGCACAGAAACCGGCTTCGCACTTCTGGGTGGACATCCCTGTT
TTCTGACGACGCAGGATATACACCTGGGCGTGAATGAGAGTCTGACGGACACAG
CTAGGGTGTTGAGCAGCATGGCCGATGCAGTACTGGCCCGCGTTTATAAGCAGA
GCGACTTGGACACACTGGCCAAGGAAGCGTCAATTCCGATTATCAATGGGCTGT
CAGACCTGTATCATCCCATTCAAATCTTGGCTGACTATCTGACCCTGCAAGAACA
TTACAGCTCCCTGAAGGGCCTCACGTTGTCCTGGATTGGCGACGGAAACAACATT
CTGCATTCGATCATGATGAGCGCTGCTAAGTTTGGCATGCACCTCCAAGCCGCTA
CACCTAAGGGATATGAGCCTGATGCCAGCGTAACCAAGCTGGCCGAACAGTACG
CGAAGGAGAATGGCACGAAACTGCTGTTGACAAATGACCCACTGGAGGCAGCTC
ACGGTGGCAACGTGCTGATCACCGACACGTGGATATCTATGGGACAGGAAGAAG
AGAAGAAGAAGCGGCTGCAGGCATTCCAAGGGTATCAGGTCACCATGAAAACG
GCCAAGGTTGCTGCATCCGACTGGACATTTCTGCATTGCTTGCCCCGCAAACCAG
AAGAAGTAGACGACGAAGTCTTTTATTCCCCACGGTCGCTGGTGTTCCCCGAGGC
GGAGAATCGAAAGTGGACGATTATGGCCGTGATGGTGTCCCTGCTGACTGATTA
CTCTCCCCAACTGCAAAAGCCTAAGTTTTAG

-continued

SEQUENCE LISTING

>pARM567 (SEQ ID NO: 132)
ATGCTTTTCAACCTGAGGATCCTCCTGAACAACGCCGCCTTTCGCAATGGTCACA
ACTTTATGGTCCGGAACTTCAGATGCGGCCAGCCGCTGCAGAACAAGGTCCAGC
TGAAGGGACGGGATCTGCTGACTCTGAAGAACTTCACCGGAGAAGAGATCAAGT
ACATGCTGTGGCTGTCGGCCGACCTGAAGTTCAGGATCAAGCAGAAGGGAGAAT
ACCTCCCGCTGCTGCAAGGAAAGTCCCTGGGCATGATTTTCGAGAAGCGCTCGAC
CAGAACTCGGTTGTCCACCGAAACCGGGTTTGCGCTGCTGGGCGGACATCCTTGC
TTCCTGACGACTCAGGATATTCACCTGGGAGTGAACGAGTCGCTGACCGACACC
GCCAGAGTGCTGAGCTCGATGGCCGACGCCGTGTTGGCACGCGTGTACAAGCAG
TCCGATCTGGATACCCTGGCCAAAGAAGCTTCCATCCCGATCATTAACGGGCTGA
GCGACCTCTACCACCCCATTCAAATCCTGGCCGACTACCTGACTCTGCAAGAACA
CTACAGCTCGCTGAAGGGGTTGACTCTGTCCTGGATCGGCGACGGAAACAACAT
CCTGCACTCCATCATGATGTCGGCCGCAAAGTTCGGCATGCATTTGCAAGCCGCC
ACCCCAAAGGGCTACGAACCAGACGCGAGCGTCACCAAGCTGGCCGAACAGTAC
GCGAAGGAAAATGGTACTAAGCTGCTGCTGACCAACGACCCATTGGAAGCTGCC
CATGGTGGAAACGTGCTGATCACCGACACCTGGATCTCGATGGGCCAGGAAGAG
GAGAAGAAGAAGCGGCTGCAGGCGTTCCAGGGGTATCAGGTCACCATGAAAAC
AGCCAAAGTGGCAGCGTCAGACTGGACCTTCCTCCACTGTCTGCCTCGCAAGCCA
GAGGAGGTGGACGACGAGGTGTTCTACTCCCCTCGGTCCCTCGTGTTCCCTGAGG
CTGAGAACCGGAAGTGGACCATTATGGCCGTGATGGTGTCACTCCTGACTGATTA
CTCCCCGCAACTGCAGAAGCCCAAGTTCTAG

>pARM568 (SEQ ID NO: 133)
ATGCTGTTTAACCTGAGGATCCTATTGAACAATGCTGCTTTTCGTAATGGCCATA
ACTTTATGGTTCGGAACTTTAGATGCGGGCAGCCACTGCAGAACAAGGTCCAGTT
GAAAGGCCGCGATCTGTTGACATTGAAGAACTTTACCGGCGAAGAGATTAAGTA
TATGCTGTGGCTGTCTGCTGACCTCAAGTTTCGAATCAAGCAGAAGGGCGAATAT
CTCCCCCTGCTGCAAGGAAAGTCTCTCGGCATGATCTTTGAGAAGCGGAGTACCC
GAACACGGCTGAGCACCGAAACGGGCTTCGCACTGCTGGGGGGCCATCCCTGTT
TTCTGACAACGCAGGACATCCACTTGGGGGTTAACGAATCATTGACTGATACCGC
CCGCGTACTGTCATCCATGGCCGACGCTGTGCTGGCTAGGGTGTACAAGCAGTCA
GATCTGGATACACTGGCCAAGGAAGCTAGCATACCAATCATCAATGGACTGAGT
GACCTTTATCACCCGATTCAAATACTAGCCGATTATCTGACCCTGCAAGAGCATT
ACTCCTCGCTGAAAGGCCTCACGCTGTCCTGGATCGGCGACGGCAACAACATTCT
GCATAGTATTATGATGTCTGCTGCCAAATTCGGCATGCATCTGCAAGCTGCTACG
CCGAAGGGTTATGAACCCGACGCGTCAGTTACGAAGCTCGCTGAGCAGTATGCA
AAGGAGAATGGCACAAAGCTGTTGCTTACCAACGATCCCCTGGAAGCTGCTCAT
GGCGGCAATGTGCTGATTACTGACACCTGGATTTCAATGGGCCAGGAGGAGGAG
AAGAAGAAGAGGTTACAGGCTTTTCAAGGTTACCAAGTCACGATGAAAACCGCT
AAGGTCGCAGCCAGCGACTGGACATTCCTGCACTGTCTGCCAAGAAAGCCGGAA
GAAGTGGACGACGAGGTGTTCTATTCCCCGCGGTCTTTGGTGTTTCCGGAGGCCG
AAAACAGGAAATGGACCATTATGGCCGTGATGGTATCGTTGCTGACGGACTACA
GCCCTCAGTTGCAAAAGCCCAAGTTCTAG

>pARM569 (SEQ ID NO: 134)
ATGCTCTTTAACCTCCGCATCCTCCTCAACAACGCCGCCTTCCGGAATGGGCATA
ACTTCATGGTCCGGAACTTCAGATGCGGCCAGCCCCTGCAAAACAAGGTCCAGTT
GAAGGGACGGGACCTCCTTACGCTGAAGAACTTTACCGGAGAAGAGATTAAGTA
CATGCTGTGGTTGTCCGCTGACCTCAAGTTCCGCATTAAGCAGAAGGGAGAATAT
CTGCCGCTGCTGCAAGGAAAGAGCCTGGGCATGATCTTCGAAAAGCGCTCCACT
AGAACCCGGCTGTCGACTGAGACTGGATTCGCCTTGCTCGGTGGACACCCGTGCT
TCCTGACGACCCAGGACATCCACCTGGGAGTGAACGAGTCACTTACGGATACCG
CGAGGGTGCTGTCCTCAATGGCCGACGCAGTGCTCGCGCGCGTGTACAAGCAGT
CAGATCTGGATACCCTGGCCAAGGAAGCCAGCATTCCCATCATCAACGGACTGA
GCGACCTTTACCACCCAATCCAGATCCTCGCCGACTACTTAACCCTGCAAGAGCA
CTACAGCTCCCTGAAGGGACTGACTCTGTCCTGGATCGGGGATGGAAACAACAT
CCTGCACTCCATCATGATGTCTGCCGCTAAGTTTGGGATGCATCTGCAAGCCGCA
ACCCCTAAGGGATACGAGCCCGACGCCTCGGTGACCAAACTTGCGGAACAGTAC
GCCAAGGAAAACGGTACCAAGCTGCTGCTGACCAACGACCCTCTGGAAGCGGCC
CACGGAGGAAATGTGCTGATTACCGACACCTGGATTTCGATGGGCCAGGAGGAG
GAGAAGAAGAAGAGACTGCAGGCGTTCCAGGGATATCAGGTCACCATGAAAAC
CGCCAAGGTCGCCGCCAGCGACTGGACCTTCCTGCACTGTCTCCCTCGGAAACCG
GAAGAAGTGGATGACGAGGTGTTCTACTCCCCGCGCTCGCTGGTGTTCCCGGAG
GCTGAAAACAGGAAGTGGACAATCATGGCCGTGATGGTGTCCCTGTTGACCGAC
TACTCCCCACAACTGCAGAAGCCCAAGTTCTAG

>pARM570 (SEQ ID NO: 135)
ATGCTTTTCAATCTGCGCATCCTCCTGAACAACGCCGCCTTCCGCAATGGACACA
ACTTTATGGTCCGCAACTTCCGCTGTGGGCAGCCGCTGCAGAACAAGGTCCAGCT
CAAGGGGAGAGATCTCCTGACCCTGAAGAACTTCACTGGAGAGGAGATCAAGTA
CATGCTGTGGCTGTCCGCCGACCTGAAATTTCGGATTAAGCAGAAGGGCGAATA
CCTCCCACTGCTGCAAGGAAAGTCTTTGGGCATGATCTTCGAAAAGAGAAGCAC
CCGGACCCGGTTGAGCACCGAAACTGGGTTCGCGCTCCTCGGTGGACACCCGTG
CTTCCTGACCACCCAAGATATTCATCTGGGTGTCAACGAAAGCCTGACCGACACC
GCCAGGGTGCTGTCATCCATGGCTGACGCAGTGCTCGCCCGGGTGTACAAGCAG
TCAGACCTGGACACCCTCGCCAAGGAAGCTTCGATCCCTATCATCAACGGACTTT
CCGACCTGTACCACCCCATCCAAATTCTGGCCGACTACCTGACTCTGCAAGAACA

-continued

SEQUENCE LISTING

CTATAGCTCGCTGAAAGGACTTACTCTGTCCTGGATCGGGGACGGCAACAACATT
CTCCATTCCATCATGATGTCCGCTGCCAAGTTCGGAATGCACCTTCAAGCAGCGA
CTCCCAAGGGATACGAACCTGATGCCTCCGTGACTAAGCTGGCAGAGCAGTACG
CCAAGGAGAACGGTACAAAGCTGCTGCTCACGAACGACCCCCTGGAGGCGGCCC
ACGGCGGAAACGTGCTGATTACCGATACCTGGATCTCAATGGGCCAGGAAGAGG
AGAAGAAGAAGCGGCTCCAGGCGTTTCAAGGCTACCAGGTCACCATGAAAACCG
CGAAGGTCGCCGCCTCCGACTGGACTTTCTTGCACTGCCTGCCGCGGAAGCCCGA
GGAAGTGGATGACGAAGTGTTCTACTCGCCGAGATCGTTGGTGTTCCCTGAGGCC
GAAAACAGGAAGTGGACCATCATGGCCGTGATGGTGTCCCTGCTGACTGATTAC
AGCCCACAGCTGCAGAAGCCTAAGTTCTAG

>pARM571 (SEQ ID NO: 136)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM572 (SEQ ID NO: 137)
ATGCTTTTCAACCTGAGAATCCTCCTGAACAACGCCGCCTTCCGCAATGGTCATA
ACTTCATGGTCCGCAACTTTCGCTGCGGACAGCCTCTCCAAAACAAGGTCCAGCT
CAAGGGGCGCGACCTCCTCACACTGAAGAACTTCACTGGAGAAGAAATCAAGTA
CATGCTGTGGCTGAGCGCCGATCTGAAGTTCCGGATCAAGCAGAAGGGAGAGTA
CCTTCCTCTGCTGCAAGGGAAGTCCTTGGGAATGATTTTCGAGAAGCGGTCCACC
CGGACCAGGCTGAGCACTGAAACTGGCTTCGCCCTGCTGGGAGGCCACCCTTGTT
TCCTGACCACTCAGGACATCCACCTGGGCGTGAACGAGTCCCTGACCGATACTGC
CAGAGTGCTGTCCTCCATGGCCGACGCCGTGCTCGCCCGGGTGTACAAGCAGTCA
GACCTCGATACGCTGGCCAAGGAAGCCTCCATTCCCATTATCAATGGTCTGTCGG
ACCTCTACCATCCAATCCAAATCCTCGCCGACTACCTGACTCTGCAAGAACACTA
CAGCTCACTCAAGGGCCTCACCCTCTCCTGGATCGGCGACGGAAACAACATCCTT
CACTCGATTATGATGTCGGCCGCGAAGTTCGGGATGCACCTCCAAGCTGCCACTC
CAAAAGGCTACGAGCCGGATGCCTCAGTGACTAAGTTGGCGGAACAGTATGCGA
AGGAGAACGGTACCAAGCTCCTGCTGACTAACGACCCGCTGGAGGCCGCCCACG
GGGGAAACGTGCTCATCACCGATACTTGGATTTCCATGGGACAGGAGGAAGAGA
AGAAGAAGCGGTTGCAGGCATTTCAGGGCTACCAGGTCACCATGAAAACTGCCA
AAGTCGCCGCCAGCGACTGGACCTTCCTGCACTGCCTGCCCCGCAAGCCTGAAG
AAGTGGACGACGAGGTGTTCTACTCTCCCCGGTCCCTCGTGTTCCCTGAGGCCGA
AAACAGGAAGTGGACCATCATGGCTGTGATGGTGTCCCTCCTGACCGACTACAG
CCCTCAGCTCCAAAAACCCAAGTTTTAG

>pARM573 (SEQ ID NO: 138)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTGAAGAACTTTACTGGGGAGGAGATTAAGTA
TATGCTGTGGCTGTCCGCTGACCTGAAGTTTAGGATCAAGCAGAAGGGCGAATA
TCTGCCGCTGCTGCAAGGGAAAAGTCTGGGCATGATTTTTGAAAAGCGCTCTACC
CGGACCAGACTGTCTACGGAAACAGGCTTTGCCCTGCTGGGCGGCCACCCCTGTT
TTCTGACAACGCAGGACATCCATCTGGGCGTGAACGAATCACTGACCGATACTG
CTCGGGTACTCAGTTCTATGGCTGACGCAGTGCTGGCTAGGGTGTACAAGCAGA
GCGACTTGGACACACTGGCTAAGGAGGCCAGCATCCCCATTATCAATGGCCTGTC
TGATTTGTACCATCCCATTCAAATCCTGGCTGATTATCTGACACTACAAGAGCAT
TACTCAAGTCTGAAGGGTTTGACTCTCTCCTGGATCGGCGACGGCAACAACATTT
TACATTCCATTATGATGAGTGCTGCTAAGTTTGGCATGCATTTGCAAGCTGCTAC
CCCAAAGGGCTATGAACCTGACGCTAGCGTAACCAAGTTGGCCGAACAGTATGC
TAAAGAGAATGGCACCAAGCTGCTCCTGACGAATGACCCCCTGGAAGCTGCTCA
TGGCGGAAACGTACTTATAACTGATACATGGATTAGCATGGGCCAGGAAGAGGA
GAAGAAGAAGAGACTGCAGGCCTTCCAAGGCTATCAGGTCACCATGAAAACTGC
CAAGGTTGCAGCTAGCGACTGGACCTTCCTGCACTGTTTGCCGAGGAAACCCGA
GGAGGTGGACGATGAAGTCTTTTATTCTCCCCGCTCCTTGGTGTTTCCCGAGGCT
GAAAATCGAAAGTGGACGATAATGGCAGTGATGGTGTCCCTACTGACCGACTAT
TCTCCACAACTGCAGAAGCCTAAATTCTAG

-continued

SEQUENCE LISTING

```
>pARM574 (SEQ ID NO: 139)
ATGCTTTTCAATCTGAGGATCCTGCTGAACAACGCTGCTTTTCGCAACGGTCATA
ACTTTATGGTTCGCAATTTTCGTTGTGGCCAGCCGCTGCAGAACAAGGTTCAGCT
GAAGGGCAGAGATCTGCTGACTCTGAAGAACTTCACTGGGGAAGAAATCAAGTA
TATGTTATGGCTGTCCGCGGATCTGAAATTTCGAATCAAGCAGAAGGGCGAATAT
CTTCCCCTGCTGCAAGGGAAATCCTTGGGCATGATTTTTGAGAAGAGGAGCACTA
GGACTAGATTGTCAACAGAAACAGGCTTTGCTTTGTTGGGCGGACATCCCTGCTT
TCTGACGACACAGGATATCCACCTCGGCGTAAACGAGTCCCTCACCGACACTGCT
AGGGTACTGAGCAGCATGGCCGACGCTGTGCTAGCCCGGGTTTACAAGCAGTCA
GACCTGGACACCCTTGCCAAGGAAGCTTCTATTCCAATTATCAACGGCCTGAGTG
ACCTGTATCACCCTATTCAAATACTCGCCGACTATTTGACGCTTCAAGAACATTA
CAGCAGCCTCAAGGGCTTAACCTTGAGTTGGATAGGCGACGGCAACAATATCCT
GCATTCCATTATGATGTCTGCCGCTAAGTTTGGCATGCATCTACAAGCCGCAACA
CCCAAGGGCTATGAACCCGACGCTAGCGTGACCAAGCTGGCCGAGCAGTATGCT
AAGGAAAATGGCACAAAGCTCCTTCTTACCAACGATCCCCTGGAGGCTGCTCAC
GGCGGCAACGTGCTGATTACCGATACATGGATTAGCATGGGCCAGGAGGAGGAG
AAAAAGAAGCGGCTCCAGGCTTTTCAAGGCTATCAGGTCACCATGAAAACTGCA
AAGGTCGCTGCCTCCGACTGGACTTTCCTGCATTGTCTACCCCGCAAGCCTGAGG
AAGTGGACGATGAGGTGTTCTACTCCCCACGGAGTCTGGTGTTCCCGGAAGCAG
AGAATCGGAAGTGGACCATCATGGCTGTCATGGTGTCGCTCTTGACTGACTATTC
TCCCCAACTGCAAAAACCCAAGTTTTAG

>pARM575 (SEQ ID NO: 140)
ATGCTTTTCAATCTGAGGATCCTGCTGAACAACGCTGCTTTTCGCAACGGTCATA
ACTTTATGGTTCGCAATTTTCGTTGTGGCCAGCCGCTGCAGAACAAGGTTCAGCT
GAAGGGCAGAGATCTGCTGACTCTGAAGAACTTCACTGGGGAAGAAATCAAGTA
TATGTTATGGCTGTCCGCGGATCTGAAATTTCGAATCAAGCAGAAGGGCGAATAT
CTTCCCCTGCTGCAAGGGAAATCCTTGGGCATGATTTTTGAGAAGAGGAGCACTA
GGACTAGATTGTCAACAGAAACAGGCTTTGCTTTGTTGGGCGGACATCCCTGCTT
TCTGACGACACAGGATATCCACCTCGGCGTAAACGAGTCCCTCACCGACACTGCT
AGGGTACTGAGCAGCATGGCCGACGCTGTGCTAGCCCGGGTTTACAAGCAGTCA
GACCTGGACACCCTTGCCAAGGAAGCTTCTATTCCAATTATCAACGGCCTGAGTG
ACCTGTATCACCCTATTCAAATACTCGCCGACTATTTGACGCTTCAAGAACATTA
CAGCAGCCTCAAGGGCTTAACCTTGAGTTGGATAGGCGACGGCAACAATATCCT
GCATTCCATTATGATGTCTGCCGCTAAGTTTGGCATGCATCTACAAGCCGCAACA
CCCAAGGGCTATGAACCCGACGCTAGCGTGACCAAGCTGGCCGAGCAGTATGCT
AAGGAAAATGGCACAAAGCTCCTTCTTACCAACGATCCCCTGGAGGCTGCTCAC
GGCGGCAACGTGCTGATTACCGATACATGGATTAGCATGGGCCAGGAGGAGGAG
AAAAAGAAGCGGCTCCAGGCTTTTCAAGGCTATCAGGTCACCATGAAAACTGCA
AAGGTCGCTGCCTCCGACTGGACTTTCCTGCATTGTCTACCCCGCAAGCCTGAGG
AAGTGGACGATGAGGTGTTCTACTCCCCACGGAGTCTGGTGTTCCCGGAAGCAG
AGAATCGGAAGTGGACCATCATGGCTGTCATGGTGTCGCTCTTGACTGACTATTC
TCCCCAACTGCAAAAACCCAAGTTTTAG

>pARM708 (SEQ ID NO: 141)
ATGCTTTTTAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCCATCATCAACGGCCTGA
GCGACCTGTACCACCCAATCCAAATCCTGGCTGACTACCTGACCCTGCAAGAGCA
CTACAGCAGCCTGAAGGGTCTGACCCTGTCATGGATTGGCGATGGAAACAATAT
TCTGCACTCCATCATGATGTCCGCCGCGAAGTTCGGAATGCATCTGCAAGCCGCC
ACGCCAAAAGGATACGAACCGGATGCGTCCGTGACGAAGTTGGCGGAACAGTAC
GCGAAGGAGAACGGAACCAAGCTTCTGCTGACTAACGACCCCCTCGAGGCTGCG
CATGGGGGCAACGTGCTGATTACCGACACCTGGATCTCCATGGGGCAGGAGGAA
GAGAAGAAGAAGAGACTGCAGGCATTCCAGGGGTACCAGGTCACCATGAAAAC
CGCAAAAGTGGCAGCTTCGGACTGGACTTTCCTGCATTGCCTGCCGAGGAAGCC
GGAGGAAGTCGACGACGAAGTGTTCTACTCGCCTCGGTCCCTGGTGTTCCCCGAG
GCCGAAAACCGGAAGTGGACCATCATGGCCGTGATGGTGTCCTTGCTGACTGAC
TATAGCCCGCAGCTGCAGAAGCCTAAGTTCTAG

>pARM709 (SEQ ID NO: 142)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTGAAGAACTTTACTGGAGAAGAGATCAAGTA
CATGCTGTGGCTGTCGGCCGACCTGAAGTTCAGGATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
```

-continued

SEQUENCE LISTING

TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCGTCCGTGACCAAGTTGGCGGAACAGTACG
CGAAGGAGAACGGAACCAAGCTTCTGCTGACTAACGACCCCCTCGAGGCTGCGC
ATGGGGGCAACGTGCTGATTACCGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTAG

>pARM710 (SEQ ID NO: 143)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTAAAGAACTTTACTGGAGAAGAGATCAAGTA
CATGCTATGGCTGTCGGCCGACCTGAAGTTCCGTATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCATCCGTGACCAAGTTGGCGGAACAGTACG
CGAAGGAGAACGGAACCAAGCTCCTGCTGACTAACGACCCGCTCGAGGCTGCGC
ATGGGGGTAACGTGCTGATTACGGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTAG

>pARM711 (SEQ ID NO: 144)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTAAAGAACTTTACTGGAGAAGAGATCAAGTA
CATGCTATGGCTGTCGGCCGACCTGAAGTTCCGTATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCGTCCGTGACCAAGTTGGCGGAACAGTACG
CGAAGGAGAACGGAACCAAGCTTCTGCTGACTAACGACCCCCTCGAGGCTGCGC
ATGGGGGCAACGTGCTGATTACCGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTAG

>pARM712 (SEQ ID NO: 145)
ATGCTGTTCAACCTGCGAATCCTGCTGAACAACGCCGCTTTTCGGAACGGGCACA
ACTTTATGGTGAGGAACTTTCGCTGCGGACAGCCCCTCCAGAATAAGGTCCAGCT
GAAGGGCAGGGACCTGCTGACCCTGAAAAATTTCACAGGGGAGGAAATCAAGTA
TATGCTGTGGCTGTCAGCTGATCTGAAGTTCCGGATCAAGCAGAAGGGCGAATA
TCTGCCTCTGCTCCAGGGCAAAAGCCTGGGGATGATCTTCGAAAAGCGCAGTACT
CGGACCAGACTGTCAACCGAGACTGGATTCGCTCTGCTGGGAGGACACCCTTGTT
TTCTGACCACTCAGGACATTCACCTGGGAGTGAACGAGTCCCTGACCGACACTGC
TCGCGTCCTGAGCTCTATGGCCGACGCTGTGCTGGCTCGAGTCTACAAACAGTCC
GACCTGGATACCCTGGCCAAGGAAGCTTCTATCCCAATTATTAACGGCCTGTCAG
ACCTGTATCACCCCATCCAGATTCTGGCCGATTACCTGACCCTCCAGGAGCACTA
TTCTAGTCTGAAAGGGCTGACACTGAGTTGGATTGGGGACGGAAACAATATCCT
GCACTCTATTATGATGTCAGCCGCCAAGTTTGGAATGCACCTCCAGGCTGCAACC
CCAAAAGGCTACGAACCCGATGCCTCAGTGACAAAGCTGGCTGAACAGTACGCC
AAAGAGAACGGCACTAAGCTGCTGCTGACCAACGACCCTCTGGAGGCCGCTCAC
GGAGGCAACGTGCTGATCACCGATACCTGGATTAGTATGGGACAGGAGGAAGAG
AAGAAGAAGCGGCTCCAGGCCTTCCAGGGCTACCAGGTGACAATGAAAACCGCT
AAGGTCGCAGCCAGCGATTGGACCTTTCTGCACTGCCTGCCCAGAAAGCCCGAA
GAGGTGGACGACGAGGTCTTCTACTCTCCCAGAAGCCTGGTGTTTCCCGAAGCTG
AGAATAGGAAGTGGACAATTATGGCAGTGATGGTCAGCCTGCTGACTGATTATTC
ACCTCAGCTCCAGAAACCAAAGTTCTGA

-continued

SEQUENCE LISTING

>pARM713 (SEQ ID NO: 146)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM714 (SEQ ID NO: 147)
ATGCTGTTCAACCTGCGAATCCTGCTGAACAACGCCGCTTTTCGGAACGGGCACA
ACTTTATGGTGAGGAACTTTCGCTGCGGACAGCCCCTCCAGAATAAGGTCCAGCT
GAAGGGCAGGGACCTGCTGACCCTGAAAAATTTCACAGGGGAGGAAATCAAGTA
TATGCTGTGGCTGTCAGCTGATCTGAAGTTCCGGATCAAGCAGAAGGGCGAATA
TCTGCCTCTGCTCCAGGGCAAAAGCCTGGGGATGATCTTCGAAAAGCGCAGTACT
CGGACCAGACTGTCAACCGAGACTGGATTCGCTCTGCTGGGAGGACACCCTTGTT
TTCTGACCACTCAGGACATTCACCTGGGAGTGAACGAGTCCCTGACCGACACTGC
TCGCGTCCTGAGCTCTATGGCCGACGCTGTGCTAGCTCGAGTCTACAAACAGTCC
GACCTGGATACCCTGGCCAAGGAAGCTTCTATCCCAATTATTAACGGCCTGTCAG
ACCTGTATCACCCCATCCAGATTCTGGCCGATTACCTGACCCTCCAGGAGCACTA
TTCTAGTCTGAAAGGGCTGACACTGAGTTGGATTGGGGACGGAAACAATATCCT
GCACTCTATTATGATGTCAGCCGCCAAGTTTGGAATGCACCTCCAGGCTGCAACC
CCAAAAGGCTACGAACCCGATGCCTCAGTGACAAAGCTGGCTGAACAGTACGCC
AAAGAGAACGGCACTAAGCTGCTGCTGACCAACGACCCTCTGGAGGCCGCTCAC
GGAGGCAACGTGCTGATCACCGATACCTGGATTAGTATGGGACAGGAGGAAGAG
AAGAAGAAGCGGCTCCAGGCCTTCCAGGGCTACCAGGTGACAATGAAAACCGCT
AAGGTCGCAGCCAGCGATTGGACCTTTCTGCACTGCCTGCCCAGAAAGCCCGAA
GAGGTGGACGACGAGGTCTTCTACTCTCCCAGAAGCCTGGTGTTTCCCGAAGCTG
AGAATAGGAAGTGGACAATTATGGCAGTGATGGTCAGCCTGCTGACTGATTATTC
ACCTCAGCTCCAGAAACCAAAGTTCTGA

>pARM715 (SEQ ID NO: 148)
ATGCTGTTCAACCTGCGAATCCTGCTGAACAATGCCGCTTTTCGGAACGGGCACA
ATTTCATGGTGAGGAACTTTCGCTGCGGACAGCCCCTCCAGAACAAGGTCCAGCT
GAAGGGCAGGGACCTGCTGACCCTGAAAAATTTCACAGGGGAGGAAATCAAGTA
CATGCTGTGGCTGTCAGCCGATCTGAAGTTCCGGATCAAGCAGAAGGGCGAATA
TCTGCCTCTGCTCCAGGGCAAAAGCCTGGGGATGATCTTCGAAAAGCGCAGTACT
CGGACCAGACTGTCAACAGAGACTGGATTCGCACTGCTGGGAGGACACCCATGT
TTTCTGACCACACAGGACATTCATCTGGGAGTGAACGAGTCCCTGACCGACACA
GCACGCGTCCTGAGCTCCATGGCTGATGCAGTGCTGGCTCGAGTCTACAAACAGT
CTGACCTGGATACCCTGGCCAAGGAAGCTTCTATCCCAATCATTAATGGCCTGAG
TGACCTGTATCACCCCATCCAGATTCTGGCCGATTACCTGACCCTCCAGGAGCAT
TATTCTAGTCTGAAAGGGCTGACACTGAGCTGGATTGGGGACGGAAACAATATC
CTGCACTCCATTATGATGAGCGCCGCCAAGTTTGGAATGCACCTCCAGGCTGCAA
CCCCAAAAGGCTACGAACCCGATGCCTCCGTGACAAAGCTGGCAGAACAGTATG
CCAAAGAGAACGGCACTAAGCTGCTGCTGACCAATGACCCTCTGGAGGCCGCTC
ACGGAGGCAACGTGCTGATCACTGATACCTGGATTAGTATGGGACAGGAGGAAG
AGAAGAAGAAGCGGCTCCAGGCCTTCCAGGGCTACCAGGTGACAATGAAAACTG
CTAAGGTCGCAGCCAGCGACTGGACCTTTCTGCATTGCCTGCCCAGAAAGCCTGA
AGAGGTGGACGATGAGGTCTTCTACTCACCCAGAAGCCTGGTGTTTCCTGAAGCT
GAGAATAGGAAGTGGACAATCATGGCAGTGATGGTCAGCCTGCTGACTGATTAT
TCCCCTCAGCTCCAGAAACCAAAGTTCTGA

>pARM716 (SEQ ID NO: 149)
ATGCTTTTCAACCTTCGCATTCTCCTCAACAACGCCGCGTTTAGAAACGGACACA
ACTTCATGGTCCGCAACTTCCGCTGCGGACAGCCGCTGCAGAACAAGGTCCAGCT
CAAGGGTCGGGATCTCCTGACGCTGAAGAACTTTACCGGCGAAGAGATTAAGTA
CATGCTGTGGCTGTCCGCCGACCTTAAGTTCCGGATCAAGCAGAAGGGCGAATA
CCTTCCCCTGCTGCAAGGAAAGTCCCTGGGCATGATCTTCGAGAAGCGCAGTACC
AGAACCAGACTCTCCACTGAAACCGGGTTCGCGCTGCTTGGCGGCCACCCGTGTT
TCCTCACTACGCAAGACATCCATCTTGGCGTGAACGAGTCCCTTACCGACACCGC
CAGGGTGCTGTCAAGCATGGCCGACGCCGTCCTTGCGCGCGTGTACAAGCAGTC
AGACCTTGATACTCTGGCCAAGGAAGCCTCCATCCCTATTATCAACGGCCTATCC
GACCTTTACCACCCGATCCAGATCCTCGCTGACTACCTGACCCTGCAAGAACACT

-continued

SEQUENCE LISTING

ACAGCAGCCTCAAGGGACTGACTCTGTCCTGGATCGGCGACGGGAACAACATCC
TGCACTCAATCATGATGAGCGCAGCCAAGTTCGGCATGCATCTCCAAGCCGCTAC
ACCCAAGGGTTATGAACCGGACGCCTCTGTGACCAAGTTGGCAGAACAGTACGC
CAAGGAGAACGGTACTAAGCTCCTTTTAACCAACGACCCCCTCGAAGCAGCCCA
TGGCGGGAATGTGCTCATTACCGATACCTGGATTTCGATGGGCCAGGAGGAGGA
GAAGAAGAAGCGGCTGCAGGCGTTCCAGGGCTACCAGGTCACCATGAAAACTGC
CAAAGTGGCCGCCTCGGATTGGACCTTTCTCCACTGCCTGCCTCGGAAGCCTGAG
GAGGTGGACGACGAAGTGTTCTACTCCCCACGGTCCCTCGTGTTCCCCGAGGCCG
AAAATAGGAAGTGGACCATCATGGCCGTGATGGTGTCCCTCTTGACCGATTACA
GCCCGCAGCTTCAGAAGCCTAAATTCTAG

>pARM717 (SEQ ID NO: 150)
ATGCTTTTCAATCTTCGCATCCTGTTGAACAACGCCGCCTTCCGCAATGGTCACA
ACTTCATGGTCCGGAACTTCAGATGTGGACAGCCTCTCCAAAACAAGGTCCAGCT
GAAGGGAAGGGACCTCTTAACCCTCAAAAACTTTACTGGAGAGGAGATCAAGTA
CATGCTGTGGCTTAGCGCCGACCTTAAGTTCCGGATCAAGCAGAAGGGAGAGTA
CCTCCCGCTGCTGCAAGGAAAGAGTCTTGGAATGATCTTCGAGAAGCGGTCCAC
CAGAACTCGCCTCTCCACTGAAACCGGATTCGCACTCCTGGGTGGACACCCGTGC
TTTCTGACCACCCAAGACATCCACCTCGGAGTGAACGAGAGCCTCACGGACACC
GCGAGAGTGCTGTCATCCATGGCCGACGCCGTGCTTGCACGGGTCTACAAGCAG
TCCGATCTGGACACTCTTGCCAAGGAAGCCTCCATTCCTATCATTAACGGTCTGT
CGGATCTGTACCACCCGATTCAGATCCTTGCGGACTACCTCACACTTCAAGAACA
CTATTCAAGCCTAAAGGGTCTGACCCTGTCCTGGATCGGAGATGGAAACAACATT
CTCCATTCCATCATGATGAGCGCTGCCAAGTTCGGAATGCATCTCCAAGCAGCGA
CTCCTAAGGGTTACGAGCCGGACGCCTCAGTGACTAAGCTGGCCGAGCAGTACG
CCAAGGAGAACGGTACCAAACTGTTGCTTACTAACGACCCGCTTGAAGCGGCCC
ATGGAGGAAACGTGCTGATTACCGACACCTGGATTTCGATGGGACAGGAAGAGG
AGAAGAAGAAGCGGCTCCAGGCGTTCCAGGGATACCAGGTCACCATGAAAACG
GCCAAAGTGGCCGCTAGCGATTGGACCTTTCTGCACTGCCTCCCGCGCAAGCCTG
AAGAAGTGGACGACGAAGTGTTCTACTCCCCTCGCTCTCTTGTGTTCCCGGAAGC
CGAAAACAGGAAGTGGACCATCATGGCCGTGATGGTGTCCCTCCTGACCGATTA
CAGCCCGCAGCTGCAGAAGCCTAAGTTCTAG

>pARM718 (SEQ ID NO: 151)
ATGCTTTTCAATCTCCGCATCCTCCTCAACAACGCCGCGTTTAGAAACGGCCACA
ACTTCATGGTCCGGAACTTCAGATGTGGCCAGCCGCTTCAGAACAAGGTCCAGCT
CAAGGGCCGGGATCTTCTGACCCTGAAGAACTTTACTGGCGAAGAAATCAAGTA
CATGCTCTGGCTCTCCGCCGACTTGAAGTTCCGCATTAAGCAGAAGGGGGAATAC
CTTCCGCTGCTGCAAGGAAAGTCGCTCGGCATGATCTTTGAGAAGCGCTCAACCC
GCACCAGGCTGTCCACTGAAACCGGGTTCGCGCTGCTTGGTGGCCACCCCTGCTT
CCTGACCACCCAAGACATTCACCTCGGAGTGAACGAATCGCTCACTGATACTGCC
CGGGTGCTGTCGTCGATGGCCGATGCAGTGCTGGCCAGGGTGTACAAACAGTCC
GATCTGGACACTCTGGCCAAGGAGGCGTCCATCCCTATTATCAACGGCCTTTCCG
ACCTCTACCACCCGATTCAGATCCTTGCCGATTACCTCACCCTGCAAGAACACTA
CTCGTCACTGAAGGGTCTGACCTTGTCCTGGATCGGCGACGGCAACAACATCCTC
CATTCCATTATGATGTCCGCCGCCAAATTCGGCATGCATCTTCAAGCCGCAACCC
CTAAGGGTTACGAGCCGGACGCTTCCGTGACCAAGCTCGCCGAGCAGTACGCTA
AGGAGAACGGAACCAAGCTTCTGCTGACTAACGACCCCCTAGAGGCAGCCCACG
GGGGCAACGTGCTTATTACTGACACCTGGATCTCCATGGGACAGGAAGAAGAGA
AGAAGAAGCGGTTACAGGCGTTCCAGGGCTATCAGGTCACCATGAAAACCGCCA
AGGTCGCTGCCTCGGACTGGACCTTCCTGCATTGCCTGCCTCGCAAGCCCGAAGA
AGTGGACGACGAGGTGTTCTACTCGCCACGGTCCCTTGTGTTCCCTGAGGCCGAG
AATAGAAAGTGGACCATTATGGCCGTGATGGTGTCCCTTCTCACCGACTACTCGC
CGCAACTGCAGAAACCCAAGTTCTAG

>pARM719 (SEQ ID NO: 152)
ATGCTTTTCAATCTTCGCATCCTCCTCAACAACGCCGCCTTCCGGAACGGTCACA
ACTTCATGGTCCGGAACTTCCGCTGCGGCCAGCCGCTCCAAAACAAAGTGCAGCT
TAAGGGCCGCGATCTCCTGACCCTGAAGAACTTCACCGGAGAGGAAATCAAGTA
CATGCTGTGGCTCTCGGCGGACCTGAAGTTTAGGATTAAGCAGAAGGGGGAGTA
TCTGCCGCTGCTCCAAGGGAAGTCCCTTGGCATGATCTTCGAAAAGAGGTCCACC
CGGACTCGGCTCAGCACCGAAACAGGTTTTGCACTTCTGGGGGGCCACCCGTGCT
TCCTGACGACCCAGGACATCCATCTGGGTGTCAACGAGAGTTTGACCGACACTGC
CAGAGTGCTGTCATCCATGGCGGACGCGGTGCTCGCGAGAGTGTACAAGCAGTC
CGATCTTGACACCCTGGCAAAAGAGGCTTCAATCCCGATCATTAACGGACTCTCG
GATCTGTACCACCCTATCCAAATCTTGGCCGACTACCTGACCCTGCAAGAACACT
ACAGCTCCCTGAAGGGCCTGACTCTTTCCTGGATTGGCGATGGAAACAACATTCT
CCATTCTATTATGATGTCCGCCGCCAAGTTCGGCATGCACCTTCAAGCCGCCACC
CCGAAGGGCTACGAACCTGACGCCTCCGTGACTAAGCTAGCCGAACAGTACGCT
AAGGAGAACGGCACTAAGCTTCTCCTTACCAACGATCCGCTGGAGGCGGCCCAT
GGCGGAAATGTGCTTATCACCGACACCTGGATTAGCATGGGGCAGGAAGAAGAG
AAGAAGAAACGGCTCCAGGCATTCCAGGGCTACCAGGTCACCATGAAAACTGCC
AAGGTCGCCGCTAGCGACTGGACCTTCCTCCACTGTCTGCCTCGCAAGCCTGAAG
AAGTGGACGACGAGGTGTTCTACTCCCCGCGCTCCCTCGTGTTTCCTGAGGCCGA
GAACAGAAAGTGGACCATCATGGCCGTGATGGTGTCATTACTTACGGACTACAG
CCCGCAGCTGCAGAAGCCGAAGTTCTAG

-continued

SEQUENCE LISTING

>pARM720 (SEQ ID NO: 153)
ATGCTTTTTAACTTGAGAATCCTTCTGAACAACGCCGCTTTCCGCAACGGTCATA
ACTTCATGGTCCGGAACTTCAGATGTGGCCAGCCCCTCCAAAACAAAGTGCAGCT
GAAGGGCCGGGACCTTCTTACGCTGAAGAATTTCACCGGCGAAGAAATCAAGTA
CATGCTCTGGCTGTCCGCCGATCTTAAGTTCCGCATTAAGCAGAAGGGGGAATAC
CTCCCGCTGCTGCAAGGGAAGTCGCTGGGCATGATTTTTGAGAAGCGGTCAACTC
GCACCCGCCTGTCCACTGAAACTGGATTCGCACTGCTCGGTGGCCATCCCTGCTT
CCTGACCACCCAAGACATCCACCTCGGCGTGAACGAGTCCCTGACTGACACCGC
CCGGGTCTTATCCTCGATGGCCGATGCTGTGCTTGCGAGGGTGTACAAGCAGTCC
GACCTCGACACACTCGCGAAGGAGGCCTCCATCCCCATCATCAACGGCCTGTCCG
ACCTTTACCACCCAATTCAGATCCTCGCCGATTACCTGACCCTGCAAGAGCACTA
CTCGTCGCTCAAGGGGCTTACCCTCTCGTGGATTGGCGACGGCAACAACATCCTT
CACTCCATCATGATGTCGGCAGCGAAGTTCGGCATGCATCTGCAAGCCGCCACGC
CTAAGGGTTATGAACCGGATGCCTCAGTGACCAAGCTCGCCGAACAGTACGCGA
AAGAGAATGGAACCAAGCTACTTCTGACCAACGACCCCCTGGAGGCCGCTCACG
GCGGCAACGTCCTCATTACCGATACTTGGATTTCGATGGGACAGGAAGAGGAAA
AGAAGAAGAGACTGCAGGCGTTCCAGGGATACCAGGTCACCATGAAAACTGCCA
AAGTGGCAGCCTCCGACTGGACCTTCCTTCACTGCCTGCCGAGGAAGCCTGAAG
AGGTGGACGACGAGGTGTTCTACTCCCCGCGCTCCTTGGTGTTTCCTGAGGCCGA
AAACCGGAAGTGGACTATCATGGCCGTGATGGTGTCCCTCCTCACCGACTACTCG
CCGCAACTGCAGAAGCCTAAGTTCTAG

>pARM721 (SEQ ID NO: 154)
ATGTTATTCAACCTTAGAATTCTCCTTAACAACGCCGCCTTCCGGAATGGGCATA
ACTTTATGGTCCGCAATTTCCGCTGTGGACAGCCTCTGCAAAACAAGGTCCAGCT
CAAGGGCCGGGATCTGCTGACTCTCAAGAACTTCACTGGGGAAGAAATCAAGTA
CATGCTCTGGCTGAGCGCCGACCTCAAGTTCCGCATCAAGCAGAAGGGAGAGTA
CCTCCCGCTGCTCCAAGGGAAGTCCCTGGGCATGATCTTCGAGAAGAGATCCACC
CGCACCAGACTTTCCACTGAGACTGGCTTCGCCTTGCTGGGAGGCCACCCATGCT
TCCTGACGACCCAGGACATTCACCTTGGCGTGAACGAGTCCCTGACTGACACCGC
AAGGGTGTTGTCCTCGATGGCCGACGCCGTGCTTGCCCGGGTGTACAAGCAGAG
CGATCTTGACACCCTGGCTAAGGAAGCTTCCATTCCCATCATCAACGGTCTGAGC
GACCTGTACCACCCGATTCAGATCCTGGCGGACTACCTAACCCTGCAAGAGCACT
ATAGCTCCCTGAAGGGCCTCACACTTTCATGGATCGGCGACGGCAACAACATCCT
GCACTCTATTATGATGAGCGCTGCCAAATTCGGCATGCACCTCCAAGCCGCCACG
CCTAAAGGCTACGAGCCCGACGCCTCGGTGACCAAGCTTGCGGAGCAGTACGCG
AAGGAAAACGGCACCAAGCTGCTTCTCACCAACGATCCTCTGGAAGCGGCCCAT
GGTGGCAACGTGCTCATTACCGACACTTGGATCTCCATGGGACAGGAGGAGGAA
AAGAAGAAGCGGCTCCAGGCGTTTCAGGGTTACCAGGTCACCATGAAAACCGCC
AAGGTCGCAGCCTCCGACTGGACCTTCCTTCATTGCCTTCCGCGCAAGCCCGAAG
AAGTGGACGATGAAGTGTTTTACTCACCTCGGTCACTCGTGTTCCCGGAAGCAGA
GAACAGGAAATGGACCATTATGGCCGTGATGGTGTCCCTGCTCACCGATTACAGT
CCGCAACTGCAGAAGCCCAAGTTCTAG

>pARM722 (SEQ ID NO: 155)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAAATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCTAAGGGTTACGAACCCGACGCTTCCGTGACTAAGCTCGCCGAGCAGTACGC
TAAGGAGAACGGAACCAAGCTGCTGCTGACTAACGACCCGCTAGAAGCAGCCCA
CGGGGGCAACGTGCTTATTACTGACACCTGGATCTCCATGGGCCAGGAGGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTTCTCACCGACTAC
AGCCCGCAGCTTCAGAAGCCCAAGTTCTAG

>pARM723 (SEQ ID NO: 156)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
TAAGGGCCGGGATCTCCTCACCCTTAAAAACTTCACCGGCGAAGAGATCAAGTA
CATGCTCTGGCTCTCCGCGGACCTTAAGTTCCGCATTAAGCAGAAGGGGGAATAC
CTTCCGCTGCTTCAAGGAAAGAGCCTCGGCATGATCTTTGAGAAGCGCTCAACCA
GGACCAGGCTTTCTACTGAAACTGGGTTCGCGCTTCTCGGCGGTCATCCCTGCTT
CCTCACGACCCAAGACATCCACCTCGGAGTGAACGAATCCCTCACGGATACTGC
CCGCGTGCTTTCGAGCATGGCAGACGCCGTGCTCGCCCGGGTGTACAAACAGTCC
GATCTCGACACTCTCGCCAAGGAGGCGTCAATTCCTATTATCAACGGTCTTAGTG
ACCTTTACCACCCGATCCAGATCCTCGCCGATTACCTCACACTCCAAGAACACTA

-continued

SEQUENCE LISTING

CAGCTCCCTTAAGGGTCTTACCCTCTCCTGGATCGGCGACGGCAACAACATTCTC
CACTCCATCATGATGTCCGCCGCAAAGTTCGGCATGCATCTTCAAGCCGCCACCC
CGAAGGGCTACGAGCCTGATGCTTCCGTGACTAAGCTCGCCGAGCAGTACGCTA
AGGAGAACGGAACCAAGCTTCTTCTCACTAACGACCCACTCGAAGCAGCCCATG
GGGGCAACGTGCTTATCACTGACACCTGGATCTCCATGGGCCAGGAAGAAGAGA
AGAAGAAGCGGCTCCAGGCGTTCCAGGGATATCAGGTCACCATGAAAACCGCCA
AGGTCGCTGCCTCCGACTGGACCTTTCTCCACTGCCTCCCTCGCAAACCTGAAGA
AGTGGACGACGAGGTGTTCTACTCGCCCCGGAGCCTCGTGTTCCCCGAGGCCGA
GAATAGAAAGTGGACCATTATGGCCGTGATGGTGTCACTCCTCACCGACTACAG
CCCGCAGCTTCAGAAGCCCAAGTTCTAG

>pARM724 (SEQ ID NO: 157)
ATGCTTTTCAATCTCCGCATCCTCCTTAACAACGCCGCGTTTAGAAACGGACATA
ACTTCATGGTCCGGAACTTCAGATGTGGACAGCCGCTTCAAAACAAGGTCCAGCT
GAAGGGTCGGGATCTTCTGACCCTGAAGAACTTTACCGGAGAAGAGATCAAGTA
CATGCTCTGGCTCTCCGCGGACTTGAAGTTCCGCATTAAGCAGAAGGGAGAATA
CCTCCCGCTGCTTCAAGGAAAGAGCCTCGGAATGATTTTTGAGAAGCGCTCAACC
AGGACCCGCCTTTCTACTGAAACTGGATTCGCGCTGCTGGGTGGACACCCCTGCT
TCCTGACGACCCAGGACATCCACCTCGGAGTGAACGAATCCCTCACTGATACCGC
CCGGGTGTTATCGAGCATGGCAGATGCCGTGCTGGCCAGGGTGTACAAACAGTC
CGATCTGGACACTCTGGCCAAGGAGGCGTCAATTCCTATCATCAACGGACTTAGT
GACCTCTACCATCCGATTCAAATCCTGGCCGACTACCTCACCCTGCAAGAACACT
ACAGCTCCCTGAAGGGTCTGACATTGTCCTGGATCGGAGATGGAAACAACATTCT
CCACTCCATCATGATGTCCGCCGCAAAATTCGGAATGCATCTTCAAGCCGCCACG
CCTAAGGGTTACGAACCCGACGCTTCCGTGACTAAGCTCGCCGAGCAGTACGCT
AAGGAGAACGGTACCAAGCTTCTCCTGACCAACGACCCACTAGAAGCAGCCCAC
GGTGGAAACGTGCTTATTACTGACACTTGGATCTCCATGGGACAGGAGGAAGAG
AAAAAGAAGCGGCTGCAGGCGTTCCAGGGATATCAGGTCACCATGAAAACCGCC
AAGGTCGCTGCCTCCGACTGGACCTTCCTGCACTGCCTGCCTCGCAAGCCTGAAG
AAGTGGACGACGAGGTGTTCTACTCGCCGCGGAGCCTCGTGTTCCCCGAGGCCG
AGAATAGAAAGTGGACCATCATGGCCGTGATGGTGTCACTGCTCACCGACTACA
GCCCGCAGCTTCAGAAGCCCAAGTTCTAG

>pARM725 (SEQ ID NO: 158)
ATGCTTTTCAACCTCCGCATTCTCCTCAACAACGCTGCCTTCCGGAATGGACATA
ACTTCATGGTCCGGAACTTCAGATGCGGACAGCCGCTTCAGAACAAGGTCCAGC
TTAAGGGGAGAGATCTCCTTACCCTCAAAAACTTCACTGGCGAAGAAATCAAGT
ACATGCTCTGGCTTAGTGCGGATCTCAAGTTCCGCATCAAGCAGAAGGGAGAAT
ACCTCCCGCTCCTTCAAGGAAAGAGCCTCGGCATGATTTTTGAGAAGAGGTCCAC
CAGAACTCGCCTTTCAACCGAGACTGGGTTCGCCCTGCTTGGCGGTCACCCCTGC
TTCCTCACTACCCAAGACATCCACCTCGGCGTGAACGAGAGCCTTACCGACACCG
CCCGCGTGCTCTCCTCAATGGCCGACGCTGTGCTCGCCCGGGTGTACAAGCAGTC
CGACCTTGATACTCTCGCCAAGGAGGCCTCCATCCCAATTATCAACGGGCTCTCT
GATCTCTACCACCCTATCCAAATCCTCGCGGACTACCTCACCCTCCAAGAGCACT
ATAGCTCGCTCAAGGGCCTCACCCTTTCCTGGATTGGCGACGGCAACAACATTCT
TCACTCGATCATGATGTCCGCCGCCAAGTTCGGCATGCATCTCCAAGCCGCGACC
CCCAAGGGCTACGAGCCTGACGCATCCGTGACCAAGCTCGCCGAGCAGTACGCG
AAGGAAAATGGCACCAAGCTTCTTCTCACCAACGACCCCCTTGAGGCCGCTCATG
GCGGCAACGTGCTCATCACTGACACTTGGATCAGCATGGGCCAGGAGGAGGAAA
AGAAGAAGCGCCTTCAGGCATTCCAGGGTTACCAGGTCACCATGAAAACCGCCA
AAGTGGCCGCCTCCGACTGGACCTTTCTTCACTGTCTCCCGCGGAAGCCTGAAGA
AGTGGATGACGAAGTGTTTTACTCCCCTCGGTCACTCGTGTTCCCGGAAGCAGAA
AACAGGAAGTGGACCATTATGGCGGTCATGGTGTCCCTCCTCACCGACTACAGCC
CGCAGCTTCAGAAACCCAAGTTCTAG

>pARM726 (SEQ ID NO: 159)
ATGCTTTTCAATCTCCGCATCCTCCTTAACAACGCAGCGTTTAGAAACGGTCACA
ACTTCATGGTCCGGAACTTCCGCTGTGGACAGCCGCTTCAAAACAAGGTCCAGCT
GAAGGGTCGGGACCTTCTGACCCTGAAGAACTTTACTGGAGAAGAGATCAAGTA
CATGCTTTGGCTGTCCGCGGACTTGAAGTTCCGCATTAAGCAGAAGGGAGAATA
CCTTCCGCTGCTCCAAGGAAAGAGCCTGGGAATGATCTTTGAGAAGCGCTCAAC
CAGGACCCGCCTTTCTACTGAAACTGGATTCGCGCTGCTGGGTGGTCACCCTTGC
TTCCTGACGACCCAGGACATTCACCTCGGAGTGAACGAGTCCCTCACTGATACCG
CCAGAGTGTTATCGAGCATGGCAGATGCCGTGCTGGCTAGGGTGTACAAACAGT
CCGATCTGGACACCCTGGCCAAGGAGGCATCAATTCCTATTATCAACGGACTTAG
TGACCTCTACCATCCGATTCAAATCCTGGCCGATTACCTCACCCTGCAAGAACAC
TACAGCTCCCTGAAGGGTCTGACATTGTCCTGGATCGGAGATGGAAACAACATTC
TCCATTCCATCATGATGTCCGCGGCCAAGTTCGGAATGCATCTCCAAGCCGCCAC
GCCGAAAGGATACGAGCCGGACGCTTCCGTGACTAAGCTCGCCGAGCAGTACGC
TAAGGAGAACGGAACCAAGCTTCTGCTGACTAACGACCCGCTAGAAGCCGCCCA
CGGTGGAAACGTGCTTATTACTGACACCTGGATCTCCATGGGACAGGAAGAAGA
GAAAAAGAAGCGGCTGCAGGCGTTCCAGGGATATCAGGTCACCATGAAAACCGC
CAAGGTCGCCGCCTCCGACTGGACCTTCCTTCACTGCCTGCCTCGGAAGCCTGAA
GAAGTGGACGACGAGGTGTTCTACTCGCCGCGGAGCCTCGTGTTCCCTGAGGCC
GAGAATAGAAAGTGGACCATCATGGCCGTGATGGTGTCACTCCTCACCGACTAC
AGCCCGCAGCTTCAGAAGCCTAAGTTCTAG

-continued

SEQUENCE LISTING

>pARM727 (SEQ ID NO: 160)
ATGCTTTTCAATCTCCGCATTCTCCTCAACAACGCAGCCTTTAGAAACGGCCACA
ACTTCATGGTCCGGAACTTCAGATGTGGCCAGCCGCTTCAGAACAAGGTCCAGCT
CAAGGGCCGGGACCTCCTCACCCTCAAAAACTTTACCGGCGAAGAGATCAAGTA
CATGCTCTGGCTTTCGGCCGACCTTAAGTTCCGCATCAAGCAGAAGGGGGAATAC
CTTCCGCTGCTTCAAGGAAAGTCCCTCGGCATGATCTTTGAAAAGCGCTCGACCA
GGACCCGCCTTTCCACTGAAACCGGGTTCGCGCTTCTCGGTGGCCACCCCCTGCTT
CCTCACCACCCAAGACATTCACCTCGGAGTGAACGAATCCCTTACCGATACCGCA
AGAGTGCTTTCGTCGATGGCCGATGCCGTGCTTGCGCGGGTGTACAAGCAGTCAG
ATCTCGACACTCTCGCCAAGGAGGCGTCCATTCCTATTATCAACGGCCTTTCCGA
CCTTTACCACCCGATTCAGATCCTCGCCGATTACCTCACCCTGCAAGAGCACTAC
TCGTCACTCAAGGGTCTTACCCTCTCCTGGATCGGCGACGGAAACAACATCCTCC
ATTCGATCATGATGTCCGCCGCCAAATTCGGCATGCACCTCCAAGCCGCGACCCC
GAAGGGTTACGAGCCCGACGCTTCCGTGACCAAGCTCGCCGAACAGTACGCTAA
GGAAAACGGCACCAAGCTCCTCCTCACTAACGACCCTCTCGAAGCAGCCCATGG
GGGCAACGTGCTCATTACTGACACTTGGATCTCGATGGGCCAGGAAGAGGAGAA
AAAGAAGCGGCTTCAGGCGTTCCAGGGATATCAGGTCACCATGAAAACCGCCAA
GGTCGCTGCCTCGGACTGGACCTTCCTTCACTGCCTTCCGCGCAAGCCTGAAGAG
GTGGACGATGAGGTGTTCTACTCCCCACGGTCCCTTGTGTTCCCCGAGGCCGAGA
ATAGGAAGTGGACCATCATGGCCGTGATGGTGTCGCTCCTCACTGACTACTCCCC
GCAACTTCAGAAGCCTAAGTTCTAG

>pARM728 (SEQ ID NO: 161)
ATGCTGTTTAATCTGAGAATACTTCTAAACAACGCCGCCTTCCGGAATGGCCATA
ACTTTATGGTTCGGAATTTCCGCTGCGGCCAGCCGCTGCAGAACAAGGTCCAGCT
GAAGGGAAGAGACTTGCTGACCCTCAAGAACTTCACCGGAGAAGAAATCAAGTA
TATGCTGTGGCTGTCCGCCGACCTGAAATTCCGCATCAAGCAGAAGGGCGAATA
TCTGCCGCTGTTGCAAGGGAAGTCCCTGGGGATGATCTTCGAGAAGAGGTCCAC
CAGAACACGGCTTTCAACCGAAACCGGGTTTGCACTGCTGGGTGGACACCCCTGT
TTTCTGACCACTCAAGATATCCACCTGGGCGTGAACGAGTCCCTTACCGACACTG
CTAGGGTGTTGTCCAGCATGGCCGATGCCGTCCTGGCTCGCGTGTACAAGCAGTC
CGACCTGGATACCCTGGCAAAGGAAGCGTCCATTCCCATTATCAACGGGCTGTCC
GACCTGTACCATCCGATTCAAATCCTGGCGGACTACCTGACTCTGCAAGAGCATT
ACAGCAGCTTGAAGGGGCTTACTCTCTCGTGGATCGGCGACGGGAACAACATCC
TGCACTCCATCATGATGTCCGCCGCCAAGTTCGGGATGCATTTGCAAGCTGCGAC
CCCGAAAGGTTACGAGCCCGATGCTAGCGTAACTAAGCTTGCCGAACAGTACGC
CAAAGAGAATGGTACAAAACTGCTTCTGACTAACGACCCGCTGGAAGCAGCCCA
CGGCGGGAACGTGCTGATAACCGACACCTGGATTTCAATGGGGCAGGAGGAAGA
GAAGAAGAAGCGACTGCAGGCGTTCCAAGGCTATCAGGTTACCATGAAAACCGC
CAAAGTGGCAGCCAGCGATTGGACTTTCCTGCACTGTCTGCCGCGGAAGCCCGA
GGAAGTTGATGACGAAGTATTCTACTCACCCCGGAGCCTCGTGTTCCCCGAGGCC
GAAAACCGGAAGTGGACTATTATGGCCGTGATGGTGTCGCTGTTGACCGACTAC
AGCCCGCAACTGCAGAAGCCGAAGTTTTAG

>pARM729 (SEQ ID NO: 162)
ATGCTTTTCAACCTGAGGATCCTTTTGAACAACGCCGCCTTTCGCAACGGCCACA
ACTTTATGGTCCGCAATTTCCGCTGCGGGCAGCCGCTGCAGAACAAGGTCCAGCT
GAAGGGCCGGGATCTGCTGACCCTGAAGAACTTCACCGGGGAGGAAATCAAGTA
CATGCTTTGGCTCTCCGCCGATCTGAAGTTCAGAATCAAGCAGAAGGGAGAGTA
CCTCCCGTTGCTGCAAGGAAAGTCACTCGGAATGATTTTCGAAAAGAGAAGCAC
TAGGACCCGCCTCTCAACTGAAACCGGGTTCGCGCTGCTCGGGGGCCATCCGTGT
TTCCTGACTACCCAAGACATCCACCTGGGAGTGAACGAGTCGCTGACCGACACC
GCACGCGTGCTGTCATCCATGGCGGACGCAGTGCTTGCCCGGGTGTACAAGCAG
TCGGACCTGGACACTCTTGCCAAGGAGGCATCAATCCCCATCATTAACGGACTGT
CCGATCTCTACCACCCGATTCAGATCCTGGCTGACTACCTAACCCTGCAAGAGCA
CTACTCAAGCCTGAAGGGGCTGACCCTGTCGTGGATCGGGGACGGCAACAACAT
TCTGCACTCCATCATGATGTCGGCGGCTAAGTTCGGGATGCATTTGCAAGCGGCA
ACTCCGAAGGGTTATGAACCCGACGCCTCCGTGACCAAGCTGGCCGAACAGTAC
GCCAAGGAAAACGGAACCAAGTTGCTGCTGACTAATGATCCCCTGGAGGCGGCC
CACGGGGGGAACGTGCTGATAACCGATACCTGGATCTCCATGGGGCAGGAAGAA
GAGAAGAAAAAGCGGCTGCAGGCATTCCAGGGATACCAGGTCACCATGAAAAC
CGCAAAAGTGGCAGCCAGCGACTGGACTTTCCTCCATTGCCTGCCGCGAAAGCC
GGAGGAGGTCGATGACGAGGTGTTCTACTCCCCGCGGTCGCTGGTGTTCCCGGA
GGCGGAAAACCGGAAGTGGACCATTATGGCCGTGATGGTGTCACTCCTGACTGA
CTACAGCCCGCAACTGCAGAAGCCGAAGTTCTAG

>pARM1787 (SEQ ID NO: 163)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC

SEQUENCE LISTING

TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAGATAAGTGAA

>pARM1788 (SEQ ID NO: 164)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGA

>pARM1789 (SEQ ID NO: 165)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGA

>pARM1790 (SEQ ID NO: 166)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAGATAAGTGAA

-continued

SEQUENCE LISTING

>pARM1791 (SEQ ID NO: 167)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTAAAGAACTTTACTGGAGAAGAGATCAAGTA
CATGCTATGGCTGTCGGCCGACCTGAAGTTCCGTATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCATCCGTGACCAAGTTGGCGGAACAGTACG
CGAAGGAGAACGGAACCAAGCTCCTGCTGACTAACGACCCGCTCGAGGCTGCGC
ATGGGGGTAACGTGCTGATTACGGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTAGATAAGTGA

>pARM1792 (SEQ ID NO: 168)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGA

>pARM1793 (SEQ ID NO: 169)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAGATAAGTGAA

>pARM1794 (SEQ ID NO: 170)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA

-continued

SEQUENCE LISTING

```
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGA

>pARM1795 (SEQ ID NO: 171)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTAAAGAACTTTACTGGAGAAGAGATCAAGTA
CATGCTATGGCTGTCGGCCGACCTGAAGTTCCGTATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCATCCGTGACCAAGTTGGCGGAACAGTACG
CGAAGGAGAACGGAACCAAGCTCCTGCTGACTAACGACCCGCTCGAGGCTGCGC
ATGGGGGTAACGTGCTGATTACGGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTAGATAAGTGA

>pARM1796 (SEQ ID NO: 172)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAGATAAGTGAA

>pARM1797 (SEQ ID NO: 173)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGA
```

-continued

SEQUENCE LISTING

>pARM1798 (SEQ ID NO: 174)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTAAAGAACTTTACTGGAGAAGAGATCAAGTA
CATGCTATGGCTGTCGGCCGACCTGAAGTTCCGTATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCATCCGTGACCAAGTTGGCGGAACAGTACG
CGAAGGAGAACGGAACCAAGCTCCTGCTGACTAACGACCCGCTCGAGGCTGCGC
ATGGGGGTAACGTGCTGATTACGGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTAGATAAGTGA

>pARM1799 (SEQ ID NO: 175)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1800 (SEQ ID NO: 176)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1801 (SEQ ID NO: 177)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA

-continued

SEQUENCE LISTING

GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1802 (SEQ ID NO: 178)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGAA

>pARM1803 (SEQ ID NO: 179)
ATGGGCGTCTTCAACCTGCGGATCCTGCTGAACAACGCCGCCTTCCGGAACGGCC
ACAACTTCATGGTCCGCAACTTCAGATGCGGCCAGCCCCTGCAGAACAAGGTGC
AGCTGAAGGGCCGGGACCTGCTGACCCTGAAGAACTTCACCGGCGAAGAGATCA
AGTACATGCTGTGGCTGAGCGCCGACCTGAAGTTCCGGATCAAGCAGAAGGGCG
AGTACCTGCCCCTGCTGCAAGGCAAGAGCCTGGGCATGATCTTCGAGAAGCGGA
GCACCCGGACCCGGCTGAGCACCGAGACAGGCTTTGCCCTGCTGGGAGGCCACC
CCTGCTTTCTGACCACCCAGGACATCCACCTGGGCGTGAACGAGAGCCTGACCG
ACACCGCCAGAGTGCTGAGCAGCATGGCCGACGCCGTGCTGGCCCGGGTGTACA
AGCAGAGCGACCTGGACACCCTGGCCAAAGAGGCCAGCATCCCCATCATCAACG
GCCTGAGCGACCTGTACCACCCCATCCAGATCCTGGCCGACTACCTGACCCTGCA
GGAACACTACAGCTCCCTGAAGGGCCTGACCCTGAGCTGGATCGGCGACGGCAA
CAACATCCTGCACAGCATCATGATGAGCGCCGCCAAGTTCGGCATGCATCTGCA
GGCCGCCACCCCCAAGGGCTACGAGCCTGATGCCAGCGTGACCAAGCTGGCCGA
GCAGTACGCCAAAGAGAACGGCACCAAGCTGCTGCTGACCAACGACCCCCTGGA
AGCCGCCCACGGCGGCAACGTGCTGATCACCGACACCTGGATCAGCATGGGCCA
GGAAGAGGAAAAGAAGAAGCGGCTGCAGGCCTTCCAGGGCTACCAGGTCACAA
TGAAGACCGCCAAGGTGGCCGCCAGCGACTGGACCTTCCTGCACTGCCTGCCCC
GGAAGCCCGAAGAGGTGGACGACGAGGTGTTCTACAGCCCCCGGTCCCTGGTGT
TCCCCGAGGCCGAGAACCGGAAGTGGACCATTATGGCCGTGATGGTGTCCCTGC
TGACCGACTACTCCCCCCAGCTGCAGAAGCCCAAGTTCTAGATAAGTGAA

>pARM1804 (SEQ ID NO: 180)
ATGGGCGTCTTCAACCTGCGGATCCTGCTGAACAACGCCGCCTTCCGGAACGGCC
ACAACTTCATGGTCCGCAACTTCAGATGCGGCCAGCCCCTGCAGAACAGGGTGC
AGCTGAAGGGCCGGGACCTGCTGACCCTGAAGAACTTCACCGGCGAAGAGATCA
GGTACATGCTGTGGCTGAGCGCCGACCTGAAGTTCCGGATCAAGCAGAAGGGCG
AGTACCTGCCCCTGCTGCAAGGCAAGAGCCTGGGCATGATCTTCGAGAAGCGGA
GCACCCGGACCCGGCTGAGCACCGAGACAGGCTTTGCCCTGCTGGGAGGCCACC
CCTGCTTTCTGACCACCCAGGACATCCACCTGGGCGTGAACGAGAGCCTGACCG
ACACCGCCAGAGTGCTGAGCAGCATGGCCGACGCCGTGCTGGCCCGGGTGTACA
AGCAGAGCGACCTGGACACCCTGGCCAAAGAGGCCAGCATCCCCATCATCAACG
GCCTGAGCGACCTGTACCACCCCATCCAGATCCTGGCCGACTACCTGACCCTGCA
GGAACACTACAGCTCCCTGAAGGGCCTGACCCTGAGCTGGATCGGCGACGGCAA
CAACATCCTGCACAGCATCATGATGAGCGCCGCCAAGTTCGGCATGCATCTGCA
GGCCGCCACCCCCAAGGGCTACGAGCCTGATGCCAGCGTGACCAAGCTGGCCGA
GCAGTACGCCAAAGAGAACGGCACCAAGCTGCTGCTGACCAACGACCCCCTGGA
AGCCGCCCACGGCGGCAACGTGCTGATCACCGACACCTGGATCAGCATGGGCCA
GGAAGAGGAAAAGAAGAAGCGGCTGCAGGCCTTCCAGGGCTACCAGGTCACAA
TGAAGACCGCCAAGGTGGCCGCCAGCGACTGGACCTTCCTGCACTGCCTGCCCC
GGAAGCCCGAAGAGGTGGACGACGAGGTGTTCTACAGCCCCCGGTCCCTGGTGT
TCCCCGAGGCCGAGAACCGGAAGTGGACCATTATGGCCGTGATGGTGTCCCTGC
TGACCGACTACTCCCCCCAGCTGCAGAAGCCCAAGTTCTAGATAAGTGAA

-continued

SEQUENCE LISTING

>pARM1805 (SEQ ID NO: 181)
ATGCTGGTCTTCAACCTGCGGATCCTGCTGAACAACGCCGCCTTCCGGAACGGCC
ACAACTTCATGGTCCGCAACTTCAGATGCGGCCAGCCCCTGCAGAACAGGGTGC
AGCTGAAGGGCCGGGACCTGCTGACCCTGAAGAACTTCACCGGCGAAGAGATCA
GGTACATGCTGTGGCTGAGCGCCGACCTGAAGTTCCGGATCAAGCAGAAGGGCG
AGTACCTGCCCCTGCTGCAAGGCAAGAGCCTGGGCATGATCTTCGAGAAGCGGA
GCACCCGGACCCGGCTGAGCACCGAGACAGGCTTTGCCCTGCTGGGAGGCCACC
CCTGCTTTCTGACCACCCAGGACATCCACCTGGGCGTGAACGAGAGCCTGACCG
ACACCGCCAGAGTGCTGAGCAGCATGGCCGACGCCGTGCTGGCCCGGGTGTACA
AGCAGAGCGACCTGGACACCCTGGCCAAAGAGGCCAGCATCCCCATCATCAACG
GCCTGAGCGACCTGTACCACCCCATCCAGATCCTGGCCGACTACCTGACCCTGCA
GGAACACTACAGCTCCCTGAAGGGCCTGACCCTGAGCTGGATCGGCGACGGCAA
CAACATCCTGCACAGCATCATGATGAGCGCCGCCAAGTTCGGCATGCATCTGCA
GGCCGCCACCCCCAAGGGCTACGAGCCTGATGCCAGCGTGACCAAGCTGGCCGA
GCAGTACGCCAAAGAGAACGGCACCAAGCTGCTGCTGACCAACGACCCCCTGGA
AGCCGCCCACGGCGGCAACGTGCTGATCACCGACACCTGGATCAGCATGGGCCA
GGAAGAGGAAAAGAAGAAGCGGCTGCAGGCCTTCCAGGGCTACCAGGTCACAA
TGAAGACCGCCAAGGTGGCCGCCAGCGACTGGACCTTCCTGCACTGCCTGCCCC
GGAAGCCCGAAGAGGTGGACGACGAGGTGTTCTACAGCCCCCGGTCCCTGGTGT
TCCCCGAGGCCGAGAACCGGAAGTGGACCATTATGGCCGTGATGGTGTCCCTGC
TGACCGACTACTCCCCCCAGCTGCAGAAGCCCAAGTTCTAGATAAGTGAA

>pARM1806 (SEQ ID NO: 182)
ATGCTGTTCAACCTGAGGATCCTGCTGAACAACGCAGCTTTCAGGAACGGCCAC
AACTTCATGGTGAGGAACTTCCGGTGCGGCCAGCCCCTGCAGAACAAGGTGCAG
CTGAAGGGCAGGGACCTGCTGACCCTGAAGAACTTCACCGGAGAGGAGATCAAG
TACATGCTGTGGCTGAGCGCAGACCTGAAGTTCAGGATCAAGCAGAAGGGAGAG
TACCTGCCCCTGCTGCAGGGGAAGTCCCTGGGCATGATCTTCGAGAAGAGGAGT
ACCAGGACCAGGCTGAGCACCGAAACCGGCTTCGCCCTGCTGGGAGGACACCCC
TGCTTCCTGACCACCCAGGACATCCACCTGGGCGTGAACGAGAGTCTGACCGAC
ACCGCCAGGGTGCTGTCTAGCATGGCCGACGCCGTGCTGGCCAGGGTGTACAAG
CAGTCAGACCTGGACACCCTGGCTAAGGAGGCCAGCATCCCCATCATCAACGGC
CTGAGCGACCTGTACCACCCCATCCAGATCCTGGCTGACTACCTGACCCTGCAGG
AGCACTACAGCTCTCTGAAGGGCCTGACCCTGAGCTGGATCGGCGACGGGAACA
ACATCCTGCACAGCATCATGATGAGCGCCGCCAAGTTCGGCATGCACCTGCAGG
CCGCTACCCCCAAGGGTTACGAGCCCGACGCCAGCGTGACCAAGCTGGCAGAGC
AGTACGCCAAGGAGAACGGCACCAAGCTGCTGCTGACCAACGACCCCCTGGAGG
CCGCCCACGGAGGCAACGTGCTGATCACCGACACCTGGATCAGCATGGGACAGG
AGGAGGAGAAGAAGAAGCGGCTGCAGGCTTTCCAGGGTTACCAGGTGACCATGA
AGACCGCCAAGGTGGCTGCCAGCGACTGGACCTTCCTGCACTGCCTGCCCAGGA
AGCCCGAGGAGGTGGACGACGAGGTGTTCTACTCTCCCAGGAGCCTGGTGTTCC
CCGAGGCCGAGAACAGGAAGTGGACCATCATGGCTGTGATGGTGTCCCTGCTGA
CCGACTACAGCCCCCAGCTGCAGAAGCCCAAGTTCTGAATAAGTGAA

>pARM1808 (SEQ ID NO: 183)
ATGCTGTTCAACCTGAGGATCCTGCTGAACAACGCAGCTTTCAGGAACGGCCAC
AACTTCATGGTGAGGAACTTCCGGTGCGGCCAGCCCCTGCAGAACAAGGTGCAG
CTGAAGGGCAGGGACCTGCTGACCCTGAAGAACTTCACCGGAGAGGAGATCAAG
TACATGCTGTGGCTGAGCGCAGACCTGAAGTTCAGGATCAAGCAGAAGGGAGAG
TACCTGCCCCTGCTGCAGGGGAAGTCCCTGGGCATGATCTTCGAGAAGAGGAGT
ACCAGGACCAGGCTGAGCACCGAAACCGGCTTCGCCCTGCTGGGAGGACACCCC
TGCTTCCTGACGACCCAGGACATCCACCTCGGAGTGAACGAATCCCTCACCGATA
CCGCCCGGGTGTTATCAAGCATGGCAGATGCCGTGCTGGCCAGGGTGTACAAAC
AGTCCGATCTGGACACTCTGGCTAAGGAGGCCAGCATCCCCATCATCAACGGCCT
GAGCGACCTGTACCACCCCATCCAGATCCTGGCTGACTACCTGACCCTGCAGGAG
CACTACAGCTCTCTGAAGGGCCTGACCCTGAGCTGGATCGGCGACGGGAACAAC
ATCCTGCACTCCATCATGATGTCCGCCGCGAAGTTCGGAATGCATCTGCAAGCCG
CCACGCCAAAAGGATACGAACCGGATGCGCCCGTGACAAAGTTGGCGGAACAGT
ACGCTAAGGAGAACGGAACCAAGCTGCTGCTGACCAACGACCCCCTGGAGGCCG
CCCACGGAGGCAACGTGCTGATCACCGACACCTGGATCAGCATGGGACAGGAGG
AGGAGAAGAAGAAGCGGCTGCAGGCTTTCCAGGGTTACCAGGTGACCATGAAGA
CCGCCAAGGTGGCTGCCAGCGACTGGACCTTCCTGCACTGCCTGCCCAGGAAGC
CCGAGGAGGTGGACGACGAGGTGTTCTACTCTCCCAGGAGCCTGGTGTTCCCCG
AGGCCGAGAACAGGAAGTGGACCATCATGGCTGTGATGGTGTCCCTGCTGACCG
ACTACAGCCCCCAGCTGCAGAAGCCCAAGTTCTGAATAAGTGAA

>pARM1809 (SEQ ID NO: 184)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA

-continued

| SEQUENCE LISTING |
| --- |

GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGAA

>pARM1816 (SEQ ID NO: 185)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTGAA

>pARM1822 (SEQ ID NO: 186)
ATGCTTTTCAACTTGAGAATCCTGCTGAACAACGCCGCCTTTCGCAACGGTCACA
ATTTTATGGTCAGAAACTTCAGATGCGGACAGCCCCTCCAAAACAAGGTCCAGCT
GAAGGGCCGCGATCTCCTCACCCTGAAGAACTTCACGGGGGAGGAGATCAAGTA
CATGCTGTGGCTCTCCGCTGACCTGAAGTTCAGGATCAAGCAGAAGGGAGAATA
TCTGCCGCTGCTGCAAGGGAAGTCCCTGGGGATGATTTTCGAGAAGCGGAGCAC
CCGGACTCGGCTCTCCACTGAAACTGGTTTCGCCCTTCTGGGCGGTCACCCCTGC
TTCCTGACCACTCAAGACATTCACCTCGGAGTGAACGAGTCCTTGACTGACACCG
CCCGGGTGCTGTCGAGCATGGCAGACGCCGTGCTAGCCCGCGTGTACAAGCAGT
CAGACCTCGATACCCTGGCCAAGGAGGCTTCGATCCCGATCATCAACGGGTTGTC
CGACCTGTACCACCCGATTCAGATTCTCGCCGACTACCTCACCCTGCAAGAGCAT
TACAGCTCCCTGAAGGGGCTTACCCTGTCCTGGATTGGCGACGGAAACAACATCC
TGCACTCCATTATGATGTCGGCGGCCAAGTTCGGCATGCACCTCCAAGCCGCGAC
CCCTAAGGGTTACGAACCAGACGCGTCAGTGACTAAGCTGGCCGAACAGTACGC
AAAGGAAAATGGCACGAAGCTGCTCCTGACCAACGATCCGTTGGAAGCCGCCCA
TGGCGGAAATGTGCTCATCACCGACACCTGGATCTCGATGGGACAGGAGGAAGA
GAAGAAGAAGCGGCTGCAGGCGTTCCAGGGCTACCAGGTCACCATGAAAACTGC
CAAGGTGGCCGCCAGCGACTGGACCTTCCTGCACTGCCTTCCGCGCAAGCCTGAG
GAGGTGGACGATGAAGTGTTCTACTCTCCACGGTCCCTGGTGTTCCCCGAGGCGG
AGAACCGCAAATGGACCATCATGGCTGTGATGGTCAGCCTGCTGACCGATTACA
GCCCTCAGTTGCAAAAGCCGAAGTTTTGA

>pARM1823 (SEQ ID NO: 187)
ATGCTGTTCAACCTCCGCATCCTCCTCAACAACGCCGCATTCAGAAACGGGCACA
ACTTCATGGTCAGAAACTTCCGCTGCGGGCAACCCCTACAAAACAAGGTCCAGC
TCAAGGGGCGGGACCTCCTGACCCTGAAGAACTTCACCGGCGAAGAGATCAAGT
ACATGCTGTGGCTCTCCGCCGACCTGAAGTTCCGCATCAAGCAGAAGGGAGAGT
ACCTCCCGCTGCTGCAAGGGAAGTCGCTGGGGATGATCTTCGAGAAGCGGTCAA
CCAGAACCCGGCTGTCAACCGAAACCGGGTTCGCACTGCTGGGGGGACACCCGT
GCTTCCTGACCACCCAAGACATCCACCTGGGAGTGAACGAATCGCTGACCGACA
CCGCCCGCGTGCTGAGCTCAATGGCGGACGCCGTGCTGGCCCGCGTGTACAAGC
AGTCCGACCTGGACACCCTGGCCAAGGAAGCGTCCATCCCGATCATCAACGGAC
TGTCCGACCTGTACCACCCGATCCAGATCCTGGCAGACTACCTGACCCTGCAAGA
ACACTACAGCTCCCTGAAGGGCCTGACCCTGTCATGGATCGGGGACGGGAACAA
CATCCTGCACTCCATAATGATGTCAGCCGCCAAGTTCGGAATGCACCTCCAAGCC
GCAACCCCGAAGGGCTACGAACCGGACGCATCAGTGACCAAACTGGCCGAGCAG
TACGCCAAGGAAAACGGCACCAAGCTCCTGCTGACCAACGACCCGCTGGAGGCC
GCACACGGGGGGAACGTGCTGATCACCGACACCTGGATCTCCATGGGACAGGAG
GAGGAAAAGAAGAAGCGGCTGCAGGCGTTCCAGGGGTACCAGGTCACCATGAA
AACCGCGAAGGTCGCGGCATCAGACTGGACCTTCCTGCACTGCCTGCCCCGGAA
GCCGGAAGAGGTGGACGACGAGGTGTTCTACTCGCCGCGCTCGCTGGTGTTCCCC
GAGGCGGAGAACAGGAAGTGGACCATCATGGCGGTGATGGTCAGCCTCCTGACC
GACTACTCGCCGCAGCTGCAGAAGCCGAAGTTCTGA

-continued

SEQUENCE LISTING

>pARM1840 (SEQ ID NO: 188)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTGAATAAGTAGA

>pARM1841 (SEQ ID NO: 189)
ATGCTTTTCAACCTGAGAATCCTCTTGAACAATGCTGCTTTTCGGAATGGCCACA
ACTTTATGGTTCGGAACTTCCGTTGCGGCCAGCCTTTACAAAACAAGGTCCAGCT
GAAGGGCCGGGATTTGCTCACACTAAAGAACTTTACTGGAGAAGAGATCAAGTA
CATGCTATGGCTGTCGGCCGACCTGAAGTTCCGTATCAAGCAGAAGGGAGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTCGATACCTTGGCAAAGGAGGCTTCCATTCCCATCATCAACGGCCTGAG
CGACCTGTACCACCCAATCCAAATCCTGGCTGACTACCTGACCCTGCAAGAGCAC
TACAGCAGCCTGAAGGGTCTGACCCTGTCATGGATTGGCGATGGAAACAATATT
CTGCACTCCATCATGATGTCCGCCGCGAAGTTCGGAATGCATCTGCAAGCCGCCA
CTCCAAAAGGATACGAACCGGATGCATCCGTGACCAAGTTGGCGGAACAGTACG
CGAAGGAGAACGGAACCAAGCTCCTGCTGACTAACGACCCGCTCGAGGCTGCGC
ATGGGGGTAACGTGCTGATTACGGACACCTGGATCTCCATGGGGCAGGAGGAAG
AGAAGAAGAAGAGACTGCAGGCATTCCAGGGGTACCAGGTCACCATGAAAACC
GCAAAAGTGGCAGCTTCGGACTGGACTTTCCTGCATTGCCTGCCGAGGAAGCCG
GAGGAAGTCGACGACGAAGTGTTCTACTCGCCTCGGTCCCTGGTGTTCCCCGAGG
CCGAAAACCGGAAGTGGACCATCATGGCCGTGATGGTGTCCTTGCTGACTGACT
ATAGCCCGCAGCTGCAGAAGCCTAAGTTCTGAATAAGTAGA

>pARM1842 (SEQ ID NO: 190)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCCTGGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGAATAAGTAGA

>pARM1843 (SEQ ID NO: 191)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC

-continued

SEQUENCE LISTING

TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM1844 (SEQ ID NO: 192)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM1845 (SEQ ID NO: 193)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM1846 (SEQ ID NO: 194)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

-continued

SEQUENCE LISTING

>pARM1847 (SEQ ID NO: 195)
ATGCTTTTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM1882 (SEQ ID NO: 196)
ATGGTGTTCAACCTCCGCATCCTCCTCAACAACGCCGCATTCAGAAACGGGCACA
ACTTCATGGTCAGAAACTTCCGCTGCGGGCAACCCCTACAAAACAAGGTCCAGC
TCAAGGGGCGGGACCTCCTGACCCTGAAGAACTTCACCGGCGAAGAGATCAAGT
ACATGCTGTGGCTCTCCGCCGACCTGAAGTTCCGCATCAAGCAGAAGGGAGAGT
ACCTCCCGCTGCTGCAAGGGAAGTCGCTGGGGATGATCTTCGAGAAGCGGTCAA
CCAGAACCCGGCTGTCAACCGAAACCGGGTTCGCACTGCTGGGGGGACACCCGT
GCTTCCTGACCACCCAAGACATCCACCTGGGAGTGAACGAATCGCTGACCGACA
CCGCCCGCGTGCTGAGCTCAATGGCGGACGCCGTGCTGGCCCGCGTGTACAAGC
AGTCCGACCTGGACACCCTGGCCAAGGAAGCGTCCATCCCGATCATCAACGGAC
TGTCCGACCTGTACCACCCGATCCAGATCCTGGCAGACTACCTGACCCTGCAAGA
ACACTACAGCTCCCTGAAGGGCCTGACCCTGTCATGGATCGGGGACGGGAACAA
CATCCTGCACTCCATAATGATGTCAGCCGCCAAGTTCGGAATGCACCTCCAAGCC
GCAACCCCGAAGGGCTACGAACCGGACGCATCAGTGACCAAACTGGCCGAGCAG
TACGCCAAGGAAAACGGCACCAAGCTCCTGCTGACCAACGACCCGCTGGAGGCC
GCACACGGGGGGAACGTGCTGATCACCGACACCTGGATCTCCATGGGACAGGAG
GAGGAAAAGAAGAAGCGGCTGCAGGCGTTCCAGGGGTACCAGGTCACCATGAA
AACCGCGAAGGTCGCGGCATCAGACTGGACCTTCCTGCACTGCCTGCCCCGGAA
GCCGGAAGAGGTGGACGACGAGGTGTTCTACTCGCCGCGCTCGCTGGTGTTCCCC
GAGGCGGAGAACAGGAAGTGGACCATCATGGCGGTGATGGTCAGCCTCCTGACC
GACTACTCGCCGCAGCTGCAGAAGCCGAAGTTCTGA

>pARM1883 (SEQ ID NO: 197)
ATGGTGTTCAACCTCCGCATCCTCCTCAACAACGCCGCATTCAGAAACGGGCACA
ACTTCATGGTCAGAAACTTCCGCTGCGGGCAACCCCTACAAAACCGGGTCCAGCT
CAAGGGGCGGGACCTCCTGACCCTGAAGAACTTCACCGGCGAAGAGATCAAGTA
CATGCTGTGGCTCTCCGCCGACCTGAAGTTCCGCATCAAGCAGAAGGGAGAGTA
CCTCCCGCTGCTGCAAGGGAAGTCGCTGGGGATGATCTTCGAGAAGCGGTCAAC
CAGAACCCGGCTGTCAACCGAAACCGGGTTCGCACTGCTGGGGGGACACCCGTG
CTTCCTGACCACCCAAGACATCCACCTGGGAGTGAACGAATCGCTGACCGACAC
CGCCCGCGTGCTGAGCTCAATGGCGGACGCCGTGCTGGCCCGCGTGTACAAGCA
GTCCGACCTGGACACCCTGGCCAAGGAAGCGTCCATCCCGATCATCAACGGACT
GTCCGACCTGTACCACCCGATCCAGATCCTGGCAGACTACCTGACCCTGCAAGAA
CACTACAGCTCCCTGAAGGGCCTGACCCTGTCATGGATCGGGGACGGGAACAAC
ATCCTGCACTCCATAATGATGTCAGCCGCCAAGTTCGGAATGCACCTCCAAGCCG
CAACCCCGAAGGGCTACGAACCGGACGCATCAGTGACCAAACTGGCCGAGCAGT
ACGCCAAGGAAAACGGCACCAAGCTCCTGCTGACCAACGACCCGCTGGAGGCCG
CACACGGGGGGAACGTGCTGATCACCGACACCTGGATCTCCATGGGACAGGAGG
AGGAAAAGAAGAAGCGGCTGCAGGCGTTCCAGGGGTACCAGGTCACCATGAAA
ACCGCGAAGGTCGCGGCATCAGACTGGACCTTCCTGCACTGCCTGCCCCGGAAG
CCGGAAGAGGTGGACGACGAGGTGTTCTACTCGCCGCGCTCGCTGGTGTTCCCCG
AGGCGGAGAACAGGAAGTGGACCATCATGGCGGTGATGGTCAGCCTCCTGACCG
ACTACTCGCCGCAGCTGCAGAAGCCGAAGTTCTGA

>pARM1884 (SEQ ID NO: 198)
ATGGTGTTCAACCTCCGCATCCTCCTCAACAACGCCGCATTCAGAAACGGGCACA
ACTTCATGGTCAGAAACTTCCGCTGCGGGCAACCCCTACAAAACCGGGTCCAGCT
CAAGGGGCGGGACCTCCTGACCCTGAAGAACTTCACCGGCGAAGAGATCCGGTA
CATGCTGTGGCTCTCCGCCGACCTGAAGTTCCGCATCAAGCAGAAGGGAGAGTA
CCTCCCGCTGCTGCAAGGGAAGTCGCTGGGGATGATCTTCGAGAAGCGGTCAAC
CAGAACCCGGCTGTCAACCGAAACCGGGTTCGCACTGCTGGGGGGACACCCGTG
CTTCCTGACCACCCAAGACATCCACCTGGGAGTGAACGAATCGCTGACCGACAC
CGCCCGCGTGCTGAGCTCAATGGCGGACGCCGTGCTGGCCCGCGTGTACAAGCA
GTCCGACCTGGACACCCTGGCCAAGGAAGCGTCCATCCCGATCATCAACGGACT
GTCCGACCTGTACCACCCGATCCAGATCCTGGCAGACTACCTGACCCTGCAAGAA

-continued

SEQUENCE LISTING

CACTACAGCTCCCTGAAGGGCCTGACCCTGTCATGGATCGGGGACGGGAACAAC
ATCCTGCACTCCATAATGATGTCAGCCGCCAAGTTCGGAATGCACCTCCAAGCCG
CAACCCCGAAGGGCTACGAACCGGACGCATCAGTGACCAAACTGGCCGAGCAGT
ACGCCAAGGAAAACGGCACCAAGCTCCTGCTGACCAACGACCCGCTGGAGGCCG
CACACGGGGGGAACGTGCTGATCACCGACACCTGGATCTCCATGGGACAGGAGG
AGGAAAAGAAGAAGCGGCTGCAGGCGTTCCAGGGGTACCAGGTCACCATGAAA
ACCGCGAAGGTCGCGGCATCAGACTGGACCTTCCTGCACTGCCTGCCCCGGAAG
CCGGAAGAGGTGGACGACGAGGTGTTCTACTCGCCGCGCTCGCTGGTGTTCCCCG
AGGCGGAGAACAGGAAGTGGACCATCATGGCGGTGATGGTCAGCCTCCTGACCG
ACTACTCGCCGCAGCTGCAGAAGCCGAAGTTCTGA

>pARM1885 (SEQ ID NO: 199)
ATGCTGGTCAACCTCCGCATCCTCCTCAACAACGCCGCATTCAGAAACGGGCACA
ACTTCATGGTCAGAAACTTCCGCTGCGGGCAACCCCTACAAAACAAGGTCCAGC
TCAAGGGGCGGGACCTCCTGACCCTGAAGAACTTCACCGGCGAAGAGATCAAGT
ACATGCTGTGGCTCTCCGCCGACCTGAAGTTCCGCATCAAGCAGAAGGGAGAGT
ACCTCCCGCTGCTGCAAGGGAAGTCGCTGGGGATGATCTTCGAGAAGCGGTCAA
CCAGAACCCGGCTGTCAACCGAAACCGGGTTCGCACTGCTGGGGGGACACCCGT
GCTTCCTGACCACCCAAGACATCCACCTGGGAGTGAACGAATCGCTGACCGACA
CCGCCCGCGTGCTGAGCTCAATGGCGGACGCCGTGCTGGCCCGCGTGTACAAGC
AGTCCGACCTGGACACCCTGGCCAAGGAAGCGTCCATCCCGATCATCAACGGAC
TGTCCGACCTGTACCACCCGATCCAGATCCTGGCAGACTACCTGACCCTGCAAGA
ACACTACAGCTCCCTGAAGGGCCTGACCCTGTCATGGATCGGGGACGGGAACAA
CATCCTGCACTCCATAATGATGTCAGCCGCCAAGTTCGGAATGCACCTCCAAGCC
GCAACCCCGAAGGGCTACGAACCGGACGCATCAGTGACCAAACTGGCCGAGCAG
TACGCCAAGGAAAACGGCACCAAGCTCCTGCTGACCAACGACCCGCTGGAGGCC
GCACACGGGGGGAACGTGCTGATCACCGACACCTGGATCTCCATGGGACAGGAG
GAGGAAAAGAAGAAGCGGCTGCAGGCGTTCCAGGGGTACCAGGTCACCATGAA
AACCGCGAAGGTCGCGGCATCAGACTGGACCTTCCTGCACTGCCTGCCCCGGAA
GCCGGAAGAGGTGGACGACGAGGTGTTCTACTCGCCGCGCTCGCTGGTGTTCCCC
GAGGCGGAGAACAGGAAGTGGACCATCATGGCGGTGATGGTCAGCCTCCTGACC
GACTACTCGCCGCAGCTGCAGAAGCCGAAGTTCTGA

>pARM1886 (SEQ ID NO: 200)
ATGCTGGTCAACCTCCGCATCCTCCTCAACAACGCCGCATTCAGAAACGGGCACA
ACTTCATGGTCAGAAACTTCCGCTGCGGGCAACCCCTACAAAACCGGGTCCAGCT
CAAGGGGCGGGACCTCCTGACCCTGAAGAACTTCACCGGCGAAGAGATCAAGTA
CATGCTGTGGCTCTCCGCCGACCTGAAGTTCCGCATCAAGCAGAAGGGAGAGTA
CCTCCCGCTGCTGCAAGGGAAGTCGCTGGGGATGATCTTCGAGAAGCGGTCAAC
CAGAACCCGGCTGTCAACCGAAACCGGGTTCGCACTGCTGGGGGGACACCCGTG
CTTCCTGACCACCCAAGACATCCACCTGGGAGTGAACGAATCGCTGACCGACAC
CGCCCGCGTGCTGAGCTCAATGGCGGACGCCGTGCTGGCCCGCGTGTACAAGCA
GTCCGACCTGGACACCCTGGCCAAGGAAGCGTCCATCCCGATCATCAACGGACT
GTCCGACCTGTACCACCCGATCCAGATCCTGGCAGACTACCTGACCCTGCAAGAA
CACTACAGCTCCCTGAAGGGCCTGACCCTGTCATGGATCGGGGACGGGAACAAC
ATCCTGCACTCCATAATGATGTCAGCCGCCAAGTTCGGAATGCACCTCCAAGCCG
CAACCCCGAAGGGCTACGAACCGGACGCATCAGTGACCAAACTGGCCGAGCAGT
ACGCCAAGGAAAACGGCACCAAGCTCCTGCTGACCAACGACCCGCTGGAGGCCG
CACACGGGGGGAACGTGCTGATCACCGACACCTGGATCTCCATGGGACAGGAGG
AGGAAAAGAAGAAGCGGCTGCAGGCGTTCCAGGGGTACCAGGTCACCATGAAA
ACCGCGAAGGTCGCGGCATCAGACTGGACCTTCCTGCACTGCCTGCCCCGGAAG
CCGGAAGAGGTGGACGACGAGGTGTTCTACTCGCCGCGCTCGCTGGTGTTCCCCG
AGGCGGAGAACAGGAAGTGGACCATCATGGCGGTGATGGTCAGCCTCCTGACCG
ACTACTCGCCGCAGCTGCAGAAGCCGAAGTTCTGA

>pARM1887 (SEQ ID NO: 201)
ATGCTGGTCAACCTCCGCATCCTCCTCAACAACGCCGCATTCAGAAACGGGCACA
ACTTCATGGTCAGAAACTTCCGCTGCGGGCAACCCCTACAAAACCGGGTCCAGCT
CAAGGGGCGGGACCTCCTGACCCTGAAGAACTTCACCGGCGAAGAGATCCGGTA
CATGCTGTGGCTCTCCGCCGACCTGAAGTTCCGCATCAAGCAGAAGGGAGAGTA
CCTCCCGCTGCTGCAAGGGAAGTCGCTGGGGATGATCTTCGAGAAGCGGTCAAC
CAGAACCCGGCTGTCAACCGAAACCGGGTTCGCACTGCTGGGGGGACACCCGTG
CTTCCTGACCACCCAAGACATCCACCTGGGAGTGAACGAATCGCTGACCGACAC
CGCCCGCGTGCTGAGCTCAATGGCGGACGCCGTGCTGGCCCGCGTGTACAAGCA
GTCCGACCTGGACACCCTGGCCAAGGAAGCGTCCATCCCGATCATCAACGGACT
GTCCGACCTGTACCACCCGATCCAGATCCTGGCAGACTACCTGACCCTGCAAGAA
CACTACAGCTCCCTGAAGGGCCTGACCCTGTCATGGATCGGGGACGGGAACAAC
ATCCTGCACTCCATAATGATGTCAGCCGCCAAGTTCGGAATGCACCTCCAAGCCG
CAACCCCGAAGGGCTACGAACCGGACGCATCAGTGACCAAACTGGCCGAGCAGT
ACGCCAAGGAAAACGGCACCAAGCTCCTGCTGACCAACGACCCGCTGGAGGCCG
CACACGGGGGGAACGTGCTGATCACCGACACCTGGATCTCCATGGGACAGGAGG
AGGAAAAGAAGAAGCGGCTGCAGGCGTTCCAGGGGTACCAGGTCACCATGAAA
ACCGCGAAGGTCGCGGCATCAGACTGGACCTTCCTGCACTGCCTGCCCCGGAAG
CCGGAAGAGGTGGACGACGAGGTGTTCTACTCGCCGCGCTCGCTGGTGTTCCCCG
AGGCGGAGAACAGGAAGTGGACCATCATGGCGGTGATGGTCAGCCTCCTGACCG
ACTACTCGCCGCAGCTGCAGAAGCCGAAGTTCTGA

-continued

SEQUENCE LISTING

>pARM1888 (SEQ ID NO: 202)
ATGCTGGTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1889 (SEQ ID NO: 203)
ATGCTGGTCAACCTGCGCATCCTGCTGAACAACGCCGCCTTCCGCAACGGCCACA
ACTTCATGGTGCGCAACTTCCGCTGCGGCCAGCCCCTGCAGAACCGGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1890 (SEQ ID NO: 204)
ATGCTTGTCAATCTCCGCATCCTCCTTAACAACGCCGCGTTTAGAAACGGCCACA
ACTTCATGGTCCGGAACTTCAGATGTGGCCAGCCGCTTCAAAACAAGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC
TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM1891 (SEQ ID NO: 205)
ATGCTTGTCAATCTCCGCATCCTCCTTAACAACGCCGCGTTTAGAAACGGCCACA
ACTTCATGGTCCGGAACTTCAGATGTGGCCAGCCGCTTCAAAACCGGGTCCAGCT
GAAGGGCCGGGATCTTCTGACCCTGAAGAACTTTACTGGCGAAGAGATCAAGTA
CATGCTCTGGCTCTCCGCGGACTTGAAGTTCCGCATTAAGCAGAAGGGGGAATA
CCTTCCGCTGCTTCAAGGAAAGAGCCTCGGCATGATCTTTGAGAAGCGCTCAACC
AGGACCCGCCTTTCTACTGAAACTGGGTTCGCGCTGCTCGGTGGCCACCCCTGCT
TCCTGACGACCCAGGACATCCACCTCGGAGTGAACGAATCCCTCACCGATACCG
CCCGGGTGTTATCGAGCATGGCAGATGCCGTGCTGGCCAGGGTGTACAAACAGT
CCGATCTGGACACTCTGGCCAAGGAGGCGTCAATTCCTATTATCAACGGCCTTAG
TGACCTCTACCATCCGATTCAGATCCTGGCCGATTACCTCACCCTGCAAGAACAC

-continued

SEQUENCE LISTING

TACAGCTCCCTGAAGGGTCTGACATTGTCCTGGATCGGCGACGGCAACAACATTC
TCCATTCCATCATGATGTCCGCCGCAAAATTCGGCATGCATCTTCAAGCCGCCAC
GCCGAAGGGTTACGAGCCCGACGCTTCCGTGACTAAGCTCGCCGAGCAGTACGC
TAAGGAGAACGGAACCAAGCTTCTGCTGACTAACGACCCACTAGAAGCAGCCCA
CGGGGGCAACGTGCTTATTACTGACACCTGGATCTCCATGGGCCAGGAAGAAGA
GAAAAAGAAGCGGCTGCAGGCGTTCCAGGGATATCAGGTCACCATGAAAACCGC
CAAGGTCGCTGCCTCCGACTGGACCTTCCTGCACTGCCTGCCTCGCAAGCCTGAA
GAAGTGGACGACGAGGTGTTCTACTCGCCACGGAGCCTCGTGTTCCCCGAGGCC
GAGAATAGAAAGTGGACCATCATGGCCGTGATGGTGTCACTGCTCACCGACTAC
AGCCCGCAGCTTCAGAAGCCCAAGTTCTAG

>pARM1898 (SEQ ID NO: 206)
ATGGGCCTTGTCAATCTCCGCATCCTCCTTAACAACGCCGCGTTTAGAAACGGCC
ACAACTTCATGGTCCGGAACTTCAGATGTGGCCAGCCGCTTCAAAACAAGGTCC
AGCTGAAGGGCCGGGATCTTCTGACCCTGAAGAACTTTACTGGCGAAGAGATCA
AGTACATGCTCTGGCTCTCCGCGGACTTGAAGTTCCGCATTAAGCAGAAGGGGG
AATACCTTCCGCTGCTTCAAGGAAAGAGCCTCGGCATGATCTTTGAGAAGCGCTC
AACCAGGACCCGCCTTTCTACTGAAACTGGGTTCGCGCTGCTCGGTGGCCACCCC
TGCTTCCTGACGACCCAGGACATCCACCTCGGAGTGAACGAATCCCTCACCGATA
CCGCCCGGGTGTTATCGAGCATGGCAGATGCCGTGCTGGCCAGGGTGTACAAAC
AGTCCGATCTGGACACTCTGGCCAAGGAGGCGTCAATTCCTATTATCAACGGCCT
TAGTGACCTCTACCATCCGATTCAGATCCTGGCCGATTACCTCACCCTGCAAGAA
CACTACAGCTCCCTGAAGGGTCTGACATTGTCCTGGATCGGCGACGGCAACAAC
ATTCTCCATTCCATCATGATGTCCGCCGCAAAATTCGGCATGCATCTTCAAGCCG
CCACGCCGAAGGGTTACGAGCCCGACGCTTCCGTGACTAAGCTCGCCGAGCAGT
ACGCTAAGGAGAACGGAACCAAGCTTCTGCTGACTAACGACCCACTAGAAGCAG
CCCACGGGGGCAACGTGCTTATTACTGACACCTGGATCTCCATGGGCCAGGAAG
AAGAGAAAAAGAAGCGGCTGCAGGCGTTCCAGGGATATCAGGTCACCATGAAA
ACCGCCAAGGTCGCTGCCTCCGACTGGACCTTCCTGCACTGCCTGCCTCGCAAGC
CTGAAGAAGTGGACGACGAGGTGTTCTACTCGCCACGGAGCCTCGTGTTCCCCG
AGGCCGAGAATAGAAAGTGGACCATCATGGCCGTGATGGTGTCACTGCTCACCG
ACTACAGCCCGCAGCTTCAGAAGCCCAAGTTCTAG

>pARM1899 (SEQ ID NO: 207)
ATGGGCCTTGTCAATCTCCGCATCCTCCTTAACAACGCCGCGTTTAGAAACGGCC
ACAACTTCATGGTCCGGAACTTCAGATGTGGCCAGCCGCTTCAAAACCGGGTCCA
GCTGAAGGGCCGGGATCTTCTGACCCTGAAGAACTTTACTGGCGAAGAGATCAA
GTACATGCTCTGGCTCTCCGCGGACTTGAAGTTCCGCATTAAGCAGAAGGGGGA
ATACCTTCCGCTGCTTCAAGGAAAGAGCCTCGGCATGATCTTTGAGAAGCGCTCA
ACCAGGACCCGCCTTTCTACTGAAACTGGGTTCGCGCTGCTCGGTGGCCACCCCT
GCTTCCTGACGACCCAGGACATCCACCTCGGAGTGAACGAATCCCTCACCGATAC
CGCCCGGGTGTTATCGAGCATGGCAGATGCCGTGCTGGCCAGGGTGTACAAACA
GTCCGATCTGGACACTCTGGCCAAGGAGGCGTCAATTCCTATTATCAACGGCCTT
AGTGACCTCTACCATCCGATTCAGATCCTGGCCGATTACCTCACCCTGCAAGAAC
ACTACAGCTCCCTGAAGGGTCTGACATTGTCCTGGATCGGCGACGGCAACAACA
TTCTCCATTCCATCATGATGTCCGCCGCAAAATTCGGCATGCATCTTCAAGCCGC
CACGCCGAAGGGTTACGAGCCCGACGCTTCCGTGACTAAGCTCGCCGAGCAGTA
CGCTAAGGAGAACGGAACCAAGCTTCTGCTGACTAACGACCCACTAGAAGCAGC
CCACGGGGGCAACGTGCTTATTACTGACACCTGGATCTCCATGGGCCAGGAAGA
AGAGAAAAAGAAGCGGCTGCAGGCGTTCCAGGGATATCAGGTCACCATGAAAA
CCGCCAAGGTCGCTGCCTCCGACTGGACCTTCCTGCACTGCCTGCCTCGCAAGCC
TGAAGAAGTGGACGACGAGGTGTTCTACTCGCCACGGAGCCTCGTGTTCCCCGA
GGCCGAGAATAGAAAGTGGACCATCATGGCCGTGATGGTGTCACTGCTCACCGA
CTACAGCCCGCAGCTTCAGAAGCCCAAGTTCTAG

>pARM1900 (SEQ ID NO: 208)
ATGGGCGGACTTGTCAATCTCCGCATCCTCCTTAACAACGCCGCGTTTAGAAACG
GCCACAACTTCATGGTCCGGAACTTCAGATGTGGCCAGCCGCTTCAAAACAAGG
TCCAGCTGAAGGGCCGGGATCTTCTGACCCTGAAGAACTTTACTGGCGAAGAGA
TCAAGTACATGCTCTGGCTCTCCGCGGACTTGAAGTTCCGCATTAAGCAGAAGGG
GGAATACCTTCCGCTGCTTCAAGGAAAGAGCCTCGGCATGATCTTTGAGAAGCG
CTCAACCAGGACCCGCCTTTCTACTGAAACTGGGTTCGCGCTGCTCGGTGGCCAC
CCCTGCTTCCTGACGACCCAGGACATCCACCTCGGAGTGAACGAATCCCTCACCG
ATACCGCCCGGGTGTTATCGAGCATGGCAGATGCCGTGCTGGCCAGGGTGTACA
AACAGTCCGATCTGGACACTCTGGCCAAGGAGGCGTCAATTCCTATTATCAACGG
CCTTAGTGACCTCTACCATCCGATTCAGATCCTGGCCGATTACCTCACCCTGCAA
GAACACTACAGCTCCCTGAAGGGTCTGACATTGTCCTGGATCGGCGACGGCAAC
AACATTCTCCATTCCATCATGATGTCCGCCGCAAAATTCGGCATGCATCTTCAAG
CCGCCACGCCGAAGGGTTACGAGCCCGACGCTTCCGTGACTAAGCTCGCCGAGC
AGTACGCTAAGGAGAACGGAACCAAGCTTCTGCTGACTAACGACCCACTAGAAG
CAGCCCACGGGGGCAACGTGCTTATTACTGACACCTGGATCTCCATGGGCCAGG
AAGAAGAGAAAAAGAAGCGGCTGCAGGCGTTCCAGGGATATCAGGTCACCATG
AAAACCGCCAAGGTCGCTGCCTCCGACTGGACCTTCCTGCACTGCCTGCCTCGCA
AGCCTGAAGAAGTGGACGACGAGGTGTTCTACTCGCCACGGAGCCTCGTGTTCC
CCGAGGCCGAGAATAGAAAGTGGACCATCATGGCCGTGATGGTGTCACTGCTCA
CCGACTACAGCCCGCAGCTTCAGAAGCCCAAGTTCTAG

-continued

SEQUENCE LISTING

>pARM1903 (SEQ ID NO: 209)
ATGGCCCTTTTCAATCTCCGCATCCTCCTTAACAACGCCGCGTTTAGAAACGGCC
ACAACTTCATGGTCCGGAACTTCAGATGTGGCCAGCCGCTTCAAGGCAAGGTCC
AGCTGAAGGGCCGGGATCTTCTGACCCTGAAGAACTTTACTGGCGAAGAGATCA
AGTACATGCTCTGGCTCTCCGCGGACTTGAAGTTCCGCATTAAGCAGAAGGGGG
AATACCTTCCGCTGCTTCAAGGAAAGAGCCTCGGCATGATCTTTGAGAAGCGCTC
AACCAGGACCCGCCTTTCTACTGAAACTGGGTTCGCGCTGCTCGGTGGCCACCCC
TGCTTCCTGACGACCCAGGACATCCACCTCGGAGTGAACGAATCCCTCACCGATA
CCGCCCGGGTGTTATCGAGCATGGCAGATGCCGTGCTGGCCAGGGTGTACAAAC
AGTCCGATCTGGACACTCTGGCCAAGGAGGCGTCAATTCCTATTATCAACGGCCT
TAGTGACCTCTACCATCCGATTCAGATCCTGGCCGATTACCTCACCCTGCAAGAA
CACTACAGCTCCCTGAAGGGTCTGACATTGTCCTGGATCGGCGACGGCAACAAC
ATTCTCCATTCCATCATGATGTCCGCCGCAAAATTCGGCATGCATCTTCAAGCCG
CCACGCCGAAGGGTTACGAGCCCGACGCTTCCGTGACTAAGCTCGCCGAGCAGT
ACGCTAAGGAGAACGGAACCAAGCTTCTGCTGACTAACGACCCACTAGAAGCAG
CCCACGGGGGCAACGTGCTTATTACTGACACCTGGATCTCCATGGGCCAGGAAG
AAGAGAAAAAGAAGCGGCTGCAGGCGTTCCAGGGATATCAGGTCACCATGAAA
ACCGCCAAGGTCGCTGCCTCCGACTGGACCTTCCTGCACTGCCTGCCTCGCAAGC
CTGAAGAAGTGGACGACGAGGTGTTCTACTCGCCACGGAGCCTCGTGTTCCCCG
AGGCCGAGAATAGAAAGTGGACCATCATGGCCGTGATGGTGTCACTGCTCACCG
ACTACAGCCCGCAGCTTCAGAAGCCCAAGTTCTAGATAAGTGAA

>pARM1904 (SEQ ID NO: 210)
ATGGCCCTTTTCAATCTCCGCATCCTCCTTAACAACGCCGCGTTTAGAAACGGCC
ACAACTTCATGGTCCGGAACTTCAGATGTGGCCAGCCGCTTCAAGGCCGGGTCCA
GCTGAAGGGCCGGGATCTTCTGACCCTGAAGAACTTTACTGGCGAAGAGATCAA
GTACATGCTCTGGCTCTCCGCGGACTTGAAGTTCCGCATTAAGCAGAAGGGGGA
ATACCTTCCGCTGCTTCAAGGAAAGAGCCTCGGCATGATCTTTGAGAAGCGCTCA
ACCAGGACCCGCCTTTCTACTGAAACTGGGTTCGCGCTGCTCGGTGGCCACCCCT
GCTTCCTGACGACCCAGGACATCCACCTCGGAGTGAACGAATCCCTCACCGATAC
CGCCCGGGTGTTATCGAGCATGGCAGATGCCGTGCTGGCCAGGGTGTACAAACA
GTCCGATCTGGACACTCTGGCCAAGGAGGCGTCAATTCCTATTATCAACGGCCTT
AGTGACCTCTACCATCCGATTCAGATCCTGGCCGATTACCTCACCCTGCAAGAAC
ACTACAGCTCCCTGAAGGGTCTGACATTGTCCTGGATCGGCGACGGCAACAACA
TTCTCCATTCCATCATGATGTCCGCCGCAAAATTCGGCATGCATCTTCAAGCCGC
CACGCCGAAGGGTTACGAGCCCGACGCTTCCGTGACTAAGCTCGCCGAGCAGTA
CGCTAAGGAGAACGGAACCAAGCTTCTGCTGACTAACGACCCACTAGAAGCAGC
CCACGGGGGCAACGTGCTTATTACTGACACCTGGATCTCCATGGGCCAGGAAGA
AGAGAAAAAGAAGCGGCTGCAGGCGTTCCAGGGATATCAGGTCACCATGAAAA
CCGCCAAGGTCGCTGCCTCCGACTGGACCTTCCTGCACTGCCTGCCTCGCAAGCC
TGAAGAAGTGGACGACGAGGTGTTCTACTCGCCACGGAGCCTCGTGTTCCCCGA
GGCCGAGAATAGAAAGTGGACCATCATGGCCGTGATGGTGTCACTGCTCACCGA
CTACAGCCCGCAGCTTCAGAAGCCCAAGTTCTAGATAAGTGAA

>pARM1905 (SEQ ID NO: 211)
ATGGCCCTTTTCAATCTCCGCATCCTCCTTAACAACGCCGCGTTTAGAAACGGCC
ACAACTTCATGGTCCGGAACTTCAGATGTGGCCAGCCGCTTCAAGGCCGGGTCCA
GCTGAAGGGCCGGGATCTTCTGACCCTGAAGAACTTTACTGGCGAAGAGATCAG
GTACATGCTCTGGCTCTCCGCGGACTTGAAGTTCCGCATTAAGCAGAAGGGGGA
ATACCTTCCGCTGCTTCAAGGAAAGAGCCTCGGCATGATCTTTGAGAAGCGCTCA
ACCAGGACCCGCCTTTCTACTGAAACTGGGTTCGCGCTGCTCGGTGGCCACCCCT
GCTTCCTGACGACCCAGGACATCCACCTCGGAGTGAACGAATCCCTCACCGATAC
CGCCCGGGTGTTATCGAGCATGGCAGATGCCGTGCTGGCCAGGGTGTACAAACA
GTCCGATCTGGACACTCTGGCCAAGGAGGCGTCAATTCCTATTATCAACGGCCTT
AGTGACCTCTACCATCCGATTCAGATCCTGGCCGATTACCTCACCCTGCAAGAAC
ACTACAGCTCCCTGAAGGGTCTGACATTGTCCTGGATCGGCGACGGCAACAACA
TTCTCCATTCCATCATGATGTCCGCCGCAAAATTCGGCATGCATCTTCAAGCCGC
CACGCCGAAGGGTTACGAGCCCGACGCTTCCGTGACTAAGCTCGCCGAGCAGTA
CGCTAAGGAGAACGGAACCAAGCTTCTGCTGACTAACGACCCACTAGAAGCAGC
CCACGGGGGCAACGTGCTTATTACTGACACCTGGATCTCCATGGGCCAGGAAGA
AGAGAAAAAGAAGCGGCTGCAGGCGTTCCAGGGATATCAGGTCACCATGAAAA
CCGCCAAGGTCGCTGCCTCCGACTGGACCTTCCTGCACTGCCTGCCTCGCAAGCC
TGAAGAAGTGGACGACGAGGTGTTCTACTCGCCACGGAGCCTCGTGTTCCCCGA
GGCCGAGAATAGAAAGTGGACCATCATGGCCGTGATGGTGTCACTGCTCACCGA
CTACAGCCCGCAGCTTCAGAAGCCCAAGTTCTAGATAAGTGAA

>pARM1906 (SEQ ID NO: 212)
ATGGCCCTTGTCAATCTCCGCATCCTCCTTAACAACGCCGCGTTTAGAAACGGCC
ACAACTTCATGGTCCGGAACTTCAGATGTGGCCAGCCGCTTCAAGGCAGGGTCC
AGCTGAAGGGCCGGGATCTTCTGACCCTGAAGAACTTTACTGGCGAAGAGATCA
AGTACATGCTCTGGCTCTCCGCGGACTTGAAGTTCCGCATTAAGCAGAAGGGGG
AATACCTTCCGCTGCTTCAAGGAAAGAGCCTCGGCATGATCTTTGAGAAGCGCTC
AACCAGGACCCGCCTTTCTACTGAAACTGGGTTCGCGCTGCTCGGTGGCCACCCC
TGCTTCCTGACGACCCAGGACATCCACCTCGGAGTGAACGAATCCCTCACCGATA
CCGCCCGGGTGTTATCGAGCATGGCAGATGCCGTGCTGGCCAGGGTGTACAAAC
AGTCCGATCTGGACACTCTGGCCAAGGAGGCGTCAATTCCTATTATCAACGGCCT
TAGTGACCTCTACCATCCGATTCAGATCCTGGCCGATTACCTCACCCTGCAAGAA

-continued

SEQUENCE LISTING

CACTACAGCTCCCTGAAGGGTCTGACATTGTCCTGGATCGGCGACGGCAACAAC
ATTCTCCATTCCATCATGATGTCCGCCGCAAAATTCGGCATGCATCTTCAAGCCG
CCACGCCGAAGGGTTACGAGCCCGACGCTTCCGTGACTAAGCTCGCCGAGCAGT
ACGCTAAGGAGAACGGAACCAAGCTTCTGCTGACTAACGACCCACTAGAAGCAG
CCCACGGGGGCAACGTGCTTATTACTGACACCTGGATCTCCATGGGCCAGGAAG
AAGAGAAAAAGAAGCGGCTGCAGGCGTTCCAGGGATATCAGGTCACCATGAAA
ACCGCCAAGGTCGCTGCCTCCGACTGGACCTTCCTGCACTGCCTGCCTCGCAAGC
CTGAAGAAGTGGACGACGAGGTGTTCTACTCGCCACGGAGCCTCGTGTTCCCCG
AGGCCGAGAATAGAAAGTGGACCATCATGGCCGTGATGGTGTCACTGCTCACCG
ACTACAGCCCGCAGCTTCAGAAGCCCAAGTTCTAAGTGAATAGA

>pARM1907 (SEQ ID NO: 213)
ATGGCCCTTTTCAATCTCCGCATCCTCCTTAACAACGCCGCGTTTAGAAACGGCC
ACAACTTCATGGTCCGGAACTTCAGATGTGGCCAGCCGCTTCAAGTCAAGGTCCA
GCTGAAGGGCCGGGATCTTCTGACCCTGAAGAACTTTACTGGCGAAGAGATCAA
GTACATGCTCTGGCTCTCCGCGGACTTGAAGTTCCGCATTAAGCAGAAGGGGGA
ATACCTTCCGCTGCTTCAAGGAAAGAGCCTCGGCATGATCTTTGAGAAGCGCTCA
ACCAGGACCCGCCTTTCTACTGAAACTGGGTTCGCGCTGCTCGGTGGCCACCCCT
GCTTCCTGACGACCCAGGACATCCACCTCGGAGTGAACGAATCCCTCACCGATAC
CGCCCGGGTGTTATCGAGCATGGCAGATGCCGTGCTGGCCAGGGTGTACAAACA
GTCCGATCTGGACACTCTGGCCAAGGAGGCGTCAATTCCTATTATCAACGGCCTT
AGTGACCTCTACCATCCGATTCAGATCCTGGCCGATTACCTCACCCTGCAAGAAC
ACTACAGCTCCCTGAAGGGTCTGACATTGTCCTGGATCGGCGACGGCAACAACA
TTCTCCATTCCATCATGATGTCCGCCGCAAAATTCGGCATGCATCTTCAAGCCGC
CACGCCGAAGGGTTACGAGCCCGACGCTTCCGTGACTAAGCTCGCCGAGCAGTA
CGCTAAGGAGAACGGAACCAAGCTTCTGCTGACTAACGACCCACTAGAAGCAGC
CCACGGGGGCAACGTGCTTATTACTGACACCTGGATCTCCATGGGCCAGGAAGA
AGAGAAAAAGAAGCGGCTGCAGGCGTTCCAGGGATATCAGGTCACCATGAAAA
CCGCCAAGGTCGCTGCCTCCGACTGGACCTTCCTGCACTGCCTGCCTCGCAAGCC
TGAAGAAGTGGACGACGAGGTGTTCTACTCGCCACGGAGCCTCGTGTTCCCCGA
GGCCGAGAATAGAAAGTGGACCATCATGGCCGTGATGGTGTCACTGCTCACCGA
CTACAGCCCGCAGCTTCAGAAGCCCAAGTTCTAGATAAGTGAA

>pARM1908 (SEQ ID NO: 214)
ATGGCCCTTTTCAATCTCCGCATCCTCCTTAACAACGCCGCGTTTAGAAACGGCC
ACAACTTCATGGTCCGGAACTTCAGATGTGGCCAGCCGCTTCAAGTCAGGGTCCA
GCTGAAGGGCCGGGATCTTCTGACCCTGAAGAACTTTACTGGCGAAGAGATCAA
GTACATGCTCTGGCTCTCCGCGGACTTGAAGTTCCGCATTAAGCAGAAGGGGGA
ATACCTTCCGCTGCTTCAAGGAAAGAGCCTCGGCATGATCTTTGAGAAGCGCTCA
ACCAGGACCCGCCTTTCTACTGAAACTGGGTTCGCGCTGCTCGGTGGCCACCCCT
GCTTCCTGACGACCCAGGACATCCACCTCGGAGTGAACGAATCCCTCACCGATAC
CGCCCGGGTGTTATCGAGCATGGCAGATGCCGTGCTGGCCAGGGTGTACAAACA
GTCCGATCTGGACACTCTGGCCAAGGAGGCGTCAATTCCTATTATCAACGGCCTT
AGTGACCTCTACCATCCGATTCAGATCCTGGCCGATTACCTCACCCTGCAAGAAC
ACTACAGCTCCCTGAAGGGTCTGACATTGTCCTGGATCGGCGACGGCAACAACA
TTCTCCATTCCATCATGATGTCCGCCGCAAAATTCGGCATGCATCTTCAAGCCGC
CACGCCGAAGGGTTACGAGCCCGACGCTTCCGTGACTAAGCTCGCCGAGCAGTA
CGCTAAGGAGAACGGAACCAAGCTTCTGCTGACTAACGACCCACTAGAAGCAGC
CCACGGGGGCAACGTGCTTATTACTGACACCTGGATCTCCATGGGCCAGGAAGA
AGAGAAAAAGAAGCGGCTGCAGGCGTTCCAGGGATATCAGGTCACCATGAAAA
CCGCCAAGGTCGCTGCCTCCGACTGGACCTTCCTGCACTGCCTGCCTCGCAAGCC
TGAAGAAGTGGACGACGAGGTGTTCTACTCGCCACGGAGCCTCGTGTTCCCCGA
GGCCGAGAATAGAAAGTGGACCATCATGGCCGTGATGGTGTCACTGCTCACCGA
CTACAGCCCGCAGCTTCAGAAGCCCAAGTTCTAGATAAGTGAA

>pARM1915 (SEQ ID NO: 215)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

-continued

| SEQUENCE LISTING |
| --- |

>pARM1916 (SEQ ID NO: 216)
ATGGGAGTATTCAACCTGCGCATCCTGCTGAACAACGCCGCCTTCCGCAACGGCC
ACAACTTCATGGTGCGCAACTTCCGCTGCGGCCAGCCCCTGCAGAACAAGGTGC
AGCTGAAGGGCCGCGACCTGCTGACCCTGAAGAACTTCACCGGCGAGGAGATCA
AGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM1917 (SEQ ID NO: 217)
ATGGGAGTATTCAACCTGCGCATCCTGCTGAACAACGCCGCCTTCCGCAACGGCC
ACAACTTCATGGTGCGCAACTTCCGCTGCGGCCAGCCCCTGCAGAACCGGGTGC
AGCTGAAGGGCCGCGACCTGCTGACCCTGAAGAACTTCACCGGCGAGGAGATCC
GGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM1918 (SEQ ID NO: 218)
ATGCTGGTATTCAACCTGCGCATCCTGCTGAACAACGCCGCCTTCCGCAACGGCC
ACAACTTCATGGTGCGCAACTTCCGCTGCGGCCAGCCCCTGCAGAACCGGGTGC
AGCTGAAGGGCCGCGACCTGCTGACCCTGAAGAACTTCACCGGCGAGGAGATCC
GGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM1919 (SEQ ID NO: 219)
ATGGGAGTATTCAACCTGCGCATCCTGCTGAACAACGCCGCCTTCCGCAACGGCC
ACAACTTCATGGTGCGCAACTTCCGCTGCGGCCAGCCCCTGCAGAACAAGGTGC
AGCTGAAGGGCCGCGACCTGCTGACCCTGAAGAACTTCACCGGCGAGGAGATCA
AGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA

-continued

SEQUENCE LISTING

GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM1920 (SEQ ID NO: 220)
ATGGGAGTATTCAACCTGCGCATCCTGCTGAACAACGCCGCCTTCCGCAACGGCC
ACAACTTCATGGTGCGCAACTTCCGCTGCGGCCAGCCCCTGCAGAACCGGGTGC
AGCTGAAGGGCCGCGACCTGCTGACCCTGAAGAACTTCACCGGCGAGGAGATCC
GGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM1921 (SEQ ID NO: 221)
ATGCTGGTATTCAACCTGCGCATCCTGCTGAACAACGCCGCCTTCCGCAACGGCC
ACAACTTCATGGTGCGCAACTTCCGCTGCGGCCAGCCCCTGCAGAACCGGGTGC
AGCTGAAGGGCCGCGACCTGCTGACCCTGAAGAACTTCACCGGCGAGGAGATCC
GGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM1925 (SEQ ID NO: 222)
ATGTTGTTCAACTTGAGGATCTTGTTGAACAACGCCGCCTTCAGGAACGGACACA
ACTTCATGGTAAGGAACTTCAGGTGCGGACAGCCCTTGCAGAACAAAGTACAGT
TGAAAGGAAGGGACTTGTTGACATTGAAAAACTTCACAGGAGAAGAAATCAAAT
ACATGTTGTGGTTGTCGGCCGACTTGAAATTCAGGATCAAACAGAAAGGAGAAT
ACTTGCCCTTGTTGCAGGGAAAATCGTTGGGAATGATCTTCGAAAAAAGGTCGA
CAAGGACAAGGTTGTCGACAGAAACAGGATTCGCCTTGTTGGGAGGACACCCCT
GCTTCTTGACAACACAGGACATCCACTTGGGAGTAAACGAATCGTTGACAGACA
CAGCCAGGGTATTGTCGTCGATGGCCGACGCCGTATTGGCCAGGGTATACAAAC
AGTCGGACTTGGACACATTGGCCAAAGAAGCCTCGATCCCCATCATCAACGGAT
TGTCGGACTTGTACCACCCCATCCAGATCTTGGCCGACTACTTGACATTGCAGGA
ACACTACTCGTCGTTGAAAGGATTGACATTGTCGTGGATCGGAGACGGAAACAA
CATCTTGCACTCGATCATGATGTCGGCCGCCAAATTCGGAATGCACTTGCAGGCC
GCCACACCCAAAGGATACGAACCCGACGCCTCGGTAACAAAATTGGCCGAACAG
TACGCCAAAGAAAACGGAACAAAATTGTTGTTGACAAACGACCCCTTGGAAGCC
GCCCACGGAGGAAACGTATTGATCACAGACACATGGATCTCGATGGGACAGGAA
GAAGAAAAAAAAAAAAGGTTGCAGGCCTTCCAGGGATACCAGGTAACAATGAA
AACAGCCAAAGTAGCCGCCTCGGACTGGACATTCTTGCACTGCTTGCCCAGGAA
ACCCGAAGAAGTAGACGACGAAGTATTCTACTCGCCCAGGTCGTTGGTATTCCCC
GAAGCCGAAAACAGGAAATGGACAATCATGGCCGTAATGGTATCGTTGTTGACA
GACTACTCGCCCCAGTTGCAGAAACCCAAATTCTGAATAGTGAA

-continued

SEQUENCE LISTING

>pARM1926 (SEQ ID NO: 223)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGGGCAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1927 (SEQ ID NO: 224)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGGGCCGGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1928 (SEQ ID NO: 225)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGGGCCGGGTGCAGCT
GAAGGGCCGCGACCTGCTGACCCTGAAGAACTTCACCGGCGAGGAGATCCGGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM1929 (SEQ ID NO: 226)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGGGCAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA

SEQUENCE LISTING

GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM2016 (SEQ ID NO: 227)
ATGCTGTTCAACCTGCGCATCCTGCTGAACAACGCCGCCTTCCGCAACGGCCACA
ACTTCATGGTGCGCAACTTCCGCTGCGGCCAGCCCCTGCAGAACAAGGTGCAGCT
GAAGGGCCGCGACCTGCTGACCCTGAAGAACTTCACCGGCGAGGAGATCAAGTA
CATGCTGTGGCTGAGCGCCGACCTGAAGTTCCGCATCAAGCAGAAGGGCGAGTA
CCTGCCCCTGCTGCAGGGCAAGAGCCTGGGCATGATCTTCGAGAAGCGCAGCAC
CCGCACCCGCCTGAGCACCGAGACAGGCTTCGCCCTGCTGGGCGGCCACCCCTG
CTTCCTGACCACCCAGGACATCCACCTGGGCGTGAACGAGAGCCTGACCGACAC
CGCCCGCGTGCTGAGCAGCATGGCCGACGCCGTGCTGGCCCGCGTGTACAAGCA
GAGCGACCTGGACACCCTGGCCAAGGAGGCCAGCATCCCCATCATCAACGGCCT
GAGCGACCTGTACCACCCCATCCAGATCCTGGCCGACTACCTGACCCTGCAGGA
GCACTACAGCAGCCTGAAGGGCCTGACCCTGAGCTGGATCGGCGACGGCAACAA
CATCCTGCACAGCATCATGATGAGCGCCGCCAAGTTCGGCATGCACCTGCAGGC
CGCCACCCCCAAGGGCTACGAGCCCGACGCCAGCGTGACCAAGCTGGCCGAGCA
GTACGCCAAGGAGAACGGCACCAAGCTGCTGCTGACCAACGACCCCCTGGAGGC
CGCCCACGGCGGCAACGTGCTGATCACCGACACCTGGATCAGCATGGGCCAGGA
GGAGGAGAAGAAGAAGCGCCTGCAGGCCTTCCAGGGCTACCAGGTGACCATGA
AGACCGCCAAGGTGGCCGCCAGCGACTGGACCTTCCTGCACTGCCTGCCCCGCA
AGCCCGAGGAGGTGGACGACGAGGTGTTCTACAGCCCCCGCAGCCTGGTGTTCC
CCGAGGCCGAGAACCGCAAGTGGACCATCATGGCCGTGATGGTGAGCCTGCTGA
CCGACTACAGCCCCCAGCTGCAGAAGCCCAAGTTCTGA

>pARM2260 (SEQ ID NO: 228)
ATGCTGGTATTCAACCTGCGCATCCTGCTGAACAACGCCGCCTTCCGCAACGGCC
ACAACTTCATGGTGCGCAACTTCCGCTGCGGCCAGCCCCTGCAGAACCGGGTGC
AGCTGAAGGGCCGCGACCTGCTGACCCTGAAGAACTTCACCGGCGAGGAGATCC
GGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

>pARM2262 (SEQ ID NO: 229)
ATGCTGGTATTCAACCTGCGCATCCTGCTGAACAACGCCGCCTTCCGCAACGGCC
ACAACTTCATGGTGCGCAACTTCCGCTGCGGCCAGCCCCTGCAGAACCGGGTGC
AGCTGAAGGGCCGCGACCTGCTGACCCTGAAGAACTTCACCGGCGAGGAGATCC
GGTACATGCTGTGGCTGAGCGCCGACCTGAAGTTCCGCATCAAGCAGAAGGGCG
AGTACCTGCCCCTGCTGCAGGGCAAGAGCCTGGGCATGATCTTCGAGAAGCGCA
GCACCCGCACCCGCCTGAGCACCGAGACAGGCTTCGCCCTGCTGGGCGGCCACC
CCTGCTTCCTGACCACCCAGGACATCCACCTGGGCGTGAACGAGAGCCTGACCG
ACACCGCCCGCGTGCTGAGCAGCATGGCCGACGCCGTGCTGGCCCGCGTGTACA
AGCAGAGCGACCTGGACACCCTGGCCAAGGAGGCCAGCATCCCCATCATCAACG
GCCTGAGCGACCTGTACCACCCCATCCAGATCCTGGCCGACTACCTGACCCTGCA
GGAGCACTACAGCAGCCTGAAGGGCCTGACCCTGAGCTGGATCGGCGACGGCAA
CAACATCCTGCACAGCATCATGATGAGCGCCGCCAAGTTCGGCATGCACCTGCA
GGCCGCCACCCCCAAGGGCTACGAGCCCGACGCCAGCGTGACCAAGCTGGCCGA
GCAGTACGCCAAGGAGAACGGCACCAAGCTGCTGCTGACCAACGACCCCCTGGA
GGCCGCCCACGGCGGCAACGTGCTGATCACCGACACCTGGATCAGCATGGGCCA
GGAGGAGGAGAAGAAGAAGCGCCTGCAGGCCTTCCAGGGCTACCAGGTGACCA
TGAAGACCGCCAAGGTGGCCGCCAGCGACTGGACCTTCCTGCACTGCCTGCCCC
GCAAGCCCGAGGAGGTGGACGACGAGGTGTTCTACAGCCCCCGCAGCCTGGTGT
TCCCCGAGGCCGAGAACCGCAAGTGGACCATCATGGCCGTGATGGTGAGCCTGC
TGACCGACTACAGCCCCCAGCTGCAGAAGCCCAAGTTCTGA

-continued

| SEQUENCE LISTING | | |
|---|---|---|
| AT5G61250 | AACCAAUCGAAAGAAACCAAA | SEQ ID NO: 230 |
| AT5G46430 | CUCUAAUCACCAGGAGUAAAA | SEQ ID NO: 231 |
| AT5G47110 | GAGAGAGAUCUUAACAAAAAA | SEQ ID NO: 232 |
| AT1G03110 | UGUGUAACAACAACAACAACA | SEQ ID NO: 233 |
| AT3G12380 | CCGCAGUAGGAAGAGAAAGCC | SEQ ID NO: 234 |
| AT5G45910 | AAAAAAAAAGAAAUCAUAAA | SEQ ID NO: 235 |
| AT1G07260 | GAGAGAAGAAAGAAGAAGACG | SEQ ID NO: 236 |
| AT3G55500 | CAAUUAAAAAUACUUACCAAA | SEQ ID NO: 237 |
| AT3G46230 | GCAAACAGAGUAAGCGAAACG | SEQ ID NO: 238 |
| AT2G36170 | GCGAAGAAGACGAACGCAAAG | SEQ ID NO: 239 |
| AT1G10660 | UUAGGACUGUAUUGACUGGCC | SEQ ID NO: 240 |
| AT4G14340 | AUCAUCGGAAUUCGGAAAAAG | SEQ ID NO: 241 |
| AT1G49310 | AAAACAAAAGUUAAAGCAGAC | SEQ ID NO: 242 |
| AT4G14360 | UUUAUCUCAAAUAAGAAGGCA | SEQ ID NO: 243 |
| AT1G28520 | GGUGGGGAGGUGAGAUUUCUU | SEQ ID NO: 244 |
| AT1G20160 | UGAUUAGGAAACUACAAAGCC | SEQ ID NO: 245 |
| AT5G37370 | CAUUUUUCAAUUUCAUAAAAC | SEQ ID NO: 246 |
| AT4G11320 | UUACUUUUAAGCCCAACAAAA | SEQ ID NO: 247 |
| AT5G40850 | GGCGUGUGUGUGUGUUGUUGA | SEQ ID NO: 248 |
| AT1G06150 | GUGGUGAAGGGGAAGGUUUAG | SEQ ID NO: 249 |
| AT2G26080 | UUGUUUUUUUUUGGUUUGGUU | SEQ ID NO: 250 |

mARM2260 (SEQ ID NO: 251)
AGGAUUAUUACAUCAAAACAAAAAGCCGCCACCAUGCUGGUAUUCAACCUGCG
CAUCCUGCUGAACAACGCCGCCUUCCGCAACGGCCACAACUUCAUGGUGCGCA
ACUUCCGCUGCGGCCAGCCCCUGCAGAACCGGGUGCAGCUGAAGGGCCGCGAC
CUGCUGACCCUGAAGAACUUCACCGGCGAGGAGAUCCGGUACAUGCUGUGGCU
GAGCGCCGACCUGAAGUUCCGCAUCAAGCAGAAGGGCGAGUACCUGCCCCUGC
UGCAGGGCAAGAGCCUGGGCAUGAUCUUCGAGAAGCGCAGCACCCGCACCCGC
CUGAGCACCGAGACAGGCUUCGCCCUGCUGGGCGGCCACCCCUGCUUCCUGAC
CACCCAGGACAUCCACCUGGGCGUGAACGAGAGCCUGACCGACACCGCCCGCG
UGCUGAGCAGCAUGGCCGACGCCGUGCUGGCCCGCGUGUACAAGCAGAGCGAC
CUGGACACCCUGGCCAAGGAGGCCAGCAUCCCCAUCAUCAACGGCCUGAGCGA
CCUGUACCACCCCAUCCAGAUCCUGGCCGACUACCUGACCCUGCAGGAGCACU
ACAGCAGCCUGAAGGGCCUGACCCUGAGCUGGAUCGGCGACGGCAACAACAUC
CUGCACAGCAUCAUGAUGAGCGCCGCCAAGUUCGGCAUGCACCUGCAGGCCGC
CACCCCCAAGGGCUACGAGCCCGACGCCAGCGUGACCAAGCUGGCCGAGCAGU
ACGCCAAGGAGAACGGCACCAAGCUGCUGCUGACCAACGACCCCCUGGAGGCC
GCCCACGGCGGCAACGUGCUGAUCACCGACACCUGGAUCAGCAUGGGCCAGGA
GGAGGAGAAGAAGAAGCGCCUGCAGGCCUUCCAGGGCUACCAGGUGACCAUGA
AGACCGCCAAGGUGGCCGCCAGCGACUGGACCUUCCUGCACUGCCUGCCCCGC
AAGCCCGAGGAGGUGGACGACGAGGUGUUCUACAGCCCCCGCAGCCUGGUGUU
CCCCGAGGCCGAGAACCGCAAGUGGACCAUCAUGGCCGUGAUGGUGAGCCUGC
UGACCGACUACAGCCCCCAGCUGCAGAAGCCCAAGUUCUGAGGUCUCUAGUAA
UGAGCUGGAGCCUCGGUAGCCGUUCCUCCUGCCCGCUGGGCCUCCCAACGGGC
CCUCCUCCCCUCCUUGCACCGGCCCUUCCUGGUCUUUGAAUAAAGUCUGAGUG
GGCAGCAUCUAGAAAAAAAAAAAAAAAAAAAAAAAAAAAAAAAAAAAAAAAAA
AAAAAAAAAAAAAAAAAAAAAAAAAAAAAAAAAAAAAAAAAAAAAAAAAAAAA
AAAAAAAA mARM2262 (SEQ ID NO: 252)
AGGAUUAUUACAUCAAAACAAAAAGCCGCCACCAUGCUGGUAUUCAACCUGCG
CAUCCUGCUGAACAACGCCGCCUUCCGCAACGGCCACAACUUCAUGGUGCGCA
ACUUCCGCUGCGGCCAGCCCCUGCAGAACCGGGUGCAGCUGAAGGGCCGCGAC
CUGCUGACCCUGAAGAACUUCACCGGCGAGGAGAUCCGGUACAUGCUGUGGCU
GAGCGCCGACCUGAAGUUCCGCAUCAAGCAGAAGGGCGAGUACCUGCCCCUGC
UGCAGGGCAAGAGCCUGGGCAUGAUCUUCGAGAAGCGCAGCACCCGCACCCGC

-continued

| SEQUENCE LISTING |
|---|
| CUGAGCACCGAGACAGGCUUCGCCCUGCUGGGCGGCCACCCCUGCUUCCUGAC<br>CACCCAGGACAUCCACCUGGGCGUGAACGAGAGCCUGACCGACACCGCCCGCG<br>UGCUGAGCAGCAUGGCCGACGCCGUGCUGGCCCGCGUGUACAAGCAGAGCGAC<br>CUGGACACCCUGGCCAAGGAGGCCAGCAUCCCCAUCAUCAACGGCCUGAGCGA<br>CCUGUACCACCCCAUCCAGAUCCUGGCCGACUACCUGACCCUGCAGGAGCACU<br>ACAGCAGCCUGAAGGGCCUGACCCUGAGCUGGAUCGGCGACGGCAACAACAUC<br>CUGCACAGCAUCAUGAUGAGCGCCGCCAAGUUCGGCAUGCACCUGCAGGCCGC<br>CACCCCCAAGGGCUACGAGCCCGACGCCAGCGUGACCAAGCUGGCCGAGCAGU<br>ACGCCAAGGAGAACGGCACCAAGCUGCUGCUGACCAACGACCCCCUGGAGGCC<br>GCCCACGGCGGCAACGUGCUGAUCACCGACACCUGGAUCAGCAUGGGCCAGGA<br>GGAGGAGAAGAAGAAGCGCCUGCAGGCCUUCCAGGGCUACCAGGUGACCAUGA<br>AGACCGCCAAGGUGGCCGCCAGCGACUGGACCUUCCUGCACUGCCUGCCCCGC<br>AAGCCCGAGGAGGUGGACGACGAGGUGUUCUACAGCCCCCGCAGCCUGGUGUU<br>CCCCGAGGCCGAGAACCGCAAGUGGACCAUCAUGGCCGUGAUGGUGAGCCUGC<br>UGACCGACUACAGCCCCCAGCUGCAGAAGCCCAAGUUCUGAGGUCUCUAGUAA<br>UGAGCUGGAGCCUCGGUAGCCGUUCCUCCUGCCCGCUGGGCCUCCCAACGGGC<br>CCUCCUCCCCUCCUUGCACCGGCCCUUCCUGGUCUUUGAAUAAAGUCUGAGUG<br>GGCAGCAUCUAGAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAA<br>AAAAAAAAAGCU<br><br>mARM2016 (SEQ ID NO: 253)<br>AGGAUUAUUACAUCAAAACAAAAAGCCGCCACCAUGCUGUUCAACCUGCGCAU<br>CCUGCUGAACAACGCCGCCUUCCGCAACGGCCACAACUUCAUGGUGCGCAACU<br>UCCGCUGCGGCCAGCCCCUGCAGAACAAGGUGCAGCUGAAGGGCCGCGACCUG<br>CUGACCCUGAAGAACUUCACCGGCGAGGAGAUCAAGUACAUGCUGUGGCUGAG<br>CGCCGACCUGAAGUUCCGCAUCAAGCAGAAGGGCGAGUACCUGCCCCUGCUGC<br>AGGGCAAGAGCCUGGGCAUGAUCUUCGAGAAGCGCAGCACCCGCACCCGCCUG<br>AGCACCGAGACAGGCUUCGCCCUGCUGGGCGGCCACCCCUGCUUCCUGACCAC<br>CCAGGACAUCCACCUGGGCGUGAACGAGAGCCUGACCGACACCGCCCGCGUGC<br>UGAGCAGCAUGGCCGACGCCGUGCUGGCCCGCGUGUACAAGCAGAGCGACCUG<br>GACACCCUGGCCAAGGAGGCCAGCAUCCCCAUCAUCAACGGCCUGAGCGACCU<br>GUACCACCCCAUCCAGAUCCUGGCCGACUACCUGACCCUGCAGGAGCACUACA<br>GCAGCCUGAAGGGCCUGACCCUGAGCUGGAUCGGCGACGGCAACAACAUCCUG<br>CA<br>CAGCAUCAUGAUGAGCGCCGCCAAGUUCGGCAUGCACCUGCAGGCCGCCACCC<br>CCAAGGGCUACGAGCCCGACGCCAGCGUGACCAAGCUGGCCGAGCAGUACGCC<br>AAGGAGAACGGCACCAAGCUGCUGCUGACCAACGACCCCCUGGAGGCCGCCCA<br>CGGCGGCAACGUGCUGAUCACCGACACCUGGAUCAGCAUGGGCCAGGAGGAGG<br>AGAAGAAGAAGCGCCUGCAGGCCUUCCAGGGCUACCAGGUGACCAUGAAGACC<br>GCCAAGGUGGCCGCCAGCGACUGGACCUUCCUGCACUGCCUGCCCCGCAAGCC<br>CGAGGAGGUGGACGACGAGGUGUUCUACAGCCCCCGCAGCCUGGUGUUCCCCG<br>AGGCCGAGAACCGCAAGUGGACCAUCAUGGCCGUGAUGGUGAGCCUGCUGACC<br>GACUACAGCCCCCAGCUGCAGAAGCCCAAGUUCUGAGGUCUCUAGUAAUGAGC<br>UGGAGCCUCGGUAGCCGUUCCUCCUGCCCGCUGGGCCUCCCAACGGGCCCUCC<br>UCCCCUCCUUGCACCGGCCCUUCCUGGUCUUUGAAUAAAGUCUGAGUGGGCAG<br>CAUCUAGAAAAAAAAAAAAAAAAAAAAAAAAAAAAAAAAAAAAAAAAAAAAAA<br>AAAAAAAAAAAAAAAAAAAAAAAAAAAAAAAAAAAAAAAAAAAAAAAAAAAAA<br>AAA |

What is claimed is:

1. A polynucleotide encoding an ornithine transcarbamylase (OTC) protein comprising an amino acid sequence of SEQ ID NO: 4 and having OTC enzymatic activity, wherein the polynucleotide comprises an optimized coding region encoding SEQ ID NO: 4, and wherein the polynucleotide is an mRNA comprising a sequence of SEQ ID NO: 119.

2. The polynucleotide of claim 1, comprising a 3' poly A tail having from about 60 sequential adenine nucleotides to about 125 sequential adenine nucleotides.

3. The polynucleotide of claim 1, comprising a 5' cap.

4. The polynucleotide of claim 3, wherein the 5' cap is m7GpppGm having the following structure:

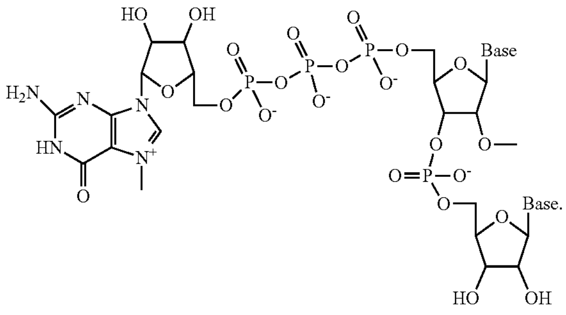

5. The polynucleotide of claim 1, wherein the percentage of uracil nucleobases in the coding region of the polynucleotide is reduced with respect to the percentage of uracil nucleobases in the wild-type OTC nucleic acid sequence.

6. The polynucleotide of claim 1, wherein 1-100% of the uridine nucleotides are each independently a modified uridine analog selected from the group consisting of 5-methoxyuridine, $N^1$-methylpseudouridine, 5-hydroxyuridine, 5-methyluridine, 5-hydroxymethyluridine, 5-carboxyuridine, 5-carboxymethylesteruridine, 5-formyluridine, 5-propynyluridine, 5-bromouridine, 5-fluorouridine, 5-iodouridine, 2-thiouridine, 6-methyluridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, $N^1$-hydroxymethylpseudouridine, 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

7. The polynucleotide of claim 6, wherein 100% of the uridine nucleotides are 5-methoxyuridine.

8. The polynucleotide of claim 1, wherein 1-100% of the uridines of the polynucleotide are modified uridine analogs.

9. A pharmaceutical composition comprising the polynucleotide of claim 1.

10. The pharmaceutical composition of claim 9, comprising a pharmaceutically acceptable carrier, wherein the pharmaceutically acceptable carrier is a lipid formulation.

11. A method of treating OTC deficiency in a patient identified as suffering from OTC deficiency comprising: administering to the patient a pharmaceutical composition of claim 9, wherein upon administration of the pharmaceutical composition to the patient, the protein of SEQ ID NO: 4 is expressed in the patient.

12. An mRNA encoding an OTC protein having an amino acid sequence of SEQ ID NO: 4, wherein the mRNA has a polynucleotide sequence of SEQ ID NO: 119 and wherein the encoded protein has OTC enzymatic activity.

13. The mRNA of claim 12, wherein 1-100% of the uridine nucleotides are each independently a modified uridine analog selected from the group consisting of 5-methoxyuridine, $N^1$-methylpseudouridine, 5-hydroxyuridine, 5-methyluridine, 5-hydroxymethyluridine, 5-carboxyuridine, 5-carboxymethylesteruridine, 5-formyluridine, 5-propynyluridine, 5-bromouridine, 5-fluorouridine, 5-iodouridine, 2-thiouridine, 6-methyluridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, $N^1$-hydroxymethylpseudouridine, 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2'-O-methylpseudouridine, 2-thio-2'O-methyluridine, and 3,2'-O-dimethyluridine.

14. The mRNA of claim 13, wherein 100% of the uridine nucleotides are 5-methoxyuridine.

15. A pharmaceutical composition comprising the mRNA of claim 12 and a pharmaceutically acceptable carrier, wherein the pharmaceutically acceptable carrier is a lipid formulation.

16. A method of treating OTC deficiency in a patient identified as suffering from OTC deficiency comprising: administering to the patient an mRNA of claim 12, wherein the mRNA expresses a protein having a sequence of SEQ ID NO: 4 in the patient.

17. A DNA molecule encoding the mRNA of claim 1.

18. A polynucleotide encoding an ornithine transcarbamylase (OTC) protein comprising an amino acid sequence of SEQ ID NO: 4 and having OTC enzymatic activity, wherein the polynucleotide comprises a sequence of SEQ ID NO: 119.

19. The polynucleotide of claim 1, comprising (a) a sequence of SEQ ID NO: 221, wherein T is substituted with U; or (b) a sequence of SEQ ID NO: 221, wherein T is substituted with U, and a sequence of SEQ ID NO: 6; or (c) a sequence of SEQ ID NO: 221, wherein T is substituted with U, and a sequence of SEQ ID NO: 21; or (d) a sequence of SEQ ID NO: 221, wherein T is substituted with U, a sequence of SEQ ID NO: 6, and a sequence of SEQ ID NO: 21.

20. The polynucleotide of claim 1, comprising (i) a sequence of SEQ ID NO: 221, wherein T is substituted with U, a sequence of SEQ ID NO: 6, and a sequence of SEQ ID NO: 21;

(ii) a sequence of SEQ ID NO: 251; or (iii) a sequence of SEQ ID NO: 252;

wherein 1-100% of the uridines of the polynucleotide are modified uridine analogs.

21. The polynucleotide of claim 1, wherein the polynucleotide is an mRNA having a polynucleotide sequence comprising (i) a sequence of SEQ ID NO: 221, wherein T is substituted with U, a sequence of SEQ ID NO: 6, and a sequence of SEQ ID NO: 21;

(ii) a sequence of SEQ ID NO: 251; or (iii) a sequence of SEQ ID NO: 252.

22. The mRNA of claim 21, wherein 1-100% of the uridine nucleotides are each independently a modified uridine analog selected from the group consisting of 5-methoxyuridine, $N^1$-methylpseudouridine, 5-hydroxyuridine, 5-methyluridine, 5-hydroxymethyluridine, 5-carboxyuridine, 5-carboxymethylesteruridine, 5-formyluridine, 5-propynyluridine, 5-bromouridine, 5-fluorouridine, 5-iodouridine, 2-thiouridine, 6-methyluridine, $N^1$-ethylpseudouridine, $N^1$-propylpseudouridine, $N^1$-cyclopropylpseudouridine, $N^1$-phenylpseudouridine, $N^1$-aminomethylpseudouridine, $N^3$-methylpseudouridine, $N^1$-hydroxypseudouridine, $N^1$-hydroxymethylpseudouridine, 5-methoxycarbonylmethyl-2-thiouridine, 5-methylaminomethyl-2-thiouridine, 5-carbamoylmethyluridine, 5-carbamoylmethyl-2'-O-methyluridine, 1-methyl-3-(3-amino-3-carboxypropy)pseudouridine, 5-methylaminomethyl-2-selenouridine, 5-carboxymethyluridine, 5-methyldihydrouridine, 5-taurinomethyluridine, 5-taurinomethyl-2-thiouridine, 5-(isopentenylaminomethyl)uridine, 2' methylpseudouridine, 2-thio-2'O-methyluridine, and 3,2'-O-dimethyluridine.

23. The mRNA of claim 22, wherein 100% of the uridine nucleotides are 5-methoxyuridine.

24. A pharmaceutical composition comprising the mRNA of claim 21 and a pharmaceutically acceptable carrier, wherein the pharmaceutically acceptable carrier is a lipid formulation.

25. A method of treating OTC deficiency in a patient identified as suffering from OTC deficiency comprising: administering to the patient an mRNA of claim 21, wherein the mRNA expresses a protein having a sequence of SEQ ID NO: 4 in the patient.

* * * * *